US012630845B2

(12) United States Patent
Zolotukhin et al.

(10) Patent No.: US 12,630,845 B2
(45) Date of Patent: May 19, 2026

(54) AAV CAPSID VARIANTS FOR TARGETING HUMAN GLIOBLASTOMA CELLS

(71) Applicant: University of Florida Research Foundation, Incorporated, Gainesville, FL (US)

(72) Inventors: Sergei Zolotukhin, Gainesville, FL (US); David Tran, Gainesville, FL (US); Oleksandr Kondratov, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1085 days.

(21) Appl. No.: 17/633,769

(22) PCT Filed: Aug. 7, 2020

(86) PCT No.: PCT/US2020/045526
§ 371 (c)(1),
(2) Date: Feb. 8, 2022

(87) PCT Pub. No.: WO2021/030225
PCT Pub. Date: Feb. 18, 2021

(65) Prior Publication Data
US 2022/0333136 A1 Oct. 20, 2022

Related U.S. Application Data

(60) Provisional application No. 62/884,716, filed on Aug. 9, 2019.

(51) Int. Cl.
*C12N 15/861* (2006.01)
*C07K 14/005* (2006.01)

(52) U.S. Cl.
CPC .......... *C12N 15/861* (2013.01); *C07K 14/005* (2013.01)

(58) Field of Classification Search
CPC ........................... C12N 15/861; C07K 14/005
See application file for complete search history.

(56) References Cited

U.S. PATENT DOCUMENTS

| | | | |
|---|---|---|---|
| 6,156,303 | A | 12/2000 | Russell et al. |
| 7,186,552 | B2 | 3/2007 | Wilson et al. |
| 7,220,577 | B2 | 5/2007 | Zolotukhin |
| 7,723,112 | B2 | 5/2010 | Clarke et al. |
| 7,812,124 | B2 | 10/2010 | Palm |
| 7,927,585 | B2 | 4/2011 | Snyder |
| 8,445,267 | B2 | 5/2013 | Zhong et al. |
| 9,157,098 | B2 | 10/2015 | Zhong et al. |
| 9,677,088 | B2 | 6/2017 | Nakai et al. |
| 9,725,485 | B2 | 8/2017 | Srivastava et al. |
| 10,011,640 | B2 | 7/2018 | Srivastava et al. |
| 10,308,957 | B2 | 6/2019 | Boye et al. |
| 10,426,844 | B2 | 10/2019 | Agbandje-McKenna et al. |
| 10,648,000 | B2 | 5/2020 | Hauswirth et al. |
| 10,723,768 | B2 | 7/2020 | Zhong et al. |
| 10,793,606 | B2 | 10/2020 | Zolotukhin et al. |
| 10,815,279 | B2 | 10/2020 | Srivastava et al. |
| 11,000,597 | B2 | 5/2021 | Muzyczka et al. |
| 11,091,777 | B2 | 8/2021 | Marsic et al. |
| 11,332,502 | B2 | 5/2022 | Zolotukhin et al. |
| 11,767,346 | B2 | 9/2023 | Zolotukhin et al. |
| 11,827,884 | B2 | 11/2023 | Tran et al. |
| 2004/0219575 | A1 | 11/2004 | Neuman et al. |
| 2005/0106700 | A1 | 5/2005 | Nomura et al. |
| 2006/0034805 | A1 | 2/2006 | Fang et al. |
| 2006/0127358 | A1 | 6/2006 | Muzyczka et al. |
| 2006/0188484 | A1 | 8/2006 | Rabinowitz et al. |
| 2007/0036760 | A1 | 2/2007 | Wilson et al. |
| 2007/0196275 | A1 | 8/2007 | Li et al. |
| 2008/0269149 | A1 | 10/2008 | Bowles et al. |
| 2009/0075357 | A1 | 3/2009 | Snyder |
| 2009/0197338 | A1 | 8/2009 | Vandenberghe et al. |
| 2009/0286321 | A1 | 11/2009 | Warrington et al. |
| 2012/0009268 | A1 | 1/2012 | Asokan et al. |
| 2013/0109742 | A1 | 5/2013 | Hewitt et al. |
| 2014/0005249 | A1 | 1/2014 | Hugnot et al. |

(Continued)

FOREIGN PATENT DOCUMENTS

| | | |
|---|---|---|
| EP | 1486567 A1 | 12/2004 |
| EP | 1 487 501 B1 | 12/2012 |

(Continued)

OTHER PUBLICATIONS

La Bella T, Bertin B, Mihaljevic A, et al. Predictive power of deleterious single amino acid changes to infer on AAV2 and AAV2-13 capsids fitness. 2024., Mol Ther Methods Clin Dev. 2024;32(3):101327., doi: 10.1016/j.omtm.2024.101327 (Year: 2024).*

(Continued)

*Primary Examiner* — Maria G Leavitt
*Assistant Examiner* — Kodye Lee Abbott
(74) *Attorney, Agent, or Firm* — Wolf, Greenfield & Sacks, P.C.

(57) ABSTRACT

Described herein are AAV particles having capsid proteins with amino acid substitutions that confer increased affinity for and transduction of glioma cells. The disclosed capsid proteins may be used in conjunction with any therapeutic transgene for treatment of cancer, including in the manufacture of an AAV particle. Also described are methods of identifying AAV variants having increased affinity for and transduction of specific tumor cell types.

10 Claims, 11 Drawing Sheets

Specification includes a Sequence Listing.

(56) References Cited

U.S. PATENT DOCUMENTS

| | | |
|---|---|---|
| 2014/0134168 A1 | 5/2014 | Zurawski et al. |
| 2014/0227268 A1 | 8/2014 | Banchereau et al. |
| 2014/0341852 A1 | 11/2014 | Srivastava et al. |
| 2015/0024036 A1 | 1/2015 | Saydam et al. |
| 2016/0017005 A1 | 1/2016 | Asokan et al. |
| 2016/0074389 A1 | 3/2016 | Lisanto |
| 2016/0116474 A1 | 4/2016 | Suva et al. |
| 2016/0289275 A1 | 10/2016 | Chiorini et al. |
| 2016/0369298 A1 | 12/2016 | Marsic et al. |
| 2016/0369299 A1 | 12/2016 | Boye et al. |
| 2017/0051288 A1 | 2/2017 | Byrne et al. |
| 2018/0015172 A1 | 1/2018 | Muzyczka et al. |
| 2018/0066285 A1 | 3/2018 | Ojala et al. |
| 2018/0193489 A1 | 7/2018 | Hobbs et al. |
| 2018/0244727 A1 | 8/2018 | Zhong et al. |
| 2018/0245098 A1 | 8/2018 | Yazicioglu et al. |
| 2019/0048041 A1 | 2/2019 | Asokan et al. |
| 2019/0127424 A1 | 5/2019 | Srivastava et al. |
| 2019/0249195 A1 | 8/2019 | Marsic et al. |
| 2019/0382452 A1 | 12/2019 | Samulski et al. |
| 2020/0002386 A1 | 1/2020 | Zolotukhin et al. |
| 2020/0165614 A1 | 5/2020 | Tran et al. |
| 2020/0181644 A1 | 6/2020 | Zolotukhin et al. |
| 2021/0061863 A1 | 3/2021 | Zolotukhin et al. |
| 2021/0290771 A1 | 9/2021 | Muzyczka et al. |
| 2022/0135971 A1 | 5/2022 | Tran et al. |
| 2022/0267383 A1 | 8/2022 | Zolotukhin et al. |

FOREIGN PATENT DOCUMENTS

| | | |
|---|---|---|
| EP | 3118306 A1 | 1/2017 |
| JP | 2008-523813 A | 7/2008 |
| JP | 2016-520311 A | 7/2016 |
| JP | 2016-533709 A | 11/2016 |
| WO | WO 2004/096826 A2 | 11/2004 |
| WO | WO 2004/112727 A2 | 12/2004 |
| WO | WO 2005/028675 A2 | 3/2005 |
| WO | WO 2005/033321 A2 | 4/2005 |
| WO | WO 2007/089632 A2 | 8/2007 |
| WO | WO 2008/124724 A1 | 10/2008 |
| WO | WO 2010/011404 A2 | 1/2010 |
| WO | WO 2010/093784 A2 | 8/2010 |
| WO | WO 2010/108126 A2 | 9/2010 |
| WO | WO 2012/057363 A1 | 5/2012 |
| WO | WO 2012/109570 A1 | 8/2012 |
| WO | WO 2013/170078 A1 | 11/2013 |
| WO | WO 2013/188813 A2 | 12/2013 |
| WO | WO 2014/062454 A1 | 4/2014 |
| WO | WO 2014/193716 A2 | 12/2014 |
| WO | WO 2015/048534 A1 | 4/2015 |
| WO | WO 2015/108610 A1 | 7/2015 |
| WO | WO 2015/121501 A1 | 8/2015 |
| WO | WO 2015/134643 A1 | 9/2015 |
| WO | WO 2017/032869 A1 | 3/2017 |
| WO | WO 2017/070476 A2 | 4/2017 |
| WO | WO 2018/069891 A2 | 4/2018 |
| WO | WO 2018/211409 A1 | 11/2018 |

OTHER PUBLICATIONS

Schmit, Pauline F et al. "Cross-Packaging and Capsid Mosaic Formation in Multiplexed AAV Libraries." Molecular therapy. Methods & clinical development vol. 17 107-121. Nov. 26, 2019, doi:10.1016/j.omtm.2019.11.014 (Year: 2019).*

(Unitprot, UniProtKB/TrEMB entry Q6JC12_9VIRU, 2007) (Year: 2007).*

Amberger et al., Spreading and migration of human glioma and rat C6 cells on central nervous system myelin in vitro is correlated with tumor malignancy and involves a metalloproteolytic activity. Cancer Res. Jan. 1, 1998;58(1):149-58.

Burger et al., Recombinant AAV viral vectors pseudotyped with viral capsids from serotypes 1, 2, and 5 display differential efficiency and cell tropism after delivery to different regions of the central nervous system. Mol Ther. Aug. 2004;10(2):302-17. doi: 10.1016/j.ymthe.2004.05.024.

Chelban et al., Mutations in NKX6-2 Cause Progressive Spastic Ataxia and Hypomyelination. Am J Hum Genet. Jun. 1, 2017;100(6):969-977. doi: 10.1016/j.ajhg.2017.05.009.

Dalkara et al., In vivo-directed evolution of a new adeno-associated virus for therapeutic outer retinal gene delivery from the vitreous. Sci Transl Med. Jun. 12, 2013;5(189):189ra76. doi: 10.1126/scitranslmed.3005708.

Dmitrenko et al., Determination of molecular glioblastoma subclasses on the basis of analysis of gene expression. Cytology and genetics. Nov. 2014;48:383-91.

Fontanet et al., Pea3 Transcription Factors, Etv4 and Etv5, Are Required for Proper Hippocampal Dendrite Development and Plasticity. Cereb Cortex. Jan. 1, 2018;28(1):236-249. doi: 10.1093/cercor/bhw372.

Huang et al., Microarray analysis of the hypoxia-induced gene expression profile in malignant C6 glioma cells. Asian Pac J Cancer Prev. 2012;13(9):4793-9. doi: 10.7314/apjcp.2012.13.9.4793.

Kanaan et al., Rationally Engineered AAV Capsids Improve Transduction and Volumetric Spread in the CNS. Mol Ther Nucleic Acids. Sep. 15, 2017;8:184-197. doi: 10.1016/j.omtn.2017.06.011. Epub Jun. 21, 2017.

Muraguchi et al., NKX2.2 suppresses self-renewal of glioma-initiating cells. Cancer Res. Feb. 1, 2011;71(3):1135-45. doi: 10.1158/0008-5472.CAN-10-2304. +A56:N56.

Neuner-Jehle et al., Characterization and sleep deprivation-induced expression modulation of dendrin, a novel dendritic protein in rat brain neurons. J Neurosci Res. Oct. 15, 1996;46(2):138-51. doi: 10.1002/(SICI)1097-4547(19961015)46:2<138::AID-JNR2>3.0. CO;2-I.

Sebastian et al., Abstract 4072: Direct transdifferentiation of glioblastoma cells to antigen-presenting cells: A novel immunotherapeutic approach, Cancer Research, American Association for Cancer Research, Apr. 14, 2018 (Apr. 14, 2018), pp. 1-4, XP55969302, Retrieved from the Internet: URL:https://aacrjournals.org/cancerres/article/78/13Supplement/4072/628678/Abstract-4072-Direct-transdifferentiation-of [retrieved on Oct. 10, 2022].

Sirek et al., Insulin stimulates the expression of carbohydrate response element binding protein (ChREBP) by attenuating the repressive effect of Pit-1, Oct-1/Oct-2, and Unc-86 homeodomain protein octamer transcription factor-1. Endocrinology. Aug. 2009;150(8):3483-92. doi: 10.1210/en.2008-1702. Epub Apr. 9, 2009.

Sunayama et al., Crosstalk between the PI3K/mTOR and MEK/ERK pathways involved in the maintenance of self-renewal and tumorigenicity of glioblastoma stem-like cells. Stem Cells. Nov. 2010;28(11):1930-9. doi: 10.1002/stem.521.

Vastrad et al., Molecular mechanisms underlying gliomas and glioblastoma pathogenesis revealed by bioinformatics analysis of microarray data. Med Oncol. Sep. 26, 2017;34(11):182. doi: 10.1007/s12032-017-1043-x.

Wick et al., Phase III study of enzastaurin compared with lomustine in the treatment of recurrent intracranial glioblastoma. J Clin Oncol. Mar. 1, 2010;28(7):1168-74. doi: 10.1200/JCO.2009.23.2595. Epub Feb. 1, 2010.

Invitation to Pay Additional Fees for Application No. PCT/US2020/045526 mailed Nov. 16, 2020.

International Search Report and Written Opinion for Application No. PCT/US2020/45526 mailed Feb. 8, 2021.

International Preliminary Report on Patentability for International Application No. PCT/US2020/045526, mailed Feb. 17, 2022.

Andersen, Jimena. Study of Ascl1 Function In The Neurogenic Lineage Of The Adult Mouse Hippocampus, Division of Molecular Neurobiology, MRC National Institute for Medical Research, Mar. 2015, pp. 1-212. [Retrieved from the Internet Feb. 5, 2020] <http://discovery.ucl.ac.uk/1469969/1/PhD%20thesis_Jimena%20Andersen_Reduced.pdf>.

Appleyard et al., Pretreatment with the probiotic VSL#3 delays transition from inflammation to dysplasia in a rat model of colitis-

(56)        References Cited

OTHER PUBLICATIONS associated cancer. Am J Physiol Gastrointest Liver Physiol. Dec. 2011;301(6):G1004-13. doi: 10.1152/ajpgi.00167.2011. Epub Sep. 8, 2011.

Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine. 2012.03.079. Epub Apr. 10, 2012. Author Manuscript, 23 pages.

Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.

Aydemir et al., Mutants at the 2-Fold Interface of Adeno-associated Virus Type 2 (AAV2) Structural Proteins Suggest a Role in Viral Transcription for AAV Capsids. J Virol. Jul. 27, 2016;90(16):7196-7204. doi: 10.1128/JVI.00493-16.

Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.

Bozzetti et al., Metabolic Bone Disease in preterm newborn: an update on nutritional issues. Ital J Pediatr. Jul. 14, 2009;35(1):20. doi: 10.1186/1824-7288-35-20.

Choudhury et al., Novel Methodology for Creating Macaque Retinas with Sortable Photoreceptors and Ganglion Cells. Front Neurosci. Dec. 1, 2016;10:551. eCollection 2016.

Clavairoly, Adrien. Ascll and Olig2 Transcriptional Regulations of Oligodendrogenesis, Neurons and Cognition [q-bio.NC], Université Pierre et Marie Curie, Paris VI, (2014), (257 pages), English, NNT: 2014PA066316. [Retrieved from the Internet Feb. 5, 2020] <https://tel.archives-ouvertes.fr/tel-01133659/file/2014PA066316.pdf>.

Crommentuijin et al., Systemically administered AAV9-sTRAIL combats invasive glioblastoma in a patient-derived orthotopic xenograft model. Mol Ther Oncolytics. Jun. 22, 2016;3:16017. doi: 10.1038/mto.2016.17.

Galindo, Alkaline Phosphatase (ALP). Aug. 23, 2010. Retrieved on May 8, 2018. http://www.isu.edu/~galisusa/alp_sop.html. 4 pages.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Clades of Adeno-associated viruses are widely disseminated in human tissues. J Virol. Jun. 2004;78(12):6381-8.

Genbank Submission; NIH/NCBI, Accesion No. AAS99272.1. Gao et al., Jun. 24, 2004.

Grimm et al., E Pluribus Unum: 50 Years of Research, Millions of Viruses, and One Goal—Tailored Acceleration of AAV Evolution. Mol Ther. Dec. 2015;23(12):1819-31.

Guhasarkar et al., Systemic AAV9-IFNβ gene delivery treats highly invasive glioblastoma. Neuro Oncol. Nov. 2016;18(11):1508-1518. doi: 10.1093/neuonc/now097. Epub May 18, 2016.

Guo et al., Protein tolerance to random amino acid change. PNAS. Jun. 22, 2004;101(25):9205-10.

Gurda et al., Capsid antibodies to different adeno-associated virus serotypes bind common regions. J Virol. Aug. 2013;87(16):9111-24. doi: 10.1128/JVI.00622-13. Epub Jun. 12, 2013.

Haapa-Paananen et al., HES6 gene is selectively overexpressed in glioma and represents an important transcriptional regulator of glioma proliferation. Oncogene. Mar. 8, 2012;31(10):1299-310. doi: 10.1038/onc.2011.316. Epub Jul. 25, 2011.

Hoffmann et al., Stem Cell Factor Sox2 and Its Close Relative Sox3 Have Differentiation Functions In Oligodendrocytes, The Company of Biologists Ltd. I Development, vol. 141, (2014), pp. 39-50. DOI: 10.1242/dev.098418. [Retrieved from the Internet Feb. 5, 2020] <https://dev.biologists.org/content/develop/141/1/39.full.pdf>.

Johansson, Térèse A. et al. Identification of Achaete-Scute Complex-Like 1 (ASCL1) Target Genes and Evaluation of DKK1 and TPH1 Expression In Pancreatic Endocrine Tumours, BMC Cancer, BioMed Central, vol. 9, No. 1, Sep. 10, 2009, pp. 1-13. XP021057699. ISSN: 1471-2407. DOI: 10.1186/1471-2407-9-321. [Retrieved from the Internet Feb. 5, 2020] <https://bmccancer.biomedcentral.com/articles/10.1186/1471-2407-9-321>.

Klimczak, Molecular evolution of adeno-associated virus for improved retinal gene therapies. University of California, Berkeley. Jan. 1, 2010. Retrieved from the internet <https://digitalassets.lib.berkeley.edu/etd/ucb/text/Klimczak_berkeley_0028E_10444.pdf> 116 pages.

Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008. Author Manuscript, 17 pages.

Lan et al., IA-2, a transmembrane protein of the protein tyrosine phosphatase family, is a major autoantigen in insulin-dependent diabetes mellitus. Proc Natl Acad Sci U S A. Jun. 25, 1996;93(13):6367-70.

Lerch et al., The structure of adeno-associated virus serotype 3B (AAV-3B): insights into receptor binding and immune evasion. Virology. Jul. 20, 2010;403(1):26-36. doi: 10.1016/j.virol.2010.03.027. Epub May 4, 2010.

Lochrie et al., Mutations on the external surfaces of adeno-associated virus type 2 capsids that affect transduction and neutralization. J Virol. Jan. 2006;80(2):821-34. doi: 10.1128/JVI.80.2.821-834.2006.

Maersch et al., Optimization of stealth adeno-associated virus vectors by randomization of immunogenic epitopes. Virology. Feb. 5, 2010;397(1):167-75. doi: 10.1016/j.virol.2009.10.021. Epub Nov. 18, 2009.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009. Author Manuscript, 16 pages.

Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.

Marsic et al., Vector design Tour de Force: integrating combinatorial and rational approaches to derive novel adeno-associated virus variants. Mol Ther. Nov. 2014;22(11):1900-9. doi: 10.1038/mt.2014.139. Epub Jul. 22, 2014.

Méndez-Gómez et al., Transcytosis in the blood-cerebrospinal fluid barrier of the mouse brain with an engineered receptor/ligand system. Mol Ther Methods Clin Dev. Oct. 7, 2015;2:15037. doi: 10.1038/mtm.2015.37. eCollection 2015.

Muramatsu et al., Nucleotide sequencing and generation of an infectious clone of adeno-associated virus 3. Virology. Jul. 1, 1996;221(1):208-17.

Opie et al., Identification of amino acid residues in the capsid proteins of adeno-associated virus type 2 that contribute to heparan sulfate proteoglycan binding. J Virol. Jun. 2003;77(12):6995-7006.

Ozawa, [Gene therapy using AAV]. Uirusu. Jun. 2007;57(1):47-55. Article in Japanese.

Pang et al., AAV-mediated cone rescue in a naturally occurring mouse model of CNGA3-achromatopsia. PLoS One. 2012;7(4):e35250. doi: 10.1371/journal.pone.0035250. Epub Apr. 11, 2012.

Perabo et al., Combinatorial engineering of a gene therapy vector: directed evolution of adeno-associated virus. J Gene Med. Feb. 2006;8(2):155-62.

Rheinbay et al., An aberrant transcription factor network essential for Wnt signaling and stem cell maintenance in glioblastoma. Cell Rep. May 30, 2013;3(5):1567-79. doi: 10.1016/j.celrep.2013.04.021. Epub May 23, 2013. Author Manuscript, 27 pages.

Romero et al., Exploring protein fitness landscapes by directed evolution. Nat Rev Mol Cell Biol. Dec. 2009;10(12):866-76. Author Manuscript, 25 pages.

Santiago-Ortiz Set al., Adeno-associated virus (AAV) vectors in cancer gene therapy. J Control Release. Oct. 28, 2016;240:287-301. doi: 10.1016/j.jconrel.2016.01.001. Epub Jan. 12, 2016. Author Manuscript, 39 pages.

Shannon et al., ID of Optimal Gene Delivery Vectors in Primate Retina for Treatment of Human Disorders: Labels Non-Human Primate Eyes with Fluorescent Proteins and/or Fluorescent Dyes, Creating Sortable Cell Populations, Allowing for Screening of Capsid and Promoter Libraries. Office of Technology Licensing, University of Florida. Feb. 11, 2017. Retrieved from the Internet: http://technologylicensing.research.ufl.edu/technologies/16134.pdf> on Apr. 12, 2017. 4 pages.

(56)  References Cited

OTHER PUBLICATIONS

Suvà, Mario L. et al. Reconstructing and Reprogramming The Tumor-Propagating Potential of Glioblastoma Stem-Like Cells, Cell Press, vol. 157, No. 3, Apr. 24, 2014, pp. 580-594. [Retrieved from the Internet Feb. 5, 2020] <https://www.sciencedirect.com/science/article/pii/S0092867414002293>.

Swartling, Fredrik J. Myc Proteins In Brain Tumor Development and Maintenance, Upsula Journal of Medical Sciences, vol. 117, No. 2, Feb. 2012, pp. 122-131. ISSN: 0300-9734. DOI: 10.3109/03009734.2012.658975. [Retrieved from the Internet Feb. 5, 2020] <https://www.tandfonline.com/doi/full/10.3109/03009734.2012.658975>.

Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.

Wu et al., Mutational analysis of the adeno-associated virus type 2 (AAV2) capsid gene and construction of AAV2 vectors with altered tropism. J Virol. Sep. 2000;74(18):8635-47. doi: 10.1128/jvi.74.

Xie et al., The atomic structure of adeno-associated virus (AAV-2), a vector for human gene therapy. Proc Natl Acad Sci U S A. Aug. 6, 2002;99(16):10405-10. doi: 10.1073/pnas.162250899. Epub Jul. 22, 2002.

Zhong et al., Next generation of adeno-associated virus 2 vectors: point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.

Zolotukhin et al., Improved Adeno-associated Viral Gene Transfer to Murine Glioma. J Genet Syndr Gene Ther. Apr. 29, 2013;4(133):12815. doi: 10.4172/2157-7412.

U.S. Appl. No. 17/009,536, filed Sep. 1, 2020, Zolotukhin et al.

U.S. Appl. No. 17/689,324, filed Mar. 8, 2022, Zolotukhin et al.

U.S. Appl. No. 17/228,298, filed Apr. 12, 2021, Muzyczka et al.

U.S. Appl. No. 16/613,402, filed Nov. 18, 2019, Tran et al.

U.S. Appl. No. 17/428,722, filed Aug. 5, 2021, Tran et al.

PCT/US2020/045526, Nov. 16, 2020, Invitation to Pay Additional Fees.

PCT/US2020/45526, Feb. 8, 2021, International Search Report and Written Opinion.

PCT/US2020/045526, Feb. 17, 2022, International Preliminary Report on Patentability.

Berezovsky et al., Sox2 promotes malignancy in glioblastoma by regulating plasticity and astrocytic differentiation. Neoplasia. Mar. 2014;16(3):193-206, 206.e19-25. doi: 10.1016/j.neo.2014.03.006. Epub Apr. 13, 2014.

Goyal et al., Engineering a prokaryotic Cys-loop receptor with a third functional domain. J Biol Chem. Oct. 7, 2011;286(40):34635-42. doi: 10.1074/jbc.M111.269647. Epub Aug. 15, 2011.

Kleine et al., Immune surveillance of the human central nervous system (CNS): different migration pathways of immune cells through the blood-brain barrier and blood-cerebrospinal fluid barrier in healthy persons. Cytometry A. Mar. 2006;69(3):147-51. doi: 10.1002/cyto.a.20225.

Kügler et al., Differential transgene expression in brain cells in vivo and in vitro from AAV-2 vectors with small transcriptional control units. Virology. Jun. 20, 2003;311(1):89-95. doi: 10.1016/s0042-6822(03)00162-4.

Schultz et al., Recombinant adeno-associated virus transduction and integration. Mol Ther. Jul. 2008;16(7):1189-99. doi: 10.1038/mt.2008.103. Epub May 20, 2008.

Tan et al., Selective and quickly reversible inactivation of mammalian neurons in vivo using the Drosophila allatostatin receptor. Neuron. Jul. 20, 2006;51(2):157-70. doi: 10.1016/j.neuron.2006.06.018.

Weins et al., Dendrin ablation prolongs life span by delaying kidney failure. Am J Pathol. Aug. 2015; 185(8):2143-57. doi: 10.1016/j.ajpath.2015.04.011. Epub Jun. 12, 2015.

Zolotukhin et al., Recombinant adeno-associated virus purification using novel methods improves infectious titer and yield. Gene Ther. Jun. 1999;6(6):973-85. doi: 10.1038/sj.gt.3300938.

* cited by examiner

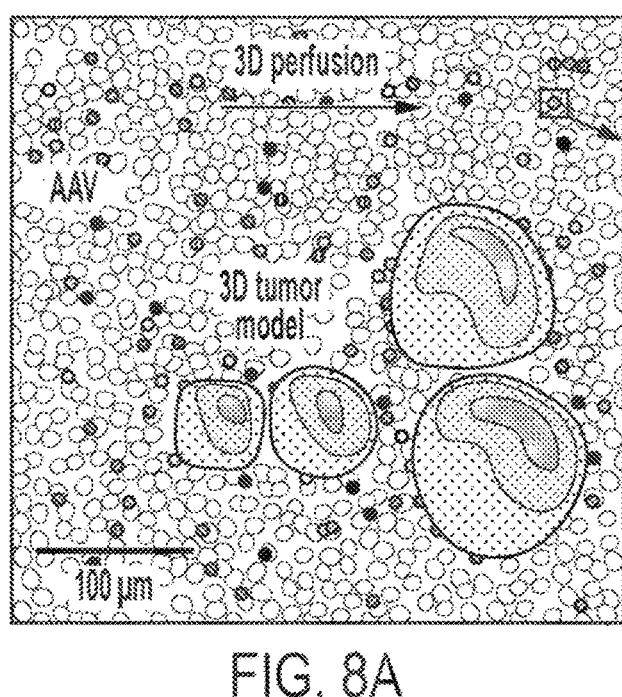
FIG. 8A
FIG. 8B
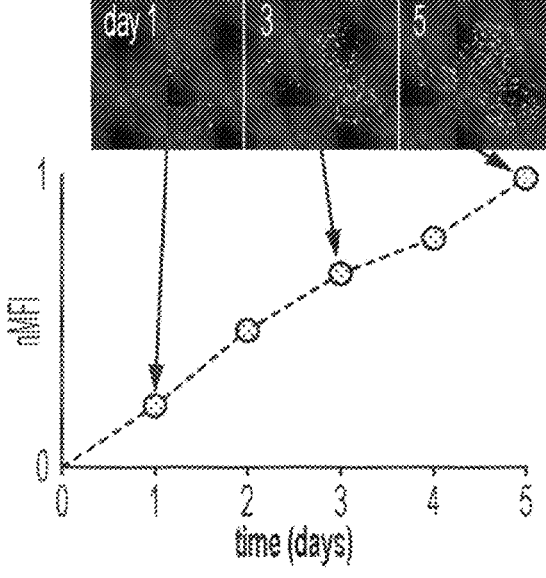
FIG. 8C
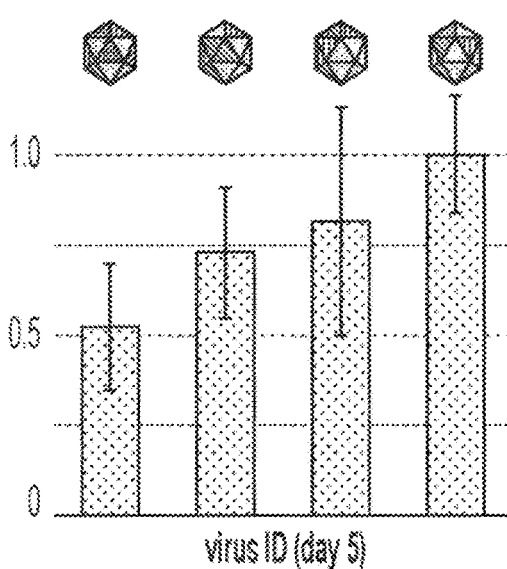
FIG. 8D

AAV CAPSID VARIANTS FOR TARGETING HUMAN GLIOBLASTOMA CELLS

RELATED APPLICATIONS

This application is a national stage filing under 35 U.S.C. § 371 of International Patent Application Serial No. PCT/US2020/045526, filed Aug. 7, 2020, which claims the benefit under 35 U.S.C. § 119 (e) of the filing date of U.S. Provisional Application Ser. No. 62/884,716, filed Aug. 9, 2019. The contents of the above-referenced applications are incorporated herein in their entirety by reference.

GOVERNMENT SUPPORT

This invention was made with government support under grant number CA228875 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Feb. 7, 2022, is named U119670041US01-SEQ-EPG and is 20,759,730 bytes in size.

BACKGROUND OF THE INVENTION

Adeno-associated virus (AAV) is a small (20 nm) replication-defective, non-enveloped virus. AAV can infect non-dividing cells and has the ability to stably integrate into the host cell genome. Because AAV is generally non-pathogenic, it is an attractive tool for delivering genes to cells in vivo. Several serotypes of naturally occurring and artificial AAVs having different affinities for different cells in vivo are known. These serotypes are determined by the AAV capsid proteins. AAV contains three capsid proteins, VP1, VP2 and VP3 (87, 72 and 62 kilodaltons, respectively) typically present in a ratio of about 1:1:10. While different AAV serotypes have particular organ tropisms that can be taken advantage of to target gene-based therapies to a target organ (see e.g., Surace et al., *Vision Res.* 2008, 48(3):353-9; Zincarelli et al., *Mol Ther.* 2008, 16(6):1073-80), the increased efficiency in AAV for targeting certain organs or tissues would be of great benefit. An example of such tissue or cell type is glioma.

SUMMARY OF THE INVENTION

Provided herein are viral vectors, and in particular recombinant AAV (rAAV) vectors, for treatment of cancers such as glioblastoma. Further provided herein are novel rAAV capsid protein variants that exhibit improved transduction of glioblastoma, glioma, glioblastoma stem-like cells (GSC) and glioma stem-like cells. The disclosed capsid variants may be used in conjunction with any therapeutic transgene in the manufacture of an AAV particle for treatment of cancer. Accordingly, the disclosure provides rAAV particles, compositions comprising rAAV particles, and methods for treatment of cancer in a subject suffering from or diagnosed with glioblastoma or glioma. Further provided herein are methods of identifying AAV variants having increased affinity for and transduction of specific tumor cell type.

Further disclosed herein are methods for generating rAAV capsids having enhanced tumor cell-type specific binding. In some aspects, these methods comprise multiple iterations of evolution, such as in directed evolution screening. In some aspects, the methods comprise generating a library of rAAV capsid variants. The methods comprise use of a dynamic mode of administration of an AAV library reagent. Delivery of the AAV library may be at least partially synchronized with tumor progression in a subject tumor, such as a mouse model tumor.

Accordingly, in some aspects, an AAV library containing different cap proteins is administered to a mouse harboring a tumor. The tumor may either be implanted (such as by injection of tumor cells), arise spontaneously, or be induced. The AAV library may be administered to the tumor by infusion. As the tumor develops and grows, the level of infusion is increased. In some embodiments, the intratumoral infusion of the AAV library is continuous. Initially, the infusion rate is slow. As the tumor grows, the infusion rates synchronized with early and late stage of tumor growth. By synchronizing intratumoral infusion rate of the AAV library with early and late stage of tumor growth, a nearly 10-fold increase in AAV binding to the tumor cell and gene delivery may be observed when compared to a single intratumor injection.

Glioma is a tumor of the glial cells in the brain and spinal cord. Three types of glial cells can produce tumors. Gliomas are classified according to the type of glial cell involved in the tumor, as well as the tumor's genetic features, which can help predict how the tumor will behave over time and the treatments most likely to work. The types of glioma include astrocytomas (tumors of astrocytes), which includes astrocytoma, anaplastic astrocytoma and glioblastoma multiforme (GBM); ependymoma; and oligodendroglioma. Inherited polymorphisms of DNA repair genes ERCC1, ERCC2 (XPD) and XRCC1 increase the risk of glioma. Surgical procedures are often the preferred initial treatments for gliomas. GBM is the most aggressive form of astrocytoma. In adults, GBM occurs most often in the cerebral hemispheres, especially in the frontal and temporal lobes of the brain. GBM is a devastating cancer that typically results in death in the first 15 months after diagnosis.

The current standard of care including surgical resection, adjuvant chemotherapy, and radiation does not result in remission for the majority of patients. Recently, gene therapy and immunotherapy approaches for treating glioma and glioblastoma have been developed. However, gene therapy treatments that have reached clinical trials for glioblastoma have failed. In particular, viral vector-based treatments have not achieved FDA approval due to issues with viral delivery, inefficient tumor penetration, and limited efficacy. There remains a need in the art for viral vector-based constructs for gene delivery to specific cell types, such as tumor cells.

This disclosure is based, at least in part, on the identification of variant AAV capsid proteins and particles comprising the variant capsid proteins that show a tropism for transducing glioma, in some embodiments, to a greater extent compared to wild-type AAV (such as rAAV2) particles comprising wild-type capsid proteins. Identification of variant rAAV proteins disclosed herein was based on in vivo screening of a rAAV2 capsid library containing capsid variants with amino acid substitutions or mutations in the capsid proteins of AAV2 in a mouse model.

As disclosed in the Examples provided herein, synchronized delivery of an AAV library reagent in a directed evolution screening for variants specific for slow or fast cycling glioblastoma stem-like cell (GSC) populations resulted in infection of target cells. And synchronized delivery of an AAV library reagent in a directed evolution screening for variants specific for glioblastoma multiforme (GBM) populations resulted in infection of target cells. Accordingly, the disclosure provides methods of synchronized delivery of an AAV library reagent in screening for variants specific for GBM cells and for GSC cells.

Described are rAAV capsid variants having increase specificity for binding and/or transduction of GBM and GSC. The variants, or altered capsid proteins, may contain amino acid substitutions in the regions corresponding to amino acids 263-267, amino acids 444-461, amino acids 490-507, amino acids 527-532, amino acids 545-556, and amino acids 585-596, of the wild-type AAV2 VP1 amino acid sequence, or amino acid substitutions in corresponding positions of other wild-type serotype VP1 sequences (such as AAV5, AAV8, and AAV9).

In some aspects, the disclosed rAAV capsids and particles comprising these capsids have increased recognition and/or binding to certain cell markers, such as cell markers associated with glioblastoma or glioma. Without being bound to any theory, the increased recognition may confer improved binding to and transduction of tumor cells that exhibit these cell markers. This improved binding and transduction may lead to increased therapeutic effects in these cells, including the suppression of growth or death of such cells. These cell markers may comprise glycoproteins. In some embodiments, the cell markers comprise CD133 and CD44. In some embodiments, AAV particles having increased recognition of CD133+ GSC cells, CD44+ GSC cells, CD44+/CD133+ GSC cells, and CD44−/CD133− GBM cells are described. Amino acid substitutions in the AAV capsid proteins that may contribute to or confer an increase in specificity for transduction of GSC and/or GBM are shown in Tables 1-9.

In some embodiments, the disclosure provides rAAV capsids and viral particles for transducing glioblastoma cells (GBM) and/or glioma stem-like cells (GSC) comprising a capsid protein comprising the amino acid substitutions as described in any of Table 1, Table 2, Table 3, Table 4, Table 5, Table 6, Table 7, Table 8, or Table 9. In some embodiments, the capsid protein of any of the disclosed particles comprises substitutions at one of the following combinations of amino acid positions:

(a) Q263, S264, Y444, T450, P451, S452, T454, Q457, R459, Q461, S492, A493, D494, E499, and Y500F, or (b) E531, K532, S547, E548, D553, R585, and R588;

of the amino acid sequence of wild-type AAV2 VP1 capsid (SEQ ID NO: 1), or homologous amino acid positions of a wild-type VP1 capsid sequence of an AAV serotype other than AAV2. The capsis may further comprise substitutions at E530, E531, and K532 of a wild-type AAV2 VP1 capsid sequence as set forth in SEQ ID NO: 1.

The amino acid substitutions of any of these rAAV capsids particles may comprise one or more of Q263G, S264T, Y444F, T450A, P451E, S452G, T454L, T455K, Q457M, R459H, Q461L, S492D, A493G, D494E, E499D, and Y500F relative to the amino acid sequence of AAV2 VP1 capsid (SEQ ID NO: 1), or homologous amino acids of a wild-type VP1 capsid sequence of an AAV serotype other than AAV2.

In some aspects, the disclosure further provides methods of identifying rAAV variants having affinity for a tumor cell type comprising providing a continuous intratumor graded infusion of a viral vector library into a tumor. In some embodiments, the rate of infusion is proportional to the rate of tumor growth.

In some aspects, provided herein are compositions and methods of treatment comprising administering any of the described rAAV particle compositions to a subject in need thereof. In some embodiments, the subject is a mammalian subject, such as a human subject.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 8A. Diagram of a 3D perfused neurosphere formation assay for AAV screen and validation, in accordance with the Examples.

FIG. 8B. Diagram of AAV perfusion (passage) between microgel (PEG μgel) particles.

FIG. 8C. Kinetics of AAV transduction using Mutant #9 in the original DE screen. Mutant #9 is engineered to express Antares. Fluorescence in cells is measured in nMFI.

FIG. 8D. Ranking of GBM tropism of the top 4 GBM-specific AAV2 mutants selected in the original DE screen.

FIG. 9A: AAV2 Mutant 9 (evaluated in the original DE screen) containing a GFP expression cassette with or without one of a scrambled short hairpin RNA (shRNA) (X), shRNA targeting Nkx6-2 and Ascl-1 genes (Y), and shRNA targeting Nkx6-2 alone (Z) (not shown) efficiently transduced CA7 GSC cells.

FIG. 9B: The extent of shRNA depletion of these genes, leading to increased cell death, was captured by propidium iodide (PI) uptake (darkened squares) using an expert confocal algorithm. GFP expression is indicated as lighter-

Figure 9A:
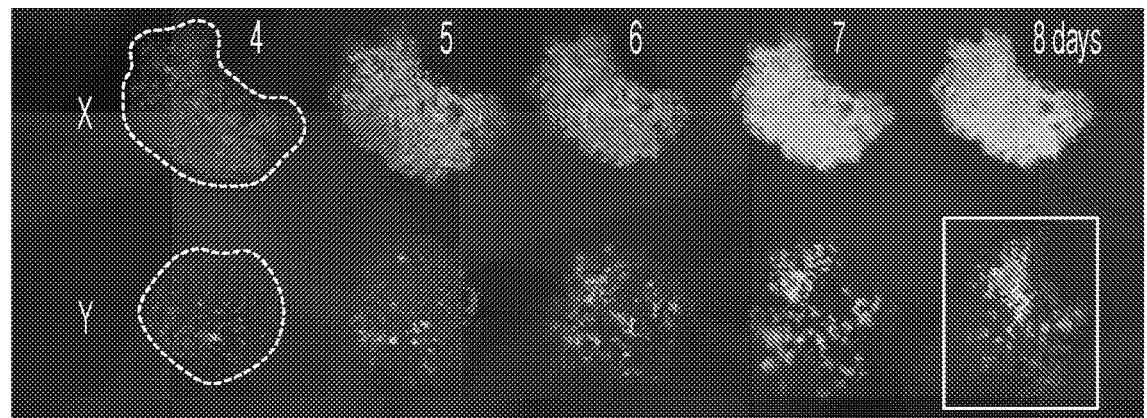
FIGS. 9A-9C. pNSA assay for AAV evaluation.
Figure 9B:
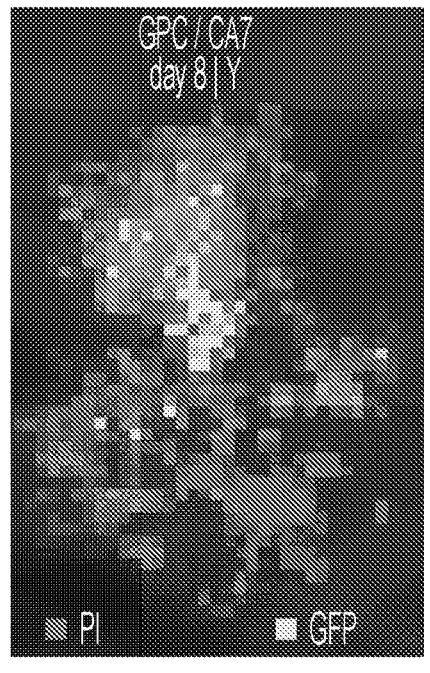
Figure 9C:
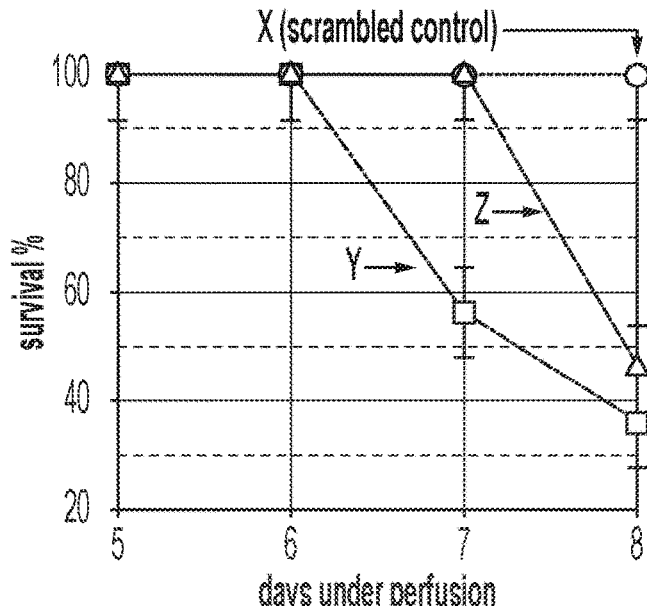

5 shaded squares. FIG. 9C is a chart that shows differential killing kinetics of the 3 shRNA as measured by pNSA, enabling dynamic screening of lead AAV variants targeting shRNA cassettes.

DETAILED DESCRIPTION

Provided herein are viral capsid protein variants that exhibit improved transduction of glioblastoma, glioma, glioblastoma stem-like cells (GSC) and glioma stem-like cells. The disclosed capsid variants may be used in conjunction with any therapeutic transgene for treatment of cancer. The disclosure provides viral particles comprising any of these capsid variants that have improved tumor penetration relative to existing viral particle treatments for tumors. The disclosure also provides viral particles that achieve improved efficacy and/or achieve equal or improved efficacy at lower vector titers (amounts) than existing viral particle treatments. In particular embodiments, the capsid protein variants are AAV variants.

Accordingly, the disclosure also provides rAAV particles and compositions comprising rAAV particles having mutant capsid proteins. The disclosure provides methods and compositions for delivering rAAV particles having mutant capsid proteins to neural tissue, such as central nervous system (CNS) tissue. In particular embodiments, methods are provided for delivery to CNS tissue such as brain tissue (e.g., human brain tissue). The disclosure further provides methods for treatment of cancer in a subject suffering from or diagnosed with glioblastoma or glioma. The disclosure further provides methods of treatment of a subject in need thereof (such as a human subject) by administering one or more of these rAAV particles or compositions. In some embodiments, these methods comprise delivering a heterologous gene or targeting construct to a glioma cell comprising inserting the heterologous gene or targeting contruct into any of the disclosed AAV particles, and contacting the glioma cell with the AAV. The step of contacting the glioma cell may comprise a single AAV particle administration or multiple AAV administrations (such as a regimen of multiple administrations). In some embodiments, any of the disclosed methods of treatment provide a reduction, either partial or complete, of a glioma tumor. In some embodiments, the disclosed methods of treatment induce apoptosis or cell death in a glioma.

Provided herein are methods of transducing GBM and GSC cells and tissue. In some embodiments, methods of transducing GBM and GSC comprise providing to the cell any one of the compositions of variant rAAV particles as disclosed herein, wherein the rAAV particles in the composition comprise a nucleic acid comprising a heterologous nucleic acid. The disclosure also provides host cells (such as mammalian cells) comprising any of these particles or compositions. In some embodiments, these host cells comprise GBM or GSC. Further provided herein are methods of identifying AAV variants having increased affinity for and transduction of specific tumor cell type.

Glioblastoma multiforme (GBM), the most common and fatal form of a primary brain tumor, accounts for approximately 60% of all glioma cases and is categorized as grade IV glioma. Local invasiveness, neoangiogenesis, and intratumor heterogeneity are among the most important hallmarks of the aggressiveness of GBM. GBM tumors contain functional subsets of cells called glioblastoma stem-like cells (GSCs), which are resistant to radiation therapy and chemotherapy and eventually lead to tumor recurrence. Recent studies showed that GSCs reside in particular tumor niches (such as perivascular niches) that are necessary to support their behavior. The presence of GSCs was first demonstrated by the identification of a CD133$^+$ cell subpopulation that is capable of tumor initiation in vivo (Singh et al., 2004). CD133, a glycoprotein cell surface marker of normal neural stem cells, is commonly used to distinguish GSCs. The percentage of CD133$^+$ cells may be significantly higher in recurrent GBMs after radiotherapy and chemotherapy as compared with primary tumors. Apart from CD133, other cell surface markers, such as SSEA-1 and CD44, have been used to enrich or distinguish stem-like populations in GBM. In particular, CD44 is highly expressed in the mesenchymal subtype of GBM, and its expression has been used to enrich for stem-like cells (Anido et al., 2010). It has been reported that Cd44$^{-/-}$ and Cd44$^{+/-}$ mice survived longer than Cd44$^{+/+}$ mice with PDGF-driven gliomas, indicating that CD44 actively contributes to aggressive glioma growth (Pietras et al., *Cell Stem Cell*. 2014). It was recently shown that patient-derived glioma stem-like cells exhibited a characteristic equilibrium of distinct CD133$^+$ and CD44$^+$ subpopulations (Brown et al., *PLoS One*. 2017; 12(2): e0172791, herein incorporated by reference). GSC populations are further characterized by their rate of growth and movement, i.e., fast-cycling (fast-dividing and fast-moving, or simply "fast") and slow-cycling (slow-dividing and slow-moving, or simply "slow") populations (see id.).

In some embodiments, the amino acid substitutions in the capsids of any of the described particles confer increased transduction of GBM or GSC compared to an AAV particle comprising a capsid protein without the substitutions (such as a wild-type capsid protein).

In some aspects, the disclosed AAV particles comprise a recombinant AAV genome (or vector) comprising a polynucleotide. This polynucleotide may encode at least one heterologous nucleic acid region. In some embodiments, the heterologous nucleic acid region encodes a peptide or protein. In certain embodiments, the heterologous nucleic acid region encodes a therapeutic peptide or protein. In certain embodiments, the heterologous nucleic acid region encodes a short hairpin RNA (shRNA). In some embodiments, the heterologous nucleic acid region encodes a short hairpin RNA targeting a gene encoding a transcription factor involved in neurogegenesis, such as a master regulator gene. In certain embodiments, the heterologous nucleic acid region encodes a short hairpin RNA targeting one or more of the Ascl-1 or Nkx6-2 genes, such as the human ASCL-1 or NKX6-2 genes. In some aspects, the therapeutic peptide or protein comprises a repair enzyme, a checkpoint inhibitor, a transcription factor, a growth factor receptor a growth factor ligand, or a tumor suppressor protein. In some embodiments, the therapeutic peptide is the repair enzyme MGMT, known to be an important prognostic indicator in GBM. Accordingly, the disclosure provides AAV particles comprising rAAV vectors encoding the enzyme MGMT.

In some embodiments, any of the described rAAV particles comprise a capsid having an amino acid sequence having at least 85%, at least 90%, at least 92.5%, at least 95%, at least 98%, or at least 95% identity to any one of SEQ ID NOs: 4-7 and 9-7010. In some embodiments, any of the described rAAV particles comprise a capsid having an amino acid sequence having at least 85%, at least 90%, at least 92.5%, at least 95%, at least 98%, or at least 95% identity to any one of SEQ ID NOs: 4-7 and 9-28. In some embodiments, any of the described rAAV particles comprise a capsid having an amino acid sequence having at least 85% or at least 90% identity to any one of SEQ ID NOs: 4-7 and 9-28. In some embodiments, any of the described rAAV particles comprise a capsid having an amino acid sequence comprising any one of SEQ ID NOs: 4-7 and 9-28. In some embodiments, any of the described rAAV particles comprise a capsid having an amino acid sequence having at least 85%, at least 90%, at least 92.5%, at least 95%, at least 98%, or at least 95% identity to any one of SEQ ID NOs: 4-7. In particular embodiments, the rAAV capsid comprises the sequence of any one of SEQ ID NOs: 4-7. In certain embodiments, the rAAV capsid comprises SEQ ID NO: 4.

In some embodiments, the disclosed capsids may comprise a sequence having 1, 2, 3, 4, 5, 6, 7, 8, 9, 10, 11, 12, 13, 14, 15, 16, 17, or 18 amino acids that differ relative to the sequence of any one of SEQ ID NOs: 4-7 and 9-28. These differences may comprise amino acids that have been inserted, deleted, or substituted relative to the sequence of any one of SEQ ID NOs: 4-7 and 9-28. In some embodiments, the disclosed capsids may comprise a sequence having 1, 2, 3, 4, 5, 6, 7, 8, 9, 10, 11, 12, 13, 14, 15, 16, 17, or 18 amino acids that differ relative to the sequence of any one of SEQ ID NOs: 4-7.

The amino acid substitutions of any of these rAAV capsids particles may comprise one or more of Q263G, S264T, Y444F, T450A, P451E, S452G, T454L, T455K, Q457M, R459H, Q461L, S492D, A493G, D494E, E499D, and Y500F relative to the amino acid sequence of AAV2 VP1 capsid (SEQ ID NO: 1) or homologous amino acids of a wild-type VP1 capsid sequence of an AAV serotype other than AAV2 (e.g., AAV1, AAV3, AAV4, AAV5, AAV6, AAV7, AAV8, AAV9, AAV10, AAVrh.74, and AAVrh.10). In some embodiments, the amino acid substitutions of the capsid proteins of any of the described rAAV particles comprise E531G, K532R, S547A, E548G, T550N, V552A, D553A, E555G, K556Q, R585A, and R588A relative to the amino acid sequence of AAV2 VP1 capsid. In some embodiments, the amino acid substitutions comprise S264A, Y444F, T450D, P451R, S452G, T454S, Q457T, R459A, Q461S, S492D, A493G, D494E, E499D, and Y500F. In some embodiments, the amino acid substitutions comprise Q263A, S264A, Y444F, T450D, P451R, S452G, T454S, Q457T, R459A, Q461S, S492D, A493G, D494E, E499D, and Y500F. In some embodiments, the amino acid substitutions comprise E530N, E531D, K532R, S547A, E548K, K549G, D553A, I554V, R585A, and R588A. In some embodiments, the amino acid substitutions comprise Q263E, Y444F, T450A, P451S, S452A, T454S, Q457T, R459T, Q461G, T491Q, S492P, A493G, E499D, Y500F, E530D, E531D, and K532R.

In some embodiments, any of the disclosed capsids comprise a T491 substitution. In some embodiments, these capsids comprise a T491Q or T491V substitution. In some embodiments, any of the disclosed capsids comprise a DZGXSUXT motif at amino acid positions 450-457 of wild-type AAV2 capsid VP1 (SEQ ID NO: 1), where X is the wild-type position, Z is a mutation selected from T or R, and U is K or T. In some embodiments, any of the disclosed capsids comprise a DDR motif at amino acid positions 530-532 of SEQ ID NO: 1. In some embodiments, any of the disclosed capsids comprises a K527R mutation.

In some aspects, provided herein is a rAAV vector comprising a capsid and a genome, wherein the capsid comprises a VP1, VP2, and/or VP3 protein having amino acid substitutions as described in any of Tables 1-9, wherein these substitutions confer an increased transduction of GBM cells or GSC compared to an AAV particle comprising a capsid protein without the substitutions (such as a wild-type capsid protein). In some embodiments, the capsid has amino acid substitutions as described in any of Tables 1-8. In certain embodiments, the capsid comprises SEQ ID NO: 4.

Generation of Glioma Cell-Type Specific AAV.

In some embodiments, methods for generating AAV having enhanced tumor cell-type specific binding and transduction are described. The methods comprising use of a dynamic mode of administration of an AAV library reagent. Delivery of the AAV library is at least partially synchronized with tumor progression in a mouse model tumor. The AAV library, containing different cap proteins, is administered to a mouse harboring a tumor. The tumor may either be implanted (such as by injection of tumor cells), arise spontaneously, or be induced. The AAV library in administered to the tumor by infusion. As the tumor develops and grows, the infusion level is increased. In some embodiments, the intratumoral infusion of the AAV library is continuous. Initially, the infusion rate is slow. As the tumor grows, the infusion rates synchronized with early and late stage of tumor growth. By synchronized intratumoral infusion rate of the AAV library with early and late stage of tumor growth, a nearly 10-fold increase in AAV binding to the tumor and gene delivery is observed when compared to a single intratumor injection.

In some embodiments, synchronized delivery of an AAV library reagent in directed evolution screening for variants specific for slow GSC and fast GSC populations, and non-GSC GBM cell populations, resulted in infection of target cells.

AAV Having Increased Specificity for and/or Transduction of GSC and Non-GSC GBM Cell.

In some embodiments, AAV variants having increased specificity for binding and/or transduction of GBM and GSC are described. Such AAV variants contain altered capsid proteins. The altered capsid proteins contain amino acid substitutions in regions corresponding to amino acids 263-267, amino acids 444-461, amino acids 490-507, amino acids 527-532, amino acids 545-556, and amino acids 585-596, of the wild-type AAV2 VP1 capsid protein (SEQ ID NO: 1) (i.e, variable regions I, IV, V, VI, VII and VIII). These groupings of amino acids indicate the variable regions of AV2 VP1. The wild type amino acid sequences of the above regions are shown below (corresponds to SEQ ID NO: 8):

```
263     444                     490             527
QSGAS   YLSRTNTPSGTTTQSRLQ  KTSADNNNSEYSWTGATK  KDDEEK 545             585
QGSEKTNVDIEK  RGNRQAATADVN
```

The AAV variants can comprise altered VP2 and VP3 capsid proteins having amino acid substitutions corresponding to the amino acid substitutions of VP1. Amino acids 263-267, 444-461, 490-507, 527-532, 545-556, and 585-596 of capsid protein VP1 are underlined in SEQ ID NO: 1 below. Corresponding amino acids positions are underlined in capsid proteins VP2 and VP3, shown in SEQ ID 2 and SEQ ID NO: 3, respectively.

```
wild.type AAV2 VP1 amino acid sequence:
                             (SEQ ID NO: 1)
MAADGYLPDWLEDTLSEGIRQWWKLKPGPPPPKPA

ERHKDDSRGLVLPGYKYLGPFNGLDKGEPVNEADA

AALEHDKAYDRQLDSGDNPYLKYNHADAEFQERLK
```

-continued
```
EDTSFGGNLGRAVFQAKKRVLEPLGLVEEPVKTAP

GKKRPVEHSPVEPDSSSGTGKAGQQPARKRLNFGQ

TGDADSVPDPQPLGQPPAAPSGLGTNTMATGSGAP

MADNNEGADGVGNSSGNWHCDSTWMGDRVITTSTR

TWALPTYNNHLYKQISSQSGASNDNHYFGYSTPWG

YFDFNRFHCHFSPRDWQRLINNNWGFRPKRLNFKL

FNIQVKEVTQNDGTTTIANNLTSTVQVFTDSEYQL

PYVLGSAHQGCLPPFPADVFMVPQYGYLTLNNGSQ

AVGRSSFYCLEYFPSQMLRTGNNFTFSYTFEDVPF

HSSYAHSQSLDRLMNPLIDQYLYYLSRTNTPSGTT

TQSRLQFSQAGASDIRDQSRNWLPGPCYRQQRVSK

TSADNNNSEYSWTGATKYHLNGRDSLVNPGPAMAS

HKDDEEKFFPQSGVLIFGKQGSEKTNVDIEKVMIT

DEEEIRTTNPVATEQYGSVSTNLQRGNRQAATADV

NTQGVLPGMVWQDRDVYLQGPIWAKIPHTDGHFHP

SPLMGGFGLKHPPPQILIKNTPVPANPSTTFSAAK

FASFITQYSTGQVSVEIEWELQKENSKRWNPEIQY

TSNYNKSVNVDFTVDTNGVYSEPRPIGTRYLTRNL wild.type AAV2 VP2 amino acid sequence:
                                (SEQ ID NO: 2)
MAPGKKRPVEHSPVEPDSSSGTGKAGQQPARKRLN

FGQTGDADSVPDPQPLGQPPAAPSGLGTNTMATGS

GAPMADNNEGADGVGNSSGNWHCDSTWMGDRVITT

STRTWALPTYNNHLYKQISSQSGASNDNHYFGYST

PWGYFDFNRFHCHFSPRDWQRLINNNWGFRPKRLN

FKLFNIQVKEVTQNDGTTTIANNLTSTVQVFTDSE

YQLPYVLGSAHQGCLPPFPADVFMVPQYGYLTLNN

GSQAVGRSSFYCLEYFPSQMLRTGNNFTFSYTFED

VPFHSSYAHSQSLDRLMNPLIDQYLYYLSRTNTPS

GTTTQSRLQFSQAGASDIRDQSRNWLPGPCYRQQR

VSKTSADNNNSEYSWTGATKYHLNGRDSLVNPGPA

MASHKDDEEKFFPQSGVLIFGKQGSEKTNVDIEKV

MITDEEEIRTTNPVATEQYGSVSTNLQRGNRQAAT

ADVNTQGVLPGMVWQDRDVYLQGPIWAKIPHTDGH

FHPSPLMGGFGLKHPPPQILIKNTPVPANPSTTFS

AAKFASFITQYSTGQVSVEIEWELQKENSKRWNPE

IQYTSNYNKSVNVDFTVDTNGVYSEPRPIGTRYLT

RNL wild.type AAV2 VP3 amino acid sequence:
                                (SEQ ID NO: 3)
MATGSGAPMADNNEGADGVGNSSGNWHCDSTWMGD

RVITTSTRTWALPTYNNHLYKQISSQSGASNDNHY

FGYSTPWGYFDFNRFHCHFSPRDWQRLINNNWGFR
```

-continued
```
PKRLNFKLFNIQVKEVTQNDGTTTIANNLTSTVQV

FTDSEYQLPYVLGSAHQGCLPPFPADVFMVPQYGY

LTLNNGSQAVGRSSFYCLEYFPSQMLRTGNNFTFS

YTFEDVPFHSSYAHSQSLDRLMNPLIDQYLYYLSR

TNTPSGTTTQSRLQFSQAGASDIRDQSRNWLPGPC

YRQQRVSKTSADNNNSEYSWTGATKYHLNGRDSLV

NPGPAMASHKDDEEKFFPQSGVLIFGKQGSEKTNV

DIEKVMITDEEEIRTTNPVATEQYGSVSTNLQRGN

RQAATADVNTQGVLPGMVWQDRDVYLQGPIWAKIP

HTDGHFHPSPLMGGFGLKHPPPQILIKNTPVPANP

STTFSAAKFASFITQYSTGQVSVEIEWELQKENSK

RWNPEIQYTSNYNKSVNVDFTVDTNGVYSEPRPIG

TRYLTRNL
```

The amino acid substitutions in exemplary capsid proteins of AAV variants having enhanced specificity for and/or transduction of GBM and GSC are shown in Tables 1-9. In certain embodiments, capsid proteins shown in Table 9 are used in the disclosed methods, rAAV particles, and compositions thereof, for enhanced transduction of GBM and GSC cells, and accordingly, for use in treatments of glioma in subjects suffering therefrom.

VP1, VP2, and VP3 (collectively VPX) capsid protein amino acid substitutions providing increased specificity for and/or transduction of GBM and GSC are listing in Tables 1-8. Each row in the tables represents capsid protein amino acid substitutions in an AAV variant selected for binding and/or transduction of GSC in a combinatorial library directed evolution screen.

In some embodiments, the AAV particles can have altered VP1 capsid proteins, wherein the VP1 capsid proteins comprise a capsid protein having an amino acid sequence greater than 75%, greater than 80%, greater than 85%, greater than 90%, greater than 95%, greater than 96%, greater than 97%, greater than 98%, greater than 99%, or 100% identical to SEQ ID NO: 1, and having one or more of the amino acid substitutions as described in any of Tables 1-8.

In some embodiments, the AAV particles can have altered VP2 capsid proteins, wherein the VP2 capsid proteins comprises a capsid protein having an amino acid sequence greater than 75%, greater than 80%, greater than 85%, greater than 90%, greater than 95%, greater than 96%, greater than 97%, greater than 98%, greater than 99%, or 100% identical or similar to SEQ ID NO: 2, and having one or more of the amino acid substitutions as described in any of Tables 1-8.

In some embodiments, the AAV particles can have altered VP3 capsid proteins, wherein the VP3 capsid proteins comprises a capsid protein having an amino acid sequence greater than 75%, greater than 80%, greater than 85%, greater than 90%, greater than 95%, greater than 96%, greater than 97%, greater than 98%, greater than 99%, or 100% identical or similar to SEQ ID NO: 3, and having one or more of the amino acid substitutions as described in any of Tables 1-8.

In some embodiments, the AAV particles can have altered VP1 capsid proteins, altered VP2 capsid proteins, altered VP3 capsid proteins, or any combination thereof, each as described above.

In some embodiments, the AAV variants have increased specificity for and/or transduction of CD133+ GSC, CD44+ GSC, CD44−/CD133+ GSC, CD44+/CD133− GSC, CD44+/CD133+ GSC and/or CD44−/CD133− GBM cells. CD133+ GSC tend to be slow GSC; CD44+ GSC tend to be fast GSC. In some embodiments, CD133+ and/or CD44+ cells are GSC and CD133−/CD44− (double negative) cells are GBM cells. In some embodiments, GBM cells includes both GSC and non-GSC GBM cancer cells. In some embodiments, GSC can be CD133−/CD44−.

In some embodiments, AAV variants having increased specificity for and/or transduction of CD133+ GSC are described. CD133+ GSC can be CD44+ or CD44−. Such AAV variants comprise one or more VPX capsid proteins having amino acid substitutions as described in Table 1 and/or Table 2.

In some embodiments, AAV variants having increased specificity for and/or transduction of CD44+ GSC are described. CD44+ GSC can be CD133+ or CD133−. Such AAV variants comprise one or more VPX capsid proteins having amino acid substitutions as described in Table 7 and/or Table 8.

In some embodiments, AAV variants having increased specificity for and/or transduction of CD44−/CD133− GBM cells are described. Such AAV variants comprise one or more VPX capsid proteins having amino acid substitutions as described in Table 3 and/or Table 4.

In some embodiments, AAV variants having increased specificity for and/or transduction of CD44+/CD133+ GSC are described. Such AAV variants comprise one or more VPX capsid proteins having amino acid substitutions as described in Table 5 and/or Table 6.

In certain embodiments, an AAV variant having increased binding specificity for and/or transduction of GSC and/or non-GSC-GBM cells comprises an AAV having a capsid protein having amino acid substitutions E531G, K532R, S547A, E548G, T550N, V552A, D553A, E555G, K556Q, R585A, and R588A relative to the amino acid sequence of SEQ ID NO: 1.

In some embodiments, an AAV variant having increase binding specificity for and/or transduction of GSC and/or non-GSC-GBM cells comprises an AAV having a capsid protein having amino acid substitutions Q263G, S264T, Y444F, T450A, P451E, S452G, T454L, T455K, Q457M, R459H, Q461L, S492D, A493G, D494E, E499D, and Y500F relative to the amino acid sequence of SEQ ID NO: 1.

In some embodiments, an AAV variant having increased binding specificity for and/or transduction of GSC and/or non-GSC-GBM cells comprises an AAV having a capsid protein having amino acid substitutions S264A, Y444F, T450D, P451R, S452G, T454S, Q457T, R459A, Q461S, S492D, A493G, D494E, E499D, and Y500F relative to the amino acid sequence of SEQ ID NO: 1. In some embodiments, an AAV variant having increased binding specificity for and/or transduction of GSC and/or non-GSC-GBM cells comprises an AAV having a capsid protein having amino acid substitutions Q263A, S264A, Y444F, T450D, P451R, S452G, T454S, Q457T, R459A, Q461S, S492D, A493G, D494E, E499D, and Y500F relative to the amino acid sequence of SEQ ID NO: 1.

In some embodiments, an AAV variant having increased binding specificity for and/or transduction of GSC and/or non-GSC-GBM cells comprises an AAV having a capsid protein having amino acid substitutions E530N, E531D, K532R, S547A, E548K, K549G, D553A, I554V, R585A, and R588A relative to the amino acid sequence of SEQ ID NO: 1. In some embodiments, an AAV variant having increased binding specificity for and/or transduction of GSC and/or non-GSC-GBM cells comprises an AAV having a capsid protein having amino acid substitutions Q263E, Y444F, T450A, P451S, S452A, T454S, Q457T, R459T, Q461G, T491Q, S492P, A493G, E499D, Y500F, E530D, E531D, and K532R relative to the amino acid sequence of SEQ ID NO: 1.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. The portion of one polynucleotide or amino acid sequence in the comparison window may comprise additions or deletions (i.e., gaps) as compared to the other sequence (which does not comprise additions or deletions) for optimal alignment of the two sequences. Unless otherwise indicated the window of comparison between two sequences is defined by the entire length of the shorter of the two sequences.

For percent sequence identity in reference to proteins, it is understood that amino acids that are not identical can differ by conservative substitutions, wherein amino acid residues are substituted for amino acid residues with similar chemical properties (e.g., charge or hydrophobicity). Such substitutions are less likely to change the functional properties of the protein. When sequences differ in conservative substitutions, the percent sequence identity may be adjusted upwards to correct for the conservative nature of the substitution. Sequences that differ by such conservative substitutions are said to have "sequence similarity" or "similarity." Such analyses are well known in the art. Conservative substitution can be scored as a partial mismatch rather than a full mismatch, thereby increasing the percentage sequence identity (or similarity). The scoring of conservative substitutions is calculated, e.g., as implemented in the program PC/GENE (Intelligenetics, Mountain View, California).

Sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. Other methods of determining similarity include, BLAST, PSI-BLAST, SSEARCH, and FASTA.

As used herein, "specificity" refers to the ability of an AAV particle to recognize and bind to a target cell. Such as a GBM cell or GSC. Increased specificity for GBM cells or GSC means that the AAV variant binds to the GBM cells or GSC with greater binding affinity than a similar AAV without the amino acid substitutions (such as a wild-type AAV capsid).

As used herein, "increased transduction" of GBM cells or GSC refers to that the AAV variant transduces GBM cells or GSC with greater efficiency than a similar AAV without the amino acid substitutions. As used herein, "transduction" refers to the intracellular introduction of a polynucleotide by a virus or viral vector, such as AAV, into a cell.

In some embodiments, nucleic acid molecules encoding any of the described AAV capsid proteins are contemplated. In some embodiments, gene delivery vectors containing any of the described AAV variants or AAV particles containing any of the described AAV capsid proteins are contemplated.

In some embodiments, host cells containing any of the described AAV variants or AAV particles containing any of the described AAV capsid proteins are contemplated. In various embodiments, host cells comprise GBM or GSC cells. In some embodiments, host cells comprise any one of CD133 and CD44 single positive, CD133/CD44 double positive and CD133/CD44 double negative GBM cells, or CD133 and CD44 single positive, CD133/CD44 double positive and CD133/CD44 double negative GSC cells.

In some embodiments, any of the described AAV variants can be used as a gene therapy vector. The described AAV variants are particularly useful in delivering heterologous nucleic acid regions transgenes (or heterologous genes or transgenes) to GBM or GSC cells. Any of the described AAV particles or an AAV particle comprising any of the described capsid proteins can comprise a genome containing a heterologous nucleic acid region. The heterologous nucleic acid sequence can encode a protein or ribonucleotide. The protein or ribonucleotide can be a therapeutic protein or ribonucleotide. A heterologous gene can contain an entire gene sequence of a partial gene sequence or a function fragment thereof. In some embodiments, a heterologous gene encodes an functional RNA. In some embodiments, a heterologous gene encodes a polypeptide or protein.

In some embodiments, methods of delivering a heterologous gene to a GBM cell or GSC are described, the methods comprising contacting a GBM cell or GSC cell with any of the described AAV variants or an AAV comprising any of the described capsid proteins.

Recombinant AAV Particles

Provided herein are variant rAAV (e.g., variant rAAV2) particles. In some embodiments, a particle is an empty particle (e.g., one that does not contain a nucleic acid vector comprising a heterologous gene). In some embodiments, an AAV2 particle contains a nucleic acid vector comprising a heterologous nucleic acid or heterologous gene. A heterologous gene is a gene that encodes a RNA or protein of interest.

In some embodiments, a rAAV2 particle containing any one of the variant rAAV (e.g., variant rAAV2) capsid proteins disclosed herein comprises ITRs and/or rep ORF of serotype 2. In some embodiments, a rAAV2 particle is a pseudotyped rAAV particle, which comprises (a) a capsid comprised of capsid proteins derived from serotype 2, and (b) a nucleic acid vector comprising ITRs from another serotype (e.g., AAV1, AAV3, AAV4, AAV5, AAV6, AAV7, AAV8, AAV9, or AAV10). For example, a particle may have ITRs of serotype 5 and a capsid of serotype 2. Such a pseudotyped rAAV particle would be designated AAV5/2.

A protein of interest may be a detectable marker or a therapeutic protein. A detectable marker is a molecule that can be visualized (e.g., using a naked eye or under a microscope). In some embodiments, the detectable marker is a fluorescent molecule, a bioluminescent molecule, or a molecule that provides color (e.g., β-galactosidase or Antares). In some embodiments, a detectable marker is a fluorescent protein or functional peptide or functional polypeptide thereof.

In some embodiments, a heterologous gene encodes a therapeutic protein and is referred to as a "therapeutic gene." A therapeutic gene may provide a therapeutic effect in a cell, tissue or organ to which it is delivered. In some embodiments, a therapeutic gene provides a therapeutic benefit to a cell, tissue or organ other than the one to which it is delivered. For example, a gene delivered to the brain tissue (e.g., the temporal or frontal lobe) may reach glioma or glioblastoma cells. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, a short hairpin RNA, an siRNA, a guide RNA, or other nucleic acid or protein for gene editing.

In some embodiments, a heterologous gene encodes a therapeutic RNA, e.g., a small interfering RNA or a short hairpin RNA. In certain embodiments, the heterologous gene encodes a shRNA targeting a master regulator gene. In certain embodiments, the heterologous gene encodes a shRNA targeting one or more of the Ascl-1 or Nkx6-2 genes, such as shRNA targeting one or more of the human ASCL-1 or NKX6-2 genes. In some embodiments, a therapeutic gene encodes a repair enzyme (e.g., MGMT), a checkpoint inhibitor, a transcription factor, a growth factor receptor, a growth factor ligand, or a tumor suppressor protein.

In some embodiments, a nucleic acid vector comprised in a rAAV particle comprises one or more of the following: (a) one or more heterologous nucleic acid regions comprising a heterologous gene, and (b) one or more regions comprising inverted terminal repeat (ITR) sequences (e.g., wild-type ITR sequences or engineered ITR sequences) flanking the one or more nucleic acid regions (e.g., heterologous nucleic acid regions). In some embodiments, a nucleic acid vector in a rAAV particle comprises one or more nucleic acid regions comprising a control sequence that facilitates expression of the heterologous nucleic acid region (e.g., a promoter). In some embodiments, a nucleic acid vector in a rAAV particle comprises one or more nucleic acid regions comprising a sequence that facilitates integration of the heterologous nucleic acid region (optionally with the one or more nucleic acid regions comprising a sequence that facilitates expression) into the genome of the subject.

Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

In some embodiments, one or more promoters may be operably linked to a coding nucleotide sequence in the heterologous nucleic acid. A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. In some embodiments, chimeric viral/mammalian promoters may include a chimeric CMV/chicken beta actin (CBA, CB or CAG) promoters. In some embodiments, a shortened or truncated promoter is used.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. In some embodiments, it may be beneficial to combine a variant rAAV (e.g., variant rAAV2) particle as disclosed herein, with a promoter that also targets the same cells, tissue, or organ as the variant rAAV (e.g., variant rAAV2) particle. For example, a variant rAAV (e.g., variant rAAV2) particle that targets glioma or glioma stem-like cells might encapsidate a nucleic acid comprising a promoter that targets neural cells or neural stem cells.

Synthetic promoters are also contemplated herein. A synthetic promoter may comprise, for example, regions of known promoters, regulatory elements, transcription factor binding sites, enhancer elements, repressor elements, and the like.

It is to be understood that a promoter may be a fragment of any one of the promoters disclosed herein, or one that retains partial promoter activity (e.g., 10-90, 30-60, 50-80, 80-99 or 90-99.9% of the activity) of a whole promoter.

Any nucleic acid vector described herein may be encapsidated by a viral capsid. In some embodiments a cap gene is modified to express a fusion protein comprising a detectable marker and VP proteins of AAV serotype 2. In some embodiments, a peptide is inserted into the capsid protein either at position 587/588 or at the C-terminus of VP2. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complementary vector that contains a region of the nucleic acid vector that is complementary to another region of the nucleic acid vector, initiating the formation of the double-strandedness of the nucleic acid vector.

Method of Making rAAV Particles

Various methods of producing rAAV particles and nucleic acid vectors are known (see, e.g., Zolotukhin et al. Production and purification of serotype 1, 2, and 5 recombinant adeno-associated viral vectors. *Methods* 28 (2002) 158-167; and U.S. Patent Publication Nos. 2007/0015238 and 2012/0322861, which are incorporated herein by reference; and plasmids and kits available from ATCC and Cell Biolabs, Inc.). In some embodiments, a vector (e.g., a plasmid) comprising a heterologous gene may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprises rep and/or cap genes that encode the Rep protein and/or Cap proteins. In some embodiments, the packaging is performed in vitro (e.g., outside of a cell).

In some embodiments, a nucleic acid vector (e.g., a plasmid) containing the heterologous gene is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca.; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), J Virology, 6:3096-3101).

ITR sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca.; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). Genebank reference numbers for sequences of AAV serotypes 1, 2, 3, 3B, 4, 5, 6, 7, 8, 9, 10, 11, 12, and 13 are listed in patent publication WO 2012/064960, which is incorporated herein by reference.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO4-mediated transfection, lipids or polymeric molecules such as polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Methods for large-scale production of AAV using a herpesvirus-based system are also known. See for example, Clement et al. (Hum Gene Ther. 2009, 20(8):796-806). Methods of producing exosome-associated AAV, which can be more resistant to neutralizing anti-AAV antibodies, are also known (Hudry et al., Gene Ther. 2016, 23(4):380-92; Macguire et al., Mol Ther. 2012, 20(5):960-71).

Methods for producing and using pseudotyped rAAV vectors are also known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Compositions

Various formulations have been developed to facilitate rAAV particle use. For example, for administration of an injectable aqueous solution of rAAV particles, the solution may be suitably buffered, if necessary, and the liquid diluent first rendered isotonic with sufficient saline or glucose. In some embodiments, a composition as provided herein comprises a plurality of any one of the variant rAAV (e.g., variant rAAV2) particles disclosed herein. In some embodiments, a composition comprises pluralities of more than one of the variant rAAV (e.g., variant rAAV2) particles disclosed herein. In some embodiments, "administering" or "administration" means providing a material to a subject in a manner that is pharmacologically useful.

Accordingly, in some embodiments, a composition of variant rAAV particles comprises a pharmaceutically acceptable carrier. The term "carrier" refers to a diluent, adjuvant, excipient, or vehicle with which the rAAV particle is administered. Such pharmaceutical carriers can be sterile liquids (e.g., water, oils, saline solutions, aqueous dextrose and glycerol solutions), suspending agents, preserving agents (e.g., methyl-, ethyl-, and propyl-hydroxy-benzoates), and pH adjusting agents (such as inorganic and organic acids and bases). In some embodiments, carriers include buffered saline solutions (e.g., phosphate buffered saline, HEPES-buffered saline). USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, a composition comprising any one of the rAAV particles disclosed herein comprises Balanced Salt Solution (BSS) supplemented with 0.014% Tween 20 (polysorbate 20). In some embodiments, a composition comprising any one of the rAAV particles disclosed herein comprises 100 mM sodium citrate, 10 mM Tris, pH 8.0, supplemented with 0.001% Pluronic F-68.

In some embodiments, the number of rAAV particles administered to a host cell may be on the order ranging from 500 to 5,000 vector genomes (vgs)/cell. In particular embodiments, the disclosed methods comprise administration of rAAV particles in doses of about 500 vgs/cell, 1000 vgs/cell, 2000 vgs/cell, 3000 vgs/cell, 4000 vgs/cell, 5000 vgs/cell, 6000 vgs/cell or 7000 vgs/cell.

In some embodiments, the number of rAAV particles administered to a subject may be on the order ranging from $10^6$ to $10^{14}$ particles/mL or $10^3$ to $10^{13}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the number of rAAV particles administered to a subject may be on the order ranging from $10^6$ to $10^{14}$ vgs/mL or $10^3$ to $10^{15}$ vgs/mL, or any values there between for either range, such as for example, about $10^6$, $10^7$, $10^8$, $10^9$, $10^{10}$, $10^{11}$, $10^{12}$, $10^{13}$, or $10^{14}$ vgs/mL. In certain embodiments, the disclosed methods comprise administration of rAAV particle compositions in doses of $3 \times 10^3$–$1 \times 10^4$ vgs/mL. In one embodiment, rAAV particles of higher than $10^{13}$ vgs/mL are be administered.

The rAAV particles can be administered as a single dose, or divided into two or more administrations as may be required to achieve therapy of the particular disease or disorder being treated. In some embodiments, 0.0001 mL to 10 mL are delivered to a subject.

In some embodiments, the disclosure provides formulations of compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particle or preparation and nucleic acid segments may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles or preparations and nucleic acid segments may thus be delivered along with various other agents as required in the particular instance. Such compositions may be purified from host cells or other biological sources, or alternatively may be chemically synthesized as described herein. As used herein, the term "vector" can refer to a nucleic acid segment (e.g., a plasmid or recombinant viral genome) or a viral vector (e.g., an rAAV particle comprising a recombinant genome).

Typically, compositions may contain at least about 0.1% of the therapeutic agent (e.g., rAAV particle) or more, although the percentage of the active ingredient(s) may be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms of rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

Preparation of compositions for administration to a subject are known in the art. For example, a dosage may be dissolved in 1 ml of isotonic NaCl solution and either added to 1000 ml of hypodermoclysis fluid or injected at the proposed site of infusion, (see for example, Remington's Pharmaceutical Sciences, 15th Ed., 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

In some embodiments, a cell, tissue or organ is transduced in vivo, for example, for the purposes of treating a disease. In some embodiments, a cell, tissue or organ of the CNS is transduced in vivo. In some embodiments, brain tissue or brain cells is transduced in vivo. In some embodiments, a disease associated with the CNS is treated by administering one or more of the disclosed rAAV particles or compositions. In particular embodiments, a disease associated with glioma or glioblastoma is treated.

In some embodiments, "administering" or "administration" means providing a material to a subject in a manner that is pharmacologically useful. In some embodiments, a rAAV particle is administered to a subject enterally. In some embodiments, an enteral administration of the essential metal element/s is oral. In some embodiments, a rAAV particle is administered to the subject parenterally. In some embodiments, a rAAV particle is administered to a subject intratumorally, intraocularly, subcutaneously, intravenously (IV), intra-arterially, intracerebrally, intraventricularly, intramuscularly, intrathecally (IT), intracisternally, intraperitoneally, via inhalation, topically, or by direct injection to one or more cells, tissues, or organs (e.g., the brain). In certain embodiments, rAAV particle delivery is intratumoral.

In some embodiments, a subject in which a cell, tissue or organ is transduced is a vertebrate animal (e.g., a mammal or reptile). In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a model for a particular disease or used to study the pharmacokinetics and/or pharmacokinetics of a protein or siRNA encoded by a heterologous gene.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host cell, tissue or organ. A therapeutically acceptable amount may be an amount that is capable of treating a disease, e.g., stroke. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

EXAMPLES

Example 1

AAV2 Delivery

Figure 1A:
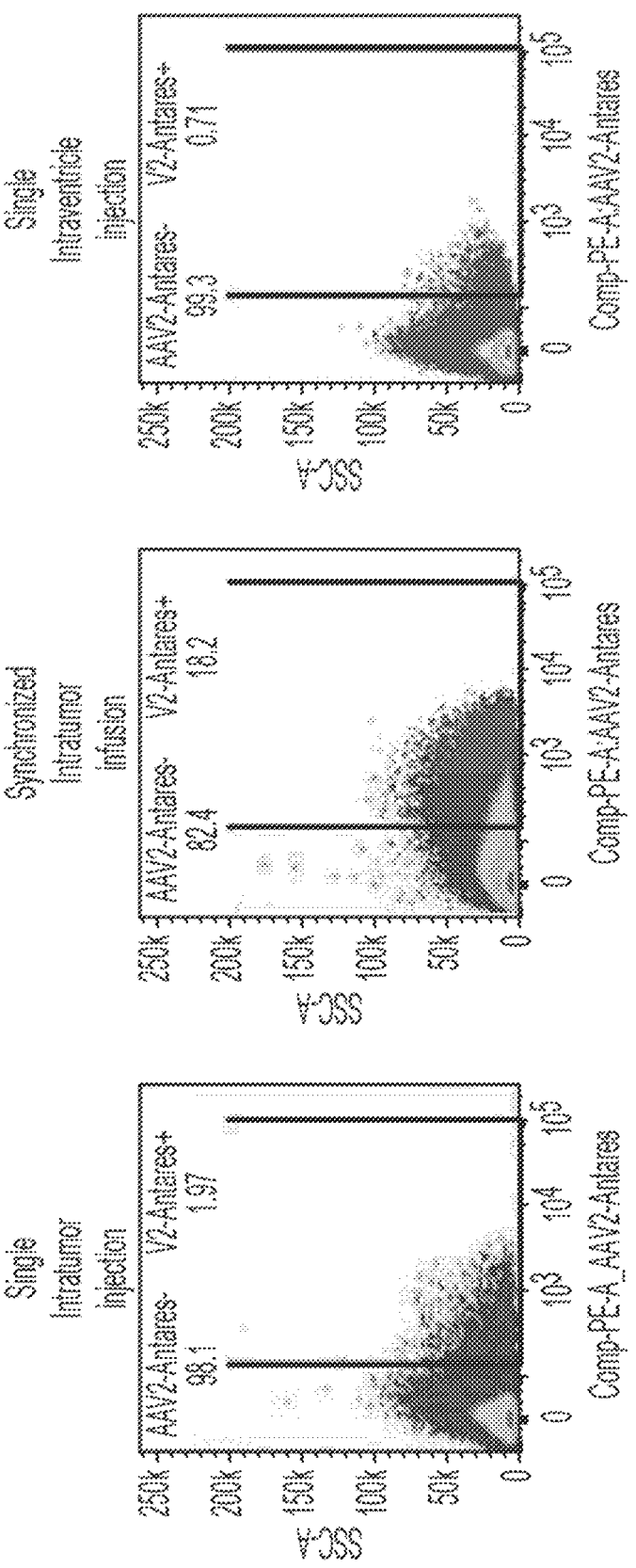
FIG. 1A. AAV delivery synchronized with tumor progression was superior in tumor infection compared to single injections intra-tumoral or intra-ventricular injections.
Figure 1B:
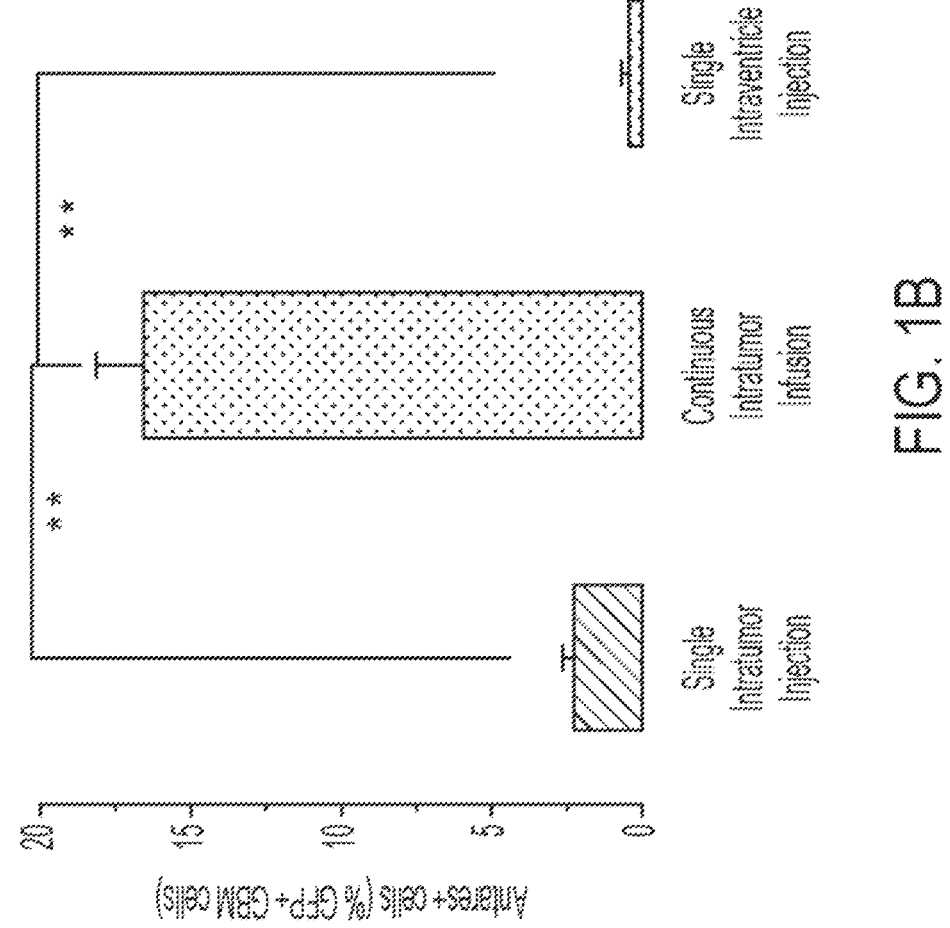
FIG. 1B. Dissociated GPP+ tumor cells were sorted for Antares expression.
Figure 1C:
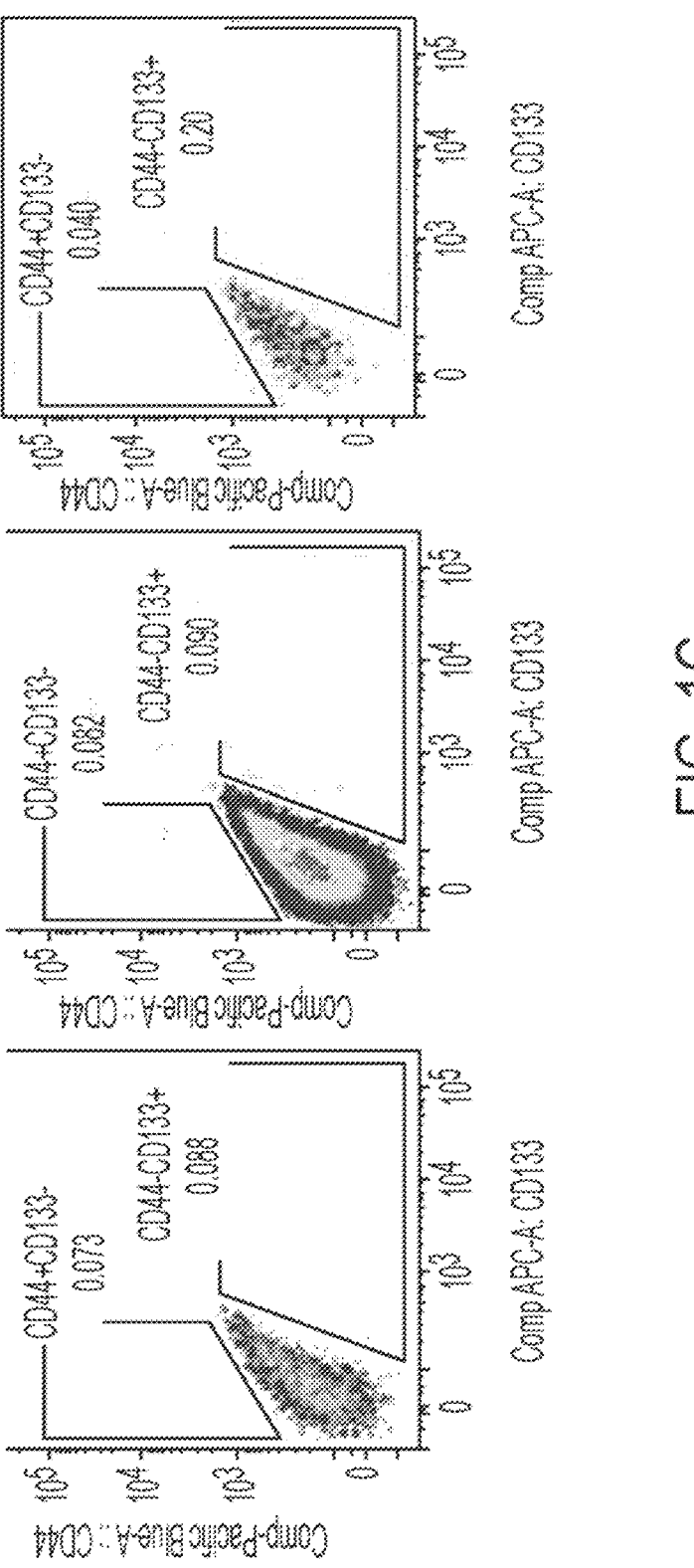
FIG. 1C. The fraction of Antares-expressing cells is one order of magnitude when using higher in synchronized continuous infusions, Ttest $p<0.01$.

A dynamic mode of administration of a library reagent synchronized with tumor progression was evaluated. The AAV vector under evaluation expressed Antares, a cyan-excitable orange fluorescent reporter gene. The Antares gene consists of an optimized fusion of CyOFP1 and NanoLuc luciferase and functions as a highly sensitive bioluminescent reporter in vivo, producing substantially brighter signals from deep tissues than firefly luciferase and other bioluminescent proteins. (See Chu et al., Nat Biotechnol. 2016 July; 34(7): 760-767, herein incorporated by reference.) Continuous intratumor graded infusion of an AAV2-Antares vector reagent that was synchronized with tumor progression (i.e. slow to fast infusion rates synchronized with early and late stage of tumor growth) resulted in nearly 10-fold increase in Antares gene delivery when compared to a single intratumor injection. Synchronized delivery of an AAV reagent in directed evolution screening for variants specific for slow and fast GSC populations and non-GSC GBM cell population resulted in infection of target cells (FIGS. 1A-1C).

Example 2

Directed Evolution Screen of an AAV2 Library

Figure 2:
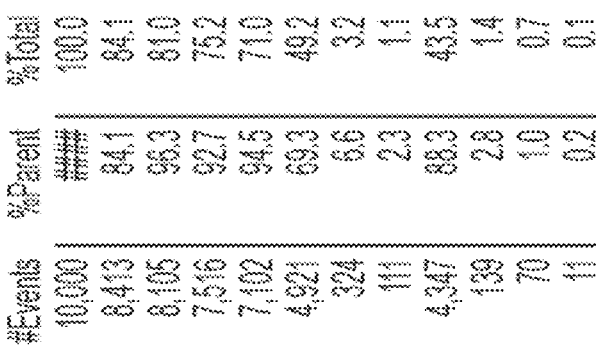
FIG. 2. A Glioblastoma (GBM) Patient derived Xenograft (PDX) in a directed evolution screen with an AAV2 library. GFP+ tumor cells were sorted for CD133 and CD44 with typical frequencies shown.
Figure 2:
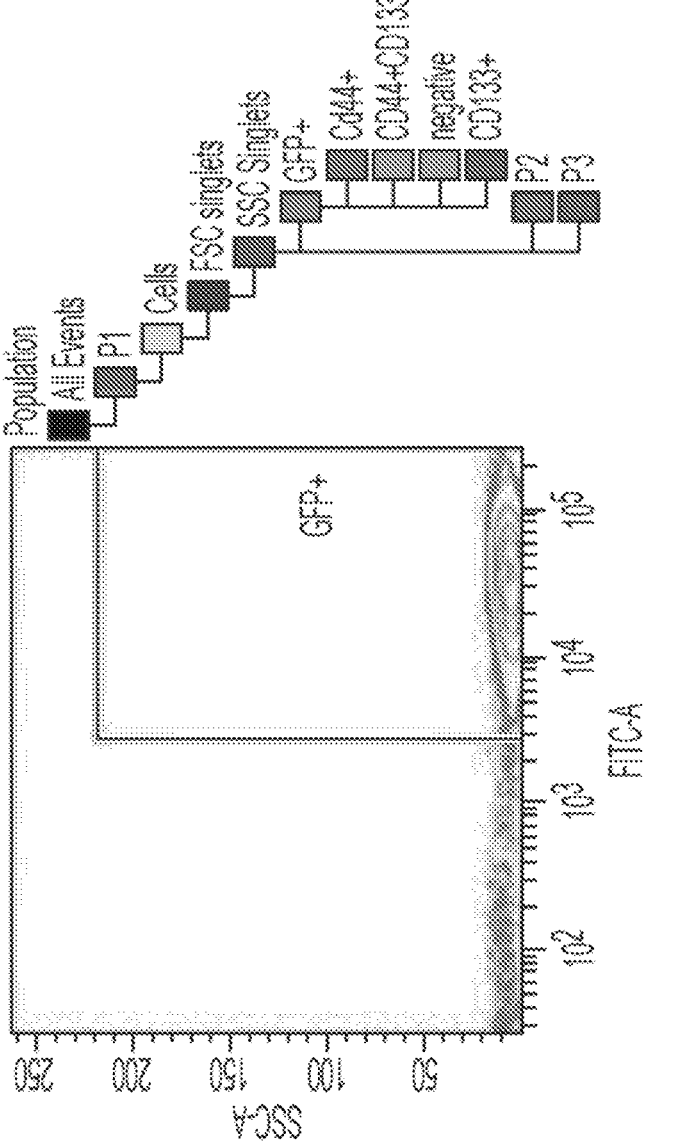

Three rounds of directed evolution screening, using an AAV2 library (~107 complexity of variants) in 3 GFP/luciferase-labeled GSC lines and at least 5 animals in each group. Tumor growth was monitored by bioluminescent imaging (BLI). For each round, AAV2 infusion was synchronized with tumor growth using an Alzet pump implanted subcutaneously (s.q.) in the animal's back. The catheter was inserted intratumorally. AAV2 library was infused over a period of at least 2 weeks, with infusion rate doubled in the second week when tumor growth accelerated, followed by a 1-week rest period to allow for maximal viral transduction. Tumors were harvested and analyzed by FACS; gated for GFP, and sorted for CD133 and CD44 single positive, CD133/CD44 double positive and CD133/CD44 double negative populations (FIG. 2). Two rounds of directed evolution screening were conducted in each cell population to provide the results shown in Tables 1-8. Subsequently, a third round of evolution was conducted to provide the 23 variants that conferred the highest increase of (or improvement in) transduction across all four cell types. These directed evolution (DE) experiments presuppose that capsid variants are homogeneously distributed among the AAV2 viral library.

Example 3

Next Generation Sequencing (NGS) and Bioinformatics

Figure 3:
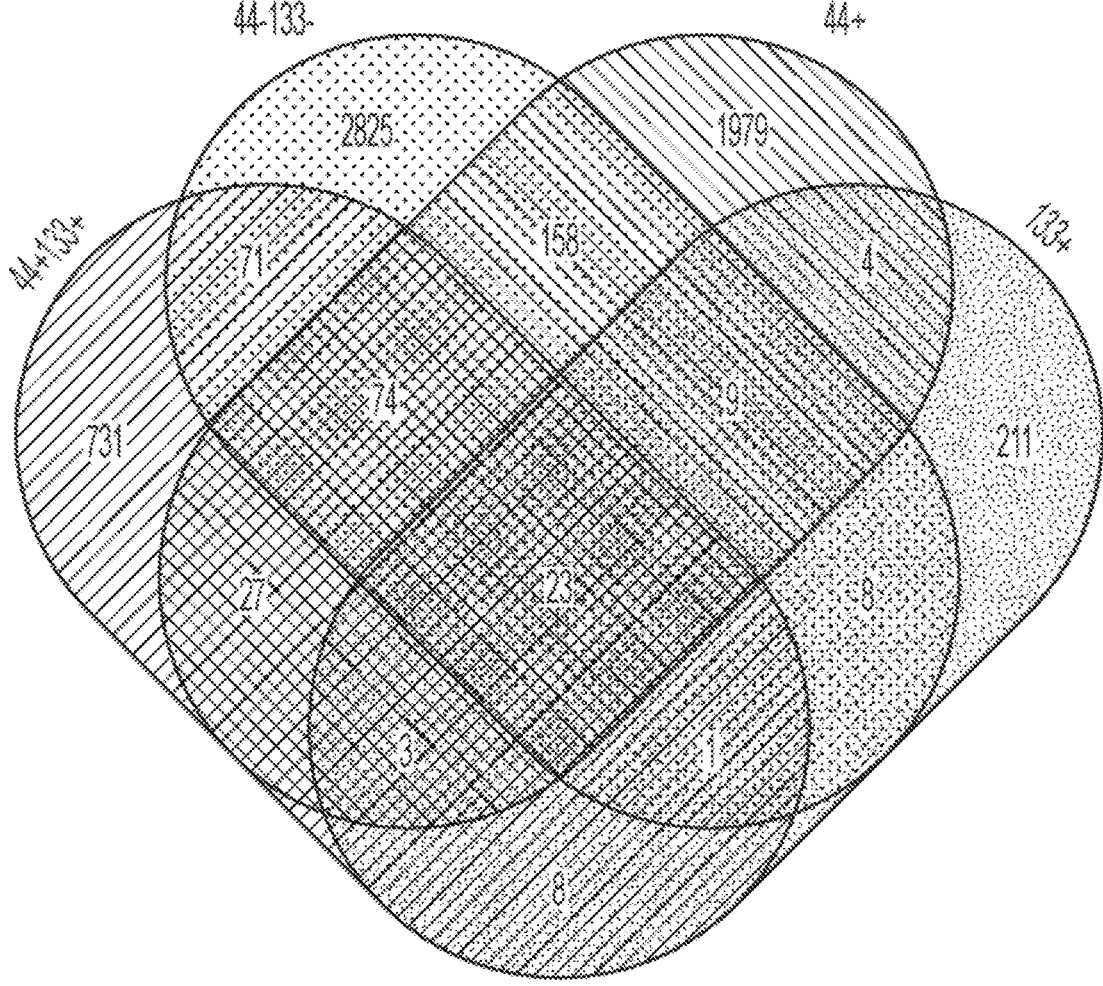
FIG. 3. Venn diagram of capsid variant sequences transducing various GSC populations and non-GSC-GBM cells after 3 rounds of directed evolution screening.
Figure 4:
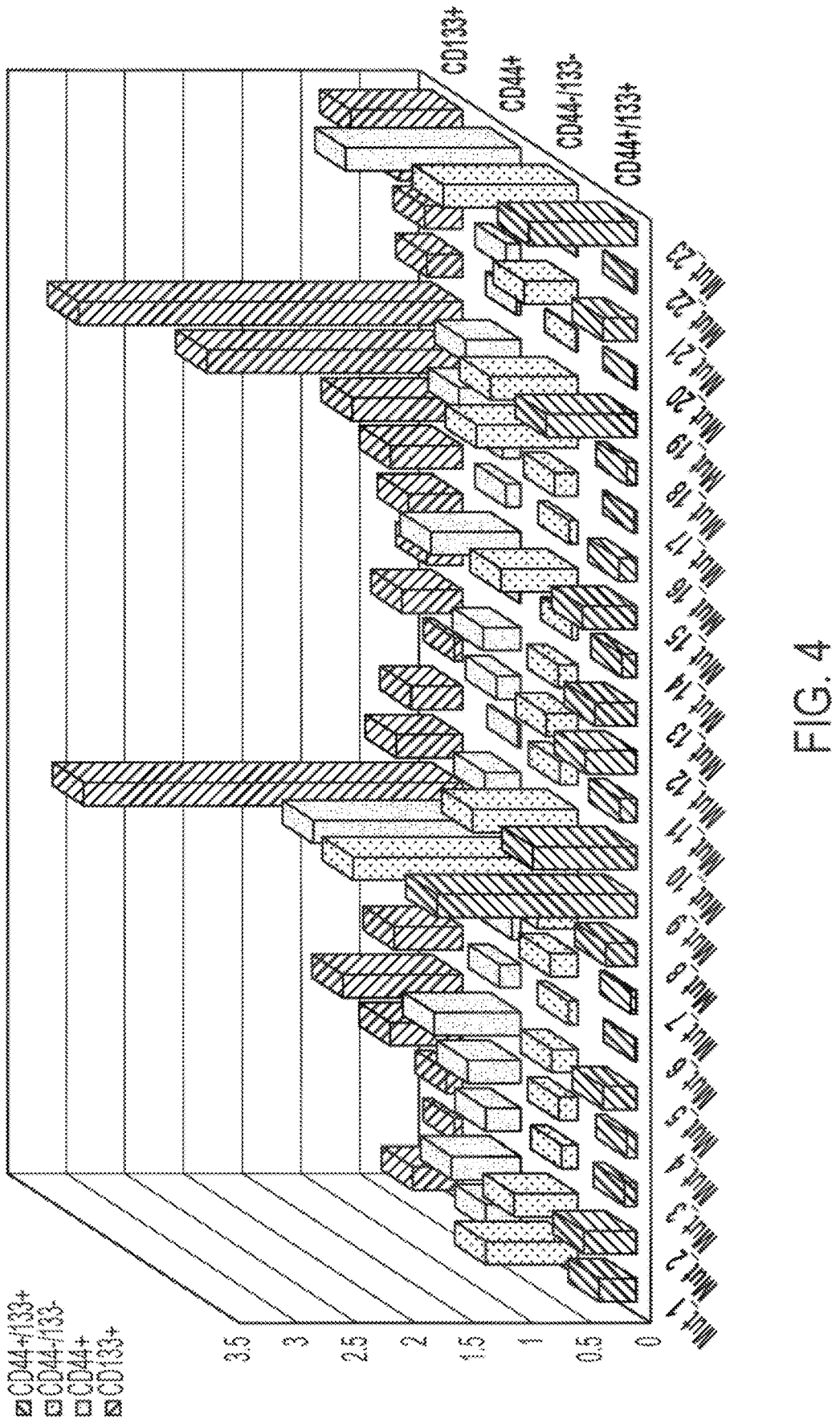
FIG. 4. The 23 mutant (Mut) sequences enriched in all GSC populations and non-GSC-GBM cell populations (see FIG. 3). Mutants 9, 10, 18, 19 and 23 had the broadest overlaps.

After each round of directed evolution, viral DNA was isolated from each cell population and subjected to next generation sequencing (NGS) and bioinformatics analysis using dedicated software. A clustering analysis identified several enriched AAV capsid variants that exhibited increased recognition and transduction of each population of GSCs and non-GSC-GBM cells. 23 AAV variants (Mut) recognized and transduced all types tested, including CD44 (+), CD133(+), and double negative cells (FIGS. 3 and 4).

Next generation sequencing was used to identify the amino acid substitutions in the capsid proteins of AAV particles identified in the directed evolution screen that conferred enhanced transduction. Results of these sequencing evaluations are shown in Tables 1-8. Variants are shown along with the "enrichment factor" of the rAAV vector (or genome) associated with each variant. The enrichment factor ("%") refers to the percentage of all nucleotide sequence reads (or "copies") that are represented by the genome associated with a particular variant, in the particular screening round. (Reads are determined through next-generation sequencing (NGS) of the genomes.) The higher the value of this percentage, the better the variant is suited to target and infect these particular cell types so that they integrate the rAAV genome. After a single screening round, variants generating a higher percentage of sequence reads may be selected as better (or the best) candidates. In that scenario, the % shown is equivalent to the fraction of (count of individual mutant genome reads)/(count of all mutant genome reads in the DNA sample). For example, if 10,000 copies of Mutant #1 were recovered after analysis of of a total of 1000,000 copies of DNA (for that sample) were screened, then the % for Mutant #1 is calculated as (10,000/1000,000)*100%, or 1%.

The fold-change values describing enrichment between two rounds of screening (e.g., rounds 1 and 2 of selection in in CD133+ GSC cells) may be calculated as:

$$\text{DNA enrichment} = \frac{\% \text{ in reads after } NGS \text{ of DNA Round 1}}{\% \text{ of reads after } NGS \text{ of in DNA Round 2}} =$$

$$\frac{5\%}{1\%} = 5 \text{ times (round 1 to 2 enrichment)}.$$

Accordingly, in some embodiments, the capsid variant of any of the disclosed rAAV particles comprises a polypeptide sequence that exhibits an enrichment factor (%) in GBM and/or GSC cells that is greater than 0.01, 0.05, 0.1, 0.15, 0.2, 0.25, 0.3, 0.35, 0.4, 0.45, 0.5, 1.0 1.5, 2.0, 2.5, 3.0, 3.5, 4.0, 4.5, 5.0, 5.5, 6.0, 6.5, 7.0, 7.5, 8.0, 8.5, 9.0, 9.50, 10.0, 11.0, 12.0, 13.0, 14.0, 15.0, 16.0, 17.0, 18.0, 19.0, 20.0, 30.0, 40.0, 50.0, 60.0, 70.0, 80.0, 90.0, or 95.0, optionally greater than 10.0, or 20.0, 30.0, 40.0, 50.0, 60.0, 70.0, 80.0, or 90.0. In particular embodiments, the capsid variants exhibit an enrichment factor of greater than 10.0, 11.0, 12.0, 13.0, 14.0, 15.0, or 20.0. For example, the capsid may comprise a sequence that comprises the mutations of any of SEQ ID NO:s 4, 5, 6, 7, or 9-7010 relative to SEQ ID NO: 8 (e.g., the mutations of SEQ ID NOs: 4-7 and 9-28) and that demonstrates an enrichment factor as described above.

A key to the tables is as follows:

Table 1 depicts an alignment of amino acid sequences of the pool of variants following Round 1 selection in CD133$^+$ GSC cells against SEQ ID NO: 8, which corresponds to the variable regions I, IV, V, VI, VII and VIII of the wild-type AAV2 VP1 capsid protein.

Table 2 depicts an alignment of amino acid sequences of the pool of variants following Round 2 selection in CD133$^+$ GSC cells.

Table 3 depicts an alignment of amino acid sequences of the pool of variants following Round 1 selection in CD44$^-$/CD133$^-$ GBM cells.

Table 4 depicts an alignment of amino acid sequences of the pool of variants following Round 2 selection in CD44$^-$/CD133$^-$ GBM cells.

Table 5 depicts an alignment of amino acid sequences of the pool of variants following Round 1 selection in CD44$^+$/CD133$^+$ GSC cells.

Table 6 depicts an alignment of amino acid sequences of the pool of variants following Round 1 selection in CD44$^+$/133$^+$ GSC cells.

Table 7 depicts an alignment of amino acid sequences of the pool of variants following Round 1 selection in CD44$^+$ GSC cells.

Table 8 depicts an alignment of amino acid sequences of the pool of variants following Round 2 selection in CD44$^+$ GSC cells.

Table 9 depicts an alignment of amino acid sequences of sequences of the top 23 capsid variants selected by three rounds of directed evolution targeting all four GSC and GBM cell populations, against SEQ ID NO: 8.

TABLE 1

AAV capsid proteins having increased specificity for and/or transduction
of CD133* GSC (pool of Round 1 selection). Amino acid numbers correspond
to the amino acid sequence of VP1 (SEQ ID NO: 1). The percentage value in
the penultimate column indicates the "enrichment factor." Sequences below
correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | ................ | ...NDR | ..AKG...AV.. | A..A........ | 3.25 | 250 |
| ..... | ................ | ................ | ....GR | ..AG.N.AA.GQ | A..A........ | 3.23 | 248 |
| GT... | F.....AEG.LK.M.H.L | ..DGE....DF...... | ...... | ........... | ............ | 2.17 | 167 |
| ..... | F................ | .V........F...... | ...... | ........... | ARRDE..ANT.H | 1.53 | 118 |
| EA... | ................ | .Q.......DF...... | ...AD. | EDGGGS..EYGS | A..A........ | 1.34 | 103 |
| SA... | ................ | ................ | E..TG. | ........... | A..A......H | 1.20 | 92 |
| .A... | ................ | ................ | R...DR | E.ARE...E.DQ | A..A........ | 1.20 | 92 |
| SA... | F....ATT.IM.T.T.R | .V........F...... | ...... | ...KANDTEY.S | A..A........ | 1.18 | 91 |
| ..... | F................ | .V........F...... | ...... | ........... | ATSDH..NR..A | 1.16 | 89 |
| EA... | ................ | T..NE....DF......T | R..DD. | ........... | ............ | 1.13 | 87 |
| ..... | ................ | .V........F...... | ...... | ........... | ............ | 1.01 | 78 |
| RA... | F.....GQG.IA.....K | ................ | ...... | ........... | A..A...... | 1.01 | 78 |
| GT... | F.......G.HK.T.N.G | ..HG.....NF......T | E..N.. | E.......... | A..A........ | 1.00 | 77 |
| ..... | ................ | ................ | ...... | ..AKA.DTEV.Q | A..A........ | 0.99 | 76 |
| ..... | ................ | ................ | ....D. | ........... | A..A........ | 0.95 | 73 |
| E.... | F.....ASA.S..T.T.G | .QPG.....DF...... | ...DDR | ........... | A..A........ | 0.95 | 73 |
| ..... | ................ | ................ | ...D.. | .NATG....VGS | A..A........ | 0.91 | 70 |
| ..... | ................ | ................ | ...DG. | ES.GT...A.DG | A..A........ | 0.90 | 69 |
| GT... | ................ | ..PDG....NF...... | ....DR | ........... | A..A........ | 0.90 | 69 |
| NT... | ................ | ..YN......F......T | ...N.. | ........... | A..A........ | 0.88 | 68 |
| ..... | ................ | .................T | R..D.R | .D.TR..AA..Q | A..A........ | 0.87 | 67 |
| RT... | ................ | TKDDR....DF...... | ...DDR | EDGATG...VDR | A..A........ | 0.85 | 65 |
| AA... | F.....G.G.HM.M.S.M | T.P......DF...... | ...D.. | ........... | A..A........ | 0.83 | 64 |
| ..... | ..........N.T.R | .QHNQ.....F......T | ...N.. | E.AA.SD.AVGG | A..A........ | 0.83 | 64 |
| ..... | ................ | ................ | ...DDR | EDGNTN.A.VDS | A..A........ | 0.83 | 64 |
| ..... | ................ | ................ | ...DDR | ..AG...IAYGN | A..A........ | 0.83 | 64 |
| ..... | F................ | .V........F...... | ...... | ........... | TSKAT..FRE.T | 0.83 | 64 |
| ST... | ...............T.N | ................ | ...... | ..TG.D..A.GG | A..A........ | 0.81 | 62 |
| ..... | F.....D.G..Q.N...R | ..A.............. | ...... | ........... | ............ | 0.79 | 61 |
| ..... | ................ | .V........F...... | ...... | ENAAGND.AVDR | A..A........ | 0.79 | 61 |
| .A... | F................ | .PPNG.....F......T | ...DDR | E.ASE...E.D. | A..A........ | 0.78 | 60 |
| ..... | ................ | ................ | G..N.. | ........... | A..A........ | 0.75 | 58 |
| ..... | F................ | .V........F...... | ...... | ........... | KTKNP...GE.H | 0.74 | 57 |
| ..... | ................ | .QPSQ....NF...... | G..DD. | ........... | A..A........ | 0.74 | 57 |
| A.... | F.....ATG.NN..I.S.G | .QPN......F......T | ...N.. | ........... | A..A........ | 0.73 | 56 |
| RT... | F.....ARG.I..T.A.K | ..DGE....DF...... | ...... | E.AG.S..E.DN | A..A........ | 0.70 | 54 |

TABLE 1-continued

AAV capsid proteins having increased specificity for and/or transduction
of CD133* GSC (pool of Round 1 selection). Amino acid numbers correspond
to the amino acid sequence of VP1 (SEQ ID NO: 1). The percentage value in
the penultimate column indicates the "enrichment factor." Sequences below
correspond to SEQ ID NOs: 8 and 29.295 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | ................. | .D.... | .DAGRN.IA.DG | A..A........ | 0.69 | 53 |
| ..... | F.....GTG.P....K.. | .........NF....... | R...D. | .DGKGND...DG | A..A........ | 0.68 | 52 |
| ..... | ................. | ................. | F...AD. | .DAG.S.A..DR | A..A........ | 0.68 | 52 |
| RA... | ................. | .PDNR..T.DF......T | ..GR | ........... | A..A........ | 0.68 | 52 |
| ..... | ................. | ................. | .DDR | E.GATG...VD. | A..A........ | 0.65 | 50 |
| TA... | F......AG.S..T.K.K | ..DD.....DF....... | ....D. | ESTDRG.A..GE | A..A........ | 0.65 | 50 |
| R.... | F.....SR...V.N.H.E | T.P......DF....... | ...D.. | ...G.S..AFGD | A..A........ | 0.65 | 50 |
| AA... | ................. | TQ..H....NF....... | ...... | ........... | A..A........ | 0.62 | 48 |
| ..... | ................. | ................. | ...N.. | ........... | A..A........ | 0.62 | 48 |
| TA..T | F.....NE..SD.H...K | Q.DR......F....... | ....D. | ..NAG.DD..DQ | A..A........ | 0.61 | 47 |
| ..... | ................. | ................. | R..DDR | ...GT..AA.GD | A..A........ | 0.61 | 47 |
| ..... | ................. | ................T | ...N.. | .SAS.N.IA..E | A..A........ | 0.61 | 47 |
| SA... | ................. | ..YN......F......T | R..DDR | .SARTGDTA..G | A..A........ | 0.60 | 46 |
| TA..T | ................. | .PPNG.....F......T | ...DDR | ........... | A..A........ | 0.60 | 46 |
| ..... | ................. | .......NF..P.... | ....D. | ........... | A..A........ | 0.60 | 46 |
| .A..T | F.....SA..SM.M.T.K | .PPNG.....F......T | ...DDR | ........... | A..A........ | 0.60 | 46 |
| NA... | ................. | .QDT.....DF....... | ...N.. | E...RS...F.Q | A..A........ | 0.60 | 46 |
| AT... | F................. | T.HGR....NF......T | ....GR | ........... | A..A........ | 0.60 | 46 |
| ..... | F................. | .V......F....... | ...... | ........... | TSRGG..IT..Q | 0.59 | 45 |
| DA... | ................. | ..AGR....DF......T | R..DG. | .SGGRS..E.DQ | A..A........ | 0.59 | 45 |
| ..... | ................. | TQP.R....NF....... | ....D. | ........... | A..A........ | 0.59 | 45 |
| ..... | ................. | ................. | R..TG. | ........... | A..A........ | 0.57 | 44 |
| .A... | ................. | ..PN.....NF....... | ...DDR | ED.RGS..EVGQ | A..A........ | 0.57 | 44 |
| SA... | F.....SA..SI.M.G.R | .KDSR....DF....... | E..ND. | ESAR..DAA.DD | A..A........ | 0.57 | 44 |
| D...T | F.....DRG.PN.N.N.K | .PPNG.....F......T | ...DDR | ........... | A..A........ | 0.57 | 44 |
| ..... | F................. | .V........F...... | ...... | ........... | NTKNG..NGS.. | 0.56 | 43 |
| NA..T | F.....DHT.R..M.G.R | ................. | ...... | E.AGTADIEVD. | A..A........ | 0.56 | 43 |
| ..... | ................. | ................. | R..DD. | ..GAR.D.E.GE | A..A........ | 0.56 | 43 |
| A.... | ................. | TQ.TG....DF....... | ...DDR | ..AGT.D.EYGQ | A..A........ | 0.56 | 43 |
| .A... | F.....DRG.S..T.A.S | ..DGE....DF....... | ...... | ........... | ........... | 0.56 | 43 |
| E.... | F.....GS..NM.N.T.R | TQDS......NF.....T | ...... | E.TGRA..A..G | A..A........ | 0.56 | 43 |
| A.... | F.....DA..IA.L.K.R | .KDSR....DF......T | R..DD. | ........... | A..A........ | 0.56 | 43 |
| ..... | ................. | ................. | ...A.R | ..ANGND.A..H | A..A........ | 0.56 | 43 |
| ..... | ................. | ................. | ...DD. | ........... | A..A........ | 0.55 | 42 |
| ..... | ................. | ................. | ....G. | ........... | A..A........ | 0.53 | 41 |

TABLE 1-continued

AAV capsid proteins having increased specificity for and/or transduction
of CD133* GSC (pool of Round 1 selection). Amino acid numbers correspond
to the amino acid sequence of VP1 (SEQ ID NO: 1). The percentage value in
the penultimate column indicates the "enrichment factor." Sequences below
correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ...D.. | ESARRD.A..DG | A..A........ | 0.53 | 41 |
| E.... | F.....DRG.S..T.A.S | ..DGE....DF....... | ...... | ........... | ........... | 0.53 | 41 |
| SA... | F.....AST.PI.K.Q.K | .KDSR....DF....... | E..ND. | ........... | A..A........ | 0.52 | 40 |
| G...T | F.....DRG.H..L.S.L | .V........F....... | ...... | ........... | A..A........ | 0.52 | 40 |
| ..... | ................. | ................. | R..ND. | EDATEN.I..DR | A..A........ | 0.51 | 39 |
| ..... | ................. | .QD.E.....F..P.... | ...D.. | ........... | ........... | 0.51 | 39 |
| ..... | ................. | TQ.G.....DF....... | ...DDR | .D.R....AFDG | A..A........ | 0.51 | 39 |
| DT... | ................. | .........NF......T | G..K.. | E..G.SD.AF.G | A..A........ | 0.49 | 38 |
| ..... | ................. | .........NF | ...... | E.AG...IAVDR | A..A........ | 0.49 | 38 |
| ..... | ................. | ................. | ...DD. | ...KRA.TE.GE | A..A........ | 0.48 | 37 |
| ..... | F................. | .V........F....... | ...... | ........... | GPSSG...NK.Q | 0.48 | 37 |
| T.... | F.....NG..SN.M...K | .........NF......T | R..AG. | ..GT.DD...DN | A..A..... | 0.47 | 36 |
| A.... | F................. | ..DGE....DF....... | R..DD. | ........... | ........... | 0.46 | 35 |
| ..... | ................. | ................. | E...DR | .SAGAN..E..S | A..A........ | 0.46 | 35 |
| NT..T | F.....ASA.S..T.T.G | .QPG.....DF......T | E..KD. | ........... | ........... | 0.46 | 35 |
| ..... | ................. | ................. | ...... | ........... | A..A........ | 0.46 | 35 |
| AA..T | ................. | ................. | R...D. | .D.TGN.I...Q | A..A........ | 0.44 | 34 |
| ..... | ................. | ..........F....... | R...D. | F..GATG...VD. | A..A........ | 0.44 | 34 |
| NT..T | F................. | .V........DF...... | ...... | ........... | A..A........ | 0.44 | 34 |
| R.... | F......GA.NM.T.A.R | .QPTR....DF....... | E..NG. | .DAG.S.A...E | A..A........ | 0.44 | 34 |
|  | F................. | .V........F....... | ...... | ........... | G.KG...SG..E | 0.44 | 34 |
| .A... | ................. | .........DF......T | ...AG. | E..DRS..EFDN | A..A........ | 0.43 | 33 |
| SA... | F.....NGG.NV.L.N.R | ..DGE....DF....... | ...... | ........... | A..A........ | 0.43 | 33 |
| ....T | F......KT.NV.K.T.H | ..YN......F......T | ...D.R | E..R.N.AEFGE | A..A........ | 0.43 | 33 |
| ..... | ................. | ................. | G..DG. | ........... | ........... | 0.43 | 33 |
| RA... | F.....DTG.SK.T.T.R | .Q.S......F....... | ...D.. | .NGR.G..A..E | A..A........ | 0.43 | 33 |
| AA... | F......DA..IA.M.K.R | T.PTG....DF....... | ...DDR | .NAG.AD.AV.Q | A..A........ | 0.43 | 33 |
| ..... | ................. | ................. | R..D.. | E..A.A....GE | A..A........ | 0.43 | 33 |
| .A... | ................. | ..DGE....DF....... | R..DD. | ........... | ........... | 0.43 | 33 |
| TA... | F.....SKA.S..L.E.R | .Q.S......F....... | R..... | E.GTEGDA..D. | A..A........ | 0.43 | 33 |
| ..... | ................. | ....E....DF......N | R..AGR | E.ATA.DTAV.D | A..A........ | 0.42 | 32 |
| ..... | F................. | .V........F....... | ...... | ........... | TAHSA..ITV.. | 0.42 | 32 |
| ..... | ................. | ................. | ...D.. | E.T..S..A..R | A..A........ | 0.42 | 32 |
| .A... | F.....GKG.NV.I.Q.G | .Q.DH....NF....... | ...DD. | ..TK...AE..D | A..A........ | 0.42 | 32 |
| N.... | F.....GGT.IV.K.G.K | ................. | ...... | ..ARGADAE..S | A..A........ | 0.40 | 31 |
| R.... | F................. | .KPDQ.....F....... | G..ND. | ..TGAS..EV.N | A..A........ | 0.40 | 31 |

TABLE 1-continued

AAV capsid proteins having increased specificity for and/or transduction of CD133* GSC (pool of Round 1 selection). Amino acid numbers correspond to the amino acid sequence of VP1 (SEQ ID NO: 1). The percentage value in the penultimate column indicates the "enrichment factor." Sequences below correspond to SEQ ID NOs: 8 and 29.295 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................. | .V........F....... | ...... | ............ | S.RSN..FDV.Q | 0.40 | 31 |
| .A..T | F.....SRT..M.K.A.S | .Q.DR.....F....... | ...D.. | ............ | A..A........ | 0.40 | 31 |
| N.... | F.....STG.LQ.L.D.R | .KYT.....NF......T | ...DD. | E.AK.N..AVDG | A..A........ | 0.39 | 30 |
| TA..T | F.....SGA..K.N.S.S | ..HG.....NF......T | ...D.. | ..ADRS...VGS | A..A........ | 0.38 | 29 |
| ..... | ................. | ................. | ...DDR | .DAGRN.IA.DG | A..A........ | 0.38 | 29 |
| .A... | ................. | ..DGE....DF....... | ...... | .DTGAD.IAV.N | A..A........ | 0.38 | 29 |
| .A..T | ......GT..NQ.K.G.R | .KPDQ.....F....... | ...DDR | ..A...AD.E.GG | A..A........ | 0.38 | 29 |
| .A... | F.....NTG.RN.T.T.L | ........NF....... | R...D. | ES.GRGD...DR | A..A........ | 0.38 | 29 |
| EA... | F.....NGG.HV.....L | ..HG.....NF......T | ...D.. | E..GASD.A..Q | A..A........ | 0.36 | 28 |
| G.... | F.....SN..PL.K.T.. | .Q.......DF....... | ...... | .N.AAG..E.GD | A..A........ | 0.36 | 28 |
| ..... | ................. | ................. | R..DD. | ............ | A..A........ | 0.36 | 28 |
| A.... | F.....DR..SL.H.D.R | ..D.E....DF....... | ...DD. | E.GR.DD.E.GE | A..A........ | 0.34 | 26 |
| ..... | ................. | ................. | R...DR | E.T..S..A..R | A..A........ | 0.34 | 26 |
| ..... | ................. | ................. | ...... | ENTDAS.A...N | A..A........ | 0.34 | 26 |
| ..... | ................. | ................. | ...DG. | ..ASE..AAYDS | A..A........ | 0.34 | 26 |
| ..... | F................. | .V........F....... | ...... | ............ | SRQNG..APT.. | 0.34 | 26 |
| TT..T | F.....S...PN.T.G.V | .Q.GQ....DF....... | ...D.. | ............ | A..A........ | 0.34 | 26 |
| ..... | ................. | ................. | R..DD. | ............ | A..A........ | 0.33 | 2 |
| E.... | ................. | .Q.S.....NF....... | R..DD. | ENAAES.IE.GR | A..A........ | 0.33 | 2 |
| G.... | F.....GHA.SK.T.E.K | .QPSQ....NF....... | R...D. | ............ | A..A........ | 0.33 | 2 |
| SA... | ................. | .........NF....... | ...TG. | E.AGGS..AVDG | A..A........ | 0.31 | 24 |
| ..... | ................. | ................. | R..AGR | ............ | A..A........ | 0.30 | 23 |
| ..... | ................. | ................. | G..KGR | ............ | A..A........ | 0.30 | 23 |
| ..... | ................. | .Q.DR.....F....... | ...D.. | E.TD.A....DG | A..A........ | 0.30 | 23 |
| .A... | F................. | ................. | ...D.. | E..AGS.AA.DN | A..A........ | 0.30 | 23 |
| ..... | F....ASA.S...T.T.G | .QPG.....DF....... | ...DDR | ............ | ............ | 0.30 | 23 |
| ..... | F....NR..N..I.T.G | ..DGE....DF....... | ...... | ............ | A..A........ | 0.30 | 23 |
| ..... | ................. | .Q.DR.....F....... | ...D.. | ............ | A..A........ | 0.30 | 23 |
| S.... | ................. | .........NF....... | R...D. | .SASGND..FD. | A..A........ | 0.29 | 23 |
| AA..T | ................. | .QPG.....NF......T | ...DDR | ENGTEN..A.D. | A..A........ | 0.29 | 22 |
| ..... | F................. | .V........F....... | ...... | ............ | KPKNG..NHE.Q | 0.29 | 22 |
| ..... | ................. | ................. | R...D. | .D.TGN.I...Q | A..A........ | 0.27 | 22 |
| ..... | ................. | .........DF....... | G..KGR | E.ASTSD.A.DH | A..A........ | 0.27 | 21 |
| NT..T | ................. | ................. | ...... | ............ | ............ | 0.26 | 21 |
| H.... | F.....ATG.NN.I.S.G | TQPTH....NF....... | R..DD. | ............ | A..A........ | 0.26 | 20 |

TABLE 1-continued

AAV capsid proteins having increased specificity for and/or transduction
of CD133* GSC (pool of Round 1 selection). Amino acid numbers correspond
to the amino acid sequence of VP1 (SEQ ID NO: 1). The percentage value in
the penultimate column indicates the "enrichment factor." Sequences below
correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| SA... | F.....SAT.PV.T.Q.G | ..AGR....DF......T | R.D... | ............ | A..A........ | 0.26 | 20 |
| SA... | F.....GTG.S..H.T.N | .Q.GQ....DF....... | ...G.. | E..G...D.AVGE | A..A........ | 0.26 | 20 |
| G.... | ......GKG.S..M.K.M | T.PGG....NF....... | ...DD. | .D.G.D..AF.Q | A..A........ | 0.26 | 20 |
| ..... | F................. | .V........F....... | ...... | ............ | GTKGS..IEN.. | 0.25 | 20 |
| R.... | ................. | .QHTH....NF......T | G..DD. | ............ | A..A........ | 0.25 | 19 |
| .A..T | F.....GT..NQ.K.G.R | .KPDQ.....F....... | ...DDR | ..A..AD.E.GG | A..A........ | 0.25 | 19 |
| ..... | ................. | .........NF....... | R..DD. | E.AG..D.A.GR | A..A........ | 0.25 | 19 |
| .A..T | F.....ASA.S..T.T.G | .QPG.....DF......T | E..KD. | ............ | ............ | 0.23 | 18 |
| RA... | ................. | .QPTG....NF....... | R..D.R | ES.S.SDAE..E | A..A........ | 0.23 | 18 |
| ..... | .............L... | ..DD.....DF....... | E..DD. | ..AGAD...FDG | A..A........ | 0.23 | 18 |
| G.... | F.....SRA.SK.N.A.H | .Q.......DF....... | ...AD. | ..AARS..AF.Q | A..A........ | 0.23 | 18 |
| ..... | ................. | ................. | ...D.. | E.TAEN...FDD | A..A........ | 0.22 | 17 |
| AA... | F.....DA..IA.L.K.R | T.PTG....DF...... | ...DDR | .NAG.AD.AV.Q | A..A........ | 0.22 | 17 |
| ..... | ................. | ................. | ...DD. | ...GEA..EF.G | A..A........ | 0.22 | 17 |
| A.... | F.....DA..IA.L.K.R | .KDSR....DF......T | R..DG. | ............ | A..A........ | 0.22 | 17 |
| ..... | F................. | .V........F....... | ...... | ............ | T.RNT..ASG.E | 0.22 | 17 |
| GA... | ................. | .Q.GQ....DF....... | ....GR | ESAKTADAAVDD | A..A........ | 0.21 | 16 |
| ..... | ................. | ................. | ...... | EDGGG..IE.D. | A..A........ | 0.21 | 16 |
| NT..T | ......DRG.S..T.A.S | ..DGE....DF....... | ...... | ............ | ............ | 0.21 | 16 |
| ..... | ................. | ................. | ....D. | E.GAT.DAE.DR | A..A........ | 0.20 | 15 |
| ..... | ................. | .........DF....... | G..DD. | ED.NGN.IA.D. | A..A........ | 0.18 | 14 |
| ..... | F.....DA..IA.L.K.R | .KDSR....DF......T | R..DD. | ............ | A..A........ | 0.17 | 13 |
| DA... | F......NG.LQ.H...N | T.P......DF....... | ...D.. | ............ | ............ | 0.17 | 13 |
| NT..T | F.....ASA.S..T.T.G | .QPG.....DF....... | ...DDR | ............ | A..A........ | 0.17 | 13 |
| H.... | F.....DK..NV.T.G.R | ...DG....DF....... | ...... | .NAAG.DI.VD. | A..A........ | 0.17 | 13 |
| ..... | ................. | ................. | ....G. | E.AAGSD.EVDR | A..A........ | 0.16 | 12 |
| ..... | ................. | ....E....DF....T | ...D.. | .NA.RA.T..G. | A..A........ | 0.16 | 12 |
| DT... | F......KT.NK...A.G | ..HG.....NF......T | ...D.. | ............ | A..A........ | 0.16 | 12 |
| G.... | F.....DHT.NI.M.T.S | .QPSQ....NF....... | R..DD. | ............ | A..A........ | 0.16 | 12 |
| G.... | ................. | .QDT.....DF....... | G..DG. | ............ | ............ | 0.16 | 12 |
| ..... | ........E........ | ................. | R..DD. | ............ | A..A........ | 0.16 | 12 |
| ..... | ................. | ....E....DF....... | R..AGR | E.ATA.DTAV.D | A..A........ | 0.14 | 11 |
| RT... | ................. | .QPN.....DF......T | R..TG. | ............ | A..A........ | 0.14 | 11 |
| ..... | F................. | .V........F....... | ...... | ............ | SHRTG..SNE.T | 0.14 | 11 |
| ..... | ................. | ................. | ....G. | ..AA.D.IA... | A..A........ | 0.14 | 11 |
| ..... | F................. | .V........F....... | ...... | ............ | A..A........ | 0.14 | 11 |

TABLE 1-continued

AAV capsid proteins having increased specificity for and/or transduction of CD133* GSC (pool of Round 1 selection). Amino acid numbers correspond to the amino acid sequence of VP1 (SEQ ID NO: 1). The percentage value in the penultimate column indicates the "enrichment factor." Sequences below correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | ...DDR | E.ADRSD...GN | A..A........ | 0.14 | 11 |
| NT..T | F.....AEG.LK.M.H.L | .KPDQ....DF....... | ...DDR | ............ | ............ | 0.13 | 11 |
| ..... | .................. | ...............T | E..AD. | .NADRN..E.GE | A..A........ | 0.13 | 10 |
| SA... | .................. | ..HG.....NF....... | ...TD. | .NATG....VGS | A..A........ | 0.13 | 10 |
| R.... | F.....GGG....K.G.R | .................. | ...... | ...AAS.A.VGQ | A..A........ | 0.13 | 10 |
| ..... | .................. | .................. | E...G. | ENATRGDIA..D | A..A........ | 0.12 | 10 |
| ..... | .................. | .................. | ...N.. | EDTSRGD.E... | A..A........ | 0.12 | 9 |
| ..... | .................. | .........NF....... | ...A.. | .S.RT...A.DD | A..A........ | 0.12 | 9 |
| A.... | F.....GKA.SE.N...K | .................. | ...D.. | E.GG.N.I.V.G | A..A........ | 0.12 | 9 |
| SA... | F.....ST...N...A.K | T.P......DF....... | ...D.. | ............ | ............ | 0.12 | 9 |
| ..... | .................. | TKDDR....DF....... | ...DDR | E.AG.S..E.DN | A..A........ | 0.10 | 9 |
| ..... | .................. | .................. | ...D.. | E.TR.M.....Q | A..A........ | 0.10 | 8 |
| ..... | .................. | .................. | E..ND. | ............ | ............ | 0.09 | 8 |
| ..... | .................. | .........DF....... | ...D.. | ..AAGSDTA.DE | A..A........ | 0.09 | 7 |
| E.... | F.....GT..NQ.K.G.R | T.PTR....DF....... | R...D. | ............ | A..A........ | 0.09 | 7 |
| ..... | F.....NGT.L..M.K.R | ..YN......F......T | ...... | ESGTAND...DR | A..A........ | 0.09 | 7 |
| ..... | .................. | .................. | ...... | .DAAGA.IE.GN | A..A........ | 0.09 | 7 |
| SA... | .................. | .KD.E.....F..P...T | R..ND. | ............ | A..A........ | 0.09 | 7 |
| ..... | .................. | .................. | ...DDR | E..NG.DI..D. | A..A........ | 0.09 | 7 |
| ..... | F................. | .V........F....... | ...... | ............ | DRRG...S.A.H | 0.09 | 7 |
| N...T | F......KT.NV.K.T.H | T.P......DF....... | ....GR | ............ | A..A........ | 0.08 | 6 |
| NT..T | F......KG.RV.T.A.G | ...TE.....F......T | ...NGR | .SAKAA.AA.DE | A..A........ | 0.08 | 6 |
| GA..T | .................. | .KYT......F....... | G..KD. | E.AGTSD.AFGE | A..A........ | 0.08 | 6 |
| E.... | .................. | ..HG.....NF....... | ...TD. | .NATG....VGS | A..A........ | 0.08 | 6 |
| RT... | F.....ATT.NV.T.K.S | T.A.Q....DF....... | G..A.R | E.ANG..AE.GE | A..A........ | 0.08 | 6 |
| TA... | .................. | .QANH....DF....... | ...DDR | ............ | A..A........ | 0.07 | 5 |
| ..... | F................. | .V........F....... | ...... | ............ | TRSAP..FNT.E | 0.07 | 5 |
| SA... | .................. | ..YN......F......T | ...D.R | ............ | A..A........ | 0.07 | 5 |
| ..... | F.....NGG.NN.K.T.R | .QPSE....DF....... | ....GR | ES.G.S.IAV.G | A..A........ | 0.07 | 5 |
| S.... | F.....SRA.SK.N.A.H | T.P......DF....... | ...D.. | ..TR.ND.A.DE | A..A........ | 0.07 | 5 |
| ..... | .................. | .PPNG.....F......T | ...DDR | E.ATRA..A.DE | A..A........ | 0.07 | 5 |
| ..... | .................. | ..DGG....DF....... | ...... | ED.R.N..AY.G | A..A........ | 0.05 | 4 |
| A.... | F.....DHT.SQ.L...K | .KYT.....NF......T | E..TD. | ............ | A..A........ | 0.05 | 4 |
| ..... | .................. | .................. | ...... | E.ATAS.AAFDE | A..A........ | 0.05 | 4 |
| ..... | F................. | .V........F....... | ...... | ............ | TAQA....GA.D | 0.05 | 4 |

TABLE 1-continued

AAV capsid proteins having increased specificity for and/or transduction
of CD133* GSC (pool of Round 1 selection). Amino acid numbers correspond
to the amino acid sequence of VP1 (SEQ ID NO: 1). The percentage value in
the penultimate column indicates the "enrichment factor." Sequences below
correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................. | .V........F....... | ...... | ............ | D.RAA..N...A | 0.05 | 4 |
| ..... | .................. | .........DF....... | ...TG. | ..ASGD....GR | A..A........ | 0.05 | 4 |
| E.... | F.....AEG.LK.M.H.L | ..DGE....DF....... | ...... | ............ | ............ | 0.05 | 4 |
| ..... | .................. | .................. | R..DD. | .NGST.....GG | A..A........ | 0.04 | 4 |
| E.... | F................. | .QPG.....DF....... | ...DDR | ............ | ............ | 0.04 | 3 |
| ..... | .................. | .................. | ...... | ESANGNDIE..D | A..A........ | 0.04 | 3 |
| .A... | F......R..PN.T.A.M | T..NE....DF....... | ...D.. | ..AGGN..E.GG | A..A........ | 0.04 | 3 |
| NA..T | F................. | .V........F....... | ...... | ............ | GTRT...Y.M.Q | 0.04 | 3 |
| NA..T | F.....ASA.S..T.T.G | .QPG.....DF....... | ...DDR | ............ | ............ | 0.04 | 3 |
| ..... | .................. | .................. | ...DDR | E.GATG...VD. | A..A.......D | 0.03 | 2 |
| TA..T | F................. | .QD......DF..P.... | G..K.. | ............ | A..A........ | 0.03 | 2 |
| ....T | F......KT.NV.K.T.H | ..YN......F......T | ...D.R | E..R.N.SEFGE | A..A........ | 0.03 | 2 |
| ..... | .................. | .........DF....... | ...DDR | ...GTSDI.VGQ | A..A........ | 0.03 | 2 |
| ..... | F................. | .V........F....... | ...... | ............ | GQKSR..VEA.T | 0.03 | 2 |
| N.... | F.....STG.LQ.L.D.R | .KYT.....NF......T | E..DD. | E.AK.N..AVDG | A..A........ | 0.03 | 2 |
| .A..T | F.....SA..SM.M.T.K | .PPNG.....F......T | ...DDR | ............ | A..A.......K | 0.03 | 2 |
| ..... | F................. | .V........F....... | ...... | ............ | GTRT...Y.M.Q | 0.03 | 2 |
| TA... | .................. | TQYDR....NF....... | ...DDR | ............ | A..A........ | 0.03 | 2 |
| ..... | ..............R.... | .................. | ...DD. | ............ | A..A........ | 0.03 | 2 |
| TA... | F.....SKA.S..L.E.R | .Q.S......F....... | G..... | E.GTEGDA..D. | A..A........ | 0.03 | 2 |
| ..... | .................. | ..DGE....DF....... | ...... | F...STG.IAY.D | A..A........ | 0.03 | 2 |
| RT... | .................. | TKDDR....DF....... | ...DDR | ............ | A..A........ | 0.03 | 2 |
| ..... | .................. | .................. | R..D.R | ..TNESD..... | A..A........ | 0.03 | 2 |
| ..... | .................. | .QDT.....DF....... | G..DG. | ............ | ............ | 0.03 | 2 |
| ..... | .................. | .................. | R..... | .NGDTG....GG | A..A........ | 0.03 | 2 |
| E.... | F.....NTT..V.N.K.R | ..DD.....DL....... | E..DD. | ............ | A..A........ | 0.03 | 2 |
| ..... | .................. | .........DF....... | ...D.. | E.TTRSDIE.DR | A..A........ | 0.03 | 2 |
| ..... | .................. | SQ.G.....DF....... | ...DDR | .D.R....AFDG | A..A........ | 0.01 | 1 |
| ..... | F.....NA..RM.M.K.. | .Q.S......F....... | E.N... | ............ | A..A........ | 0.01 | 1 |
| SA... | ......NGG.NV.L.N.R | .................. | ...DDR | .DAGRN.IA.DG | A..A........ | 0.01 | 1 |
| ..... | .................. | TKDDR....DF....... | ...DDR | ............ | A..A........ | 0.01 | 1 |
| ..... | F.....GG..SL.L...M | ..DGE....DF....... | ...... | ES.DRN.....Q | A..A........ | 0.01 | 1 |
| ..... | .................. | .................. | E..DD. | ............ | A..A........ | 0.01 | 1 |
| ..... | .................. | .................. | ...N.R | .NAT.D.TAY.S | A..A........ | 0.01 | 1 |
| NT... | F.....DQT.PL.T...R | ..AGQ....NF....... | ...D.. | .DGGGAD.A.D. | A..A........ | 0.01 | 1 |
| ..... | F................. | .V........F....... | ...... | ....E....... | TSRGG..TT..Q | 0.01 | 1 |

TABLE 1-continued

AAV capsid proteins having increased specificity for and/or transduction of CD133* GSC (pool of Round 1 selection). Amino acid numbers correspond to the amino acid sequence of VP1 (SEQ ID NO: 1). The percentage value in the penultimate column indicates the "enrichment factor." Sequences below correspond to SEQ ID NOs: 8 and 29.295 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .........NF....... | ...... | E.AG...IAVDR | A..A......I. | 0.01 | 1 |
| ..... | F................. | .V........F....... | ...... | ............ | KP.GP..V.M.. | 0.01 | 1 |
| ..... | ................. | TQ.TG.....F....... | ...DDR | ..AGT.D.EYGQ | A..A........ | 0.01 | 1 |
| NA... | ................. | .RDT.....DF....... | ...N.. | E...RS...F.Q | A..A........ | 0.01 | 1 |
| ..... | ................. | ................. | R..... | ............ | A..A........ | 0.01 | 1 |
| GT... | F.....AEG.LK.M.H.L | ..DGE....DF....... | .....S | ............ | ............ | 0.01 | 1 |
| ..... | ................. | ................. | .....S | EDGGG..IE.D. | A..A........ | 0.01 | 1 |
| ..... | ................. | ..YN......F......T | ...N.. | ............ | A..A........ | 0.01 | 1 |
| .A..T | ......GT..NQ.K.G.R | .KPDQS....F....... | ...DDR | ..A..AD.E.GG | A..A........ | 0.01 | 1 |
| ....A | ................. | ................. | ....D. | ............ | A..A........ | 0.01 | 1 |
| .A... | ................. | TP.DG....NF....... | ...DDR | ............ | A..A........ | 0.01 | 1 |
| ..... | ................. | ..AD.....DF......T | ...DG. | EN.ARG..E..R | A..A........ | 0.01 | 1 |
| NT..T | F......KG.RV.T.A.G | ...TE.....F......T | ...NGR | .SAKAA.AA.DE | ............ | 0.01 | 1 |
| ..... | ................. | ................. | ...DDR | .RRR...IAYGN | A..A........ | 0.01 | 1 |
| AA... | F.....G.G.HM.M.S.M | T.P......DF....... | ...D.. | H........... | A..A........ | 0.01 | 1 |
| D...T | F......KT.NK...A.G | .V........F....... | ...... | .S.ARGDI..DN | A..A........ | 0.01 | 1 |
| AA... | ................. | TQ..N....NF....... | ...... | ............ | A..A........ | 0.01 | 1 |
| ..... | F................. | .V........F....... | .....S | ............ | G.KG...SG..E | 0.01 | 1 |

TABLE 2

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | R..... | ............ | A..A........ | 18.79 | 1309 |
| GT... | F.....AEG.LK.M.H.L | ..DGE....DF....... | ...... | ............ | ............ | 3.45 | 240 |
| ..... | F................. | .QAS......F....... | R..ND. | ............ | A..A........ | 2.63 | 183 |
| ..... | ................. | ................. | ...... | ............ | A..A........ | 2.51 | 175 |
| ..... | F.....ASA.S..T.T.G | .QPG.....DF....... | ...DDR | ............ | ............ | 2.30 | 160 |
| ..... | ................. | .QD.E.....F..P.... | ...D.. | ............ | ............ | 2.10 | 146 |
| ..... | ................. | ................. | ...D.. | ............ | ............ | 2.08 | 145 |
| ..... | F.....AEG.LK.M.H.L | ..DGE....DF....... | ...... | ............ | ............ | 1.94 | 135 |
| ..... | ................. | ................. | ...D.. | .NATG....VGS | A..A........ | 1.62 | 113 |
| ..... | ................. | ................. | R..DD. | ............ | A..A........ | 1.29 | 90 |
| AA... | F.....DRG.S..T.A.S | ..DGE....DF....... | ...... | ............ | ............ | 1.26 | 88 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....SGT.S..T.T.. | TQ.S.....DF....... | R..DD. | E..TAA.AAFDE | A..A........ | 1.19 | 83 |
| ..... | ................. | .................. | ...DDR | ............ | A..A........ | 1.13 | 79 |
| ..... | F................. | .V........F....... | ...... | ............ | KTKNP...GE.H | 1.13 | 79 |
| ..... | ................. | .................. | R..AD. | ............ | A..A........ | 1.00 | 70 |
| ..... | F................. | ..DGE....DF...R. | ...D.. | ............ | ............ | 0.95 | 66 |
| GA... | F.....ASA.S..T.T.G | .QPG.....DF....... | ...DDR | ............ | A..A........ | 0.89 | 62 |
| E.... | F.....ASA.S..T.T.G | .QPG.....DF....... | ...DDR | ............ | A..A........ | 0.88 | 61 |
| ..... | ................. | T.HTE....NF..T.... | ...NDR | ............ | A..A........ | 0.88 | 61 |
| ..... | ................. | .................. | G..N.. | ............ | ............ | 0.86 | 60 |
| D.... | F.....GQG.IA.....K | .................. | ...... | ............ | A..A........ | 0.83 | 58 |
| ..... | ................. | .................. | ...D.. | .STGAD...... | A..A........ | 0.79 | 55 |
| SA... | F.....ASA.S..T.T.G | .Q.S......F....... | ....D. | ............ | ............ | 0.76 | 53 |
| A.... | ................. | .................. | ...N.. | ...G.N.A.... | A..A........ | 0.75 | 52 |
| AT... | ................. | .Q.G.....NF....... | ...DDR | ............ | A..A........ | 0.75 | 52 |
| .A... | ................. | .................. | ...D.. | ............ | ............ | 0.75 | 52 |
| TA... | F.....DGA.R..P.A.K | ..YN......F......T | R..DD. | ............ | A..A........ | 0.75 | 52 |
| ..... | ................. | .................. | ...... | .SAT.N.IA..H | A..A........ | 0.75 | 52 |
| ..... | ................. | .................. | ...... | GDTTGS.AA..E | A..A........ | 0.75 | 52 |
| ..... | ................. | .V........F....... | ...... | ............ | TARSA..VDG.A | 0.73 | 51 |
| ..... | ................. | .................. | G..DD. | EDAG.AD.E..R | ............ | 0.72 | 50 |
| E.... | F.....GAT.IN.M.K.L | T.ANE....DF....... | ...DDR | ............ | ............ | 0.70 | 49 |
| ..... | ................. | .................. | R..DD. | ............ | ............ | 0.70 | 49 |
| ..... | ................. | .V........F....... | ...... | ............ | GR.DT..FTE.D | 0.70 | 49 |
| ..... | F................. | .V........F....... | ...... | ............ | SRHNE..S.V.Q | 0.69 | 48 |
| ..... | ................. | .................. | ...DDR | .NAAAN..EF.H | A..A........ | 0.69 | 48 |
| GT... | ................. | .PDNR..T.DF......T | ....GR | ............ | A..A........ | 0.69 | 48 |
| TT..T | ................. | .........DF.P....T | ...AD. | ............ | A..A........ | 0.69 | 48 |
| ..... | ................. | .................. | E..N.. | E.ATAS.AAFDE | A..A........ | 0.67 | 47 |
| DT... | ....AST.IN.L.T.. | ..DGE....DF....... | ...... | ............ | ............ | 0.67 | 47 |
| ..... | ................. | .........F....... | R..AD. | .NAR.A.I..GE | A..A........ | 0.65 | 45 |
| ST... | ............T.N | .................. | ...... | ..TG.D..A.GG | A..A........ | 0.63 | 44 |
| GA..T | P.....SNG.P....T.R | ..A......DF....... | ...DG. | ............ | A..A........ | 0.63 | 44 |
| ..... | F.....GG..SL.L...M | ..DGE....DF....... | ...... | ES.DRN.....Q | A..A........ | 0.62 | 43 |
| ..... | ................. | .................. | R..DD. | ES.DRN..A.DN | A..A........ | 0.60 | 42 |
| ..... | ................. | .................. | ....GR | EDAGT..AA..H | A..A........ | 0.60 | 42 |
| ..... | ................. | .................. | ...... | ............ | A..A........ | 0.60 | 42 |
| ..... | F................. | .V........F....... | ...... | ............ | GPRTA...SG.H | 0.60 | 42 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................. | .V.......F....... | ...... | ............ | GTRDG..AE..A | 0.60 | 42 |
| NT... | ................. | ..YN......F......T | .N.D.R | ............ | A..A........ | 0.59 | 41 |
| ..... | ................. | ................. | ...... | EDANG...EV.N | A..A........ | 0.59 | 41 |
| ..... | ................. | .V.......F....... | ...... | ............ | NPRDK..FEG.. | 0.57 | 40 |
| ..... | ................. | ................. | R..D.. | ............ | A..A........ | 0.56 | 39 |
| ..... | F................. | .V.......F....... | ...... | ............ | DQRGT...RG.D | 0.56 | 39 |
| ..... | .........SP.H.E.V | ..HG.....NF......T | ...DDR | E.AGAND.AV.H | A..A........ | 0.56 | 39 |
| ..... | F................. | .V.......F....... | ...... | ............ | GARGG..FNM.Q | 0.56 | 39 |
| T...T | ................. | ..A......DF....... | ...DG. | EDAGT...AFD. | A..A........ | 0.56 | 39 |
| HA... | F.....GKT.SL...G.R | ..A......DF....... | ...DG. | ENANGN.IAFD. | A..A........ | 0.55 | 38 |
| ..... | F................. | .V.......F....... | ...... | ............ | ERSGA..IE..D | 0.55 | 38 |
| G.... | ................. | .V.......F....... | ...... | ............ | A..A........ | 0.52 | 36 |
| ..... | F................. | .V.......F....... | ...... | ............ | .EKGG...QN.. | 0.50 | 35 |
| ..... | ................. | ................. | ...... | E.AG.S...... | A..A........ | 0.50 | 35 |
| .A... | F.....ASA.S..T.T.G | .QPG.....DF....... | ...DDR | ............ | ............ | 0.49 | 34 |
| ..... | ................. | ................. | ....GR | ..ARRGD.A.DE | A..A........ | 0.49 | 34 |
| G.... | ................. | .........NF....... | R...D. | ............ | A..A........ | 0.49 | 34 |
| ..... | F................. | .V.......F....... | ...... | ............ | NQHNA..FQT.P | 0.49 | 34 |
| H.... | F................. | ................. | ...DDR | ............ | A..A........ | 0.47 | 33 |
| .A... | F.....DAA.IK.T.Q.N | ..DGE....DF....... | ...... | E........... | ............ | 0.47 | 33 |
| .A... | F.....DRG.S..T.A.S | ..DGE....DF....... | ...... | ............ | ............ | 0.46 | 32 |
| AA... | F.....SG..IK.K.D.R | ..P.E....NF......T | E..DG. | E.GAR..AA..Q | A..A........ | 0.45 | 31 |
| ..... | ................. | ................. | ...... | ............ | DHRNP..DQA.. | 0.43 | 30 |
| ..... | ................. | ................. | R...D. | ............ | A..A........ | 0.43 | 30 |
| TA... | ................. | .QANH....DF....... | ...DDR | ............ | A..A........ | 0.43 | 30 |
| ..... | F................. | .Q.GQ....DF....... | ....G. | EDAGRN...V.N | A..A........ | 0.42 | 29 |
| TA..T | F.....GDG....K.Q.R | .V.......F....... | ...DDR | .SAKAA.AA.DE | A..A........ | 0.42 | 29 |
| ..... | ................. | ................. | ...D.. | ...G.D..EVGQ | A..A........ | 0.42 | 29 |
| ..... | ................. | ................. | R..D.. | ..ASAAD.E..D | A..A........ | 0.40 | 28 |
| EA... | ................. | ................. | ..ND.. | ..ATT..T.F.Q | A..A........ | 0.40 | 28 |
| ..... | ................. | ..DNH....NF......T | E..ND. | ............ | A..A........ | 0.40 | 28 |
| ..... | ................. | ................. | ...DD | E.AGGN..E.DD | A..A........ | 0.36 | 25 |
| ..... | F................. | .V.......F....... | ...... | ............ | TARTA..SQV.H | 0.36 | 25 |
| ..... | ................. | ................. | G..KD. | ESAGAN....GG | A..A........ | 0.36 | 25 |
| ....T | ................. | ................. | ...... | ............ | ............ | 0.36 | 25 |
| ..... | ................. | ................. | R..ND. | ..AGEN..A..G | A..A........ | 0.34 | 24 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| RA... | ................. | .................... | ...AG. | ........... | A........... | 0.33 | 23 |
| ..... | ...........M..... | .................... | ...NDR | ..AKG...AV.. | A..A........ | 0.33 | 23 |
| R...T | ................. | .V........F....... | E..TD. | ........... | ........... | 0.33 | 23 |
| ..... | F................ | .V........F....... | ...... | ........... | GPKNP..DRT.D | 0.32 | 22 |
| ..... | F................ | .V........F....... | ...... | ........... | DSRGG..FSE.. | 0.32 | 22 |
| EA... | F.....DAA.IK.T.Q.N | ..DGE....DF....... | ...... | E.......... | ........... | 0.30 | 21 |
| ..... | ......GN..IK.L...G | .QAS......F....... | ...... | ........... | A..A........ | 0.29 | 20 |
| E.... | F.....DRG.S..T.A.S | ..DGE....DF....... | ...... | ........... | ........... | 0.29 | 20 |
| ..... | ...............T.N | .................... | ...... | ..TG.D..A.GG | A..A........ | 0.27 | 19 |
| E.... | ................. | .................... | R...D. | .DAKGD.A.F.D | A..A........ | 0.27 | 19 |
| GT... | F.....AEG.LK.M.H.L | ..DGE....DF....... | ...DDR | ........... | A..A........ | 0.27 | 19 |
| ..... | F......AG.NP.P.D.R | .QAS.....NF....... | ...... | ........... | A..A........ | 0.26 | 18 |
| ..... | ................. | ..P.G....NF....... | R...D. | R..NG....VDG | A..A........ | 0.26 | 18 |
| GT... | ................. | ..HG.....NF......T | E..DD. | ........... | ........... | 0.26 | 18 |
| ..... | ................. | .................... | R..A.. | ........... | A..A........ | 0.26 | 18 |
| TT..T | ................. | .................... | ...... | ........... | ........... | 0.26 | 18 |
| .A..T | P.....ASA.S..T.T.G | .QPG.....DF......T | F..KD. | ........... | ........... | 0.24 | 17 |
| ..... | F................ | .V.V......F....... | ...... | ........... | GARAT..SQ... | 0.23 | 16 |
| ..... | F.....NGG.NV.L.N.R | ..DGE....DF....... | ...... | ........... | A..A........ | 0.23 | 16 |
| ..... | ................. | ..AGR....DF....... | ...D.. | .NAG.DD...DQ | A..A........ | 0.23 | 16 |
| ..... | ................. | .................... | R...D. | E.AG..D.A.GR | A..A........ | 0.22 | 15 |
| ..... | ................. | .........DF....... | ...D.. | E.ASGG.A..GS | A..A........ | 0.22 | 15 |
| ..... | ................. | .................... | ...N.. | E..G.SDAA.GD | ...A........ | 0.20 | 14 |
| SA... | ................. | .QAS......F....... | ...... | E.TNAA.I.FDR | A..A........ | 0.20 | 14 |
| A.... | ................. | .................... | ...D.R | ESATGG.T..GG | A..A........ | 0.20 | 14 |
| AT... | F.....ATG.NV.T.G.R | ..HDG.....F....... | ...... | ........... | A..A........ | 0.20 | 14 |
| ..... | ................. | .................... | R..DD | ESGGAD.I...R | A..A........ | 0.19 | 13 |
| ..... | ................. | .................... | ...D.. | .SG.TN.T..D. | A..A........ | 0.19 | 13 |
| ..... | ................. | .................T | R..D.R | ........... | A..A........ | 0.19 | 13 |
| ..... | F................ | .V........F....... | ...... | ........... | TRRDG..I.S.E | 0.19 | 13 |
| ..... | ................. | .................... | R..D.R | E.AAAA.I..D. | A..A........ | 0.19 | 13 |
| ..... | ................. | .QANH....DF....... | ...DDR | ........... | ........... | 0.19 | 13 |
| ..... | ................. | .................... | ...D.. | E.AGAND.AY.N | A..A........ | 0.17 | 12 |
| ..... | ................. | .................... | ...TG. | .SAKAA.AA.DE | A..A........ | 0.17 | 12 |
| ..... | F................ | .V........F....... | ...... | ........... | AQRAG..VDA.Q | 0.17 | 12 |
| D...T | F................ | .Q.S......F....... | ...... | ........... | ........... | 0.17 | 12 |
| ..... | F................ | .V........F....... | ...... | ........... | TERGT..SD... | 0.17 | 12 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .................. | R..AGR | ........... | A..A........ | 0.16 | 11 |
| AA..T | ................. | .................. | R...D. | .D.TGN.I...Q | A..A........ | 0.16 | 11 |
| ..... | F................ | .V........F....... | ...... | ........... | GTRST..FRE.T | 0.16 | 11 |
| ..... | F................ | .V........F....... | ...... | .SADGSD...DR | A..A........ | 0.14 | 10 |
| ..... | ................. | .................. | ...D.. | .SAGRGDAAVDE | A..A........ | 0.14 | 10 |
| ..... | ................. | .................. | ...DD. | .NGST.....GG | A..A........ | 0.14 | 10 |
| ..... | F................ | .V........F....... | ...... | ........... | SQRAS..SDK.D | 0.14 | 10 |
| ..... | ................. | .................. | R..... | ........... | ........... | 0.14 | 10 |
| GT... | F......KG.NL...Q.S | .QPG.....NF....... | ...DDR | ........... | A..A........ | 0.13 | 9 |
| ..... | ................. | .................. | ...... | .NGGAADAE..H | A..A........ | 0.13 | 9 |
| HT... | F.....NTG.HP.T.G.M | T.P......DF....... | ...D.. | ........... | ........... | 0.13 | 9 |
| RT... | ................. | .................. | G..A.R | ........... | A..A........ | 0.13 | 9 |
| A.... | ................. | .QD.E....F..P..... | ...D.. | ........... | ........... | 0.13 | 9 |
| ..... | F................ | .V........F....... | ...... | ........... | GRQDS..NR..E | 0.13 | 9 |
| GT... | ................. | .KYT.....DF....... | G..KGR | .DAS.N...VDG | A..A........ | 0.13 | 9 |
| ..... | ................. | .................. | ...... | ESAN...I...H | A..A........ | 0.11 | 8 |
| ..... | ................. | .................. | ....D. | ........... | ...A........ | 0.11 | 8 |
| TA... | F................ | .V........F....... | ...... | ........... | AK.TE...G... | 0.11 | 8 |
| ..... | ................. | .................. | ...D.R | ESATGG.T..GG | A..A........ | 0.11 | 8 |
| ..... | ................. | .................. | R..TG. | ........... | A..A........ | 0.10 | 7 |
| ..... | F................ | .V........F....... | ...... | ........... | GKRD...AGE.K | 0.10 | 7 |
| ..... | ................. | .................. | ...N.. | E..TAA.AAFDE | A..A........ | 0.10 | 7 |
| ..... | F.....D...S..M.T.R | .................. | ...... | ........... | A..A...A.R | 0.10 | 7 |
| G.... | ...........K..... | .................. | ...D.R | ..TGAS.A..DH | A..A........ | 0.09 | 6 |
| GT... | ................. | .................. | ...DDR | ...GT..AA.GD | A..A........ | 0.09 | 6 |
| ..... | F................ | .V................ | ...... | E.AAGND.EFDQ | A..A........ | 0.09 | 6 |
| ..... | ................. | .................. | ...NDR | ..AKG...AV.. | A..A........ | 0.09 | 6 |
| E.... | F................ | .Q.S......F....... | R..DD. | ........... | ........... | 0.07 | 5 |
| ..... | F................ | .V........F....... | ...... | ........... | ........... | 0.07 | 5 |
| ..... | ................. | .................. | ...DG. | ........... | A..A........ | 0.07 | 5 |
| ....T | F................ | .V........F....... | ...... | ........... | A..A........ | 0.07 | 5 |
| HT... | F................ | .V........F....... | ...... | ........... | A..A........ | 0.07 | 5 |
| ..... | ................. | .................. | ...ADR | .....K..... | A..A........ | 0.06 | 4 |
| ..... | ................. | .KYT.....DF......T | E..ND. | E.AGRDD...DR | A..A........ | 0.06 | 4 |
| ..... | ................. | .................. | ...D.R | ..ARTADTE.DS | A..A........ | 0.06 | 4 |
| A.... | ................. | .................. | ...... | ........... | ........... | 0.06 | 4 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| AA... | ................. | .V........F....... | ...... | ............ | A..A........ | 0.06 | 4 |
| E.... | ................. | ................. | R..DD. | ............ | ............ | 0.04 | 3 |
| E.... | F.....AEG.LK.M.H.L | ..DGE....DF....... | ...... | ............ | ............ | 0.04 | 3 |
| ..... | F................. | .V........F....... | ...... | ............ | A..A........ | 0.04 | 3 |
| TA..T | ................. | ........DF....... | ....D. | ESGS.S.IA.DQ | A..A........ | 0.04 | 3 |
| ..... | F................. | .V........F....... | ...... | ............ | GARAT..SQ... | 0.04 | 3 |
| A.... | F.....AEG.LK.M.H.L | ..DGE....DF....... | ...... | ............ | ............ | 0.04 | 3 |
| ..... | ................. | ..HG......F....... | ...... | ............ | GTRGG...K..D | 0.04 | 3 |
| SA... | ................. | ................. | ...D. | ............ | ............ | 0.03 | 2 |
| ..... | F................. | .V........F....... | ...... | .NAAAN..EF.H | A..A........ | 0.03 | 2 |
| ..... | F................. | .V........F....... | ...... | ............ | THRDA...EG.E | 0.03 | 2 |
| ..... | ................. | ................. | ....G. | E.AAGSD.EVDR | A..A........ | 0.03 | 2 |
| .A... | F.....DAA.IK.T.Q.N | ..DGE....DF....... | ...D.. | ............ | ............ | 0.03 | 2 |
| ET..T | F.....AT...N.T...G | .QPNQ....NF..P...T | .....R | ............ | A..A........ | 0.03 | 2 |
| TA..T | F.....GDG....K.Q.R | .V........F....... | ...DDR | .SAKAA.AA.DE | A..A........ | 0.03 | 2 |
| ..... | ................. | ................. | R..... | ............ | A..A........ | 0.03 | 2 |
| D.... | ..........A...T.N | T.P......DF....... | ...D.. | ............ | ............ | 0.03 | 2 |
| ..... | ................. | ................. | ...D.. | E.TR.N.....Q | A..A........ | 0.03 | 2 |
| ..... | ................. | ..YN......F......T | ...D.R | ............ | A..A........ | 0.03 | 2 |
| R...T | ................. | ................. | ...DDR | .NAAAN..EF.H | A..A........ | 0.03 | 2 |
| ..... | ................. | ......S.......... | ...DDR | ............ | A..A........ | 0.03 | 2 |
| ..... | C................. | ................. | ...... | E.AG.S...... | A..A........ | 0.03 | 2 |
| ..... | F................. | .V........F....... | ...... | .......A.... | DQRGT...RG.D | 0.03 | 2 |
| ..... | ................. | ................. | E..NG. | ............ | ............ | 0.03 | 2 |
| TT..T | ................. | ................. | .....R | ............ | ............ | 0.03 | 2 |
| GT... | F.....AEG.LK.M.HRL | ..DGE....DF....... | ...... | ............ | ............ | 0.03 | 2 |
| ..... | ................. | ................. | E..AG. | ............ | ............ | 0.03 | 2 |
| ..... | ..N.............. | ................. | ...... | ............ | A..A........ | 0.03 | 2 |
| GT... | F.....A.A.RE.I.... | TKAT.....NF......T | R..AG. | ESAG....A.GE | A..A........ | 0.03 | 2 |
| ..... | ................. | .KYT.....DF....... | G..KGR | .DAS.N...VDG | A..A........ | 0.03 | 2 |
| GT..T | F......GA..K.M...E | ................. | ...... | ..AG.N..AF.R | A..A........ | 0.03 | 2 |
| ..... | ...............H. | ................. | ...D.. | .STGAD...... | A..A........ | 0.03 | 2 |
| GT... | ................. | ................. | ...D.. | .STGAD...... | A..A........ | 0.03 | 2 |
| TA... | ................. | .QD.E.....F..P.... | ...D.. | ............ | ....P....... | 0.03 | 2 |
| ..... | ................. | ................. | R..D.. | ESAAGD.IE.GD | A..A........ | 0.03 | 2 |
| ..... | ................. | ................. | ...D.R | ............ | A..A........ | 0.03 | 2 |
| NT... | ................. | ................. | ...... | EDANG...EV.N | A..A........ | 0.01 | 1 |

TABLE 2-continued

AAV capsid proteins having increased specificity for and/or transduction of CD133+ GSC (pool of Round 2 selection). Amino acid numbers correspond to the amino acid sequence of VP1 (SEQ ID NO: 1). Sequences below correspond to SEQ ID NOs: 8 and 296.523 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ......D........... | ...DDR | ........... | A..A........ | 0.01 | 1 |
| ..... | ................. | ......S........... | R..... | ........... | A..A........ | 0.01 | 1 |
| ..... | F.....AEG.LK.M.H.L | .QPG.....DF....... | ...DDR | ........... | ........... | 0.01 | 1 |
| ..... | F.....AEG.LK.M.H.L | ................. | ...DDR | ........... | A..A........ | 0.01 | 1 |
| ..... | ................. | ................. | R....E | ........... | A..A........ | 0.01 | 1 |
| ..... | F................ | .V........F....... | .....S | ........... | GARGG..FNM.Q | 0.01 | 1 |
| ..... | ................. | .PDNR..T.DF......T | ....GR | ........... | A..A........ | 0.01 | 1 |
| GT... | ................. | ................. | ....GR | EDAGT..AA..H | A..A........ | 0.01 | 1 |
| ..... | ................. | ................. | R...GR | EDTG.A....GN | A..A........ | 0.01 | 1 |
| ..... | F................ | .V........F....... | ....D. | ........... | GPKNP..DRT.D | 0.01 | 1 |
| E.... | ................. | T.HTE...NF......T | ...NDR | ........... | A..A........ | 0.01 | 1 |
| ..... | F................ | .QAS......F....... | R..ND. | ....E....... | A..A........ | 0.01 | 1 |
| TT... | F.....ASA.S..T.T.G | ................. | ...DDR | ........... | A..A........ | 0.01 | 1 |
| ..... | F................ | ..HG....NF......T | ...A.. | ........... | A..A........ | 0.01 | 1 |
| ..... | ................. | .V........F....... | ..G... | ........... | TARSA..VDG.A | 0.01 | 1 |
| RT... | ................. | ................. | G..A.R | ........... | A..T........ | 0.01 | 1 |
| ..... | F.....DRG.S..T.A.S | ..DGE....DF....... | ...... | ........... | ........... | 0.01 | 1 |
| ..... | F.....ASA.S..T.T.G | .Q.S.....F........ | ....D. | ........... | ........... | 0.01 | 1 |
| SA... | F.....ASA.S..T.T.G | .QPG.....DF....... | ...DDR | ........... | ........... | 0.01 | 1 |
| ..... | ................. | .Q.S............. | ...... | ........... | ........... | 0.01 | 1 |
| ..... | ................. | .V........F....... | ...... | ........... | A..A........ | 0.01 | 1 |
| ....P | ...........M..... | ................. | ...NDR | ..AKG...AV.. | A..A........ | 0.01 | 1 |
| DT... | F.....AEG.LK.M.H.L | ..DGE....DF....... | ...... | ........... | ........... | 0.01 | 1 |
| ..... | ................. | .QAS......F....... | ...... | E.TNAA.I.FDR | A..A........ | 0.01 | 1 |
| GT... | F.....AEG.LM.M.H.L | ..DGE....DF....... | ...... | ........... | ........... | 0.01 | 1 |
| ..... | ................. | ................. | G..N.E | ........... | ........... | 0.01 | 1 |
| ..... | ................. | ................. | ...DDR | E.A........ | A..A........ | 0.01 | 1 |
| G.... | ................. | .Q.GQ....DF....... | ....G. | EDAGRN...V.N | A..A........ | 0.01 | 1 |
| ..... | ................. | ................. | R..... | ....E....... | A..A........ | 0.01 | 1 |
| GA... | F.....ASA.S..T.T.G | ................. | ...DDR | ........... | A..A........ | 0.01 | 1 |
| ..... | ................. | ...........R... | ...D.. | ........... | ........... | 0.01 | 1 |
| ..... | F................ | .V....D...F....... | ...... | ........... | SQRAS..SDK.D | 0.01 | 1 |
| ..... | F................ | ................. | R..... | ........... | A..A........ | 0.01 | 1 |
| ..... | ................. | R................ | E..N.. | E.ATAS.AAFDE | A..A........ | 0.01 | 1 |

TABLE 3

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | .................. | .................. | ....GR | ..AG.N.AA.GQ | A..A........ | 1.91 | 216 |
| E.... | F.....ASA.S..T.T.G | .QPG.....DF....... | ...DDR | ............ | A..A........ | 1.15 | 130 |
| ..... | .................. | .................. | R...D. | E.AG..D.A.GR | A..A........ | 0.96 | 109 |
| GA... | F.....GNG.HV.H.G.R | TQ.TG....DF....... | ...DDR | ............ | A..A........ | 0.94 | 106 |
| .A... | F.....DRG.S..T.A.S | ..DGE....DF....... | ...... | ............ | ............ | 0.88 | 100 |
| GT... | F.....AEG.LK.M.H.L | ..DGE....DF....... | ...... | ............ | ............ | 0.85 | 96 |
| ..... | .................. | .................. | ...DDR | ............ | A..A........ | 0.80 | 90 |
| ..... | .................. | .................. | R..DD. | ............ | ............ | 0.80 | 90 |
| ..... | .................. | .................. | G..DG. | ............ | ............ | 0.80 | 90 |
| ..... | .................. | .................. | ...... | ............ | ............ | 0.79 | 89 |
| D...T | F......GT.NM.L.Q.G | .Q.S.....F........ | ....D. | ..AKG...AV.. | A..A........ | 0.74 | 84 |
| ..... | .................. | .................. | ...... | ............ | ............ | 0.72 | 82 |
| ..... | .................. | .................. | ...NDR | ............ | A..A........ | 0.65 | 74 |
| TA... | .................. | .QANH....DF....... | ...DDR | ............ | A..A........ | 0.55 | 62 |
| D.... | F.....AN...N.L.H.R | ..D......NF....... | R...D. | .SGAG.D..Y.E | A..A........ | 0.51 | 58 |
| ..... | .................. | .................. | R..DD. | ............ | A..A........ | 0.47 | 53 |
| ..... | F................. | .V........F....... | ...... | ............ | ............ | 0.43 | 49 |
| ..... | F................. | .V........F....... | ...... | ............ | S.KAG...EG.Q | 0.42 | 48 |
| GT... | .................. | ..HG.....NF......T | E..DD. | ............ | ............ | 0.42 | 47 |
| ..... | F.....ASA.S..T.T.G | .QPG.....DF....... | ...DDR | ............ | ............ | 0.38 | 43 |
| A.... | F.....DA..IA.L.K.R | .KDSR....DF......T | R..DD. | ............ | A..A........ | 0.34 | 38 |
| ..... | ..............P.A.K | .QPG.....NF....... | ...DDR | E.GGEN..EF.S | A..A........ | 0.31 | 35 |
| ..... | F.....AEG.LK.M.H.L | ..DGE....DF....... | ...... | ............ | ............ | 0.30 | 34 |
| TA... | F.....DRA.IN.M.K.L | .Q.S......F....... | ...DDR | ............ | A..A........ | 0.28 | 32 |
| ..... | .................. | .................. | E..KD. | ............ | ............ | 0.28 | 32 |
| ..... | .................. | .................. | ...D.R | ............ | ............ | 0.27 | 30 |
| ..... | .................. | .................. | E..AG. | ............ | ............ | 0.26 | 29 |
| ..... | .................. | .PPNG.....F......T | ...DDR | ............ | ............ | 0.26 | 29 |
| GA... | .................. | ..DGE....DF....... | E..TG. | E.ATRA..A.DE | A..A........ | 0.25 | 28 |
| ..... | .................. | .................. | R...D. | ............ | A..A........ | 0.25 | 28 |
| ..... | .................. | .................. | ...AG. | ............ | A..A........ | 0.25 | 28 |
| RA... | .................. | .................. | E..N.. | ............ | A..A........ | 0.25 | 28 |
| ..... | .................. | .................. | ...DDR | ............ | A..A........ | 0.24 | 27 |
| TT..T | .................. | ..........F......T | ...DG. | ............ | A..A........ | 0.23 | 26 |
| ..... | F.......T.SV...H.R | ..A......DF....... | E..ND. | E.TN.GD..Y.S | A..A........ | 0.23 | 26 |
| ..... | .................. | .................. | E..NG. | ............ | ............ | 0.22 | 25 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | E..ND. | .......... | ............ | 0.21 | 24 |
| ..... | .................. | .................. | ...DDR | .......... | A..A........ | 0.21 | 24 |
| ..... | .................. | .................. | E..AD. | .......... | ............ | 0.20 | 23 |
| ..... | .................. | .................. | E..AD. | .......... | ............ | 0.20 | 23 |
| ..... | .................. | .................. | ...D.. | .......... | A..A........ | 0.19 | 22 |
| ..... | .................. | .................. | R...D. | .......... | A..A........ | 0.19 | 22 |
| ..... | .................. | .................. | ...D.. | ESATGD..E.GQ | A..A........ | 0.19 | 21 |
| ..... | .................. | .................T | ...D.R | .......... | A..A........ | 0.19 | 21 |
| G.... | F.....GS..NK.M.A.R | ..YN......F......T | ...... | .......... | A..A........ | 0.19 | 21 |
| GA... | F.....AKG.NM.L...K | ..DGE....DF....... | ...... | .......... | A..A........ | 0.18 | 20 |
| ..... | F................. | .V........F....... | E..AD. | .......... | TQRDA...SSG.T | 0.18 | 20 |
| GA... | .................. | ...GG....NF....... | ...AG. | .......... | A..A........ | 0.18 | 20 |
| ..... | .................. | .................. | R...D. | .......... | A..A........ | 0.18 | 20 |
| ..... | .................. | ..P.G....NF....... | ...ADR | ...NG....VDG | A..A........ | 0.17 | 19 |
| ..... | .................. | .................. | ...... | .......... | A..A........ | 0.17 | 19 |
| EA... | F.....DAA.IK.T.Q.N | ..DGE....DF....... | R..AGR | E.......... | A..A........ | 0.17 | 19 |
| ..... | .................. | ..PNG....DF....... | ...D.. | .......... | A..A........ | 0.17 | 19 |
| ..... | .................. | .................. | ...D.. | .......... | A..A........ | 0.16 | 18 |
| ..... | .................. | .....QD.E.F..P.... | ...DDR | E.GGRGD.E..E | A..A........ | 0.16 | 18 |
| A.... | F.....NGG.NV.K.K.K | TKDDR....DF....... | ...... | E.AG...TAVGN | A..A........ | 0.16 | 18 |
| ..... | .................. | .................. | ...N.. | .......... | A..A........ | 0.16 | 18 |
| ..... | .................. | .................. | ...DDR | .......... | A..A........ | 0.16 | 18 |
| E.... | F.....SGA..N...G.R | .QPG.....NF....... | ...... | .......... | A..A........ | 0.16 | 18 |
| ..... | F................. | .V.......DF....... | ...... | .......... | A..A........ | 0.16 | 18 |
| H.... | .................. | ..DGE....DF....... | R...D. | .......... | ............ | 0.15 | 17 |
| ..... | F................. | .V.......F....... | ...... | .......... | ARQSG..AGS.. | 0.15 | 17 |
| AT... | .................. | .................. | G..KGR | .......... | A..A........ | 0.15 | 17 |
| RA... | F.....DTG.SK.T.T.R | .Q.S......F....... | ...D.. | .NGR.G..A..E | A..A........ | 0.15 | 17 |
| ..... | F................. | .................F. | ...... | .......... | ............ | 0.15 | 17 |
| ..... | ......DRG.S..T.A.S | ..DGE....DF....... | ...... | .......... | ............ | 0.15 | 17 |
| ..... | .................. | .................. | R...D. | .......... | A..A........ | 0.15 | 17 |
| ..... | .................. | .................. | ...DDR | ..AA.D.IA... | A..A........ | 0.14 | 16 |
| NA... | .................. | ..HDR....NF....... | ....D. | E.AGRN.TA..S | A..A........ | 0.14 | 16 |
| AA... | F.....SG..IK.K.D.R | ..P.E....NF......T | E..DG. | E.GAR..AA..Q | A..A........ | 0.14 | 16 |
| NA... | F.....N.T.LN.P...G | TKDDR....DF....... | ...DDR | E..SG...A.DG | A..A........ | 0.14 | 16 |
| ..... | .................. | .................. | ...D.. | .NAG.AD.AV.Q | A..A........ | 0.14 | 16 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | ..................... | ..ND.. | ENGD....E.DR | A..A........ | 0.13 | 15 |
| ..... | .................. | ..................... | ..N... | ...G.N.A.... | A..A........ | 0.13 | 15 |
| ..... | .................. | ..................... | R..ND. | E.ARGADI..GD | A..A........ | 0.13 | 15 |
| ..... | .................. | ..................... | R..N.. | ............ | A..A........ | 0.13 | 15 |
| ..... | F................. | .V........F........ | ...... | ............ | GHRAT..ND... | 0.13 | 15 |
| ..... | F......TG.KA.I.G.K | .........NF....... | E..N.. | ............ | A..A........ | 0.13 | 15 |
| ..... | .................. | .QPG.....DF....... | ...DDR | ............ | ............ | 0.13 | 15 |
| ..... | .................. | ..................... | E..DGR | .SAKAA.AA.DE | ............ | 0.12 | 14 |
| EA... | .................. | T..NE...DF......T | R..DD. | ............ | ............ | 0.12 | 14 |
| ..... | F.....SAT.PV.T.Q.G | ...TE.....F......T | ...D.. | ............ | A..A........ | 0.12 | 14 |
| A.... | F.....AAG.S..P...R | T.P......DF....... | R..DD. | EDGTRAD.AFGD | A..A........ | 0.12 | 14 |
| GT... | .................. | ..HG.....NF......T | E..DD. | EDGGGS..EYGS | ............ | 0.12 | 14 |
| ..... | F................. | .V........F......T | ...DDR | ............ | A..A........ | 0.12 | 14 |
| ..... | .................. | .Q.GQ....DF....... | R..ND. | ..AK.ADT..GN | A..A........ | 0.12 | 14 |
| ..... | .................. | ..................... | ...A.. | ............ | A..A........ | 0.12 | 14 |
| ..... | F.....NQA.SV...A.R | TQ.TQ.....F....... | ...DDR | ..A.A..AAFGE | A..A........ | 0.12 | 14 |
| GA... | F.....ASA.S..T.T.G | .QPG.....DF....... | ...DDR | ............ | ............ | 0.12 | 14 |
| RA... | F.....DGA.R..P.A.K | .........NF....... | R...D. | ............ | A..A........ | 0.11 | 13 |
| ..... | .................. | .I........F....... | ...N.. | ...G.S..AFGD | A..A........ | 0.11 | 13 |
| H.... | F.....NGA.H..N.E.L | .QPN......F......T | ...N.. | ............ | A..A........ | 0.11 | 13 |
| AA... | F.....GKA.HA...T.M | TKAT.....NF......T | ...D.. | ............ | A..A........ | 0.11 | 13 |
| ..... | .................. | ..................... | R..N.. | ..TG.A.I..D. | A..A........ | 0.11 | 13 |
| TA... | F.....SGG.SH...A.R | .Q.......DF....... | ...... | ES.GAN..EVDG | A..A........ | 0.11 | 13 |
| E.... | F.....ASA.S..T.T.G | .QPG.....DF....... | ...DDR | ............ | A..A........ | 0.11 | 13 |
| GT... | .................. | ..................... | R..DD. | ............ | ............ | 0.11 | 13 |
| ..... | .................. | ..................... | ...DDR | ..AG.DDIA.DN | A..A........ | 0.11 | 13 |
| A.... | F.....GRG.H..P.E.R | .QPN......F......T | ...N.. | E.AGAA..E.DR | A..A........ | 0.11 | 13 |
| RA... | .................. | .KPSE....DF......T | R...DR | .SAGRGDAAVDE | A..A........ | 0.11 | 13 |
| ..... | .................. | ..................... | E..NG. | ............ | A..A........ | 0.11 | 13 |
| HT..T | F.....NGG.NV.N.K.G | .........NF....... | R...D. | ............ | A..A........ | 0.11 | 13 |
| ..... | F................. | .V........F........ | ...... | ............ | A.RDP..FEV.. | 0.11 | 13 |
| ..... | .................. | ..................... | ...... | .DAGGND.A.D. | A..A........ | 0.11 | 13 |
| ..... | .................. | ..................... | ...... | ..AKG.D.AYDG | A..A........ | 0.11 | 13 |
| T.... | F.....ATA..V.H...R | .QAS.....F........ | ...... | .SGDE.D.E.DR | A..A........ | 0.11 | 13 |
| G.... | .................. | ..DGE...DF........ | ...... | .SGARD.A..DG | A..A........ | 0.11 | 12 |
| ..... | .................. | ..................... | ....D. | ............ | ............ | 0.11 | 12 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | ..DGE....DF....... | R...D. | ........... | ........... | 0.11 | 12 |
| TA... | F.........LA...H.G | .V........F....... | ...... | ........... | ........... | 0.11 | 12 |
| E.... | F.....AEG.LK.M.H.L | ..DGE....DF....... | ...... | ........... | ........... | 0.11 | 12 |
| SA... | ................ | .QAS......F....... | ...... | E.TNAA.I.FDR | A..A........ | 0.11 | 12 |
| H.... | F.....GN..NA.T...M | .Q.S......F....... | E..N.. | ..A.TS.AA.D. | A..A........ | 0.11 | 12 |
| AA... | F......S..SE.T...R | .........NF....... | R...D. | E.GT.ND.A.DG | A..A........ | 0.11 | 12 |
| NA... | ................ | .Q.DR.....F....... | ....D. | ENAS.G.A.VDS | A..A........ | 0.11 | 12 |
| ..... | ................ | ................ | R..ADR | ........... | A..A........ | 0.11 | 12 |
| ..... | ................ | ................ | ...DDR | E.GSR..AAVGD | A..A........ | 0.11 | 12 |
| ..... | ................ | ................ | E..KG. | ........... | ........... | 0.11 | 12 |
| ..... | ................ | ................ | ....D. | ........... | ........... | 0.11 | 12 |
| ....T | F.....SA..RA.....R | TKDDR....DF....... | ...DDR | ........... | A..A........ | 0.10 | 11 |
| ..... | ................ | ................T | ...... | .SA....AA.GH | A..A........ | 0.10 | 11 |
| ..... | F.....DGA.R..P.A.K | .QPTG....NF....... | E..AGR | ESA....GA.GE | A..A........ | 0.10 | 11 |
| ..... | F.....DRG.S..T.A.S | ..DGE....DF....... | ...... | ........... | ........... | 0.10 | 11 |
| TT..T | ................ | ..DGE....DF....... | R...D. | ........... | ........... | 0.10 | 11 |
| ..... | F......GT.NM.L.Q.G | .Q.S......F....... | ....D. | ........... | ........... | 0.10 | 11 |
| ..... | ................ | TKHGG....NF......T | R...D. | E.TDGNDA...N | A..A........ | 0.10 | 11 |
| ..... | ................ | ................ | ...DGR | EDAG...I..GQ | A..A........ | 0.10 | 11 |
| S.... | ..........L..L.Q.G | .QPSQ....NF....... | E..NGR | ........... | A..A........ | 0.10 | 11 |
| ..... | ................ | ................ | R..ND. | ........... | A..A........ | 0.10 | 11 |
| G.... | F.....ASG.SI.T...R | TKDDR....DF....... | ...DDR | ..GGGADAA.GE | A..A........ | 0.10 | 11 |
| E.... | ................ | ................ | R..TGR | ESGGANDI...R | A..A........ | 0.10 | 11 |
| ..... | ................ | ................ | ...DDR | ...G..DAE.DS | A..A........ | 0.10 | 11 |
| RT... | F.....SA..RA.....R | .........NF....... | R...D. | E.TGGNDAE.DD | A..A........ | 0.10 | 11 |
| ..... | ................ | ................ | G..KD. | ........... | A..A........ | 0.10 | 11 |
| ..... | ................ | ..HGH....NF......T | ...D.. | ........... | A..A........ | 0.09 | 10 |
| ..... | ................ | ................ | ...DD. | ........... | A..A........ | 0.09 | 10 |
| SA..T | ................ | .QPTR.....F....... | G...GR | ..ASE...E.D. | A..A........ | 0.09 | 10 |
| ..... | ................ | ................ | R..TG. | ........... | A..A........ | 0.09 | 10 |
| AT..T | F.....GHA.SK.T.E.K | ..DGE....NF......T | ...... | ENASG.....GN | A..A........ | 0.09 | 10 |
| RA... | F.....AAT.N..P.P.R | .PPNG.....F......T | ...DDR | ..A.G...AYD. | A..A........ | 0.09 | 10 |
| AA... | F.....GRG.SP.K...G | .QPG.....NF....... | ...DDR | ........... | A..A........ | 0.09 | 10 |
| ..... | ................ | ................ | R...D. | ...AAS.A.VGQ | A..A........ | 0.09 | 10 |
| ..... | ................ | ................ | G..DDR | ........... | A..A........ | 0.09 | 10 |
| A.... | F............... | TQ.TG....DF....... | ...DDR | ..AGT.D.EYGQ | A..A........ | 0.09 | 10 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ......STA..Q.H.Q.L | T.P......DF....... | R...D. | ............ | A..A........ | 0.09 | 10 |
| ..... | F................. | .........DF....G.T | ....GR | ENAGGD..E..R | A..A........ | 0.09 | 10 |
| ..... | F.....DRG.S..T.A.S | .V........F....... | ...... | ............ | A..A........ | 0.09 | 10 |
| ....T | F.....AQG.LH.L.G.R | .KPDQ.....F....... | ...... | EN.SAGD..... | A..A........ | 0.09 | 10 |
| GT... | F.....AEG.LK.M.H.L | ..HG.....NF......T | E..DD. | ............ | ............ | 0.09 | 10 |
| ..... | F................. | .V........F....... | ...... | ............ | NPRAP...TN.E | 0.09 | 10 |
| ..... | F................. | .V........F....... | ...... | ............ | GARAT..DTE.H | 0.09 | 10 |
| TT..T | F................. | .V........F......T | ...DDR | ............ | A..A........ | 0.09 | 10 |
| ..... | F................. | .V........F....... | ...... | ............ | GRHGG..SEG.E | 0.09 | 10 |
| ..... | .................. | .................. | ...... | ENTTGN....DR | A..A........ | 0.09 | 10 |
| ..... | F................. | .V........F....... | ...... | ............ | GT.TR..FQM.E | 0.09 | 10 |
| ..... | .................. | .................. | ....GR | ..AGA..AA.GS | A..A........ | 0.09 | 10 |
| G.... | F.....NGG.HV.....L | .QP.G.....F....... | G..KD. | .NATGND.E..H | A..A........ | 0.09 | 10 |
| ..... | F................. | .V........F....... | ...... | ............ | G.RTG..VR..H | 0.09 | 10 |
| GT... | F.....NAT.RD.M.T.K | ..YN......F......T | ...D.R | ............ | A..A........ | 0.08 | 9 |
| NA... | F.....SA..RA.....R | ..DGE....DF....... | ...... | .NGG.ND....Q | A..A........ | 0.08 | 9 |
| GA... | F.....AA..IQ.T.K.R | .Q.DH....NF....... | ...DD. | E.GAGAD...GQ | A..A........ | 0.08 | 9 |
| ..... | .................. | .................. | G..ANR | ...........N | A..A........ | 0.08 | 9 |
| ET..T | F.....NT..SH.M.D.. | .........NF....... | R...D. | ............ | A..A........ | 0.08 | 9 |
| TA... | .................. | ..HG.....NF......T | ...DDR | ............ | A..A........ | 0.08 | 9 |
| ..... | .................. | .........F......T | ...DGR | ..ADAGD.AV.Q | A..A........ | 0.08 | 9 |
| ..... | .................. | ....G....DF....... | E..AD. | ...SGSD..FDN | A..A........ | 0.08 | 9 |
| R.... | F.....DT..LK.T.H.G | .................. | R..DG. | ............ | A..A........ | 0.08 | 9 |
| D...T | F.....AET..A.T...K | .V........F....... | R...D. | ENTGAGDA.VDR | ............ | 0.08 | 9 |
| GT... | .................. | .................. | E..KD. | ............ | ............ | 0.08 | 9 |
| ..... | F................. | .V........F....... | ...... | ............ | TPRSP..FDS.T | 0.08 | 9 |
| ..... | .................. | .................. | ...DDR | ...GT..AA.GD | A..A........ | 0.08 | 9 |
| ..... | .................. | .................. | R..N.. | .DTSANDT..DG | A..A........ | 0.08 | 9 |
| ..... | .................. | .................. | ...DDR | .NGSAS..A.DN | A..A........ | 0.08 | 9 |
| ..... | .................. | .................. | E..KD. | ............ | A..A........ | 0.08 | 9 |
| AA... | F.....SN..PL.K.T.. | ..HG.....NF......T | ...A.. | ............ | A..A........ | 0.08 | 9 |
| ..... | F................. | .V........F....... | ...... | ............ | NARTA...KE.Q | 0.08 | 9 |
| E...T | F.....DTG.SK.T.T.R | .QPTG.....F....... | ...NDR | ............ | A..A........ | 0.08 | 9 |
| ..... | F.....AGG.SI.T.G.M | ..DGE....DF....... | ...... | .DTSANDT..DG | A..A........ | 0.08 | 9 |
| ..... | F................. | .V........F....... | ...... | ............ | SHRDG..SDN.E | 0.08 | 9 |
| RA... | F.....SRA.SK.N.A.H | .QDT.....DF....... | ...DDR | ...G.S..AFGD | A..A........ | 0.08 | 9 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | .V........F....... | ...... | ........... | A..A........ | 0.08 | 9 |
| ..... | ................. | .PPNG.....F......T | ...DDR | ..AGA..AA.GS | A..A........ | 0.08 | 9 |
| GT... | F.....DHT.R..M.G.R | .PPNG.....F......T | ....D. | ........... | A..A........ | 0.08 | 9 |
| H.... | F.....NKG.S..H.N.G | .QPNE.....F..P...T | R...D. | ........... | A..A........ | 0.08 | 9 |
| ..... | F................ | ................. | ...... | ........... | A..A........ | 0.08 | 9 |
| GT... | ................. | ................. | ...N. | ...G.N.A.... | A..A........ | 0.08 | 9 |
| E.... | F.....AAG.RV.L.K.R | TKDDR....DF....... | ...DDR | ..AGT.D.EYGQ | A..A........ | 0.08 | 9 |
| ..... | F................ | .V........F....... | ...... | ........... | TPRGP..VTG.H | 0.08 | 9 |
| ..... | ................. | ................. | G...D. | ........... | A..A........ | 0.08 | 9 |
| SA... | F......N..NH.L.P.S | ................. | ....GR | ........... | A..A........ | 0.08 | 9 |
| ..... | F................ | ........DF....... | ...DDR | ........... | A..A........ | 0.08 | 9 |
| ..... | ................. | ................. | ...ND. | ........... | A..A........ | 0.08 | 9 |
| ..... | F.......T.SV...H.R | .Q.G......F......T | ...D.. | ........... | A..A........ | 0.08 | 9 |
| SA..T | ................. | .K.TG....DF....... | R...DR | ..ATRS.I..GN | A..A........ | 0.08 | 9 |
| ..... | ................. | T.P......DF....... | ...D.. | .NTSTSD.E.DG | A..A........ | 0.08 | 9 |
| E.... | F.....ST..SV.K.H.M | ................. | ...... | ED.GR..I..DN | A..A........ | 0.08 | 9 |
| R.... | F.....SG..IK.K.D.R | T.PTG....DF....... | ...DDR | ES.DGN..A.DG | A..A........ | 0.08 | 9 |
| G.... | F.....DTG.SK.T.T.R | .Q.GQ....DF....... | ....G. | .SG..ND...DG | A..A........ | 0.08 | 9 |
| ..... | F................ | .V........F....... | ...... | ........... | TQRSG..IT..E | 0.08 | 9 |
| ..... | ................. | ........NF....... | ...D.R | ENGKAGD...GN | A..A........ | 0.08 | 9 |
| SA... | ................. | ..DGE....DF....... | ...... | ENGD.S.TA.DR | A..A........ | 0.08 | 9 |
| D...T | ................. | ................. | ...DG. | EDAGT..AA..H | A..A........ | 0.08 | 9 |
| NT..T | F.....SG..IK.K.D.R | .PPNG.....F......T | ...DDR | ........... | A,.A........ | 0.08 | 9 |
| ..... | ................. | ................. | R..DD. | .NTGGG.....H | A..A........ | 0.08 | 9 |
| ..... | F................ | .V........F....... | ...... | ........... | GQRNP..SDV.H | 0.07 | R |
| ..... | F................ | .V........F....... | ...... | ........... | GTRDG..AE..A | 0.07 | 8 |
| TT..T | ................. | ...GG....NF....... | E..AD. | ........... | A..A........ | 0.07 | 8 |
| ..... | ................. | ................. | ...DG. | ........... | A..A........ | 0.07 | 8 |
| RA... | ................. | T.PTG....DF....... | ...DDR | .DAS.N...VGG | A..A........ | 0.07 | 8 |
| AT..T | F.....GS..NM.N.E.R | ..DGE....DF....... | ...... | ........... | A..A........ | 0.07 | 8 |
| ..... | ................. | .Q.......DF....... | ...AD. | .D.RGN.IAYDE | A..A........ | 0.07 | 8 |
| ..... | F................ | .V........F....... | ...... | ........... | TRSGG..FSR.D | 0.07 | 8 |
| ..... | ................. | ........DF......T | R..DG. | .NAG.S.IAFGN | A..A........ | 0.07 | 8 |
| ..... | ................. | ..........F....... | R..AD. | ........... | A..A........ | 0.07 | 8 |
| ..... | ................. | TKDT.....NF......T | G..A.R | ........... | A..A........ | 0.07 | 8 |
| ..... | F................ | .V........F....... | ...... | ........... | AR.NP..YRN.D | 0.07 | 8 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | .KYT.....NF......T | ...AD. | .......... | A..A........ | 0.07 | R |
| G.... | F.....SN..PL.K.T.. | .........NF....... | R...D. | .......... | A..A........ | 0.07 | 8 |
| RA... | F.....STA..Q.H.Q.L | .Q.S......F....... | ...TG. | .......... | A..A........ | 0.07 | 8 |
| DT... | F.....GRT..L.H.E.S | .QAS.....NF......T | R..DD. | .SAS.N.IA..E | A..A........ | 0.07 | 8 |
| ..... | ................ | ................ | R..TD. | .SAS.N.IA..E | A..A........ | 0.07 | 8 |
| ..... | ................ | ................ | ...DD. | ...R.G.....E | A..A........ | 0.07 | 8 |
| G.... | F.....SRG.HH.L.D.R | .V........F....... | ...... | .SAT.N.IA..H | A..A........ | 0.07 | 8 |
| AA..T | F.....ST..SV.K.H.M | ..YN......F......T | ...D.R | .......... | A..A........ | 0.07 | 8 |
| ..... | ................ | ................ | ...D.R | ESATGG.T..GG | A..A........ | 0.07 | 8 |
| ..... | ................ | .........NF.....P. | ...... | .......... | A..A........ | 0.07 | 8 |
| ..... | ................ | ..HG.....NF......T | E..DD. | ..AG.G..E.GE | A..A........ | 0.07 | 8 |
| ..... | F............... | .V........F....... | ...... | .......... | DPKNK...GT.H | 0.07 | 8 |
| .A... | F.....ASA.S..T.T.G | .QPG.....DF....... | ....D. | .......... | A..A........ | 0.07 | 8 |
| D...T | ................ | | G..DG. | .......... | ............ | 0.07 | 8 |
| ..... | F............... | .V........F....... | ...... | .......... | SRSDN..S.E.H | 0.07 | 8 |
| ..... | F............... | .V........F....... | ...... | .......... | TQRGA..IDT.D | 0.07 | 8 |
| ..... | ................ | .QPN......F......T | ...... | .......... | ............ | 0.07 | R |
| ..... | ................ | ................ | ...DDR | E.AG..D.A.GR | A..A........ | 0.07 | 8 |
| D...T | ................ | .QPN......F......T | ...N.. | .......... | A..A........ | 0.07 | 8 |
| TT... | F.....SN..PL.K.T.. | ................ | ...... | .......... | A..A........ | 0.07 | 8 |
| G.... | F.....NKT.HL.T.A.R | ................ | ...... | ..AA.N..AV.H | A..A........ | 0.07 | 8 |
| GA... | F.....NKG.S..H.K.G | ................ | ...... | .......... | A..A........ | 0.07 | 8 |
| ..... | ................ | ................ | ...A.. | EDTGAD....DS | A..A........ | 0.07 | 8 |
| A.... | ................ | ................ | ...DDR | ESGN.N.A..GS | A..A........ | 0.07 | 8 |
| .A... | F.....NQT.RN.T.D.R | TK.T.....DF......T | ...NDR | .......... | A..A........ | 0.07 | 8 |
| ....T | F.....DRG.S..T.A.S | ..DGE....DF....... | ...... | .......... | ............ | 0.07 | 8 |
| TT..T | F.....AAA.NI.L.K.N | ..A......DF....... | ...DG. | .DAG.A.I..DG | A..A........ | 0.07 | 8 |
| SA... | F.....GN..HI.P.Q.. | .........NF....... | ....D. | .SARG.D.AVDD | A..A........ | 0.07 | 8 |
| A.... | ................ | T.PTG....DF....... | ...DDR | E..G.SDAA.GD | A..A........ | 0.07 | 8 |
| DT... | F.....A.G.RM.L.T.E | TQ.TG....DF....... | ...DDR | .......... | A..A........ | 0.07 | 8 |
| EA... | F.....AQ...A.L.... | .QPN......F......T | ...NDR | ..AGRSDI..GN | A..A........ | 0.07 | 8 |
| ..... | F............... | .V........F....... | ...... | .......... | TTRGD....K.Q | 0.07 | 8 |
| ..... | F............... | .V........F....... | ...... | .......... | NTRSG..AK..H | 0.07 | 8 |
| ..... | F............... | .V........F....... | ...... | .......... | SARTT..SSM.A | 0.07 | 8 |
| G...T | F.....SNA.PK.N.A.S | ..DGE....DF....... | ...... | EDGGGG..A..Q | A..A........ | 0.07 | 8 |
| GT... | F............... | ..HG.....NF......T | E..DD. | .......... | ............ | 0.07 | 8 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | ................. | ...D.. | .STGAD...... | A..A........ | 0.07 | R |
| ..... | F................ | .V........F....... | ...... | ............ | SPRDG..VGA.K | 0.07 | 8 |
| ..... | ................. | ..DD.....DF....... | R...D. | ESAGRNDIA.DQ | A..A........ | 0.06 | 7 |
| ..... | ................. | ................. | ...N.. | E..TAA.AAFDE | A..A........ | 0.06 | 7 |
| .A... | ................. | ..DGE....DF....... | E..AD. | ............ | A..A........ | 0.06 | 7 |
| RA... | F.....D...S..M.T.R | .RPT......F..P...T | ...ND. | ..A.G...AYD. | A..A........ | 0.06 | 7 |
| DA..T | F.....NGG.HV.....L | .Q.DR.....F....... | ...DDR | ..ARGADAE..S | A..A........ | 0.06 | 7 |
| EA..T | F.....GN..NA.T...M | ................. | G..ND. | ............ | A..A........ | 0.06 | 7 |
| ST... | F.....NRT..A.N.G.S | .Q.SG....NF....... | R..DD. | E.ATA.DA.VDQ | A..A........ | 0.06 | 7 |
| E.... | F......RT.LA.L.G.K | ................. | ...... | ............ | A..A........ | 0.06 | 7 |
| AA... | ................. | .Q.DR.....F....... | ....D. | E.GTAN..AVD. | A..A........ | 0.06 | 7 |
| ..... | ................. | ................. | ...... | E.TGT.DAAVDD | A..A........ | 0.06 | 7 |
| EA..T | F.....GSA.RV.L.A.R | ..HG.....NF......T | ...A.. | ............ | A..A........ | 0.06 | 7 |
| ..... | ................. | .V........F....... | ...... | ............ | | 0.06 | 7 |
| ..... | ................. | ................. | ...D.. | EDTSGAD...DE | A..A........ | 0.06 | 7 |
| ..... | ................. | ................. | R...D. | .NGSAS..A.DN | A..A........ | 0.06 | 7 |
| TA... | F.....SRA.SK.N.A.H | .QDT.....DF....... | ...DDR | ...G.S..AFGD | A..A........ | 0.06 | 7 |
| ..... | ................. | ................. | ...... | E.AGTNDI...R | A..A........ | 0.06 | 7 |
| AA... | F.....NT.....K.A.R | TKDT.....NF....... | ...DDR | ENG.ASD.E.GQ | A..A........ | 0.06 | 7 |
| ..... | ................. | ................. | E..N.. | E.TGT...AV.S | A..A........ | 0.06 | 7 |
| GT..T | ................. | .QHNQ.....F......T | ...DDR | ..GA.A...V.H | A..A........ | 0.06 | 7 |
| ..... | ................. | ................. | ...NGR | ............ | A..A........ | 0.06 | 7 |
| TA... | F......S..PM.T.S.K | .RPT.....DF....... | ...DD. | ..AGA..AA.GS | A..A........ | 0.06 | 7 |
| A.... | ................. | .KYT.....NF....... | ...D.. | ............ | | 0.06 | 7 |
| AT... | F.......G.N..T.P.L | ..DGE....DF....... | ...... | ...A.SD.EVGG | | 0.06 | 7 |
| AA... | F.....STG.HE.L...M | .QD......NF....... | E..AD. | ............ | A..A........ | 0.06 | 7 |
| AA... | ................. | .QHNQ.....F......T | ...N.. | ..AGG....DDQ | A..A........ | 0.06 | 7 |
| ..... | F................ | .V........F....... | ...... | ............ | G.RTA..SRV.E | 0.06 | 7 |
| ..... | ................. | ................. | E..TG. | .SA.TG.A..GQ | A..A........ | 0.06 | 7 |
| ..... | F................ | .V........F....... | ...... | ............ | ...DP..FTV.E | 0.06 | 7 |
| ..... | F.....SA..RA.....R | ..DD.....DF....... | R...D. | ESAG...TEYD. | A..A........ | 0.06 | 7 |
| ..... | F................ | .V........F....... | ...... | ............ | TARTP..DSA.E | 0.06 | 7 |
| ..... | ................. | ................. | ...D.. | E..TRS.AE.GS | A..A........ | 0.06 | 7 |
| ..... | F................ | .V........F....... | ...... | ............ | NTRSG..SSS.D | 0.06 | 7 |
| ..... | .........A.N....R | .KYT.....NF......T | R...D. | ...G.D..EVGQ | A..A........ | 0.06 | 7 |
| DA... | ................. | ................. | E..AGR | .NAG.NDT..DG | A..A........ | 0.06 | 7 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| SA..T | F.....NQG.RV.I.N.R | .........NF....... | R...D. | .DASGDD.EVD. | A..A........ | 0.06 | 7 |
| AA... | ................. | .KDSR....DF....... | E..ND. | ........... | A..A........ | 0.06 | 7 |
| EA... | F.....ASA.PN.P.A.R | .PPNG.....F......T | ...DDR | ...GRS.IEF.. | A..A........ | 0.06 | 7 |
| ..... | F.....SK..PA.K.A.G | ..DGE....DF....... | ...DD. | ........... | A..A........ | 0.06 | 7 |
| ..... | F......AG..L.T.N.R | T..NE....DF....... | ...DDR | ..AKGS.AAYDS | A..A........ | 0.06 | 7 |
| ..... | ................. | .........NF......T | E..N.. | E.TR.N.....Q | A..A........ | 0.06 | 7 |
| ..... | ................. | ................. | G..N.. | ........... | A..A........ | 0.06 | 7 |
| GT... | ................. | ..DGE....DF....... | ...... | ........... | ............ | 0.06 | 7 |
| ..... | F................ | .V........F....... | ...... | ........... | A.KTP..VQG.E | 0.06 | 7 |
| ..... | F................ | .V........F....... | ...... | ........... | SERGN..SKT.. | 0.06 | 7 |
| ..... | ................. | ................. | R...D. | E..GGG..EF.G | A..A........ | 0.06 | 7 |
| AA... | F.....GRT.S..L.G.R | .........F..P.... | R..... | .NAAEND...GE | A..A........ | 0.06 | 7 |
| GA... | F.....NGG.HN.K.G.E | ..A......DF....... | ...DG. | E.ATRA..A.DE | A..A........ | 0.06 | 7 |
| GA... | F.....GQ..LN.L.D.R | .Q.S......F....... | ...DDR | ........... | A..A........ | 0.06 | 7 |
| RA..T | F.....NDT.IP.T...K | .Q.DR.....F....... | ....D. | ........... | A..A........ | 0.06 | 7 |
| ..... | F................ | .V........F....... | ...... | ........... | GNRTT..FTG.A | 0.06 | 7 |
| ..... | ................. | ................. | G..NDR | ...G.S..AFGD | A..A........ | 0.06 | 7 |
| R.... | ................. | TKDDR....DF....... | ...DDR | ........... | A..A........ | 0.06 | 7 |
| GA... | F.....AG..PA.K.G.R | .Q.DR.....F....... | ....D. | ........... | A..A........ | 0.06 | 7 |
| ..... | F.....A.A.NH.I.Q.G | ..HG.....NF......T | ...A.. | ........... | A..A........ | 0.06 | 7 |
| ..... | F................ | .V........F....... | ...... | ........... | TRSAT..SNE.Q | 0.06 | 7 |
| ..... | ......SG..IK.K.D.R | .KPDQ....DF....... | ...D.. | .NATG....VGS | A..A........ | 0.06 | 7 |
| SA... | F................ | .V........F....... | ...... | ........... | A..A........ | 0.06 | 7 |
| ..... | ................. | ................. | ...... | ..GRRA..E.DQ | A..A........ | 0.06 | 7 |
| ..... | ................. | ..PN.....NF....... | ...N.. | E.GNGS....GR | A..A........ | 0.06 | 7 |
| D...T | F.....NKT.HL.T.A.R | ..DGE....DF....... | ...... | ........... | A..A........ | 0.06 | 7 |
| ..... | F......RG.H..L.E.G | .V........F....... | ...... | ........... | A..A........ | 0.06 | 7 |
| ..... | F................ | .V........F....... | ...... | ........... | EERNT..S.T.E | 0.06 | 7 |
| TT..T | ................. | .QPTG....NF....... | ...DDR | E.GNG.D.E.DS | A..A........ | 0.06 | 7 |
| ..... | ................. | .........DF....... | ...... | ..GG...I..GH | A..A........ | 0.05 | 6 |
| ..... | ......DAA.IK.T.Q.N | ..DGE....DF....... | ...... | E.......... | ............ | 0.05 | 6 |
| G.... | F.....SG..IK.K.D.R | ................T | ...... | ...DTN..E.DR | A..A........ | 0.05 | 6 |
| D...T | F.....AGG.P..L...G | ..PN.....NF....... | ...NDR | ........... | A..A........ | 0.05 | 6 |
| AA... | F.....STA..Q.H.Q.L | ..PDG....NF....... | ....DR | ........... | A..A........ | 0.05 | 6 |
| SA..T | ................. | ................. | ...... | ........... | ............ | 0.05 | 6 |
| SA... | F.....NGG.NN.K.T.R | .Q.DR.....F....... | ....D. | .DGGGS.....G | A..A........ | 0.05 | 6 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| DA... | F.....GET.IA.H.N.H | .QPG.....NF....... | ...DDR | E.AAGSD.E.GG | A..A........ | 0.05 | 6 |
| ..... | ................. | ................. | G..TG. | .D.TGN.I...Q | A..A........ | 0.05 | 6 |
| ..... | ................. | ........NF....... | ...DDR | ........... | A..A........ | 0.05 | 6 |
| ..... | ................. | ................. | R..NDR | E.AG..D.A.GR | A..A........ | 0.05 | 6 |
| S.... | F.......G.HK.T.N.G | .QHNQ.....F......T | ...... | ........... | A..A........ | 0.05 | 6 |
| GA... | F.....STA..Q.H.Q.L | T.P......DF....... | R...D. | ........... | ........... | 0.05 | 6 |
| E.... | ................. | .QANH.....F......T | R..D.. | .SAKAA.AA.DE | A..A........ | 0.05 | 6 |
| ..... | ................. | ................. | ...D.R | .NADRN..E.GE | A..A........ | 0.05 | 6 |
| ..... | ......N.......... | ................. | R..DG. | ........... | A..A........ | 0.05 | 6 |
| R.... | F.....GGG.PL.M.A.R | ................. | ...D.R | ........... | A..A.A..... | 0.05 | 6 |
| ..... | F.....SRA.SK.N.A.H | ..DGE....DF....... | ...DDR | .N.SGNDIE.DQ | A..A........ | 0.05 | 6 |
| TA... | ................. | TQ.GR.....F......T | ...DDR | ........... | A..A........ | 0.05 | 6 |
| ..... | ................. | ................. | ...DDR | .DAR...AEY.R | A..A........ | 0.05 | 6 |
| GA... | F.....ATT..N.L...L | .KYT.....NF......T | ...D.. | ........... | A..A........ | 0.05 | 6 |
| ..... | F................ | .V........F....... | ...... | ........... | KNKGP..AHE.H | 0.05 | 6 |
| D...T | ................. | ..PDG....NF....... | ....DR | E..G.SDAA.GD | A..A........ | 0.05 | 6 |
| G.... | F.....GR..SK.N.T.S | .Q.D.....DF....... | ...DDR | ........... | A..A........ | 0.05 | 6 |
| ..... | ................. | .QPN......F......T | ...N. | ........... | A..A........ | 0.05 | 6 |
| GT... | F.....AEG.LK.M.H.L | .QPG.....DF....... | ...... | ........... | GTRDG..AE..A | 0.05 | 6 |
| TT..T | F.....DA..IA.L.K.R | .KDSR....DF......T | R..DD. | ........... | A..A........ | 0.05 | 6 |
| ..... | ................. | ................. | ...... | E..TRSD.AFDD | A..A........ | 0.05 | 6 |
| ..... | F.....NKG.NI.N.E.R | .QPN......F......T | ...N.. | ........... | A..A........ | 0.05 | 6 |
| ..... | ................. | .........F....... | ...DDR | ES.SA..I..DR | A..A........ | 0.05 | 6 |
| ..... | ................. | ................. | ...... | ........... | ........... | 0.05 | 6 |
| ..... | ......AST.IN.L.T.. | ..DGE....DF....... | ...... | ........... | ........... | 0.05 | 6 |
| DT... | F.....ATG.NV.T.G.R | .Q.GQ....DF....... | ....G. | .DG.GA.IEFDR | A..A........ | 0.05 | 6 |
| ..... | ................. | ................. | G..TDR | E.AGGN..E.DD | ........... | 0.05 | 6 |
| ..... | ......GN..IK.L...G | .QAS......F....... | ...... | ........... | A..A........ | 0.05 | 6 |
| ..... | F................ | .V........F....... | ...... | ........... | KH.DR....G.A | 0.05 | 6 |
| A.... | F.....GE..LQ.N.T.R | .QD.E.....F..P.... | ...... | ........... | A..A........ | 0.05 | 6 |
| HA... | F.....GKG.ND.T.N.G | ..A......DF....... | ...DG. | ........... | ........... | 0.05 | 6 |
| TT..T | ................. | ................. | ...... | ........... | DHRNP..DQA.. | 0.05 | 6 |
| ..... | ................. | ................. | ....GR | ........... | A..A........ | 0.05 | 6 |
| ..... | ................. | ................. | ...... | ..TAGN..A..N | A..A........ | 0.05 | 6 |
| ..... | F................ | .V........F....... | ...... | ........... | .EKGG...QN.. | 0.05 | 6 |
| ..... | F................ | .V........F....... | ...... | ........... | GRSAD..DTS.H | 0.05 | 6 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| GA... | F.....SAG..L.H...K | ................. | ...... | ........... | A..A....... | 0.05 | 6 |
| ..... | ................. | .........DF......T | G..ND. | ........... | A..A....... | 0.05 | 6 |
| ..... | F................ | .V......F........ | ...... | ........... | GARGP..D.I.E | 0.05 | 6 |
| ..... | ................. | ................. | ...... | ENAGGD..E..R | A..A....... | 0.05 | 6 |
| ..... | ................. | ................. | E..DD. | ........... | A..A....... | 0.05 | 6 |
| TA..T | F.....NA..RM.M.K.. | ..DGE....DF...... | ...DDR | ........... | A..A....... | 0.05 | 6 |
| ..... | F................ | .V......F........ | ...... | ........... | DRRSH..S.G.D | 0.05 | 6 |
| ..... | ................. | .QAS......F...... | ...... | ........... | A..A.....A | 0.05 | 6 |
| TT..T | ................. | ..DGE....DF...... | R...D. | ........... | A..A....... | 0.05 | 6 |
| TT... | F.....AE...A.T...R | .QPN......F......T | ...A.. | ........... | A..A....... | 0.05 | 6 |
| ..... | ................. | ........R.F......T | ...DDR | E..AGS.TEFDQ | ........... | 0.05 | 6 |
| ..... | ................. | .QPD.....DF...... | ...DDR | ED.TTGDA...G | A..A....... | 0.05 | 6 |
| TA..T | F.....ARA.IE.....L | .Q.DR.....F...... | ....D. | .NGGGN..E.DG | A..A....... | 0.05 | 6 |
| TA..T | F.....NGG.IM.L.E.R | T.P......DF...... | ....D. | ........... | ........... | 0.05 | 6 |
| ..... | ................. | .Q.GQ....DF...... | R..TDR | .DAG.S.A..DR | A..A....... | 0.05 | 6 |
| ..... | ................. | ................. | ...DDR | ..ATGD..EV.Q | A..A....... | 0.05 | 6 |
| ..... | ................. | ................. | ...... | E.AAGSD..... | A..A....... | 0.05 | 6 |
| GT... | F.....SRA.SK.N.A.H | T.P......DF...... | ...DDR | ........... | A..A....... | 0.05 | 6 |
| T...T | F.....N.G.RE.H.A.R | .Q.DR.....F...... | ....D. | ........... | A..A....... | 0.05 | 6 |
| EA... | F................ | TK.NE...DF......T | ...DDR | ........... | A..A....... | 0.05 | 6 |
| ..... | F................ | .V........F...... | ...... | ........... | SDRGA..SQE.E | 0.05 | 6 |
| ..... | ................. | .KYT.....NF......T | ...... | ED.GGN.IE..R | A..A....... | 0.05 | 6 |
| E.... | F.....A.A.NH.I.Q.G | ..HG.....NF......T | ...DDR | E.TGAN.AE.GE | A..A....... | 0.05 | 6 |
| ..... | F................ | .V........F...... | ...... | ........... | DR.NK..DSG.Q | 0.05 | 6 |
| SA... | ................. | TQA.H....DF...... | ...... | ........... | A..A....... | 0.05 | 6 |
| R...T | F.....DKG.HM.L.G.R | .........DF...... | ...... | ........... | A..A....... | 0.05 | 6 |
| ..... | F.....DSA..A.I...R | ........NF...... | ...DDR | ........... | A..A....... | 0.05 | 6 |
| ..... | F................ | .V........F...... | ...... | ........... | THRT...VRN.D | 0.05 | 6 |
| ....T | ................. | ..AGQ....NF...... | ...DDR | ........... | A..A....... | 0.05 | 6 |
| RA... | F.....ATT..N.L...L | .QPN......F......T | ...N.. | E.ANG...E.G. | A..A....... | 0.05 | 6 |
| GT... | F................ | .V........F...... | ....G. | ........... | ........... | 0.05 | 6 |
| ..... | ................. | ................. | R...D. | EDAG...I..GQ | A..A....... | 0.05 | 6 |
| ..... | F................ | .V........F...... | ...... | ........... | DPKSR..FG..T | 0.05 | 6 |
| A...T | F................ | .V........F...... | ...... | ........... | A..A....... | 0.05 | 6 |
| ..... | ................. | .V........F...... | ...... | ........... | NPRGE...RS.A | 0.05 | 6 |
| ..... | ................. | ................. | ...NDR | ........... | A..A....... | 0.05 | 6 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | ...NGR | .DAG.S.A..DR | A..A........ | 0.05 | 6 |
| ..... | F.....NR..N..I.T.G | .QD......DF..P.... | G..K.. | ........... | A..A........ | 0.05 | 6 |
| GT... | .................. | ..HG.....NF......T | E..DD. | ........... | A..A........ | 0.05 | 6 |
| ..... | .................. | .................. | ...DDR | ..AS..D.AVGH | A..A........ | 0.05 | 6 |
| RA... | .................. | TQ..H....NF....... | ...... | E.ANG...E.G. | A..A........ | 0.05 | 6 |
| ..... | .................. | .................. | R..DG. | ........... | A..A........ | 0.05 | 6 |
| GT... | .................. | .................. | ...DD. | EDTTGG.....G | A..A........ | 0.05 | 6 |
| ..... | F.....SN..PL.K.T.. | .V........F....... | ...... | ........... | ........... | 0.05 | 6 |
| ..... | .................. | TKDT.....NF....... | ...... | ........... | A..A........ | 0.05 | 6 |
| G.... | F......KT.NV.K.T.H | .Q.DR.....F....... | ....D. | ........... | A..A........ | 0.05 | 6 |
| DA... | F.....GNG.HV.H.G.R | .........DF....... | ...... | ........... | ........... | 0.05 | 6 |
| ..... | F................. | .V........F....... | ...... | ........... | TH.NR..FT..E | 0.05 | 6 |
| TA... | .................. | TQYDR....NF....... | R...D. | ........... | A..A........ | 0.05 | 6 |
| NA... | F.....NA..RM.M.K.. | ..DGE....DF....... | ...DDR | ........... | A..A........ | 0.05 | 6 |
| ..... | .................. | .........DF......T | ...DDR | E.TS.D..AFDQ | A..A........ | 0.05 | 6 |
| ..... | .................. | .................. | ...D.. | .SGK.SDI.VDD | A..A........ | 0.05 | 6 |
| ..... | F.....GEG.L..T.K.G | ..PNG....DF....... | ...NGR | ........... | A..A........ | 0.05 | 6 |
| ..... | F................. | .V........F....... | ...... | ........... | GRSNT..D.A.. | 0.05 | 6 |
| ..... | .................. | .................. | R..ND. | EDGAAA....GQ | A..A........ | 0.05 | 6 |
| ..... | .................. | .................. | ...NG. | ........... | A..A........ | 0.05 | 6 |
| AA... | F................. | .QDT.....DF....... | G..DG. | .SATAN.I..DQ | A..A........ | 0.05 | 6 |
| E.... | .................. | .................. | ...... | ........... | A..A........ | 0.05 | 6 |
| ..... | .................. | ..HG.....NF......T | E..DD. | ........... | ........... | 0.05 | 6 |
| ..... | F.....GQG.IA.....K | .QAS......F....... | ...... | ...TG.D.AY.G | A..A........ | 0.05 | 6 |
| NA..T | .................. | ..HG.....NF......T | ...A.. | EDAG.AD.E.G. | A..A........ | 0.05 | 6 |
| RA... | .................. | .................. | ...... | .DTG.GD.A..H | A..A........ | 0.05 | 6 |
| AT..T | .................. | .........DF.WGATK | ...DD. | ..AKG.D.AYDG | A..A........ | 0.05 | 6 |
| ..... | .................. | .................. | R..DDR | E.AGES.A.Y.Q | A..A........ | 0.05 | 6 |
| GA... | F.....STA..Q.H.Q.L | T.P......DF....... | ...D.. | .S.KA..TE.DS | A..A........ | 0.05 | 6 |
| ..... | .................. | .........NF....... | R..DD. | EN..EG....DS | A..A........ | 0.05 | 6 |
| G.... | .................. | .........NF....... | R...D. | .NAGA.D.AFDE | A..A........ | 0.05 | 6 |
| GT..T | F.....GNG.HV.H.G.R | .Q.G......F....... | ...DD. | ........... | A..A........ | 0.05 | 6 |
| ..... | .................. | .................. | G..AD. | .N..TN.....G | A..A........ | 0.05 | 6 |
| ..... | .................. | .................. | ...... | ...ARAD.AY.G | A..A........ | 0.05 | 6 |
| TA... | F.....AQ...A.L.... | .QD.E.....F..P.... | ...... | ........... | ........... | 0.04 | 5 |
| A.... | F.....GNG.SL.M...I | ..DGE....DF....... | ...... | ........... | A..A........ | 0.04 | 5 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| TT..T | .................. | .................. | ...DDR | ............ | ............ | 0.04 | 5 |
| ..... | .................. | .................. | R..DD. | .DTA.A.AA.GE | A..A........ | 0.04 | 5 |
| A.... | F.....SR..IK.T.H.G | .QANH.....F......T | E..T.. | E.AGAND.AV.H | A..A........ | 0.04 | 5 |
| ..... | F................. | .V........F....... | ...... | ............ | .TRNE..VH... | 0.04 | 5 |
| ..... | .................. | .................. | R...G. | ESAA.D..E.GN | A..A........ | 0.04 | 5 |
| ..... | .................. | .................. | ...DDR | E.AARS...Y.H | A..A........ | 0.04 | 5 |
| ..... | F................. | .V........F....... | ...... | ............ | GNRDG..ASE.Q | 0.04 | 5 |
| D...T | F.....NGG.HV.....L | TQ.TG....DF....... | ...DDR | ..TGRS..E.GS | A..A........ | 0.04 | 5 |
| ..... | .................. | .................. | ...KDR | ............ | A..A........ | 0.04 | 5 |
| SA..T | F.....S.A.IA.M.T.R | .Q.DR.....F....... | ....D. | ............ | A..A........ | 0.04 | 5 |
| ..... | .................. | .................. | ...ND. | ..AKG...AV.. | A..A........ | 0.04 | 5 |
| G.... | F.....AAG.S..P...R | TKDDR....DF....... | ...DDR | .STAG.D..FDQ | A..A........ | 0.04 | 5 |
| GT... | F.....AEG.LK.M.H.L | ..DGE....DF....... | R...D. | ............ | ............ | 0.04 | 5 |
| HA... | F.....GKT.SL...G.R | ..A......DF....... | ...DG. | ENANGN.IAFD. | A..A........ | 0.04 | 5 |
| ..... | F.....DA..IA.L.K.R | .KDSR....DF......T | R...DD | ............ | A..A........ | 0.04 | 5 |
| ..... | F................. | TKDDR....DF....... | ...DDR | ............ | A..A........ | 0.04 | 5 |
| AT... | .................. | .................. | ...... | ............ | A..A........ | 0.04 | 5 |
| AT... | F.....DRG.S..T.A.S | .V........F....... | ...... | ............ | A..A........ | 0.04 | 5 |
| ..... | .................. | .................. | ...... | ESADRSD..Y.H | A..A........ | 0.04 | 5 |
| TA... | .................. | ..HG.....NF......T | E..DD. | EDGGGS..EYGS | ............ | 0.04 | 5 |
| ..... | F................. | .V........F....... | ...... | ............ | TRRDG..I.S.E | 0.04 | 5 |
| ..... | .................. | .................. | R...D. | .DTA.G.AAVDQ | A..A........ | 0.04 | 5 |
| ..... | .................. | .QPN......F.....ST | ....D. | ....E.....GH | A..A........ | 0.04 | 5 |
| ..... | .................. | .................. | ...DDR | E.A.AN..AVGD | A..A........ | 0.04 | 5 |
| ..... | .................. | .................. | ...N.. | ESAAASD..VGQ | A..A........ | 0.04 | 5 |
| ..... | .................. | .................. | R..ND. | ES.TG.DA..DQ | A..A........ | 0.04 | 5 |
| ..... | .................. | ........DF......T | ...D.. | E.AGEG.I...R | A..A........ | 0.04 | 5 |
| ..... | .................. | ........DF....... | ...... | ..T.GG.IEVDD | A..A........ | 0.04 | 5 |
| DT... | .................. | .Q.GQ....DF....... | R...D. | ............ | A..A........ | 0.04 | 5 |
| ..... | F.....SA..RA.....R | .KPDQ.....F....... | ...DDR | ENAGRSDIE.GQ | A..A........ | 0.04 | 5 |
| ..... | .................. | .Q.DR.....F....... | ....D. | ............ | A..A........ | 0.04 | 5 |
| T...T | .................. | .V........F....... | ...... | ESGGTD....DR | A..A........ | 0.04 | 5 |
| RA... | .................. | TKDDR....DF....... | ...DDR | ...ARD.IA..G | A..A........ | 0.04 | 5 |
| ..... | .................. | .................. | ...DDR | .D...S..A.GG | A..A........ | 0.04 | 5 |
| GT... | F................. | .V........F....... | ...... | ............ | ST.SA..FGV.A | 0.04 | 5 |
| GT..T | .................. | ...T.....NF....... | ....D. | ............ | A..A........ | 0.04 | 5 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| NT..T | .................. | TQ.GR....NF....... | ...... | ........... | A..A........ | 0.04 | 5 |
| ..... | F................. | .V........F....... | ...... | ........... | TARCA..ASA.E | 0.04 | 5 |
| ..... | .................. | TQ.TG....DF....... | ...DDR | .SGREGDAE..D | A..A........ | 0.04 | 5 |
| ..... | F.....GRG.H..P.E.R | .V........F....... | R.A... | ........... | A,.A........ | 0.04 | 5 |
| A.... | F.....DD..IH.K.K.K | .Q.DR.....F....... | ....D. | ..AT..DIA.DR | A..A........ | 0.04 | 5 |
| RA... | .................. | .................. | E..KD. | ........... | ............ | 0.04 | 5 |
| T.... | .................. | .QD.E.....F..P.... | ...D.. | ........... | ............ | 0.04 | 5 |
| D.... | F................. | .QPSR.....F......T | ...D.. | E.ATG...A.G. | A..A........ | 0.04 | 5 |
| ..... | .................. | ..HG.....NF......T | ...A.. | ........... | A..A........ | 0.04 | 5 |
| ..... | .................. | .................. | ...D.. | EDAGT..AA..H | A..A........ | 0.04 | 5 |
| SA..T | F.....AGT..M.K.Q.G | .Q.GQ....DF....... | R..DG. | .NAAR.D.A.GE | A..A........ | 0.04 | 5 |
| ..... | F.....GG..NK.M.... | .KPSE....DF......T | R...DR | ........... | A..A........ | 0.04 | 5 |
| ..... | .................. | .................. | ...KG. | ........... | A..A........ | 0.04 | 5 |
| ..... | .................. | .................. | ....GR | ..AG.N.AA.GQ | ............ | 0.04 | 5 |
| RA... | .................. | .Q.DR.....F....... | ....D. | EDTG.A....GN | A..A........ | 0.04 | 5 |
| GT..T | F.....AAG.HV.I...K | ..DGE....DF....... | ...... | ........... | A..A........ | 0.04 | 5 |
| ..... | F................. | .................. | E..KG. | ........... | A..A........ | 0.04 | 5 |
| G.... | F.....DRG..M...K.R | .V........F....... | ...... | ..AATD.AA.DQ | A..A........ | 0.04 | 5 |
| ..... | .................. | ........DF....... | ...... | ES.DRN.....Q | A..A........ | 0.04 | 5 |
| ..... | .................. | TQ.TG....DF....... | ...DDR | ........... | A..A........ | 0.04 | 5 |
| D...T | .................. | .................. | G..K.. | ...A.SD.AY.G | A..A........ | 0.04 | 5 |
| E.... | .................. | .Q......DF....... | ...AD. | ..NAAS.AE.GE | A..A........ | 0.04 | 5 |
| E.... | .................. | .................. | ...N.. | ........... | A..A........ | 0.04 | 5 |
| ..... | F................. | .V........F....... | ...... | ........... | APRAP..IR..A | 0.04 | 5 |
| ..... | F................. | .V........F....... | ...... | ........... | NHRNT..D.E.A | 0.04 | 5 |
| ..... | F.....aqg.nv.h.k.r | .QYGQ....DF....... | ...... | E........... | ............ | 0.04 | 5 |
| GT... | F.....GG..LL.H.G.R | .QPN......F......T | ...N.. | ........... | A..A........ | 0.04 | 5 |
| GT... | F......KG.NL...Q.S | .QPG.....NF....... | ...DDR | ........... | A..A........ | 0.04 | 5 |
| ..... | .................. | .................. | R...D. | EDASTNDAAY.Q | A..A........ | 0.04 | 5 |
| NT... | .................. | ..YN......F......T | ...D.R | ........... | A..A........ | 0.04 | 5 |
| A.... | .................. | .........NF....... | R...D. | ..TGTS...YGS | A..A........ | 0.04 | 5 |
| E.... | .................. | .................. | R..DD. | ........... | A..A........ | 0.04 | 5 |
| HA... | F.....SN..PLKK.T.. | .Q......DF....... | E..N.. | ........... | A..A........ | 0.04 | 5 |
| DA..T | F.....DS..NH.I.P.R | .Q.DH....NF....... | ...DD. | ..AAE.D....N | A..A........ | 0.04 | 5 |
| ..... | .................. | .........NF....... | E..N.. | ES.GAN..EVDG | A..A........ | 0.04 | 5 |
| AT..T | F.....NTG.RN.T.T.L | .........NF....... | R...D. | ...AAS.A.VGQ | A..A........ | 0.04 | 5 |

TABLE 3-continued

AAV capsid proteins having increased specificity for and/or transduction of CD447−/133− GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | .........DF....... | E..AD. | .SAKGG..EYGD | A..A........ | 0.04 | 5 |
| ..... | F............... | .V........F....... | ...... | ............ | GRSSG..DTN.D | 0.04 | 5 |
| GA... | ................ | ..DGE....DF....... | E..AD. | ............ | A..A........ | 0.04 | 5 |
| GT... | F............... | .V........F....... | ....V. | ............ | ............ | 0.04 | 5 |
| PA..T | F............... | ................ | ...DD. | ............ | A..A........ | 0.04 | 5 |
| ..... | ................ | ................ | ...DDR | E.A......... | A,.A........ | 0.04 | 5 |
| ..... | F............... | .V........F....... | ...... | ............ | DPRAS..SSA.. | 0.04 | 5 |
| ..... | ................ | ................ | R...D. | E.TNESDT..D. | A..A........ | 0.04 | 5 |
| D.... | F.....SK..PA.K.A.G | ..A......DF....... | ...DG. | .N.GRS..E.G. | A..A........ | 0.04 | 5 |
| EA..T | ................ | T.P......DF....... | ...D.. | .SGS.NDIA..D | A..A........ | 0.04 | 5 |
| ..... | F............... | .V........F....... | ...... | ............ | TTRAT..DKI.D | 0.04 | 5 |
| NA... | F.....GRT.PQ.T.T.R | ..DGE....DF....... | R..... | .N.GA.D.A.GG | A..A........ | 0.04 | 5 |
| ..... | F............... | .V........F....... | ...... | ............ | DTRGR..DRI.H | 0.04 | 5 |
| ..... | F............... | ...T.....NF....... | ...... | .SAS.N.IA..E | A,.A........ | 0.04 | 5 |
| ..... | F............... | ..........F....... | ...... | ............ | GPQDG..ADE.H | 0.04 | 5 |
| A...T | ................ | TQP.R....NF......T | ...D.. | ............ | A..A........ | 0.04 | 5 |
| GA..T | ................ | .Q.DH....NF....... | ...DD. | ............ | A..A........ | 0.04 | 5 |
| ..... | ................ | ................ | ...D.. | E.TAGN.IE.DG | A..A........ | 0.04 | 5 |
| TA..T | F.....GN..HM.P.... | ...NG....DF....... | ...D.. | ............ | A..A........ | 0.04 | 5 |
| R...T | F.....DTA..D.K...K | .KYT.....NF......T | R..TDR | ............ | A..A........ | 0.04 | 5 |
| ..... | F............... | .V........F....... | ...... | ............ | GTRAT..IH..D | 0.04 | 5 |
| ..... | F............... | .V........F....... | ...... | ............ | TPRAP..VRG.E | 0.04 | 5 |
| ..... | ................ | ................ | ...DD. | .NGST.....GG | A..A........ | 0.04 | 5 |
| ..... | ................ | ..ADH....DF....... | G..A.R | ............ | A..A........ | 0.04 | 5 |
| .A... | F.....A.G.RV.T.A.G | .QD.E.....F..P.... | ....G. | E.TGRND.A..E | A..A........ | 0.04 | 5 |
| ..... | ................ | .Q.GQ....DF....... | ....G. | ............ | A..A........ | 0.04 | 5 |
| ..... | ................ | ................ | R...D. | ESAG...TEYD. | A..A........ | 0.04 | 5 |
| ET... | F.....NGG.NN.K.T.R | ................ | ...... | ............ | A..A........ | 0.04 | 5 |
| DT... | F.....NTG.RN.T.T.L | .Q.GQ....DF....... | E..AG. | ............ | A..A........ | 0.04 | 5 |
| ..... | ................ | ................ | G..TG. | ES.DRN.....Q | A,.A........ | 0.04 | 5 |
| ..... | ................ | ....E....DF......T | R..DG. | .N.AEA..AYDD | A..A........ | 0.04 | 5 |
| ..... | F............... | .QANH....DF....... | ...DDR | ............ | A..A........ | 0.04 | 5 |
| ..... | ................ | ................ | R..DG. | ESAAR..IE.DE | A..A........ | 0.04 | 5 |
| E.... | F.....AGG.P..L...G | .V........F....... | ...... | EN.GE..IA.DR | ............ | 0.04 | 5 |
| ..... | ...............H | .QPN......F......T | ...D.. | EDAAGNDIE.G. | A..A........ | 0.04 | 5 |
| G.... | F.....ASA.PN.P.... | .QDT.....DF....... | R...D. | EDAG.AD.E.G. | A..A........ | 0.04 | 5 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................ | .V........F....... | ...... | ........... | GPRGH...TN.D | 0.04 | 5 |
| NT..T | F......HG.LV.L.K.R | .QAS......F....... | ...... | ........... | A...A........ | 0.04 | 5 |
| TA..T | F.....SRA.SK.N.A.H | .Q.D.....DF..P.... | ...... | ........... | A...A........ | 0.04 | 5 |
| .T... | ................ | ..PDH....DF....... | ...DDR | EN.TTG.IEVDR | A...A........ | 0.04 | 5 |
| ..... | ................ | ................ | R...D. | .DAAAN.IE.DR | A...A........ | 0.04 | 5 |
| G.... | F.....A.A.NH.I.Q.G | .........NF....... | R...D. | ..AGAN...FGE | A...A........ | 0.04 | 5 |
| ..... | ................ | ..HG.....NF......T | ...A.. | .STSRGD...GG | A...A........ | 0.04 | 5 |
| ..... | F................ | .V........F....... | ...... | ........... | GARTH..YTE.A | 0.04 | 5 |
| ..... | ................ | ................ | ...NG. | ........... | ............ | 0.04 | 5 |
| ..... | F................ | .V........F....... | ...... | ........... | ETHGP..DHI.. | 0.04 | 5 |
| ..... | ................ | ................ | ...D.R | .NGST.....GG | A...A........ | 0.04 | 5 |
| NA..T | F.....G.G.HA.T.G.R | ...TE.....F......T | ...NGR | ..ATESD..FDQ | A...A........ | 0.04 | 5 |
| ..... | ................ | ........DF....... | ...AGR | ..A...AD.AYGQ | A...A........ | 0.04 | 5 |
| AT... | ................ | ........DF....... | ...DD. | ........... | ............ | 0.04 | 5 |
| .A... | F................ | .V........F....... | ...DDR | ED.GAG..AV.G | A...A........ | 0.04 | 5 |
| A.... | F.....ATA.NK.T.A.R | .........NF....... | R...D. | E.ANGG.A...D | A...A........ | 0.04 | 5 |
| RT... | ................ | TKPTQ....NF......T | ...D.R | ........... | A...A........ | 0.04 | 5 |
| TT... | F......AG.NV.N.S.R | .QAS.....NF......T | ...N.. | ........... | A...A........ | 0.04 | 5 |
| ..... | ................ | ................ | ...... | ESATGG.T..GG | A...A........ | 0.04 | 5 |
| TA... | F.....AG..RV.L.N.G | .V........F....... | ...... | EN.G.A.....Q | A...A........ | 0.04 | 5 |
| ..... | ................ | ................ | ...... | .STT.S..A.GG | A...A........ | 0.04 | 5 |
| ..... | ................ | ................ | E..ND. | .DADGD...VDQ | A...A........ | 0.04 | 5 |
| GT... | F.....DGG.LA.K...R | ..AGR.....F......T | ...... | ........... | A...A........ | 0.04 | 5 |
| ..... | ................ | ................ | ....D. | ...DGSDT..GG | A...A........ | 0.04 | 5 |
| ..... | ................ | ........DF......T | G..KGR | ........... | A...A........ | 0.04 | 5 |
| ..... | F................ | .V........F....... | ...... | ........... | AKSG...D.R.D | 0.04 | 5 |
| SA... | F.....NR..N..I.T.G | ..YGG.....F....... | E..KD. | .DAGGN.IAV.E | A...A........ | 0.04 | 5 |
| G.... | ................ | ................T | ...... | .SA....AA.GH | A...A........ | 0.04 | 5 |
| TA... | F.....AQ...A.L.... | .QD.E.....F..P.... | ...... | ........... | T.RAS..SKE.Q | 0.04 | 5 |
| ..... | ................ | ................T | G..TDR | ........... | ............ | 0.04 | 5 |
| RA... | F................ | .KAS.....NF......T | ...AD. | ........... | A...A........ | 0.04 | 5 |
| ..... | ................ | ................ | ...DDR | ...RGN...YGG | A...A........ | 0.04 | 5 |
| E.... | F.....AA..RM.P.G.. | .........NF....... | R...D. | ...AAS.A.VGQ | A...A........ | 0.04 | 5 |
| ..... | ................ | ................ | E..TD. | ........... | ............ | 0.04 | 5 |
| ..... | ................ | ................ | ...D.. | .DGSGG.TE.DG | A...A........ | 0.04 | 5 |
| EA... | F.....GTG..P.T.D.R | .QPSE....DF....... | ...DDR | ........... | ............ | 0.04 | 5 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| .A... | F.....DHA.N..P.Q.K | TQPTH....NF....... | R..DD. | .SATGS....DQ | A..A........ | 0.04 | 5 |
| ..... | ................. | ..........F......T | ...DG. | .DG.G.DI..DR | A..A........ | 0.04 | 5 |
| TT... | ................. | ................. | ...KD. | ........... | ........... | 0.04 | 5 |
| ..... | ................. | ..........NF....... | ...DDR | ...DGSDT..GG | A..A........ | 0.04 | 4 |
| ..... | ................. | ................. | R..... | E..SRND...DR | A..A........ | 0.04 | 4 |
| AA... | ......NKG.NL.N.T.E | ..DGE....DF....... | ...... | ........... | A..A........ | 0.04 | 4 |
| TT... | F.....SSA.LD.T.A.. | .V........F....... | ...... | ........... | ........... | 0.04 | 4 |
| ..... | F................ | .V........F....... | ...... | ........... | N.HSA...GE.K | 0.04 | 4 |
| ..... | F.....A...ND.T...K | .Q.DH....NF....... | ...DD. | ........... | A..A........ | 0.04 | 4 |
| ..... | ................. | ................. | ...DDR | .DGGGS.....G | A..A........ | 0.04 | 4 |
| SA..T | F................ | .V........F....... | ...... | ........... | ARHDR..SET.E | 0.04 | 4 |
| ..... | ................. | ..HG.....NF......T | ...... | ........... | ........... | 0.04 | 4 |
| SA... | F......S..PM.T.S.K | ..A......DF....... | ...DG. | .DAG.A.I..DG | A..A........ | 0.04 | 4 |
| ..... | ................. | ................. | R..DD. | ES.DRN..A.DN | A..A........ | 0.04 | 4 |
| SA... | ................. | .V........F....... | ...... | ........... | GNRDP..A.E.E | 0.04 | 4 |
| ..... | ................. | ................. | ...ADR | ..AGAN...FGQ | A..A........ | 0.04 | 4 |
| ..... | F................ | .V........F....... | ...... | ........... | T..GG......P | 0.04 | 4 |
| ..... | ................. | ..DGE....DF....... | ...... | ........... | A..A........ | 0.04 | 4 |
| GT..T | F.....SG..RV.I.G.R | .QANH....DF....... | R...D. | E.AATSDIE.DR | A..A........ | 0.04 | 4 |
| ..... | F.....SKG.NV.L.G.G | .V........F....... | ...... | ........... | A..A........ | 0.04 | 4 |
| SA..T | F......AT.I..N.K.G | ..PNG....NF....... | ...DD. | ........... | A..A........ | 0.04 | 4 |
| ..... | ................. | ........DF......T | R..AGR | ED.KAS.I...G | A..A........ | 0.04 | 4 |
| RA... | F.......KT.NK..A.G | .V........F....... | ...ND. | ..AAE.D....N | A..A........ | 0.04 | 4 |
| A...T | ................. | ...V.....NF....... | R...D. | ........... | A..A........ | 0.04 | 4 |
| HT..T | F.....ARG.IA.K.E.R | .Q.DH....NF....... | ...DD. | ........... | A..A........ | 0.04 | 4 |
| SA... | ................. | ................. | ...DG. | ...GGND...GG | A..A........ | 0.04 | 4 |
| ..... | ................. | ................. | ...... | ..TA.N..A.GG | A..A........ | 0.04 | 4 |
| ..... | F.......G.HK.T.N.G | .Q.DH....NF....... | ...DD. | E.AGAND.AY.N | A..A........ | 0.04 | 4 |
| ..... | ................. | ................. | R...D. | EDAA...AAVDQ | A..A........ | 0.04 | 4 |
| ..... | F................ | .V........F....... | ...... | ........... | GHRTG..D.T.H | 0.04 | 4 |
| AA... | F.....AN...N.L.H.R | ..........F....... | ...... | .SASRND.AVGE | A..A........ | 0.04 | 4 |
| T.... | F......TG.IL...T.R | ..YN......F......T | ...D.R | ........... | A..A........ | 0.04 | 4 |
| SA... | ................. | .QPSQ....NF....... | E..TGR | .DTGRN..E.DS | A..A........ | 0.04 | 4 |
| ..... | ................. | ................. | ...D.. | EN.GGSD.E.DE | A..A........ | 0.04 | 4 |
| ..... | ................. | ................. | ...DD. | .S.AGND..VDN | A..A........ | 0.04 | 4 |
| AA... | ................. | TQ.TG....DF....... | ...DDR | .NTGGG....DG | A..A........ | 0.04 | 4 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | .................T | ...D.R | E.GG.N.I.F.E | A..A........ | 0.04 | 4 |
| GT... | ................. | ..DGE....DF....... | R...D. | ............ | A..A........ | 0.04 | 4 |
| ET... | F.....ASA.SV.H.T.G | ..DGE....DF....... | ...... | .SAAGAD.A.DS | A..A........ | 0.04 | 4 |
| N.... | ................. | ................. | ...DDR | ............ | A..A........ | 0.04 | 4 |
| ..... | ................. | ................. | ...D.. | EDAA...AAVDQ | A..A........ | 0.04 | 4 |
| ..... | ................. | ................. | ....D. | ..GG...I..GH | A..A........ | 0.04 | 4 |
| ..... | ................. | ..E......NF......T | G..N.. | ..TK.GD..FGQ | A..A........ | 0.04 | 4 |
| ET..T | F.....SGG.IN.H.... | .........NF....... | R...D. | EDAGT...AFD. | A..A........ | 0.04 | 4 |
| NA... | F.....NGG.LN.I.G.R | .KYT.....NF......T | G..DD. | EDAAR.D.A.D. | A..A........ | 0.04 | 4 |
| ..... | .................K | ..DGE....DF....... | ...DGR | .SGTGDDT.VDG | A..A........ | 0.04 | 4 |
| ..... | ................. | ................. | G..KGR | ............ | A..A........ | 0.04 | 4 |
| ..... | ................. | ................. | ....G. | EDAGT...AFD. | A..A........ | 0.04 | 4 |
| ..... | F................ | .V........F....... | ...... | ............ | .DRDE..VGG.. | 0.04 | 4 |
| ..... | ................. | ................. | ...DD. | ...TAAD..V.E | A..A........ | 0.04 | 4 |
| ..... | F................ | .V........F....... | ...... | ............ | KRHSG..FSV.D | 0.04 | 4 |
| ..... | ................. | .RPT.....DF....... | E..N.. | .S.SGN.I..GH | A..A........ | 0.04 | 4 |
| ..... | F.....NS..SA.H.Q.G | ..HG.....NF......T | ...A.. | ..AG.SD...GR | A..A........ | 0.04 | 4 |
| ..... | F................ | .V........F....... | ...... | ............ | DPRAA..AGV.T | 0.04 | 4 |
| ..... | ................. | ................. | ....D. | ...R.ND.A.GG | A..A........ | 0.04 | 4 |
| ..... | ................. | ................. | R...D. | .S.RT...A.DD | A..A........ | 0.04 | 4 |
| ..... | ................. | ................. | ...DD. | E.TGAN.AE.GE | A..A........ | 0.04 | 4 |
| DT... | ................. | ..HG.....NF......T | ...A.. | ............ | A..A........ | 0.04 | 4 |
| AA..T | F.....D.A.HA...G.R | ..P.G....KF....... | ...D.. | ............ | ............ | 0.04 | 4 |
| RT... | F.....GKG.S..M.K.M | .........NF....... | R...D. | EDAG.AD.E.G. | CD.A........ | 0.04 | 4 |
| D...T | F.....NGG.HN.K.G.E | ..YN......F......T | ...D.R | ............ | A..A........ | 0.04 | 4 |
| N.... | ................. | ................. | ...DDR | ............ | ............ | 0.04 | 4 |
| ..... | F................ | .V........F....... | ...... | ............ | ATRNT..VDV.H | 0.04 | 4 |
| ..... | ................. | ................. | R..DG. | ..AG.DD...GG | A..A........ | 0.04 | 4 |
| ..... | ................. | ...T......F....... | R...D. | ENGKTA..A.DR | A..A........ | 0.04 | 4 |
| ..... | ................. | .PDNR..T.DF......T | ....GR | ............ | A..A........ | 0.04 | 4 |
| DT... | ................. | ................. | R..N.. | ............ | ............ | 0.04 | 4 |
| ..... | ................. | ..P.G....KF....... | ...D.R | ............ | A..A........ | 0.04 | 4 |
| ..... | F................ | .V........F....... | ...... | ............ | S.RGP..ART.D | 0.04 | 4 |
| ..... | ................. | ..DDR.....F....... | ...... | .STAEG...F.. | A..A........ | 0.04 | 4 |
| ..... | ................. | .QPN......F......T | ...N.. | .D.GGSD.AYDR | A..A........ | 0.04 | 4 |
| RA... | F................ | .PPNG.....F......T | ...DDR | EDASG....FDR | A..A........ | 0.04 | 4 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| RA... | F.....NNA.HK.T.D.R | ..........F....... | ....D. | ...DTN..E.DR | A..A........ | 0.04 | 4 |
| HT... | F.....DRG.S..T.A.S | .V........F....... | ...... | ............ | A..A........ | 0.04 | 4 |
| ..... | .................. | .................. | .DDR | .D.GRA...F.. | A..A........ | 0.04 | 4 |
| T...T | F......G..NL.T.E.R | .........NF....... | R...D. | E.AKAADAAYDE | A..A........ | 0.04 | 4 |
| RA..T | F.....DGA.R..P.A.K | .........NF....... | R...D. | ............ | A..A........ | 0.04 | 4 |
| GA... | F.....AEG.LK.M.H.L | ..DGE....DF....... | R...D. | ............ | A..A........ | 0.04 | 4 |
| TT... | F.....AE...A.T...R | .QPN......F....... | ...A.. | ............ | A..A........ | 0.04 | 4 |
| ..... | .................. | .KYT.....DF....... | ...KGR | .DAS.N...VDG | A..A........ | 0.04 | 4 |
| D...T | F.....DRG.S..T.A.S | .QHGG.....F....... | ...... | ..AGADD...DQ | A..A........ | 0.04 | 4 |
| TA... | .................. | ..HG.....NF......T | ...DDR | ............ | A..A........ | 0.04 | 4 |
| AA... | F.....DQ..R..P.S.R | T.P......DF....... | ...D.. | .DANTN.A.VDS | A..A........ | 0.04 | 4 |
| ..... | .................. | .................. | ...DDR | EDTAGA....DR | A..A........ | 0.04 | 4 |
| ..... | .................. | .................. | R...D. | ..TG.N.IAF.D | A..A........ | 0.04 | 4 |
| ..... | F.....ASA.S..T.T.G | .QPG.....DF....... | ...... | ............ | A..A........ | 0.04 | 4 |
| E.... | F.....ASA.S..T.T.G | .................. | ...... | ............ | ............ | 0.04 | 4 |
| E.... | F......KT.NV.K.T.H | ..YN......F......T | ...D.R | ............ | A..A........ | 0.04 | 4 |
| ..... | ......AEG.LK.M.H.L | ..DGE....DF....... | ...... | ............ | ............ | 0.04 | 4 |
| ..... | .................. | .................. | ...DD. | .DTA.A.AA.GE | A..A........ | 0.04 | 4 |
| ..... | .................. | .................. | R..N.. | ..AKAND...GS | A..A........ | 0.04 | 4 |
| AA... | F.....ATT.NV.T.G.R | .QPTR....DF....... | E..NG. | ENATASD...GS | A..A........ | 0.04 | 4 |
| ..... | F.....GQ..LN.L.D.R | ..A......DF....... | R...G. | ..ARRS.A.FDD | A..A........ | 0.04 | 4 |
| ..... | .................. | .................. | G..DG. | ............ | A..A........ | 0.04 | 4 |
| ..... | .................. | .........NF....... | ...N.. | ESARGSD.A.DE | A..A........ | 0.04 | 4 |
| ..... | .................. | .................. | ...D.. | .DASGS....GG | A..A........ | 0.04 | 4 |
| GT... | F.....AEG.LK.M.H.L | ..DGE....DF....... | ...N.. | ............ | A..A........ | 0.04 | 4 |
| GT... | F.....STA.HA.M.S.V | ..DGE....DF....... | ...... | .SAKAA.AA.DE | A..A........ | 0.04 | 4 |
| E.... | F.....NA..PI.P.P.R | ..DGE....DF....... | ...... | ............ | A..A........ | 0.04 | 4 |
| ....T | F.....GGG.LD.T...R | T.P......DF....... | ...D.. | ESGG.G..E..Q | A..A........ | 0.04 | 4 |
| A...T | F.....DNT.SK.L...K | ..DGE....DF....... | ...... | E.AAGD.I.V.R | A..A........ | 0.04 | 4 |
| NA... | .................. | TKHGG....NF....... | ...D.. | E.GDGS...F.R | A..A........ | 0.04 | 4 |
| ..... | .................. | .................. | ...... | .SAKAA.AA.DE | A..A........ | 0.04 | 4 |
| ..... | .................. | .................. | R..D.R | ESTKR....VGE | A..A........ | 0.04 | 4 |
| ..... | .................. | .................. | ....GR | ............ | ............ | 0.04 | 4 |
| ..... | .................. | .................. | G..TDR | E..K.NDAEVGQ | A..A........ | 0.04 | 4 |
| ..... | .................. | .........NF......T | R..AD. | ............ | A..A........ | 0.04 | 4 |
| SA... | F......GG.NA.H.Q.R | .V........F....... | ...... | ..AAA.....GR | A..A........ | 0.04 | 4 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| G...T | F.....DRG.H..L.S.L | .V........F....... | ...... | .......... | A..A........ | 0.04 | 4 |
| RT... | ................. | ..ATR....DF....... | E..N.. | E..RRA.....Y | A..A........ | 0.04 | 4 |
| ..... | ................. | ................. | ....GR | .STAAG...VDG | A..A........ | 0.04 | 4 |
| GA... | F.....S.A.N..L...L | .V........F....... | R...D. | E.AAGSD..... | A..A........ | 0.04 | 4 |
| ..... | F................. | .V........F....... | ...... | .......... | GRRAT..DDA.. | 0.04 | 4 |
| ..... | ................. | .........DF....... | ...DG. | .NGGGD....GR | A..A........ | 0.04 | 4 |
| ..... | F................. | .V........F....... | ...... | .......... | GTQSR..DRG.. | 0.04 | 4 |
| ..... | ................. | .........DF....... | ...D.. | .S.KA..TE.DS | A..A........ | 0.04 | 4 |
| ..... | ................. | ................. | ....D. | ES.TGSD..VDR | A..A........ | 0.04 | 4 |
| SA..T | F......TG.IL...T.R | .QAS.....NF......T | ....GR | .DAGA.D.EVDE | ............ | 0.04 | 4 |
| AT... | F.....GTG..P.T.D.R | ..DGE....DF....... | ...ND. | ENAAGGDT..GR | A..A........ | 0.04 | 4 |
| SA... | F.....AQ...A.L.... | T.P......DF....... | ...DDR | ENTKGD....D. | A..A........ | 0.04 | 4 |
| ..... | F.....ARA.L..L.Q.G | ..DGE....DF....... | ...... | .......... | A..A........ | 0.04 | 4 |
| ....T | ................. | ................. | ...... | .......... | | 0.04 | 4 |
| ..... | ................. | .........NF....... | ...A.. | .......... | A..A........ | 0.04 | 4 |
| ..... | ................. | ................. | ....G. | ENAGR.DI..GS | A..A........ | 0.04 | 4 |
| ..... | F.....AQ...A.L.... | .QD.E.....F..P.... | ...... | .......... | ............ | 0.04 | 4 |
| ..... | ................. | ................. | R..TG. | ..TGAS.A..DH | A..A........ | 0.04 | 4 |
| GT... | F.....ASA.S..T.T.G | .QPG.....DF....... | ...DDR | .......... | A..A........ | 0.04 | 4 |
| RA... | F.....NGG.LN.I.G.R | TQPT.....DF....... | ...... | .NAAAN..EF.H | A..A........ | 0.04 | 4 |
| G...T | ................. | .KYT.....NF....... | ...NDR | ED.R.S.A...G | A..A........ | 0.04 | 4 |
| R.... | F.....GN..HM.P.... | .........DF....... | ....GR | .NAGASDA.FDQ | A..A........ | 0.04 | 4 |
| N.... | F.....NGG.NN.K.T.R | ..PN.....NF....... | ...NDR | .......... | A..A........ | 0.04 | 4 |
| SA... | F.....DRG.HA.T...G | .QPN......F......T | ...N.. | .......... | A..A........ | 0.04 | 4 |
| ..... | ................. | ................. | ...ADR | EDGDGA..A.DR | A..A........ | 0.04 | 4 |
| ..... | ................. | .Q.S.....NF......T | E..DD. | .......... | A..A........ | 0.04 | 4 |
| ..... | ................. | ................. | R...D. | .N.AGA.AEYDD | A..A........ | 0.04 | 4 |
| ..... | F................. | .V........F....... | ...... | .......... | .HRGG...D..T | 0.04 | 4 |
| TT..T | ......GRG.SP.K.M.G | .QPG.....NF....... | ...DDR | .......... | A..A........ | 0.04 | 4 |
| ..... | ................. | ................. | R..ND. | ..AG.N.AA.GQ | A..A........ | 0.04 | 4 |
| ..... | F................. | .V........F......T | ...N.. | ..TG.D..A.GG | APRDP....S.. | 0.04 | 4 |
| ..... | ................. | .QPN......F....... | ...... | .......... | A..A........ | 0.04 | 4 |
| ..... | F.....SAT.SM.K...R | .V........F....... | ...... | .......... | A..A........ | 0.04 | 4 |
| RT... | ................. | .KDDG....NF....... | ...... | E..RRA.....Y | A..A........ | 0.04 | 4 |
| ..... | ................. | ................. | G..TG. | .......... | A..A........ | 0.04 | 4 |
| .T..T | ................. | ................. | ....D. | .......... | A..A........ | 0.04 | 4 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .................... | ...... | E.ASTA..A.GQ | A..A........ | 0.04 | 4 |
| NT... | F.....SAT.PV.T.Q.G | TQDGE....DF....... | ...DG. | ............ | A..A........ | 0.04 | 4 |
| ..... | ................. | .................... | ...... | E.AG..D.A.GR | A..A........ | 0.04 | 4 |
| E.... | ................. | .KYT.....NF....... | ...D. | ............ | ............ | 0.04 | 4 |
| ..... | ................. | .................... | ...D. | E.T..S..A..R | A..A........ | 0.04 | 4 |
| ..... | ................. | .................... | ...... | ............ | SARAP..VHN.A | 0.04 | 4 |
| G.... | F.....GRG.H..P.E.R | .KD.E.....F....... | ...D. | E..RG.D..FDG | A..A........ | 0.04 | 4 |
| ..... | ................. | T.PG.....NF....... | ...D.. | EN.TTG.IE.DR | A..A........ | 0.04 | 4 |
| ..... | ................. | .........DF......T | ....GR | E.TSGDD.EYDN | A..A........ | 0.04 | 4 |
| HT..T | ................. | .Q.DR.....F....... | ....D. | ............ | A..A........ | 0.04 | 4 |
| TT... | F.....SAG..L.P.P.. | .................... | ...... | ............ | A..A........ | 0.04 | 4 |
| ..... | ................. | .................... | ...DDR | .STAAG...VDG | A..A........ | 0.04 | 4 |
| ..... | ................. | .................... | E..DGR | ............ | ............ | 0.04 | 4 |
| ..... | F................ | .V........F....... | ...... | ............ | GARGN..AGR.D | 0.04 | 4 |
| NA... | F.....NR..N..I.T.G | .QYGQ....DF......T | E..NGR | ............ | A..A........ | 0.04 | 4 |
| GT... | F.....SRG..L.P.G.G | ..HG.....NF......T | ....GR | ............ | A..A........ | 0.04 | 4 |
| ..... | ................. | TKDDR....DF....... | ...DDR | .DAGRN.IA.DG | A..A........ | 0.04 | 4 |
| NA... | F.....DA..IA.L.K.R | .KPDQ.....F....... | ...DG. | ............ | A..A........ | 0.04 | 4 |
| ..... | ................. | .................... | ....D. | .DAGES..A.GD | A..A........ | 0.04 | 4 |
| RA... | F.....G.G.HV.H.G.R | .........NF....... | R...D. | .SAKAA.AA.DE | A..A........ | 0.04 | 4 |
| .A... | F.....D.T.HP.M...R | ..A......DF....... | ...DG. | .STSRGD...GG | A..A........ | 0.04 | 4 |
| ..... | ................. | .................... | E..KDR | ............ | ............ | 0.04 | 4 |
| ..... | F................ | .V........F....... | ...... | ............ | TPHGP..DEM.P | 0.04 | 4 |
| GT..T | F.....GT..NL.K.D.R | .Q.S......F....... | R..AD. | ..AA.D.IA... | A..A........ | 0.04 | 4 |
| E.... | F.....NGG.NN.K.T.R | .QPN......F......T | ...N.. | ............ | A..A........ | 0.04 | 4 |
| GT... | F.....DRG.SL.M...G | ..DGE....DF....... | ...... | ............ | A..A........ | 0.04 | 4 |
| T.... | F.....NGG.HV.....L | .KDDG....NF....... | ...DDR | ............ | A..A........ | 0.04 | 4 |
| ..... | F................ | .V........F....... | ...... | ............ | KD.GR..FGV.. | 0.04 | 4 |
| ..... | F.....A.T.NN.T.S.H | .........NF....... | R...D. | ............ | A..A........ | 0.04 | 4 |
| ..... | ................. | .........NF....... | ...ND. | EN.G.A.....Q | A..A........ | 0.04 | 4 |
| GA... | F.....DRA.N..P...L | ..HG.....NF......T | ...A. | ............ | A..A........ | 0.04 | 4 |
| .A... | ................. | .................... | R..DD. | ............ | ............ | 0.04 | 4 |
| ..... | F..I............. | .V........F....... | ...... | ............ | GP.GT..FNV.D | 0.04 | 4 |
| NA..T | ................. | ..HG.....NF......T | ...A. | ES.DRN.....Q | A..A........ | 0.04 | 4 |
| ..... | ................. | .................... | ...D.. | ES.NRD..A..G | A..A........ | 0.04 | 4 |
| S.... | F.....AAR..K.T.E.L | ..DGE....DF....... | ...... | EDGG.GDIA.DR | A..A........ | 0.04 | 4 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| TA... | F.....SGT.S..T.T.. | ..HG.....NF......T | ...A.. | ........... | A..A........ | 0.04 | 4 |
| ..... | .................. | ..YN......F......T | ...D.R | ........... | A..A........ | 0.04 | 4 |
| ..... | F................. | .V........F....... | ...... | ........... | DRQTK..SD... | 0.04 | 4 |
| A.... | .................. | .KPDQ.....F....... | ....G. | ...REGD...GQ | A..A.....G.. | 0.04 | 4 |
| E.... | F................. | .................. | R..AD. | ........... | A..A........ | 0.04 | 4 |
| KA... | F......S..SE.T...R | ..PNG....DF....... | G..NDR | .DGGGN.....R | A..A........ | 0.04 | 4 |
| R.... | F................. | ..ATG....NF..P...T | ...AD. | ........... | A..A........ | 0.04 | 4 |
| ..... | .................. | .................. | ...DG. | ..ARTADTE.DS | A..A........ | 0.04 | 4 |
| ..... | .................. | .V........F....... | ...DDR | ........... | A..A........ | 0.04 | 4 |
| GA... | .................. | ..HG.....NF......T | ...A.. | ..AA.SDI.... | A..A........ | 0.04 | 4 |
| ..... | .................. | TQ.TG....DF....... | ...DDR | ...AGS.IAFDG | A..A........ | 0.04 | 4 |
| ..... | F.....ARA.L..L.Q.G | .V........F....... | ...D.. | ........... | A..A........ | 0.04 | 4 |
| ..... | .................. | .................. | ...DDR | .STTGA...V.Q | A..A........ | 0.04 | 4 |
| ..... | .................. | .................. | R..A.. | ........... | A..A........ | 0.04 | 4 |
| ..... | F................. | .V........F....... | ...... | ........... | N.RAP..ATV.D | 0.04 | 4 |
| ..... | F................. | .V........F....... | ...... | ........... | ATRST...DE.A | 0.04 | 4 |
| TT... | F................. | .V........F....... | ...... | ........... | ............ | 0.04 | 4 |
| E.... | F......G..NQ.N.D.K | ...TE.....F......T | E..KD. | ..TG.A...GN | A..A........ | 0.04 | 4 |
| HT... | F.....AA.HP.P.Q.K | .QPN......F......T | ...N.. | E.TS.D..AFDQ | A..A........ | 0.03 | 3 |
| SA... | .................. | .KD.E....DF....... | R..A.. | ........... | A..A........ | 0.03 | 3 |
| AA... | F.....A.G..V.T.H.R | .KDDG....NF......T | ...... | ENGD....E.DR | A..A........ | 0.03 | 3 |
| RA... | F.....NGT.IL.T.A.K | .Q.S......F....... | R...D. | .SANESD...DQ | A..A........ | 0.03 | 3 |
| SA... | .................. | .................. | E..AD. | E.ASTND..... | A..A........ | 0.03 | 3 |
| ..... | .................. | .................. | ...D.. | ESGS.S.IA.DQ | A..A........ | 0.03 | 3 |
| ..... | F................. | .V........F....... | ...... | ........... | G.RSG..NQA.H | 0.03 | 3 |
| NA... | F.....A.G..V.T.H.R | .QPSR.....F....... | E..NG. | ..AGTSDIA.DR | A..A........ | 0.03 | 3 |
| .A..T | .................. | .................. | E..KD. | .S.ST...E.GH | A..A........ | 0.03 | 3 |
| D...T | .............K.S | .................. | ...... | E.AAGND.EFDQ | ............ | 0.03 | 3 |
| ..... | .................. | .KAS.....NF......T | ....D. | ENG.AG...V.H | A..A........ | 0.03 | 3 |
| ..... | .................. | .................. | R..AD. | ..AAAN..E.DG | A..A........ | 0.03 | 3 |
| GA... | F.....SGA..K.N.S.S | ..A......DF....... | ...DG. | E........... | A..A........ | 0.03 | 3 |
| ..... | F................. | .V........F....... | ...... | ........... | SERTP..F.T.Q | 0.03 | 3 |
| R...T | .................. | TQDGE....DF....... | ...DG. | ENTATDD...GH | A..A........ | 0.03 | 3 |
| RA..T | F.....NQG.RV.I.N.R | .........NF....... | R...D. | .DASGDD.EVD. | A..A........ | 0.03 | 3 |
| ...A. | .................. | .PANG.....F......T | ....GR | .DAS.N...VDG | A..A........ | 0.03 | 3 |
| S.... | F.....AGG.P..L...G | ..A......DF....... | ...ND. | ..GAAND....H | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| AT..T | ................. | .KDDG....NF......T | ...DDR | E.AGRN.T..DD | A..A........ | 0.03 | 3 |
| ..... | ................. | ................. | R..AD. | E.AGGS..AVDG | A..A........ | 0.03 | 3 |
| RA... | ......KT.NK...A.G | .V.......F....... | ...... | ............ | ASSNH..AKG.D | 0.03 | 3 |
| DA... | ..............S.. | .QPG.....NF....... | ...DDR | ED.G.GD.AYDR | A..A........ | 0.03 | 3 |
| ..... | ................. | ................. | R..AGR | .DAG.A.I..DG | A..A........ | 0.03 | 3 |
| ..... | F................ | .V.......F....... | ...... | ............ | GPSSA..IQK.H | 0.03 | 3 |
| D.... | F.....AGT.PK.L.D.S | .KYT.....NF......T | ...... | ............ | A..A........ | 0.03 | 3 |
| ..... | F................ | .V.......F....... | ...... | ............ | ATKTP..SDA.E | 0.03 | 3 |
| SA... | F.....DNT.SK.L...K | TKAGE....NF......T | R...G. | .SG..ND...DG | A..A........ | 0.03 | 3 |
| ..... | F................ | .V.......F....... | ...... | ............ | GTRSP..S.N.D | 0.03 | 3 |
| N...T | ......SRT..A...T.N | ..DGE....DF....... | ...... | ............ | A..A........ | 0.03 | 3 |
| TA..T | F.....DH..R..P.G.S | .V........F....... | ...... | EN.G.A....GQ | A..A........ | 0.03 | 3 |
| ..... | ................. | ................. | ...... | ..GGESD.E.D. | A..A........ | 0.03 | 3 |
| E.... | F.....ASA.S..T.T.G | ................. | E..TD. | ............ | ............ | 0.03 | 3 |
| ..... | F................ | .V.......F....... | ...... | ............ | DRRTE..SRV.A | 0.03 | 3 |
| ..... | ................. | ................. | ...DDR | ...GTND.AYDE | A..A........ | 0.03 | 3 |
| ..... | F................ | .V.......F....... | ...... | ............ | AAHDG...RE.. | 0.03 | 3 |
| ..... | ................. | ................. | ...DDR | E.T..S..A..R | A..A........ | 0.03 | 3 |
| EA... | ................. | ................. | E..AD. | ............ | ............ | 0.03 | 3 |
| ..... | ................. | TQ..H....NF....... | ...... | ..AG.DDIA.DN | A..A........ | 0.03 | 3 |
| N.... | ................. | .KDDG....NF......T | G..DD. | ...NG....VDG | A..A........ | 0.03 | 3 |
| T.... | F.......G.PE.T.G.R | .Q.GQ....DF....... | ....G. | ............ | A..A........ | 0.03 | 3 |
| TT..T | F.....ASA.S..T.T.G | .QPG.....DF....... | ...... | ............ | ............ | 0.03 | 3 |
| ..... | ................. | ................. | ...... | ..TG.N.IAF.D | A..A........ | 0.03 | 3 |
| ..... | ................. | ................. | ...... | ...G.GD.A.DR | A..A........ | 0.03 | 3 |
| NA... | F.....STA..Q.H.Q.L | TK.NE....DF....... | ...... | .N.AE...E.DG | A..A........ | 0.03 | 3 |
| HT..T | F......GT.NM.L.Q.G | .KYT.....NF......T | R...D. | E.GAGSD.E.D. | A..A........ | 0.03 | 3 |
| E.... | F................ | .V.......F....... | ...... | ............ | ............ | 0.03 | 3 |
| RA... | F.....DTG.SM.K.G.M | .Q.S......F....... | ...D.. | ............ | A..A........ | 0.03 | 3 |
| ..... | ................. | ................. | ...N.. | .DAGRN.IA.D. | A..A........ | 0.03 | 3 |
| ..... | ................. | ................. | ...... | ENAS.G.A.VDS | A..A........ | 0.03 | 3 |
| AA... | F......S..PM.T.S.K | .PPNG.....F......T | ...DDR | .D.GG.....GH | A..A........ | 0.03 | 3 |
| ..... | ................. | ................. | ...D.. | ENTSEG....GH | A..A........ | 0.03 | 3 |
| E.... | F.....ASA.S..T.T.G | .QPG.....DF....... | R..DD. | ............ | A..A........ | 0.03 | 3 |
| NT... | F.....AGA.NK.L...K | .V.......F....... | ...... | ENARASDA..GS | A..A........ | 0.03 | 3 |
| TT..T | ................. | TKDDR....DF....... | ...DDR | ............ | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................ | .V........F....... | ...... | ........... | GRHS....K..E | 0.03 | 3 |
| AT..T | F.....S.A.IA.M.T.R | TQ.TG....DF....... | ...DDR | ..TR.ND.A.DE | A..A........ | 0.03 | 3 |
| G.... | F.....G.G.RA.N.E.R | .KYT.....NF......T | ...DD. | ........... | A..A........ | 0.03 | 3 |
| NA... | ................ | TQADR....NF......T | G..ND. | ........... | A..A........ | 0.03 | 3 |
| ..... | ................ | TKHGG....DF....... | ...DD. | .D.R....AFDD | A..A........ | 0.03 | 3 |
| E.... | F......TG.IL...T.R | .QAS......F....... | ....D. | ........... | A..A........ | 0.03 | 3 |
| ..... | ................ | ..DGE....DF....... | ...... | ..T.EG.IE..H | A..A........ | 0.03 | 3 |
| ..... | ................ | ................ | .....R | ..GSA..I..GG | A..A........ | 0.03 | 3 |
| ..... | ................ | .........DF....... | ...D.. | ........... | A..A........ | 0.03 | 3 |
| ..... | ................ | ................ | ....D. | E.TVTNDA...S | A..A........ | 0.03 | 3 |
| AA... | F................ | TQ.TG....DF....... | ...DDR | E.AGR..A.FDR | A..A........ | 0.03 | 3 |
| ..... | F................ | .V........F....... | ...... | ........... | TPRGG...TM.H | 0.03 | 3 |
| DT... | F.....AQ...A.L.... | ................ | ...... | E.AS.A.TAV.H | A..A........ | 0.03 | 3 |
| ..... | ................ | ................ | ...D.. | E..TRSD.AFDD | A..A........ | 0.03 | 3 |
| N.... | ................ | T.ASH....DF....... | ...DG. | ........... | A..A........ | 0.03 | 3 |
| ..... | ................ | ...........F....... | ...... | E..AGADIE..H | A..A........ | 0.03 | 3 |
| R.... | ................ | .QAS.....NF......T | E..AGR | ........... | A..A........ | 0.03 | 3 |
| ..... | F................ | .V........F....... | ...... | ........... | KDRTP..FQA.D | 0.03 | 3 |
| ..... | F................ | .V........F....... | ...... | ........... | KDHT...S.A.A | 0.03 | 3 |
| SA... | ................ | ................ | G..ND. | ........... | A..A........ | 0.03 | 3 |
| E.... | F.....GAA.L..L.N.S | ................ | ...... | ........... | A..A........ | 0.03 | 3 |
| TA... | F.....GRG.NV.N.S.R | ..YN......F......T | R...G. | ........... | A..A........ | 0.03 | 3 |
| ..... | ................ | ................ | R..DD. | E..G.S.T.FDS | A..A........ | 0.03 | 3 |
| ..... | ................ | ..HG.....NF......T | ...A.. | E.TATDD...DG | A..A........ | 0.03 | 3 |
| ..... | ................ | ................ | E..AD. | E.AKEN.A..DE | A..A........ | 0.03 | 3 |
| EA... | F.....AST.HD.T.E.R | .PPNG.....F......T | ...DDR | ..TG.N.IAF.D | A..A........ | 0.03 | 3 |
| ..... | ................ | ................ | ...... | E.TR.N.....Q | A..A....V... | 0.03 | 3 |
| .A... | F.....ANG.HL.K.K.S | ..A......DF....... | ...DG. | E.AG.GD.EY.. | A..A........ | 0.03 | 3 |
| ..... | F.....DAA.IK.T.Q.N | ..DGE....DF....... | ...... | E.......... | ........... | 0.03 | 3 |
| ..... | ................ | ..P.E....NF....... | R...D. | ESAT.A.A..DR | A..A........ | 0.03 | 3 |
| G.... | F.....NN..SA.N...R | ..DGE....DF....... | ...DDR | .DAG.A.I..DG | A..A........ | 0.03 | 3 |
| G.... | F.......G.PE.T.G.R | .Q.GQ....DF....... | ....G. | ........... | A..A........ | 0.03 | 3 |
| ..... | ................ | ................ | R...D. | EDGSR.D.AV.E | A..A........ | 0.03 | 3 |
| ..... | F.....DAT..L.I.N.R | .KDSR....DF....... | ...D.. | ........... | A..A........ | 0.03 | 3 |
| AT... | F.....SA..RA.....R | .QAS......F....... | ...... | ESAAASD..VGQ | A..A........ | 0.03 | 3 |
| G.... | ................ | .Q.DR.....F....... | ....D. | ...GAD.IA..G | A..A........ | 0.03 | 3 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| NT..T | ................. | ................. | E..AGR | ESAT.A.A..DR | A..A........ | 0.03 | 3 |
| TA..T | F.....GDG....K.Q.R | .V........F....... | ...DDR | .SAKAA.AA.DE | A..A........ | 0.03 | 3 |
| RA..T | F.....GNG.HV.H.G.R | ..ATR....DF....... | ...... | EDADG.DT...H | A..A........ | 0.03 | 3 |
| R...T | ................. | .V........F....... | E..TD. | ............ | A..A........ | 0.03 | 3 |
| E.... | F.....DGT.SM.N.G.R | ..DGE....DF....... | ...... | ............ | A..A........ | 0.03 | 3 |
| GT... | F.....AEG.LK.M.H.L | ..DGE.....F....... | ...... | ............ | A..A........ | 0.03 | 3 |
| H.... | F.....GQG.IA.....K | .Q.......DF....... | G..DG. | ............ | A..A........ | 0.03 | 3 |
| GA... | ................. | T.ASH....DF....... | ...DDR | ..AG.A..EFGG | A..A........ | 0.03 | 3 |
| G...T | F.....DAT..L.I.N.R | T.P......DF....... | ...D.. | ...TTSD..F.H | A..A........ | 0.03 | 3 |
| D.... | F................. | .V........F....... | ...... | ............ | TAQSG..FN..D | 0.03 | 3 |
| ..... | F................. | .V........F....... | ...... | ............ | S.SNG...GG.T | 0.03 | 3 |
| A.... | ................. | ..DGE....DF....... | R...GR | ENTSRND.EV.S | ............ | 0.03 | 3 |
| ..... | F.....GK..SI.N.K.R | ................. | ...DDR | ............ | A..A........ | 0.03 | 3 |
| ..... | F................. | .Q.DH....NF....... | ...DD. | ............ | A..A........ | 0.03 | 3 |
| ..... | ................. | .................T | R..AG. | ............ | A..A........ | 0.03 | 3 |
| D.... | F.....NKT.I..K.... | .Q.DR.....F....... | G..ND. | ............ | A..A........ | 0.03 | 3 |
| ..... | ................. | ................. | E..AD. | .DTGGNDAE.DQ | A..A........ | 0.03 | 3 |
| ..... | ................. | ................. | E..NGR | .NGDTSD.A..Q | A..A........ | 0.03 | 3 |
| G.... | ................. | ........NF....... | R...D. | EN.G.G..EF.Q | A..A........ | 0.03 | 3 |
| SA... | ................. | .QAS......F....... | ...... | E.ATRGDTE.DR | A..A........ | 0.03 | 3 |
| ..... | ................. | ................. | G..DD. | ES.DRN..A.DN | A..A........ | 0.03 | 3 |
| ..... | ................. | ................. | ...DDR | E.AGAND.AV.H | A..A........ | 0.03 | 3 |
| ..... | ................. | ................. | ...... | E.ATADDA..GS | A..A........ | 0.03 | 3 |
| D...T | F.....NDG.PA.K.T.R | .QHNQ.....F......T | ...N.. | E.TGAN.AE.GE | A..A........ | 0.03 | 3 |
| DT... | F.....AEG.LK.M.H.L | ..DGE....DF....... | ...... | ............ | ............ | 0.03 | 3 |
| GT... | F................. | .V........F....... | ...... | ............ | ............ | 0.03 | 3 |
| ..... | ................. | ................. | R..DD. | .DTG.GD.A..H | A..A........ | 0.03 | 3 |
| ..... | F................. | .V........F....... | ...... | ............ | TTSA...VRV.D | 0.03 | 3 |
| ..... | ................. | ................. | ...DD. | .DAGES..AF.Q | A..A........ | 0.03 | 3 |
| ..... | ................. | ........NF......T | R...D. | ENGREND.A.DD | A..A........ | 0.03 | 3 |
| ..... | F................. | .V........F....... | ...... | ............ | NNQGR..YTG.E | 0.03 | 3 |
| ..... | ................. | ................. | ...AG. | ............ | A..A........ | 0.03 | 3 |
| ..... | ................. | .................T | ...AG. | ..ASE...E.DN | A..A........ | 0.03 | 3 |
| ..... | ................. | ................. | ...D.. | ESAKTADAAVDD | A..A........ | 0.03 | 3 |
| ..... | F.....SN..PL.K.T.. | ................. | G..A.R | E.AG..D.A.GR | A..A........ | 0.03 | 3 |
| NA... | F.....DR..II...A.R | ................. | ...AG. | E.AGGD.AA.DD | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| DT... | F.....DHT.R..M.G.R | .Q.T.....NF.......T | R...DD. | ........... | A...A........ | 0.03 | 3 |
| R.... | F.....SGA..N...G.R | .Q.DH....NF....... | ...DD. | .NAA.A...GD | A...A........ | 0.03 | 3 |
| E.... | F.....S.T.NV.L.D.. | .Q.DR.....F....... | ...DGR | E.ATG...A.G. | A...A........ | 0.03 | 3 |
| ..... | ................. | TQ.TQ.....F....... | ...DDR | ........... | A...A........ | 0.03 | 3 |
| ..... | ................. | ................. | ...N.. | ..TR.ND.A.D. | A...A........ | 0.03 | 3 |
| N.... | ................. | ..AGR....DF......T | R...D.. | ES.TTG..A..G | A...A........ | 0.03 | 3 |
| N.... | ......DAT..Q.L.G.. | .KDT......F......T | ...D.R | ........... | ............ | 0.03 | 3 |
| ..... | ................. | ....H............ | R...DD. | EDGAAA....GQ | A...A........ | 0.03 | 3 |
| .A..T | F.....GRT.ND.L.Q.R | .........NF....... | R...D. | E.TR.N.....Q | A...A........ | 0.03 | 3 |
| ..... | ................. | .........DF....... | ....D. | ESAN...I...H | A...A........ | 0.03 | 3 |
| N.... | F.....AE...A.T...R | ..PN.....NF....... | ...... | ES.TRSDI.FDH | A...A........ | 0.03 | 3 |
| TT..T | F.....AQG.NV.H.K.R | ................. | ...... | .NGSAN..E.DQ | A...A........ | 0.03 | 3 |
| ..... | F.....DA..IA.L.K.R | .KDSR....DF......T | G...DG. | ........... | ............ | 0.03 | 3 |
| ..... | F................ | .V........F....... | ...... | ........... | SHRGE..FDV.T | 0.03 | 3 |
| E.... | F......AG.NV.N.S.R | T.P......DF....... | ...DG. | E.TDGNDA..GQ | A...A........ | 0.03 | 3 |
| E.... | ......SG..IK.K.D.R | .KPDQ....DF....... | ...D.. | ........... | ............ | 0.03 | 3 |
| GA... | F.....DG..I..K.K.G | .QAS......F....... | ...... | .SAKAA.AA.DE | A...A........ | 0.03 | 3 |
| .A... | F.....DQ..R..P.S.R | T.PGG....NF....... | ...D.R | ........... | A...A........ | 0.03 | 3 |
| D.... | F.....AQA.IK.M.A.S | .QPN......F......T | ...N.. | ........... | A...A........ | 0.03 | 3 |
| H.... | ................. | ................. | ...DDR | ENGD....E.DR | A...A........ | 0.03 | 3 |
| ..... | ................. | .V.......DF....... | ...... | ........... | A...A........ | 0.03 | 3 |
| ..... | ................. | ................. | E..NGR | ........... | A...A........ | 0.03 | 3 |
| ..... | ................. | .QDT......F......T | ...D.. | ........... | A...A........ | 0.03 | 3 |
| RA... | F................ | .V........F....... | ...... | ........... | APRNS..VR..H | 0.03 | 3 |
| ..... | ................. | ................. | ...... | E.TKRA.AEVDQ | A...A........ | 0.03 | 3 |
| TA... | F................ | ................. | ...... | ........... | GQRDG...RN.A | 0.03 | 3 |
| ..... | ................. | ................T | ...NDR | E.TGAN.AE.GE | A...A........ | 0.03 | 3 |
| ..... | F................ | .V.......F....... | ...... | ........... | TRHSP..SEG.H | 0.03 | 3 |
| ..... | F.....GTG..P.T.D.R | .KYT.....NF......T | ....D. | ........... | A...A........ | 0.03 | 3 |
| GT... | F................ | .V.......F....... | ....G. | ........... | A...A........ | 0.03 | 3 |
| GT..T | ................. | ................. | ...... | ........... | ............ | 0.03 | 3 |
| ..... | ................. | ................T | R..N.. | ........... | A...A........ | 0.03 | 3 |
| TT..T | F.....NAT.RP.K.A.R | .V........F....... | ...... | ..AGT.D.EYGQ | A...A........ | 0.03 | 3 |
| ..... | ................. | ................. | E..KG. | ........... | A...A........ | 0.03 | 3 |
| ..... | ................. | ................. | ...D.R | E.ADRN....GS | A...A........ | 0.03 | 3 |
| R.... | F.....GRG.NQ.K.E.H | T.P......DF....... | ...D.. | KNARASDAAVDQ | A...A........ | 0.03 | 3 |

TABLE 3-continued

AAV capsid proteins having increased specificity for and/or transduction of CD447$^-$/133$^-$ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| G.... | F.....NQG.RV.I.N.R | ..DGE....DF....... | ...... | ........... | A..A........ | 0.03 | 3 |
| ..... | F.....SGA..K.N.S.S | TQDS.....NF....... | ...... | E.AAAA..AF.S | A..A........ | 0.03 | 3 |
| RA..T | F................. | .V.........F...... | ...... | ........... | APRNS..VR..H | 0.03 | 3 |
| GA... | .................. | ..PNG....DF....... | G..NDR | ..TGTS...YDS | A..A........ | 0.03 | 3 |
| .T..T | F.....GN..HM.P.... | TQASG.....F......T | ...D.. | ........... | A..A........ | 0.03 | 3 |
| D...T | F......Q...Q.L.K.V | ..DGE....DF....... | ...... | ........... | A..A........ | 0.03 | 3 |
| RA... | .................. | .................. | E..TG. | .NAA...A..DD | A..A........ | 0.03 | 3 |
| ..... | .................. | ..A.Q....NF....... | ...DD | E.AG.GD.EY.. | A..A........ | 0.03 | 3 |
| RA... | .................. | ..YN......F......T | ...D.R | ........... | A..A........ | 0.03 | 3 |
| ..... | F................. | .V.........F...... | ...... | ........... | AASS....RV.. | 0.03 | 3 |
| NT... | F.....NR..N..I.T.G | TKPS.....DF....... | ...DDR | ........... | A..A........ | 0.03 | 3 |
| TA..T | F.....GR..PN.N.Q.L | .KP......NF....... | R..ND. | ENTN.ADAA..E | A..A........ | 0.03 | 3 |
| E.... | F.....DTT.SH.T.T.G | T.P......DF....... | ...D.. | ..AARS..AF.Q | ............ | 0.03 | 3 |
| AT... | F.....AST.PI.K.Q.K | TQ.TH....DF....... | ...... | ........... | A..A........ | 0.03 | 3 |
| NT... | .................. | ..........F......T | R..AG. | E.ASGG.A..GS | V..A........ | 0.03 | 3 |
| SA..T | F.....DGT.SM.N.G.R | ..DD.....DF....... | ....D. | ........... | ............ | 0.03 | 3 |
| ..... | F................. | .V.........F...... | ...... | ........... | GRQDS..NR..E | 0.03 | 3 |
| ..... | .................. | .................. | R..DD. | EN.KAN....GG | A..A........ | 0.03 | 3 |
| ..... | .................. | ..DGE....DF....... | R..DD. | ........... | A..A........ | 0.03 | 3 |
| ..... | .................. | .................. | ...D.. | ESGGTD....DR | A..A........ | 0.03 | 3 |
| A.... | .................. | .................. | R..N.. | ........... | ............ | 0.03 | 3 |
| T.... | F......AG..L.T.N.R | .................. | ...... | ........... | A..A........ | 0.03 | 3 |
| ..... | F................. | .V.........F...... | ...DDR | ........... | NSRAT..S.G.H | 0.03 | 3 |
| GA... | F.....GHA.I..K.H.H | ..DGE....DF....... | ...... | ........... | A..A........ | 0.03 | 3 |
| ..... | F................. | .V.........F...... | ...... | ........... | GESG...AEM.T | 0.03 | 3 |
| ..... | .................. | .................. | R..D.R | ..AGEN..A.GN | A..A........ | 0.03 | 3 |
| ..... | .................. | ........DF......T | ...AG. | .NATG....VGS | A..A........ | 0.03 | 3 |
| ..... | ......STG.LH.T...R | ..DT.....KF......T | ...... | .NGSAN..AFGQ | A..A........ | 0.03 | 3 |
| ..... | .................. | .................. | ...DDR | E.AS.N..E.GQ | A..A........ | 0.03 | 3 |
| TA... | F................. | .................. | R...D. | ........... | ............ | 0.03 | 3 |
| NA..T | F.....SS..SL.K.E.K | .................. | ...... | .DARAADA...Q | A..A........ | 0.03 | 3 |
| ..... | F......AG.NP.P.D.R | .QAS.....NF....... | ...... | ........... | A..A........ | 0.03 | 3 |
| ..... | .................. | .................. | G..AGR | ........... | A..A........ | 0.03 | 3 |
| ..... | F.....NKT.IV.T.E.R | .........NF....... | R...D. | ........... | A..A........ | 0.03 | 3 |
| D.... | F.....SR...V.T.N.V | .I................ | ...... | E.TA.G.....G | A..A........ | 0.03 | 3 |
| ..... | F.....GR..IN...A.R | ..DGE....DF....... | E..AGR | ........... | A..A........ | 0.03 | 3 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| TA..T | F.......G.HK.T.N.G | T.PTG....DF....... | ...DDR | ..AG.N.AA.GQ | A..A........ | 0.03 | 3 |
| ..... | F................. | .V.........F....... | ...... | ............ | SPKN...AGS.H | 0.03 | 3 |
| E.... | F.....AQ...A.L.... | .................. | ...... | ............ | A..A........ | 0.03 | 3 |
| DA... | .................. | ..ATR....DF....... | ...... | ...GAD.IA..G | A..A........ | 0.03 | 3 |
| ..... | F.....GG..NK.M.... | .................. | ...D.R | ............ | A..A........ | 0.03 | 3 |
| ..... | F.....SNG.RE.L...K | TQ.TG....NF....... | ...... | .N.AGNDAAVDE | A..A........ | 0.03 | 3 |
| ..... | .................. | .V.........F....... | ...... | E.GT.G.T..GH | A..A........ | 0.03 | 3 |
| G...T | F.....AHG.HL.T.P.R | ...TE.....F......T | ...NGR | ..ANRD.A..DQ | A..A........ | 0.03 | 3 |
| ..... | F.....SRT..A...T.N | ..A.R....DF....... | R...D. | ............ | A.HAD........ | 0.03 | 3 |
| D...T | F.....NGG.NV.N.K.G | ..DNH....NF....... | R...G. | ............ | A..A........ | 0.03 | 3 |
| SA... | F......RT.LA.L.G.K | ..DGE....DF....... | R..DD. | E.AAND.EYGH | A..A........ | 0.03 | 3 |
| ..... | .................. | .................. | ...... | .NAGEG...VDS | A..A........ | 0.03 | 3 |
| ..... | .................. | .KPDQ....DF....... | R...DR | ............ | .SARGA.A.YDD | 0.03 | 3 |
| ..... | .................. | .................. | ...... | .DGGRG.AA..Q | A..A........ | 0.03 | 3 |
| ..... | ......ATT.NV.T.K.S | .Q.......DF....... | ...AD. | ............ | A..A........ | 0.03 | 3 |
| ..... | .................. | .................. | R..AGR | ............ | A..A........ | 0.03 | 3 |
| RA... | .................. | .................. | ...... | ............ | ............ | 0.03 | 3 |
| ..... | .................. | ..YN......F......T | ...... | ..ARTADTE.DS | A..A........ | 0.03 | 3 |
| ..... | F.....GG..NK.M.... | ..DGE....DF....... | ...... | .DAGRN.IA.DG | A..A........ | 0.03 | 3 |
| ..... | .................. | .................. | ...... | ESGRANDA...S | A..A........ | 0.03 | 3 |
| ..... | .................. | .................. | ...DG. | ..ASE..AAYDS | A..A........ | 0.03 | 3 |
| ..... | .................. | .................. | ....D. | ..TD.N...VGQ | A..A........ | 0.03 | 3 |
| .A... | .................. | ..HG.....NF......T | ...A.. | ............ | A..A........ | 0.03 | 3 |
| ..... | F................. | .V.........F....... | ...... | ............ | GPRGP..DGE.H | 0.03 | 3 |
| ..... | .................. | .................. | ...... | .NTGTA..E... | A..A........ | 0.03 | 3 |
| A.... | F.....GKG.ND.T.N.R | .V.........F....... | ...... | ENGGTN..E.GN | A..A........ | 0.03 | 3 |
| ..... | F................. | .V.........F....... | R..DGR | ENGGGSDAE.DD | A..A........ | 0.03 | 3 |
| ..... | .................. | .................. | ...DDR | ..ARGADAE..S | A..A........ | 0.03 | 3 |
| ..... | F......GT.NM.L.Q.G | .Q.S.............. | ...DDR | ............ | ............ | 0.03 | 3 |
| H.... | .................. | .Q.GQ....DF....... | ..G. | .NGST.....GG | A..A........ | 0.03 | 3 |
| E.... | F.....SA..SI.M.G.R | .QPN.....DF....... | ...D.. | ..TGTS...YGS | A..A........ | 0.03 | 3 |
| ..... | .................. | ........NF....... | ....D. | E.ARAN.IEVDQ | A..A........ | 0.03 | 3 |
| RA..T | .................. | TKHGG....NF......T | R...D. | ............ | A..A........ | 0.03 | 3 |
| ..... | F....DAT.NL.H.Q.L | .........F......T | ...DG. | ............ | ............ | 0.03 | 3 |
| ..... | .................. | .........DF.....T | ....D. | .DGSGD.IA.DG | A..A........ | 0.03 | 3 |
| ..... | F................. | .V.........F....... | ...... | ............ | GAHAD..FHV.D | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| G...T | ................. | .Q.S......F....... | E..N.. | ........... | ........... | 0.03 | 3 |
| A...T | ................. | .K.TG....DF....... | R...DR | ........... | A..A........ | 0.03 | 3 |
| TA... | F................ | ................. | ...NDR | | | 0.03 | 3 |
| D.... | F.....GRG.H..P.E.R | .V........F....... | ...... | ENGREG.AA..H | A..A........ | 0.03 | 3 |
| .A... | F.....ATG.NV.T.G.R | .Q.DR.....F....... | ....D. | | GQKDR..ST..H | 0.03 | 3 |
| E.... | ................. | .QPSR.....F......T | ...D.. | .DAG.S.A..DR | A..A........ | 0.03 | 3 |
| R.... | ................. | ..........F....... | R..AD. | .NAR.A.I..GE | A..A........ | 0.03 | 3 |
| ..... | ................. | ................. | ...DD. | E.TR.N.....Q | A..A........ | 0.03 | 3 |
| AA... | ................. | TQP.R....NF......T | R...D. | ..A.G...AYD. | A..A........ | 0.03 | 3 |
| RT... | F.....AT..LV.L.... | ..DGE....DF....... | ...... | | | 0.03 | 3 |
| DT... | F.....NQG.HK.P.N.G | .........NF....... | R...D. | | A..A........ | 0.03 | 3 |
| R...T | F.....DHT.R..M.G.R | TQ.TQ....F....... | R..A.. | E.ARGN.I..DE | A..A........ | 0.03 | 3 |
| ..... | ................. | ................. | R...GR | | A..A........ | 0.03 | 3 |
| RA... | ................. | ................. | ...AG. | | | 0.03 | 3 |
| ..... | ................. | ................. | R...D. | E.AGG.DI..GH | A..A........ | 0.03 | 3 |
| ..... | ................. | .........NF....... | ....G. | ESTARN.A.V.Q | A..A........ | 0.03 | 3 |
| ..... | F.....DA..IA.L.K.R | ................. | R...G. | ESGGE.....GG | A..A........ | 0.03 | 3 |
| GT... | ................. | .........NF......T | E..DD. | | | 0.03 | 3 |
| ..... | F................ | .V........F....... | ...... | | ARQNGP.A.T.E | 0.03 | 3 |
| ..... | F................ | .V........F....... | ...... | | NPKTA..AHS.E | 0.03 | 3 |
| TT..T | F.....SGT.MM.K.T.E | .Q.GQ....DF....... | ....G. | | A..A........ | 0.03 | 3 |
| ..... | ................. | ................. | E..NG. | .DTSGA.I.VDQ | A..A........ | 0.03 | 3 |
| ..... | F................ | .V........F....... | ...... | | .DRST..VQG.H | 0.03 | 3 |
| G.... | F.......T.SV...H.R | ................. | ...... | | A..A........ | 0.03 | 3 |
| ..... | ................. | .QDT......F......T | ...T.R | | A..A........ | 0.03 | 3 |
| ..... | ................. | .V........F....... | ...... | | GASSN..ATV.E | 0.03 | 3 |
| ..... | F................ | .V........F....... | ...... | | GRQSG..SR..P | 0.03 | 3 |
| ..... | ................. | ................. | ...N.. | ENAGGD..E..R | A..A........ | 0.03 | 3 |
| ..... | ................. | ................. | ....D. | ESAKTADAAVDD | A..A........ | 0.03 | 3 |
| ..... | ................. | ................. | R..AD. | | A..A........ | 0.03 | 3 |
| RA... | ................. | ................. | R..DG. | | A..A........ | 0.03 | 3 |
| ..... | ................. | ................. | E..NGR | ..AG.DD...GG | A..A........ | 0.03 | 3 |
| ..... | ................. | ................. | ...DDR | .NGST.....GG | A..A........ | 0.03 | 3 |
| RA... | F.....NGT.L..M.K.R | ..HTG....DF....... | ...D.R | | A..A........ | 0.03 | 3 |
| G.... | F.....A...H......L | .QD.E.....F..P.... | ...DDR | | A..A........ | 0.03 | 3 |
| D...T | F.....SN..PL.K.T.. | ..HG.....NF......T | ...DDR | | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| H.... | F.....AR..IE.I.G.R | T.PDH....DF......T | R...G. | ..ATTDD..VDG | A..A........ | 0.03 | 3 |
| ..... | ................. | ................. | ...N.. | E.AARS...Y.H | A..A........ | 0.03 | 3 |
| ..... | F.....DT..NI.K.S.M | .QHTH....NF......T | ...ADR | ..AST..AA..D | A..A........ | 0.03 | 3 |
| TA... | F.....AGA.HK.N.G.G | .........NF....... | R...D. | ............ | A..A........ | 0.03 | 3 |
| D...T | F......GT.NM.L.Q.G | TQP.R.....F....... | ....D. | ............ | ............ | 0.03 | 3 |
| D.... | F.....ATG.NN.I.S.G | .PPN......F....... | R..A.. | .NAGASDA.FDQ | A..A........ | 0.03 | 3 |
| ..... | ................. | ................. | ...DG. | E.AGAND.AV.H | A..A........ | 0.03 | 3 |
| ..... | F................. | ................. | R...D. | EDAGAA..EFGQ | A..A........ | 0.03 | 3 |
| ..... | F................. | .V........F....... | ...... | ............ | KDRAA..VHN.H | 0.03 | 3 |
| TA... | F.....GNT.RP.T.S.M | .Q.GQ....DF....... | ....D. | E.AAAN..E.DG | A..A........ | 0.03 | 3 |
| ..... | ................. | ................. | ...AG. | E.AAAN..E.DG | A..A........ | 0.03 | 3 |
| E.... | ................. | .........DF....... | ...DDR | ............ | ............ | 0.03 | 3 |
| DT... | F.....ANG.HL.K.K.S | ..A......DF....... | ...DG. | E.AG.GD.EY.. | A..A........ | 0.03 | 3 |
| ..... | ................. | ................. | ...DG. | E........... | A..A........ | 0.03 | 3 |
| AT... | F.....SG..IK.K.D.R | T.P......DF....... | ....D. | .DAG.A.I..DG | A..A........ | 0.03 | 3 |
| ..... | ................. | ................. | R..DG. | E.ASTA..A.GQ | A..A........ | 0.03 | 3 |
| G.... | F.....AG..RV.T.G.S | ..DGE....DF....... | ...... | EDAG...I..GQ | A..A........ | 0.03 | 3 |
| ..... | ................. | ..DGE....DF....... | R...D. | EN.GT..AA.GD | A..A........ | 0.03 | 3 |
| RA... | F.....NGG.NI.K.E.R | T.PGG....NF....... | R..DD. | ............ | A..A........ | 0.03 | 3 |
| ..... | F.....SKA.S..L.E.R | ..A......DF....... | ...DG. | ............ | A..A........ | 0.03 | 3 |
| GT... | ................. | ................. | ...... | ............ | ............ | 0.03 | 3 |
| ..... | ................. | ................. | ...DDR | ..AK.ADT..GN | A..A........ | 0.03 | 3 |
| A.... | F.....AT..PM.L.... | T.P......DF....... | ...D.. | ............ | ............ | 0.03 | 3 |
| ..... | F................. | .V........F....... | ...... | ............ | SHRTA..STA.A | 0.03 | 3 |
| ..... | F.....SD..I..H.D.R | ................. | ...... | ............ | A..A........ | 0.03 | 3 |
| ..... | F.....SD..HP.L.Q.K | .........NF....... | R...D. | ENAAA.D..FGH | A..A........ | 0.03 | 3 |
| ....T | ................. | ..AGR....DF......T | ....D. | ............ | A..A........ | 0.03 | 3 |
| ..... | ......ASA.SV.H.T.G | .V........F....... | ...... | E.AAGA.IA.GE | A..A........ | 0.03 | 3 |
| GA... | F.....AST.IN.L.T.. | .Q.......DF....... | ...DDR | ...GAD.IA..G | A..A....E... | 0.03 | 3 |
| NT... | F.....NET.NA.P...K | ................. | ...... | E.AST.DAAV.Q | A..A........ | 0.03 | 3 |
| A.... | F.....GN..NA.T...M | TQ.TG....DF....... | E..ND. | ............ | A..A........ | 0.03 | 3 |
| ..... | F................. | .V........F....... | ...... | ............ | KEHTR..VN..D | 0.03 | 3 |
| .A... | F.....ATT.L..M...G | .V........F....... | ...DDR | E........... | A..A........ | 0.03 | 3 |
| ..... | ................. | ................. | ...N.. | ...T.N.T...R | A..A........ | 0.03 | 3 |
| ..... | ................. | ................. | ....D. | EDAGAA..EFGQ | A..A........ | 0.03 | 3 |
| ..... | ................. | ................. | ...... | E.GTEGDA..D. | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................ | .V........F....... | ...... | ............ | GAHAT..VR..T | 0.03 | 3 |
| R.... | F.....NGG.NN.K.T.R | .........NF....... | R...D. | .DTG.GD.A..H | A..A........ | 0.03 | 3 |
| AA... | ................. | .KAS.....NF......T | E..DD. | ............ | A..A........ | 0.03 | 3 |
| ..... | F................ | .V........F....... | ...... | ............ | DQSDS..ITI.H | 0.03 | 3 |
| AT... | F......TG.IL...T.R | .V........F....... | ...DD. | ESTSTA..E... | A..A........ | 0.03 | 3 |
| RT... | F.....DTG.PA.L.T.K | TKAT.....NF....... | ...DD. | E..GGND....R | A..A........ | 0.03 | 3 |
| ..... | F................ | .V........F....... | ...... | ............ | TARNG..VRE.H | 0.03 | 3 |
| NT... | F......AG.L..L.K.G | ................. | ...... | ............ | A..A........ | 0.03 | 3 |
| ..... | ................. | .QAS......F....... | E..NG. | ............ | A..A........ | 0.03 | 3 |
| ..... | ................. | ................. | E..DDR | E.ARAA.I..GQ | A..A........ | 0.03 | 3 |
| A...T | F.....DQ..R..P.S.R | .Q.......DF....... | G..KGR | EDAGT...AFD. | A..A........ | 0.03 | 3 |
| ..... | F.....GGG.NH.T.D.R | TKDT.....NF....... | ...DDR | E.AAASD.EYGE | A..A........ | 0.03 | 3 |
| RA..T | F.....AQG.SN.K.G.K | .........DF....... | ...D.. | ENAATN.AA.DE | A..A........ | 0.03 | 3 |
| R.... | F.....SA..RA.....R | ..DD.....DF....... | ...A. | ............ | A..A........ | 0.03 | 3 |
| DT... | F................ | .Q.DH....NF....... | ...DD. | ............ | A..A........ | 0.03 | 3 |
| ..... | F................ | .V........F....... | ...... | ............ | .PQGE...EE.P | 0.03 | 3 |
| ..... | ................. | .PANG.....F....... | ...DDR | .DAG.A.I..DG | A..A........ | 0.03 | 3 |
| ..... | ................. | ................. | ...DDR | E..TA.D...GR | A..A........ | 0.03 | 3 |
| ..... | ................. | ................. | ...DD. | .DTGRN..E.DS | A..A........ | 0.03 | 3 |
| D.... | F......S.T.NV.L.D. | .Q.DR.....F....... | ...DGR | E.ATG...A.G. | A..A........ | 0.03 | 3 |
| T...T | F.....DS..RA.P.A.S | .QPSQ....DF....... | R...D. | ............ | A..A........ | 0.03 | 3 |
| ..... | ................. | ................. | ...DDR | E.AGRN.T..DD | A..A........ | 0.03 | 3 |
| TA... | F.....GGG.LD.T...R | .Q.S......F....... | E..N.. | ............ | A..A........ | 0.03 | 3 |
| ..... | F................ | .V........F....... | ...... | ............ | DPRGG..VQK.A | 0.03 | 3 |
| ..... | ................. | ................. | ...DDR | ENASGD..EVDS | A..A........ | 0.03 | 3 |
| ..... | F.....GN..NK.P.P.N | .Q.DR.....F....... | ....D. | ..AST..AA..D | A..A........ | 0.03 | 3 |
| ..... | F................ | .V........F....... | ...... | ............ | EARGP..IQK.D | 0.03 | 3 |
| NT..T | F.....GRG.SP.K...G | .........DF....... | ...... | .D.GG.....GH | A..A........ | 0.03 | 3 |
| A.... | F.....GRT.PQ.T.T.R | .Q.DH....NF....... | ...DD. | ENGSGGD.A.DN | A..A........ | 0.03 | 3 |
| .A... | ................. | ................. | E..DD. | ............ | A..A........ | 0.03 | 3 |
| TA... | ................. | .QPN.....F.......T | ...N.. | ..GTAG...V.G | A..A........ | 0.03 | 3 |
| HT... | F.....NTG.HP.T.G.M | T.P.....DF....... | ...D.. | ............ | ............ | 0.03 | 3 |
| NA..T | F.....G.G.HA.T.G.R | ..A.....DF....... | ...DG. | ............ | A..A........ | 0.03 | 3 |
| GA... | F.....SGA..K.N.S.S | ..A.....DF......T | ....D. | ............ | ............ | 0.03 | 3 |
| E.... | F......SG.HP.T.A.L | .KYT.....NF....... | ...D.. | ............ | A..A........ | 0.03 | 3 |
| ..... | ................. | ..HG.....NF....... | E..KD. | ............ | A..A........ | 0.03 | 3 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....SK..PA.K.A.G | TQ.TG....DF....... | ...DDR | ..ATRD.T..GH | A..A........ | 0.03 | 3 |
| ..... | F......GA.HP.K...V | .V........F....... | R...G. | E..AAS....GG | A..A........ | 0.03 | 3 |
| ..... | .................. | T.P......DF......T | G..N.. | ED......... | A..A........ | 0.03 | 3 |
| ..... | .................. | .................. | G..D.R | .SGKRA..E.DQ | A..A........ | 0.03 | 3 |
| N...T | F.....NQG..V.L.N.R | TQDGQ.....F....... | ....D. | .......... | A..A........ | 0.03 | 3 |
| RA... | .................. | TQ.TG....NF....... | F...N. | .......... | A..A........ | 0.03 | 3 |
| ..... | F................. | .................. | ...... | .......... | .......... | 0.03 | 3 |
| TA... | F.....NGG.HV.....L | TKDDR....DF....... | ...DDR | .......... | A..A........ | 0.03 | 3 |
| ..... | F.....SA..RA.....R | TKDDR....DF....... | E..AG. | .......... | .......... | 0.03 | 3 |
| ..... | F................. | .V........F....... | ...... | .......... | G.RNG..VTM.Q | 0.03 | 3 |
| AT... | F......QT.P..L.Q.R | ..PN.....NF....... | R...D. | .DGNGA..E..G | A..A........ | 0.03 | 3 |
| ..... | F................. | .V........F....... | ...... | .......... | ATRAP..DTR.D | 0.03 | 3 |
| ..... | F................. | .V........F....... | ...... | .......... | SKKTA..VET.A | 0.03 | 3 |
| ..... | .................. | .V........F....... | E..DD. | .NAA.A....GD | A..A........ | 0.02 | 2 |
| EA... | F.....ATT.NV.T.K.S | .KYT......F......T | ...D. | .......... | A..A........ | 0.02 | 2 |
| HA... | F.....NTG.RN.T.T.R | .................. | ...... | .......... | A..A........ | 0.02 | 2 |
| E.... | F.....ASA.S..T.T.G | RQPG.....DF....... | ...DDR | .......... | .......... | 0.02 | 2 |
| ..... | .................. | .................. | R..DD. | EDAGT...AFD. | A..A........ | 0.02 | 2 |
| ..... | F.....ASA.S..T.T.G | .QPG.....DF....... | ...DDR | EN.GTN.AE.DN | A..A........ | 0.02 | 2 |
| EA... | .................. | .........F......T | ...NGR | .DAG.A.I..DG | A..A........ | 0.02 | 2 |
| ..... | .................. | .................. | ...DG. | E....ND.EF.Q | A..A........ | 0.02 | 2 |
| G.... | F.....GS..NK.M.A.R | ..YN......F......T | ...D.R | .......... | .......... | 0.02 | 2 |
| GT... | F.....GS..NM.N.E.R | ..DGE....DF....... | ...... | .......... | A..A........ | 0.02 | 2 |
| NA..T | F......AG.SH.T.A.R | T.P......DF....... | ...DDR | EDGAA.DAA.DE | A..A........ | 0.02 | 2 |
| ..... | .................. | .................T | V..DD. | .......... | .......... | 0.02 | 2 |
| ..... | ......SR..NE.M...S | .........NF....... | R..AG. | .SAS.N.IA..E | A..A........ | 0.02 | 2 |
| ..... | .................. | T..NE....NF....... | ...DD. | .NAG.D..AFDG | A..A........ | 0.02 | 2 |
| R...T | .................. | .................. | E...KG | .......... | A..A........ | 0.02 | 2 |
| ..... | F.......G.SE.N...R | .................. | ...... | .......... | A..A........ | 0.02 | 2 |
| ..... | F................. | .................. | E..TG. | .......... | .......... | 0.02 | 2 |
| ..... | .................. | .................. | ...DDR | ESAG...TEYD. | A..A........ | 0.02 | 2 |
| TT... | F.....NNA..K...K.. | ..PN.....NF....... | ...NDR | .......... | A..A........ | 0.02 | 2 |
| GT... | F.....GT..NQ.K.G.R | .QHNQ.....F......T | ...N.. | .......... | A..A........ | 0.02 | 2 |
| RA... | F................. | .........NF....... | R...D. | .......... | A..A........ | 0.02 | 2 |
| TA... | F.....GHA.HD.T...I | .Q.S......F....... | ...DDR | ESGSGAD...GR | A..A........ | 0.02 | 2 |
| TT..T | .................. | .................. | G..DG. | .......... | .......... | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ...AGR | .S.G.S.IA..G | A..A........ | 0.02 | 2 |
| ..... | F......N..IL.T.T.R | .QPSQ....NF....... | G...GR | ........... | A..A........ | 0.02 | 2 |
| D.... | F.....GTG.HN.T.G.R | .PPDR....DF....... | R..DD. | .SASGSD.A.DE | A..A........ | 0.02 | 2 |
| .A... | F.....DHT.R..M.G.R | ................. | ...... | ........... | A..A........ | 0.02 | 2 |
| ..... | ................. | ................. | ....GR | ..TRRD.A.FDG | A..A........ | 0.02 | 2 |
| A...T | F...K..S..PM.T.S.K | ..YN......F......T | ...D.R | ........... | ........... | 0.02 | 2 |
| SA... | F.....NGG.RP...D.G | T..NE....DF....... | ...DDR | ........... | A..A........ | 0.02 | 2 |
| ..... | F................ | .V........F....... | ...... | ........... | ERKGT...R..D | 0.02 | 2 |
| RT... | ................. | TQHNG....NF......T | R..D.. | .DGKGS.IA..G | A..A........ | 0.02 | 2 |
| ..... | F................ | .V........F....... | ...... | ........... | GRAA..FDG..Q | 0.02 | 2 |
| ..... | .........SM.L...R | .........NF....... | R...D. | EDTG.A....GN | A..A........ | 0.02 | 2 |
| E.... | F.....AEG.LK.M.H.L | ..DGE....NF....... | R..D.. | ..GGAND.AV.Q | A..A........ | 0.02 | 2 |
| AA... | ................. | ..PN.....NF....... | ....D. | .DA.EG....GR | A..A........ | 0.02 | 2 |
| ..... | F.....AA...K.T.E.L | ..DGE....DF....... | ...... | ........... | A..A........ | 0.02 | 2 |
| A...T | ................. | T.PGG....NF....... | ....D. | EN.RAG.....E | A..A........ | 0.02 | 2 |
| ..... | ................. | TQDDR....NF......T | ...DDR | ........... | A..A........ | 0.02 | 2 |
| ..... | ................. | .........DF....... | ...D.. | ESGGAN..EYDG | A..A........ | 0.02 | 2 |
| EA..T | ................. | ................. | ....D. | E.ARE...E.DQ | ........... | 0.02 | 2 |
| AT..T | F......KG.NL...Q.S | TQPT......F....... | ...N.. | .SAKAA.AA.DE | A..A........ | 0.02 | 2 |
| NT... | F.....NR..N..I.T.G | T.P.....DF....... | ..DDR. | ........... | ........... | 0.02 | 2 |
| ..... | ................. | ................. | E..N.. | ..TK...AE..D | ........... | 0.02 | 2 |
| ..... | ................. | ................. | E..ND. | E.AST...E.GS | A..A........ | 0.02 | 2 |
| G...T | F.....ASA.S..T.T.G | .QPG.....DF....... | ...... | ESTTEA...... | A..A........ | 0.02 | 2 |
| ..... | F................ | .V........F....... | ...... | ........... | GRST...VR..H | 0.02 | 2 |
| ..... | ................. | ................. | ...... | ..ARGADAE..S | A..A........ | 0.02 | 2 |
| ..... | F................ | .V........F....... | ...... | ........... | T.AT....S..Q | 0.02 | 2 |
| RA... | F......AG..L.T.N.R | T.PGG....NF....... | ...DD. | .NANRDDAEVGD | A..A........ | 0.02 | 2 |
| GT... | ................. | ..HG.....NF....... | E..TG. | ........... | A..A........ | 0.02 | 2 |
| ..... | F.....ATT..N.L...L | .K.TG....DF....... | R...DR | ........... | A..A........ | 0.02 | 2 |
| ..... | ................. | ................. | ...DD. | E.GTG...EVD. | A..A........ | 0.02 | 2 |
| D.... | F.....STA.RD.P.S.R | ................T | ...DDR | ES.A.S..EFDS | A..A........ | 0.02 | 2 |
| ..... | ................. | ................. | ...DDR | GM...SDAAVDD | A..A........ | 0.02 | 2 |
| .A... | F.....NGG.NN.K.T.R | .........NF....... | R....D | E.ANR..IA.GE | A..A........ | 0.02 | 2 |
| ..... | ................. | ................. | ...... | ........... | GSRTA..NNE.D | 0.02 | 2 |
| G.... | F.....NG..H...I.A.R | .QANH.....F......T | ....GR | ........... | A..A........ | 0.02 | 2 |
| D.... | F.....AT..ND.K.P.K | ................. | ...... | ........... | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| SA..T | F.....DKG.NK.T.A.V | T.YNH.....F....... | E..ND. | ............ | A..A........ | 0.02 | 2 |
| ..... | .................. | .........DF....... | ...... | ..AAGG..AV.G | A..A........ | 0.02 | 2 |
| NT... | F......ET.HN.H...G | .Q.DR.....F....... | ....D. | EDAG...I..GQ | A..A........ | 0.02 | 2 |
| ..... | .................. | T.HTR....DF......T | ...... | ............ | A..A........ | 0.02 | 2 |
| .A... | .................. | .................. | ...... | ESGNTN...VGE | A..A........ | 0.02 | 2 |
| NA..T | F.....GRG.H..P.E.R | ..........F....... | ...... | .SASRND.AVGE | A..A........ | 0.02 | 2 |
| RA..T | F.....SN..PL.K.T.. | ..DGE....DF....... | ...... | ESAR..DAA.DD | A..A........ | 0.02 | 2 |
| ..... | .................. | TKHGG....NF......T | R...D. | ............ | A..A........ | 0.02 | 2 |
| ..... | .................. | .................. | ....D. | ..T.TD.....N | A..A........ | 0.02 | 2 |
| RA..T | .................. | .................. | ....GR | ..TRRD.A.FDN | A..A........ | 0.02 | 2 |
| GA..T | F.....NKT.HL.T.A.R | .QAS......F....... | ...... | .S.ARGDI..DN | A..A........ | 0.02 | 2 |
| ..... | .................. | .................. | ...... | EDGKES.IE.GD | A..A........ | 0.02 | 2 |
| ..... | F................. | .V........F....... | ...... | ............ | GAQAS..AKV.. | 0.02 | 2 |
| ..... | .................. | .................. | E..NG. | E....ND.EF.Q | ............ | 0.02 | 2 |
| A.... | .................. | .KDDG.....NF...... | ...... | E..RRA.....Y | A..A........ | 0.02 | 2 |
| E.... | F.....DNT.SK.L...K | .QPN......F......T | ...... | ..AGAN....GG | A..A........ | 0.02 | 2 |
| ..... | .................. | .................. | ...... | ..AG.N.AA.DQ | A..A........ | 0.02 | 2 |
| ..... | .................. | .................. | R..AD. | .DAG.SD...GG | A..A........ | 0.02 | 2 |
| ..... | .........V........ | .................. | E..AG. | ............ | ............ | 0.02 | 2 |
| ..... | F................. | .V........F....... | ...... | ............ | GSRTG..NR..A | 0.02 | 2 |
| ..... | .................. | .................. | ....D. | .DTAA...EF.G | A..A........ | 0.02 | 2 |
| ..... | .................. | .........NF......T | R..TDR | ............ | A..A........ | 0.02 | 2 |
| DT... | F.....NAG.LA...Q.R | .........NF....... | R,..D. | ..GT..DAAY.E | A..A........ | 0.02 | 2 |
| ..... | .................. | .................. | G..A.R | ............ | A..A........ | 0.02 | 2 |
| .A... | F.....AS..LE.M.T.R | .QDT......F......T | ...D.. | .D.RTAD.E.DH | A..A........ | 0.02 | 2 |
| ..... | F................. | .V........F....... | ...... | ............ | K.KT....RE.E | 0.02 | 2 |
| ..... | F................. | .V........F....... | ...... | ............ | .QQG...STG.. | 0.02 | 2 |
| NA... | F.....NKT.HL.T.A.R | TQHNH.....F......T | ...... | ............ | A..A........ | 0.02 | 2 |
| ..... | .................. | ....E.....F....... | ...AD. | ............ | A..A........ | 0.02 | 2 |
| D...T | F.....S...PN.T.G.E | ..YN......F......T | ...D.R | ............ | A..A........ | 0.02 | 2 |
| DT... | F.....DTG.SK.T.T.R | .QHNQ.....F......T | ....GR | ENAG.SD.E..H | A..A........ | 0.02 | 2 |
| TA... | F......EG.LQ.M.A.K | TKA......NF......T | ...D.. | ............ | A..A.....V.. | 0.02 | 2 |
| ..... | F................. | .V........F....... | ...... | ............ | GQRAA..N.N.T | 0.02 | 2 |
| ..... | .................. | .V........F....... | ...... | E.GGAN.IA.GQ | A..A........ | 0.02 | 2 |
| ..... | F................. | .V........F....... | ...... | ............ | .RQSG..FDM.D | 0.02 | 2 |
| E.... | F.....GAT.PN.H.H.G | ..DGE....DF....... | ...... | ESGR.GDI..DD | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| .T... | .................. | .........NF..P...T | R..ND. | ........... | A..A........ | 0.02 | 2 |
| ....T | F.....SA..RA.....R | .................. | ...DDR | ........... | A..A........ | 0.02 | 2 |
| TA... | F.....GNG.NE.L.P.R | .Q.DH....NF....... | ...DD. | ...GTS..EF.Q | A..A........ | 0.02 | 2 |
| GT... | F.......G.HK.T.N.G | ..HG.....NF......T | E..N.. | E.......... | A..A........ | 0.02 | 2 |
| ..... | .................. | .........DF....... | ...ADR | .D...S..A.GG | A..A........ | 0.02 | 2 |
| EA... | .................. | .QPSR.....F......T | ...D.. | .DAG.S.A..DR | A..A........ | 0.02 | 2 |
| GA..T | F.....DKG.P..T...G | ..PN.....NF....... | ...... | ........... | A..A........ | 0.02 | 2 |
| AA... | F.....GG..NK.M.... | .QPSE....DF....... | R..D.. | ........... | A..A........ | 0.02 | 2 |
| ..... | .................. | .........NF....... | R...D. | EDT.EGDI..DR | A..A........ | 0.02 | 2 |
| .A... | P.....DRG.N..I.A.K | .................. | ...... | ENASG.....GN | A..A........ | 0.02 | 2 |
| TT... | F.....SN..PL.K.T.. | .................. | ...... | ........... | A..A...A.... | 0.02 | 2 |
| ST... | .................. | .................. | ...... | ........... | ........... | 0.02 | 2 |
| SA... | .................. | .V........F....... | ...... | EDAGT...AFD. | A..A........ | 0.02 | 2 |
| T...T | F.....ATT..N.L...L | .Q.DR.....F....... | ....D. | ........... | A..A........ | 0.02 | 2 |
| R...T | F.....GTA.NV.L...M | ..DGE....DF....... | ....DR | .NAGASDA.FDQ | A..A........ | 0.02 | 2 |
| G.... | F.......T.SV...H.R | .Q.DR.....F....... | ....D. | .SAKAA.AA.DE | A..A........ | 0.02 | 2 |
| A.... | F.....GTG..P.T.D.R | TQPNH.....F....... | R..D.. | ........... | A..A........ | 0.02 | 2 |
| ..... | .................. | .PHD.....DF......T | R..DG. | ........... | A..A........ | 0.02 | 2 |
| ..... | F................. | .V........F....... | ...... | ........... | K.RTA..A.G.D | 0.02 | 2 |
| RA... | F.....ASA.S..T.T.G | .QPG.....DF......T | ...AD. | ........... | A..A........ | 0.02 | 2 |
| .A... | F.....NTG.RN.T.T.L | .........NF....... | R...D. | ES.GRGD...DR | A..A........ | 0.02 | 2 |
| HT... | F................. | .V........F....... | ...... | ........... | ........... | 0.02 | 2 |
| R.... | F.....GDG....K.Q.R | .Q.DR.....F....... | ....D. | ESAGA.D.A..R | A..A........ | 0.02 | 2 |
| ..... | .................. | .................. | ...N.. | ..TG.A.I..D. | A..A........ | 0.02 | 2 |
| ..... | F.....GKA.LD.P.D.R | .................. | ...D.. | ........... | A..A........ | 0.02 | 2 |
| H.... | .................. | ..HG.....NF......T | E..DD. | ........... | A..A........ | 0.02 | 2 |
| TA..T | F.....DQG.S..L...G | ..P.G....KF....... | ...DDR | .NAG.DD...DQ | A..A........ | 0.02 | 2 |
| HA... | F.....AGT.PM.K.K.G | .QDGH....DF.....T | ...DD. | E.AGRN.T..DD | A..A........ | 0.02 | 2 |
| ..... | .................. | .................. | ....D. | .NGR.G..A..E | A..A........ | 0.02 | 2 |
| ..... | F................. | .V........F....... | ...... | ........... | TAKGR...T..A | 0.02 | 2 |
| ..... | .................. | .................. | ...... | EDAGT...AFD. | A..A........ | 0.02 | 2 |
| TT... | F.....STA..Q.H.Q.L | ..HG.....NF......T | ...A.. | ........... | A..A........ | 0.02 | 2 |
| A...T | F......S..PM.T.S.K | ..YN......F......T | ...D.R | ........... | ........... | 0.02 | 2 |
| SA..T | F.....A...HA.K.N.R | T.AG.....NF......T | R...D. | ..GAGGDAEF.Q | A..A........ | 0.02 | 2 |
| DT..T | F.....NG..LK.T.K.K | .QANH....DF....... | ...DDR | ........... | A..A........ | 0.02 | 2 |
| AA... | .................. | .................. | R..DDR | .SGGRS..AFGD | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ....D. | E.AGAND.AY.N | A..A........ | 0.02 | 2 |
| TA... | F.....AGT..M.K.Q.G | .PPNG.....F......T | ...DDR | ............ | A..A........ | 0.02 | 2 |
| A.... | ................. | .KYT.....NF...... | ...D.. | ............ | A..A........ | 0.02 | 2 |
| ..... | ................. | ................. | ...DDR | E.GRAADAAF.E | A..A........ | 0.02 | 2 |
| RT... | F......T..HP.L.H.R | .QPG.....NF...... | ...DDR | ..TGAS.A..DH | A..A........ | 0.02 | 2 |
| DT... | ................. | ................. | ....D. | ............ | A..A........ | 0.02 | 2 |
| R.... | F.....NAT.IM.T.H.R | .QDT......F......T | ...D.. | .NAGA.D...GS | A..A........ | 0.02 | 2 |
| ..... | F................. | .V........F...... | ...... | ............ | TPRG...NTT.D | 0.02 | 2 |
| NA... | F.....GRG.NQ.K.E.H | .Q.GQ....DF...... | ....G. | E.GAGSD.E.D. | A..A........ | 0.02 | 2 |
| AA... | F.....GRG.SP.K...G | .QPG.....NF...... | ...DDR | ENGGGG.I..GH | A..A........ | 0.02 | 2 |
| T...T | ................. | T.ANE.....F...... | ...DDR | ..GDRN.AA.GE | A..A........ | 0.02 | 2 |
| NA... | F.....AQ...A.L.... | TQYNR.....F...... | ...... | ............ | A..A........ | 0.02 | 2 |
| TA... | ................. | .Q.S......F...... | E..ND. | ENAGASDIA.DH | A..A........ | 0.02 | 2 |
| TA..T | F.....AN..RH...E.K | ..DGE....DF...... | ...D.. | .NAGEG...VDS | A..A........ | 0.02 | 2 |
| ..... | ................. | ........DF...... | ...DDR | ..TTGA..AY.D | A..A........ | 0.02 | 2 |
| ..... | ................. | ................. | ...ADR | ..AS...I..G. | A..A........ | 0.02 | 2 |
| ..... | ................. | ................. | R..DD. | ...AGADIA.DE | A..A........ | 0.02 | 2 |
| G.... | ................. | ................. | E...DR | .SAGAN..E..S | A..A........ | 0.02 | 2 |
| G.... | ................. | ..ATG....NF..P...T | ...... | E..RRD.AA..H | A..A........ | 0.02 | 2 |
| GT... | ................. | ................P.... | E..KG. | ............ | A..A........ | 0.02 | 2 |
| G...T | F.....GN..IK.L...G | ...DG....DF...... | ...DDR | ..TG.S...V.E | A..A........ | 0.02 | 2 |
| SA..T | F.....GNG.HV.H.G.R | ............P.... | ...... | ............ | A..A........ | 0.02 | 2 |
| D...T | F.....SGA..K.N.S.S | .Q.DR.....F......T | ....D. | ESAR..DAA.DD | A..A........ | 0.02 | 2 |
| NT... | F................. | .V........F...... | ...... | ............ | ............ | 0.02 | 2 |
| ..... | ................. | .V........F...... | ...... | ..TGTS...YGS | A..A........ | 0.02 | 2 |
| ..... | F................. | .V........F...... | G..TG. | ............ | KDRTP..FQA.D | 0.02 | 2 |
| ..... | F.....ATG.NV.T.G.R | ..DGE....DF...... | ...... | ENGTASD.AF.E | A..A........ | 0.02 | 2 |
| TT... | ................. | TQA.H....DF...... | ...... | ............ | A..A........ | 0.02 | 2 |
| ..... | F................. | .V........F....T | ...... | ............ | GTRDA..VQE.A | 0.02 | 2 |
| TT.ST | ................. | ................. | ...... | ............ | ............ | 0.02 | 2 |
| SA... | .I................ | .QAS......F...... | ...... | ED.TTGDA...G | A..A........ | 0.02 | 2 |
| GT... | F.....AEG.LK.M.H.L | ..DGE....DF...... | ...... | E........... | ............ | 0.02 | 2 |
| T.... | F.....GS..NK.M.A.R | .QPSR.....F...... | ...... | ESAAG.D.AF.S | A..A........ | 0.02 | 2 |
| ..... | ................. | T.HDR....NF...... | ...DDR | EN.G..DIE..S | A..A........ | 0.02 | 2 |
| ..... | ................. | T.P......DF...... | ...D.. | ............ | A..A........ | 0.02 | 2 |
| ..... | ................. | ................. | R..DD. | .NGG.ND....Q | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | .................. | ...DDR | E.ASG..I.VGR | A..A........ | 0.02 | 2 |
| D.... | F.....AEA..I.K.H.. | .QPSH....DF....... | ....G. | .SA.GG....DG | A..A........ | 0.02 | 2 |
| ..... | F.....ASA.S..T.T.G | .KPDQ.....F....... | ...DDR | ............ | ............ | 0.02 | 2 |
| E.... | F................ | .V........F....... | E..NG. | ............ | ............ | 0.02 | 2 |
| SA... | F.....NGG.NV.N.K.G | ..YN............. | ...... | .NAT.ND.AFGE | A..A........ | 0.02 | 2 |
| RA... | ................. | .........NF....... | R...D. | E..RRD.AA..H | A..A........ | 0.02 | 2 |
| DA..T | F.....DHT.R..M.G.R | .QDT.....DF....... | G..TG. | ............ | A..A........ | 0.02 | 2 |
| ..... | ................. | ....G.....F....... | ....G. | .NADRN..E.GE | A..A........ | 0.02 | 2 |
| ..... | ................. | TQDGQ....NF....... | R..... | .D.GA.DIE.DR | A..A........ | 0.02 | 2 |
| TT..T | F.....NGG.NI.K.E.R | ..DGE....DF....... | ...... | ESTDGG..A.DS | A..A........ | 0.02 | 2 |
| ..... | ................. | .................. | E..DD. | ............ | ............ | 0.02 | 2 |
| ..... | F................ | .V........F....... | ...... | ............ | TQRSP..S...T | 0.02 | 2 |
| DT... | .......AST.IN.L.T. | ..DGE....DF....... | ...... | ............ | ............ | 0.02 | 2 |
| ..... | ................. | .................. | E..ND. | E.AG.D...YGR | A..A........ | 0.02 | 2 |
| RA... | ................. | .................. | ...DDR | ............ | GRSAG..AG..A | 0.02 | 2 |
| NA..T | F.....AGG.P..L...G | ..PN.....NF....... | ...NDR | ............ | A..A........ | 0.02 | 2 |
| ..... | ................. | .................. | ...... | E.AGG.D.E.DS | A..A........ | 0.02 | 2 |
| H.... | F.....SA..RA.....R | .V........F....... | ...... | ESARGS..EFDG | A..A........ | 0.02 | 2 |
| ..... | F................ | .V........F....... | ...... | ............ | GRSGR...EG.T | 0.02 | 2 |
| ..... | F.....AGA.SL.....R | T.ANE....F....... | ...D.. | ............ | A..A........ | 0.02 | 2 |
| ..... | F................ | .V........F....... | ...... | ............ | ATKTN...R... | 0.02 | 2 |
| TT... | ................. | .................. | E..KD. | ............ | ............ | 0.02 | 2 |
| D.... | ......NRG.PV.N.A.. | ..YN......F......T | ...D.R | ..ARRG..A.DE | A..A........ | 0.02 | 2 |
| H.... | F.....SN..PL.K.T.. | .KYT.....NF......T | ...... | ............ | A..A........ | 0.02 | 2 |
| AT..T | F.....A.G..V.T.H.R | .........F....... | ...... | ............ | A..A........ | 0.02 | 2 |
| ..... | P.....GS..NK.M.A.R | ..YN......F......T | ...D.R | ............ | A..A........ | 0.02 | 2 |
| ..... | F.........HK.P.N.G | TQ.TH....DF....... | ...DDR | ............ | A..A........ | 0.02 | 2 |
| ST..T | ................. | .Q.DQ.....F....... | R..DD. | ............ | A..A........ | 0.02 | 2 |
| ..... | ................. | .................. | ...RDG | ESTDRG.A..GE | A..A........ | 0.02 | 2 |
| AA... | ................. | .KDSR....DF....... | ....D. | EDGGRG...V.D | ............ | 0.02 | 2 |
| SA..T | ................. | .................. | ...... | ENTTGN....DR | A..A........ | 0.02 | 2 |
| ..... | F................ | .V........F....... | ...... | ............ | GSRAS..AT..K | 0.02 | 2 |
| NT... | F.....NR..N..I.T.G | TKPS.....DF......T | G..AD. | ............ | A..A........ | 0.02 | 2 |
| RA... | F.....GN..IK.L...G | ...NG.....F....... | R..N.. | E.AGGN..E.DD | A..A........ | 0.02 | 2 |
| .A... | F.....SNG.RE.L...K | TQ.TG....NF....... | ...... | ............ | A..A........ | 0.02 | 2 |
| ..... | F................ | .V........F....... | ...... | ............ | GPKAA..V.G.T | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | R..DG. | E..GASD.A..Q | ............ | 0.02 | 2 |
| ..... | .................. | .QD.E.....F..P.... | ...D.R | ............ | A..A........ | 0.02 | 2 |
| ..... | F.....GTG.P....K.. | .KYT.....NF......T | ...D.. | ............ | A..A........ | 0.02 | 2 |
| ..... | F................. | .V........F....... | ...... | ............ | ERRTH...TE.. | 0.02 | 2 |
| NT..T | ............H...R | .QANH.....F......T | ...D.. | ENG.AG....DQ | A..A........ | 0.02 | 2 |
| GT... | F.....GRG.H..P.E.R | .Q.S......F....... | ...... | .DGAGGD.A..Q | A..A........ | 0.02 | 2 |
| ..... | .................. | .................. | ...DDR | ESTTGADT..GG | A..A........ | 0.02 | 2 |
| ..... | F................. | .V........F....... | ...... | ............ | GPRA...FNE.H | 0.02 | 2 |
| ..... | F................. | .V........F....... | ...... | ............ | GTKAP...GE.T | 0.02 | 2 |
| ..... | .................. | .................. | ...NGR | .SAT.N.IA..H | A..A........ | 0.02 | 2 |
| ..... | .................. | ..A......DF....... | ....D. | .SATTGD..VDR | A..A........ | 0.02 | 2 |
| E.... | .................. | .........DF......T | R..DG. | .NAG.S.IAFGN | A..A........ | 0.02 | 2 |
| ..... | .................. | .V........F....... | ...... | ............ | GPHS...FQS.D | 0.02 | 2 |
| TA... | .................. | .Q.S......F....... | E..N.. | .SAGEND.E.GH | A..A........ | 0.02 | 2 |
| ..... | F................. | .V........F....... | ...... | ............ | SDRST..STG.. | 0.02 | 2 |
| ..... | .................. | .................. | G..DD. | ESGN.N.A..GS | A..A........ | 0.02 | 2 |
| ..... | .................. | .................. | ...... | ESAGTG..AY.H | A..A........ | 0.02 | 2 |
| AA... | .................. | .Q.S......F......T | ...DD. | E.TGGGD.AV.. | A..A........ | 0.02 | 2 |
| ..... | .................. | .........DF....... | ...D.. | .DAG.....VGN | A..A........ | 0.02 | 2 |
| DA... | F.....SA..RA.....R | TQDS.....NF....... | E..NG. | EN.KA.DAE..D | A..A........ | 0.02 | 2 |
| R.... | .................. | TKPN.....NF....... | R...D. | ESAGTNDAEVGD | A..A........ | 0.02 | 2 |
| SA... | F.....GG..I..P...R | .Q.GQ....DF....... | ....G. | .D.GA.DIE.DR | A..A........ | 0.02 | 2 |
| NA..T | F.....GN..NA.T...M | .Q.......DF....... | ...ADR | ............ | A..A........ | 0.02 | 2 |
| EA..T | F.....NNG..V.K.P.R | .Q.......DF....... | R...D. | .DTG.N..A..R | A..A........ | 0.02 | 2 |
| D...T | .................. | .................. | ...DG. | .NGGTG..A.DR | A..A........ | 0.02 | 2 |
| GT... | F.....GNG.HV.H.G.R | .........DF....... | ...... | ............ | ............ | 0.02 | 2 |
| ..... | F................. | .V......N.F....... | ...... | ............ | NARDN..DDS.. | 0.02 | 2 |
| .A... | F......GT.NM.L.Q.G | ..DGE....DF....... | ...... | ............ | ............ | 0.02 | 2 |
| .A... | F................. | .V......F....... | ...... | ............ | ............ | 0.02 | 2 |
| ..... | .................. | .................. | R...D. | ...SGSD..FDN | A..A........ | 0.02 | 2 |
| SA..T | .................R | .QPN......F......T | ...N.. | ..AKGNDAAV.Q | ............ | 0.02 | 2 |
| ..... | F.....ANG.HL.K.K.S | .Q.......DF....... | ...AD. | ............ | A..A........ | 0.02 | 2 |
| ..... | .................. | .................. | ...DDR | ...TG.D.AY.G | A..A........ | 0.02 | 2 |
| ..... | F................. | .V........F....... | ...... | ............ | A.HNA..DQE.Q | 0.02 | 2 |
| ...T. | .................. | .................. | ...DDR | E..TA.D...GR | A..A........ | 0.02 | 2 |
| ..... | F.......G.PK.L...H | .........NF....... | ...... | ............ | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| SA... | F.....AEG.NI.L.K.R | .........NF....... | ...DD. | ........... | A..A........ | 0.02 | 2 |
| .A... | F.....DHT.R..M...R | ................. | ...... | ........... | A..A........ | 0.02 | 2 |
| ..... | F............... | .Q.DR.....F...... | ....D. | EN.AGN.IE.GN | A..A........ | 0.02 | 2 |
| ..... | ................. | ................. | ....D. | .NTSAS..EFDR | A..A........ | 0.02 | 2 |
| DA... | F............... | ................. | ...DDR | ........... | ........... | 0.02 | 2 |
| ..... | ................. | .........DF...... | R...D. | .SAKAA.AA.DE | A..A........ | 0.02 | 2 |
| AT... | ................. | ...TG....NF...... | R..AD. | EDAKGG.....R | A..A........ | 0.02 | 2 |
| DT... | ................. | ................. | ...TG. | .S.G.S.IA..D | A..A........ | 0.02 | 2 |
| A.... | ................. | TQPTH....NF...... | ...DDR | EDAA.SD..Y.D | A..A........ | 0.02 | 2 |
| EA... | F.....GN..PL.K.T.. | ..ADH....DF...... | ...D.. | ES.TEN....GR | A..A........ | 0.02 | 2 |
| ..... | ................. | ..PN.....DF...... | ...DDR | E.AKRGD.A..G | A..A........ | 0.02 | 2 |
| ..... | F.....GRG.H..P.E.R | .QAS......F...... | ...... | ENTSEG.....R | A..A........ | 0.02 | 2 |
| E.... | ................. | ................. | ....GR | ..AG.N.AA.GQ | A..A........ | 0.02 | 2 |
| ..... | F......GT.NM.L.Q.G | TQ.TG....DF...... | ...DDR | ........... | A..A........ | 0.02 | 2 |
| ..... | ................. | T..G....DF...... | ....D. | ..ARGADAE..S | A..A........ | 0.02 | 2 |
| ..... | ................. | .........NF......T | ...D.R | .SAS.N.IA..E | A..A........ | 0.02 | 2 |
| R.... | ................. | ..DGE....DF...... | ...... | ESGSGSD..FDH | A..A........ | 0.02 | 2 |
| ..... | F............... | .V........F...... | ...... | ........... | DHRT...ADG.T | 0.02 | 2 |
| E.... | F.....DA..IA.L.K.R | .KDSR....DF......T | R..DD. | ........... | A..A........ | 0.02 | 2 |
| ..... | ................. | ................. | ...DD. | E.GT.ND.A.DG | A..A........ | 0.02 | 2 |
| D...T | F.....AG.....T.D.R | ................. | R...D. | ..A.EGD.E... | A..A........ | 0.02 | 2 |
| D.... | F.....SNG.RE.L...K | .QPN......F......T | ...N.. | ........... | A..A........ | 0.02 | 2 |
| ..... | F............... | .V........F...... | ...... | ........... | G.KAH..DRS.. | 0.02 | 2 |
| DT... | F............... | .V........F...... | ...... | ........... | GSSAG..AQV.Q | 0.02 | 2 |
| ..... | ................. | ................. | R..KD. | ........... | A..A........ | 0.02 | 2 |
| NA..T | ......NKG.NL.N.T.E | .QPG.....DF...... | ...... | ........... | A..A........ | 0.02 | 2 |
| ..... | ................. | ................. | ...D.. | EDAGRND.AFDH | A..A........ | 0.02 | 2 |
| ..... | ................. | ..........F...... | ...NDR | ESAAR.DA.FD. | A..A........ | 0.02 | 2 |
| ..... | F............... | .V........F...... | ...... | ........... | S.RAG..FQI.Q | 0.02 | 2 |
| ..... | ................. | ................. | ...D.. | .SANES.A...N | A..A........ | 0.02 | 2 |
| ..... | ................. | ..........F...... | ...D.. | ........... | A..A........ | 0.02 | 2 |
| TA..T | F............... | ................. | ...... | ........... | ........... | 0.02 | 2 |
| NA..T | F............... | ................. | ....D. | .S.G.S.IA..G | A..A........ | 0.02 | 2 |
| G.... | F.....A...ND.T...K | .Q.DH....NF...... | ...DD. | ........... | A..A........ | 0.02 | 2 |
| ..... | F.......G.HK.T.N.G | ..HG.....NF......T | E..N.. | E.......... | A..A........ | 0.02 | 2 |
| ..... | F............... | ................. | E..DG. | ........... | ........... | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................ | .V........F....... | ...... | ............ | T..DG..FTA.D | 0.02 | 2 |
| G.... | F.....SA..SI.M.G.R | ..HG.....NF......T | ...A.. | ..ANRD.A..DQ | A..A........ | 0.02 | 2 |
| DA..T | F.....NA..PI.P.P.R | .Q.DR.....F....... | ....D. | ............ | A..A........ | 0.02 | 2 |
| T.... | F.....AKG.P..H.P.R | ................. | ...D.. | E.AGAADA.VDH | A..A........ | 0.02 | 2 |
| ..... | ................ | ................. | ...DGR | ..AGEA...VDG | A..A........ | 0.02 | 2 |
| ..... | ................ | ................T | R..TGR | ............ | A..A........ | 0.02 | 2 |
| ..... | F................ | .V........F....... | ...... | ............ | TQRG...ADM.A | 0.02 | 2 |
| ..... | ................ | ................. | R..... | ED.GR..I..DN | A..A........ | 0.02 | 2 |
| ..... | F................ | .V........F....... | ...... | ............ | T.RT...VKA.D | 0.02 | 2 |
| HA... | F...........M.K.R | T.PTG....DF....... | ...DGR | ............ | A..A........ | 0.02 | 2 |
| ..... | F.....AG..RE.L...K | TQ.TG....DF....... | ...DDR | .SGAGAD.E.GE | A..A........ | 0.02 | 2 |
| ..... | F................ | .V........F....... | ...... | ............ | ..QTA..VEG.H | 0.02 | 2 |
| DA... | ................ | ................. | ...AG. | .NAG.DD...DQ | A..A........ | 0.02 | 2 |
| NA..T | F................ | TKAT.....NF......T | R..ND. | .SARG..A..DE | A..A........ | 0.02 | 2 |
| N.... | F.....DT..LK.T.H.G | .QPTG....NF....... | E..AGR | ............ | DPRDE..VEM.H | 0.02 | 2 |
| TT... | F.....ATG.NV.T.G.R | ..DGE....DF....... | ...... | ENA..ND.A.DR | A..A........ | 0.02 | 2 |
| ..... | F................ | .V........F....... | ...... | ............ | A..TG..DGT.E | 0.02 | 2 |
| E.... | F.....DAG.NA.L.S.R | .Q.S.....NF....... | ...D.R | ES.DRN.....Q | A..A........ | 0.02 | 2 |
| ..... | F................ | .V........F....... | ...... | ............ | DTKA...NS..E | 0.02 | 2 |
| ..... | ................ | ................. | ....D. | ENTATDD...GH | A..A........ | 0.02 | 2 |
| ..... | F.....SAA.NM.M.A.L | .KAS.....NF......T | ...... | ............ | A..A........ | 0.02 | 2 |
| HA... | F................ | ................. | ...DDR | EN.GTN.AE.DN | A..A........ | 0.02 | 2 |
| ..... | ................ | ................. | E..D.. | EDGKGA....GE | A..A........ | 0.02 | 2 |
| HT... | ................ | ................. | E..NG. | ............ | ............ | 0.02 | 2 |
| .A... | F.....NGG.RA.N.E.R | ..DGE....DF....... | ....GR | E.TR.N.....E | A..A........ | 0.02 | 2 |
| ..... | F................ | .V........F....... | ...... | ............ | GKRDP..NSE.. | 0.02 | 2 |
| ..... | ................ | ........DF....... | ...D.R | EDTG.A....GN | A..A........ | 0.02 | 2 |
| SA... | ................ | ........NF....... | R...D. | .DGTGGD.A..R | A..A........ | 0.02 | 2 |
| NA... | F................ | TKHGG....NF....... | R..DD. | ............ | A..A........ | 0.02 | 2 |
| ..... | ................ | ................. | R..D.. | E..GTG..E.DS | A..A........ | 0.02 | 2 |
| ..... | F................ | .V........F....... | ...... | ............ | GTRNG.TDNS.E | 0.02 | 2 |
| G.... | F.....NGG.HV...W.L | .QP.G.....F....... | G..KD. | .NATGND.E..H | A..A........ | 0.02 | 2 |
| NT... | F.....SA..RA.....R | .........NF....... | R...D. | E.TGGNDAE.DD | A..A........ | 0.02 | 2 |
| DA..T | F.....NGG.NI.K.E.R | .QAS.....NF......T | ....GR | .SAKAA.AA.DE | A..A........ | 0.02 | 2 |
| RA... | ................ | .KYT.....NF......T | ...DDR | .NGGGN...VDQ | A..A........ | 0.02 | 2 |
| ..... | F................ | .V........F....... | ...... | ............ | ERRSP...GE.D | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................ | .V........F....... | ...... | ........... | ANKNG..SSV.A | 0.02 | 2 |
| .A... | F................ | T.DT.....DF......T | R..TGR | ........... | ........... | 0.02 | 2 |
| E.... | ................ | ................ | ...... | ..ANTN.TA.DS | A..A........ | 0.02 | 2 |
| SA... | F.....GDG.RA.....V | ..DGE....DF......T | G..AD. | E.AGAA..E.DR | A..A........ | 0.02 | 2 |
| ..... | ................ | ................ | E..... | ..TGRD...F.R | A..A........ | 0.02 | 2 |
| TA... | F.....SGT.NM.K.T.E | .Q.DH....NF......T | ...D.R | ........... | A..A........ | 0.02 | 2 |
| A...T | ................ | TQ.TG....DF....... | ...DD. | ..T.G...A..E | A..A........ | 0.02 | 2 |
| TT... | F.....DK...M.K.P.M | .KPSE....DF......T | ...ADR | ........... | A..A........ | 0.02 | 2 |
| ..... | ................ | ................ | ...N.R | E.AGAND.AY.N | A..A........ | 0.02 | 2 |
| ..... | ................ | .KDSR....DF....... | R..D.. | ..TK...AE..D | A..A........ | 0.02 | 2 |
| ..... | ................ | ................ | ...TG. | ........... | A..A........ | 0.02 | 2 |
| D...T | F................ | ..........F....... | ....D. | ...GEA...YDR | A..A........ | 0.02 | 2 |
| ....T | F.....D...S..M.T.R | .........NF....... | ....D. | ESAG...TEYD. | A..A........ | 0.02 | 2 |
| ..... | F................ | .V........F....... | ...... | ........... | GRRDP..NEG.. | 0.02 | 2 |
| T.... | F.....GN..NA.T...M | T.PTG....DF....... | ...DDR | ........... | A..A........ | 0.02 | 2 |
| ..... | F.........I....... | .........NF....... | R...D. | E.AAAD.I..GQ | A..A........ | 0.02 | 2 |
| GT... | F................ | .V........F....... | ...... | ........... | A..A........ | 0.02 | 2 |
| ..... | ................ | ................ | ...AG. | E.TD.A....DG | A..A........ | 0.02 | 2 |
| ..... | ................ | ................ | ...D.. | ENGRGD..AY.D | A..A........ | 0.02 | 2 |
| ..... | F................ | .V........F....... | ...... | ........... | T.RD...ARI.. | 0.02 | 2 |
| ..... | F................ | ..HG.....NF......T | E..DD. | ........... | ........... | 0.02 | 2 |
| D.... | F.....SRA.SK.N.A.H | ..DGE....DF....... | ...... | ........... | A..A........ | 0.02 | 2 |
| ..... | ................ | .........NF....... | ...DDR | EDAG...I..GQ | A..A........ | 0.02 | 2 |
| TA... | ................ | T.P......DF....... | ...D.. | ........... | A..A........ | 0.02 | 2 |
| SA... | F.....AKG.P..H.P.R | T.PGG....NF....... | ...DD. | ...TGS.IEFDG | A..A........ | 0.02 | 2 |
| RT... | F................ | .QPTG....NF....... | ...... | ........... | A..A........ | 0.02 | 2 |
| D...T | ................ | .Q.S......F....... | R..AD. | ........... | A..A........ | 0.02 | 2 |
| NA..T | F.....GTG..P.T.D.R | T.P......DF....... | ...D.. | ........... | A..A........ | 0.02 | 2 |
| AA... | ................ | .QHNQ.....F......T | ...N.. | E.ANRN..EF.D | A..A........ | 0.02 | 2 |
| ..... | ................ | ................ | ...... | ENGD....E.DR | A..A........ | 0.02 | 2 |
| ..... | F................ | .V........F....... | ...... | ........... | .ARSP...R..E | 0.02 | 2 |
| G.... | ................ | TQ.GR....NF....... | ...... | ........... | A..A........ | 0.02 | 2 |
| R.... | ................ | TQ.NQ.....F..P.... | R...DR | ........... | A..A........ | 0.02 | 2 |
| ..... | ................ | ................ | R..N.. | ..AG.N.AA.GQ | A..A........ | 0.02 | 2 |
| ..... | ................ | ................ | ...ADR | ..AG.N.AA.GQ | A..A........ | 0.02 | 2 |
| ..... | ................ | ................ | E..A.. | ........... | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....A.A.RP.I...L | ..DGE....DF....... | R..... | .SGAG.D..F.N | A..A........ | 0.02 | 2 |
| SA... | F.....AG..PE.H.Q.V | .K.TG....DF....... | R...DR | ........... | A..A........ | 0.02 | 2 |
| ..... | ................. | ................. | ...... | ..AKG...EFG. | A..A........ | 0.02 | 2 |
| ..... | ................. | ................. | R..TGR | ..AG.SD.EVG. | A..A........ | 0.02 | 2 |
| ..... | ................. | .KYT.....NF....... | R..D. | ED.GGND.EV.D | A..A........ | 0.02 | 2 |
| ..... | ................. | ................. | ...N. | ...AAS.A.VGQ | A..A........ | 0.02 | 2 |
| ..... | ................. | ................. | ...D.R | E.GAGAD...GQ | A..A........ | 0.02 | 2 |
| RA... | ................. | .........NF..P...T | R.ND. | ........... | A..A........ | 0.02 | 2 |
| ..... | ................. | ................. | ...... | GDTTGS.AA..E | A..A........ | 0.02 | 2 |
| GT... | F.....SRA.SK.N.A.H | .QDT.....DF....... | ...DDR | ...G.S..AFGD | A..A........ | 0.02 | 2 |
| GA... | F.....NAG.IN.N...L | ..HG.....NF......T | ...DDR | ........... | A..A........ | 0.02 | 2 |
| NT..T | F......KT.NV.K.T.H | ................. | ...... | ........... | A..A........ | 0.02 | 2 |
| DA... | F.....A.G.SL.K.Q.G | ................. | G..ND. | ........... | A..A........ | 0.02 | 2 |
| EA... | F.....DKG.HM.L.G.R | .........NF....... | ...D.. | .DAS.N...VDG | A..A......I. | 0.02 | 2 |
| ..... | ................. | ................. | E..AD. | ..AT.DD..FDG | A..A........ | 0.02 | 2 |
| AA... | ......GRG..Q.T.G.R | .RPT......F..P...T | ...ND. | .NAGA.D...GS | A..A........ | 0.02 | 2 |
| D.... | ................. | ................. | R..... | EN.AADD.A.GD | A..A........ | 0.02 | 2 |
| ET..T | F................ | .V.......F....... | ...... | ........... | A..A........ | 0.02 | 2 |
| A...T | F.....SRT.IQ.....G | .Q.DR.....F....... | ....D. | ........... | A..A........ | 0.02 | 2 |
| ..... | ................. | ................. | ...D.. | E.TG.G.T...Q | A..A........ | 0.02 | 2 |
| ..... | ................. | ................. | R..ND. | ..AGEN..A..G | A..A........ | 0.02 | 2 |
| SA... | F.....SGT.S..T.T.. | ..AGR....DF......T | R..D.. | ........... | A..A........ | 0.02 | 2 |
| SA... | F.....A.A.RE.I.... | ..DGE....DF....... | ...... | ...ARD.IA..G | A..A........ | 0.02 | 2 |
| ..... | ................. | ................. | E..AD. | E.AAAN..E.DG | A..A........ | 0.02 | 2 |
| ..... | ................. | ................. | R..ADR | EN.D...A..GD | A..A........ | 0.02 | 2 |
| ..... | F.....SS..SV.P.D.H | .........DF....... | E..AD. | ........... | A..A........ | 0.02 | 2 |
| E.... | ................. | .........NF..P...T | R...D. | .D.K.G..E.GQ | A..A........ | 0.02 | 2 |
| ..... | ................. | ................. | ...DG. | ..ARGA.AE..S | A..A........ | 0.02 | 2 |
| ..... | ................. | ................. | ...D.. | ENAGASD1A.DH | A..A........ | 0.02 | 2 |
| EA... | ................. | ................. | E..DD. | ........... | A..A........ | 0.02 | 2 |
| ..... | ................. | ................. | R..... | EDAG.AD.E.G. | A..A........ | 0.02 | 2 |
| G.... | F................ | ..HG.....NF......T | E..DD. | ........... | A..A........ | 0.02 | 2 |
| ..... | ................. | .K.TG....DF....... | R...DR | ..ATRS.I..GN | A..A........ | 0.02 | 2 |
| TA..T | F.....AG..PA.K.G.R | ..YN......F.....T | ...... | E.GNGS....GR | A..A........ | 0.02 | 2 |
| G.... | F.....SRA.SK.N.A.L | ..DGE....DF....... | ...... | ..AAE.D....N | A..A........ | 0.02 | 2 |
| HT..T | F.....SA..RA.....R | .........NF....... | R...D. | E.TGGNDAE.DD | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................. | .V........F....... | ...... | ............ | TPRTA..NR..P | 0.02 | 2 |
| ..... | F................. | .V........F....... | ...... | ............ | .DRAA..IRE.H | 0.02 | 2 |
| ..... | ................. | .................T | ...D.. | ............ | A..A........ | 0.02 | 2 |
| ..... | ................. | .........DF..P...T | ...... | ESAGRS...VDR | A..A........ | 0.02 | 2 |
| EA... | F......KA.SA.T.A.G | .V........F....... | ...... | E.AAAN..E.DG | A..A........ | 0.02 | 2 |
| ..... | F......GA..K.M...E | ..PN.....NF....... | ...NDR | ............ | A..A........ | 0.02 | 2 |
| NT... | ................. | ................. | ...... | ............ | A..A........ | 0.02 | 2 |
| ..... | ................. | .........NF....... | R...D. | ............ | A..A........ | 0.02 | 2 |
| AA... | F.....A...H......L | .........NF....... | R..... | ............ | A..A........ | 0.02 | 2 |
| ..... | ................. | ..HG.....NF......T | R..DD. | E.TS.D..AY.D | A..A........ | 0.02 | 2 |
| SA... | ................. | .PPNG.....F......T | ...DDR | ............ | A..A........ | 0.02 | 2 |
| ..... | F................. | .V........F....... | ...... | ............ | GAKDR..NNA.H | 0.02 | 2 |
| ..... | F.....G.G.HA.T.G.R | TQPSQ....NF....... | ...DDR | ............ | A..A........ | 0.02 | 2 |
| ..... | F................. | .V........F....... | ...... | ............ | N.RDG..NRT.P | 0.02 | 2 |
| AT... | F.....GKG.NV.I.Q.G | TQ.TQ.....F....... | R..A.. | ESAK..DAA.DD | A..A........ | 0.02 | 2 |
| D.... | F.....AK..NV.M.G.R | TQ.TQ.....F....... | R...D. | .SGGA.D.E..N | A..A........ | 0.02 | 2 |
| ..... | ................. | ................. | ...... | .NGGRA.I...H | A..A........ | 0.02 | 2 |
| R.... | .........NP.M.E.R | TQYT.....NF......T | R...D. | ............ | A..A........ | 0.02 | 2 |
| ..... | ................. | .........F....... | ...... | ............ | KTRNT..AG..H | 0.02 | 2 |
| TA... | ................. | .........DF....... | R...D. | ............ | A..A........ | 0.02 | 2 |
| ..... | F................. | .V........F....... | ...... | ............ | GQRSH..DRN.E | 0.02 | 2 |
| GT... | F......GT.NM.L.Q.G | .KAS.....NF......T | E..DD. | ............ | A..A........ | 0.02 | 2 |
| ..... | ................. | ................. | ...D.. | ..GT.DD...DN | A..A........ | 0.02 | 2 |
| TA..T | F......TT.HN.L.G.R | T.PGG....NF....... | ...D.R | ............ | A..A........ | 0.02 | 2 |
| GA..T | ................. | ................. | ...DDR | ..A.RG.A..GH | A..A........ | 0.02 | 2 |
| ..... | ................. | ................. | ...D.. | .AGA..T..GR | A..A........ | 0.02 | 2 |
| ..... | F................. | ................. | E..NG. | ............ | ............ | 0.02 | 2 |
| ..... | F.....AST.PI.K.Q.K | TQASG....DF....... | ...D.. | EDTGAD....DS | A..A........ | 0.02 | 2 |
| RA... | ................. | .RPT......F....... | ...DDR | E.AGE...E..N | A..A........ | 0.02 | 2 |
| ..... | ................. | TQYT.....NF......T | R..AD. | ............ | A..A........ | 0.02 | 2 |
| ..... | F................. | .V........F....... | ...... | ............ | SBSP...FTE.P | 0.02 | 2 |
| TA..T | ................. | .........NF....... | R...D. | EDGGGS..E.GR | A..A........ | 0.02 | 2 |
| ..... | ................. | ................. | R..TG. | E.AGGS..AVDG | A..A........ | 0.02 | 2 |
| E.... | F.....AGA.NK.L...K | .V........F....S.. | ...... | ..TGAS..EV.N | A..A........ | 0.02 | 2 |
| ..... | ................. | ................. | ...D.. | E.TR.N.....Q | A..A........ | 0.02 | 2 |
| ..... | ................. | ................. | E..DDR | ............ | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| A.... | ................. | ................. | ....GR | ........... | A..A........ | 0.02 | 2 |
| TA... | F.....AAT.N..P.P.R | ..YN......F......T | ...D.R | ........... | A..A........ | 0.02 | 2 |
| ..... | ................. | ................. | E..NG. | EDTGGNDIA.DD | A..A........ | 0.02 | 2 |
| R.... | F.....DHT.R..M.G.R | .Q.DR.....F....... | ....D. | ..GRGSD.A.GD | A..A........ | 0.02 | 2 |
| ..... | F................ | .V........F....... | ...... | ........... | TRT....NNG.Q | 0.02 | 2 |
| GT... | ................. | .........NF....... | R...D. | EDAA...AAVDQ | A..A........ | 0.02 | 2 |
| ..... | F................ | .V........F....... | ...... | ........... | ARHSG..FNI.E | 0.02 | 2 |
| ..... | ................. | ................. | ...D.R | ESGKAS..A.GE | A..A........ | 0.02 | 2 |
| ..... | ................. | ................. | ...D.. | ........N... | A..A........ | 0.02 | 2 |
| ..... | ................. | ................. | ...DDR | E.......... | A..A........ | 0.02 | 2 |
| ..... | ................. | ................. | ...DG. | EDTA.G..E.G. | A..A........ | 0.02 | 2 |
| NA..T | ................. | .QPG.....NF....... | ...DD. | .DARAADA...Q | A..A........ | 0.02 | 2 |
| T.... | F.....AGA.NQ.N...V | .V........F....... | ...... | ..TGAS.A..DH | A..A........ | 0.02 | 2 |
| ..... | ................. | ..A......DF....... | E..ND. | ........... | ........... | 0.02 | 2 |
| ..... | F.....GKA.LQ.P.N.L | ................. | ...... | ........... | A..A........ | 0.02 | 2 |
| EA... | F.....SGA.LV.M.G.R | TQPNR.....F..P...T | ...DG. | ........... | A..A........ | 0.02 | 2 |
| GT... | ................. | .QPN......F......T | ...N.. | .DAGES..AF.Q | A..A........ | 0.02 | 2 |
| ..... | F................ | .V........F....... | ...... | ........... | AQRA....QG.E | 0.02 | 2 |
| ..... | F................ | .V........F....... | ...... | ........... | AQRAT..SNG.. | 0.02 | 2 |
| ..... | ................. | ................. | R...D. | ........... | ........... | 0.02 | 2 |
| ..... | ................. | ..A......DF....... | ...DG. | .DASGS.TAY.S | A..A........ | 0.02 | 2 |
| NA... | F.....AET..A.T...K | .QYDH....NF..P...T | R.... | ........... | A..A........ | 0.02 | 2 |
| TA... | F.....NKT.HL.T.A.R | TQASG.....F....... | R...D. | E.ATA...E.DD | A..A........ | 0.02 | 2 |
| ..... | ................. | ................. | ...D.. | .NASEN...FDR | A..A........ | 0.02 | 2 |
| ....T | F.....DNT.SK.L...K | .Q.G......F....... | R...D. | E.GSAND.EFDG | A..A........ | 0.02 | 2 |
| E.... | F.....STG.SV.M.T.L | ................. | ...DD. | ........... | ........... | 0.02 | 2 |
| ..... | ................. | ................. | E..AD. | ENAGASDIA.DH | A..A........ | 0.02 | 2 |
| GA... | ................. | .Q.DR.....F....... | ....D. | E.GTAN..AVD. | A..A........ | 0.02 | 2 |
| ..... | ................. | ................. | R..AD. | .NGG.ND....Q | A..A........ | 0.02 | 2 |
| ..... | F................ | .V........F....... | ...... | ........... | GPRNG..FGG.T | 0.02 | 2 |
| GT... | F.....DRG.S..T.A.S | ..DGE....DF....... | ...... | ........... | ........... | 0.02 | 2 |
| ..... | ................. | ................. | G..DDR | E.GGAA..EVDS | A..A........ | 0.02 | 2 |
| ..... | ................. | ...TG....NF....... | R..AD. | EDAKGG.....R | A..A........ | 0.02 | 2 |
| AT... | F.....AT..IA.K.Q.R | ..P.E....NF......T | ...DDR | ........... | A..A........ | 0.02 | 2 |
| ..... | ................. | ................. | ...DDR | ..ASE...E.D. | A..A........ | 0.02 | 2 |
| G...T | F................ | ................. | ...... | ........... | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................. | .V........F....... | ...... | ............ | NRRAT..ST..T | 0.02 | 2 |
| ..... | F................. | .V........F....... | ...... | ............ | GPRS...YSM.T | 0.02 | 2 |
| ..... | .................. | .................. | ...N.. | E..GAND.A... | A..A........ | 0.02 | 2 |
| T.... | F.....ANG.HL.K.K.S | .KPSE....DF......T | ...... | E.TD.A....DG | A..A........ | 0.02 | 2 |
| KA... | F.....GG..NK.M.... | .QPSE....DF....... | R..D.. | ............ | A..A........ | 0.02 | 2 |
| ..... | .................. | .................. | ...NDR | ..A.GD...VDH | A..A........ | 0.02 | 2 |
| ..... | .................. | .................. | ...D.R | .DATA..A.Y.H | A..A........ | 0.02 | 2 |
| GA..T | F......AG.NP.P.D.R | .QAS.....NF......T | ...... | ............ | A..A........ | 0.02 | 2 |
| SA... | F.....AQT.LA.I.K.K | TQ..H....NF....... | R..DD. | ESGR.GDA.F.E | A..A........ | 0.02 | 2 |
| ..... | .................. | .QDTQ.....F....... | ...DDR | ..ATRD.T...GH | A..A........ | 0.02 | 2 |
| ..... | .................. | .................. | ...... | EN.TR.DAA.DE | A..A........ | 0.02 | 2 |
| ..... | .................. | .................. | ...D.R | ............ | ............ | 0.02 | 2 |
| T.... | .................. | .QPNE....DF....... | G..ND. | .NGAESDIE.DG | A..A........ | 0.02 | 2 |
| RA... | F.....GKA.SE.N...L | .QPG.....NF....... | ...DDR | ............ | A..A........ | 0.02 | 2 |
| ..... | F................. | .V........F....... | ...... | ............ | GPRGR..DSE.H | 0.02 | 2 |
| TT..T | C................. | .................. | ...... | ............ | ............ | 0.02 | 2 |
| DT... | F.....SST.HI.I.T.G | .Q.S......F....... | E..ND. | ..AAE.D....N | A..A........ | 0.02 | 2 |
| ..... | .................. | .................. | G..DG. | .NGSAN..AFGQ | A..A........ | 0.02 | 2 |
| ..... | F................. | .................. | ...DDR | E.GRAADAAF.E | A..A........ | 0.02 | 2 |
| ..... | F.....NGG.NV.N.K.G | .QDT.....DF....... | ...DDR | ............ | A..A........ | 0.02 | 2 |
| ..... | .................. | .PPNG.....F......T | ...DDR | .S.......... | A..A........ | 0.02 | 2 |
| ..... | F................. | .V........F....... | ...... | ............ | TERTG..FDE.D | 0.02 | 2 |
| ..... | .................. | .................. | ...... | .STAAG...VDG | A..A........ | 0.02 | 2 |
| ..... | F................. | .V........F....... | ...... | ............ | APRGN..VTN.T | 0.02 | 2 |
| ..... | .................. | .........F....... | ...D.. | ENGKN..T.VGG | A..A........ | 0.02 | 2 |
| ..... | .................. | .........NF....... | ...DD. | ..ASE...E.D. | A..A........ | 0.02 | 2 |
| D...T | .................. | .................. | ...... | ..TTGA..AY.D | ............ | 0.02 | 2 |
| .A... | .................. | .................. | ....D. | ............ | A..A........ | 0.02 | 2 |
| .A... | F.....GQ..LN.L.D.R | .RPT......F..P...T | ...ND. | E.AG..D.A.GR | A..A........ | 0.02 | 2 |
| SA... | F.....DTG.PA.L.T.K | TQ.TG....DF....... | R..DD. | ..AAE.D....N | A..A........ | 0.02 | 2 |
| ..... | F................. | .V........F....... | ...... | ............ | EAKAR..FQ..H | 0.02 | 2 |
| ..... | .................. | .................. | ...DDR | EDGKGN..AF.. | A..A........ | 0.02 | 2 |
| ..... | .................. | .........DF....... | R...D. | ..GAEN..EF.R | A..A........ | 0.02 | 2 |
| E.... | .................. | ..A......DF....... | E..ND. | ............ | ............ | 0.02 | 2 |
| .A... | F.....SA..RA.....R | .................. | ...... | E..G.SDAA.GD | A..A........ | 0.02 | 2 |
| ..... | .................. | .................. | G..D.R | ..AGT.D.EYGQ | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| RA... | ................. | ..AGR.....F......T | R...D. | .......... | A..A........ | 0.02 | 2 |
| .A... | ................. | ................. | R..DD. | .......... | A..A........ | 0.02 | 2 |
| S...T | F.....G.G.IN.L...V | .V........F....... | ...... | ENGGGGD.A.GD | A..A........ | 0.02 | 2 |
| ..... | ................. | .Q.......DF....... | ...AD. | .NATG....VGS | A..A........ | 0.02 | 2 |
| GT..T | F.----ARG.IA.K.E.R | .QD.E.....F..P.... | ...... | ..AG.DDIA.DN | A..A........ | 0.02 | 2 |
| D...T | F............K.S | ................. | ...... | E.AAGND.EFDQ | .......... | 0.02 | 2 |
| ..... | ................. | .V........F....... | ...... | .......... | GTRG...VQS.E | 0.02 | 2 |
| A.... | F.....SN..PL.K.T.. | ................. | G..A.R | E.AG..D.A.GR | A..A........ | 0.02 | 2 |
| ..... | ................. | ........F....... | R..A.. | .......... | A..A........ | 0.02 | 2 |
| G...T | F.....DAA.HV.P...L | .QDGG....DF....... | ...D.R | .......... | A..A........ | 0.02 | 2 |
| T...T | F....DS..RA.P.A.S | ................. | ...... | .......... | A..A........ | 0.02 | 2 |
| ..... | F.....SS..SL.K.H.E | ........NF....... | R...D. | .......... | A..A........ | 0.02 | 2 |
| ..... | ................. | ................. | R..NG. | .S.G.S.IA..G | A..A........ | 0.02 | 2 |
| .A... | ................. | TQP.R....NF......T | E..DG. | ESAGRS...VDR | A..A........ | 0.02 | 2 |
| ..... | F................ | .V........F....... | ...... | .......... | TAQA...AP..T | 0.02 | 2 |
| ..... | ................. | ................T | G..KD. | .......... | A..A........ | 0.02 | 2 |
| DA... | F.....AEG.LK.M.H.L | ..DGE....DF....... | ...... | .......... | .......... | 0.02 | 2 |
| .A... | F.....ATT.NV.T.K.S | .KYT.....NF......T | R...D. | .......... | A..A........ | 0.02 | 2 |
| ..... | F................ | .V........F....... | ...... | .......... | E.RSA..VNT.P | 0.02 | 2 |
| E.... | F.....NKT.HL.T.A.R | ................. | ...... | ESTSTA..E... | A..A........ | 0.02 | 2 |
| ..... | F.....ART.P..M.A.N | .V........F....... | ...... | .......... | A..A........ | 0.02 | 2 |
| EA..T | F.....GA..SV.K.T.R | ........NF....... | R...D. | ES.SG.DIA.GE | A..A........ | 0.02 | 2 |
| E.... | F.....AGA.NQ.N...V | ..DD.....DF....... | ...DG. | E.ARGADI..GD | A..A........ | 0.02 | 2 |
| AT... | F.....AT..IA.K.Q.R | ................. | R...D. | ...AAS.A.VGQ | A..A........ | 0.02 | 2 |
| NA..T | F.....SA..RA.....R | .QDT.....F....... | R...DD. | .N.AGNDAAVDE | A..A........ | 0.02 | 2 |
| .A... | F.....DAG.LL.T.A.K | .Q.DR.....F....... | ....D. | .......... | A..A........ | 0.02 | 2 |
| ..... | F................ | .V........F....... | ...... | .......... | KPKDA...EA.A | 0.02 | 2 |
| ..... | F................ | .V........F....... | ...... | .......... | GD.DR..SEE.Q | 0.02 | 2 |
| ..... | ................. | ................. | R..DD. | EDGKGN..AF.. | A..A........ | 0.02 | 2 |
| A.... | F......KT.NV.K.T.K | TQASH.....F....... | E..TD. | ..TGGNDAE.DD | A..A........ | 0.02 | 2 |
| ..... | F................ | T..SE...DF....... | E...G. | .......... | A..A........ | 0.02 | 2 |
| RA... | F.....GEA.PL.L.N.R | ..DD.....DF....... | R...D. | .NTGGG.....H | A..A........ | 0.02 | 2 |
| TA... | F......GT.NM.L.Q.G | .Q.S......F....... | ....D. | .......... | A..A........ | 0.02 | 2 |
| DT..T | F......GT.NM.L.Q.G | .Q.S......F....... | ....D. | .......... | .......... | 0.02 | 2 |
| ..... | ................. | ...DG....DF......T | ...DDR | .DARRN.AE.GS | A..A........ | 0.02 | 2 |
| ..... | ................. | ................. | ...D.R | .D.GG.....GH | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | ...DGR | .DTG.GD.A..H | A..A........ | 0.02 | 2 |
| TA... | .................. | .................T | ...KDR | ............ | A..A........ | 0.02 | 2 |
| ..... | .................. | ..........F....... | ...DD. | .SAKAA.AA.DE | A..A........ | 0.02 | 2 |
| AT..T | F.....DTA.HV.K.G.G | .........DF....... | G..AD. | ............ | A..A........ | 0.02 | 2 |
| A.... | F.....AGA.NK.L...K | T..NE...DF.......T | ...D.. | ............ | A..A........ | 0.02 | 2 |
| ..... | .................. | .................. | ...DDR | ESAGGD..EV.R | A..A........ | 0.02 | 2 |
| ..... | .................. | .V........F....... | ...... | EDAGT...AFD. | A..A........ | 0.02 | 2 |
| ..... | .................. | .................. | ...N.. | E.GGG...E.GE | A..A........ | 0.02 | 2 |
| NA... | .................. | .................. | ...NGR | ............ | A..A........ | 0.02 | 2 |
| R.... | F................. | .QPTR.....F....... | E..NG. | ............ | A..A........ | 0.02 | 2 |
| TA... | F.....AGA.NQ.N...V | TQPTE....DF......T | ...D.R | ............ | A..A........ | 0.02 | 2 |
| HT... | F.....AEG.LK.M.H.L | ..DGE....DF....... | ...... | ............ | ............ | 0.02 | 2 |
| G.... | .................. | .................. | ...NG. | ............ | ............ | 0.02 | 2 |
| ..... | .................. | .................. | E..AD. | E.GRAADAAF.E | A..A........ | 0.02 | 2 |
| ..... | F................. | .V........F....... | ...... | ............ | SRRDA....G.E | 0.02 | 2 |
| ..... | F................. | .V........F....... | ...... | ............ | G.KSG..F.G.D | 0.02 | 2 |
| D.... | .................. | .........DF......T | ...DG. | ENTNGSD.AY.S | A..A........ | 0.02 | 2 |
| ....T | F.....ART.P..M.A.N | .V........F....... | ...... | ............ | A..A........ | 0.02 | 2 |
| G.... | F.....A...ND.T...K | ..PN.....NF....... | ...NDR | ............ | A..A........ | 0.02 | 2 |
| ..... | F......GT.NM.L.Q.G | .Q.S......F....... | ....D. | ............ | AR.AR..SR..D | 0.02 | 2 |
| T.... | F.....AEG.NI.L.K.R | .Q.DR.....F....... | ...DDR | ..AN.ADIAYDH | A..A........ | 0.02 | 2 |
| HT... | F.....ARA.P..L.G.V | .V........F....... | ...... | ESAGTN.....R | A..A........ | 0.02 | 2 |
| GT... | .................. | .................. | R..DD. | ..AG..D.A.GR | A..A........ | 0.02 | 2 |
| AA... | F.....DRG.HA.T...G | .................. | ...... | ............ | A..A........ | 0.02 | 2 |
| ..... | F................. | .KDSR....DF....... | ...DDR | .DATA..A.Y.H | A..A........ | 0.02 | 2 |
| DT... | .................. | .PPNG.....F......T | ...DDR | E.ATRA..A.DE | A..A........ | 0.02 | 2 |
| ..... | F.....AAT.N..P.P.R | .................. | R..N.. | .DGNGSDI.Y.E | A..A........ | 0.02 | 2 |
| DT... | F.....ARG.I..T.A.K | ..DGE.....F......T | R...D. | .S.G..D..FGG | A..A........ | 0.02 | 2 |
| ..... | F................. | .V........F....... | ...... | ............ | G.KGP..DKN.D | 0.02 | 2 |
| ..... | .................. | .................. | ...... | .DAKG..I.FDG | A..A........ | 0.02 | 2 |
| ..... | .................. | .................. | ...DDR | .DGGGAD.A.D. | A..A........ | 0.02 | 2 |
| ..... | .................. | ..........F......T | R..N.. | ............ | A..A........ | 0.02 | 2 |
| A...T | F.....G.G.HM.M.G.R | ..A......DF....... | ...DG. | EDAA.A.AE..Q | A..A........ | 0.02 | 2 |
| TA... | F.....NE..SD.H...K | ..DGE...DF....... | ...... | ............ | A..A........ | 0.02 | 2 |
| ..... | .................. | .........NF......T | R..TG. | .DGG.....Y.Q | A..A........ | 0.02 | 2 |
| ..... | F................. | .V........F....... | ...... | ............ | TPRNR..ANG.D | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | .........NF....... | ...AGR | ............ | A..A........ | 0.02 | 2 |
| ..... | ................. | ................. | ...D.R | .CTG.D..A.GG | A..A........ | 0.02 | 2 |
| ..... | F................ | .V.......F....... | ...... | ............ | RTP....AQ..D | 0.02 | 2 |
| RT... | F................ | TKDDR....DF....... | ...DDR | ............ | A..A........ | 0.02 | 2 |
| RT... | F.....NN..SA.N...R | T.P......DF....... | ...D.. | ES.AGGDAAFDQ | A..A........ | 0.02 | 2 |
| ..... | ................. | .................T | ...A.. | ............ | A..A........ | 0.02 | 2 |
| ..... | ................. | ..A....DF....... | ...DG. | ............ |  | 0.02 | 2 |
| TA... | F.....AA..RM.P.G.. | ..ATR....DF....... | E..N.. | ............ | A..A........ | 0.02 | 2 |
| ..... | ................. | .........F......T | ....GR | .NG..G.I...G | A..A........ | 0.02 | 2 |
| E.... | F................ | .V.......F....... | ...... | ............ | DRRSS..FEG.D | 0.02 | 2 |
| ..... | F.....STA..Q.H.Q.L | ..YN......F......T | ...D.R | .DAKRD.AAFDQ | A..A........ | 0.02 | 2 |
| DT... | F................ | T.HGR....NF......T | ....GR | ............ | A..A........ | 0.02 | 2 |
| ..... | F................ | .V........F....... | ...... | ............ | G.HTN..FEG.A | 0.02 | 2 |
| ..... | F................ | .V........F....... | ...... | ............ | AARTD..AK..H | 0.02 | 2 |
| ..... | F.....GQG.IA.....K | .QAS.....NF......T | ...DDR | ............ | A..A........ | 0.02 | 2 |
| RA... | F.....GKT.SL...S.K | .QAS......F....... | ...... | EDGSRND..... | A..A........ | 0.02 | 2 |
| ..... | F................ | .V........F....... | ...... | ............ | .QSNA..STR.D | 0.02 | 2 |
| A...T | F.....AQ...A.L.... | .V........F....... | ...... | ............ | A..A........ | 0.02 | 2 |
| A...T | F.....DN...L.I.N.R | T.PTG....DF....... | ...DDR | ...GAS..AYGE | A..A........ | 0.02 | 2 |
| ..... | ................. | ................. | ...... | ESTK..D.A.GD | A..A........ | 0.02 | 2 |
| A.... | F.....ATG.NV.T.G.R | ..DGE....DF....... | ...... | ENGTASD.AF.E | A..A........ | 0.02 | 2 |
| ..... | ................. | .........DF....... | E..AD. | .DTA.G.AAVDQ | A..A........ | 0.02 | 2 |
| ET..T | F................ | ..PN.....NF....... | E..KD. | ............ | A..A........ | 0.02 | 2 |
| ..... | F.....SA..SM.M.T.K | .PHD.....DF..P.... | E..DD. | .SAGRGDAE.GQ | A..A........ | 0.02 | 2 |
| ..... | ................. | ................. | ...DDR | ESTKAA.T..DH | A..A........ | 0.02 | 2 |
| ..... | F.....NGG..K.L...G | .QP.G.....F....... | ...... | ............ | A..A........ | 0.02 | 2 |
| ..... | ......DRG.PI.L.A.R | TQPT......F......T | ...DG. | ............ | A..A........ | 0.02 | 2 |
| AT..T | .................K | ..HGE....DF....... | ...DD. | ..AGTSD.AFGN | A..A........ | 0.02 | 2 |
| ..... | F................ | .V........F....... | ...... | ............ | GARG...S.T.T | 0.02 | 2 |
| R.... | F.....DA..IA.L.K.R | .QDT.....NF....... | ...DDR | EDAT..D.E.G. | A..A........ | 0.02 | 2 |
| ..... | ................. | ................. | E..ND. | E.TR.N.....Q | A..A........ | 0.02 | 2 |
| ..... | ................. | .KYT.....NF....... | ...NDR | ED.R.S.A...G | A..A........ | 0.02 | 2 |
| ..... | ................. | .........DF....... | R..NG. | ...G.S..AFGD | A..A........ | 0.02 | 2 |
| A...T | ................. | ................. | ...... | EDAGRND.A.D. | A..A........ | 0.02 | 2 |
| ..... | ................. | ................. | R...D. | ESTA.G.IEF.G | A..A........ | 0.02 | 2 |
| GA... | F.....AGG.HV.K.K.V | .KDT......F......T | ...DD. | ............ | A..A........ | 0.02 | 2 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| DT... | F.....R..$..T...N | ................. | ...... | ........... | A..A........ | 0.02 | 2 |
| ..... | ................. | ................. | ...... | ESGGTD....DR | A..A........ | 0.02 | 2 |
| NA... | ................. | .PPNG.....F......T | ...DDR | E.TR.N.....Q | A..A........ | 0.02 | 2 |
| H.... | F.....SGT.NM.K.T.E | ................. | ...... | ........... | A..A........ | 0.02 | 2 |
| ..... | .....GRT.ND.L.Q.R | .........NF....... | R...D. | E.TR.N.....Q | A..A........ | 0.02 | 2 |
| ..... | F................ | .V........F....... | ...... | ........... | .DRDT..D.I.Q | 0.02 | 2 |
| ..... | ................. | ................. | G..K.. | .SADGSD...DR | A..A........ | 0.02 | 2 |
| GA... | F................ | .V........F....... | ...... | ........... | G.RSG..VR..H | 0.02 | 2 |
| SA... | F......RT.IK.P.D.K | .QPN......F......T | G..N.. | ..ATGSD.A..H | A..A........ | 0.02 | 2 |
| TT..T | ................. | .V............... | ...... | ........... | A..A........ | 0.02 | 2 |
| ..... | F.....STG.SV.M.T.L | .QPSQ....NF....... | ...D.. | .DAG.A.I..DG | A..A........ | 0.02 | 2 |
| .A... | F.....SNG.RE.L...K | TKDDR....DF....... | ...DDR | ........... | A..A........ | 0.02 | 2 |
| ..... | F................ | ..........F......T | ...DDR | ........... | A..A........ | 0.02 | 2 |
| ..... | ................. | ................. | E..KG. | ENA.GAD..... | A..A........ | 0.02 | 2 |
| ..... | ................. | ................. | R..DD. | E.TS.D..AFDQ | A..A........ | 0.02 | 2 |
| SA... | F.....NGG.NV.N.K.G | ..YN......F......T | ...D.R | ........... | A..A........ | 0.02 | 2 |
| A.... | ................. | ................. | G..DG. | ........... | A..A........ | 0.02 | 2 |
| ..... | ................. | ................. | ...D.. | E.GD.A.A..DD | A..A........ | 0.02 | 2 |
| ..... | ................. | ................. | ...... | E.GGA.D.E..G | A..A........ | 0.02 | 2 |
| GA... | ................. | ..AGR....DF......T | R..D.. | .D......... | A..A........ | 0.02 | 2 |
| ..... | ................. | ................. | G..KGR | .DAG.S.A..DR | A..A........ | 0.02 | 2 |
| ..... | ................. | ................. | E..AD. | E.ATGA.....G | A..A........ | 0.02 | 2 |
| E.... | F.....GKG.ND.T.N.G | T.AG.....NF......T | ...D.R | ........... | A..A........ | 0.02 | 2 |
| ..... | ................. | ...........F...... | G..D.R | ..ASE...E.D. | A..A........ | 0.02 | 2 |
| AA... | F.....AGA.SL.....R | T.ANE.....F....... | ...D.. | ........... | A..A........ | 0.02 | 2 |
| RT... | F................ | ................. | ...... | ..GGGN.IE..R | ........... | 0.02 | 2 |
| AA... | F.....NR..NK.I.E.S | T..NE.....F......T | ...DDR | E.AGAND.AV.H | A..A........ | 0.02 | 2 |
| ..... | F.....NAT.RP.K.A.R | .........NF....... | R...D. | .DGARDDAA..D | A..A........ | 0.02 | 2 |
| TT... | F.....AEG.LK.M.H.L | ..DGE....DF....... | ...... | ........... | ........... | 0.02 | 2 |
| DT... | F......N..IL.T.T.R | .QPSQ....NF....... | G...GR | ........... | A..A........ | 0.02 | 2 |
| ..... | ................. | ................. | G..... | .DAGTA...FGG | A..A........ | 0.02 | 2 |
| ..... | ................. | ................. | R...D. | .NTAGND....R | A..A........ | 0.02 | 2 |
| RT... | ................. | ..AGR....DF......T | R..D.. | .SAKAA.AA.DE | A..A........ | 0.02 | 2 |
| ..... | ................. | ................. | ...... | .S.GAD..EV.G | A..A........ | 0.02 | 2 |
| ..... | ................. | ................. | ...D.R | ESTGEN...V.R | A..A........ | 0.02 | 2 |
| ..... | ................. | .QDGG.....F......T | ...DD. | ........... | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....NGG.IM.L.E.R | T.P......DF....... | R...D. | ........... | A..A........ | 0.02 | 2 |
| RA... | ................. | ..DGE....DF....... | ...... | E.GSR..AAVGD | A..A........ | 0.02 | 2 |
| ..... | ................. | ..A......DF..P.... | ...DD. | E.TTGND..V.S | A..A........ | 0.02 | 2 |
| ..... | F................ | .Q.GQ....DF....... | ....G. | .STTGA...V.Q | A..A........ | 0.02 | 2 |
| ..... | ................. | ................. | ...... | EDAGRND.A.D. | A..A........ | 0.02 | 2 |
| ..... | ................. | ................. | ...... | EDARGA...VGN | A..A........ | 0.02 | 2 |
| SA... | F......TG.IL...T.R | .QAS.....NF......T | ....GR | .DAGA.D.EVDE | ........... | 0.02 | 2 |
| ..... | ................. | .KPSE....DF......T | R...DR | E.ASTA..A.GQ | A..A........ | 0.02 | 2 |
| ..... | F................ | ................. | ...... | ..AG..DIAF.G | A..A........ | 0.02 | 2 |
| ..... | F................ | .V........F....... | ...... | ........... | GHRDG..FRA.Q | 0.02 | 2 |
| ..... | F................ | .V........F....... | ...... | ........... | KPRDG..DRI.. | 0.02 | 2 |
| ..... | ................. | ..........F......T | ...D.. | E.ATRGDTE.DR | A..A........ | 0.02 | 2 |
| NA..T | ................. | ..YN......F......T | ...D.R | ........... | A..A........ | 0.02 | 2 |
| NA... | F.....ATT.NV.T.K.S | ..HG.....NF......T | ...D.. | ........... | A..A........ | 0.02 | 2 |
| EA... | F................ | .V........F....... | ...... | ........... | SHRGE..FDV.T | 0.02 | 2 |
| GT... | F.....AEG.LK.M.H.L | ..DGE....DF....... | ...... | ........DR | ........... | 0.02 | 2 |
| RA... | ................. | TQ.TG....DF....... | ...... | EDGGGS..E.GR | A..A........ | 0.02 | 2 |
| ..... | F................ | .V........F....... | ...... | ........... | GPRD...I.E.T | 0.02 | 2 |
| ..... | .....NKT.HL.T.A.R | .........NF....... | ....G. | ..TK...AE..D | A..A........ | 0.02 | 2 |
| .A... | F.....GQ...M.M...H | ..A.R....DF....... | ...... | ........... | A..A........ | 0.02 | 2 |
| ..... | F................ | .V........F....... | ...... | ........... | NAKAA..VGE.H | 0.02 | 2 |
| GA... | ................. | ...T.....NF......T | ...DDR | .SAKAA.AA.DE | A..A........ | 0.02 | 2 |
| ..... | F................ | .V........F....... | ...... | ........... | TDRNH..FDE.. | 0.02 | 2 |
| E.... | F................ | .V........F....... | E..ND. | ........... | A..A........ | 0.02 | 2 |
| G.... | F.....GGG.L..N.P.K | .V........F....... | ...... | E.ATR.DT.YDQ | A..A........ | 0.02 | 2 |
| ..... | F.....NGG.HV.....L | ....E....DF....... | R...D. | ........... | A..A........ | 0.02 | 2 |
| ..... | ................. | TQ.TG....DF....... | ...DDR | ESG.AS...VDG | A..A........ | 0.02 | 2 |
| A.... | ................. | .QD.E....F..P..... | ...DG. | ........... | A..A........ | 0.02 | 2 |
| ..... | F................ | .V........F....... | ...... | ........... | A.RS...NR..D | 0.02 | 2 |
| ..... | ................. | .QPSQ....NF....... | ...D.. | ........... | ..AGAS...FDR | 0.02 | 2 |
| ..... | ................. | ..........F....... | ...... | ........... | ........... | 0.02 | 2 |
| GT... | F.....NGG.RP...D.G | .V........F....... | ...... | ........... | A..A........ | 0.02 | 2 |
| ..... | F.....SGT.SQ.K.E.. | .Q.......DF....... | ...AD. | E.AA.G..AF.S | A..A........ | 0.02 | 2 |
| GT... | ................. | ..........F....... | R..... | ..AGRG.TA.DD | A..A........ | 0.02 | 2 |
| ..... | ................. | .V........F....... | ...... | ........... | A.RTA..DTM.D | 0.02 | 2 |
| ..... | F.....AQ..RK.T.E.. | T.PNE....DF....... | R..... | ........... | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| TA... | F.....NR..IK.P...G | ..DGE....DF....... | ...... | .DAAGS..A.DE | A..A........ | 0.02 | 2 |
| EA... | .................. | .Q.S......F....... | E..N.. | .SAGAN..E..S | ............ | 0.02 | 2 |
| E.... | F.....NHA.LA.L.T.E | ..DGE....DF....... | ...... | ESGKAS..A.GE | A..A........ | 0.02 | 2 |
| GT... | F......GT.NM.L.Q.G | .Q.S......F....... | ....D. | ............ | ............ | 0.02 | 2 |
| E.... | F......G..NQ.N.A.G | TKAT.....NF......T | ...NDR | ............ | A..A........ | 0.02 | 2 |
| TA... | .................. | .................. | ...D.R | EDAGRGD...GN | A..A........ | 0.02 | 2 |
| ..... | .................. | .KYT.....DF......T | E..ND. | E.AGRDD...DR | A..A........ | 0.02 | 2 |
| ..... | .................. | .................. | ...AGR | E.TGTG..E.DS | A..A........ | 0.02 | 2 |
| ..... | .................. | ..AGR.....F......T | R..D.. | ............ | A..A........ | 0.02 | 2 |
| A.... | F.....GG..NK.M.... | .QPSE....DF....... | R..ND. | ............ | A..A........ | 0.02 | 2 |
| G...T | F.....GTG..P.T.D.R | .QPSQ....NF....... | ...D.R | E.AGTNDI...R | A..A........ | 0.02 | 2 |
| T.... | .................. | .KDT......F......T | ...DD. | ESGA.A.AAV.H | A..A........ | 0.02 | 2 |
| ..... | .................. | .................. | ...... | ..ATAD..AFDG | A..A........ | 0.02 | 2 |
| ..... | .................. | .................T | ...... | ..AS.N.IA.GD | A..A........ | 0.02 | 2 |
| D.... | F.....NNA..K...K.. | .QANH.....F......T | R..DD. | ............ | A..A........ | 0.02 | 2 |
| D...T | .................. | .................. | ...A.. | .NTGGG....DG | A..A........ | 0.02 | 2 |
| ..... | .................. | .V........F....... | ...... | .S.G.S.IA..G | A..A........ | 0.02 | 2 |
| A...T | F.....AQ...A.L.... | T.PGG....NF....... | R...D. | ............ | A..A........ | 0.02 | 2 |
| ..... | F................. | .V........F....... | ...... | ............ | .P.TS..FNE.D | 0.02 | 2 |
| NT..T | F.....S.T..I.K.N.M | .V........F....... | ...... | E.T..S..A..R | A..A........ | 0.02 | 2 |
| AA... | F.....GTG..P.T.D.R | T.PGG....NF....... | ...DD. | ............ | A..A........ | 0.02 | 2 |
| .T... | ......GRG.NQ.K.E.H | ..DGE....DF....... | ...... | ............ | ............ | 0.02 | 2 |
| ..... | .................. | .................. | R..AD. | ..AG.N.AA.GQ | A..A........ | 0.02 | 2 |
| NA... | .................. | .V........F....... | ...... | ............ | ASSNH..AKG.D | 0.02 | 2 |
| A.... | F......GG.NA.H.Q.R | ..DGE....DF......T | E..NG. | ............ | A..A........ | 0.02 | 2 |
| RT... | .................. | .Q.DR.....F....... | ....D. | .SGTRA..A.GE | A..A........ | 0.02 | 2 |
| ..... | F................. | .V........F....... | ...... | ............ | T.RAA...GE.H | 0.02 | 2 |
| TA..T | F.....SG..IK.K.D.R | .PPNG.....F......T | ...DDR | ............ | A..A........ | 0.02 | 2 |
| RA... | F.....DD..IH.K.K.K | .QPN......F......T | ...N.. | ENGGGA.I..GQ | A..A........ | 0.02 | 2 |
| ..... | F.....GQG.IA.....K | .Q......DF....... | ...AD. | .NTGGN.T..DN | A..A........ | 0.02 | 2 |
| .A... | .................. | .................. | E..NG. | E....ND.EF.Q | ............ | 0.02 | 2 |
| GA... | ............H...R | .QANH.....F......T | ...D.. | ENG.AG....DQ | A..A........ | 0.02 | 2 |
| ..... | .................. | .................. | ....D. | .D.GRA...F.. | A..A........ | 0.02 | 2 |
| ..... | .................. | .................. | ....D. | ENTTGNDAE.GQ | A..A........ | 0.02 | 2 |
| ..... | ......STA..Q.H...G | ...GG.....F..P...T | G..ND. | ............ | A..A........ | 0.02 | 2 |
| ..... | F................. | .V........F....... | R..AD. | ............ | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | .................. | ...A.. | ..GTGG.T...G | A..A........ | 0.02 | 2 |
| TT... | F.....ASA.S..T.T.G | ..DGE....DF....... | ...... | ............ | A..A........ | 0.02 | 2 |
| N.... | ................ | ..DGE....DF....... | ...... | E.TGRA..A..G | A..A........ | 0.02 | 2 |
| H.... | F......GA.NM.L.Q.G | .Q.S......F....... | ....D. | ............ | ............ | 0.02 | 2 |
| ..... | F................ | .V........F....... | T..... | ............ | .DRDE.VGG... | 0.02 | 2 |
| ..... | ................ | .................. | ...D.. | ED.TEGD...G. | A..A........ | 0.02 | 2 |
| ..... | ................ | .................. | ...D.. | ..TGGS.A.V.. | A..A........ | 0.02 | 2 |
| ..... | ......AST.IN.L.T.. | .................. | ...... | ............ | ............ | 0.02 | 2 |
| S.... | F.....DGA.R..P.A.K | ........NF....... | R...D | ............ | A..A........ | 0.02 | 2 |
| ..... | F.....SRA.SK.N.A.H | .QDT.....DF....... | ...DDR | ...G.S..AFGD | A..A........ | 0.02 | 2 |
| GT... | ................ | .................T | ...... | ............ | A..A........ | 0.02 | 2 |
| ..... | F.....DA..IA.L.K.R | .PPNG.....F......T | ...DDR | ............ | A..A........ | 0.02 | 2 |
| ..... | ................ | ..........F....... | R..AD. | .NAR.A.I..GE | A..A........ | 0.02 | 2 |
| TA... | F.....GGA.ID.I.Q.L | ..PN.....NF....... | ...NDR | ............ | A..A........ | 0.02 | 2 |
| ..... | ................ | .................. | ...DDR | E.ATRA.IE.DD | A..A........ | 0.02 | 2 |
| NT... | ................ | .PPNG.....F......T | ...DDR | ............ | A..A........ | 0.02 | 2 |
| TA... | F......A.G..V.T.H.R | TKDT.....NF....... | ...ND. | .SAARNDTAY.N | A..A........ | 0.02 | 2 |
| ..... | ................ | .................. | R..DD. | EDGGA.D.AV.N | A..A........ | 0.02 | 2 |
| E.... | F.....G.G.HM.M.G.R | ..A......DF....... | ...DG. | EDAA.A.AE..Q | A..A........ | 0.02 | 2 |
| G.... | ................ | .................. | ...... | .STSRGD...GG | A..A........ | 0.02 | 2 |
| A.... | F.....SQT.IH.K.T.R | TQ.TG....DF....... | ...D.R | E.GGANDT...G | A..A........ | 0.02 | 2 |
| ..... | ................ | .................T | ...DDR | ............ | A..A........ | 0.02 | 2 |
| D...T | ................ | ...GG....NF......T | ...... | EN.TR.DAA.DE | A..A........ | 0.02 | 2 |
| ..... | ................ | .................. | ...N.. | ..AKA.DTEV.Q | A..A........ | 0.02 | 2 |
| NT... | F.....NDG.PA.K.T.R | .Q.DR.....F....... | ....D. | ............ | A..A........ | 0.02 | 2 |
| ..... | ................ | .................. | R..DDR | ..AG.ND.EF.Q | A..A........ | 0.02 | 2 |
| A.... | F.....G.G.HM.M.G.R | ..A......DF....... | ...DG. | EDAA.A.AE..Q | A..A........ | 0.02 | 2 |
| ..... | ................ | .................. | E..A.R | ............ | A..A........ | 0.02 | 2 |
| SA... | F................ | .V........F....... | ...... | ............ | THRT...VRN.D | 0.02 | 2 |
| GA... | F.....AG..I..H.G.. | ..DGE....DF....... | ...... | E.TR.N.....Q | A..A........ | 0.02 | 2 |
| .A... | ................ | .KYT.....NF......T | ...D.R | ESATGD..E.GQ | A..A........ | 0.02 | 2 |
| ..... | F................ | ..........F....... | ...DDR | E..N...I..DR | A..A........ | 0.02 | 2 |
| D.... | ................ | .V........F....... | ...... | ............ | A..A........ | 0.02 | 2 |
| TT... | F.....SNG.P....T.R | ..DGE....DF....... | ...... | ............ | A..A........ | 0.02 | 2 |
| ..... | F................ | .V........F....... | ...... | ............ | TQHTP..AQE.E | 0.02 | 2 |
| DT... | F.....DTG.PA.L.T.K | .Q.DR.....F....... | ....D. | ............ | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .QPN.....NF....... | G..NDR | .DGREN.A..DG | A..A........ | 0.02 | 2 |
| AA... | ................. | ..P.....DF....... | ...D.. | ENAGRGDI.... | A..A........ | 0.02 | 2 |
| R.... | F.....DA..IA.L.K.R | .PPNG.....F......T | ...DDR | ............ | A..A........ | 0.02 | 2 |
| ..... | ................. | ................T | ...DDR | .DGSGG.TE.DG | A..A........ | 0.02 | 2 |
| D.... | ................. | ..ADH....DF....... | R...D. | ED.A.G.T..DN | A..A........ | 0.02 | 2 |
| AT..T | ................. | ..AGR....DF......T | R..D. | ............ | A..A........ | 0.02 | 2 |
| ..... | F.....GQA.LV.K.E.M | .V........F....... | ...... | ............ | A..A........ | 0.02 | 2 |
| ..... | ................. | ..PN.....NF....... | E..N.. | ............ | A..A........ | 0.02 | 2 |
| ..... | ................. | ................. | ...DDR | E.A.AD.AAF.. | A..A........ | 0.02 | 2 |
| D...T | ................. | .QPN......F......T | ....D. | ES.NRD....GQ | A..A........ | 0.02 | 2 |
| RA... | F.....GGT.IV.K.G.K | .Q.DR....DF....... | ...DDR | ............ | GQKDR..ST..H | 0.02 | 2 |
| ..... | ................. | ................. | R..DD. | ............ | A..A........ | 0.02 | 2 |
| ..... | ................. | ................. | ...DD. | .DAG.S.A..DR | ............ | 0.02 | 2 |
| A...T | F.....DRG.PI.L.A.R | TQPT......F......T | ...DG. | ............ | A..A........ | 0.02 | 2 |
| GA... | ................. | .QPG.....NF....... | ...DD. | E.GGA.D.E..G | A..A........ | 0.02 | 2 |
| TA... | F.....DRG.S..T.A.S | ..DGE....DF....... | ...... | ............ | ............ | 0.02 | 2 |
| A.... | F.....AEG.LK.M.H.L | .KYT.....NF......T | E..TD. | .SAKAA.AA.DE | A..A........ | 0.02 | 2 |
| D.... | F.....SR...A.L.... | ..HG.....F......T | ...... | ............ | A..A........ | 0.02 | 2 |
| ..... | F................. | .V........F....... | ...... | ............ | GNKDP..DGV.A | 0.02 | 2 |
| .A... | F.....DRG.S..T.A.S | ..DGE....DF....... | G..DG. | ............ | ............ | 0.02 | 2 |
| E.... | F.....ASA.S..T.T.G | .QPG.....DF....... | ....D. | ...R.G.....E | A..A........ | 0.02 | 2 |
| A.... | ................. | ................. | ...ADR | ..AGAN...FGQ | A..A........ | 0.02 | 2 |
| ..... | F................. | ................. | R..AD. | E.TTG..IAVDD | A..A........ | 0.02 | 2 |
| TT... | F.....GAT.IN.M.K.L | T.P......DF....... | R...D. | ..TG.N.IAF.D | A..A........ | 0.02 | 2 |
| E.... | F.....NQG.RV.I.N.R | .PANG.....F....... | ...DDR | ..AT.DDA..DQ | A..A........ | 0.02 | 2 |
| ..... | F.....SG..SH.T.G.G | TQDGE....DF....... | ...DG. | ...SRDD...GG | A..A........ | 0.02 | 2 |
| ..... | F................. | .V........F....... | ...... | ............ | NAKTR..FTT.D | 0.02 | 2 |
| R.... | ................. | .Q.DR.....F....... | ...... | ES.SA..I..DR | A..A........ | 0.02 | 2 |
| GT... | ......ATT.NV.T.K.S | ................. | ...... | ............ | A..A........ | 0.02 | 2 |
| RT... | F.....NGG.NN.K.T.R | .........NF....... | R...D. | .DTG.GD.A..H | A..A........ | 0.02 | 2 |
| GT... | ................. | .QD.E.....F..P.... | ...... | ............ | ............ | 0.02 | 2 |
| ..... | ................. | ................. | G..DG. | ............ | STRAP..STN.D | 0.02 | 2 |
| D.... | ................. | ..HG.....NF......T | ...A.. | E..AGS.AA.DN | A..A........ | 0.02 | 2 |
| ..... | F................. | .V........F....... | ...... | ............ | S.SSG..FGG.E | 0.02 | 2 |
| EA... | F.....DAA.IK.T.Q.N | ..DGE....DF....... | ...... | E........... | GTQSR..DRG.. | 0.02 | 2 |
| NT..T | ................. | ................. | E..N.. | E.TGRA..A..G | A..A........ | 0.02 | 2 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | .................. | .................. | R..D.. | ............ | ............ | 0.02 | 2 |
| ..... | .................. | .................. | ...D.. | .SG.TN.T..D. | A..A........ | 0.02 | 2 |
| ..... | F.....ATT.NV.T.K.S | TKAT.....NF......T | ...... | .SAAAA.I.F.H | A..A........ | 0.02 | 2 |
| ..... | .................. | .................. | R..ND. | ............ | A..A........ | 0.02 | 2 |
| ..... | F......S..SA.I.K.K | T.ASH....DF...... | ...D.. | .DTGTGD...GG | A..A........ | 0.02 | 2 |
| SA... | F.....SNA.HP.I.E.. | .................. | ...... | ............ | A..A........ | 0.02 | 2 |
| ..... | .................. | .Q.GQ....DF...... | ....G. | ..TG.N.IAF.D | A..A........ | 0.02 | 2 |
| ..... | F................. | .V........F...... | ...... | ............ | SAKTA..FE... | 0.02 | 2 |
| ..... | .................. | .................. | .D.R | .NASEN.AA..D | A..A........ | 0.02 | 2 |
| E.... | F.........HK.P.N.G | .V........F...... | ...... | ............ | A..A........ | 0.02 | 2 |
| AA... | F.....NRG.S..T.A.S | ..DGE....DF...... | ...... | ............ | ............ | 0.02 | 2 |
| R.... | .................. | TQ.GG....NF...... | ...DDR | ...G.A..E.GR | A..A........ | 0.02 | 2 |
| TA... | F.....GS..NM.N.E.R | .Q.GQ....DF...... | ....G. | E.TAG.DI..D. | A..A........ | 0.02 | 2 |
| ..... | F.....NAG.LA...Q.R | .........NF...... | R...D. | ..GT..DAAY.E | A..A........ | 0.02 | 2 |
| G.... | F.....AHT..H.K.G.H | ..........F...... | ...... | ............ | .A.TP..FNI.D | 0.02 | 2 |
| ..... | F.....STA..Q.H.Q.L | .QHNQ.....F......T | ...N.. | ............ | A..A........ | 0.02 | 2 |
| ..... | F................. | .................. | R..DD. | ............ | ............ | 0.02 | 2 |
| ..... | .................. | .................. | ...DDR | EN.GTN.AE.DN | A..A........ | 0.02 | 2 |
| D.... | F.....SAA.NM.M.A.L | T.ANH....NF......T | R...D. | ............ | A..A........ | 0.01 | 1 |
| ..... | F.....DGT.SM.N.G.R | .KPDQ.....F...... | ...DG. | ..ATGSD.A..H | A..A........ | 0.01 | 1 |
| ..... | .................. | .................. | ...... | ............ | SQRST..YGG.. | 0.01 | 1 |
| NA... | .................. | .........NF...... | R...D. | .D.......... | A..A........ | 0.01 | 1 |
| AA... | F......G..SE.T...R | .........NF...... | R...D. | E.GT.ND.A.DG | A..A........ | 0.01 | 1 |
| ..... | .................. | .................. | S..TDR | ............ | A..A........ | 0.01 | 1 |
| AA..T | .................. | .................. | ...... | ..TG.N.IAF.D | A..A........ | 0.01 | 1 |
| ..... | ..........L..L.Q.G | .QPSQ....NF...... | E..NGR | ............ | A..A........ | 0.01 | 1 |
| ..... | F................. | .V........F...... | ...... | ............ | NPRAD..VHM.A | 0.01 | 1 |
| ..... | .................. | .................. | ...DDR | .NASG..A.VGQ | A..A........ | 0.01 | 1 |
| E.... | F.....ASA.S..T.T.G | .QPG......F...... | ...DDR | ............ | ............ | 0.01 | 1 |
| EA... | F.....S...H......L | .................. | ...... | ES.DRN.....Q | A..A........ | 0.01 | 1 |
| AA... | F.....SGA..K.N.S.S | .V........F...... | ...... | ............ | A..A........ | 0.01 | 1 |
| ..... | ................L | TKDDR....DF...... | ...D.R | ............ | A..A........ | 0.01 | 1 |
| GT... | .................. | .QANH.....F......T | R..D.. | .SAKAA.AA.DE | A..A........ | 0.01 | 1 |
| ..... | .................. | .V........F...... | ..D... | ............ | A..A.E...... | 0.01 | 1 |
| ..... | .................. | .........DF......T | ...DDR | .SATTGD..VDR | A..A........ | 0.01 | 1 |
| ..... | .................. | .................. | ...ND. | ..ATT..T.F.Q | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| EA..T | F.....NGG.HV.....L | ................. | ...... | ............ | A..A........ | 0.01 | 1 |
| ..... | ................. | ................. | ...... | ............ | ............ | 0.01 | 1 |
| GA... | ................. | ................. | E..AD. | .SAKAA.AA.DE | A..A........ | 0.01 | 1 |
| T.... | ................. | ................. | E..N.. | ............ | ............ | 0.01 | 1 |
| E.... | ................. | ................T | E..DD. | ............ | ............ | 0.01 | 1 |
| ..... | F................. | .V........F....... | ...... | ............ | DKRG...VGV.T | 0.01 | 1 |
| TT..T | ................. | ................. | R...GR | E.AG...IAVDR | A..A........ | 0.01 | 1 |
| GA... | F.....G.G.HA.T.G.R | TKDT.....NF....... | ...DDR | .DTGASD.A.GN | A..A........ | 0.01 | 1 |
| ..... | ................. | ........NF....... | ...D.. | EDAG...I..GQ | A..A........ | 0.01 | 1 |
| G.... | F.....STG.LQ.L.D.R | .QP.G.....F....... | G..D.. | ............ | A..A........ | 0.01 | 1 |
| AA... | ................. | ........DF....... | G..KD. | ENASG.....GN | A..A........ | 0.01 | 1 |
| SA... | ................. | TQ.TG....DF....... | ...DDR | ..GTAGDI..GG | A..A........ | 0.01 | 1 |
| TT..T | ................. | ..........F......T | ...DGR | ............ | A..A........ | 0.01 | 1 |
| ST... | F......KT.NV.K.T.H | T..NE....DF......T | R..DD. | ............ | A..A........ | 0.01 | 1 |
| D...T | F.....DA..IA.L.K.R | .QPN......F......T | ...N.. | ............ | A..A........ | 0.01 | 1 |
| R.... | F.....GGG.PL.M.A.R | ................. | ....G. | ENAG.A...AVGG | A..A........ | 0.01 | 1 |
| .A... | F.....DNT.SK.L...K | ..PN.....NF......T | R..ND. | .DADGD...VDQ | A..A........ | 0.01 | 1 |
| GT... | ................. | ..HG............. | E..ND. | ............ | ............ | 0.01 | 1 |
| ..... | F................. | .V........F....... | ...... | ............ | TRRDG..FGE.H | 0.01 | 1 |
| ..... | F................. | .V........F....... | ...... | ............ | GDRGN..IS... | 0.01 | 1 |
| R.... | F.....NKT.I..K.... | ..DGE....DF....... | ...... | E.AGAADA.VDH | A..A........ | 0.01 | 1 |
| D...T | F................. | ...V.....NF....... | ....D. | ............ | ............ | 0.01 | 1 |
| DA... | ................. | .Q.DR.....F....... | ....D. | EDTAT..AE..D | A..A........ | 0.01 | 1 |
| G...T | F.....AN..RH...E.K | ..DGE....DF....... | ...... | ............ | A..A........ | 0.01 | 1 |
| TA..T | F.....NA..RM.M.K.. | ...T.....DF......T | R..DG. | ............ | A..A........ | 0.01 | 1 |
| ..... | F................. | .V........F....... | ...... | ............ | GQQA...V.K.H | 0.01 | 1 |
| ..... | F................. | .KDSR....DF....... | E..ND. | ............ | A..A........ | 0.01 | 1 |
| TA... | F.....NNG..V.K.P.R | Q.......DF....... | R...D. | .DTG.N..A..R | A..A........ | 0.01 | 1 |
| TA... | ................. | .QAS......F....... | ...... | .DATA..A.Y.H | A..A........ | 0.01 | 1 |
| T...T | ................. | .Q.DR....DF......T | ...DD. | .SGS.N..AV.D | A..A........ | 0.01 | 1 |
| ..... | F................. | .V........F....... | ...... | ............ | AQQAG...NT.E | 0.01 | 1 |
| ..... | .........IA.....K | ................. | R..D.. | ..AATADIE.D. | A..A........ | 0.01 | 1 |
| ..... | F.....SG..IK.K.D.R | T.P......DF....... | ....D. | .DAG.A.I..DG | A..A........ | 0.01 | 1 |
| GA..T | ......NN..SA.N...R | ................. | E..AD. | ............ | A..A........ | 0.01 | 1 |
| E.... | F.....G.G.HA.T.G.R | TKPS......F....... | ...... | .NTGRSDA...S | A..A........ | 0.01 | 1 |
| RA... | F.....SHG.II.K.H.R | ..DGE....DF....... | ...... | ESATGD..E.GQ | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ...V.....NF....... | ...DDR | EDAG...I..GQ | A..A........ | 0.01 | 1 |
| ..... | ................. | .........NF....... | ...DDR | E..G.A..E.GR | A..A........ | 0.01 | 1 |
| SA... | ................. | .........F......T | R..AD. | EDGKGN..AFDE | A..A........ | 0.01 | 1 |
| ..... | F................ | .........NF....... | R..D.. | ............ | A..A........ | 0.01 | 1 |
| ..... | ................. | ................. | E..T.. | ............ | ............ | 0.01 | 1 |
| GT... | F................ | .V........F...... | ...... | ............ | NTRAG..IG..K | 0.01 | 1 |
| ..... | ................. | ................. | E...ND | E.AGAND.AV.H | A..A........ | 0.01 | 1 |
| RA... | ................. | ................. | E..T.. | ............ | A..A........ | 0.01 | 1 |
| ..... | ................. | ................. | ...D.. | ED..A..IAF.D | A..A........ | 0.01 | 1 |
| D.... | F.....AEG.LK.M.H.L | ..DGE....DF....... | ...... | ............ | A..A........ | 0.01 | 1 |
| .A... | ................. | .QAS......F....... | ...... | EDAAG..A.VGS | A..A........ | 0.01 | 1 |
| ..... | F.....DAT..L.I.N.R | .KPDQ....DF....... | R...G. | E.GDGS...F.R | A..A........ | 0.01 | 1 |
| .A... | F.....GNG.HV.H.G.R | ..YN......F......T | ...D.R | E.AG...IAVDR | A..A........ | 0.01 | 1 |
| R.... | .........NP.M.E.R | TQYT.....NF......T | R..DD. | ............ | A..A........ | 0.01 | 1 |
| T.... | F.....SA..RA.....R | T.P......DF....... | ....D. | ............ | A..A........ | 0.01 | 1 |
| NA.GT | ................. | TQASG....NF....... | ....D. | E.AS...IEYGQ | A..A........ | 0.01 | 1 |
| ..... | F.....AT..NN.T.S.H | .QPG.....NF....... | ...DDR | ............ | A..A........ | 0.01 | 1 |
| A...T | ................. | ................. | E..NGR | .NAGA.D.AFDE | A..A........ | 0.01 | 1 |
| GT... | F.....ASG.SV.I.S.R | ................. | ...... | ..AG.DD...GG | A..A........ | 0.01 | 1 |
| TA... | F................ | .KDDR....DF....... | ...DDR | ESAKTADAAVDD | A..A........ | 0.01 | 1 |
| ..... | ................. | ................. | ...DD. | .D.GGGDAEV.Q | A..A........ | 0.01 | 1 |
| .A... | F.....DGT..V.H.H.V | ..V.......F....... | ...... | ............ | ............ | 0.01 | 1 |
| NA... | ................. | ................T | ...ADR | ............ | A..A........ | 0.01 | 1 |
| R.... | ................. | ..DGE....DF....... | ...... | EDGS...AE.DR | A..A........ | 0.01 | 1 |
| ..... | ................. | TQPGG....NF....... | R...D. | ..ATED..A.D. | A..A........ | 0.01 | 1 |
| ..... | ................. | ................. | ...... | .D.......... | A..A........ | 0.01 | 1 |
| TA... | F.....NDG.IV.M.... | ..DGE....DF....... | ...... | ............ | ............ | 0.01 | 1 |
| ..... | F................ | .V.......F....... | ...... | ............ | GKSSN..ANG.. | 0.01 | 1 |
| PT... | ................. | T..SG....DF....... | ...DD. | ..AKGD.A.V.S | A..A........ | 0.01 | 1 |
| G.... | F.....DKG.HM.L.G.R | ................. | ...NGR | ............ | A..A........ | 0.01 | 1 |
| ..... | ................. | ................. | ...DDR | .SAG.D..AFDG | A..A........ | 0.01 | 1 |
| D...T | F.....STA.HV.K.Q.M | ..DGE....DF....... | ...... | ..ARGADAE..S | A..A........ | 0.01 | 1 |
| ..... | ................. | ................. | R..DD. | E..KAS..AVDH | A..A........ | 0.01 | 1 |
| D.... | F......GA.HK.T.D.R | ................F. | R..AD. | ESG..N.I..DG | A..A........ | 0.01 | 1 |
| E.... | F.....NTG.LH.T...R | .Q.D.....DF..P.... | ...ND. | ............ | A..A........ | 0.01 | 1 |
| GA... | ................. | ................. | ...N.. | ...G.N.A.... | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| DT... | F.....NR..N..I.T.G | ..ADH....DF....... | R...D. | KNTTEN....DG | A..A........ | 0.01 | 1 |
| ..... | F.....GRG.H..P.E.R | .Q.DR.....F....... | ....D. | ............ | A..A........ | 0.01 | 1 |
| .A... | F.....STA..Q.H.Q.L | T.P......DF....... | R...D. | ............ | ............ | 0.01 | 1 |
| ..... | F....A...ND.T...K | ..P.E....NF......T | ...A.. | ............ | A..A........ | 0.01 | 1 |
| ..... | ................. | ..........NF....... | G..NDR | ............ | A..A........ | 0.01 | 1 |
| A.... | F.....AQ...A.L.... | .V........F....... | ...... | ............ | A..A........ | 0.01 | 1 |
| ..... | F.....AGA.HK.N.G.G | .........NF....... | R...D. | ............ | ............ | 0.01 | 1 |
| E.... | ................. | ................. | ...AG. | E.AAAN..E.DG | A..A........ | 0.01 | 1 |
| ..... | ................. | ......D.......... | E..KD. | ............ | ............ | 0.01 | 1 |
| RA..T | F......GA.HP.K...V | ..DGE....DF....... | ...... | ............ | A..A........ | 0.01 | 1 |
| ..... | ................. | ................. | ...... | E.AG.DDA...R | A..A........ | 0.01 | 1 |
| ..... | F......A..NL...A.N | ................. | G..ND. | .NGGGN...VDQ | A..A........ | 0.01 | 1 |
| EA... | F.....AST.HD.T.E.R | ................. | ...... | ............ | A..A........ | 0.01 | 1 |
| ..... | F......R..PN.T.A.M | ................. | ...... | ............ | AAQTS..AQI.T | 0.01 | 1 |
| GT..T | ................. | ................. | ...N.. | E..G.SDAA.GD | A..A........ | 0.01 | 1 |
| .A... | F.........HK.P.N.G | T.P......DF....... | ...D.. | ............ | A..A........ | 0.01 | 1 |
| ..... | ................. | ................. | G..ND. | E.ADRN....GS | A..A........ | 0.01 | 1 |
| AA..T | F.....GN..NK.H.A.L | T.P......DF....... | ...D.. | .N.AGA.AEYDD | A..A........ | 0.01 | 1 |
| ..... | ................. | ................. | ...... | E.ANGA.IE.GD | A..A........ | 0.01 | 1 |
| GA... | F.....ASG.SV.I.S.R | .........NF....... | R...D. | E.T..S..A..R | A..A........ | 0.01 | 1 |
| .A... | F.....NGG.NV.N.K.G | TQASH.....F....... | ...DDR | ............ | A..A........ | 0.01 | 1 |
| ..... | F................. | .V........F....... | ...... | ............ | .PRTA..SEG.. | 0.01 | 1 |
| ..... | F.....AAG.SE.I.G.. | .........DF....... | ...D.. | ............ | ............ | 0.01 | 1 |
| ..... | ................. | TKAG....NF....... | ....GR | ............ | A..A........ | 0.01 | 1 |
| ..... | ................. | TKAT....NF.......T | ...D.. | .DAGAN.AEVDH | A..A.......K | 0.01 | 1 |
| D...T | ................. | ................. | ...... | ............ | ............ | 0.01 | 1 |
| ..... | F................. | .V........F....... | ...D.. | ............ | A..A........ | 0.01 | 1 |
| ..... | ................. | ................. | ...... | .NTSGSDI..DE | A..A........ | 0.01 | 1 |
| G.... | ................. | .KDSR....DF....... | ...D.. | EDGGRG...V.D | ............ | 0.01 | 1 |
| E.... | F.....R..HE...N.N | .V........F....... | ...... | E.GSGS..AVD. | A..A........ | 0.01 | 1 |
| RA... | F.....GGT.PM.K.D.R | .........F......T | R..N.. | ............ | A..A........ | 0.01 | 1 |
| ..... | ................. | .QPSQ....NF....... | E..TGR | ............ | A..A........ | 0.01 | 1 |
| ..... | F................. | .V........F....... | ...... | ............ | ARRDP..F.N.E | 0.01 | 1 |
| ..... | F................. | .V........F....... | ...... | ............ | N.QDT..ARS.A | 0.01 | 1 |
| A.... | F.....AEG.LK.M.H.L | ..DGE....DF....... | ...... | ............ | ............ | 0.01 | 1 |
| .T... | ................. | ..DGE....DF....... | ...... | ENGKTND.A..G | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| KA... | F.....GRA.SV.M.K.G | ..DGE....DF....... | ...... | .DGGGS.....G | A..A........ | 0.01 | 1 |
| ..... | F................. | .V........F....... | ...... | ............ | SRSNT..YHV.. | 0.01 | 1 |
| AA... | .................. | T.P......DF....... | ...DD. | .NTRRGDIE..D | A..A........ | 0.01 | 1 |
| ..... | .................. | .................. | ...... | ESGAAA..EV.Q | A..A........ | 0.01 | 1 |
| ..... | .................. | .................. | ....D. | E.AGTNDI...R | A..A........ | 0.01 | 1 |
| .A... | F.....AKG.P..H.P.R | .KDDG....NF......T | R...DR | E..GANDI..GS | A..A........ | 0.01 | 1 |
| EA... | .................. | .KYT.....NF....... | ...NDR | ED.R.S.A...G | A..A........ | 0.01 | 1 |
| ..... | .................. | .QHNQ.....F......T | R..TG. | ............ | A..A........ | 0.01 | 1 |
| ..... | F.....DGA.R..P.A.K | .........NF....... | R...D. | ............ | A..A........ | 0.01 | 1 |
| ..... | F.....SGG.RV.P...G | .................. | ...DDR | ..AST..AA..D | A..A........ | 0.01 | 1 |
| ..... | .................. | .................. | ...N.R | E.AAAA..AF.S | A..A........ | 0.01 | 1 |
| ..... | .................. | .V........F....... | ...... | ............ | GRKDR..DKI.D | 0.01 | 1 |
| G.... | .................. | .................. | E..ND. | ............ | ............ | 0.01 | 1 |
| ..... | F.....DGT.SM.N.G.R | ..DGE....DF....... | ...... | ............ | A..A........ | 0.01 | 1 |
| ..... | .................. | .................. | R..DDR | EDTSA..A.YDG | A..A........ | 0.01 | 1 |
| A.... | .................. | .................. | G..ND. | ............ | A..A........ | 0.01 | 1 |
| A.... | F.....NA..RL.T.P.G | T.P.......F....... | R..DD. | ............ | A..A........ | 0.01 | 1 |
| .A... | F.....ASA.S..T.T.G | .QPG.....DF....... | ...DDR | ............ | ............ | 0.01 | 1 |
| ..... | .................. | .................. | R..DG. | ES.TTG..A..G | A..A........ | 0.01 | 1 |
| ..... | .................. | .................. | ....D. | .DANTN.A.VDS | A..A........ | 0.01 | 1 |
| ..... | .................. | .........DF....... | ...... | ED.GAG..AV.G | A..A........ | 0.01 | 1 |
| ..... | .................. | .................. | ....GR | EDAG.SD.E..H | A..A........ | 0.01 | 1 |
| G.... | F.....ASG.SI.T...R | ..YN......F......T | ...... | ED.G.N....GG | A..A........ | 0.01 | 1 |
| .A... | F.....ATA..V.H...R | .QAS......F....... | ...... | .SGDE.D.E.DR | A..A........ | 0.01 | 1 |
| E.... | F................. | .................. | ...... | ............ | ............ | 0.01 | 1 |
| E.... | .................. | ..DGE....DF....... | ...... | E.TGRA..A..G | A..A........ | 0.01 | 1 |
| D.... | .................. | ..DGE....DF....... | R...D. | .DGDTN.I.V.R | A..A........ | 0.01 | 1 |
| D...T | F.....SAG..L.H...K | .V........F....... | ...... | ES.G.AD.EFGE | A..A........ | 0.01 | 1 |
| TA... | F.....AEG.LK.M.H.L | ..DGE....DF....... | ...... | ............ | ............ | 0.01 | 1 |
| ..... | F.....SGA..N...G.R | .Q.DH....NF....... | ...DD. | .NAA.A....GD | A..A........ | 0.01 | 1 |
| R.... | F.....SA..RA.....R | ..DGE....DF....... | ...... | ..TKRDD.A.DE | A..A........ | 0.01 | 1 |
| ..... | .................. | .................. | ....GG | ..AG.N.AA.GQ | A..A........ | 0.01 | 1 |
| ..... | .................. | .................. | ...D.R | ............ | A..A........ | 0.01 | 1 |
| ..... | .................. | .................. | R..D.R | ..ATESD..FDQ | A..A........ | 0.01 | 1 |
| TA... | .................. | ..HG.....NF......T | ...... | ............ | A..A........ | 0.01 | 1 |
| TT... | F.....GHA.SK.T.E.K | .KYT.....NF......T | ...... | ..AGAN...FGE | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| GA... | F................. | .QDGH....DF......T | E..AGR | ..AG.DDIA.DN | A..A........ | 0.01 | 1 |
| TA..T | ................. | ..DGE....DF....... | R...D. | ........... | ............ | 0.01 | 1 |
| AA... | F.....GRG.H..P.E.R | ..DD.....DF....... | R...D. | .NGRG.D.E.DG | A..A........ | 0.01 | 1 |
| EA... | ................. | ................. | ...... | E.TGT...EVGQ | A..A........ | 0.01 | 1 |
| T.... | F.....GKG.SM.P.G.V | T.P......DF....... | ...D.. | EDAGT...AFD. | A..A........ | 0.01 | 1 |
| ..... | F.....GGG....K.G.R | TQPTE....DF....... | ...... | ..ATRSD..YGH | A..A........ | 0.01 | 1 |
| .A... | F................. | TQP.R....NF......T | G..DD. | ........... | A..A........ | 0.01 | 1 |
| R.... | F.....SGG.SH...A.R | TQASG.....F....... | ...D.. | ........... | A..A........ | 0.01 | 1 |
| G...T | ................. | .Q.GQ....DF....... | ....G. | EDAGRN...V.N | A..A........ | 0.01 | 1 |
| ..... | ................. | T.P......DF....... | ...DDR | E.AGRDD..V.E | A..A........ | 0.01 | 1 |
| G.... | ................. | ................. | ...DDR | .NATG....VGS | A..A........ | 0.01 | 1 |
| E.... | F.....DAA.IK.T.Q.N | ..DGE....DF....... | ...... | E.......... | ............ | 0.01 | 1 |
| KA... | F.....NGT.IL.T.A.K | .QAS.....NF......T | ....GR | ........... | ............ | 0.01 | 1 |
| ..... | ................. | ................. | R..DG. | EDASG....FDR | A..A........ | 0.01 | 1 |
| GT... | ................. | ..A.............. | E..ND. | ........... | ............ | 0.01 | 1 |
| ..... | ................. | TQ.GR....NF....... | ...... | ........... | A..A........ | 0.01 | 1 |
| ..... | ................. | ................. | E..AD. | .DASGS....GR | A..A........ | 0.01 | 1 |
| ..... | F................. | .V.......F....... | ...... | ........... | DRQAG..IQE.. | 0.01 | 1 |
| AT... | F.....GKA.SE.N...L | .QPG.....NF....... | ...DDR | ........... | A..A........ | 0.01 | 1 |
| H.... | ......S..NP.N.Q.K | .QPN......F......T | ...N.. | ..AGGADIEFDQ | A..A........ | 0.01 | 1 |
| .T... | F.....DAG.LK.L...G | T.P......DF....... | ...D.. | ........... | A..A........ | 0.01 | 1 |
| ....T | ................. | .KYT.....NF......T | ...D.. | ..A.A.D.AFDS | A..A........ | 0.01 | 1 |
| N.... | F......GT.NM.L.Q.G | .QDT.....DF....... | G..T.. | E.AGAND.AY.N | A..A........ | 0.01 | 1 |
| N.... | ................. | TQ.TH....DF....... | ....D. | EN.GTN.AE.DN | A..A........ | 0.01 | 1 |
| ..... | ................. | ..AGR....DF......T | ....D. | ........... | A..A........ | 0.01 | 1 |
| R.... | ................. | ..HG.....NF......T | ...A.. | ........... | A..A........ | 0.01 | 1 |
| NA... | F.....GKG.NQ...P.K | TK.NE....NF....... | ..GR | EDGG.S..E.DR | A..A........ | 0.01 | 1 |
| ..... | F................. | .V........F....... | ...... | ........... | DPRTT...NA.T | 0.01 | 1 |
| G.... | F.....SA..RA.....R | .QPN......F......T | ...N.. | .D.TAG..E..E | A..A........ | 0.01 | 1 |
| ET..T | F.....GDT..L...K.K | TQASG.....F....... | ...... | .SARG..A..DE | A..A........ | 0.01 | 1 |
| A.... | ................. | .K.TG....DF....... | R...DR | EN.GGS.IEVGG | A..A........ | 0.01 | 1 |
| ..... | ................. | ................. | G..N.. | E.......... | A..A........ | 0.01 | 1 |
| ..... | F.....SAA.NK.L.G.L | TK.NE....NF....... | ....GR | ........... | A..A........ | 0.01 | 1 |
| ..... | F.....DRG.PI.L.A.R | TQPT......F......T | ...DG. | ........... | A..A........ | 0.01 | 1 |
| ..... | ................. | ................T | G..TG. | ........... | ............ | 0.01 | 1 |
| E.... | ................. | ................. | E..AG. | ........... | ............ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.......T.SV...H.R | .Q.S......F....... | ...A.. | ENAG.SD.E..H | A..A........ | 0.01 | 1 |
| ..... | F................. | .V........F....... | ...... | ............ | NSRT...FQS.Q | 0.01 | 1 |
| ..... | ................. | ................. | ...D.. | EN.G.A.....Q | A..A........ | 0.01 | 1 |
| ..... | ................. | .........DF..P.... | R..DD. | .DGTTA.A.VDQ | A..A........ | 0.01 | 1 |
| A.... | ................. | .K.TG....DF...... | R...DR | ..ATRS.I..GN | A..A........ | 0.01 | 1 |
| ..... | ................. | ................. | ...DDR | ..AG..D..YGE | ............ | 0.01 | 1 |
| ..... | ................. | ................. | ...D.. | E.AGGN...FGE | A..A........ | 0.01 | 1 |
| AA... | F.....SK..PA.K.A.G | ................. | ...... | E.AGG.DI..GH | A..A........ | 0.01 | 1 |
| ..... | ................. | ................. | E..KD. | ...RRND...DR | A..A........ | 0.01 | 1 |
| .A... | F................. | .V........F....... | ...... | ............ | SSRGP..FTG.D | 0.01 | 1 |
| G.... | F.....SRG.PV.P.N.R | .Q.DR.....F....... | ...D.. | E.TGRND.A..E | A..A........ | 0.01 | 1 |
| EA. | ................. | ................. | ...N.. | ES.TTG.IE.DR | A..A........ | 0.01 | 1 |
| ..... | ................. | ................. | ...DDR | .STAES.I..DG | A..A........ | 0.01 | 1 |
| ..... | F................. | .V........F....... | ...... | ............ | SARTG..SNT.D | 0.01 | 1 |
| H.... | F.....GNG.HV.H.G.R | ..........DF...... | ...DDR | ............ | ............ | 0.01 | 1 |
| ..... | ................. | .KDSR....DF....... | P,.NDR | ............ | A..A........ | 0.01 | 1 |
| ..... | ................. | .QPN......F......T | ....D. | ES.NRD....GQ | A..A........ | 0.01 | 1 |
| ..... | F................. | .V........F....... | ...... | ............ | DSKAG...RG.. | 0.01 | 1 |
| ..... | ................. | T.HTR....DF......T | ...... | ............ | ............ | 0.01 | 1 |
| AA... | ................. | T..NE....DF......T | R..DD. | ............ | ............ | 0.01 | 1 |
| NT..T | F.....GKT.I..N...S | ..DGE....DF....... | ...DDR | ............ | A..A........ | 0.01 | 1 |
| ..... | ................. | ................. | ...... | ............ | GQRSH..DRN.E | 0.01 | 1 |
| ..... | ................. | ................. | ...DDR | EDGKGA....GE | A..A........ | 0.01 | 1 |
| H.... | ................. | .V........F....... | ...... | .DAAGA.IE.GN | A..A........ | 0.01 | 1 |
| TA... | F.....DTG.SK.T.T.R | .V........F....... | ...... | .NATEGDI..GG | A..A........ | 0.01 | 1 |
| ..... | ................. | .V........F....... | ...DDR | ............ | ............ | 0.01 | 1 |
| ..... | ................. | ...TG....NF......T | ...... | .DTAAA...VGE | A..A........ | 0.01 | 1 |
| A.... | ................. | TQASG.....F....... | R..DDR | E..K.GDA...S | A..A........ | 0.01 | 1 |
| ..... | F.....SKA.S..L.E.R | .QPTG....DF....... | R..... | E.T..S.....R | A..A........ | 0.01 | 1 |
| TA... | ................. | .Q.DR....F........ | ....GR | ESAGAD..AY.. | A..A........ | 0.01 | 1 |
| ..... | ................. | ................. | R..DD. | ............ | TQRSP..S...T | 0.01 | 1 |
| ..... | F.....NGG.NN.K.T.R | TQ.TG....NF....... | ...... | E.AAESD.A..Q | A..A........ | 0.01 | 1 |
| ..... | F................. | .V........F....... | ...... | ............ | TSKDA..I.T.A | 0.01 | 1 |
| ..... | F................. | .V........DF...... | R...D. | ............ | ............ | 0.01 | 1 |
| T...T | F.....NS..LV.I.S.R | ..DGE....DF....... | ...... | ............ | ............ | 0.01 | 1 |
| .A... | F.....GS..NM.N.T.R | ................. | ...... | ............ | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| G.... | F................. | .V........F....... | ...... | ............ | TTKAA..SQ..P | 0.01 | 1 |
| ..... | F................. | .V........F....... | ...... | ............ | ARSDG..AGA.. | 0.01 | 1 |
| G.... | F.....AEG.LK.M.H.L | ..DGE....DF....... | ...... | ............ | ............ | 0.01 | 1 |
| H.... | F.....DNT.SK.L...K | ..DGE....DF....... | ...... | E.AAGD.I.V.R | A..A........ | 0.01 | 1 |
| ..... | ................. | .........F......T | R..TGR | .SAS.ADAE.GS | A..A........ | 0.01 | 1 |
| ..... | ................. | .KDDR....DF....... | ...DDR | ESAKTADAAVDD | A..A........ | 0.01 | 1 |
| DA... | F.....STG.NP.M.E.R | TQYDR....NF....... | R...D. | ............ | A..A........ | 0.01 | 1 |
| G.... | F.....NQT.RN.T.D.R | .........NF....... | R...D. | ............ | A..A........ | 0.01 | 1 |
| GA... | ................. | ................. | R..N.. | ES.GAA..AVDG | A..A........ | 0.01 | 1 |
| R...T | ...........H.S.V | TQ.TG....DF....... | ...DDR | ............ | A..A........ | 0.01 | 1 |
| ..... | F.....SRT..A...T.N | ..DGE....DF....... | ...... | ............ | A..A........ | 0.01 | 1 |
| ..... | F................. | .V........F....... | ...... | ............ | .DHSP..FHE.A | 0.01 | 1 |
| ..... | F......AG..L.T.N.R | .KAS.....DF....... | E..ND. | E.TGRA..A..G | A..A........ | 0.01 | 1 |
| ..... | F................. | .V........F....... | ...... | ............ | GARNP...GN.A | 0.01 | 1 |
| A.... | ................. | ................. | ...DD. | ............ | ............ | 0.01 | 1 |
| NT... | F.....NAT.LV.T.H.R | ................. | ...... | ............ | ............ | 0.01 | 1 |
| G.... | ................. | .V........F....... | ...... | E.AA.SD.AVGG | A..A........ | 0.01 | 1 |
| E.... | ................. | ..DGE....DF....... | R...D. | ............ | ............ | 0.01 | 1 |
| ..... | ................. | .Q.......DF....... | R..A.. | .DAGGN.IAY.S | A..A........ | 0.01 | 1 |
| ..... | ......GHA.SK.T.E.K | T.PTG....DF....... | ...... | ............ | A..A........ | 0.01 | 1 |
| ..... | F................. | .V........F....... | ...... | ............ | GQRGE..ATA.H | 0.01 | 1 |
| EA... | F.....ANG.HL.K.K.S | .QAS......F....... | R,.N.. | ............ | A..A........ | 0.01 | 1 |
| ..... | ................. | ................. | ....GR | .DARGN..E.DQ | A..A........ | 0.01 | 1 |
| ..... | ................. | ................. | ...... | EDANG...EV.N | A..A........ | 0.01 | 1 |
| GT... | ................. | ..HG.....NF......T | ...DD. | ............ | ............ | 0.01 | 1 |
| R.... | ................. | .PPNG.....F......T | ...DDR | E..NA....YDR | A..A........ | 0.01 | 1 |
| ..... | F.....NR..N..I.T.G | ..ADH....DF....... | R...D. | KNTTEN....DG | A..A........ | 0.01 | 1 |
| RA... | F.....GRG.NN.T.G.. | ...DG...DF....... | ...D.. | ............ | A..A........ | 0.01 | 1 |
| ..... | ................. | ................. | E..TD. | ............ | A..A........ | 0.01 | 1 |
| RA... | F.....DTA.N....E.R | T.P......DF....... | ...DDR | ..GGGS..A.DG | ............ | 0.01 | 1 |
| GT... | F.....ASA.S..T.T.G | ..HG.....NF......T | E..DD. | ............ | ........R..H | 0.01 | 1 |
| RA..T | F.....GS..NM.N.T.R | .QP.G....DF....... | ...... | ..A.A.D.AFDS | A..A........ | 0.01 | 1 |
| ..... | F................. | .V........F....... | ...... | ............ | GRQST..SDE.A | 0.01 | 1 |
| GA... | F.....DRA.IN.M.K.L | .Q.S......F....... | ...DDR | ............ | A..A........ | 0.01 | 1 |
| ..... | F................. | .V........F....... | ...... | ............ | TTRGP..SKA.E | 0.01 | 1 |
| ..... | F................. | .V........F....... | ...... | ............ | GNRNN..I.V.T | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....NKT.HL.T.A.R | .QANH.....F......T | ...DDR | .SGKTADAEVGD | A..A........ | 0.01 | 1 |
| ..... | F.....NQA.RK.P.P.L | .V........F....... | ...... | ............ | A..A........ | 0.01 | 1 |
| ..... | F................. | .V........F....... | ...... | ............ | NPHTH..NT..P | 0.01 | 1 |
| ..... | .................. | .................. | R...D. | EDADGS..AF.Q | A..A........ | 0.01 | 1 |
| TA... | .................. | .Q.DH....NF....... | ...DD. | .NAG.NDT..DG | A..A........ | 0.01 | 1 |
| ..... | .................. | .................. | R..AD. | ESAGRNDIA.DQ | A..A........ | 0.01 | 1 |
| ..... | .................. | .................. | ...... | ............ | TQRSG..IT..E | 0.01 | 1 |
| GT..T | .................. | .................. | E..DDR | ............ | A..A........ | 0.01 | 1 |
| .A... | .................. | T.P......DF....... | ...D.. | .SGT.GD.AVGE | A..A........ | 0.01 | 1 |
| ..... | F................. | .V........F....... | R..G.. | ..GAEN..EF.R | A..A........ | 0.01 | 1 |
| ..... | .................. | .KYT.....NF..P...T | R..D.. | ............ | A..A........ | 0.01 | 1 |
| ..... | .................. | .................. | R..DD. | ..AN.A..AV.G | A..A........ | 0.01 | 1 |
| SA... | F.....GDG.RA.....V | ..DGE....DF......T | G..AD. | ............ | A..A........ | 0.01 | 1 |
| ..... | .................. | .................. | ...TGR | .......A.YDQ | A..A........ | 0.01 | 1 |
| G.... | .................. | .................. | E..ND. | E.TR.N.....Q | A..A........ | 0.01 | 1 |
| ..... | .................. | .................. | R..N.. | ENGAR....... | A..A........ | 0.01 | 1 |
| ..... | .................. | .................. | ...D.R | E.GRGA..AV.E | A..A........ | 0.01 | 1 |
| AA... | F.....SN..PL.K.T.. | .QAS.....NF......T | ...DDR | ............ | A..A........ | 0.01 | 1 |
| D...T | .................. | .................. | ....D. | ............ | ............ | 0.01 | 1 |
| G.... | .................. | .PPNG.....F......T | ...DDR | .SGS.NDIA..D | A..A........ | 0.01 | 1 |
| ..... | .................. | ..HG.....NF....... | ...DDR | ............ | ............ | 0.01 | 1 |
| ..... | .................. | .................. | ...... | E.TGT...EVGQ | A..A........ | 0.01 | 1 |
| DA... | .................. | .................. | ...D.. | EDAGT..AA..H | A..A........ | 0.01 | 1 |
| ..... | F.....GDG....K.Q.R | .QP.G.....F....... | R..NG. | E..G.S.T.FDS | A..A........ | 0.01 | 1 |
| ..... | .................. | ....E....NF......T | G..N.. | E.AAGSD..... | A..A........ | 0.01 | 1 |
| ..... | .................. | ..AGR....DF......T | R..D.. | .D.......... | A..A........ | 0.01 | 1 |
| NA... | .................. | ..........NF...... | ...D.. | .DASGS....GG | A..A........ | 0.01 | 1 |
| NT... | F................. | .V........F....... | ...... | ............ | TPRSP..Y.N.T | 0.01 | 1 |
| ..... | .................. | .................. | R...D. | .DAKGD.A.F.D | A..A........ | 0.01 | 1 |
| ..... | F.....DGA.R..P.A.K | T.P......DF....... | ...D.. | ............ | A..A........ | 0.01 | 1 |
| ..... | F................. | .KYT.....NF......T | R...D. | E.GAGSD.E.D. | A..A........ | 0.01 | 1 |
| ..... | F......KG.SH.H.G.. | ....Q.S...F....... | ...DDR | .NTGGG....DG | A..A........ | 0.01 | 1 |
| ..... | .................. | .................. | ...AGR | .N.NRN.....G | A..A........ | 0.01 | 1 |
| ..... | F................. | .V........F....... | ...... | ............ | GARDG..VRG.E | 0.01 | 1 |
| A.... | ......AEG.LK.M.H.L | ..DGE....DF....... | ...... | ............ | ............ | 0.01 | 1 |
| E.... | .................. | .................. | ....D. | ............ | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| DT... | ................. | ................. | ...DD. | ........... | A..A........ | 0.01 | 1 |
| TT... | ................. | ..HGH....NF......T | ...D.. | ........... | A..A........ | 0.01 | 1 |
| ..... | F................ | .V........F....... | ...... | ........... | SQRST..YGG.. | 0.01 | 1 |
| A.... | ................. | ................. | ...DG. | E.TGRA..A..G | A..A........ | 0.01 | 1 |
| GA... | ................. | ........NF...... | ...... | .DAKG..I.FDG | ............ | 0.01 | 1 |
| ..... | ................. | .QPTG....NF....... | ...... | .SAGRGDAAVDE | A..A........ | 0.01 | 1 |
| AT... | ................. | .PPNG.....F......T | ...DDR | E.ATRA..A.DE | A..A........ | 0.01 | 1 |
| ..... | F......AG.SH.T.A.R | T.P......DF....... | ...DDR | EDGAA.DAA.DE | A..A........ | 0.01 | 1 |
| RT... | F.....DSG.NM.H.A.R | ..HG.....NF.....T | ....G. | ........... | A..A........ | 0.01 | 1 |
| A.... | F.....GQG.IA.....K | .........NF......T | ...... | ........... | A..A........ | 0.01 | 1 |
| ..... | ................. | ................. | ...DD. | E.GNGS....GR | A..A........ | 0.01 | 1 |
| GA... | F................ | .Q.DH....NF....... | ...DD. | ........... | A..A........ | 0.01 | 1 |
| NA..T | ................. | ..AGR.....F.....T | R..D.. | .N.TA.DI.VDG | A..A........ | 0.01 | 1 |
| E.... | ................. | .Q.DR....DF....... | ...NGR | .SAKAA.AA.DE | A..A........ | 0.01 | 1 |
| NA... | ................. | ................. | ...... | ........... | ............ | 0.01 | 1 |
| NT... | F.....NQG.RV.T...L | .V........F.... | ...... | ESAGAA....GE | A..A........ | 0.01 | 1 |
| ..... | ................. | ................. | ...A.. | E..RRA..AV.D | A..A........ | 0.01 | 1 |
| ..... | ................. | ................. | ...... | EDAS....A.GQ | A..A........ | 0.01 | 1 |
| ..... | ................. | ................. | ...... | E.AKTD....GR | A..A........ | 0.01 | 1 |
| ..... | ................. | .Q.S......F....... | R..DD. | E.AGTDD.EVDE | A..A........ | 0.01 | 1 |
| DA... | F.....NR..LD.T...R | ................. | ...... | ........... | A..A........ | 0.01 | 1 |
| A.... | F.....NAG.LL.T.H.M | ................. | ...... | E.AG.S..E.DN | A..A.....Y.. | 0.01 | 1 |
| DT... | F................ | ..DGE....DF....... | R...D. | ........... | ............ | 0.01 | 1 |
| ..... | ................. | .QPN......F......T | ...N.. | E.AGAND.AV.H | A..A........ | 0.01 | 1 |
| TT..T | ................. | .V............... | ...DDR | ........... | ............ | 0.01 | 1 |
| ..... | F................ | .V........F....... | ...... | ........... | TQRAG..FNS.E | 0.01 | 1 |
| ..... | ......NAT.IM.T.H.R | T.P......DF....... | ...D.R | ........... | ............ | 0.01 | 1 |
| NT..T | ................. | ................. | E..ND. | ........... | ............ | 0.01 | 1 |
| ..... | ................. | ................. | ...N.R | ..AG.N.AA.GQ | A..A........ | 0.01 | 1 |
| DA... | F......NG.LQ.H...N | T.P......DF....... | ...D.. | ........... | ............ | 0.01 | 1 |
| HA... | F.....NGG.HN.H...G | TQASG.....F....... | ...... | ........... | A..A........ | 0.01 | 1 |
| ..... | ................. | ................. | ...T.R | ........... | A..A........ | 0.01 | 1 |
| TA... | ................. | ..DNH....NF....... | ...D.. | .NGGTG..A.DR | A..A........ | 0.01 | 1 |
| HT... | ................. | ................. | ...... | ........... | ............ | 0.01 | 1 |
| SA... | F.....NG...A.L.E.K | ..P.G....DF....... | ...D.. | .N.A.SD....G | A..A........ | 0.01 | 1 |
| G.... | ................. | .Q.......DF....... | E..AD. | ........... | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| D...T | F.....AT..ND.K.P.K | .QPN......F.....T | ...N.. | .SAS.N.IA..E | A..A........ | 0.01 | 1 |
| G.... | .................. | ..........F....... | ...... | ............ | DRSST..DTG.D | 0.01 | 1 |
| ..... | .................. | ..PNQ.....F......T | E..NGR | ............ | A..A........ | 0.01 | 1 |
| A.... | .................. | ..DGE....DF....... | R...D. | ............ | GARNA..AEG.E | 0.01 | 1 |
| ..... | F................. | .PHD.....DF......T | R..DG. | ............ | A..A........ | 0.01 | 1 |
| AA... | .......QG.NQ...A.R | ..ADR.....F....... | ....D. | E.GD.A.A...S | A..A........ | 0.01 | 1 |
| .A... | F................. | .................. | ....GR | ..AG.N.AA.GQ | ............ | 0.01 | 1 |
| .A... | F.....NQG..V.L.N.R | .Q.DR.....F....... | ...DDR | ............ | ............ | 0.01 | 1 |
| ..... | .................. | .................. | ...D.R | EDAKGG.....R | A..A........ | 0.01 | 1 |
| ..... | F................. | .V........F....... | ...... | ............ | DPHTR..D.M.. | 0.01 | 1 |
| E.... | F......A..IH.T.T.. | .V........F....... | ...... | E..RG.D..FDG | A..A........ | 0.01 | 1 |
| G.... | F.....SN..PL.K.T.. | .KYT.....NF......T | ...DDR | E.ATA.DAA.DQ | A..A........ | 0.01 | 1 |
| NT..T | P.....SA..RA.....R | .V........F....... | ...... | ESGSGND.E.DR | A..A........ | 0.01 | 1 |
| ..... | .................. | .................. | ...DDR | ENGDTSD.A.DN | A..A........ | 0.01 | 1 |
| ..... | .................. | .................. | ...DG. | .NGGTG..A.DR | A..A........ | 0.01 | 1 |
| TA... | F.....GKG.NQ.K.E.H | .................. | R..ND. | E.AAGN.AAV.E | A..A........ | 0.01 | 1 |
| G.... | F.....DA..IA.L.K.R | TQASG.....F....... | ....D. | .D.D...AEFGD | A..A........ | 0.01 | 1 |
| ..... | F................. | .V........F....... | ...... | ES.SA..I..DR | A..A........ | 0.01 | 1 |
| ..... | .................. | ..YN.............. | ...... | ..AA.N..AV.H | A..A........ | 0.01 | 1 |
| ..... | .................. | ..A......DF....... | ...T.. | ............ | A..A........ | 0.01 | 1 |
| NA... | F................. | .V........F....... | ...... | ............ | GPRTG..VR..Q | 0.01 | 1 |
| ..... | F................. | .V........F....... | ...... | ............ | ..KSG..F.V.E | 0.01 | 1 |
| R.... | .................. | T..NE....DF......T | R..DD. | ............ | ............ | 0.01 | 1 |
| ..... | .................. | .................. | ...DDR | .SAGG..I.YDS | A..A........ | 0.01 | 1 |
| ..... | F................. | .V........F....... | ...... | ............ | GPRA...FTV.H | 0.01 | 1 |
| ..... | F.....SH..LN.N.E.N | ..DGE....DF....... | ...... | ............ | A..A........ | 0.01 | 1 |
| ..... | F.....ST..SV.K.H.M | TQPTH....NF....... | R..DD. | ENGGGGD...DR | A..A........ | 0.01 | 1 |
| G.... | F.....GRT.IN.M.K.L | .........NF....... | ...... | ............ | A..A........ | 0.01 | 1 |
| ..... | .................. | .................. | ...... | E.AG.S...... | A..A........ | 0.01 | 1 |
| EA... | F.....AEG.LK.M.H.L | .KD.E....DF....... | ...... | ............ | ............ | 0.01 | 1 |
| R.... | F.....G.G.RA.N.E.R | T.PTG....DF....... | ...DDR | EDAGT...AFD. | A..A........ | 0.01 | 1 |
| AA... | F.....DTT.LH.K.T.G | .KYT.....NF......T | R...D. | ............ | A..A........ | 0.01 | 1 |
| ..... | F................. | .V........F....... | ...... | ............ | TQRT...DRS.. | 0.01 | 1 |
| ..... | .................. | .QPGQ....NF....... | E..AD. | .SASEN.I..DR | A..A........ | 0.01 | 1 |
| ..... | F.....DRT.PA.....M | .QPN......F.....T | ...N.. | .SAGAN..E..S | A..A........ | 0.01 | 1 |
| E.... | F.....DRG.S..T.A.S | ..DGE....DF....... | ...... | ............ | ............ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....SG..IK.K.D.R | .KYT.....NF......T | R..AGR | ............ | ............ | 0.01 | 1 |
| ..... | ................. | ................. | ...DG. | ..AK.ADT..GN | A..A........ | 0.01 | 1 |
| NT... | .......QG.NQ...A.R | ..ADR.....F....... | ....D. | E.GD.A.A...S | A..A........ | 0.01 | 1 |
| G.... | ................. | ................. | ...... | .SGKRA..E.DQ | A..A........ | 0.01 | 1 |
| SA..T | ................. | ..YT.....NF......T | ...DG. | ............ | A..A........ | 0.01 | 1 |
| A.... | F.....SRG.PV.P.N.R | T.P......DF....... | ...D.. | ...KGS.IEYGD | A..A........ | 0.01 | 1 |
| T.... | F.....AST.IN.L.T.. | ................. | ...D.. | ............ | A..A........ | 0.01 | 1 |
| ..... | F................ | .V........F....... | ...... | ............ | GKQS...YST.. | 0.01 | 1 |
| H.... | ................. | ..DGE....DF....... | G..DG. | ............ | ............ | 0.01 | 1 |
| ..... | ................. | ................. | ...... | ..TGAS..EV.N | A..A........ | 0.01 | 1 |
| AT... | ................. | ................. | R..DD. | ............ | ............ | 0.01 | 1 |
| DT... | ................. | ................. | ...... | ENGRGG.AEV.D | A..A........ | 0.01 | 1 |
| RA... | F................ | .V........F....... | ...... | ............ | KDRAA..VHN.H | 0.01 | 1 |
| TT... | F.....DSG.NM.H.A.R | .Q.DH....NF....... | ...... | ............ | A..A........ | 0.01 | 1 |
| AA... | ................. | ................. | ...DDR | E.AG..D.A.GR | A..A........ | 0.01 | 1 |
| RT... | F.....GNG.HV.H.G.R | TKDDR....DF....... | ...D.. | E.AGTNDI...R | A..A........ | 0.01 | 1 |
| ..... | F................ | ..........F....... | ...D.. | ..AG.DDIA.DN | TRQTT...D..P | 0.01 | 1 |
| TA... | F......EG.S..T.K.K | ..A......DF....... | ...DG. | EDGKA.DA..GQ | A..A........ | 0.01 | 1 |
| .A... | F.....GGT.HD.T.S.V | .V........F....... | ...... | .SAKAA.AA.DE | A..A........ | 0.01 | 1 |
| ..... | F................ | .V........F....... | ...... | ............ | ETRDR..STV.D | 0.01 | 1 |
| GT..T | F......GA..K.M...E | ................. | ...... | ..AG.N..AF.R | A..A........ | 0.01 | 1 |
| TT... | ................. | ................. | ....GR | ............ | ............ | 0.01 | 1 |
| TA... | ................. | ................. | ...N.. | ...G.N.A.... | A..A........ | 0.01 | 1 |
| ..... | ................. | ................. | ...D.. | .SAS.N.IA..E | A..A........ | 0.01 | 1 |
| E.... | ................. | .QPG.....NF....... | ...DDR | EDAG.AD.E.G. | A..A........ | 0.01 | 1 |
| DT... | F.....NKT.HL.T.A.R | ..YN......F......T | ...D.R | ............ | A..A........ | 0.01 | 1 |
| ..... | F................ | .V........F....... | ...... | ............ | GPRGG..DEE.. | 0.01 | 1 |
| E...T | F.....DTG.SK.T.T.R | .QPTG.....F....... | ...NGR | ............ | ............ | 0.01 | 1 |
| GT... | ................. | .PANG.....F....... | ...DDR | ...DGSDA..DE | A..A........ | 0.01 | 1 |
| NA... | ................. | ................. | ...DD. | ..GGGS..A.DG | A..A........ | 0.01 | 1 |
| RA... | ................. | ..YN......F......T | ...D.R | ..AGE....VG. | A..A........ | 0.01 | 1 |
| N.... | F.....SG..IK.K.D.R | .........F....... | R..AD. | .NAR.A.I..GE | A..A........ | 0.01 | 1 |
| ..... | ................. | ................. | G..KD. | E..AAS....GG | A..A........ | 0.01 | 1 |
| .A... | F.....GK..LA.K.N.G | .Q.S......F....... | E..N.. | ............ | A..A........ | 0.01 | 1 |
| ..... | ................. | .V........F....... | .....R | ESA.GG..E.GS | A..A........ | 0.01 | 1 |
| ..... | ................. | ................. | ...AD. | ESGSA..I.F.D | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| SA..T | F.....DKG..L.N...R | ..DGE....NF......T | ...D.. | .SANESD...DQ | A..A........ | 0.01 | 1 |
| GT... | F.....GRG.NN.T.G.. | ...DG....DF....... | ...D.. | ............ | A..A........ | 0.01 | 1 |
| G.... | F.....DQ..R..P.S.R | .KD.E.....F..P...T | R...D. | ............ | A..A........ | 0.01 | 1 |
| ET... | F.....NKT.HL.T.T.G | ..DGE....DF....... | ...... | ............ | A..A........ | 0.01 | 1 |
| NA..T | .................. | .........DF....... | ...AD. | ............ | A..A........ | 0.01 | 1 |
| DT... | F.....AGT.PM.K.K.G | .QDGH....DF......T | ...DD. | E.AGRN.T..DD | A..A........ | 0.01 | 1 |
| ..... | .........NM.L...K | .KDT......F......T | ...ND. | ............ | A..A........ | 0.01 | 1 |
| ..... | .................. | .........DF....... | ...D.. | E.TTR.D.E.GS | A..A........ | 0.01 | 1 |
| ..... | .................. | .................. | ...D.. | .DARRN.AE.GS | A..A........ | 0.01 | 1 |
| D.... | F.....ASA.S..T.T.G | .QPG.....DF....... | R...D. | ..ARG.D.AF.H | A..A........ | 0.01 | 1 |
| ..... | F.....SA..RA.....R | TKDDR....DF....... | ...DDR | ............ | A..A........ | 0.01 | 1 |
| ..... | .................. | ..HG.....NF......T | R..AD. | ............ | A..A........ | 0.01 | 1 |
| ..... | .................. | TQP.R....NF......T | R..ND. | ............ | A..A........ | 0.01 | 1 |
| ..... | .................. | TQ.TG....NF....... | ...... | ............ | | 0.01 | 1 |
| G.... | .................. | .QAS......F....... | ...... | .SGNGN...F.H | A..A........ | 0.01 | 1 |
| EA... | F.....GK..SH...E.K | .................. | ...... | E.AT.S.AAF.E | A..A........ | 0.01 | 1 |
| ..... | F.....SGA..N...G.R | .V........F....... | ...... | ..GGESD.E.D. | A..A........ | 0.01 | 1 |
| ..... | F.....GTG.P....K.. | .QPN......F......T | ..D.R | .S.G.S.IA..G | A..A........ | 0.01 | 1 |
| ..... | F................. | .V........F....... | ...... | ............ | GSSSG...TM.Q | 0.01 | 1 |
| SA..T | F.....AEG.NI.L.K.R | ..P.E....NF......T | E..A.. | E.A.A.DIA.D. | A..A........ | 0.01 | 1 |
| H.... | .................. | .QPSQ....NF....... | ...DDR | E.AG...IAVDR | A..A........ | 0.01 | 1 |
| ..... | .................. | .........DF....... | ...DDR | ENASG.....GN | A..A........ | 0.01 | 1 |
| SA... | F......KT.NK...A.G | ...NG....DF....... | G..K.. | ............ | A..A........ | 0.01 | 1 |
| ..... | .................. | .................. | ....GR | ..AG.N.AT.GQ | A..A........ | 0.01 | 1 |
| N.... | .................. | .KYT.....NF......T | ...... | ............ | A..A........ | 0.01 | 1 |
| ..... | .................. | .................. | ...DD. | .SGTG.D...GR | A..A........ | 0.01 | 1 |
| ..... | .................. | .................. | G..K.. | E.TGAA.I..GE | A..A........ | 0.01 | 1 |
| ..... | .................. | .................. | ...NGR | E.AK.N..AFDG | A..A........ | 0.01 | 1 |
| ..... | F......R..PN.T.A.M | .................. | ....D. | ESAG....A.GE | A..A........ | 0.01 | 1 |
| RA... | F.....A.A.NH.T.K.N | TQPTH....DF....... | ...DDR | ............ | A..A........ | 0.01 | 1 |
| ..... | .................. | .........NF....... | ...T.. | ..TGAS.A..DH | A..A........ | 0.01 | 1 |
| ..... | .................. | .................. | ...D.. | ESG..N.I..DG | A..A........ | 0.01 | 1 |
| ..... | .................. | .................. | ...NDR | ..AST..AA..D | A..A........ | 0.01 | 1 |
| G.... | F.....DTG.PA.L.T.K | T.P......DF....... | ...... | ...........K. | ............ | 0.01 | 1 |
| ..... | .................. | .................. | ...DD. | ............ | A..A........ | 0.01 | 1 |
| ..... | F.....AEG.LK.M.H.L | ..DT.....NF......T | ...DD. | ............ | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| NT... | .................. | .Q.......DF....... | ...DDR | .......... | GTKAA..ITS.Q | 0.01 | 1 |
| RA... | F.....G...SP.P.A.R | .V........F....... | ...... | ENGRGS.I..G. | A..A........ | 0.01 | 1 |
| G.... | F.....NN..SA.N...R | T.P......DF....... | ...D.. | EN.G.A.....Q | A..A........ | 0.01 | 1 |
| ..... | .................. | .................. | E..AGR | .......... | A..A........ | 0.01 | 1 |
| ..... | F................. | .V........F....... | ...... | .......... | T.QGR..AH..D | 0.01 | 1 |
| ..... | F................. | .V........F....... | ...... | .......... | N.SAS...SS.K | 0.01 | 1 |
| E.... | F......G..NQ.T.A.G | .V........F....... | ...... | E.AG.ADIE.G. | A..A........ | 0.01 | 1 |
| G.... | F................. | .V........F....... | ...... | .......... | A..A........ | 0.01 | 1 |
| ET..T | F.....AT...N.T...G | .QPNQ....NF...P..T | .....R | .......... | A..A........ | 0.01 | 1 |
| AA... | .................. | TKPSG....NF......T | ...DDR | ..ASAAD.E..D | A..A........ | 0.01 | 1 |
| ..... | .................. | .................. | R..D. | .......... | A..A........ | 0.01 | 1 |
| SA... | .................. | .Q.GQ....DF....... | ....G. | .......... | A..A........ | 0.01 | 1 |
| ..... | .................. | .................. | R..DD. | E.AAAN..E.DG | A..A........ | 0.01 | 1 |
| ..... | F.....ANG.NQ.I.S.G | TQDGQ....NF....... | G..... | .......... | A..A........ | 0.01 | 1 |
| R.... | F.....GS..NK.H...G | T.P......DF......T | ....D. | .......... | A..A........ | 0.01 | 1 |
| AA... | F.....A.G..V.T.H.R | TQASG.....F....... | ...... | .DGG..D.AF.E | A..A........ | 0.01 | 1 |
| SA..T | F......AAG.SE.I.G.. | .........DF....... | ...D. | .......... | ............ | 0.01 | 1 |
| DT... | F................. | .V........F....... | ...... | .......... | DR.AT..FSV.D | 0.01 | 1 |
| ..... | .................. | .................. | E..AD. | .SAKAA.AA.DE | A..A........ | 0.01 | 1 |
| GT... | F......GG.NA.I...R | ..ADH....DF......T | ...D.R | E.TS.GD.A.GD | A..A........ | 0.01 | 1 |
| R...T | .................. | TKDDR....DF....... | ...DDR | EDTG.A....GN | A..A........ | 0.01 | 1 |
| G...T | .................. | .................. | ...DDR | .......... | A..A........ | 0.01 | 1 |
| DT... | F......N..IL.T.T.R | ..HG.....NF......T | ...A.. | .......... | THKNG..SGE.T | 0.01 | 1 |
| RA... | F.....STG.LQ.L.D.R | .PDNR..T.DF......T | ....GR | .......... | A..A........ | 0.01 | 1 |
| ..... | F................. | .V........F....... | ...... | .......... | GPRAA..YTT.D | 0.01 | 1 |
| NT... | .................. | ..PNG....DF....... | R..AGR | .SGGRS..E.DQ | A..A........ | 0.01 | 1 |
| ..... | .................. | .................. | ...DD. | ..GAGSD.AY.D | A..A........ | 0.01 | 1 |
| ..... | F.....DTG.SK.T.T.R | .Q.S......F....... | ...D.. | .NGR.G..A..E | A..A........ | 0.01 | 1 |
| T.... | F......SA.IN.L.N.H | .QD.E....NF....... | ...... | .DAGGND.A.D. | A..A........ | 0.01 | 1 |
| NA... | F.....SRG.PV.P.N.R | .................. | ...... | .......... | A..A........ | 0.01 | 1 |
| D...T | F................. | .................. | R..DD. | .......... | ............ | 0.01 | 1 |
| EA... | F.....ASA.S..T.T.G | .QPG.....DF....... | ...DDR | .......... | ............ | 0.01 | 1 |
| ..... | F................. | .V........F....... | ...... | .......... | TSRDT..NNK.E | 0.01 | 1 |
| SA... | F................. | .V........F....... | ...... | .......... | ASSNH..AKG.D | 0.01 | 1 |
| GT... | F................. | ...GG....NF....... | E..AD. | .......... | A..A........ | 0.01 | 1 |
| ..... | F................. | .V........F....... | ...... | .......... | NPRG...DNG.D | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| R.... | ................. | .KPDQ.....F....... | ....GR | EDTG.A....GN | A..A........ | 0.01 | 1 |
| ..... | ................. | ................. | ...... | ES.SA..I..DR | A..A........ | 0.01 | 1 |
| D.... | F.....G..NQ.N.D.K | ...TE....F.......T | E..KD. | ........... | A..A........ | 0.01 | 1 |
| ..... | ................. | ................. | R...D. | .DAGRND.EFD. | ........... | 0.01 | 1 |
| D...T | F.....ASA.S..T.T.G | .QPG....DF....... | ...DDR | ........... | ........... | 0.01 | 1 |
| GA... | ................. | .Q......DF....... | ...AD. | .DGARDDAA..D | A..A........ | 0.01 | 1 |
| A.... | ................. | ................. | ...... | E.ARAN...F.N | A..A........ | 0.01 | 1 |
| E.... | F.....GT..NQ.K.G.R | .QHNQ.....F......T | ...N.. | ........... | A..A........ | 0.01 | 1 |
| E.... | F................ | ................. | ...DDR | ........... | ........... | 0.01 | 1 |
| ..... | ................. | T.A.H....DF....... | ...DD. | ENGREG.AA..H | A..A........ | 0.01 | 1 |
| ..... | ................. | ..DGE....DF....... | R...D. | ........... | GARNA..AEG.E | 0.01 | 1 |
| ..... | ................. | ................. | G..ND. | E.T..S..A..H | A..A........ | 0.01 | 1 |
| ..... | ................. | ................. | E..ND. | E.TGRND.A..E | A..A........ | 0.01 | 1 |
| E.... | ................. | .KD.E.....F..P...T | R..ND. | ........... | A..A........ | 0.01 | 1 |
| ..... | ................. | ................. | ...... | .STA..DA.FDS | A..A........ | 0.01 | 1 |
| GA... | F.....GDT.H..I...G | .QAS......F....... | ...D.. | ........... | A..A........ | 0.01 | 1 |
| TA... | ................. | ................. | ...D.. | ........... | A..A........ | 0.01 | 1 |
| ..... | ................. | ................. | ...DD. | ........... | KDRAA..VHN.H | 0.01 | 1 |
| G.... | ......A.......... | .........NF......T | ....D. | EN.GR.D.E.GE | A..A........ | 0.01 | 1 |
| ..... | ................. | ................. | ...... | E.AGGS..AVDG | A..A........ | 0.01 | 1 |
| ..... | F.....NNA..K...K.. | .QPN......F......T | ...N.. | ........... | A..A........ | 0.01 | 1 |
| ..... | F.....AEG.NI.L.K.R | .QD.E.....F..P.... | ...... | E.TKTN.AAVDE | A..A........ | 0.01 | 1 |
| D.... | F.....NKT.HL.T.A.R | .QANH.....F......T | ...DDR | .SGKTADAEVGD | A..A........ | 0.01 | 1 |
| ..... | ................. | .........NF......T | R..DD. | EDAKGS.A..DH | A..A........ | 0.01 | 1 |
| ..... | ................. | F................ | ...... | ED.GAG..AV.G | A..A........ | 0.01 | 1 |
| .A... | F.....AST.HD.T.E.R | T.P.....DF....... | ...DG. | ........... | ........... | 0.01 | 1 |
| TA... | ................. | .................T | ...NDR | E.TGAN.AE.GE | A..A........ | 0.01 | 1 |
| TA... | F.....NGG.NN.K.T.R | .KYT....NF......T | ...... | ........... | A..A........ | 0.01 | 1 |
| ..... | ................. | .........NF...... | ...DDR | ........... | ARSNR..FDV.H | 0.01 | 1 |
| GT... | ................. | ................. | ...ND. | ESTRG..I..GD | A..A........ | 0.01 | 1 |
| TA... | ................. | .................T | ...D.. | ........... | ........... | 0.01 | 1 |
| .A... | ................. | ................. | ...... | EN.TR.DAA.DE | A..A........ | 0.01 | 1 |
| RT... | F.....AEG.NI.L.K.R | .KP......NF....... | ..D.. | ..TGGSD.A.DN | A..A........ | 0.01 | 1 |
| ..... | ................. | .PPNG....F......T | ...DDR | ........... | A..A........ | 0.01 | 1 |
| ..... | ................. | .QPG.....DF....... | ...DDR | ..AKG.D.AYDG | A..A........ | 0.01 | 1 |
| G.... | F................ | .V........F....... | ...... | ........... | GHRNG..D.N.E | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | E..KDR | .DADA.D.A.DR | A..A........ | 0.01 | 1 |
| ..... | ................. | .........DF..P.... | G..K.. | ........... | A..A........ | 0.01 | 1 |
| ..... | F.....SN..PL.K.T.. | ..ADG.....F......T | ....D. | ........... | ........... | 0.01 | 1 |
| D.... | F.....GKG.ND.T.N.G | ................. | ...... | ........... | A..A........ | 0.01 | 1 |
| ..... | ................. | ................. | ...DG. | ........... | ........... | 0.01 | 1 |
| TA... | ................. | .QPSQ....NF....... | E..TGR | E.TD.A....DG | A..A........ | 0.01 | 1 |
| ..... | ................. | F................ | E..DDR | ...GRDDI..DR | A..A........ | 0.01 | 1 |
| PA..T | ................. | ................. | E..NG. | ........... | ........... | 0.01 | 1 |
| ..... | F................ | .V........F....... | ...... | ........... | DRKDT...NN.A | 0.01 | 1 |
| RA... | F.....GKG.S..M.K.M | .Q.S......F....... | R..DD. | ESGTRGD..VGQ | A..A........ | 0.01 | 1 |
| NA..T | ................. | TQASG....NF....... | ....D. | E.AS...IEYGQ | A..A........ | 0.01 | 1 |
| ..... | ................. | ................. | ...D.. | .N.TAN...VGS | A..A........ | 0.01 | 1 |
| GT... | F.....SRG.HP.H.D.G | ..A......DF....... | R..AGR | EDAGT...AFD. | A..A........ | 0.01 | 1 |
| ..... | F......S..PM.T.S.K | ..DGE....DF....... | ...... | ........... | ........... | 0.01 | 1 |
| ..... | ................. | .V........F....... | ...... | ........... | DPRGG..VQK.A | 0.01 | 1 |
| ..... | ................. | T.HTE....NF......T | ...NDR | ........... | A..A........ | 0.01 | 1 |
| ..... | ................. | ................. | ....D. | ENA.GAD..... | A..A........ | 0.01 | 1 |
| ..... | F................ | .V........F....... | ...... | ........... | GPRST..D.E.Q | 0.01 | 1 |
| ..... | ................. | ...TE.....F......T | R..DD. | ........... | A..A........ | 0.01 | 1 |
| AA... | F.....S.A.N..L...L | .KYT....NF.......T | ....GR | ENAG.SD.E..H | A..A........ | 0.01 | 1 |
| AA... | F......S..PM.T.S.K | .Q.GQ....DF....... | ....G. | ........... | A..A........ | 0.01 | 1 |
| AA... | ................. | TQPT......F....... | ...N.. | ...AAA.IE..Q | A..A........ | 0.01 | 1 |
| ..... | ................. | TKHGG....NF......T | ...... | ........... | A..A........ | 0.01 | 1 |
| ..... | F................ | ................. | ....D. | ........... | A..A........ | 0.01 | 1 |
| G...T | ......NS..II...A.R | ...TE.....F......T | ...DD. | .N.SGNDIE.DQ | A,.A........ | 0.01 | 1 |
| ..... | ................. | ................. | ....D. | .NTGGG.....H | A..A........ | 0.01 | 1 |
| ..... | ................. | ................. | R..DD. | ..TNESD..... | A..A........ | 0.01 | 1 |
| GT..T | F.....ARG.NA.P.Q.I | ...DG....DF....... | E..KD. | ENASG.....GN | A..A........ | 0.01 | 1 |
| ..... | ................. | ................. | R...D. | .DTSTN..E..G | A..A........ | 0.01 | 1 |
| .A... | F.....NAG.P..T.T.M | .KAS.....NF....... | ...DDR | ........... | A..A........ | 0.01 | 1 |
| ..... | ......ASA.S..T.T.G | .QPG.....DF....... | ...DDR | ........... | ........... | 0.01 | 1 |
| ..... | F................ | .V........F....... | ...... | ........... | SPRAT..VKG.D | 0.01 | 1 |
| DT... | F......N..IL.T.T.R | .........NF....... | R...D. | E.AR...I..DE | A..A........ | 0.01 | 1 |
| ..... | ................. | T.P......DF....... | ...DD. | .NTRRGDIE..D | A..A........ | 0.01 | 1 |
| ..... | ................. | .................T | ...... | ..T......... | A..A........ | 0.01 | 1 |
| ....T | F.....DTT.LH.K.T.G | .........NF....... | R...D. | ........... | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................ | .................. | R...D. | .DAKGD.A.F.D | A..A........ | 0.01 | 1 |
| GA... | F.....DNA.NA.M.N.K | ..HG.....NF......T | ...DD. | ............ | A..A........ | 0.01 | 1 |
| DA... | ................ | .................. | ...DDR | ..ARGADAE..S | A..A........ | 0.01 | 1 |
| GA... | F.....DQG.S..L...G | .Q.DR.....F....... | ....D. | ............ | A..A........ | 0.01 | 1 |
| E.... | F................ | .V........F....... | ...... | ............ | GTRDG..AE..A | 0.01 | 1 |
| .A... | ................ | ...G.....DF....... | R..DD. | ............ | A..A........ | 0.01 | 1 |
| SA..T | F.....GNG.HV.H.G.R | .................. | ...... | ............ | A..A........ | 0.01 | 1 |
| ..... | F................ | .V........F....... | ...... | ............ | AP.GR...QI.D | 0.01 | 1 |
| TA..T | F.....AEG.LK.M.H.L | ..DGE...DF....... | ...... | ............ | ............ | 0.01 | 1 |
| A.... | F.....DGG.NL.....N | TKDDR....DF....... | ...DDR | ............ | A..A........ | 0.01 | 1 |
| ..... | ................ | .Q.DR.....F....... | ....D. | ..GGA.D.E.GN | A,.A........ | 0.01 | 1 |
| GT... | F.....AEG.LK.M.H.L | ..DGE....DF....... | ....D. | ............ | ............ | 0.01 | 1 |
| SA... | F.....G.G..H.L.H.L | TQ.TQ.....F......T | ...D.R | E.AGAND.AY.N | A..A........ | 0.01 | 1 |
| ..... | F................ | .V........F....... | ...... | ............ | K.SGG..NTE.T | 0.01 | 1 |
| ..... | ................ | .KDSR....DF....... | E..ND. | ............ | A..A........ | 0.01 | 1 |
| AT..T | ................ | .................. | E..TG. | .SA.TG.A..GQ | A..A........ | 0.01 | 1 |
| G...T | F.....AEG.LK.M.H.L | ..DGE....DF....... | ...... | ............ | ............ | 0.01 | 1 |
| ..... | ................ | .................. | R...D. | ESA..S.AA..R | A..A........ | 0.01 | 1 |
| E...T | F.....AEG.LK.M.H.L | ..HG.....NF......T | E..DD. | ............ | ............ | 0.01 | 1 |
| TT... | F.....A.G..V.T.H.R | .Q.DR.....F....... | ....D. | E..AGS.AA.DN | A..A........ | 0.01 | 1 |
| ..... | F.....SG..IK.K.D.R | .................T | ...... | ...DTN..E.DR | A..A........ | 0.01 | 1 |
| ..... | ...........M..... | .................. | ...NDR | ..AKG...AV.. | A..A........ | 0.01 | 1 |
| E.... | ................ | .V........F....... | ...... | .DAAGA.IE.GN | A,.A........ | 0.01 | 1 |
| R.... | F.....AQ...A.L.... | .PPNG.....F......T | ...DDR | ..AST..AA..D | A..A........ | 0.01 | 1 |
| EA... | ................ | .QANH....DF....... | ...DDR | ............ | ............ | 0.01 | 1 |
| .A... | .......KT.NV.K.T.H | .Q.......DF....... | G..TG. | ............ | A..A........ | 0.01 | 1 |
| G...T | F.....GHG.NK.I.N.R | TQ.TG....DF....... | ...... | ..GGG.D.E... | A..A........ | 0.01 | 1 |
| ..... | ................ | T.P......DF....... | ...DG. | .SG..ND...DG | A..A........ | 0.01 | 1 |
| A...T | ......AEG.LK.M.H.L | ..DGE....DF....... | ...... | ............ | ............ | 0.01 | 1 |
| GT... | ................ | .................. | ...DDR | EN.DAS...V.E | A..A........ | 0.01 | 1 |
| ..... | F................ | .V........F....... | ...... | ............ | GAHAH..F.E.. | 0.01 | 1 |
| D...T | F.....N.G.PL.K.P.R | .Q.DR.....F....... | ....D. | ............ | A..A........ | 0.01 | 1 |
| ..... | F................ | .V........F....... | ...... | ............ | SNST...YHV.E | 0.01 | 1 |
| ..... | ................ | .................. | ...... | .NAGASDA.FDQ | A..A........ | 0.01 | 1 |
| ..... | F.....SRG..L.P.G.G | ..HG.....NF......T | .....R | ............ | A..A........ | 0.01 | 1 |
| ..... | ................ | TQASG....NF....... | ....D. | E.AS...IEYGQ | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....DQ..R..P.S.R | TQYDR....NF....... | R...D. | ............ | A..A........ | 0.01 | 1 |
| ..... | ......GRT..L.H.E.S | .V........F....... | ...... | ............ | A..A........ | 0.01 | 1 |
| ..... | ................ | ..PNG....DF......T | ...ADR | E.AG.D...YGR | A..A........ | 0.01 | 1 |
| ..... | ................ | ................ | ...DDR | .DANTN.A.VDS | A,.A........ | 0.01 | 1 |
| ..... | F................ | T.P......DF....... | R...D. | ............ | A,.A........ | 0.01 | 1 |
| G.... | F................ | .V........F....... | ...... | ............ | ETRSE..YDE.. | 0.01 | 1 |
| ..... | ................ | ........DF....... | ...DDR | .DGSGG.TE.DG | A..A........ | 0.01 | 1 |
| ....T | F......AG.NV.N.S.R | .QAS.....NF......T | ...N.. | ............ | A..A........ | 0.01 | 1 |
| E...T | ................ | ..DGE....DF..K...T | ...AG. | .D.GA.DIE.DR | A,.A........ | 0.01 | 1 |
| AT... | F.....ATG.NV.T.G.R | .Q.DR.....F....... | ....D. | ............ | GQKDR..ST..H | 0.01 | 1 |
| .A... | F................ | .QD.E.....F..P.... | ...D.. | ............ | ............ | 0.01 | 1 |
| ..... | ................ | ................ | ...DDR | ............ | GAQTR..SKE.H | 0.01 | 1 |
| TT... | ................ | .V........F....... | ...... | E.AGT.DTEY.Q | A..A........ | 0.01 | 1 |
| ..... | F.....NA..RM.M.K.. | ..DGE....DF....... | ...DDR | ............ | ............ | 0.01 | 1 |
| SA... | ................ | ........NF......T | ...N.. | ..TG.A.I..GR | A..A........ | 0.01 | 1 |
| TA... | F.....DE..PN.T.G.K | ..PNG....DF....... | R..AGR | ESGS.S.IA.DQ | A..A........ | 0.01 | 1 |
| ..... | ................ | ................ | R..NG. | .DANRN..E.GQ | A..A........ | 0.01 | 1 |
| RA..T | F.....AGA.NK.L...K | .KYT.....NF......T | ...... | ............ | A..A........ | 0.01 | 1 |
| ..... | ................ | ...GG.....F....... | R..D.. | ............ | A..A........ | 0.01 | 1 |
| TT..T | ................ | ................ | .....S | ............ | ............ | 0.01 | 1 |
| TA... | F.....NKT.HL.T.A.R | TQDS.....NF....... | ...... | E.GT.ND.A.DG | A..A........ | 0.01 | 1 |
| GT... | F.....DKG.HM.L.G.R | ........DF....... | ...... | ............ | A..A........ | 0.01 | 1 |
| ..... | ................ | ..HG.....NF......T | ...A.. | EDAG.AD.E.G. | A..A........ | 0.01 | 1 |
| ..... | ................ | ................ | ...N.. | ............ | DPRGG..VQK.A | 0.01 | 1 |
| ..... | F................ | .V........F....... | ...... | ............ | THKNG..SGE.T | 0.01 | 1 |
| ..... | ................ | ........NF......T | ...DDR | EDAS....A.GQ | A..A........ | 0.01 | 1 |
| ..... | ................ | .R........F......T | ...DDR | E..AGS.TEFDQ | A..A........ | 0.01 | 1 |
| ..... | ................ | ................ | ...DDR | ESTGGND.EYDQ | ............ | 0.01 | 1 |
| .A... | F.....SN..PL.K.T.. | TKHGG....NF......T | ...... | ............ | A..A........ | 0.01 | 1 |
| ..... | ................ | ................ | ...... | EDASG....FDR | A..A........ | 0.01 | 1 |
| .A... | F.....AGG.P..L...G | .QAS......F....... | ...... | ............ | A..A........ | 0.01 | 1 |
| ..... | F................ | .QPG.....DF....... | ...DDR | ............ | ............ | 0.01 | 1 |
| AA..T | F................ | .QANH....DF....... | ...DDR | ............ | A..A........ | 0.01 | 1 |
| TA... | ................ | .V........F....... | ...... | ............ | G.KAH..DRS.. | 0.01 | 1 |
| ..... | ................ | ........F......T | ....GR | ...RGND..V.E | A..A........ | 0.01 | 1 |
| ..... | ...............R | .KDDG....NF....... | R..DD. | ..AT.DD..FDG | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ...DDR | ENAGGD..E..R | A..A........ | 0.01 | 1 |
| RA... | F.....SK..PA.K.A.G | ..DGE....DF....... | ...... | E.DR.S..EVGE | A..A........ | 0.01 | 1 |
| ..... | F.....STA..Q.H.Q.L | TK.NE....DF....... | ...... | .N.AE...E.DG | A..A........ | 0.01 | 1 |
| G...T | F.....AEG.LK.M.H.L | ..DGE....DF......T | ...... | ............ | ............ | 0.01 | 1 |
| ..... | F................. | ...T.....NF....... | ...... | ............ | A..A........ | 0.01 | 1 |
| E.... | ................. | ................. | R..DD. | EN.KAN....GG | A..A........ | 0.01 | 1 |
| ..... | ................. | .........NF....... | ...DDR | EDAG...I..GQ | ............ | 0.01 | 1 |
| ..... | ................. | .V........F....... | ...DDR | H........... | ............ | 0.01 | 1 |
| GA... | ................. | ................. | ...... | ..TAGN..A..N | A..A........ | 0.01 | 1 |
| ..... | ................. | ................. | R...D. | ...SRA..A.GG | A..A........ | 0.01 | 1 |
| AT... | F.....GN..NK.P.P.N | .Q.S......F....... | ...DD. | ............ | A..A........ | 0.01 | 1 |
| ..... | F................. | .QPG.....NF....... | ...DD. | E.GGA.D.E..G | A..A........ | 0.01 | 1 |
| T.... | F.....NTG.LH.T...R | .Q.S......F......T | R...D. | E.GRGA..AV.E | A..A........ | 0.01 | 1 |
| ..... | ................. | ................. | ...A.. | .NAG.DD...DQ | A..A........ | 0.01 | 1 |
| .A... | F.....NA..HE.L.G.R | T.P......DF....... | ...D.. | ............ | ............ | 0.01 | 1 |
| ..... | ................. | .KAS.....NF......T | ...AG. | ............ | A..A........ | 0.01 | 1 |
| G.... | ................. | ..............P...T | G..ND. | ............ | A..A........ | 0.01 | 1 |
| RT... | ................. | ................. | ...DDR | ............ | A..A........ | 0.01 | 1 |
| ..... | F.....SGT.S..P.A.K | T.PG.....NF....... | ...DDR | ............ | A..A........ | 0.01 | 1 |
| .A... | F................. | .V........F....... | .Y.... | ............ | KH.SS..SGN.T | 0.01 | 1 |
| ..... | ................. | .........DF....... | ...DDR | E.GD.A..E.GQ | A..A........ | 0.01 | 1 |
| ..... | F................. | ..AGQ....NF....... | ...... | ..AG.DDIA.DN | A..A........ | 0.01 | 1 |
| ..... | ................. | ................. | R...D. | ..AAGSDIE..E | A..A........ | 0.01 | 1 |
| ..... | ................. | .Q.......DF....... | ...AD. | E.GNGS....GR | A..A........ | 0.01 | 1 |
| ..... | ................. | ................. | R...D. | EDAGAA..EFGQ | A..A........ | 0.01 | 1 |
| ..... | F.....SAG..L.H...K | T.PNE....DF....... | R...D. | ............ | ............ | 0.01 | 1 |
| ..... | ................. | ........F......T | ...ADR | ............ | A..A........ | 0.01 | 1 |
| ..... | ................. | ................. | ...D.. | ...RRND...DR | A..A........ | 0.01 | 1 |
| ..... | ................. | ................. | G..ND. | ............ | A..A........ | 0.01 | 1 |
| ..... | ................. | ................. | E..DD. | .SAS.N.IA..E | A..A........ | 0.01 | 1 |
| ..... | ................. | .......D......... | E..NG. | ............ | ............ | 0.01 | 1 |
| ..... | F................. | .........DF....... | ...D.R | ............ | ............ | 0.01 | 1 |
| ..... | ................. | .........NF....... | E..KG. | ............ | A..A........ | 0.01 | 1 |
| D...T | F......GT.NM.L.Q.G | .Q.S......F....... | ....D. | E.ADRAD.A..G | A..A........ | 0.01 | 1 |
| .A... | F.....SD..R..P.T.L | ..DGE....DF....... | R...D. | ............ | A..A........ | 0.01 | 1 |
| ..... | F.....GS..NM.N.E.R | .QPN......F......T | ...N.. | ............ | A..A........ | 0.01 | 1 |

TABLE 3-continued

AAV capsid proteins having increased specificity for and/or transduction of CD447−/133− GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| D.... | F.....NGG.NN.K.T.R | .Q.DR.....F....... | ....D. | .DAGA.D.A.GE | A..A........ | 0.01 | 1 |
| ..... | F.....SN..PL.K.T.. | ..........F..P.... | R..... | ........... | ............ | 0.01 | 1 |
| A.... | F.....DA..IA.L.K.R | .Q.GQ....DF....... | ....G. | ........... | A..A........ | 0.01 | 1 |
| G.... | .................. | .................. | ...NGR | E.AK.N..AFDG | A..A........ | 0.01 | 1 |
| ..... | F................. | .V........F....... | ...... | ........... | SSRNG...DV.Q | 0.01 | 1 |
| E.... | F......TG.RL.T.K.N | ..DGE....DF....... | ...... | ........... | A..A........ | 0.01 | 1 |
| G.... | .................. | .................. | ...... | E.A.RA.IE.D. | A..A........ | 0.01 | 1 |
| ..... | .................. | .PPNG.....F......T | ...DDR | E.TS.D..AFDQ | A..A........ | 0.01 | 1 |
| ..... | F................. | .V........F....... | ...... | ........... | GERTG..SRA.E | 0.01 | 1 |
| GT... | .................. | .................. | ...... | ........... | ANRS....R..H | 0.01 | 1 |
| ..... | F................. | .V........F....... | ...... | ........... | GPRGR..YE... | 0.01 | 1 |
| GA... | .................. | .Q.......NF....... | ...AD. | E.AGE...E..N | A..A........ | 0.01 | 1 |
| ..... | .................. | .................. | ...... | ...AAS.A.VGQ | A..A........ | 0.01 | 1 |
| ..... | F................. | .V........F....... | ...... | ........... | S.KNS..I...Q | 0.01 | 1 |
| D.... | ......SSG.II.H.D.R | .........NF....... | R...D. | ........... | A..A........ | 0.01 | 1 |
| RT... | F.....DEG.SI.L...L | ..DGE....DF....... | ...... | .SAKAA.AA.DE | A..A........ | 0.01 | 1 |
| NA... | F................. | T.PTG....DF....... | ...DDR | .SAKAA.AA.DE | ............ | 0.01 | 1 |
| ..... | F................. | .V........F....... | ...... | ........... | GPKNP..ADM.T | 0.01 | 1 |
| ..... | .................. | ....E............. | ...NDR | ..AKG...AV.. | A..A........ | 0.01 | 1 |
| EA... | F.....DH..ID.K...V | TQ.TG....DF....... | ...DDR | ENAGGG...YDQ | A..A........ | 0.01 | 1 |
| ..... | F.....A.G..V.T.H.R | .QPN......F......T | ...N.. | ........... | A..A........ | 0.01 | 1 |
| R.... | F......KT.NV.K.T.H | .QDT.....DF....... | G..DG. | ........... | A..A........ | 0.01 | 1 |
| ..... | F......QG.NQ...A.R | .KDSR....DF....... | ....D. | E.AK.SD.AYDE | ............ | 0.01 | 1 |
| ..... | F................. | .V........F....... | ...DG. | ........... | A..A........ | 0.01 | 1 |
| TT..T | F................. | .............P.... | ...... | ..TRRD.A.FDG | A..A........ | 0.01 | 1 |
| E.... | F.....DGT..I.H.S.R | .Q.S......F....... | R..DD. | ........... | A..A........ | 0.01 | 1 |
| ..... | .................. | .KTSADNN...NF.GATK | R..DD. | ........... | ............ | 0.01 | 1 |
| D...T | F.....GRT.S..L.G.R | .................. | ...... | .DGNAS....DR | A..A........ | 0.01 | 1 |
| AT... | F.....AEG.LK.M.H.L | ..DGE....DF....... | ...... | ........... | ............ | 0.01 | 1 |
| TT..T | .................. | .................. | R..DD. | ........... | ............ | 0.01 | 1 |
| ..... | .................. | T.A.Q....DF....... | ...DDR | ..AG.N.AA.GQ | A..A........ | 0.01 | 1 |
| KA... | .................. | TQ.TG....DF....... | ...... | ..ARAA.I..GQ | A..A........ | 0.01 | 1 |
| DA..T | F.....SH..PV.L.G.G | .QDT.....DF....... | G..DG. | ........... | ............ | 0.01 | 1 |
| T.... | F.....DGA.R..P.A.K | .........NF....... | R...D. | ........... | A..A........ | 0.01 | 1 |
| .A... | .................. | .KDDG....DF......T | ....GR | ESGGEN.AE..H | A..A........ | 0.01 | 1 |
| ..... | .................. | .................. | ...DDR | ..GTTG....GR | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .QAS......F....... | ...... | ENGTASD.AF.E | A..A........ | 0.01 | 1 |
| ..... | .................. | .................. | ...N.. | ESGG.G..E..Q | A..A........ | 0.01 | 1 |
| ..... | .................. | .................. | ...D.R | ..TG.D..A.GG | A..A........ | 0.01 | 1 |
| ..... | .................. | .................. | ....GR | ...NRG.IA.DE | A..A........ | 0.01 | 1 |
| .A... | F.....DRG.S..T.A.S | ........DF....... | ...DDR | ........... | A..A........ | 0.01 | 1 |
| NA..T | .................. | .QLG.....NF....... | ...DD. | .DARAADA...Q | A..A........ | 0.01 | 1 |
| GT... | .................. | T.P.....DF....... | ...D.. | .SGT.GD.AVGE | A..A........ | 0.01 | 1 |
| EA..T | F......KG.S..T.P.K | ........NF....... | ...... | ........... | A..A........ | 0.01 | 1 |
| EA..T | F.....GS..NA.T...M | .................. | G..ND. | ........... | A..A........ | 0.01 | 1 |
| ..... | .................. | TKDDR....DF....... | ...DDR | ........... | A..A........ | 0.01 | 1 |
| TA... | F.....SG..IK.K.D.R | .QPG.....NF....... | ...... | ..ATAA..AVDN | A..A........ | 0.01 | 1 |
| ..... | .................. | .................. | R..DD. | EDAG...I..GQ | A..A........ | 0.01 | 1 |
| D...T | F................. | .V........F....... | ...... | ........... | GAHNN..FDV.A | 0.01 | 1 |
| SA... | .................. | .PPNG.....F......T | ...DDR | ........... | GRKTG..AEV.A | 0.01 | 1 |
| ..... | .................. | ....N............. | R..NDR | E.AG..D.A.GR | A..A........ | 0.01 | 1 |
| KA... | F.....NGT.IL.T.A.K | .QAS.....NF......T | ....GR | ........... | A..A........ | 0.01 | 1 |
| NA... | .................. | TQ.TG....DF....... | ...DDR | .NAGASDA.FDQ | A..A........ | 0.01 | 1 |
| SA... | F.....GN..NA.T...M | .Q.GQ....DF....... | ...DDR | E.TGAN.AE.GE | A..A........ | 0.01 | 1 |
| GA... | F.----GRG.N......H | .Q.S......F....... | E..N.. | ........... | A..A........ | 0.01 | 1 |
| R.... | .................. | .KD.E....DF....... | ...DDR | ES.A.S..EFDS | A..A........ | 0.01 | 1 |
| GT... | .................. | .................. | ...DDR | .NAT.A.A.FGD | A..A........ | 0.01 | 1 |
| A...T | F.....SGT.SQ.K.E.. | .KYT.....NF......T | E..TD. | ........... | A..A........ | 0.01 | 1 |
| DT... | F.....ARA.L..L.Q.G | ..DGE....DF....... | ...D.. | ........... | A..A........ | 0.01 | 1 |
| ..... | .................. | .................. | E..AD. | ENGGGA.I..GQ | A..A........ | 0.01 | 1 |
| AA... | .................. | .................. | E..N.. | ........... | A..A........ | 0.01 | 1 |
| TA... | F.....SRG.PV.P.N.R | .QDT.....DF....... | G..DG. | ..AG..DIAF.G | A..A........ | 0.01 | 1 |
| ..... | .................. | .................. | G..ND. | E.GGRGD....G | A..A........ | 0.01 | 1 |
| T.... | .................. | .................. | R...D. | ..AG.DD...GG | A..A........ | 0.01 | 1 |
| N.... | F.....SA..SM.M.T.K | .QAS......F....... | ...... | E....ND.EF.Q | A..A........ | 0.01 | 1 |
| ..... | .................. | ...............T | ....D. | .NGST.....GG | A..A........ | 0.01 | 1 |
| EA... | F.....GRG.H..P.E.R | .V........F....... | R..DD. | ........... | A..A........ | 0.01 | 1 |
| A.... | F.....SRG.PV.P.N.R | ..AGR....DF......T | ...D.. | ........... | A..A........ | 0.01 | 1 |
| .A... | F................. | .QANH....DF....... | ...DDR | ........... | A..A........ | 0.01 | 1 |
| ..... | .................. | .................. | ...D.. | E.TGTA.AEVGE | A..A........ | 0.01 | 1 |
| ..... | .................. | .................. | ...A.. | .D.TR..AA..Q | A..A........ | 0.01 | 1 |
| ..... | .................. | .QPSQ....NF....... | ....GR | ........... | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....ARA.L..L.Q.K | .QHNQ.....F......T | ...D.. | E.AG.GD.EY.. | A..A........ | 0.01 | 1 |
| ..... | ................. | .........NF....... | ...NDR | E.AGAA..E.DR | A..A........ | 0.01 | 1 |
| KA... | ................. | ................. | .....S | E.AS.A.TAV.H | A..A........ | 0.01 | 1 |
| ..... | F.....G.G.RA.N.E.R | .QDT......F......T | ...D.. | EDAGT...AFD. | A..A........ | 0.01 | 1 |
| ..... | F.....DKG.HM.L.G.R | ...TE....NF......T | ...NGR | ............ | A..A........ | 0.01 | 1 |
| T.... | ................. | .V........F....... | ...ADR | EDGDGA..A.DR | A..A........ | 0.01 | 1 |
| GT... | F.....GRG.SE.N.P.H | .V........F....... | ...... | EDAG...I..GQ | A..T........ | 0.01 | 1 |
| ..... | F................ | .K.TG....DF....... | R...DR | ..ATRS.I..GN | A..A........ | 0.01 | 1 |
| ..... | ................. | ................. | R...D. | ESAAGD.IE.GD | A..A........ | 0.01 | 1 |
| ..... | ................. | ................. | ...N.. | ............ | E..A........ | 0.01 | 1 |
| ..... | ................. | ................. | ...DDR | ..AS...I..G. | A..A........ | 0.01 | 1 |
| E.... | ................. | .V........F....... | ...... | ............ | NAKTR..FTT.D | 0.01 | 1 |
| ..... | ................. | ................. | E..KD. | .DTGGA.I..GQ | A..A........ | 0.01 | 1 |
| E.... | ................. | .V........F....... | ...... | ............ | NAKTR..FTT.D | 0.01 | 1 |
| ..... | ................. | ................. | E..KD. | .DTGGA.I..GQ | A..A........ | 0.01 | 1 |
| R.... | F.....DE..PK.L.A.R | TQ.TG....DF....... | ...DDR. | ............ | A..A........ | 0.01 | 1 |
| ..... | ................. | ................. | E..DDR | ............ | A..A........ | 0.01 | 1 |
| DT... | F.....SKT.LV.M.T.G | .K.TG....DF....... | R...DR | ............ | A..A........ | 0.01 | 1 |
| RA... | ................. | TKDT.....NF....... | ...... | ............ | A..A........ | 0.01 | 1 |
| ..... | ................. | ................. | ...D.R | E.T..S..A..R | A..A........ | 0.01 | 1 |
| ..... | F.....NKT.I..K.... | .Q.DR.....F....... | G..ND. | ............ | A..A........ | 0.01 | 1 |
| R.... | ................. | .KDSR....DF....... | ....D. | EDGGRG...V.D | A..A........ | 0.01 | 1 |
| ..... | ................. | ..........F......T | G..NDR | ............ | A..A........ | 0.01 | 1 |
| ..... | ................. | ..DNH....NF......T | E..ND. | ............ | A..A........ | 0.01 | 1 |
| ..... | ................. | ................. | ...... | .DG.RA...V.R | A..A........ | 0.01 | 1 |
| T...T | F......GA.HP.K...V | T.P......DF....... | ...D.. | ............ | A..A........ | 0.01 | 1 |
| TA... | F.....GGG.HK.T...G | .V........F....... | ....D. | E.T..S..A..R | A..A........ | 0.01 | 1 |
| E...T | F.....AQG.SN.K.G.K | ..DGE....DF....... | ...... | E.AGE...E..N | A..A........ | 0.01 | 1 |
| RA... | ................. | TQ.TG....NF....... | ...DDR | E.AGG.DI..GH | A..A........ | 0.01 | 1 |
| ..... | ................. | ..YN............. | ...... | ED.GG...E.GR | A..A........ | 0.01 | 1 |
| T.... | F.....A.A.NH.I.Q.G | .QAS......F....... | R..DD. | ............ | A..A........ | 0.01 | 1 |
| ..... | F................ | .V........F....... | ...... | ............ | GKSGH..ARE.A | 0.01 | 1 |
| ..... | ................. | ................. | G..N.. | E.AGTNDI...R | A..A........ | 0.01 | 1 |
| N.... | ................. | .KPSE....DF......T | R...DR | E.AG.ADIE.G. | A..A........ | 0.01 | 1 |
| E.... | F................ | ................. | ...ADR | .DTSAND.A.DE | A..A........ | 0.01 | 1 |
| A.... | F.....AR..SL...H.G | .Q.DR.....F....... | ....D. | ..AATD.AA.DQ | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | E...N. | ............ | A..A........ | 0.01 | 1 |
| RA... | ................. | .Q.S......F......T | G..A.R | ............ | A..A........ | 0.01 | 1 |
| ..... | ................. | TKAT.....NF | ...... | ............ | A..A........ | 0.01 | 1 |
| D...T | F.....DAT..L.I.N.R | T.ADG....NF......T | R..N.. | ............ | A..A........ | 0.01 | 1 |
| SA... | F.....SGT.S..T.T.. | .K.T......F | R..AD. | ............ | A..A........ | 0.01 | 1 |
| ..... | F................. | ................. | ...DD. | E.T..S..A..R | A..A........ | 0.01 | 1 |
| ..... | ................. | ................. | ...... | .NAT.ND.AFGE | A..A........ | 0.01 | 1 |
| RA..T | F.....SG..IK.K.D.R | T.A.Q....DF....... | G..A.R | ............ | A..A........ | 0.01 | 1 |
| ..... | F.....SA..RA.....R | TKDDR....DF....... | ...DDR | ............ | A..A........ | 0.01 | 1 |
| ..... | F................. | .V........F....... | ...... | ............ | G.RSG..VR..H | 0.01 | 1 |
| TA..T | F.....SET.NN.P.H.L | .Q.DR.....F....... | ....D. | E.ANG...E.G. | A..A........ | 0.01 | 1 |
| .A... | ................. | ..YN......F......T | ...D.R | E.TGRA..A..R | A..A........ | 0.01 | 1 |
| N.... | ................. | ..HGG.....F......T | ...... | ES.TRSDI.FDH | A..A........ | 0.01 | 1 |
| ..... | F................. | .V........F....... | ...... | ............ | SRRDP..NDG.. | 0.01 | 1 |
| T.... | F.....GRG.R..P.T.L | ...DG....DF....... | E..KD. | ............ | A..A........ | 0.01 | 1 |
| ..... | ................. | T.AG.....NF......T | R...D. | .S.G.S.IA..G | A..A........ | 0.01 | 1 |
| ..... | F.....STA..Q.H.Q.L | ..........F......T | ...ND. | ...GTS..EF.Q | A..A........ | 0.01 | 1 |
| ....T | F................. | .V........F....... | ...... | ............ | A..A........ | 0.01 | 1 |
| .A... | ................. | ..ADH....DF....... | ...... | ENAGASDIA.DH | A..A........ | 0.01 | 1 |
| ..... | ................. | ..HG.....NF......T | ...DD. | ............ | ............ | 0.01 | 1 |
| GT... | F................. | .V........F....... | ...... | ............ | TERTG..FDE.D | 0.01 | 1 |
| .A... | F.....DR..SL.H.D.R | .Q.......DF....... | ...AD. | ............ | A..A........ | 0.01 | 1 |
| D.... | ......Q.......... | .Q.DH....NF....... | ...DD. | E.GGASD....S | A..A........ | 0.01 | 1 |
| RA... | ................. | .PPNG.....F......T | ...DDR | E.ADGA..AYDR | A..A........ | 0.01 | 1 |
| ..... | ................. | ................. | ...... | ............ | AARSG..SEG.D | 0.01 | 1 |
| TA... | ................. | .Q.DR.....F....... | ....D. | ............ | A..A........ | 0.01 | 1 |
| ..... | ................. | ................. | R...D. | EDGNAA.....R | A..A........ | 0.01 | 1 |
| RA... | F.....SG..IK.K.D.R | ..DGE....DF....... | ...... | EDARGADAE.GE | A..A........ | 0.01 | 1 |
| ..... | F................. | .V........F....... | ...... | ............ | GSSAG..AQV.Q | 0.01 | 1 |
| R.... | ................. | .V...........T | ...D.R | E.A.G..A...N | A..A........ | 0.01 | 1 |
| ..... | ................. | ................. | ...DDR | ............ | A..A........ | 0.01 | 1 |
| ..... | F................. | .V........F....... | ...... | ............ | ANKDH..YTT.D | 0.01 | 1 |
| SA... | F......T..PN.I...E | .Q.DR.....F....... | ....D. | ............ | A..A........ | 0.01 | 1 |
| .A... | F.....DAA.SA.K.A.R | TKHGG....NF....... | R..DDR | ............ | A..A........ | 0.01 | 1 |
| ..... | ................. | T.P......DF....... | ...DDR | ESGD.A..AVDE | A..A........ | 0.01 | 1 |
| ..... | ................. | TK.NE....DF......T | R..D.. | ...SAG....DR | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| GT... | .................. | .................. | R..AD. | .NGG.ND....Q | A..A........ | 0.01 | 1 |
| ..... | F................. | .V........F....... | ...... | .......... | DTRTA..IRT.. | 0.01 | 1 |
| GT... | ......DAA.IK.T.Q.N | ..DGE....DF....... | ...... | E.......... | .......... | 0.01 | 1 |
| H.... | F................. | .................. | ...DDR | .......... | .......... | 0.01 | 1 |
| ..... | .................. | .........F....... | ...... | ESAKT.DT.VDG | A..A........ | 0.01 | 1 |
| ..... | .................. | .........NF......T | E..AD. | ..ATESD..FDQ | A..A........ | 0.01 | 1 |
| ..... | .................. | TQPGG............. | G..NDR | .D.T.A.A...G | A..A........ | 0.01 | 1 |
| NT..T | F.....DTG.SK.T.T.R | .QPTG.....F....... | ...NGR | .......... | A..A........ | 0.01 | 1 |
| NA... | F................. | .................. | ...... | ENGD....E.DR | A..A........ | 0.01 | 1 |
| ..... | F................. | .................. | R...D. | ESA..S.AA..R | A..A........ | 0.01 | 1 |
| ..... | F................. | .V........F....... | ...... | .......... | EHRNT..SRE.E | 0.01 | 1 |
| GT... | F.....NT.....K.A.R | ..DGE....DF....... | ...... | .......... | .......... | 0.01 | 1 |
| TT..T | .................. | .................. | E..AD. | E.AKEN.A..DE | A..A........ | 0.01 | 1 |
| ..... | .................. | .................. | E..NG. | .......... | GPRAG..VE..D | 0.01 | 1 |
| RA... | F................. | TQ.TQ....DF....... | R...D. | E.AGTND.AV.H | A..A........ | 0.01 | 1 |
| ..... | .................. | TKHGG....NF......T | ...DDR | .S.G..D..FGG | .......... | 0.01 | 1 |
| HA... | .................. | .Q.S......F....... | E..N.. | .STSRGD...GG | A..A........ | 0.01 | 1 |
| ..... | .................. | .................T | ...ADR | .......... | A..A........ | 0.01 | 1 |
| ..... | .................. | .................. | ...ND. | ES.AA..AA..Q | A..A........ | 0.01 | 1 |
| ..... | F.....GRG.NV.N.S.R | ..YN......F......T | R...G. | .......... | A..A........ | 0.01 | 1 |
| ..... | F.....DTG.SK.T.T.R | .V........F....... | ...... | .NATEGDI..GG | A..A........ | 0.01 | 1 |
| GT... | .................. | .................. | R...D. | .NTAGND....R | A..A........ | 0.01 | 1 |
| AT... | .................. | .................. | ...N.. | ...G.N.A.... | A..A........ | 0.01 | 1 |
| D.... | F.....DRG.S..T.A.S | ..DGE....DF....... | ...... | .......... | A..A........ | 0.01 | 1 |
| RA... | .................. | ..DGE....DF....... | R...D. | .......... | .......... | 0.01 | 1 |
| ..... | .................. | .................. | ....G. | .DGGTA..EY.Q | A..A........ | 0.01 | 1 |
| GA... | F......N..NH.L.P.S | ..PNG....DF....... | ...DDR | E.AGGN..E.DD | A..A........ | 0.01 | 1 |
| TA... | .................. | TQ..H....NF....... | ...... | E.ANG...E.G. | A..A........ | 0.01 | 1 |
| DT... | F.....ASG.SV.I.S.R | ..DGE....DF....... | ...... | .......... | A..A........ | 0.01 | 1 |
| GT... | F.....AEG.LK.M.H.L | ..DT.....NF......T | ...DD. | .......... | A..A........ | 0.01 | 1 |
| DA... | F.....ATT.IM.T.T.R | .........NF....... | R...D. | EDAAR.D.A.D. | A..A........ | 0.01 | 1 |
| ..... | .................. | .................. | ...D.R | E..R.N.AEFGE | A..A........ | 0.01 | 1 |
| AA..T | F.....A.G..V.T.H.R | T.P......DF....... | ...D.. | .N.GA.D.A.GG | A..A........ | 0.01 | 1 |
| GA... | F.....DQ..R..P.S.R | .QPSQ....NF......T | ...N.. | .......... | A..A........ | 0.01 | 1 |
| .A..T | F.....NN..N..M...G | T.YNH.....F....... | ...D.. | .......... | A..A........ | 0.01 | 1 |
| ..... | F................. | .QPSQ....NF....... | ...DDR | .......... | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .QAS.....DF....... | ...T.. | ........... | A..A........ | 0.01 | 1 |
| EA... | F.....DA..IA.L.K.R | ..DGE....DF....... | ...... | ESG.GN..EVDR | A..A........ | 0.01 | 1 |
| RA... | F.....DTG.SK.T.T.R | .Q.S......F....... | ...D.. | ........... | A..A........ | 0.01 | 1 |
| ..... | .................. | .................. | ...ADR | E........... | A..A........ | 0.01 | 1 |
| ..... | .................. | .................. | ...ND. | ESATGN..A.DN | A..A........ | 0.01 | 1 |
| TA... | F.....NRA.LA.....G | ..........F......T | ...ADR | ........... | A..A........ | 0.01 | 1 |
| ..... | .................. | .Q.S......F....... | ...... | EDAA.S..EV.R | A..A........ | 0.01 | 1 |
| E.... | F.....ASA.S..T.T.G | TQ.TH....DF....... | ....D. | E.AGAA..E.DR | A..A........ | 0.01 | 1 |
| TA... | .................. | E.HG.....NF......T | ...DDR | ........... | ........... | 0.01 | 1 |
| ..... | F................. | .V........F....... | ...... | ........... | A.KGS....R.E | 0.01 | 1 |
| RT... | F................. | .................. | ....D. | ........... | A..A........ | 0.01 | 1 |
| ..... | F.....SAG..L.H...K | TKDDR....DF....... | ...DDR | ........... | A..A........ | 0.01 | 1 |
| R.... | F.....SN...P.H.T.K | .........NF....... | R...D. | ........... | A..A........ | 0.01 | 1 |
| ..... | .................. | .................. | ...DD. | EDGNGSDT..DS | A..A........ | 0.01 | 1 |
| .T... | F.....GS..NM.N.T.R | ..DGE....DF....... | ...... | E...GA.AA..E | A..A........ | 0.01 | 1 |
| N.... | F.....AR..L..P.D.K | .QPN......F......T | ...N.. | EDGKGA....GE | A..A........ | 0.01 | 1 |
| GT... | F.....AEG.LK.M.H.L | .................. | ...... | ........... | ........... | 0.01 | 1 |
| GT... | F.....GQI.LN.L.D.R | .QPG.....NF....... | ...DDR | .DASGDD.EVD. | A..A........ | 0.01 | 1 |
| AA... | .................. | T.PNE....DF....... | R...D. | ..ATRS.I..GN | A..A........ | 0.01 | 1 |
| ..... | F................. | .V........F....... | ...... | ........... | GPHS...FQS.D | 0.01 | 1 |
| D...T | F.....SN..PL.K.T.. | ..HG.....NF......T | R..ADR | ........... | A..A........ | 0.01 | 1 |
| RT... | .................. | .QHNQ.....F......T | ...N.. | ........... | A..A........ | 0.01 | 1 |
| ..... | .................. | F................. | ...DDR | EDGNTN.A.VDS | A..A........ | 0.01 | 1 |
| AA... | F.....NAT.RD.M.T.K | .QPN......F......T | ...N.. | ........... | A..A........ | 0.01 | 1 |
| .A... | .................. | F................. | ...AG. | ........... | A..A........ | 0.01 | 1 |
| DA... | .................. | .........DF......T | R..D.. | ........... | A..A........ | 0.01 | 1 |
| ..... | F.....AKG.P..H.P.R | .QANH.....F......T | ...D.. | ........... | A..A........ | 0.01 | 1 |
| TA... | .................. | ..........F....... | ...... | E........... | A..A........ | 0.01 | 1 |
| ..... | F.....GG..NK.M.... | F................. | ....GR | ........... | A..A........ | 0.01 | 1 |
| E.... | F.....SHG.II.K.G.R | ..HG.....NF......T | R...D. | ESAK..D.E..N | A..A........ | 0.01 | 1 |
| A.... | F.....G.G.HA.T.G.R | ..HDG.....F....... | R...D. | E.GAGAD...GQ | A..A........ | 0.01 | 1 |
| ..... | F................. | F................. | R..DD. | .D.GAG.T...G | A..A........ | 0.01 | 1 |
| ..... | F................. | F................. | ...... | E.TSTS.A.VGE | A..A........ | 0.01 | 1 |
| G...T | F.....SGT.SQ.K.E.. | .KYT.....NF......T | ...DDR | ........... | A..A........ | 0.01 | 1 |
| G.... | F................. | .Q.S......F....... | E..N.. | ........... | ........... | 0.01 | 1 |
| ..... | F................. | .QPG.....DF....... | E..AG. | .SGGA.D.E..N | A..A........ | 0.01 | 1 |

TABLE 3-continued

AAV capsid proteins having increased specificity for and/or transduction of CD447$^-$/133$^-$ GBM cells (pool of Round 1 selection). Amino acid numbers correspond to the amino acid sequence of VP1 (SEQ ID NO: 1). Sequences below correspond to SEQ ID NOs: 8 and 524-3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| AA... | ................. | ..YN......F......T | ....G. | ...G.S..AFGD | A..A........ | 0.01 | 1 |
| A.... | F.....NKT.HL.T.A.R | TQASG.....F....... | R...D. | E.ATA...E.DD | A..A........ | 0.01 | 1 |
| ..... | ................. | ................. | G..N.. | ............ | ............ | 0.01 | 1 |
| ..... | ................. | ..PNG....DF....... | E..N.. | E..RRA.....Y | A..A........ | 0.01 | 1 |
| ..... | ................. | ..........DF...... | ...D.. | .DTS.A.AA.GE | A..A........ | 0.01 | 1 |
| ..... | F.....SGT.NM.K.T.E | ................. | ...... | ............ | A..A........ | 0.01 | 1 |
| ..... | F................ | .V......F....... | ...... | ............ | DRSDP..Y.A.Q | 0.01 | 1 |
| RT... | F......GG.NV...G.M | .Q.GQ....DF....... | ....G. | ............ | A..A........ | 0.01 | 1 |
| TA... | ................. | .KYT.....NF....... | R...D. | ED.GGND.EV.D | A..A........ | 0.01 | 1 |
| ET..T | F.....NGG.NN.K.T.R | ................. | ...... | ............ | A..A........ | 0.01 | 1 |
| ..... | ................. | ................. | R..DG. | ..GG...I..GH | A..A........ | 0.01 | 1 |
| ..... | ................. | .........NF......T | ...... | .SGKTADAEVGD | A..A........ | 0.01 | 1 |
| NA... | F.....DA..IA.L.K.R | ................. | ...... | .NTGTA..E... | A..A........ | 0.01 | 1 |
| AA... | F.....D.G.LK.T.N.V | .........NF....... | R...D. | ENAKG..AEF.D | A..A........ | 0.01 | 1 |
| ..... | ................. | ................. | ....GR | ..AG.N.AA.GQ | A..A........ | 0.01 | 1 |
| NA... | F.....GGT.PM.K.D.R | .QPSQ....NF....... | E..TD. | ENTSEG.....R | A..A........ | 0.01 | 1 |
| G.... | F.....SNG.RE.L...K | TKDDR....DF....... | ...DDR | ............ | A..A........ | 0.01 | 1 |
| A...T | F.....GAG.HV.M...R | ................. | ...... | ............ | A..A........ | 0.01 | 1 |
| ..... | F.....GS..NK.M.A.R | ..ADH....DF....... | ...... | E.AGAND.AV.H | A..A........ | 0.01 | 1 |
| ..... | F......QG.NQ...A.R | .Q.S......F....... | ...D.. | ............ | A..A........ | 0.01 | 1 |
| EA..T | F.....NG..IQ.M.N.R | ..DGG.....F...P...T | R..D.R | ............ | A..A........ | 0.01 | 1 |
| ..... | ................. | .........NF....... | R...D. | ..TGTS...YGS | A..A........ | 0.01 | 1 |
| TA... | F.....AGA.NK.L...K | .QPTG....NF....... | ...D.R | E.ANGG.A...D | A..A........ | 0.01 | 1 |
| GA..T | ......NGT..V.P.E.G | T..G.....NF......T | ....G. | ............ | A..A........ | 0.01 | 1 |
| R...T | ................. | .QPN......F......T | ...N.. | ............ | A..A........ | 0.01 | 1 |
| .A... | F................ | ................. | ....D. | ............ | A..A.......H | 0.01 | 1 |
| ..... | F................ | .V........F....... | ...... | .......G... | SPRDA..N.G.D | 0.01 | 1 |
| TT... | F.....ASA.S..T.T.G | .QPG.....DF....... | ...DDR | .D.GRA..E.GE | A..A........ | 0.01 | 1 |
| ..... | ................. | ................. | R..DG. | ............ | A..A........ | 0.01 | 1 |
| GT... | F.....S.G.RQ.T.E.R | .Q.DR....DF....... | R..A.. | .N.SRA.AE..E | A..A........ | 0.01 | 1 |
| ..... | ................. | ................. | R..D.. | .SAS.N.IA..E | A..A........ | 0.01 | 1 |
| ..... | ................. | ..........DF......T | E..TGR | ESGTAA.AA..E | A..A........ | 0.01 | 1 |
| SA..T | ................. | ..DGE....DF....... | R...D. | ............ | A..A........ | 0.01 | 1 |
| DA..T | F.....NR..N..I.T.G | TQ.TQ.....F....... | ...DDR | E.ADRN....GS | A..A........ | 0.01 | 1 |
| ..... | ................. | ................. | E..N.. | E..D.N...Y.S | A..A........ | 0.01 | 1 |
| ..... | F.....GS..NM.N.T.R | T.PGG....NF....... | ...DD. | ............ | A..A........ | 0.01 | 1 |

TABLE 3-continued

AAV capsid proteins having increased specificity for and/or transduction of CD447⁻/133⁻ GBM cells
(pool of Round 1 selection). Amino acid numbers correspond to the amino acid sequence
of VP1 (SEQ ID NO: 1). Sequences below correspond to SEQ ID NOs: 8 and
524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| HA... | F.....SN..PLKK.T.. | .QPN......F......T | ...N.. | E.AGAA..E.DR | A..A........ | 0.01 | 1 |
| ..... | ................ | ................ | ...DDR | ..ANRD.A..DQ | A..A........ | 0.01 | 1 |
| ..... | F................ | .V.......F....... | ...... | .DAAGA.IE.GN | A..A........ | 0.01 | 1 |
| ....T | F................ | .........DF...... | ...NDR | ..TTGA..AY.D | A..A........ | 0.01 | 1 |
| ..... | ................ | .....D........... | ...DDR | ............ | ............ | 0.01 | 1 |
| R.... | ................ | TKDDR....DF...... | ...DDR | E.AAGND.EFDQ | A..A........ | 0.01 | 1 |
| RT... | F.....D.T.HP.M...R | .QPTR....DF...... | ...D.. | ESGTGND.E.DG | A..A........ | 0.01 | 1 |
| ..... | ................ | T.P......DF...... | ...DDR | .NASG..A.VGQ | A..A........ | 0.01 | 1 |
| G...T | F.....GGG.NQ.I.S.G | TQ.TG....DF...... | ...DDR | ESAG.DD.A.DQ | A..A........ | 0.01 | 1 |
| GA... | F.....GRG.SE.N.P.H | .V........F...... | ...... | EDAG...I..GQ | A..A........ | 0.01 | 1 |
| TT... | ................ | ................ | ...... | E.AAGND.EFDQ | A..A........ | 0.01 | 1 |
| ..... | F................ | .........DF...... | ....GR | ESGTAND...DR | A..A........ | 0.01 | 1 |
| NT... | F......AT.SN.I.Q.R | TKAT.....NF......T | ...... | E.ATA.DAA.DQ | A..A........ | 0.01 | 1 |
| ..... | ................ | .KYT.....DF...... | ...AD. | .SAA.S.TEVDS | A..A........ | 0.01 | 1 |
| RA... | F.....DGA.R..P.A.K | .QPNQ....DF...... | ...... | ............ | A..A........ | 0.01 | 1 |
| ..... | F................ | .V.......F....... | ...... | ............ | DTRSG..SNA.P | 0.01 | 1 |
| AT... | F................ | .V.......F....... | ...... | ............ | DPRTR..ATE.A | 0.01 | 1 |
| D...T | F.....NAT.IM.T.H.R | T.P......DF...... | ...D.R | ............ | ............ | 0.01 | 1 |
| ..... | ................ | .QDT......F......T | R..KD. | ............ | A..A........ | 0.01 | 1 |
| ..... | F......G..NQ.N.D.K | .QHNQ.....F......T | E..KD. | ..TG.A...VGN | A..A........ | 0.01 | 1 |
| ..... | ................ | ................ | ....D. | E.GGGA.AEVGD | A..A........ | 0.01 | 1 |
| ..... | F................ | .V.......F....... | ...... | ............ | GRDN....RV.E | 0.01 | 1 |
| SA... | F.....SG..IK.K.D.R | T.A.Q....DF...... | G..A.R | ............ | A..A........ | 0.01 | 1 |
| ..... | ................ | ................ | E..ND. | .DGKGND...DG | A..A........ | 0.01 | 1 |
| ..... | ................ | ................ | R...D. | ..AKG...AV.. | A..A........ | 0.01 | 1 |
| ..... | F.....ATA..V.H...R | .QAS......F...... | ...... | .SGDE.D.E.DR | A..A........ | 0.01 | 1 |
| ..... | ................ | ................ | ...DDR | ENASG.....GN | A..A........ | 0.01 | 1 |
| R.... | ................ | ................ | G..K.. | ............ | A..A........ | 0.01 | 1 |
| E.... | F......TG.IL...T.R | .QAS.....NF......T | ....GR | ............ | ............ | 0.01 | 1 |
| GT... | F.....AEG.LK.M.H.L | ..DGE....DF...... | R...D. | ..........G. | ............ | 0.01 | 1 |
| ..... | ................ | ................ | ...TD. | ............ | A..A........ | 0.01 | 1 |
| ..... | F.....SA..RA.....R | ................ | ...... | ............ | A..A........ | 0.01 | 1 |
| ..... | ................ | ................ | G..ND. | ............ | ............ | 0.01 | 1 |
| ..... | ................ | .QPN......F......T | ...N.. | ESGD.A.AA.GE | A..A........ | 0.01 | 1 |
| ..... | F................ | .V.......F....... | E..ND. | ............ | A..A........ | 0.01 | 1 |
| ..... | ......KT.NV.K.T.H | .Q.......DF...... | G..TG. | ............ | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| AA... | ................. | T.AG......F......T | ...DD. | ..TKRDD.A.DE | A..A........ | 0.01 | 1 |
| SA... | F......GA.HP.K...V | .V........F....... | R...G. | E..AAS....GG | A..A........ | 0.01 | 1 |
| G.... | F.....GS..NK.M.A.R | ..YN......F......T | R..N.. | ENGGAAD.A..N | A..A........ | 0.01 | 1 |
| ET..T | F................. | .V........F....... | R..DG. | E..GASD.A..Q | ............ | 0.01 | 1 |
| N.... | F.....GTT.IL.M...K | ..DGE....DF...... | E..NGR | ............ | A..A........ | 0.01 | : |
| G.... | F................. | .V........F....... | ...... | ............ | KDRAA..VHN.H | 0.01 | : |
| D.... | F.....GKG.ND.T.N.G | T.AG.....NF......T | ...D.R | ............ | A..A........ | 0.01 | 1 |
| ..... | F.....SN..PL.K.T.. | ..HG.....NF......T | R..ADR | ............ | A..A........ | 0.01 | 1 |
| E.... | F.....AQG.SN.K.G.K | ................. | G..ND. | ............ | A..A........ | 0.01 | 1 |
| AT... | ................. | ..HG.....NF......T | R..DG. | ............ | A..A........ | 0.01 | 1 |
| DA... | F.....AHG.PP.L.N.K | .K.TG.....F......T | ...DDR | ............ | A..A........ | 0.01 | : |
| ..... | ................. | .QPN......F......T | ...N.. | .DGRAG..E.GE | A..A........ | 0.01 | 1 |
| AT... | ................. | .QHNQ.....F....... | ...... | ............ | A..A........ | 0.01 | 1 |
| A.... | ................. | ................. | R..DD. | ............ | ............ | 0.01 | 1 |
| ..... | ................. | ........NF......T | ...DDR | ED.R.S.A...G | A..A........ | 0.01 | 1 |
| G.... | F.....A...ND.T...K | TQ.TG....DF....... | ...DDR | E.AAGSDI...H | A..A........ | 0.01 | 1 |
| TT..T | ................. | ..DGE....DF...... | ....D. | ............ | ............ | 0.01 | 1 |
| A.... | F.....SRG.IE.K...L | .KYT.....NF......T | ...DDR | ............ | A..A........ | 0.01 | 1 |
| ..... | F.....DGT..V.H.H.V | .V........F....... | ...... | ............ | ............ | 0.01 | 1 |
| .A... | ................. | ..HG.....NF...... | F...KD | ............ | A..A........ | 0.01 | 1 |
| ..... | F................. | ..HG.....NF......T | ...A.. | ............ | A..A........ | 0.01 | 1 |
| H.... | F.....DRG.S..T.A.S | ..DGE....DF...... | ...... | ............ | ............ | 0.01 | 1 |
| TA... | F................. | ................. | ....GR | ...RGND..V.E | A..A........ | 0.01 | 1 |
| ..... | ................. | ................. | R..DD. | ESGGAD.I...R | A..A........ | 0.01 | 1 |
| ..... | ................. | ................. | ...D.. | ....GS.IA..N | A..A........ | 0.01 | 1 |
| ..... | ................. | ................. | G..TDR | E.AGGN..E..S | A..A........ | 0.01 | 1 |
| NT..T | ................. | T.P......DF...... | ...D.R | EDANGGDAE.GH | A..A........ | 0.01 | 1 |
| AA... | ................. | ................. | G..NDR | ...G.S..AFGD | A..A........ | 0.01 | : |
| R.... | ................. | TQ.TG....DF...... | ...DDR | E..KAS..AVDH | A..A........ | 0.01 | 1 |
| ..... | ......DRG.S..T.A.R | ..A......DF...... | ...DG. | ............ | ............ | 0.01 | 1 |
| NT..T | ................. | ..DGE....DF...... | R...D. | ..GNAD.AAV.D | A..A........ | 0.01 | 1 |
| ..... | F................. | .V........F....... | ...... | ............ | SARNT..YNN.T | 0.01 | 1 |
| H.... | F................. | .V........F......E | ...... | ............ | D.KG...VDR.E | 0.01 | 1 |
| .A... | F.....NQG..V.L.N.R | T.P......DF...... | ...D.. | E.AKTADA..GH | A..A........ | 0.01 | 1 |
| ..... | F................. | .V........F....... | ...... | ............ | S.RNP..NEV.H | 0.01 | 1 |
| RA... | ................. | ................T | ...D.. | ............ | ............ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| RA... | ................. | .QHNQ.....F......T | R..D.. | .DTG.N..A..R | EKKTH..ADS.A | 0.01 | 1 |
| NA..T | ................. | .Q.DR.....F....... | ....D. | E.AT.S.AAF.E | A..A........ | 0.01 | 1 |
| G.... | ................. | ................. | ...DDR | ..AG..D..YGE | ............ | 0.01 | 1 |
| .A... | ......NN..SA.N...R | ................. | E..AD. | ............ | A..A........ | 0.01 | 1 |
| GA... | F.....SGT.S..T.T.. | ..AGR....DF......T | R..D.. | ............ | A..A........ | 0.01 | 1 |
| ..... | ................. | ................. | ...N.. | .STSRGD...GG | A..A........ | 0.01 | 1 |
| ..... | ................. | ................. | ....GR | .NGGGA.I.FDG | A..A........ | 0.01 | 1 |
| ..... | F................ | .V........F....... | ...... | ............ | GPRTA...SG.H | 0.01 | 1 |
| NT..T | ......AST.IN.L.T.. | ..DGE....DF....... | ...... | ............ | ............ | 0.01 | 1 |
| D.... | F.....AN...N.L.H.R | .V........F....... | ...... | .SGGRS..E.DQ | A..A........ | 0.01 | 1 |
| DA... | F.....SGG.RV.P...G | T.AG.....DF....... | ...D.. | ............ | A..A........ | 0.01 | 1 |
| A...T | ................. | ................. | E..ND. | .DAS.N...VDG | A..A........ | 0.01 | 1 |
| GA... | ................. | ................. | ....D. | ..GGGA.AEVGD | A..A........ | 0.01 | 1 |
| DT... | ................. | ...............F. | ...... | ..AA.N..AFGE | A..A........ | 0.01 | 1 |
| TA..T | F.....SKT.NE.P...M | .QHNQ....NF......T | ....GR | .NAGA.D.AFDE | A..A........ | 0.01 | : |
| ..... | F.....G.G.HA.T.G.R | ..HDG.....F....... | R...D. | E.GAGAD...GQ | A..A........ | 0.01 | 1 |
| RA... | ................. | .Q.GQ....DF....... | ....G. | E..TEG...VDS | A..A........ | 0.01 | 1 |
| T...T | F.....NGG.NV.N.K.G | T.ASH....DF....... | ...D.. | ..ARRS.A.FDD | A..A........ | 0.01 | 1 |
| ..... | F................ | .V........F....... | ...... | ............ | GQRNG...ST.T | 0.01 | 1 |
| G.... | F.....SAT.PV.T.Q.G | ...TE.....F......T | ...D.. | ............ | A..A........ | 0.01 | 1 |
| ..... | ................. | .Q.......DF....... | E..AD. | ............ | A..A........ | 0.01 | : |
| EA... | F.....SSA..V.H.H.. | ................. | ...... | ............ | ............ | 0.01 | 1 |
| ..... | ................. | ................. | ...... | ENGRGG.AEV.D | A..A........ | 0.01 | 1 |
| AT... | F.....S.G.RQ.T.E.R | .Q.......DF....... | ...AD. | ............ | A..A........ | 0.01 | i |
| SA... | F.....NGT.IL.T.A.K | .Q.S......F....... | R...D. | .SANESD...DQ | A..A........ | 0.01 | : |
| ..... | F................ | ................. | ...ADR | ............ | A..A........ | 0.01 | 1 |
| ..... | ................. | ...........F..... | R..AGR | .NA.RA.T..G. | A..A........ | 0.01 | 1 |
| NT... | ................. | ................. | R..DD. | E..G.S.T.FDS | A..A........ | 0.01 | 1 |
| ..... | F................ | .V........F....... | ...... | ............ | GPKDR..AQE.P | 0.01 | 1 |
| TT... | F.....SGT.NM.K.T.E | .........NF....... | R...D. | ............ | A..A........ | 0.01 | 1 |
| SA... | F.....GHG.NK.I.N.R | .QPG.....DF....... | ...DDR | ............ | ............ | 0.01 | 1 |
| ..... | F................ | .V........F....... | ...... | ............ | S.RSG..F.I.Q | 0.01 | 1 |
| ..... | ................. | T.PSH....DF......T | ...DDR | ............ | A..A........ | 0.01 | 1 |
| T.... | F.....GS..NK.M.A.R | .QPSR.....F....... | ...... | ............ | A..A........ | 0.01 | 1 |
| ..... | ................. | ................. | G..NDR | .NA.AS.A..DR | A..A........ | 0.01 | 1 |
| ..... | ................. | ................. | ...N.. | ...TG.D.AY.G | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....AGA.SL.....R | .QDGG....F.......T | R..DD. | ENAGASDIA.DH | A..A........ | 0.01 | 1 |
| ..... | .................. | .................. | ...D.R | .D.D...AEFGD | A..A........ | 0.01 | 1 |
| TT... | .................. | .................. | ...... | ............ | ............ | 0.01 | 1 |
| G.... | .................. | ..HG.....NF......T | E..DD. | ............ | ............ | 0.01 | 1 |
| TT..T | .................. | .PPN......F....... | R...D. | ............ | A..A........ | 0.01 | 1 |
| ..... | .................. | .................. | ...D.. | .D.TGN.I...Q | A..A........ | 0.01 | 1 |
| ..... | F......NA.IA.K.H.G | .........NF....... | R...D. | E.AA.NDA..DD | A..A........ | 0.01 | 1 |
| AA... | F.....SAT.NL.P.N.L | .................. | ...... | .NARGNDAEF.E | A..A........ | 0.01 | 1 |
| ..... | F................. | .V........F....... | ...... | ............ | DQKAT..SQM.A | 0.01 | 1 |
| ..... | .................. | .................. | ....D. | E.TS.D..AFDQ | A..A........ | 0.01 | 1 |
| ..... | .................. | .................. | G..TDR | ............ | A..A........ | 0.01 | 1 |
| RT... | F.....DR..LE.K...R | ....A............. | ...... | ............ | A..A........ | 0.01 | 1 |
| ..... | .................. | T.HTE....NF......T | G..K.R | ...ARAD.AY.G | A..A........ | 0.01 | 1 |
| SA... | .................. | .................. | ...... | ............ | ............ | 0.01 | 1 |
| .A... | F.....DRG.S..T.A.S | ..DGE....DF....... | R...D. | ............ | ............ | 0.01 | 1 |
| E.... | .................. | .................. | R...D. | E.AKGSD.AY.G | A..A........ | 0.01 | 1 |
| .A... | F.....ATG.S..P.... | TKHDR....DF....... | ...... | ............ | A..A........ | 0.01 | 1 |
| G...T | .................. | .................. | R..DD. | ............ | A..A........ | 0.01 | 1 |
| A.... | F.....DRA..K.I.K.H | .QAS......F....... | R..... | .SGGESDAA..E | A..A........ | 0.01 | 1 |
| DT..T | F.....GS..NM.N.T.R | .................. | ...... | ............ | A..A........ | 0.01 | 1 |
| ..... | F................. | .V........F....... | ...... | ............ | ARQGT..SS... | 0.01 | 1 |
| ..... | .................. | .KDSR....DF....... | ...DDR | E..GGD.A...G | A..A........ | 0.01 | 1 |
| A...T | F......KT.NV.K.T.H | .................. | ...... | ............ | A..A........ | 0.01 | 1 |
| RA... | .................. | TQ.TG....DF....... | ...DDR | E..RRD.AA..H | A..A........ | 0.01 | 1 |
| ..... | .................. | .................. | R...D. | .SARG.D.AVDD | A..A........ | 0.01 | 1 |
| ..... | F.....SGG.NL.L.N.L | T.P......DF....... | ...D.. | ............ | A..A........ | 0.01 | 1 |
| RA... | .................. | .................. | R..DD. | EN.KAN....GG | A..A........ | 0.01 | 1 |
| ..... | .................. | .PPNG.....F......T | ...DDR | .DAG.S.A..DR | A..A........ | 0.01 | 1 |
| ..... | F................. | .V........F....... | ...... | ............ | AARAG...SA.. | 0.01 | 1 |
| ..... | .................. | .........NF..P.... | G..K.. | ............ | A..A........ | 0.01 | 1 |
| AA..T | F.....SQ..RA...D.S | ..DGE....DF....... | ...... | E.AKES....GQ | A..A........ | 0.01 | 1 |
| SA... | .................. | TQPNH....NF......T | ...... | ...TAND.A.DG | A..A........ | 0.01 | 1 |
| ..... | F................. | .................. | ....D. | ...ARS.A.FDG | A..A........ | 0.01 | 1 |
| AT..T | .................. | .................. | ...NGR | ............ | A..A........ | 0.01 | 1 |
| ..... | .................. | TQ.TG....DF....... | ...AD. | .NAGASDA.FDQ | A..A........ | 0.01 | 1 |
| ..... | .................. | ..HGH....NF......T | ...D.R | ............ | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524..3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .................. | ...D.. | E.AGAN.A...S | A..A........ | 0.01 | 1 |
| DT... | ................. | .V........F....... | ...... | ............ | SRKAP..FE..A | 0.01 | 1 |
| GA... | ................. | .QDT......F......T | R..KD. | ............ | A..A........ | 0.01 | 1 |
| ..... | ................. | TKAT.....NF......T | ...D.. | .DAGAN.AEVDH | A..A........ | 0.01 | 1 |
| TT..T | ................. | .Q.G......F..P.... | ...... | ES.GEG...VDS | A..A........ | 0.01 | 1 |
| TA... | .....NQG..V.L.N.R | .V........F....... | ....DR | ............ | ............ | 0.01 | 1 |
| ..... | ................. | ...TE.....F......T | ...NGR | ............ | A..A........ | 0.01 | 1 |
| R.... | ................. | TKDDR....DF....... | ...DDR | .NARASDAAVDQ | A..A........ | 0.01 | 1 |
| ..... | ................. | .QANH....DF....... | ...DDR | ............ | A..A........ | 0.01 | 1 |
| TA..T | F.....ARA.IE.....L | .Q.DR.....F....... | ....DE | .NGGGN..E.DG | A..A........ | 0.01 | 1 |
| ..... | F................. | .V........F....... | ...... | ............ | D.SDP..STK.E | 0.01 | 1 |
| ET..T | ................. | TQASG.....F....... | ...... | .SGGGD..E.DD | A..A........ | 0.01 | 1 |
| ..... | F.....AA..IQ.T.K.R | .................. | ...... | ............ | A..A........ | 0.01 | 1 |
| ..... | F................. | .............F..... | E..AD. | ............ | GAHDN..FET.Q | 0.01 | 1 |
| AT... | ................. | .QPG.....DF....... | ...DDR | ............ | ............ | 0.01 | 1 |
| ..... | F................. | .V........F....... | ...... | ............ | NPRAR..DDV.Q | 0.01 | 1 |
| ..... | ................. | ........DF....... | G..KD. | ENASG.....GN | A..A........ | 0.01 | 1 |
| A.... | ................. | .V........F....... | ...... | ............ | T.HTR..DDV.A | 0.01 | 1 |
| ..... | F................. | .V........F....... | ...... | ............ | GPRAP..VRT.D | 0.01 | 1 |
| ..... | F.....SA..SM.M.T.K | TKDT.....NF....... | R...D. | ............ | A..A........ | 0.01 | 1 |
| ..... | ................. | .................. | ...... | E.GSGS.AVD. | A..A........ | 0.01 | 1 |
| R.... | F................. | ..DGE....DF....... | E..AD. | ............ | A..A........ | 0.01 | 1 |
| AA... | ................. | .................. | R.AD. | ............ | A..A........ | 0.01 | 1 |
| D...T | ................. | .................. | ...DD. | ESAA.D.E.GN | A..A........ | 0.01 | 1 |
| .A... | F....ASA.S...T.A.S | ..DGE....DF....... | ...... | ............ | ............ | 0.01 | 1 |
| ..... | F.....ADA..H.K.S.. | .Q.S......F....... | ...... | ............ | A..A........ | 0.01 | 1 |
| GA... | F.....S.A.M..L...L | .V........F....... | R...D. | E.AAGSD..... | S.SNG...GG.T | 0.01 | 1 |
| RA... | F....A.A.RE.I.... | .QDT.............. | R..DD. | ............ | ............ | 0.01 | 1 |
| TA... | F.....AGG.SH.M.N.K | .Q.S......F....... | R..NG. | EDAG..I..GQ | A..A........ | 0.01 | 1 |
| DT... | ................. | .PDNR..T.DF......T | ....GR | ............ | A..A........ | 0.01 | 1 |
| .A... | F................. | .................. | R..DG. | ..GG..I..GH | A..A........ | 0.01 | 1 |
| ..... | F................. | .V........F....... | ...... | ............ | AKHTA..SEG.T | 0.01 | 1 |
| R.... | ................. | ..HG.....NF......T | E....R | ..A.AN..AF.D | A..A........ | 0.01 | 1 |
| RT... | F.....GNG.HV.H.G.R | T.P......DF.L..... | ...D.. | ............ | A..A........ | 0.01 | 1 |
| ..... | F.....SAG.SK.H.Q.S | .Q.S......F....... | R..A. | ............ | A..A........ | 0.01 | 1 |
| TT... | F.....SRT..Q.H.Q.L | .QPTG....NF....... | ...... | .NAA.A....GD | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| DT... | ................. | .V........F....... | ...... | ........... | ............ | 0.01 | 1 |
| ..... | ................. | ................. | ...D.. | .DAT....A.DG | A..A........ | 0.01 | 1 |
| SA... | F.....NRT.LL.T.G.R | ..YN......F......T | ...D.R | ........... | A..A........ | 0.01 | 1 |
| EA... | F.....SR..PN.M.K.I | .V........F....... | ...... | ........... | GQHD...V.N.E | 0.01 | 1 |
| A.... | F.....DR..LE.K...R | ....A............. | ...... | ........... | A..A........ | 0.01 | 1 |
| ..... | ................. | E.........F..P...T | R.A.R | ........... | A..A........ | 0.01 | 1 |
| SA... | ................. | ................. | ...... | ........... | A..A........ | 0.01 | 1 |
| ..... | ................. | ................. | E..AG. | ........... | A..A........ | 0.01 | 1 |
| .A... | F.....AKG.NM.L...K | ..DGE....DF....... | ...... | ESGGTD...DH | A..A........ | 0.01 | 1 |
| D...T | ................. | .Q.......DF....... | G..ND. | E.TATAI.VGS | A..A........ | 0.01 | 1 |
| AT... | ................. | .Q.G.....NF....... | ...DDR | ........... | A..A........ | 0.01 | 1 |
| ..... | ................. | ................T | R...D. | ........... | ............ | 0.01 | 1 |
| ..... | ................. | .PPNG.....F......T | ...DDR | E.TR.N.....Q | A..A........ | 0.01 | 1 |
| ..... | ................. | ................. | ...D.. | ENAGAA..EFGQ | A..A........ | 0.01 | 1 |
| D...T | F......GT.NM.L.Q.S | .Q.S.....DF....... | ...... | ........... | ............ | 0.01 | 1 |
| TA... | F.....NGG.LM.I.G.R | ................. | ...DDR | E.GSGS..AVD. | A..A........ | 0.01 | 1 |
| ..... | ................. | ................. | ...... | ..ANTNTA.DS | A..A........ | 0.01 | 1 |
| ..... | F.....NGG.NV.N.K.G | .........NF....... | R...D. | ........... | A..A........ | 0.01 | 1 |
| SA... | F.....STA..Q.H.Q.L | ..PNG....DF....... | G..NDR | ........... | A..A........ | 0.01 | 1 |
| R...T | F.....AAA.NI.L.K.N | ..PNG....DF....... | G..NDR | ........... | A..A........ | 0.01 | 1 |
| ..... | ................. | .........NF......T | ...K.. | .NAKGA.....H | A..A........ | 0.01 | 1 |
| ..... | ................. | ................. | ....D. | EDASG....FDR | A..A........ | 0.01 | 1 |
| ..... | ................. | ................. | ...DG. | .SAS.N.I..GD | A..A........ | 0.01 | 1 |
| S.... | ................. | ..YN......F......T | ...D.R | E.TGRA..A..R | A..A........ | 0.01 | 1 |
| ..... | ................. | ................. | ...... | ...TG..T..GQ | A..A........ | 0.01 | 1 |
| ..... | ................. | .QPSQ....NF....... | R..DD. | ........... | ............ | 0.01 | 1 |
| ..... | ................. | ................. | G..ND. | .DADAA..AVD. | A..A........ | 0.01 | 1 |
| E.... | F.....ASA.S..T.T.G | ................. | R..ND. | ..AG.N.AA.GQ | ............ | 0.01 | 1 |
| A.... | ................. | ................. | R..ADR | EN.D...A..GD | A..A........ | 0.01 | 1 |
| T.... | F.....NKT.IV.T.E.R | ..HG.....NF......T | ...DD. | ........... | A..A........ | 0.01 | 1 |
| ..... | F.....GK..LA.K.N.G | .Q.S......F....... | E..N.. | ........... | A..A........ | 0.01 | 1 |
| ..... | ................. | ................. | ....GR | E.AGRDD...DR | A..A........ | 0.01 | 1 |
| ..... | F................ | .V........F....... | ...... | ........... | GKSNP..SQA.P | 0.01 | 1 |
| ..... | ................. | ................. | ....G. | ........... | ............ | 0.01 | 1 |
| ..... | ................. | ................. | E..AD. | ..TAAD...VGG | A..A........ | 0.01 | 1 |
| GT... | F.....AEG.P..L...G | .V........F....... | ...... | EN.GE..IA.DR | ............ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| NAT.. | ................. | ................. | E..KD. | ........... | ........... | 0.01 | 1 |
| ..... | ................. | ................. | ...DDR | ........... | ARHNA..DSM.A | 0.01 | 1 |
| G.... | ......DKG.HM.L.G.R | .Q.......DF...... | ...AD. | .SADGSD...DR | A..A....... | 0.01 | 1 |
| D...T | F.....DSG.NM.H.A.R | .........NF...... | R...D. | ........... | A..A....... | 0.01 | 1 |
| A.... | ................. | ................. | ...DDR | ..AS.N.IA.GD | A..A....... | 0.01 | 1 |
| .A... | ................. | ..PN.....NF...... | ...NDR | E.GA.N..A..H | A..A....... | 0.01 | 1 |
| TA... | F.....AG.....N.E.R | .QPN......F......T | ...N.. | ........... | A..A....... | 0.01 | 1 |
| ..... | F.....NKT.HL.T.A.R | ..YN......F......T | ...D.R | ........... | A..A....... | 0.01 | 1 |
| .A... | ................. | .QAS......F...... | ...... | E..NTA.A..GE | A..A....... | 0.01 | 1 |
| TA... | ......A.......... | ................. | ...... | ..GGGN.IE..R | ........... | 0.01 | 1 |
| E.... | F.....GAT.IN.M.K.L | T.ANE....DF...... | ...DDR | ........... | ........... | 0.01 | . |
| ..... | ................. | ..........F...... | ....G. | E.GNGS....GR | A..A....... | 0.01 | 1 |
| RA... | F.....DGG.NL.....N | TKDDR....DF...... | ...DDR | ........... | A..A....... | 0.01 | 1 |
| E.... | F................. | ................. | ...DG. | E.TT.A...VGD | A..A....... | 0.01 | 1 |
| SA..T | F.....SA..SM.M.T.K | TKDT.....NF...... | R...D. | ........... | A..A....... | 0.01 | 1 |
| AA... | F.....SN..PL.K.T.. | ................. | R..ND. | ED.GR....F.R | A..A....... | 0.01 | 1 |
| A.... | F.....AET..A.T...K | .QPTG....NF...... | E..AGR | ESAGRS...VDR | A..A....... | 0.01 | 1 |
| ..... | F................. | ................. | R..DDR | E.AGES.A.Y.Q | A..A....... | 0.01 | 1 |
| .T... | F................. | .V........F...... | ...... | ........... | GRKGG..DRE.. | 0.01 | 1 |
| EA... | F.....GSA.RV.L.A.R | .Q.DR.....F...... | ....GR | ED.G.SD..FDE | A..A....... | 0.01 | 1 |
| ..... | ................. | .........NF...... | ...D.. | .NGNTGD....N | A..A....... | 0.01 | 1 |
| RA... | ................. | ................. | ...NDR | ..AKG...AV.. | A..A....... | 0.01 | 1 |
| ..... | ................. | ................. | ...DDR | .SGDAG..EV.G | A..A....... | 0.01 | 1 |
| ..... | ................. | .........NF...... | R...D. | E........... | A..A....... | 0.01 | 1 |
| ..... | F................. | .V........F...... | ...... | ........... | ESRAE..V.G.H | 0.01 | 1 |
| ..... | F................. | .V........F...... | ...... | ........... | GHRNS..FSI.T | 0.01 | 1 |
| AA... | F.....DA..IA.L.K.R | .KDSR....DF......T | R..DD. | ........... | A..A....... | 0.01 | 1 |
| D...T | F.....GGT.IV.K.G.K | ..DGE....DF...... | ...... | .SA.GG....DG | A..A....... | 0.01 | 1 |
| .A... | ................. | .........F...... | ...... | ........... | ATRNT..VDV.H | 0.01 | 1 |
| NT... | F......H..NV.T.G.R | .QHNQ.....F......T | ...D.. | ........... | A..A....... | 0.01 | 1 |
| ..... | F................. | .V........F...... | ...... | ........... | G..NA..DHV.H | 0.01 | 1 |
| ..... | ................. | ................. | G..ND. | .SAS.N.IA..E | A..A....... | 0.01 | 1 |
| ..... | ................. | ................. | ...DDR | .SANTG....GE | A..A....... | 0.01 | 1 |
| RA... | ................. | .QYGQ....DF......T | E..NGR | ........... | A..A....... | 0.01 | 1 |
| ..... | F.....SRG..L.P.G.G | .K.TG....DF...... | R...DR | .NAA...A..DD | A..A....... | 0.01 | 1 |
| RA... | ................. | TQHNG....NF......T | R..D.. | ........... | A..A....... | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F................. | .V........F....... | ...... | ........... | ARQSG..NGV.T | 0.01 | 1 |
| A...T | F.....GRG.H..P.E.R | TKDDR.....F......T | ...DG. | ........... | A..A........ | 0.01 | 1 |
| NT..T | F.....SA..RA.....R | .V........F....... | ...... | ........... | KDRTH..FDM.. | 0.01 | 1 |
| DT... | ................. | .Q.GQ....DF....... | ....G. | .NASEG..E..G | A..A........ | 0.01 | 1 |
| ..... | F................. | .V........F....... | ...... | ........... | GRHNP..SR..Q | 0.01 | 1 |
| ..... | ................. | .V........F....... | ...... | ........... | GRKTG..AEV.A | 0.01 | 1 |
| ..... | ................. | ................. | R...D. | .DARAADA...Q | A..A........ | 0.01 | 1 |
| ..... | F................. | .Q.......DF....... | ...AD. | ........... | A..A........ | 0.01 | 1 |
| GA... | ................. | .Q.S......F....... | E..ND. | ........... | A..A........ | 0.01 | 1 |
| ..... | ................. | ................. | ...DDR | .NATG....VGS | A..A........ | 0.01 | 1 |
| ..... | F................. | .V........F....... | ...... | ........... | AAKTP..AGG.A | 0.01 | 1 |
| D...T | F.......T.SV...H.R | .PPNG.....F......T | ...DDR | .NAGA.D.AFDE | A..A........ | 0.01 | 1 |
| ..... | ................. | .................T | ...ND. | ........... | A..A........ | 0.01 | 1 |
| N.... | F................. | .V........F....... | ...... | ........... | NE.NA..FDV.T | 0.01 | 1 |
| NT... | F.....GTT.IL.M...K | .Q.......DF....... | ...AD. | ........... | A..A........ | 0.01 | 1 |
| A.... | F.....AKG.P..H.P.R | .KDDG....NF......T | R...DR | E..GANDI..GS | A..A........ | 0.01 | 1 |
| ..... | ................. | ................. | ...DDR | E.AAAN.IEV.E | A..A........ | 0.01 | 1 |
| ..... | F......GG.NV...G.M | .Q.GQ....DF....... | ....G. | ........... | A..A........ | 0.01 | 1 |
| TA... | F................. | ................. | ....D. | ........... |  | 0.01 | 1 |
| ..... | F.........N....... | .V........F....... | ...... | ........... | GT.TR..FQM.E | 0.01 | 1 |
| E.... | F................. | ..HG.....NF......T | E..DD. | ........... |  | 0.01 | 1 |
| ..... | ................. | ................. | ...D.. | ES.SA..I..DR | A..A........ | 0.01 | 1 |
| SA... | F.....GKG.NQ...P.K | .V........F....... | ...... | ........... | A..A........ | 0.01 | 1 |
| ..... | ................. | ........NF......T | ...... | ESGTGND.E.DG | A..A........ | 0.01 | 1 |
| ..... | F.....DA..IA.L.K.R | .PPN......F......T | R..A.. | ........... | A..A........ | 0.01 | 1 |
| ..... | ................. | ................. | ...... | ESA.AG..E.GE | A..A........ | 0.01 | 1 |
| ..... | ...........K.R | ...T.....NF.....T | ...D.. | E.GT.G.T..GH | A..A........ | 0.01 | 1 |
| ..... | F......AG..L.T.N.R | T..NE....DF....... | ...DDR | H.AKGS.AAYDS | A..A........ | 0.01 | 1 |
| AT..T | F.....SA..RA.....R | .Q.S......F....... | E..N.. | ...G.SDI.FDE | A..A........ | 0.01 | 1 |
| ..... | F................. | .V........F....... | ...... | ........... | AQRNP....M.Q | 0.01 | 1 |
| ..... | ................. | ................. | R..DD. | .NGGAADAE..H | A..A........ | 0.01 | 1 |
| G...T | F.....AQ...A.L.... | ........NF........ | R...D. | ........... | A..A........ | 0.01 | 1 |
| ..... | ................. | ........F.......T | ...DDR | E..G.SDAA.GD | A..A........ | 0.01 | 1 |
| ..... | F................. | .V........F....... | ...... | ........... | ASRA...SG..A | 0.01 | 1 |
| .A... | ................. | TKAS.....NF......T | G.A.R | ........... | A..A........ | 0.01 | 1 |
| GA... | ................. | ................. | ...DDR | .NATG....VGS | A..A........ | 0.01 | 1 |

TABLE 3-continued

AAV capsid proteins having increased specificity for and/or transduction of CD447⁻/133⁻ GBM cells (pool of Round 1 selection). Amino acid numbers correspond to the amino acid sequence of VP1 (SEQ ID NO: 1). Sequences below correspond to SEQ ID NOs: 8 and 524.3691 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| AT..T | F.....ATG.NV.T.G.R | .QDT......F......T | ...D.. | ENAGASDIA.DH | A..A........ | 0.01 | 1 |
| G.... | ................. | .........NF....... | R..D. | ........... | A..A........ | 0.01 | 1 |
| DA... | F................ | ................. | ...... | ........... | A..A........ | 0.01 | 1 |
| ..... | F......AA.RH.L.Q.N | .Q.DH....NF....... | ....D. | E..AAS....GG | A..A........ | 0.01 | 1 |
| ..... | ................. | ................. | ...AGR | ........... | A..A........ | 0.01 | 1 |
| G...T | F......GT.NM.L.Q.G | .Q.S......F....... | ....D. | ........... | A..A........ | 0.01 | 1 |
| G.... | ................. | TQ.TG....DF....... | ...DDR | EDAA...AAVDQ | A..A........ | 0.01 | 1 |
| .T... | F.....AAT.N..P.P.R | TQADR....NF......T | R...D. | ........... | A..A........ | 0.01 | 1 |
| TA... | ................. | .PPNG.....F....... | E..KD. | ........... | A..A........ | 0.01 | 1 |
| .A... | F.....AGT.N..P.A.. | .KDSR....DF....... | R..DD. | ........... | A..A........ | 0.01 | 1 |
| ..... | F................ | .V........F....... | ...... | ........... | APQNP...DI.P | 0.01 | 1 |
| ..... | ................. | .K.TG....DF....... | R...DR | E.TAGN.IE.GE | A..A........ | 0.01 | 1 |
| .A... | F................ | .V........F....... | ...... | ........... | TTKGK..Y.E.E | 0.01 | 1 |
| D.... | F......AG.SH.T.A.R | T.P......DF....... | ...DDR | EDGAA.DAA.DE | A..A........ | 0.01 | 1 |
| TA..T | F.....NGT.IL.T.A.K | .Q.DH....NF....... | ...DD. | ..ARGADAE..S | A..A........ | 0.01 | 1 |
| ..... | F.....A.A.RE.I.... | .K.TG....DF....... | R...DR | ........... | A..A........ | 0.01 | 1 |
| E.... | p.....SN..PL.K.T.. | .........F..P.... | R..... | ........... | ........... | 0.01 | 1 |
| GT... | ................. | ................. | R..A.. | ........... | ........... | 0.01 | 1 |
| ..... | F................ | .V........F....... | ...... | ........... | GT.NA..FGV.D | 0.01 | 1 |
| TT..T | F.....DS..NH.I.P.R | .KYT.....NF......T | .....R | ENTSEG.....R | A..A........ | 0.01 | 1 |
| RA... | ......A...H......L | ..DGE....DF....... | ...... | ........... | ........... | 0.01 | 1 |
| A...T | P.......G.SE.N...R | .V........F....... | ...... | ..ATRD.T..GH | A..A........ | 0.01 | 1 |
| GA... | ................. | ..PNG....DF....... | R..AGR | ........... | A..A........ | 0.01 | 1 |
| ..... | ................. | ................. | ...... | .SAD.R....GG | A..A........ | 0.01 | 1 |
| SA... | F.....NET.P..K.K.G | TKYTG....DF....... | ...DDR | ........... | A..A........ | 0.01 | 1 |
| ..... | ................. | ................. | ...DDR | EN.DAS...V.E | A..A........ | 0.01 | 1 |
| A.... | F......QG.RL.L.T.R | .........NF....... | R...D. | .SAS.N.IA..E | A..A........ | 0.01 | 1 |
| ..... | ................. | ................. | ....G. | ..ASE...E.D. | A..A........ | 0.01 | 1 |
| ..... | ................. | ...............T | ...DDR | ........... | ASSNH..AKG.D | 0.01 | 1 |
| ..... | ................. | ..........F...... | ...DDR | ........... | A..A........ | 0.01 | 1 |
| ST... | F.....SGT.S..P.A.K | T.PG.....NF....... | ...DDR | ........... | A..A........ | 0.01 | 1 |
| RA... | ................. | .KAS.....NF......T | E..DD. | ..TGAS..EV.N | A..A........ | 0.01 | 1 |
| AA... | F.....ASA.S..T.T.G | .QPG.....DF....... | ...... | ESTTEA...... | A..A........ | 0.01 | 1 |
| ET..T | ................. | .KD.E....DF......T | ...... | E.AG..D.A.GR | A..A........ | 0.01 | 1 |

TABLE 4

AAV capsid proteins having increased specificity for and/or transduction of
CD44⁻/133⁻ GBM cells (pool of Round 2 selection). Amino acid numbers correspond
to the amino acid sequence of VP1 (SEQ ID NO: 1). Sequences below correspond
to SEQ ID NOs: 8 and 3692-3730 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F.....ASA.S..T.T.G | .QPG.....DF....... | ...D.. | ............ | ............ | 11.75 | 304 |
| ..... | ................ | .Q.S......F....... | ...T.. | ............ | A..A........ | 9.39 | 243 |
| ..... | ................ | ................ | R..DD. | ............ | ............ | 6.42 | 166 |
| ..... | ................ | ..DGE....DF....... | R...D. | ............ | ............ | 5.91 | 153 |
| ..... | ................ | TQASG....NF....... | ....D | E.AS...IEYGQ | A..A........ | 4.79 | 124 |
| ..... | ................ | ................ | ...... | .DTAAA...VGE | A..A........ | 4.56 | 118 |
| ..... | ................ | ................ | G..DG. | ............ | ............ | 4.41 | 114 |
| ..... | F.....DAA.IK.T.Q.N | ..DGE....DF....... | ...... | E........... | ............ | 4.14 | 107 |
| ..... | F................ | .V......F....... | ...... | ............ | DPHTR..D.M.. | 4.06 | 105 |
| ..... | ................ | ................ | ....GR | ..AG.N.AA.GA | A..A........ | 4.06 | 105 |
| ..... | ................ | ................ | R...GR | EDTG.A....GN | A..A........ | 4.02 | 104 |
| ..... | ................ | ................ | ....D | E.GGTG.AEFDQ | A..A........ | 3.75 | 97 |
| ..... | ................ | ................ | R...D. | ............ | A.KA........ | 2.82 | 73 |
| R.... | ................ | ................ | ....G | E.AG...IAVDR | A..A........ | 2.71 | 70 |
| ..... | ................ | ................ | ....DR | ESGTTA...VGQ | A..A........ | 2.71 | 70 |
| ..... | ................ | .QD.E.....F..P.... | ...D.. | ............ | ............ | 2.55 | 66 |
| ....T | ................ | ................ | ...ADR | ............ | A..A........ | 2.32 | 60 |
| GA... | F.....STA..Q.H.Q.L | T.P.....DF....... | R...D. | ............ | ............ | 2.16 | 56 |
| ..... | ................ | ................ | ....GR | ..AGA..AA.GS | A..A........ | 2.05 | 53 |
| ..... | ................ | ................ | ...AG. | ............ | A........... | 2.05 | 53 |
| ..... | ................ | ................ | ...D.R | ES.DGN..A.DG | A..A........ | 1.70 | 44 |
| SA... | ................ | ...........T | ...D.. | ............ | ............ | 1.66 | 43 |
| E.... | ................ | ................ | G..KD. | ............ | A..A........ | 1.39 | 36 |
| NA... | F.....SK..PA.K.A.H | .KPDQ.....F....... | R..DGR | ............ | A..A........ | 1.04 | 27 |
| A.... | ................ | .QD.E.....F..P.... | ...D.. | ............ | ............ | 0.89 | 23 |
| DT... | ................ | ........NF....... | ...DDR | ESGRR...E..Q | A..A........ | 0.43 | 11 |
| TT..T | F.....SGT.NM.K.T.E | .Q.GQ....DF....... | ....G. | ............ | A..A........ | 0.39 | 10 |
| G.... | ................ | .KD.E.....F..P...T | R..ND. | ............ | A..A........ | 0.19 | 5 |
| ....T | ................ | .........G........ | ...ADR | ............ | A..A........ | 0.08 | 2 |
| AT... | .......GT.NM.L.Q.G | .Q.S......F....... | ...D. | ............ | ............ | 0.08 | 2 |
| ..... | F.....ASA.S..T.TPG | .QPG.....DF....... | ...D.. | ............ | ............ | 0.08 | 2 |
| ..... | F................ | .V......F....... | ...... | .C.......... | .EKGG...QN.. | 0.08 | 2 |
| ..... | F.....DAA.IK.T.Q.N | ..DGE....DF....... | .....S | E........... | ............ | 0.08 | 2 |
| ..... | ................ | ....G....DF....... | E..AD. | ...SGSD..FDN | A..A........ | 0.04 | 1 |
| ..... | F................ | .V......F....... | ...... | ............ | GERTP..ART.D | 0.04 | 1 |
| G...T | ................ | ..HDR....NF....... | ....D. | ............ | A..A........ | 0.04 | 1 |

TABLE 4-continued

AAV capsid proteins having increased specificity for and/or transduction of CD44⁻/133⁻ GBM cells (pool of Round 2 selection). Amino acid numbers correspond to the amino acid sequence of VP1 (SEQ ID NO: 1). Sequences below correspond to SEQ ID NOs: 8 and 3692-3730 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ...... | .DAGGND.A.D. | A..A........ | 0.04 | 1 |
| ..... | ................. | ................. | E..NG. | ............ | ............ | 0.04 | 1 |
| ..... | ................. | ................. | ...... | .DTAAA...VGE | A..A........ | 0.04 | 1 |

TABLE 5

AAV capsid proteins having increased specificity for and/or transduction of CD44⁺/133⁺ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................. | .V........F....... | ...... | ............ | ERSGA..IE..D | 10.81 | 1378 |
| ..... | ..........SP.H.E.V | ..HG.....NF......T | ...DDR | E.AGAND.AV.H | A..A........ | 6.51 | 830 |
| ..... | ................. | T.HTE....NF......T | ...NDR | ............ | A..A........ | 5.33 | 679 |
| ..... | ................. | ................. | ....GR | ..AG.N.AA.GQ | A..A........ | 1.70 | 217 |
| E.... | F.....ASA.S..T.T.G | .QPG.....DF....... | ...DDR | ............ | ............ | 0.92 | 117 |
| .A... | F.....DRG.S..T.A.S | ..DGE....DF....... | ...... | ............ | ............ | 0.88 | 112 |
| ..... | ................. | ................. | ...NDR | ..AKG...AV.. | A..A........ | 0.78 | 100 |
| ..... | F................. | .V........F....... | ...... | ............ | GRRDP..DTI.P | 0.75 | 96 |
| AA... | F.....GQG.IA.....K | .Q.GQ....DF....... | ....G. | .NAGA.D...GS | A..A........ | 0.64 | 82 |
| E.... | F.....ASA.S..T.T.G | .QPG.....DF....... | ...DDF | ............ | A..A........ | 0.60 | 76 |
| EA..T | ......NQG..V.L.N.R | .QPN......F......T | ...N.. | .NGGGN...VDQ | ............ | 0.58 | 74 |
| A.... | ................. | ................. | ...... | ............ | ............ | 0.53 | 68 |
| TT..T | ................. | ................. | ...... | ............ | ............ | 0.53 | 67 |
| ..... | ................. | ................. | R...D. | ............ | A..A........ | 0.49 | 63 |
| ..... | F......TG.KA.I.G.K | .PHD.....DF......T | ...D.R | ............ | A..A........ | 0.46 | 59 |
| ..... | ................. | ................. | ...DDR | ............ | ............ | 0.46 | 59 |
| ..... | ................. | ................. | ...... | ............ | A..A........ | 0.46 | 59 |
| GT... | ................. | ..HG.....NF......T | E..DD. | ............ | ............ | 0.46 | 58 |
| TA... | ................. | .QANH....DF....... | ...DDR | ............ | A..A........ | 0.45 | 57 |
| ..... | ................. | .PPNG.....F......T | ...DDR | E.ATRA..A.DE | A..A........ | 0.43 | 55 |
| ..... | ................. | .V........F....... | ...... | ............ | GR.DT..FTE.D | 0.42 | 53 |
| ..... | ................. | .QD.E....F..P.... | ...D.. | ............ | ............ | 0.35 | 44 |
| .A... | F.....G.T.II.P.F.R | ................. | ...DG. | ............ | A..A........ | 0.33 | 42 |
| ..... | ................. | T..NH....NF......T | ....GR | .DAGAN.AEVDH | A..A........ | 0.33 | 42 |
| GA... | ................. | ...............T | G..TG. | ............ | ............ | 0.31 | 40 |
| ..... | .......KA.SA.T.A.G | .QPN......F......T | ...N.. | ............ | A..A........ | 0.31 | 40 |
| ..... | F.....GDT.H..I...G | .QAS......F....... | G..DG. | ............ | ............ | 0.31 | 39 |

TABLE 5-continued

AAV capsid proteins having increased specificity for and/or transduction of CD44⁺/133⁺ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | G..DG. | ........... | ........... | 0.31 | 39 |
| ..... | .................. | .................. | ....GR | ........... | A..A........ | 0.30 | 38 |
| H.... | .................. | .........DF....... | ...D.. | ........... | .RQDP..NEA.T | 0.30 | 38 |
| D...T | F......GT.NM.L.Q.G | .Q.S.....F....... | ....D. | ........... | ........... | 0.30 | 38 |
| ..... | F................. | .V........F....... | ...... | ........... | ........... | 0.29 | 37 |
| ..... | .................. | .................T | G..TG. | ........... | ........... | 0.29 | 37 |
| ..... | .................. | .................. | R..DD. | ........... | A..A........ | 0.29 | 37 |
| ..... | .................. | .........DF....... | ...D.. | E.ASGG.A..GS | A..A........ | 0.29 | 37 |
| ..... | .................. | .................. | R..D.R | E.AAAA.I..D. | A..A........ | 0.29 | 37 |
| ..... | F.....AEG.LK.M.H.L | ..DGE....DF....... | ...... | ........... | ........... | 0.28 | 36 |
| ..... | .................. | .................. | R..D.. | ES.TG..I.FDR | A..A........ | 0.27 | 35 |
| TA... | F.....SRA.SG.N.A.H | .QDT.....DF....... | ...DDR | ...G.S..AFGD | A..A........ | 0.27 | 35 |
| A.... | F.....DA..IA.L.K.R | .KDSR....DF......T | R..DD. | ........... | A..A........ | 0.27 | 34 |
| ..... | .................. | .........DF....... | ...DDR | ESGTGA.A.FG. | A..A........ | 0.27 | 34 |
| ..... | .................. | .................. | E..NG. | ........... | ........... | 0.27 | 34 |
| R.... | F.....NKT.I..K.... | ..DGE....DF....... | ...... | E.AGAADA.VDH | A..A........ | 0.26 | 33 |
| ..... | .................. | .................. | ...... | .DGKTGD..VGE | A..A........ | 0.26 | 33 |
| G.... | F.....GS..NK.M.A.R | ..YN......F......T | ...D.R | ........... | A..A........ | 0.26 | 33 |
| ..... | F................. | .V........F....... | ...... | ........... | TSKDA..I.T.A | 0.26 | 33 |
| E.... | F.....ASA.S..T.T.G | ...T.....DF..P...T | ...DDR | ........... | ........... | 0.26 | 33 |
| ..... | .................. | .................. | ...NDR | ........... | A..A........ | 0.26 | 33 |
| ..... | .................. | .................. | G..ND. | E.GTR...A..S | A..A........ | 0.25 | 32 |
| ..... | .................. | .V........F....... | ...... | ENATRSDTE.DQ | A..A........ | 0.25 | 32 |
| GA... | F.....GDT.H..I...G | .QAS.....F....... | ...D.. | ........... | ........... | 0.25 | 32 |
| A.... | F................. | .V........F....... | ...... | ........... | E..A........ | 0.25 | 32 |
| AT... | .................. | .................. | E..ADR | .S.KA..TE.DS | A..A........ | 0.24 | 31 |
| RA... | .................. | .................. | E...G. | EN.NR..I...G | A..A........ | 0.24 | 31 |
| ..... | F......N..IL.T.T.R | .QPN......F......T | ...N.. | ........... | A..A........ | 0.24 | 31 |
| ..... | .................. | .........DF....... | E..ND. | ........... | A..A........ | 0.24 | 31 |
| H.... | F.....GRA.RQ.M.G.G | .Q.DR....F....... | ...DG. | ........... | A..A........ | 0.24 | 30 |
| ..... | .................. | .................. | R...DR | E.GG.....F.S | A..A........ | 0.24 | 30 |
| ..... | F................. | .V........F....... | ...... | ........... | AARGG.VSN... | 0.24 | 30 |
| SA... | .................. | .PPNG.....F......T | ...DDR | ........... | A..A........ | 0.24 | 30 |
| A.... | .................. | .QD.E.....F..P.... | ...D.. | ........... | ........... | 0.23 | 29 |
| T.... | F.....GK..LA.K.N.G | ..DGE....DF....... | ...... | ..AN.A..AV.D | A..A........ | 0.23 | 29 |
| ..... | F................. | .V........F....... | ...... | ........... | G.RTT..DRV.E | 0.22 | 28 |

TABLE 5-continued

AAV capsid proteins having increased specificity for and/or transduction of CD44$^+$/133$^+$ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................. | .V........F....... | ...... | ........... | GR.DT..FTE.E | 0.22 | 28 |
| ..... | ................. | ................. | ...D.R | ........... | A..A........ | 0.22 | 28 |
| ..... | ................. | ................. | ...... | .DAGGND.A.D. | A..A........ | 0.22 | 28 |
| DT..T | F.....NG..LK.T.K.K | .QANH....DF....... | ...DDR | ........... | A..A........ | 0.22 | 28 |
| .A... | ................. | .KYT.....NF......T | E..TD. | ........... | A..A........ | 0.22 | 28 |
| ..... | ................. | ................. | G..KGR | ..AG.N.AA.GQ | A..A........ | 0.21 | 27 |
| TA... | F.....NN..SA.N...R | .KDDG....NF......T | ...DDR | .S.G.S.IA..G | A..A........ | 0.21 | 27 |
| ..... | ................. | ................. | E..DGR | ........... | ............ | 0.21 | 27 |
| .T... | ................. | ........NF..P...T | R..ND. | ........... | A..A........ | 0.21 | 27 |
| ..... | ................. | .Q.GQ....DF....... | R..AD. | ..ARGADAE... | A..A........ | 0.21 | 27 |
| TA... | F.....AQ...A.L.... | .QD.E.....F..P.... | ...... | ........... | ............ | 0.20 | 26 |
| ..... | ................. | ..AGR....DF......T | R..D.. | .D......... | A..A........ | 0.20 | 26 |
| RA... | F.....DGA.R..P.A.K | .........NF....... | R...D. | ........... | A..A........ | 0.20 | 25 |
| ..... | ................. | ................T | ....GR | ...AAS.A.VGQ | A..A........ | 0.20 | 25 |
| ..... | ................. | ................. | ...DD. | ........... | ............ | 0.20 | 25 |
| ..... | ................. | ................. | ...ND. | ..ATT..T.F.Q | A..A........ | 0.20 | 25 |
| ..... | ................. | ................. | R..ND. | ..ARAN..A.DR | A..A........ | 0.19 | 24 |
| ..... | F.....SR..NE.M...S | .QPSE....DF....... | ...DG. | ..ATESD..FDQ | A..A........ | 0.19 | 24 |
| T.... | F......KG.RV.T.A.G | .V........F....... | R..ADR | E.AGG.DI..GN | A..A........ | 0.19 | 24 |
| EA... | ................. | T..NE....DF......T | R..DD. | ........... | ............ | 0.19 | 24 |
| ..... | F................. | .V........F....... | ...... | ........... | E.KSP..ARA.. | 0.19 | 24 |
| ..... | F.....SA..RA.....R | TKDDR....DF....... | ...DDR | E..A.ADA..GD | A..A........ | 0.19 | 24 |
| ..... | F................. | .V........F....... | ...... | ........... | A.RAG..STI.H | 0.19 | 24 |
| ..... | ................. | .V........F....... | ...... | ........... | EKRGA..V...H | 0.18 | 23 |
| RT..T | F.....G.G.HA.T.G.R | TQPTE....DF....... | ...DDR | ........... | A..A........ | 0.18 | 23 |
| GA... | F.....STA..Q.H.Q.L | T.P......DF....... | R...D. | ........... | ............ | 0.18 | 23 |
| E.... | ................. | T..NH....NF......T | ....GR | .DAGAN.AEVDH | A..A........ | 0.18 | 23 |
| ..... | ................. | ................. | G..N.. | ..GAGAD..... | A..A........ | 0.17 | 22 |
| ..... | F.....SN..PL.K.T.. | .V........F....... | ...... | ........... | ............ | 0.17 | 22 |
| ..... | ................. | ................. | ...D.. | ENAG.G.IA.DG | A..A........ | 0.17 | 22 |
| ..... | ................. | ................. | R..DD. | ........... | ............ | 0.17 | 22 |
| A.... | F.....AG..PA.K.G.R | ..A......DF....... | ....D. | ........... | A..A........ | 0.17 | 22 |
| .T... | ................. | ........NV..P...T | R..ND. | ........... | A..A........ | 0.17 | 22 |
| ..... | ................. | ........DF....... | ...D.. | ........... | .RQDP..NEA.T | 0.17 | 22 |
| GT... | ................. | ................. | R...D. | ........... | ............ | 0.17 | 22 |
| DT... | F.....AG..SD.L...K | .KDSR....DF....... | E..ND. | ........... | A..A........ | 0.16 | 21 |

TABLE 5-continued

AAV capsid proteins having increased specificity for and/or transduction of
CD44[+]/133[+] GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | .................. | .................. | ...... | E..TGS..EYDR | A..A........ | 0.16 | 21 |
| ..... | .................. | .........DF....... | R...D. | .S.GGA.IE.DD | A..A........ | 0.16 | 21 |
| ..... | .................. | .................. | E..AD. | ........... | ........... | 0.16 | 21 |
| G.... | F......G..NL.T.E.R | .QDT......F......T | ...D.. | ........... | A..A.....T | 0.16 | 21 |
| ..... | F.....STA..Q.H.E.L | T.P......DF....... | R...D. | ........... | ........... | 0.16 | 21 |
| ..... | F................. | .V.......F....... | ...... | ........... | S.HT...FGG.T | 0.16 | 21 |
| .A..T | .................. | .........DF....... | ...AD. | ........... | A..A........ | 0.16 | 21 |
| ..... | ......SG..IK.K.D.R | .KPDQ....DF....... | ...D.. | .NATG....VGS | A..A........ | 0.16 | 21 |
| GT... | .................. | .................. | E..ADR | .S.KA..TE.DS | A..A........ | 0.16 | 21 |
| ..... | .................. | ...............T | ...D.. | ........... | ........... | 0.16 | 20 |
| ..... | .................. | .........NF....... | R...D. | ESASTN...VDQ | A..A........ | 0.16 | 20 |
| TA... | F................. | .V.......F....... | ...... | ENAAGGDT..GR | A..A........ | 0.16 | 20 |
| ..... | .................. | .................. | ...DDR | E.ANR..IA.GE | A..A........ | 0.16 | 20 |
| E.... | F.....AT..PL.H.G.N | ..DD.....DF....... | ...ND. | ........... | ........... | 0.16 | 20 |
| ..... | .................. | ..AG.....NF......T | R..DF. | ........... | A..A........ | 0.16 | 20 |
| AA... | F.....DAA.SA.K.A.R | .Q.GQ....DF....... | ....G. | E..N...I..DR | A..A........ | 0.16 | 20 |
| ..... | .................. | .................. | ...DDR | .SGGRS..E.DQ | A..A........ | 0.16 | 20 |
| ..... | F................. | .V.......F....... | ...... | ........... | GPSNR..IEI.D | 0.16 | 20 |
| A.... | F.....NGT.HV.T.K.N | T.YNG....DF....... | ...DG. | ESAR..DAA.DD | A..A........ | 0.15 | 19 |
| ..... | F................. | .V.......F....... | ...... | ........... | TPRSG..FT..H | 0.15 | 19 |
| ..... | .................. | .................. | ...DDR | ...GT..AA.GD | A..A........ | 0.15 | 19 |
| ..... | .................. | .................. | ...DG. | ........... | A..A........ | 0.15 | 19 |
| ..... | .................. | .................. | ...DDR | .N.G.N.A.VDN | A..A........ | 0.15 | 19 |
| ..... | .................. | ...........NF | ...NDR | ........... | A..A........ | 0.15 | 19 |
| ..... | .................. | .................. | R..N.. | ........... | A..A........ | 0.15 | 19 |
| ..... | F................. | .V.......F....... | ...... | ........... | APQDR..DTN.T | 0.15 | 19 |
| T.... | .................. | .KDT......F......T | ...DD. | ESGA.A.AAV.H | A..A........ | 0.15 | 19 |
| ..... | .................. | .................. | R..DD. | .DTG.GD.A..H | A..A........ | 0.15 | 19 |
| TT... | F.....ARG.IA.K.E.L | .QPN......F......T | ...N.. | EDGKGN..AFDE | A..A........ | 0.15 | 19 |
| ..... | F.....GNG.HV.H.G.R | ..YN......F......T | ...D.R | ........... | A..A........ | 0.15 | 19 |
| ..... | .................. | .V.......F....... | ...... | ........... | GRRDP..DTI.P | 0.15 | 19 |
| E.... | .................. | .................. | E..A.. | ........... | A..A........ | 0.15 | 19 |
| ..... | F................. | .V.......F....... | ...... | ........... | S.QDR..D.N.A | 0.15 | 19 |
| AA... | F.....NAT.LV.T.H.R | .Q.......DF....... | ...AD. | ........... | A..A........ | 0.15 | 19 |
| AA... | F.....GS..NK.M.A.R | ..YN......F......T | ...D.R | ........... | A..A........ | 0.15 | 19 |
| R.... | F.....A...ND.T...K | TPPG.....DF....... | R..DD. | .DAGGND.A.D. | A..A........ | 0.14 | 18 |

TABLE 5-continued

AAV capsid proteins having increased specificity for and/or transduction of
CD44$^+$/133$^+$ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | .................. | E..ND. | ............ | A..A........ | 0.14 | 18 |
| ..... | .................. | .................. | R..ND. | .DGSGG.TE.DG | A..A........ | 0.14 | 18 |
| ..... | .................. | .................. | E..T.. | ............ | ............ | 0.14 | 18 |
| ..... | .................. | .................. | T..AGR | .DAG.A.I..DG | A..A........ | 0.14 | 18 |
| RA... | F.....DTG.SK.T.T.R | .Q.S.....F....... | ...D.. | .NGR.G..A..E | A..A........ | 0.14 | 18 |
| NA..T | F.....GGG.RP.T.G.L | .Q.S.....F....... | E..N.. | ............ | A..A........ | 0.14 | 18 |
| ..... | .................. | .................. | ...DDR | E..GRD.IA.DH | A..A........ | 0.14 | 18 |
| E.... | F.....DRG.N..I.A.K | .KYT.....NF....... | R..D.. | ............ | ............ | 0.14 | 18 |
| ..... | F................. | .V........F....... | ...... | ........E... | TARTT..FKV.D | 0.14 | 18 |
| ..... | .................. | ...DG....DF......T | ...DDR | .DARRN.AE.GS | A..A........ | 0.14 | 18 |
| ..... | .................. | .Q.G.....F..P.... | ...... | .SASEN....GR | ............ | 0.14 | 18 |
| ..... | .................. | .................. | ...D.. | EDAGGS.TE.DQ | A..A........ | 0.14 | 18 |
| ..... | .................. | .................. | R..DG. | ENAGT...AFD. | A..A........ | 0.14 | 18 |
| ..... | .................. | .QPN......F......T | E..AD. | ............ | A..A........ | 0.14 | 18 |
| ..... | F................. | .V........F....... | ...... | ............ | SDRT.....A.D | 0.14 | 18 |
| ..... | .................. | .................. | ....D. | ESA.GG..E.GS | A..A........ | 0.13 | 17 |
| ..... | .................. | .................. | ...DDR | E.TG.N.AA.GQ | A..A........ | 0.13 | 17 |
| T...T | F.....N.G.RE.H.A.R | .Q.DR.....F....... | ....D. | ............ | A..A........ | 0.13 | 17 |
| ..... | .................. | .........F......T | R...G. | .NASEN...FDR | ............ | 0.13 | 17 |
| ..... | .................. | .........DF....... | ...D.. | ..TTTGDTA.DN | A..A........ | 0.13 | 17 |
| NA..T | .................. | .........DF....... | ...D.. | .D..TA....GE | A..A........ | 0.13 | 17 |
| A.... | F.....DNT.SK.L...K | .Q.DQ.....F....... | ...DD. | .DA..N..A..E | A..A........ | 0.13 | 17 |
| ..... | .................. | .................. | ...... | ..GSRN..EYGE | A..A........ | 0.13 | 17 |
| ..... | .................. | .................. | R..... | ............ | A..A........ | 0.13 | 17 |
| .T... | .................. | .QPSQ....NF....... | ...... | ENGK.D..A.DG | A..A........ | 0.13 | 17 |
| GA... | .................. | TQ.TG....DF....... | ...DDR | E..KAS..AVDH | A..A........ | 0.13 | 17 |
| D.... | .................. | .........NF......T | R..TG. | .DGG.....Y.Q | A..A........ | 0.13 | 17 |
| G.... | .................. | .KYT.....NF....... | E..NG. | ENTTGN....DR | A..A........ | 0.13 | 17 |
| ..... | .................. | .Q.DR.....F....... | ....D. | ............ | A..A........ | 0.13 | 17 |
| GT... | .................. | .................. | R...D. | E.A.AN.TAY.Q | A..A........ | 0.13 | 16 |
| RA... | F.....G.G.HA.T.G.R | .Q.GQ....DF....... | R...D. | .DGTGA..E..E | A..A........ | 0.13 | 16 |
| E.... | F.....SN..PL.K.T.. | .........F..P.... | R..... | ............ | ............ | 0.13 | 16 |
| ..... | F................. | .................. | ...NDR | ..AKG...AV.. | A..A........ | 0.13 | 16 |
| ..... | F................. | .V........F....... | ...... | ............ | .AHTG...RE.A | 0.13 | 16 |
| D...T | F.....D...S..M.T.R | .................. | ...... | ............ | A..A........ | 0.13 | 16 |
| ..... | .................. | .................. | ....G. | ............ | A..A........ | 0.13 | 16 |

TABLE 5-continued

AAV capsid proteins having increased specificity for and/or transduction of CD44+/133+ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| .A... | F.....SA..RA.....R | T.P......DF....... | ...D.. | ........... | A..A........ | 0.13 | 16 |
| ..... | ................. | .QAS.....NF....... | ....GR | ........... | A..A........ | 0.13 | 16 |
| ..... | F................ | .V.......F....... | ...... | ........... | AQQNP..IRG.A | 0.13 | 16 |
| T...T | ................. | ..A......DF....... | ...DG. | EDAGT...AFD. | A..A........ | 0.13 | 16 |
| ..... | ................. | ................. | ...DDR | ........... | A..A........ | 0.13 | 16 |
| ..... | F................ | .V.......F....... | ...... | ........... | EPRGN..IKV.D | 0.13 | 16 |
| ..... | ................. | ................. | ....GR | E.GG.....F.S | A..A........ | 0.13 | 16 |
| E.... | ................. | .QANH....DF....... | R..AD. | ........... | A..A........ | 0.13 | 16 |
| ..... | ................. | .Q.......DF....... | E..KG. | E..G.D.IAF.. | A..A........ | 0.13 | 16 |
| .A... | F.....AAG.S..P...R | T.DNE....NF....... | ...DD. | ..A.EGD.E... | A..A........ | 0.13 | 16 |
| ..... | ................. | ................. | ...DDR | ENGGTA.I..GS | A..A........ | 0.12 | 15 |
| ..... | F................ | .V.......F....... | ...... | ........... | GNRDP..SRE.P | 0.12 | 15 |
| ..... | ................. | ................. | ...ADR | ........... | A..A........ | 0.12 | 15 |
| TA... | F.....AGG.IV.L.G.R | .QAS......F....... | ...... | ........... | TRRTE..FEG.A | 0.12 | 15 |
| E.... | F.....ARG.PQ.N.G.G | ..HG.....NF......T | ...DD. | ........... | A..A........ | 0.12 | 15 |
| .A... | F.....NGG.NN.K.T.R | .V.......F....... | ...... | ........... | A..A........ | 0.12 | 15 |
| ..... | F................ | .V.......F....... | ...... | ........... | GTRTP..VR..T | 0.12 | 15 |
| ..... | ................. | T..NH....NF......T | ....GR | .DAGAN.AEVGE | A..A........ | 0.12 | 15 |
| ..... | ................. | ...SH....DF....... | ...... | E..GGSDIAF.G | A..A........ | 0.12 | 15 |
| SA... | ......SA..RA.....R | .QHNQ.....F......T | ...N.. | ..AGADD.EYDE | A..A........ | 0.12 | 15 |
| ..... | ................. | ................. | ....D. | ES.TED....GR | A..A........ | 0.12 | 15 |
| ..... | F................ | .V.......F....... | ...... | ........... | NRQDG..FSG.T | 0.12 | 15 |
| NT... | ................. | ................. | E..DG. | ........... | A..A........ | 0.11 | 14 |
| .A... | ................. | ................. | E..ND. | ........... | A..A........ | 0.11 | 14 |
| E.... | ................. | ................. | E..ADR | .S.KA..TE.DS | A..A........ | 0.11 | 14 |
| ..... | ................. | ................. | ....GR | E.AAGD.I.V.R | A..A........ | 0.11 | 14 |
| ..... | F................ | .V.......F....... | ...... | ........... | NPRAP..SET.A | 0.11 | 14 |
| ..... | ................. | ................. | E..TG. | ........... | ............ | 0.11 | 14 |
| ..... | ................. | ................. | ....GR | EDAGT..AA..H | A..A........ | 0.11 | 14 |
| GA... | ................. | ................T | E..AD. | ..A.ASDA.V.Q | A..A........ | 0.11 | 14 |
| R.... | F.....NGG.NN.K.T.R | ........NF....... | R...D. | .DTG.GD.A..H | A..A........ | 0.11 | 14 |
| ..... | F................ | .V.......F....... | ...... | ........... | GTQSP..F.S.P | 0.11 | 14 |
| GT..T | ................. | ..A......DF....... | ...DG. | E.AAA..A.FG. | A..A........ | 0.11 | 14 |
| ..... | ................. | ................. | R...DR | ESTN....A..R | A..A........ | 0.11 | 14 |
| TA... | ................. | ................. | ....D. | .D.TGN.I...Q | A..A........ | 0.11 | 14 |
| ..... | F................ | .V.......F....... | ...... | ........... | G.RNP..SSA.H | 0.11 | 14 |

TABLE 5-continued

AAV capsid proteins having increased specificity for and/or transduction of CD44⁺/133⁺ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | .................. | .................. | ...DDR | ED.R.S.A...G | A..A........ | 0.11 | 14 |
| DR... | F.....ATT.IM.T.T.R | .........NF....... | R..ND. | ENAG.ND.E.DH | A..A........ | 0.11 | 14 |
| ..... | .................. | .................. | ...DDR | ES.DRN.....Q | A..A........ | 0.11 | 14 |
| ..... | .................. | .................. | E..NG. | ............ | A..A........ | 0.11 | 14 |
| ..... | .................. | ..........NF....... | ...D.. | E.AAGD.TA..G | A..A........ | 0.11 | 14 |
| TA... | F.....GK..LA.K.N.G | T.PNE....DF....... | R...D. | ............ | A..A........ | 0.11 | 14 |
| R.... | F.....GDG...K.Q.R | TKDDR....DF....... | ...DDR | ..GGA.D.E.GN | A..A........ | 0.11 | 14 |
| ..... | .................. | ..YG.....DF..P...T | R..ND. | ..TGRAD.A.DE | A..A........ | 0.11 | 14 |
| ..... | .................. | .................. | G..TD. | ............ | A..A........ | 0.11 | 14 |
| HT... | .................. | ..HG.....NF......T | ....A. | ............ | A..A........ | 0.11 | 14 |
| EA... | F.....GRT.ND.L.Q.R | .Q.G.....NF......T | E..NG. | .NAGA.D...GS | A..A........ | 0.11 | 14 |
| ..... | .................. | .................. | G..KD. | ............ | A..A........ | 0.11 | 14 |
| ..... | .................. | ................T | R..TG. | ESAN...I...H | A..A........ | 0.11 | 14 |
| ..... | .................. | .................. | R..A.. | ............ | A..A........ | 0.11 | 14 |
| RA..T | F.....GN..HM.P.... | ..DNH....NF....... | R...D. | ............ | A..A........ | 0.11 | 14 |
| ..... | .................. | .........NF......T | ...DDR | ESGGTDDA..DE | A..A........ | 0.10 | 13 |
| ..... | F................. | .V........F....... | ...... | ............ | A..A........ | 0.10 | 13 |
| ..... | .................. | .................. | G..K.. | .SADGSD..... | A..A........ | 0.10 | 13 |
| G.... | .................. | .Q.S......F....... | E..N.. | E.AS.N.IE.GS | A..A........ | 0.10 | 13 |
| GA... | .................. | ..PNH....NF......T | R..DG. | ............ | A..A........ | 0.10 | 13 |
| ..... | .................. | TQDTQ....NF....... | ...... | ............ | A..A........ | 0.10 | 13 |
| R.... | .................. | .................. | ....G. | E.AG...IAVDR | A..A........ | 0.10 | 13 |
| ..... | .................. | ..PGR....DF....... | ...D.. | E.GDGS...F.R | A..A........ | 0.10 | 13 |
| ..... | F................. | .V........F....... | ...... | ............ | NQRTH..NNM.D | 0.10 | 13 |
| ..... | F................. | T..NH....NF......T | ....GR | .DAGAN.AEVDH | A..A........ | 0.10 | 13 |
| G...T | F.....SGT.SQ.K.E.. | .KYT.....NF......T | ...DDR | ............ | ............ | 0.10 | 13 |
| TA... | .................. | ...TE.....F....... | ...NGR | ..AATD.AA.DQ | A..A........ | 0.10 | 13 |
| N.... | F.....GKG.S..M.K.M | .Q.......DF....... | ...AD. | ............ | A..A........ | 0.10 | 13 |
| SA... | .................. | ..DGE....DF....... | ...... | ENASGG.AE.DS | A..A........ | 0.10 | 13 |
| DT... | F.....NKT.HL.T.A.R | ..DGE....DF....... | ...DD. | .SAS.N.IA..E | A..A........ | 0.10 | 13 |
| A.... | F.....NGG.HN.K.G.. | TKDDR....DF....... | ...DDR | EDAGT...AFD. | A..A........ | 0.10 | 13 |
| ..... | F................. | .V........F....... | ...... | ............ | ..SNH..AKE.H | 0.10 | 13 |
| ..... | .................. | ..........F....... | ...... | ............ | TQKSE..FRT.H | 0.10 | 13 |
| A.... | F.....GKA.SE.N...K | T.AG.....NF......T | ...N.. | ............ | A..A........ | 0.10 | 13 |
| TA... | F.....AKG.P..H...G | .Q.S......F....... | E..N.. | ............ | A..A........ | 0.10 | 13 |
| GA..T | F.....ATT.NV.T.K.S | .KDHH.....F....... | R...D. | ..A.AN..AF.D | A..A........ | 0.10 | 13 |

TABLE 5-continued

AAV capsid proteins having increased specificity for and/or transduction of
CD44$^+$/133$^+$ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | ................. | R...D. | E.GAR.D.E.GE | A..A........ | 0.10 | 13 |
| ..... | ................. | ................. | E..... | ............ | GPRTT..VDA.T | 0.10 | 13 |
| ..... | ................. | .Q.DH...NF....... | ...DD. | .SAKAA.AA.DE | A..A........ | 0.10 | 13 |
| ..... | F................ | .V.......F....... | ...... | ............ | GHRAT..ND... | 0.10 | 13 |
| EA... | ................. | ...TE...DF....... | ...... | .NGST.....GG | A..A........ | 0.10 | 13 |
| TA... | ................. | TQPTH...NF....... | R..DD. | .NGG.ND....Q | A..A........ | 0.09 | 12 |
| H.... | F................ | ..AGR.....F......T | ...T.. | ............ | A..A........ | 0.09 | 12 |
| GT... | F.....ST..SV.K.H.M | .........DF....... | ...D.R | .SAKAA.AA.DE | A..A........ | 0.09 | 12 |
| ..... | ................. | ................. | ...DDR | .NGST.....GG | A..A........ | 0.09 | 12 |
| ..... | F................ | .V.......F....... | ...... | ............ | GRRD...VRM.T | 0.09 | 12 |
| ..... | F.....NGT.IL.T.A.K | .QPG.....NF....... | ...DDR | ............ | A..A........ | 0.09 | 12 |
| ..... | F.....GRG.H..P.E.R | .QPTG....NF....... | E..TG. | ............ | A..A........ | 0.09 | 12 |
| ..... | ................. | ................. | ...DDR | ...NAND.AY.G | A..A........ | 0.09 | 12 |
| ..... | ................. | ................. | ...DDR | ..ATG..I.F.R | A..A........ | 0.09 | 12 |
| ..... | ................. | ..DDG....NF..P.... | R..DD. | EN...A..EVGE | A..A........ | 0.09 | 12 |
| ..... | ..........A.N...R | .KYT.....NF......T | R...D. | ...G.D..EVGQ | A..A........ | 0.09 | 12 |
| ..... | ................. | ................. | ...DG. | .SAS.N.I..GD | A..A........ | 0.09 | 12 |
| ..... | F.....DKA.H..P.H.G | .QPSQ....DF....... | ....D. | .........D. | A..A........ | 0.09 | 12 |
| ..... | ................. | .........DF....... | ...DDR | ...T.G..A..Q | A..A........ | 0.09 | 12 |
| DA... | F.....AST.HD.T.E.R | T.PGG....NF....... | ...DDR | ESAKTSDAAVDD | A..A........ | 0.09 | 12 |
| ..... | F................ | .V.......F....... | ...... | ............ | SRQNG..F.A.T | 0.09 | 12 |
| R.... | ................. | ..AGR....DF......T | R..D.. | .D......... | A..A........ | 0.09 | 12 |
| ..... | F................ | .........NF....... | R...D. | E..G.A..A.D. | A..A........ | 0.09 | 12 |
| S.... | F.....AGT..M.K.Q.G | .PPNG.....F......T | ...DDR | ............ | A..A........ | 0.09 | 12 |
| GT... | F.....NKT.HL.T.A.R | .V.......F....... | ...... | ............ | A..A........ | 0.09 | 12 |
| ..... | ................. | ...TG....NF......T | R..DD. | ............ | A..A........ | 0.09 | 12 |
| RA... | F.....NGG.NN.K.T.R | TKPSG....DF....... | ...D.. | .DARGND.EFGE | A..A........ | 0.09 | 12 |
| ..... | ................. | ................. | R..DD. | ..TENSD..... | A..A........ | 0.09 | 12 |
| .A... | ................. | TQASG.....F....... | ...DDR | ESG..N.I..DG | A..A........ | 0.09 | 12 |
| ..... | ................. | ................. | ...DDR | EDAG...I..GQ | A..A........ | 0.09 | 12 |
| ..... | ................. | ................. | ...DGR | ...TG..T..GQ | A..A........ | 0.09 | 11 |
| ..... | ................. | ................. | ....D. | ENTATDD...GH | A..A........ | 0.09 | 11 |
| ..... | ................. | .........DF..P...T | ...AD. | ............ | A..A........ | 0.09 | 11 |
| ..... | ................. | ................. | ...... | ............ | GRRDP..DRI.P | 0.09 | 11 |
| ....T | ................. | ................. | G..K. | .SADGSD...DR | A..A........ | 0.09 | 11 |
| .A... | F.....DHT.R..M.G.R | ................. | ...... | ............ | A..A........ | 0.09 | 11 |

TABLE 5-continued

AAV capsid proteins having increased specificity for and/or transduction of
CD44+/133+ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | ................. | .KYT.....NF......T | ...ND. | ED.R.S.A...G | A..A........ | 0.09 | 11 |
| ..... | ................. | TQYT.....NF......T | ...D.. | ............ | A..A........ | 0.09 | 11 |
| .A... | F......GT.NM.L.Q.G | .Q.S......F....... | ...... | ............ | SR.DR..FNG.T | 0.09 | 11 |
| DA... | F................. | .V........F....... | ...... | ............ | A.RAG..STI.H | 0.09 | 11 |
| GA... | F......S..PM.T.S.K | ..HG.....NF......T | ...A.. | ..AGAN...FGE | A..A........ | 0.09 | 11 |
| AA... | F.....DKG.HM.L.G.R | TKDDR....DF....... | ...DDR | ...TG.D.AY.G | A..A........ | 0.09 | 11 |
| ..... | F....AGA.NK.L...K | TQASG............ | ...DDR | ED.R.S.A...G | A..A........ | 0.09 | 11 |
| NA... | ......AT...N.T...G | .QPG.....NF....... | ...... | EDGSG.DI.F.G | A..A........ | 0.09 | 11 |
| SA... | ......NQG....P.K.I | .Q.DR.....F....... | ....D. | ESGG.GDA.F.G | A..A........ | 0.09 | 11 |
| ..... | ................. | ..YN......F......T | R...G. | E.GSTSDAEFDQ | A..A........ | 0.09 | 11 |
| ..... | ................. | ................. | ...T.. | .SAKAA.AA.DE | A..A........ | 0.09 | 11 |
| ..... | ................. | ................. | ...... | .NGR..DAEV.H | A..A........ | 0.09 | 11 |
| NT... | ................. | .KYT.....DF....... | ...... | EN.KGGD.AFDN | A..A........ | 0.09 | 11 |
| ..... | ................. | ................. | R..ND. | .N.GA.D.A.GG | A..A........ | 0.09 | 11 |
| A.... | F.....G...I..M.A.G | ................. | ....GR | E.AGGN..E.DD | A..A........ | 0.09 | 11 |
| ..... | ................. | ................. | G..DD. | E.AG...TAVGN | A..A........ | 0.09 | 11 |
| A.... | ................. | ................. | E..TGR | ............ | A..A........ | 0.09 | 11 |
| NT..T | F......G..HP.T.Q.R | TKDT.....NF....... | R...D. | ..GGA.D.E.GN | A..A........ | 0.09 | 11 |
| NA... | ................. | TQADR....NF......T | G..ND. | ............ | A..A........ | 0.09 | 11 |
| ..... | ................. | T.AG.....NF......T | ...... | .D.GGGD.EVDE | A..A........ | 0.09 | 11 |
| HT..T | F.....NGG.NV.N.K.G | .........NF....... | R...D. | ............ | A..A........ | 0.09 | 11 |
| ..... | ................. | ................. | E..A.. | ............ | A..A........ | 0.09 | 11 |
| ..... | F................. | .V........F....... | ...... | ............ | GASNG..VDI.H | 0.09 | 11 |
| ..... | F.....DTG.SK.T.T.R | .Q.DR.....F....... | ....D. | ............ | A..A........ | 0.09 | 11 |
| DA..T | F.....AGT.RD.M.A.L | ..HG.....NF......T | ...A.. | ............ | A..A........ | 0.09 | 11 |
| ..... | ................. | .V........F....... | ...... | ............ | TDRAG..ST..Q | 0.09 | 11 |
| EA..T | F.....ANG.HL.K.K.S | ..DGE....DF....... | ...D.. | ............ | A..A........ | 0.08 | 10 |
| RA... | F.....DTA.N....E.R | T.P......DF....... | ...DDR | ..GGGS..A.DG | ............ | 0.08 | 10 |
| ..... | F................. | .V........F....... | ...... | ............ | ADRSG..ISV.Q | 0.08 | 10 |
| ..... | ................. | ................. | ...DDR | E.GG.....FD. | A..A........ | 0.08 | 10 |
| ST... | ................. | T.AT.....NF......T | ...DG. | E.TG.GD.A.GE | A..A........ | 0.08 | 10 |
| TA..T | F.....SKT.NE.P...M | .QHNQ....NF......T | ....GR | .NAGA.D.AFDE | A..A........ | 0.08 | 10 |
| ..... | ................. | ................. | ...DDR | EDAGGN.I.VDR | A..A........ | 0.08 | 10 |
| ..... | ................. | .........NF....... | G..TDR | E.AGGN..E.DD | A..A........ | 0.08 | 10 |
| TA..T | F.....ATG.S...P.... | .V........F....... | ...... | EDAGGS.AEYD. | A..A........ | 0.08 | 10 |
| ..... | ................. | ................. | ...... | .NGSAS..A.DN | A..A........ | 0.08 | 10 |

TABLE 5-continued

AAV capsid proteins having increased specificity for and/or transduction of CD44⁺/133⁺ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F..........K.M.Q.N | ..DGE....DF....... | ...... | ........... | ........... | 0.08 | 10 |
| G.... | ................. | .QDT.....DF....... | G..DG. | ........... | ........... | 0.08 | 10 |
| ..... | ................. | ................. | ...DDR | ENATAGDAA.GD | A..A........ | 0.08 | 10 |
| E.... | F................ | ................T | G..D.R | ........... | A..A........ | 0.08 | 10 |
| ..... | F.....SG..IK.K.D.R | ................. | ...... | EDAGAND.AV.H | A..A........ | 0.08 | 10 |
| ..... | F................ | .V.......F....... | ...... | ........... | GNRTP..NQV.Q | 0.08 | 10 |
| ..... | ................. | ................. | R..DDR | ..AA.D.IA... | A..A........ | 0.08 | 10 |
| ....T | ................. | ................. | G..TDR | E.AGGN..E.DS | ........... | 0.08 | 10 |
| ..... | ................. | ..........NF | ...D.. | .DASGS....GG | A..A........ | 0.08 | 10 |
| ..... | F................ | .V.......F....... | ...... | ........... | DRQGN..IGV.. | 0.08 | 10 |
| ..... | ................. | ................. | ...A.. | ........... | A..A........ | 0.08 | 10 |
| ..... | ................. | ..DGE....DF....... | ...... | E........... | A..A........ | 0.08 | 10 |
| EA... | ................. | ..........NF | R...D. | .NGRTGDA.V.Q | A..A........ | 0.08 | 10 |
| ..... | F................ | .V.......F....... | ...... | ........... | GQRD...AQT.Q | 0.08 | 10 |
| ..... | F................ | .V.......F....... | ...... | ........... | T.RNP..VKE.Q | 0.08 | 10 |
| TA..T | F.....NGG.IM.L.E.R | T.P......DF....... | ....D. | ........... | ........... | 0.08 | 10 |
| ..... | ................. | ..........DF | ...... | ..ATAA..AVDN | A..A........ | 0.08 | 10 |
| TA... | ................. | .KDSR....DF....... | R..DD. | ..AAE.D....N | A..A........ | 0.08 | 10 |
| DT... | ................. | ................. | E..ND. | ........... | ........... | 0.08 | 10 |
| ..... | ................. | ................. | ...D.. | ........... | A..A........ | 0.08 | 10 |
| ..... | ................L | .QAS......F....... | R..ND. | ........... | A..A........ | 0.08 | 10 |
| GA... | F.....SGT.S..T.T.. | .KYT.....NF......T | R..AGR | ........... | A..A........ | 0.08 | 10 |
| TT... | F.....DAA.SA.K.A.R | .PPNG.....F......T | ...DDR | ........... | A..A........ | 0.08 | 10 |
| ..... | ................. | .Q.GQ....DF....... | R..TDR | .DAG.S.A..DR | A..A........ | 0.08 | 10 |
| ..... | ................. | ................. | ...N.. | ........... | A..A........ | 0.08 | 10 |
| GT... | F.....AEG.LK.M.H.L | ..DGE....DF....... | ...... | ........... | ........... | 0.08 | 10 |
| ..... | F................ | .V.......F....... | ...... | ........... | ERRNP..F.T.T | 0.08 | 10 |
| G.... | ................. | .QYT.....NF......T | R...D. | ENGGAAD.A..N | A..A........ | 0.08 | 10 |
| ..... | F.....DQ..R..P.S.R | .QD.E....F..P.... | ...... | E.GKGSD...GG | A..A........ | 0.08 | 10 |
| ..... | ................. | TQASG....NF....... | ....D. | E.AS...IEYGQ | A..A........ | 0.08 | 10 |
| AA... | F.....SGT.NM.K.T.E | ..HG.....NF......T | R..DD. | .SAKAA.AA.DE | A..A........ | 0.08 | 10 |
| TT..T | ................. | .QHNQ.....F | ...... | ........... | A..A........ | 0.08 | 10 |
| R.... | F.....ATG.NN.I.S.G | .AGR....DF......T | R..D.. | ........... | A..A........ | 0.08 | 10 |
| D.... | F.....DKG..L.N...R | .Q.DR........... | ...DDR | ........... | A..A........ | 0.08 | 10 |
| DT... | F.....NGT.HN.K.G.K | .PDR.....F......T | ...... | .DAGGND.A.D | A..A........ | 0.08 | 10 |
| SA... | F.....AEG.LK.M.H.L | ..DGE....DF....... | ...... | ........... | ........... | 0.08 | 10 |

TABLE 5-continued

AAV capsid proteins having increased specificity for and/or transduction of CD44+/133+ GSC (pool of Round 1 selection). Amino acid numbers correspond to the amino acid sequence of VP1 (SEQ ID NO: 1). Sequences below correspond to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| EA... | .................. | .K.TG....DF....... | R...DR | .STREGD....N | A..A........ | 0.08 | 10 |
| SA... | F................. | .V.......F....... | ...... | ............ | GRRDP..DTI.P | 0.07 | 9 |
| ..... | .................. | ..YNR....NF....... | ...D.. | E.AGAND.AY.N | A..A........ | 0.07 | 9 |
| AA..T | F.....DKG.SH.T.K.V | .................. | ...... | ............ | A..A........ | 0.07 | 9 |
| E.... | .................. | ..HG.....NF......T | E..DD. | ............ | A..A........ | 0.07 | 9 |
| ..... | F................. | ..HG.....NF......T | ...A. | ............ | A..A........ | 0.07 | 9 |
| ..... | .................. | .V.......F....... | ...... | ............ | NP.NA..FRI.T | 0.07 | 9 |
| T.... | F.....G.G.HA.T.G.R | .........DF....... | ...... | .S.KA..TE.DS | A..A........ | 0.07 | 9 |
| ..... | F................. | .V.......F....... | ...... | ............ | GT.TS..DQ..T | 0.07 | 9 |
| NA..T | F.....GRG.H..P.E.R | .........F....... | ...... | .SASRND.AVGE | A..A........ | 0.07 | 9 |
| ..... | .................. | .................. | ...DDR | E..G.SDAA.GD | A..A........ | 0.07 | 9 |
| ..... | .................. | .................. | ...NGR | ............ | A..A........ | 0.07 | 9 |
| TT... | .................. | TQ.TG....DF....... | ...DDR | ............ | A..A........ | 0.07 | 9 |
| A...T | F......KT.NV.K...S | .................. | ...... | ............ | A..A........ | 0.07 | 9 |
| ..... | .................. | .................. | R..N.. | ..G..AD.A.DE | A..A........ | 0.07 | 9 |
| AT... | .................. | .........NF....... | R...D. | .NGST.....GG | A..A........ | 0.07 | 9 |
| ..... | .................. | .KPDQ.....F....... | R...D. | .DANRN..E.GQ | A..A........ | 0.07 | 9 |
| E.... | F.....NG..SN.M...K | ..DGE....NF....... | ...... | .N.G.N.I.V.G | A..A........ | 0.07 | 9 |
| ..... | .................. | .................. | ...DD. | .........K. | A..A........ | 0.07 | 9 |
| .A... | .................. | ..HG.....NF......T | E..DD. | ............ | ............ | 0.07 | 9 |
| ..... | .................. | .................. | R..D.. | ............ | A..A........ | 0.07 | 9 |
| ..... | .................. | .................. | ...DDR | ESAGE.DAA.DE | A..A........ | 0.07 | 9 |
| ..... | .................. | ..HG.....NF......T | E..DD. | ............ | ............ | 0.07 | 9 |
| ..... | F.....GNG.HV.H.G.R | ........DF....... | ...... | ............ | ............ | 0.07 | 9 |
| A.... | ..........A.N...R | .KYT.....NF......T | R...D. | ...G.D..EVGQ | A..A........ | 0.07 | 9 |
| .A... | F.....GKT.SL...... | .V............... | ...DDR | E.AG..D.A.DG | A..A........ | 0.07 | 9 |
| ..... | F................. | .V.......F....... | ...... | ............ | EPHAG..DNT.H | 0.07 | 9 |
| ..... | F................. | .V.......F....... | ...... | ............ | DKQGT..FRA.. | 0.07 | 9 |
| G.... | F.....SGG.RV.P...G | .QPTG....NF....... | ...... | ............ | ............ | 0.07 | 9 |
| AT..T | F.....NR..SP.T.N.G | .Q.G.....F....... | G..N.. | ............ | A..A........ | 0.07 | 9 |
| SA..T | ......AHT.LK.N...G | T.P......DF....... | ....GR | .DAGA.D.AV.E | A..A........ | 0.07 | 9 |
| ..... | .................. | .................. | ...... | ENGKAGD...GN | A..A........ | 0.07 | 9 |
| RA... | F.....AEG.LK.M.H.L | ..DGE....DF....... | ...... | ............ | ............ | 0.07 | 9 |
| ..... | F................. | .V.......F....... | ...... | ............ | KDRTH..FDM.. | 0.07 | 9 |
| ..... | .................. | .................. | R..ND. | E.TGT.DAAVDD | A..A........ | 0.07 | 9 |
| AA... | F.....AGA.SL.....R | .QP.G.....F....... | R...D. | ...AAS.A.VGQ | A..A........ | 0.07 | 9 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | ................. | ...AGR | .NA.RA.T..G. | A..A........ | 0.07 | 9 |
| ..... | ................. | ................. | ...A.. | ..GG.N.I..DR | A..A........ | 0.07 | 9 |
| ..... | ................. | ................. | R..AD. | ........... | A..A........ | 0.07 | 9 |
| GT... | F.....DQ..R..P.S.R | .QD.E.....F..P.... | ...... | E.GKGSD...GG | ........... | 0.07 | 9 |
| .A... | F......GT.NM.L.Q.G | .Q.S......F...... | ....D. | ........... | ........... | 0.07 | 9 |
| A.... | ................. | .........NF....... | R...D. | ..AK.ADT..GN | A..A........ | 0.07 | 9 |
| T.... | ................. | ..AGR....DF......T | R..D.. | E..RRD.AA..H | A..A........ | 0.07 | 9 |
| ..... | F.....AGA.NK.L...K | TQ.TG....DF....... | ...DDR | ........... | A..A........ | 0.07 | 9 |
| ..... | ................. | ................. | ...A.. | E.AS.N.IA..E | A..A........ | 0.07 | 9 |
| R.... | ................. | ..HG.....NF......T | ...A.. | ........... | A..A........ | 0.07 | 9 |
| ..... | ................. | ................. | ...D.. | E.ASTSD.AFDS | A..A........ | 0.07 | 9 |
| SA... | ................. | .........NF....... | ...TG. | E.AGGS..AVDG | A..A........ | 0.07 | 9 |
| ..... | ................. | ................. | ...D.R | ........... | ........... | 0.06 | 8 |
| DT... | F.....ARG.LV.N.Q.S | .........NF......T | R..D.R | E.AA.A....GD | A..A........ | 0.06 | 8 |
| RT... | F.....SGT.SQ.K.D.. | ..PN.....NF....... | ...NDR | ........... | A..A........ | 0.06 | 8 |
| ..... | F............... | .V.......F....... | ...... | ........... | NSRAT..S.G.H | 0.06 | 8 |
| ..... | ................. | .........F......T | ...DDR | ENTSENDIE.DR | A..A........ | 0.06 | 8 |
| ..... | ................. | ................. | R..TGR | ........... | A..A........ | 0.06 | 8 |
| .A... | F.........A.M.K.H | .QPG.....NF....... | ...DDR | E.ANG...E.G. | A..A........ | 0.06 | 8 |
| ..... | F............... | .V.......F....... | ...... | ........... | NHKGG....V.T | 0.06 | 8 |
| ..... | F.....NGG.NI.K.E.R | ..DGE....DF....... | ...... | ESTDGG..A.DS | A..A........ | 0.06 | 8 |
| ..... | ................. | ................. | ...... | .D.RTSDA.F.S | A..A........ | 0.06 | 8 |
| NA..T | ................. | ..YN......F......T | ...D.R | ........... | A..A........ | 0.06 | 8 |
| ..... | F.....ST..SV.K.H.M | TQ.TG....DF....... | ...DDR | E..AAS....GG | A..A........ | 0.06 | 8 |
| TA... | ................. | ................. | R..D.. | ........... | A..A........ | 0.06 | 8 |
| ..... | ................. | ................. | ...DDR | ..TTGA.I.FDG | A..A........ | 0.06 | 8 |
| D...T | F......GT.NM.L.Q.G | .........NF......T | ....D. | .SASEN....GR | A..A........ | 0.06 | 8 |
| ..... | ................. | .V.......F....... | ...... | ........... | G.RSG..FTG.. | 0.06 | 8 |
| ..... | ................. | .........F......T | R..DD. | ESGG.S.AA.GQ | A..A........ | 0.06 | 8 |
| ..... | ......GTG.P....K.. | ...NG.....F....... | R..DD. | E.AG...IAVDR | A..A........ | 0.06 | 8 |
| ..... | ................. | ................. | ....GR | .NA.AN..A.GE | A..A........ | 0.06 | 8 |
| ..... | F............... | .V.......F....... | ...... | ........... | SQRDK..FES.T | 0.06 | 8 |
| G.... | F.....G.G.RA.N.E.R | .KYT.....NF......T | ...DD. | ........... | A..A........ | 0.06 | 8 |
| TA... | ................. | .QANH....DF....... | ...DDR | ........... | ........... | 0.06 | 8 |
| .A... | F.....GNG.HV.H.G.R | .KDDG....NF......T | G..NG. | E.AAAN..E.DG | A..A........ | 0.06 | 8 |
| ..... | F............... | .V.......F....... | ...... | ........... | E.KTK..SSM.D | 0.06 | 8 |

TABLE 5-continued

AAV capsid proteins having increased specificity for and/or transduction of
CD44+/133+ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................. | .KYT.....NF......T | ...DDR | ........... | ........... | 0.06 | 8 |
| ..... | F.....NNG.LN.I.G.R | TQ.TG....DF....... | ...DDR | ES.SGNDIE.DQ | A..A........ | 0.06 | 8 |
| AT..T | F.....ARA.L..L.Q.G | .Q.DR.....F....... | ....D. | ........... | A..A........ | 0.06 | 8 |
| ..... | F................. | .V.......F....... | ...... | ........... | KA.TA..NST.T | 0.06 | 8 |
| TA... | F.....NS..HP.H.G.K | T.P......DF....... | ...D.. | ..NG.RGD..DG | A..A........ | 0.06 | 8 |
| AT... | .......GT.NM.L.Q.G | .Q.S......F....... | ....D. | ........... | ........... | 0.06 | 8 |
| ET... | F.....DAG.PN.L...H | T.P......DF....... | ...D.. | ........... | ........... | 0.06 | 8 |
| EA... | ................. | ................. | ....D. | ..ASE...E.D. | A..A........ | 0.06 | 8 |
| ..... | F.....DRG.N..I.A.K | .KYT.....NF......T | R..D.. | ........... | A..A........ | 0.06 | 8 |
| ..... | ................. | ..P.G............ | R...D. | ...NG....VDG | A..A........ | 0.06 | 8 |
| H.... | F................. | ................. | ...DDR | E.......... | A..A........ | 0.06 | 8 |
| ..... | ................. | ................. | R...G. | E.AR...I..DE | A..A........ | 0.06 | 8 |
| ..... | ................. | ..DGE....DF....... | ...... | .NG..G.I...G | A..A........ | 0.06 | 8 |
| GA... | F.....NG..IQ.M.N.R | ..A......DF....... | ...DG. | E.GR.DD.E.GE | A..A........ | 0.06 | 8 |
| .A... | F.......G.PE.T.G.R | ................. | G..AD. | ...G.SDI.FDE | A..A........ | 0.06 | 8 |
| ..... | ................. | ..YN......F......T | ...... | EDANG...EVDR | A..A........ | 0.06 | 8 |
| G.... | F.....SA..RA....F | ..HNH.....F......T | ...DD. | ESGTAND...DR | A..A........ | 0.06 | 8 |
| EA... | F.......G.N..T.P.L | TQ.TG....DF....... | ...DDR | ........... | A..A........ | 0.06 | 8 |
| ..... | ................. | .............P.... | E..KG. | ........... | ........... | 0.06 | 8 |
| ..... | ................. | ................. | ...AGR | ........... | A..A........ | 0.06 | 8 |
| ..... | ................. | ................. | R..ND. | ..ATRN.A.FDR | A..A........ | 0.06 | 8 |
| TA..T | F.....DE.....N...G | .QD.E....DF......T | ...... | .D..GA..EVGD | A..A........ | 0.06 | 8 |
| ..... | ................. | .V.......F....... | ...... | .N.G.G..A.DR | A..A........ | 0.06 | 8 |
| ..... | ................. | ................. | R..AD. | .SAS.N.IA..E | A..A........ | 0.06 | 8 |
| .A... | F......GT.NM.L.Q.G | ................. | ....D. | ........... | ........... | 0.06 | 8 |
| RA... | ................. | TQPTH....NF........ | R..DD. | ........... | A..A........ | 0.05 | 7 |
| NA..T | ................. | .........DF....... | ...AD. | ........... | A..A........ | 0.05 | 7 |
| ..... | ................. | ................. | ...D.. | ........... | TQKSE..FRT.H | 0.05 | 7 |
| ..... | ................. | TQYDR....NF....... | ...DDR | E..G.SDAA.GD | A..A........ | 0.05 | 7 |
| ..... | ................. | .........DF....... | ...AG. | .S.RGN...... | A..A........ | 0.05 | 7 |
| EA... | F.....DTG.SK.T.T.R | .Q.S......F....... | ...D.. | .NGR.G..A..E | A..A........ | 0.05 | 7 |
| S.... | F......KT.NV.K.T.H | T.P......DF....... | ...D.. | EDAA...AAVDQ | A..A........ | 0.05 | 7 |
| ..... | ................. | ................. | E..N.. | ..TK...AE..D | ........... | 0.05 | 7 |
| AT... | F.....ATA.RN.T.A.G | ................. | ...... | ........... | A..A........ | 0.05 | 7 |
| ..... | F.....DRG.S...T.A.A | ..DGE....DF....... | ...... | ........... | ........... | 0.05 | 7 |
| GT... | F.....SK..PA.K.A.G | .Q.DR.....F....... | ....D. | ........... | A..A........ | 0.05 | 7 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| NT..T | F.....DTG.SK.T.T.R | .QPTG.....F....... | ...NGR | ........... | A..A........ | 0.05 | 7 |
| ..... | F................. | .V.......F....... | ...... | ..SGGES.....R | ETKTR..Y.A.. | 0.05 | 7 |
| A.... | ................. | ................. | ...... | ESATRG.....R | A..A........ | 0.05 | 7 |
| ..... | F.....G.G.NQ.I.K.N | ..DGE....DF....... | ...... | ........... | A..A........ | 0.05 | 7 |
| ..... | F.....DAG.SA...... | ................. | ...N.. | E..G.SD.AYDE | A..A........ | 0.05 | 7 |
| HA... | F.....DRA.PK...P.R | ................T | ...... | ...A.SD.A.DE | A..A........ | 0.05 | 7 |
| ..... | ................. | ................. | ....GR | ........... | ........... | 0.05 | 7 |
| ..... | F................. | .V.......F....... | ...... | ........... | G..AG..VKG.Q | 0.05 | 7 |
| ..... | ................. | ................. | ...K.. | .SADGSD...DR | A..A........ | 0.05 | 7 |
| ..... | F................. | ................. | ...... | .D......... | A..A........ | 0.05 | 7 |
| ..... | F................. | .V.......F....... | ...... | ........... | DARGT..SDG.A | 0.05 | 7 |
| ..... | F.....SG..IK.K.D.R | .Q.S.....F....... | E..ND. | ...R.G.....E | A..A........ | 0.05 | 7 |
| ..... | ................. | ..AGR.....F......T | G..ND. | ........... | A..A........ | 0.05 | 7 |
| ..... | ................. | .......DF....... | ...... | ..AGRNDIA.GQ | A..A........ | 0.05 | 7 |
| ..... | ................. | .......NF....... | ...DG. | ED.GG...E.GR | A..A........ | 0.05 | 7 |
| ..... | ................. | .K.TG....DF....... | R...DR | ........... | A..A........ | 0.05 | 7 |
| GT... | F.....DRT.H..I.K.R | .V.......F....... | ...... | ........... | A..A........ | 0.05 | 7 |
| G.... | F.....SN..I..L.G.G | .Q.GQ....DF....... | ....G. | ........... | A..A........ | 0.05 | 7 |
| ..... | F................. | .V.......F....... | ...... | .N.ARSDI...G | A..A........ | 0.05 | 7 |
| G...T | ................. | .Q.GQ....DF....... | ....G. | EDAGRN...V.N | A..A........ | 0.05 | 7 |
| ..... | ................. | ................. | ...DG. | ........... | GTRDG..VN..T | 0.05 | 7 |
| AT... | F.......G.N..T.P.L | ..DGE....DF....... | ...... | ...A.SD.EVGG | ........... | 0.05 | 7 |
| DA... | F.......G.N..T.P.L | .......NF....... | R...D. | ........... | A..A........ | 0.05 | 7 |
| ..... | F.....GRT..L.H.E.S | .Q.NE....DF...... | ...ND. | ........... | A..A........ | 0.05 | 7 |
| GA... | F.....ST..SV.K.H.M | TQTPE....DF....... | G..ND. | ........... | ........... | 0.05 | 7 |
| DA... | F......AT..D.H.G.L | .K.DQ....DF....... | E..NDR | ........... | A..A........ | 0.05 | 7 |
| ..... | F.....SGT.SQ.K.... | .KYT.....NF......T | ...ND. | ........... | A..A........ | 0.05 | 7 |
| ..... | ................. | ................. | R..AGR | E.T..S..A..R | A..A........ | 0.05 | 7 |
| ..... | ................. | ................T | ...D.. | ESGGES...V.H | A..A........ | 0.05 | 7 |
| ..... | ................. | .QP.G.....F....... | R...D. | E.ANGA.IE.GD | A..A........ | 0.05 | 7 |
| ..... | ................. | ................. | E..ND. | ........... | ........... | 0.05 | 7 |
| ..... | ................. | TQP.R....NF......T | ...D.. | ........... | A..A........ | 0.05 | 7 |
| ..... | F.....NS..RI.T.N.R | .HG......F......T | ...DDR | .DTAG.D.A.DG | A..A........ | 0.05 | 7 |
| D...T | F......GG.NA.H.Q.R | ................. | ....GR | ..ATAN.TEF.H | A..A........ | 0.05 | 7 |
| AA... | ................. | ................. | ....D. | E.AGAND.AY.N | ........... | 0.05 | 7 |
| HA... | F.....ANG.HL.K.K.S | T.PTG....DF....... | ...DDR | .SAS.N.IA..E | A..A........ | 0.05 | 7 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | ................ | ................ | ....D. | ESAGAN.....E | A..A........ | 0.05 | 7 |
| D.... | F.....SRA.SK.N.A.H | ................ | ...... | ........... | A..A........ | 0.05 | 7 |
| ..... | ................ | ................ | R..AGR | .SAKAA.AA.DE | A..A........ | 0.05 | 7 |
| ..... | F............... | .V.......F....... | ...... | ........... | AQRT...YGT.. | 0.05 | 7 |
| ..... | ................ | .KYT.....NF......T | ....G. | ...AGS.IAFDG | A..A........ | 0.05 | 7 |
| ..... | F............... | .V.......F....... | ...... | ........... | ASRTG..FQG.H | 0.05 | 7 |
| SA... | F.....SN..PL.K.T.. | .Q.DR....NF....... | E..N.. | ........... | A..A........ | 0.05 | 7 |
| ..... | ................ | ................ | R..DD. | EN.KAN....GG | A..A........ | 0.05 | 7 |
| ..... | F............... | .V.......F....... | ...... | ........... | SASTT..VTE.K | 0.05 | 6 |
| G.... | F.....DS..NH.I.P.R | ..PNG....DF....... | ....DR | ESAREN.AE.DE | A..A........ | 0.05 | 6 |
| ..... | F.....DAA.IK.T.Q.N | ..DGE....DF....... | ...... | E.......... | ............ | 0.05 | 6 |
| AA... | ................ | TYQT.....NF......T | ...DDR | E.T..S..A..R | A..A........ | 0.05 | 6 |
| ..... | F............... | .V.......F....... | ...... | ........... | GHRTP..IDG.A | 0.05 | 6 |
| ..... | ......G.T.II.P.D.R | .........NF....... | R...D. | ........... | A..A........ | 0.05 | 6 |
| NA... | F.....SA..RA.....R | .V.......F....... | ...... | .SAN..DA..DN | A..A........ | 0.05 | 6 |
| TA..T | ................ | ................ | ....D. | .DTAA...EF.G | A..A........ | 0.05 | 6 |
| DT... | F.....D...S..M.T.R | TQ.TG....DF....... | ...DDR | ES.SGNDIE.DQ | A..A........ | 0.05 | 6 |
| ..... | F.....ATG.NN.I.S.G | .KDSR....DF....... | ...DDR | ........... | A..A........ | 0.05 | 6 |
| ..... | F............... | ................ | ...... | ........... | GRRDP..DTI.P | 0.05 | 6 |
| ..... | .............H.S.V | ..YN......F......T | ...D.R | ........... | ............ | 0.05 | 6 |
| NA... | F......Q..IE....R | ..P.E....NF......T | E..NDR | .NAGRDD.A..E | A..A........ | 0.05 | 6 |
| ..... | ................ | ................ | ...... | E.AG.S...... | A..A........ | 0.05 | 6 |
| EA... | ................ | .V.......F....... | ...... | .N.G.G..A.DR | A..A........ | 0.05 | 6 |
| GA... | ................ | ..PNG....DF...... | G..NDR | ES.GGD.I.VDE | A..A........ | 0.05 | 6 |
| EA... | F.....DAA.IK.T.Q.N | ..DGE....DF....... | ...... | E.......... | ............ | 0.05 | 6 |
| ..... | ................ | ..HG.....NF......T | ...A.. | ........... | A..A........ | 0.05 | 6 |
| G.... | F.....SG..IK.K.D.R | T.P......DF....... | G..K.. | ........... | A..A........ | 0.05 | 6 |
| ..... | ................ | .........NF....... | ...DDR | ESAGTSD..FDR | A..A........ | 0.05 | 6 |
| ..... | ................ | ....E....DF....... | T..AGR | E.ATA.DTAV.D | A..A........ | 0.05 | 6 |
| ..... | ................ | TQ.TG....DF....... | ...DDR | E.GD.SD..V.H | A..A........ | 0.05 | 6 |
| ..... | ................ | ................ | E..KG. | ........... | ............ | 0.05 | 6 |
| AA... | ................ | ................ | ....D. | E.AGAND.AY.N | A..A........ | 0.05 | 6 |
| ..... | ................ | ................ | E..AD. | ........... | A..A........ | 0.05 | 6 |
| ..... | ................ | ................ | R...D. | E.AR.S..EVGE | A..A........ | 0.05 | 6 |
| ..... | ................ | ................ | R...D. | EDGK.A..EVGQ | A..A........ | 0.05 | 6 |
| R...T | ................ | T.P......DF....... | R..AD. | ENGKT.D.AFDQ | A..A........ | 0.05 | 6 |

TABLE 5-continued

AAV capsid proteins having increased specificity for and/or transduction of
CD44+/133+ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....AS..LE.M.T.R | ..DGE....DF....... | R..ND. | EDAGGSDA.V.Q | A..A........ | 0.05 | 6 |
| ..... | .................. | .Q.......DF....... | ...DDR | ............ | A..A........ | 0.05 | 6 |
| SA... | F.....SN...P.H.T.K | TQPNH....DF....... | ...... | EN.G.A.....Q | A..A........ | 0.05 | 6 |
| DA... | F.....DR..LE.K...R | ..DGE....DF....... | ...... | ............ | A..A........ | 0.05 | 6 |
| ..... | .......GT.NM.L.Q.G | .Q.S......F....... | ....D. | ............ | ............ | 0.05 | 6 |
| R.... | .................. | TKDDR....DF....... | ...DDR | ............ | A..A........ | 0.05 | 6 |
| ..... | .................. | .................. | ...D.R | ES.DGN..A.DG | A..A........ | 0.05 | 6 |
| ..... | .................. | T.P......DF....... | ...D.. | .NTSTSD.E.DG | ............ | 0.05 | 6 |
| NT... | F.....ARG.HP.P.T.E | .........DF....... | R..D.. | ............ | A..A........ | 0.05 | 6 |
| G.... | F................. | .V.......F....... | ...... | ............ | GARGG...K..Q | 0.05 | 6 |
| ..... | .................. | .................. | R...D. | E.AG..D.A.GR | A..A........ | 0.05 | 6 |
| ..... | .................. | .................. | R..TG. | ............ | GR.DP..FNN.D | 0.05 | 6 |
| TT... | F.....SNG.RE.L...K | .................. | ...... | ............ | A..A........ | 0.05 | 6 |
| D.... | .................. | .................. | ...N.. | ............ | A..A........ | 0.05 | 6 |
| ..... | .................. | .................. | ...D.R | ...RRND...DR | A..A........ | 0.05 | 6 |
| ..... | F................. | .V.......F....... | ...... | ............ | GPRNA..NSV.D | 0.05 | 6 |
| .T... | F.....GT..I..N.T.G | .KYT.....NF......T | ...... | ............ | A..A........ | 0.05 | 6 |
| TA..T | F......KT.NV.K.T.H | .QPG.....DF......T | ...DG. | ..A.A.D.AFDI | A..A........ | 0.05 | 6 |
| ..... | .........NV...T... | ..PDH....DF....... | ....GR | .DTGAS..A.DR | A..A........ | 0.05 | 6 |
| N.... | .................. | .Q.GQ....DF....... | ....G. | .D.TTA....D. | A..A........ | 0.05 | 6 |
| G.... | .................. | .QPN......F......T | ...N.. | EDTTGA.A..GQ | A..A........ | 0.04 | 5 |
| D...T | F.....AGA.HK.N.G.G | .........NF....... | R...D. | ............ | A..A........ | 0.04 | 5 |
| TA..T | F.....SGA..N...G.R | .Q.S......F....... | E..AD. | E.ATEGD.A... | A..A........ | 0.04 | 5 |
| ..... | .................. | .................. | ...D.R | ENAAEG.I..DR | A..A........ | 0.04 | 5 |
| ..... | .................. | .................. | ...DDR | .SA.GG....DG | A..A........ | 0.04 | 5 |
| N.... | F......GG.NA.I...R | ..YN......F....... | ...... | ............ | GPKGR..DQN.. | 0.04 | 5 |
| EA..T | F.....S.A.N..L...L | .V.......F....... | ...N.. | .SASE.D...DS | A..A........ | 0.04 | 5 |
| DT..T | F......G..NQ.N.D.K | ..YN......F......T | ...D.R | ............ | ............ | 0.04 | 5 |
| ..... | .................. | .................. | ...DD. | ES.A.S..A.D. | A..A........ | 0.04 | 5 |
| R.... | .................. | .Q.DH....NF....... | ...DD. | .SGREGDAE..D | A..A........ | 0.04 | 5 |
| RA... | F.....SK..PA.K.A.G | .Q.DR......F....... | ....D. | ............ | A..A........ | 0.04 | 5 |
| S.... | F.....DTG.PA.L.T.K | ..AGR....DF......T | ....GR | E.AG.SDIA.DG | A..A........ | 0.04 | 5 |
| ..... | .................. | .Q.S......F....... | E..N.. | .DAGGS..EFGG | A..A........ | 0.04 | 5 |
| A...T | F.......T.SV...H.R | T.DNG....DF....... | ...DDR | ...G.S..AFGD | A..A........ | 0.04 | 5 |
| ..... | F.....SK.PA.K.A.G | .Q.DR......F....... | ....D. | ............ | A..A........ | 0.04 | 5 |
| AT... | .................. | .................. | E..TGR | ............ | A..A........ | 0.04 | 5 |

TABLE 5-continued

AAV capsid proteins having increased specificity for and/or transduction of
CD44$^+$/133$^+$ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | F.....ATT..N.L...L | .QPN......F......T | ...DDR | ............ | A..A........ | 0.04 | 5 |
| ..... | ................. | ................. | E..KDR | ............ | ............ | 0.04 | 5 |
| ..... | ................. | ................. | R..N.. | E..K.G..E.DQ | A..A........ | 0.04 | 5 |
| ..... | F.....NGT.IL.T.A.K | T.P......DF....... | ...D.. | ............ | A..A........ | 0.04 | 5 |
| GT... | F................. | ..HG......F...... | ...... | ............ | DRRTT..FT..P | 0.04 | 5 |
| G.... | F.....NGG.NN.K.T.R | .QPG.....NF....... | ...DDR | ..GA.A...V.H | A..A........ | 0.04 | 5 |
| EA... | ................. | ................. | R..AG. | ............ | A..A........ | 0.04 | 5 |
| ..... | ................. | .........NF....... | E...G. | ............ | A..A........ | 0.04 | 5 |
| EA... | F.....ATT.HA.T.T.L | .Q.......DF....... | ...AD. | E.AA.SD.AVGG | A..A........ | 0.04 | 5 |
| SA... | ................. | TK.NE....DF......T | ...D.R | .NAAAN.A.Y.S | A..A........ | 0.04 | 5 |
| TA..T | F......K.....L.G.L | T.AG.....DF....... | ...D.. | ............ | A..A........ | 0.04 | 5 |
| RA... | F................. | .QATR.....F....... | E..DG. | ............ | A..A........ | 0.04 | 5 |
| TT..T | F.....SGG.SH...A.R | ..P.E....NF.....T | R...D. | ............ | A..A........ | 0.04 | 5 |
| ..... | ................. | ................. | R..... | ..TG.A.I..D. | A..A........ | 0.04 | 5 |
| ..... | F................. | ................. | R..AD. | ............ | A..A........ | 0.04 | 5 |
| ..... | ................. | ................. | ...D.. | ...G.D..EVGQ | A..A........ | 0.04 | 5 |
| ..... | F.....G.G.IN.L...V | .........NF....... | ...DDR | ............ | A..A........ | 0.04 | 5 |
| GA..T | F.....STG.LQ.L.D.R | ................. | ...... | ..TGGSDAA.DG | A..A........ | 0.04 | 5 |
| ..... | ................. | TQDS.....NF....... | ...A.. | ............ | A..A........ | 0.04 | 5 |
| D...T | F.....NRT.NM.T.P.G | ..PDG....NF....... | ....DR | .NAT.A.A.FGD | A..A........ | 0.04 | 5 |
| A.... | F................. | ..DGE....DF....... | E..DD. | ............ | A..A........ | 0.04 | 5 |
| RA... | F......AG.RA.....V | ..DGE....DF....... | ...... | ............ | A..A........ | 0.04 | 5 |
| DA... | F.....ST..SV.K.H.M | TQ.TG....DF....... | ...DDR | E..AAS....GG | A..A........ | 0.04 | 5 |
| ..... | ................. | ..HG......F...... | ...... | ............ | GTRGG...K..D | 0.04 | 5 |
| ..... | F.....ARG.SK.L.A.L | .QPN......F......T | ...N.. | ............ | A..A........ | 0.04 | 5 |
| ..... | ................. | ................. | G..DD. | EDAG.AD.E..R | ............ | 0.04 | 5 |
| ..... | F................. | .V.......F....... | ...... | ............ | G.SGN..FQT.. | 0.04 | 5 |
| ..... | F................. | .V.......F....... | ...... | ............ | KKHS...D.M.. | 0.04 | 5 |
| ..... | F................. | .V.......F....... | ...... | ............ | S.RAG..VSE.K | 0.04 | 5 |
| ..... | ................. | ................. | ...D.R | ..ADGN..AFGE | A..A........ | 0.04 | 5 |
| TT..T | ................. | .QAS.....NF......T | E...G. | ..ARGADAE..S | A..A........ | 0.04 | 5 |
| ..... | ................. | ................. | E..AD. | ENASG.....GN | A..A........ | 0.04 | 5 |
| ..... | ................. | ................. | E..KD. | ............ | ............ | 0.04 | 5 |
| ..... | ................. | .V.......F....... | ...... | ............ | TARSA..VDG.A | 0.04 | 5 |
| N.... | ................. | .Q.GQ....DF....... | ...NGR | .DADGND.A.DQ | A..A........ | 0.04 | 5 |
| A.... | ................. | .QDNE....DF......T | ...N.. | .NATG....VGS | A..A........ | 0.04 | 5 |

TABLE 5-continued

AAV capsid proteins having increased specificity for and/or transduction of
CD44+/133+ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| H.... | .................. | ..DGE....DF....... | R...D. | ............ | ............ | 0.04 | 5 |
| RA... | F.....SG..RV.I.G.R | ..DGE....DF....... | .....R | EN.G.SD.A.D. | A..A........ | 0.04 | 5 |
| ..... | .................. | .................. | ....DR | ESGTTA...VGQ | A..A........ | 0.04 | 5 |
| ..... | .................. | .................. | E..NGR | ............ | A..A........ | 0.04 | 5 |
| ..... | .................. | .................. | ...... | ENTN.D.....R | A..A........ | 0.04 | 5 |
| ..... | .................. | .................. | ....D. | ...R.G.....E | A..A........ | 0.04 | 5 |
| ..... | .................. | ..........F....... | R...D. | ............ | .PKAP..DTT.. | 0.04 | 5 |
| ..... | .................. | .................. | ....D. | ES.TTG..A..G | A..A........ | 0.03 | 4 |
| H.... | F................. | .................. | ...DDR | ............ | A..A........ | 0.03 | 4 |
| ..... | .................. | .KYT.....NF......T | ...... | E.GG.....FD. | A..A........ | 0.03 | 4 |
| E...T | ............K.S.S | .QPNQ....NF....... | R...D. | ES.GAN..EVDG | A..A........ | 0.03 | 4 |
| D.... | .................. | .................. | ...DDR | .STAAG...VDG | A..A........ | 0.03 | 4 |
| ..... | .................. | .QPSQ....NF....... | ...DDR | E.AG...IAVDR | A..A........ | 0.03 | 4 |
| ..... | .................. | .................. | ...DDR | E.GR.G.A..DE | A..A........ | 0.03 | 4 |
| ..... | ......NQG....P.K.I | .Q.DR.....F....... | ...DDR | E..N...I..DR | A..A........ | 0.03 | 4 |
| SA... | F.....NR..N..I.T.G | .Q.DR.....F....... | ....D. | ............ | A..A........ | 0.03 | 4 |
| D...T | F.....DAA.IK.T.Q.N | ..DGE....DF....... | ...... | E........... | ............ | 0.03 | 4 |
| ..... | .................. | .................. | ...D.R | .N.AE...E.DG | A..A........ | 0.03 | 4 |
| .A... | F.....ANG.HL.K.K.S | T.PTG....DF....... | ...DDR | .SAS.N.IA..E | A..A........ | 0.03 | 4 |
| ..... | F................. | .V.......F........ | ...... | ............ | .R.SA..FSG.D | 0.03 | 4 |
| ..... | .................. | .QPGQ....NF....... | E..AD. | .SASEN.I..DR | A..A........ | 0.03 | 4 |
| G.... | F.....GHA.SK.T.E.K | .QPSQ....NF....... | R...D. | ............ | A..A........ | 0.03 | 4 |
| R.... | .................. | ..AGR....DF......T | ....D. | ............ | A..A........ | 0.03 | 4 |
| ..... | .................. | .................. | E..ND. | ESGRANDA...S | A..A........ | 0.03 | 4 |
| G.... | F.....GTT.NI.I.K.R | .................. | ...... | ............ | A..A........ | 0.03 | 4 |
| ..... | .................. | ..YN......F......T | ...D.R | .S.TRG.AAVDE | A..A........ | 0.03 | 4 |
| D.... | F.....SRA.SK.N.A.H | .Q.GQ....DF....... | ....G. | ............ | A..A........ | 0.03 | 4 |
| ..... | .................. | .................. | R..DD. | EDAA.SDAAY.E | A..A........ | 0.03 | 4 |
| ....T | ...............G.. | .........DF....... | ...DDR | ............ | A..A........ | 0.03 | 4 |
| SA... | F.....SA..RA.....R | .Q.G......F....... | ...... | ENATGGDAE.DQ | A..A........ | 0.03 | 4 |
| ..... | .................. | .................. | ...DDR | .STAES.I..DG | A..A........ | 0.03 | 4 |
| G.... | .................. | .KYT.....NF......T | ...ND. | ED.R.S.A...G | A..A........ | 0.03 | 4 |
| ..... | .................. | .Q.D.....DF..P.... | ...ND. | ............ | A..A........ | 0.03 | 4 |
| TT... | F.....NAT.RD.M.T.K | ..HG.....NF......T | ....G. | ............ | A..A........ | 0.03 | 4 |
| R.... | F.....SG..IK.K.D.R | .................. | ...... | ..GTGDD.A.D. | A..A........ | 0.03 | 4 |
| TA... | .................. | TQYDR....NF....... | ...DDR | E..G.SDAA.GD | A..A........ | 0.03 | 4 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| ..... | .................. | .................. | R..N.. | ..AKAND...GS | A..A........ | 0.03 | 4 |
| DA... | F.....ASA.S..T.T.G | .QPG.....DF....... | ...DDR | ........... | ............ | 0.03 | 4 |
| ..... | F.....GTT.PM.M.A.R | .V........F....... | ...... | ........... | ANKDP..FKE.. | 0.03 | 4 |
| ..... | .................. | .................. | R..DG. | ........... | A..A........ | 0.03 | 4 |
| ..... | .................. | ........DF..P.... | ...AD. | ........... | A..A........ | 0.03 | 4 |
| DT... | .................. | ..........NF....... | ...DDR | ESGRR...E..Q | A..A........ | 0.03 | 4 |
| ..... | .................. | .................. | ...DDR | .NG.EG....GR | A..A........ | 0.03 | 4 |
| ..... | .................. | .................. | R..TG. | ..TK...AE..D | A..A........ | 0.03 | 4 |
| ..... | .................. | .KYT.....NF......T | R..D.. | .SAKAA.AA.DE | A..A........ | 0.03 | 4 |
| R.... | .................. | .................. | E..N.. | ........... | AV.V........ | 0.03 | 4 |
| RA... | F......TT.HN.L.G.R | T.PGG....NF....... | ...DD. | ........... | A..A........ | 0.03 | 4 |
| .A... | F.....A...HV.L.... | ..DGE....DF....... | ...... | ........... | ............ | 0.03 | 4 |
| A.... | F.....DDG.SM.L...R | .Q.S......F....... | E..AD. | ED.RGG....GG | A..A........ | 0.03 | 4 |
| ..... | F................ | .V........F....... | ...... | ........... | GTRS...AE..K | 0.03 | 4 |
| EA... | .................. | ..YN......F..P.... | ...... | .S.TRG.AAVDE | A..A........ | 0.03 | 4 |
| ..... | .................. | .................. | ...D.. | .NATAG...FD. | A..A........ | 0.03 | 4 |
| ..... | .................. | .................. | ...DDR | .NASG..A.VGQ | A..A........ | 0.03 | 4 |
| .A... | ..............K.K | .QHNQ.....F......T | ...D.. | ESTKRA.AE.GE | A..A........ | 0.03 | 4 |
| GA... | .................. | ..T............... | ...DDR | ........... | A..A........ | 0.03 | 4 |
| ..... | .................. | .................. | R..DDR | E.AGES.A.Y.Q | A..A........ | 0.03 | 4 |
| AT... | F.....AST.PI.K.Q.K | TQ.TH....DF....... | ...... | ........... | A..A........ | 0.03 | 4 |
| ..... | F................ | .V........F....... | ...... | ........... | G.KSG..N...Q | 0.03 | 4 |
| ..... | .................. | ...............NF | ...DG. | .DTTRG.A.VDQ | A..A........ | 0.03 | 4 |
| R.... | .................. | .................. | E..N.. | ........... | AV.A........ | 0.03 | 4 |
| T...T | F.....AET..A.T...K | .KAS.....NF......T | E..DD. | ........... | A..A........ | 0.03 | 4 |
| E.... | .................. | TQ.TR....NF......T | G..NDR | ........... | A..A........ | 0.03 | 4 |
| ..... | F................ | .V........F....... | ...... | ........... | G.RTG..VR..H | 0.03 | 4 |
| SA... | .................. | ..YN......F......T | ...DD. | ........... | A..A........ | 0.03 | 4 |
| ..... | F................ | .V........F....... | ...... | ........... | SKRGG..FTT.E | 0.02 | 3 |
| HT... | .................. | .V........F....... | ...... | ........... | A..A........ | 0.02 | 3 |
| ..... | .................. | .........F....... | E..ND. | ESAGAN....GG | A..A........ | 0.02 | 3 |
| ..... | F.....DN..IK.H.S.G | ..DGE....DF....... | ...DDR | ........... | A..A........ | 0.02 | 3 |
| ..... | .................. | .................. | ...D.. | ESGS.S.IA.DQ | A..A........ | 0.02 | 3 |
| ..... | F.....G.G.HA.T.G.R | TQPTE....DF....... | ...DDR | ........... | A..A........ | 0.02 | 3 |
| NA..T | F.....SGT.SQ.K.E.. | .QPSR.....F....... | ...... | ........... | A..A........ | 0.02 | 3 |
| ..... | F................ | .V........F....... | ...... | ........... | TDQSR..FTE.D | 0.02 | 3 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| GT..T | F.....STG.LQ.L.D.R | ..HNH....DF....... | ....D. | .SAKAA.AA.DE | A..A........ | 0.02 | 3 |
| ..... | F................. | ................. | E..ND. | ............ | ............ | 0.02 | 3 |
| ..... | ................. | ................. | E..AD. | ..GGA.D.E.GN | A..A........ | 0.02 | 3 |
| ..... | ................. | ................. | R..ND. | ............ | A..A........ | 0.02 | 3 |
| ..... | ................. | ................. | G..ND. | ............ | A..A........ | 0.02 | 3 |
| N.... | F.....DR..LE.K...R | TQ.GR....DF..P...T | ....D. | ............ | A..A....... | 0.02 | 3 |
| ..... | F................. | ................. | ...... | ............ | ..SNH..AKE.H | 0.02 | 3 |
| ..... | ................. | ................. | R..N.. | ...G.D..EVGQ | A..A........ | 0.02 | 3 |
| E.... | F......KT.NV.K.T.H | ...NG.....F....... | R...DR | .SGS.NDIA..D | A..A........ | 0.02 | 3 |
| .A... | F......S..SE.T...R | .V................ | ...DDR | ............ | A..A........ | 0.02 | 3 |
| ..... | ................. | ................. | R..AGR | ............ | A..A........ | 0.02 | 3 |
| EA... | ................. | ................. | R...D. | ED.R.S.A...G | ............ | 0.02 | 3 |
| ..... | ................. | ................. | ...... | ESAT.A.A..DR | A..A........ | 0.02 | 3 |
| ..... | ................. | ................. | ...N.. | E..TAA.AAFDE | A..A........ | 0.02 | 3 |
| ..... | ................. | ................. | ...... | ............ | GARGH..VR..A | 0.02 | 3 |
| ..... | ................. | ................. | E..ND. | .S.ATGDTE.DG | A..A........ | 0.02 | 3 |
| ..... | ................. | .QANH.....F......T | ...D.R | E..G.ND.EVDR | A..A........ | 0.02 | 3 |
| ..... | F................. | .V.......F....... | ...... | ............ | TPKAN..AQI.E | 0.02 | 3 |
| ..... | F................. | .V.......F.....R | ...... | ............ | ERSGA..IE..D | 0.02 | 3 |
| ..... | ................. | .QANH....DF....... | ...DDR | ............ | A..A........ | 0.02 | 3 |
| AA... | F.....STG.PI.M...R | ..DGE....DF....... | ...... | ............ | A..A........ | 0.02 | 3 |
| TA... | ................. | ................. | ....GR | ............ | A..A........ | 0.02 | 3 |
| ..... | ................. | ................. | R...D. | ESGSGSD..FDH | A..A........ | 0.02 | 3 |
| ..... | F................. | .V.......F....... | ...... | ............ | TP.SD..NDK.D | 0.02 | 3 |
| ..... | F................. | .V.......F....... | ...... | ............ | SDRAP...ST.K | 0.02 | 3 |
| ..... | ................. | .KPDQ.....F....... | R..AGR | .NAGASDA.FDQ | A..A........ | 0.02 | 3 |
| ..... | ................. | ................T | T..TG. | ESAN...I...H | A..A........ | 0.02 | 3 |
| A.... | F.....ATT.L..M...G | .V.......F....... | ...... | ED.KAN..A.D. | A..A........ | 0.02 | 3 |
| GA... | ................. | .........F.....T | ....GR | ...RGND..V.E | A..A........ | 0.02 | 3 |
| ..... | F................. | .V.......F....... | ...... | ............ | ANRDG..VRV.H | 0.02 | 3 |
| EA... | ................. | TKDDR....DF....... | R..ND. | E.TARN.AAFDE | A..A........ | 0.02 | 3 |
| NA..T | ................. | .........NF....... | E..ND. | ............ | A..A........ | 0.02 | 3 |
| R.... | F......HG.I..M.Q.R | TKDT.....NF....... | ...... | E.AG.A..EF.R | A..A........ | 0.02 | 3 |
| TA... | ................. | .........NF....... | R...D. | .NGRTGDA.V.Q | A..A........ | 0.02 | 3 |
| ..... | ................. | .........DF....... | ...DDR | ............ | A..A........ | 0.02 | 3 |
| ..... | ................. | .........NF......T | ...... | .ST..D..AV.Q | A..A........ | 0.02 | 3 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| E.... | F.....STG.LQ.L.D.R | T..NE....DF......T | R..D.R | ..TG.N.IAF.D | A..A........ | 0.02 | 3 |
| EA... | ................. | ..........F........ | ...DDR | ............ | AHSDG...TT.D | 0.02 | 3 |
| ..... | F.....AA..P..L.K.N | ...TE.....F......T | ...NGR | ............ | A..A........ | 0.02 | 3 |
| NT... | ................. | ........DF........ | R...D. | EDAA...AAVDQ | A..A........ | 0.02 | 3 |
| ..... | ................. | ................. | ...DDR | E.T..S..A..R | A..A........ | 0.02 | 3 |
| ..... | ................. | ................. | ...... | ............ | A..T........ | 0.02 | 3 |
| ..... | ................. | ........DF........ | ...... | ..AG...IAYGN | A..A........ | 0.02 | 3 |
| ..... | ................. | ................. | ...D.. | ..ATGS..EYGS | A..A........ | 0.02 | 3 |
| ..... | ................. | ........NF........ | R...D. | ............ | A..A........ | 0.02 | 3 |
| ..... | ................. | ................. | ...... | ESTK..D.A.GD | A..A........ | 0.02 | 3 |
| ..... | F................. | .V........F........ | ...... | ............ | NR.AD..VDE.. | 0.02 | 3 |
| ..... | ................. | .Q.GQ....DF........ | R..ND. | ..AK.ADT..GN | A..A........ | 0.02 | 3 |
| NT... | ................. | ..PN.....NF........ | R..AGN | ..TNE..I..DG | A..A........ | 0.02 | 3 |
| AA... | F.....ANG.HL.K.K.S | ................. | ...... | ............ | A..A........ | 0.02 | 3 |
| DA... | ................. | ................. | ...T.. | ............ | A..A........ | 0.02 | 3 |
| NA... | F.....AST.HD.T.E.R | TKAGE....NF..P...T | ...DDR | ............ | A..A........ | 0.02 | 3 |
| G.... | F.......T.HH.P.G.K | .KHDH....DF........ | ...DDR | ............ | A..A........ | 0.02 | 3 |
| G.... | F.....SSA.NV.K.G.R | ..HG.....NF......T | R..N.. | .SAGAN..E..S | A..A........ | 0.02 | 3 |
| ..... | ................. | ................. | G..DD. | .NAGGNDIA.GE | A..A........ | 0.02 | 3 |
| G.... | F.....A.A.RE.I.... | .KPDQ.....F........ | ...... | E..TGS..EYDR | A..A........ | 0.02 | 3 |
| ..... | F................. | .V........F........ | ...... | ............ | .PSAT....G.A | 0.02 | 3 |
| ..... | F.....ARG.PQ.N.G.G | ..HG.....NF......T | ...DD. | ............ | A..A........ | 0.02 | 2 |
| A.... | F.....DNT.SK.L...K | .Q.DQ.....F........ | ...DD. | .DA..ND.A..E | A..A........ | 0.02 | 2 |
| RT... | F......SG.HP.T.A.L | TQ.TG....DF........ | ...DDR | ............ | A..A........ | 0.02 | 2 |
| HT..T | F.....NGG.NV.N.K.G | .........NF........ | R...D. | .DAGAN.AEVGE | A..A........ | 0.02 | 2 |
| G.... | F.....NGG.NN.K.T.R | .QPG.....NF........ | ...DDR | .CGA.A...V.H | A..A........ | 0.02 | 2 |
| .A... | ................. | .KPDQ.....F........ | ...NDR | .SAGGSD.AFDE | A..A........ | 0.02 | 2 |
| ..... | ................. | ................. | ...A.. | ..TR.ND.A.DE | A..A........ | 0.02 | 2 |
| ..... | ................. | ................. | Q...GR | ..AG.N.AA.GQ | A..A........ | 0.02 | 2 |
| ..... | ................. | ................. | ...... | ..AKA.DTEV.Q | A..A........ | 0.02 | 2 |
| ..... | F................. | T.PNE....DF........ | R..DDR | ............ | A..A........ | 0.02 | 2 |
| ..... | ................. | TQHGH....DF........ | ...DD. | .SGREGDAE..D | A..A........ | 0.02 | 2 |
| R...T | ................. | .V........F........ | E..TD. | ............ | A..A........ | 0.02 | 2 |
| .A... | F.......G.PE.T.G.R | .KDSR....DF........ | E..NGR | ............ | A..A........ | 0.02 | 2 |
| ..... | ................. | ................. | ...DDR | .SGGRS..G.DQ | A..A........ | 0.02 | 2 |
| ..... | ................. | ................. | N...GR | ..AG.N.AA.GQ | A..A........ | 0.02 | 2 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| SA... | F.....NGT.IL.T.A.K | .QHNQ.....F......T | ...D.. | ...NG....VDG | A..A........ | 0.02 | 2 |
| R.... | F.....NGG.NI.K.E.R | ................. | ...... | .NASEN.AA..D | A..A........ | 0.02 | 2 |
| E.... | F.....DRG.S..T.A.S | ..DGE....DF...... | ...... | ........... | ........... | 0.02 | 2 |
| TA... | F.....AQ...A.L.... | .QD.E.....F..P.... | .G.... | ........... | ........... | 0.02 | 2 |
| ..... | ................. | ................. | R..DG. | ..AG.DD...GG | A..A........ | 0.02 | 2 |
| ..... | ................. | ..........NF...... | ...TG. | E.AGGS..AVDG | A..A........ | 0.02 | 2 |
| SA..T | F.....AR..L..P.D.K | .KYT.....NF......T | R...D. | E.......... | A..A........ | 0.02 | 2 |
| ..... | ............P.D.R | TQANH.....F....... | E..AGR | .DAAG.D.AFDG | A..A........ | 0.02 | 2 |
| ..... | ................. | ..........NF......T | ...DDR | ...AASDI..DR | A..A........ | 0.02 | 2 |
| ..... | ................. | ................. | ...DD. | ..TTGA..AY.D | A..A........ | 0.02 | 2 |
| .A... | F.....S.A.N..L...L | ..A......DF...... | ...DG. | ........... | A..A........ | 0.02 | 2 |
| ..... | ................. | ................. | ...... | .SAKAA.AA.DE | A..A........ | 0.02 | 2 |
| T...T | ................. | T.YNH.....F...... | ...DDR | ENAG.SD.E..H | A..A........ | 0.02 | 2 |
| E.... | F.....AG..LP.L.N.R | ................. | ...... | E.AGG.DTE..R | A..A........ | 0.02 | 2 |
| ..... | ................. | .QANH.....F......T | G..ND. | EDAG...I..GQ | A..A........ | 0.02 | 2 |
| .A... | F.....ARA.IE....L | .........NF...... | R...D. | E..G.A..A.DR | A..A........ | 0.02 | 2 |
| SA... | F.....DRG.S..T.A.S | ..DGE....DF...... | ...... | ........... | ........... | 0.02 | 2 |
| ..... | ...............I. | ................. | ...... | .NGR..DAEV.H | A..A........ | 0.02 | 2 |
| R...T | F.....DKG.HM.L.G.R | .........DF...... | ...... | ........... | A..A........ | 0.02 | 2 |
| ..... | F.....GNG.HV.H.G.R | .PPNG.....F......T | ...DDR | E.ATRA..A.DE | A..A........ | 0.02 | 2 |
| ..... | F................. | .V........F...... | ...... | ........... | TRKG...S.E.. | 0.02 | 2 |
| EA... | ................. | .Q.G......F..P.... | ...... | ES.GEG...VDS | ............ | 0.02 | 2 |
| A.... | ............H...N | ..DGE....DF...... | ...... | E.TDAND..VGQ | A..A........ | 0.02 | 2 |
| ..... | F................. | .V........F...... | ...... | ........... | KA.TR..AQ..Q | 0.02 | 2 |
| ..... | ................. | ................. | ...AG. | ........... | A..A........ | 0.02 | 2 |
| SA... | F.....NGT.IL.T.A.K | .QHNQ.....F......T | ...D.. | .D.GA.DAEVDG | A..A........ | 0.02 | 2 |
| T.... | F.....N.G.IV.....R | TQDTQ....DF...... | R...DR | ........... | A..A........ | 0.02 | 2 |
| ..... | ................. | ................. | R..TG. | ........... | A..A........ | 0.02 | 2 |
| D.... | F.....SGG.IN.H.... | .........NF...... | R...D. | ........... | A..A........ | 0.02 | 2 |
| .A..T | ................. | .........DF...... | N..AD. | ........... | A..A........ | 0.02 | 2 |
| ..... | ................. | ................. | R...D. | ED.R.S.A...G | ............ | 0.02 | 2 |
| GT..T | F.....GRG.N.....H | ...TE.....F......T | ...... | ........... | A..A........ | 0.02 | 2 |
| ..... | ..........SP.H.E.V | ..HG.....NF......T | ...NDR | E.AGAND.AV.H | A..A........ | 0.02 | 2 |
| DT... | F.....NKT.HL.T.A.R | ..YN......F......T | ...D.R | ........... | A..A........ | 0.02 | 2 |
| E.... | F.....N...IN.P...L | .QPN......F......T | ...NDR | E.AR.NDAE.GS | A..A........ | 0.02 | 2 |
| A...T | F.....K....L.G.L | .Q.S......F...... | E..N.. | ........... | A..A........ | 0.02 | 2 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| TA..T | ................... | .PPNG.....F......T | ...DDR | ........... | A..A........ | 0.02 | 2 |
| D...T | ................... | ................... | R..AD. | E.T..S..A..R | A..A........ | 0.02 | 2 |
| .A... | ................... | .KYT.....NF......T | ...D.R | ESATGD..E.GQ | A..A........ | 0.02 | 2 |
| ..... | F.................. | .V.......F....... | ...... | ........... | GRSAP..SG..T | 0.02 | 2 |
| ..... | ................... | ................... | ...DD. | .SG..ND...DG | A..A........ | 0.02 | 2 |
| ....T | ................... | ..AGR....DF......T | ....D. | ........... | A..A........ | 0.02 | 2 |
| ..... | ................... | .V......F....... | ...... | ........... | NP.AP..DRG.P | 0.02 | 2 |
| GA... | ................... | ..HG.....NF......T | R..DD. | ........... | ........... | 0.02 | 2 |
| ..... | ................... | ...........NF..... | R...D. | EDAGAA..EFGQ | A..A........ | 0.02 | 2 |
| E.... | F.....GTG.P....K.. | ...NG.....F....... | R..DD. | E.AG...IAVDR | A..A........ | 0.02 | 2 |
| RT... | F.................. | .V.......F....... | ...... | ........... | AQQNP..IRG.A | 0.02 | 2 |
| ..... | F.....DRG.N..I.A.K | .KYT.....NF....... | R..D.. | ........... | ETKSG..YR..T | 0.02 | 2 |
| SA... | F.....NGT.IL.T.A.K | .QHNQ.....F......T | ...... | .D.GA.DAEVDG | A..A........ | 0.02 | 2 |
| ..... | F.................. | .V.......F....... | ...... | ........... | GAKG....HV.. | 0.02 | 2 |
| ..... | ................... | ................... | E..DG. | ........... | GRRDP..DTI.P | 0.02 | 2 |
| GA... | ................... | ................... | ...... | ........... | ........... | 0.02 | 2 |
| ..... | ................... | ................... | ...D.. | EDAGR..IEY.. | A..A........ | 0.02 | 2 |
| ..... | F.......G.N..T.P.L | TQ.TG....DF....... | ...DDR | ........... | A..A........ | 0.02 | 2 |
| ..... | ................... | ................... | R...D. | ...TAS.IA..G | A..A........ | 0.02 | 2 |
| RA... | ................... | .Q.S......F....... | E..AGR | E..GA.D.EYGQ | A..A........ | 0.02 | 2 |
| ..... | S.................. | .V.......F....... | ...... | ........... | NPRAP..SET.A | 0.02 | 2 |
| G...T | ................... | ...........F..... | R..DG. | ..ATESD..FDQ | A..A........ | 0.02 | 2 |
| ..... | ................... | ................... | ...KD. | ........... | A..A........ | 0.02 | 2 |
| ..... | ................... | ................... | R..DD. | .NGG.ND....Q | A..A........ | 0.02 | 2 |
| ..... | F.....SG..IK.K.D.R | ........NF......T | ...DDR | ........... | ........... | 0.02 | 2 |
| S.... | ................... | .QANH.....F......T | G..ND. | EDAG...I..GQ | A..A........ | 0.02 | 2 |
| GA... | F.....DH..R..P.G.S | .Q.DQ.....F....... | ....D. | ........... | A..A........ | 0.02 | 2 |
| D...T | F.................. | ................... | E..AD. | E.......... | A..A........ | 0.02 | 2 |
| ..... | ................... | ................... | ....D. | ........... | A..A........ | 0.02 | 2 |
| R.... | ................... | ...........F..... | R..TGR | ...G.D..EVGQ | A..A........ | 0.02 | 2 |
| ..... | ..........SP.H.E.V | ..HC.....NF......T | ...DDR | E.AGAND.AV.H | A..A........ | 0.02 | 2 |
| ..... | ................... | .KYT.....NF..P...T | R..D.. | ........... | A..A........ | 0.02 | 2 |
| DT... | ................... | ...........NF..... | ...DDR | ESGRRS..E..Q | A..A........ | 0.02 | 2 |
| ..... | ................... | ................... | ...ADR | E.AG..D.A.GR | A..A........ | 0.02 | 2 |
| ..... | ................... | ..PNG....DF....... | R..AGR | ........... | A..A........ | 0.02 | 2 |
| ..... | ................... | .........DF....... | ...DG. | ESAAAADT..GN | A..A........ | 0.02 | 2 |

TABLE 5-continued

AAV capsid proteins having increased specificity for and/or transduction of
CD44+/133+ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| GA... | F.....DRG.S..T.A.S | ..DGE....DF....... | ...... | .......... | ............ | 0.02 | 2 |
| S.... | F......HG.I..M.Q.R | TKDT.....NF....... | ...... | E.AG.A..EF.R | A..A........ | 0.01 | 1 |
| NT..T | F......HG.LV.L.K.R | .QAS......F....... | ...... | .......... | A..A........ | 0.01 | 1 |
| .T... | .....ASA.S..T.T.G | .QPG.....DF....... | ...DDR | .......... | A..A........ | 0.01 | 1 |
| ..... | ................. | ............. | ....D. | ..ASE...E.D. | A..A........ | 0.01 | 1 |
| S.... | ................. | TKDDR....DF....... | ....D. | ...AAA.IE..Q | A..A........ | 0.01 | 1 |
| TT..T | ................. | ................. | ...... | .......... | .D.......... | 0.01 | 1 |
| T.... | ................. | .........NF....... | R..DG. | .DTTRG.A.VDQ | A..A........ | 0.01 | 1 |
| TA..T | F.....ST..SV.K.H.M | TQPTE....DF....... | G..ND. | .......... | ............ | 0.01 | 1 |
| ..... | F.....A.G..V.T.H.R | .Q.DR.....F....... | ....D. | ..AAGAD.EV.. | A..A........ | 0.01 | 1 |
| EA..T | .....NQG..V.L.N.R | .QPN......F......T | ...N.. | .NGGGN...VDQ | .........Y.. | 0.01 | 1 |
| ..... | ................. | .QPG.............. | G..DD. | .......... | ............ | 0.01 | 1 |
| ..... | ................. | ................. | R...D. | .......... | A........... | 0.01 | 1 |
| ..... | F.....AST.HD.T.E.R | TKAGE....NF..P...T | E..AD. | ..A.ASDA.V.Q | A..A........ | 0.01 | 1 |
| ..... | F................. | .V.....D..F....... | ...... | .......... | ERSGA..IE..D | 0.01 | 1 |
| ..... | ..........SPAH.E.V | ..HG.....NF......T | ...DDR | E.AGAMD.AV.H | A..A........ | 0.01 | 1 |
| DA... | F.....AST.HDMT.E.R | T.PGG....NF....... | ...DDR | ESAKTSDAAVDD | A..A........ | 0.01 | 1 |
| ..... | ................. | ................. | R..DG. | .DAGA.D.AV.E | A..A........ | 0.01 | 1 |
| ..... | ................. | ................. | ....DR | .......... | ............ | 0.01 | 1 |
| ..... | ................. | ................. | R..DD. | .NAGGNDIA.GE | A..A........ | 0.01 | 1 |
| GT... | ................. | ..HG.....NF......T | E..DD. | .......... | EKRGA..V...H | 0.01 | 1 |
| ..... | F.....ANG.HL.K.K.S | ..DGE....DF....... | ...... | .......... | A..A........ | 0.01 | 1 |
| EA... | F.....SSA..V.H.H.. | ................. | ...... | .......... | ............ | 0.01 | 1 |
| RA..T | F......GA.HP.K...V | ..DGE....DF....... | ...... | .......... | A..A........ | 0.01 | 1 |
| ..... | F................. | .V.......F....... | ...... | .......... | NARGT..AQV.D | 0.01 | 1 |
| EA... | F.....AGT..M.K.Q.G | .PPNG.....F......T | ...DDR | .......... | A..A........ | 0.01 | 1 |
| ..... | F.....D...S..M.T.R | ................. | ...... | .......... | A..A........ | 0.01 | 1 |
| SA... | ......NQG....P.K.I | .Q.DR.....F....... | E..AD. | .......... | ............ | 0.01 | 1 |
| ..... | ................. | ................. | ...D.. | ENAG.G.IT.DQ | A..A........ | 0.01 | 1 |
| T.... | ................. | TKDT.....NF....... | R...D. | ..GGA.D.E.GN | ANKDP..FKE.. | 0.01 | 1 |
| ..... | F.....GNG.HV.H.G.R | ..YN......F......T | ...... | .......... | APQDR..DTN.T | 0.01 | 1 |
| NA..T | ................. | .........DF....... | ...D.. | .D..TA....GE | ............ | 0.01 | 1 |
| EA... | ................. | .QANH....DF....... | ...DDR | .......... | A..A........ | 0.01 | 1 |
| ..... | ................. | ..DGE....DF....... | .....S | .NG..G.I...G | A..A........ | 0.01 | 1 |
| ..... | ................. | ................. | ....D. | .DART.D.A.DE | A..A........ | 0.01 | 1 |
| G.... | F......G..NL.T.E.R | .QDT......F......T | ...... | .......... | ............ | 0.01 | 1 |

TABLE 5-continued

AAV capsid proteins having increased specificity for and/or transduction of
CD44⁺/133⁺ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| GA... | F......S..PM.T.S.K | .Q.S......F....... | R..D.. | ............ | A..A........ | 0.01 | 1 |
| ..... | F................. | .V.......F....... | ...... | ............ | G.KTT..FTM.T | 0.01 | 1 |
| EA... | ................. | ................. | R..D.. | ............ | A..A........ | 0.01 | 1 |
| ..... | F......GT.NM.L.Q.G | ................. | ....D. | ............ | ............ | 0.01 | 1 |
| ..... | ................. | .V.......F....... | ...... | ............ | KEHTR..VN..D | 0.01 | 1 |
| ..... | ................. | ................. | ....GR | R.AG.N.AA.GQ | A..A........ | 0.01 | 1 |
| E.... | F.....STA..Q.H.Q.L | T.P......DF....... | R...D. | ............ | ............ | 0.01 | 1 |
| ..... | F................. | .V.......F....... | ...NG. | ENTTGN....DR | A..A........ | 0.01 | 1 |
| ..... | .........SP.H.EPV | ..HG.....NF......T | ...DDR | E.AGAND.AV.H | A..A........ | 0.01 | 1 |
| TA..T | F.....NGG.IM.L.E.R | T.P....D.DF....... | ....D. | ............ | ............ | 0.01 | 1 |
| DT... | F.....AEG.LK.M.H.L | ..DGE....DF....... | ...... | ............ | ............ | 0.01 | 1 |
| E.... | ................. | ................. | R..DG. | ENAGT...AFD. | A..A........ | 0.01 | 1 |
| SA... | ................. | ..A......DF....... | ...DG. | EDAGT...AFD. | A..A........ | 0.01 | 1 |
| N.... | ................. | TQ.TH....DF....... | ....D. | EN.GTN.AE.DN | A..A........ | 0.01 | 1 |
| ..... | ................. | .v.......F....... | ...... | ............ | AARGG..VSN.. | 0.01 | 1 |
| TA..T | F.....DE.....N...G | .QD.E....DF......T | .....S | .D..GA..EGVD | A..A........ | 0.01 | 1 |
| .A... | ................. | .V.......F....... | ...... | ............ | TARSA..VDG.A | 0.01 | 1 |
| ..... | F................. | .V.......F....... | ...... | ............ | GDRTT..DRV.E | 0.01 | 1 |
| RT... | F.....ANG.HL.K.K.S | ..DGE....DF....... | ...... | ............ | A..A........ | 0.01 | 1 |
| E.... | F................. | ................. | R...DR | E.GG.....F.S | A..A........ | 0.01 | 1 |
| HT... | F.........A.M.K.H | .QPG.....NF....... | ...DDR | E.ANG...E.G. | A..A........ | 0.01 | 1 |
| ..... | ................. | ................. | ....D. | E.AGAND.AY.N | A..A........ | 0.01 | 1 |
| TA... | F.....G....K.L...G | .KD.E.....F....... | ....D. | ENGSAA.A...E | A..A........ | 0.01 | 1 |
| ..... | F.....GRG.H..P.E.M | TQ.TG....DF...... | ...DDR | E..AAS....GG | A..A........ | 0.01 | 1 |
| ..... | ................. | .KYT.....NF......T | ...... | ............ | A..A........ | 0.01 | 1 |
| ..... | F.....GRG.H..P.E.R | .........F....... | ...... | .SASRND.AVGE | A..A........ | 0.01 | 1 |
| GA... | F.....STA..Q.H.Q.L | T.P......GF....... | R...D. | ............ | ............ | 0.01 | 1 |
| ..... | ................. | ................. | ...... | ..GGTD....DR | A..A........ | 0.01 | 1 |
| ..... | F.........A.M.K.H | TQ.TG....DF....... | ...DDR | E.AGGN...FGE | A..A........ | 0.01 | 1 |
| TA..T | ................. | ..HG.....NF......T | ...TDR | .SA....AEVDD | A..A........ | 0.01 | 1 |
| TT..T | ................. | ................. | ...... | ............ | .......T... | 0.01 | 1 |
| ..... | .........SP.H.EV | ..HGN....NF......T | ...DDR | E.AGAND.AV.H | A..A........ | 0.01 | 1 |
| ....P | ................. | ................. | R..N.. | ............ | A..A........ | 0.01 | 1 |
| TA..T | G.....SGA..K.N.S.S | ..HG.....NF......T | ...D.. | ..ADRS...VGS | A..A........ | 0.01 | 1 |
| ..... | ................. | ................. | ...DDR | .NAGAND.EV.G | A..A........ | 0.01 | 1 |
| G.... | ................. | ................. | ...... | ............ | GRRDP..DTI.P | 0.01 | 1 |

TABLE 5-continued

AAV capsid proteins having increased specificity for and/or transduction of
CD44$^+$/133$^+$ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263<br>QSGAS | 444<br>YLSRTNTPSGTTTQSRLQ | 490<br>KTSADNNNSEYSWTGATK | 527<br>KDDEEK | 545<br>QGSEKTNVDIEK | 585<br>RGNRQAATADVN | % | # |
|---|---|---|---|---|---|---|---|
| E.... | F.....GAT.IN.M.K.L | T.ANE....DF....... | ...DDR | ............ | ............ | 0.01 | 1 |
| GA... | F................. | TKDDR....DF....... | R..ND. | E.TARN..AAFDE | A..A........ | 0.01 | 1 |
| ..... | N................. | ................. | R..D.R | E.AAAA.I..D. | A..A........ | 0.01 | 1 |
| ..... | ................. | ................. | ....GR | E.AGGD..EV.R | A..A........ | 0.01 | 1 |
| ..... | ................. | .........P...... | ...... | ENGKAGD...GN | A..A........ | 0.01 | 1 |
| ..... | ................. | ......NF......T | R..AD. | ............ | A..A........ | 0.01 | 1 |
| ..... | ................. | .......F....... | ...... | .DT.RS.I...R | A..A........ | 0.01 | 1 |
| GT... | F.....AEG.LK.M.H.L | ..DGE....DF....... | ...... | E.ATRA..A.DE | A..A........ | 0.01 | 1 |
| .A... | ................. | ..DGE....DF....... | R..DD. | ............ | ............ | 0.01 | 1 |
| ..... | ................. | ...............T | ...ADR | ............ | A..A........ | 0.01 | 1 |
| ..... | ................. | ......NF..P.... | ....D. | ............ | A..A........ | 0.01 | 1 |
| .T... | ................. | .V.......F....... | ...... | ............ | GR.DT..FTE.D | 0.01 | 1 |
| .A... | F.....G.T.II.P.D.R | E................. | ...DG. | ............ | A..A........ | 0.01 | 1 |
| G.... | F.....SGG.RV.P...G | .QPTG....NF....... | R...D. | ............ | ............ | 0.01 | 1 |
| T.... | F.....GH..HE.T.T.E | ..DGE....DF....... | ...... | ............ | A..A........ | 0.01 | 1 |
| ..... | F.....SA..RA.....R | TKDR.....DF..I.... | ...DDR | E..A.ADA..GD | A..A........ | 0.01 | 1 |
| ..... | ..RQNKH...SP.H.E.V | ..HG.....NF......T | ...DDR | E.AGAND.AV.H | A..A........ | 0.01 | 1 |
| GA... | ................. | .PPNG....F......T | ...DDR | ............ | A..A........ | 0.01 | 1 |
| ..... | ................. | T.HTE....NF......T | ...NDR | ............ | A..T........ | 0.01 | 1 |
| ..... | F......TG.KA.I.G.K | .PHD.....DF......T | ...D.R | ........E... | A..A........ | 0.01 | 1 |
| ..... | F.....NN..N..M...G | .Q.DR.....F....... | ...DDR | ............ | AC.A........ | 0.01 | 1 |
| ..... | F.....N.G.RE.H.A.R | .Q.DR.....F....... | ....D. | ............ | A..A........ | 0.01 | 1 |
| ..... | .........SP.H.E.V | ..HG.....NF......T | ...DDR | ECAGAND.AV.H | A..A........ | 0.01 | 1 |
| A.... | ................. | TQASG....NF....... | ....D. | E.AS...IEYGQ | A..A........ | 0.01 | 1 |
| D...T | F......QA.IN.H.H.K | .KD.E.....F..P...T | R..TG. | ............ | A..A........ | 0.01 | 1 |
| ..... | F.....SGT.SQ.K.E.. | .KYT.....NF......T | ...DDR | ............ | ............ | 0.01 | 1 |
| ..... | F.....AAG..E.T.... | .QPNY.....F......T | ...N.. | ............ | A..A........ | 0.01 | 1 |
| ....T | ................. | ................. | G..KG. | .SADGSD...DR | A..A........ | 0.01 | 1 |
| ..... | ................. | TK.NW....DF......T | ...D.R | .NAAAN.A.Y.S | A..A........ | 0.01 | 1 |
| GT... | F................. | .V.......F....... | ...... | ............ | GRRDP..DTI.P | 0.01 | 1 |
| ..... | F................. | .V.......F....... | ...... | ............ | E.RSP..FTI.Q | 0.01 | 1 |
| TA... | ................. | .KYT.....NF | R...D. | ED.GGND.EV.D | A..A........ | 0.01 | 1 |
| T.... | F......EG.NA.P.E.R | ..PN.....NF....... | ...D.R | .SAKAA.AA.DE | A..A........ | 0.01 | 1 |
| EA... | F.....GG.NA.I...R | T.YNH....F....... | ...D.. | ............ | A..A........ | 0.01 | 1 |
| ..... | F.....DQ..R..P.S.R | .QD.E.....F..P.... | ....S | E.GKGSD...GG | A..A........ | 0.01 | 1 |
| ..... | ................. | ................. | ...... | ESATRG.....R | A..A........ | 0.01 | 1 |

TABLE 5-continued

AAV capsid proteins having increased specificity for and/or transduction of
CD44$^+$/133$^+$ GSC (pool of Round 1 selection). Amino acid numbers correspond
to the amino acid sequence of VP1 (SEQ ID NO: 1). Sequences below correspond
to SEQ ID NOs: 8 and 3731-4667 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | F................. | .V.......F....... | ...... | ............ | GRQSP..DRA.E | 0.01 | 1 |
| ..... | ................. | E................. | ....GR | ..AG.N.AA.GQ | A..A........ | 0.01 | 1 |
| D.... | F.....SG..SH.T.G.G | ..P......DF....... | ...DDR | .SG..ND...DG | A..A........ | 0.01 | 1 |
| .A... | F.....SGG.SH...A.R | ..P.E....NF......T | R...D. | ............ | A..A........ | 0.01 | 1 |
| ..... | F................. | .V.......F....... | ...... | ............ | AP.SK..DN..T | 0.01 | 1 |
| ..... | ................. | .V.......F....... | ...... | ............ | ............ | 0.01 | 1 |
| ..... | ......NQG..V.L.N.R | .QPN......F......T | ...N.. | .NGGGN...VDQ | ............ | 0.01 | 1 |
| NA... | ................. | ................. | ...DDR | ..TTGA.I.FDG | A..A........ | 0.01 | 1 |
| TT..T | ................. | ................. | .....S | ............ | ............ | 0.01 | 1 |
| AA... | ................. | T.Y.G....NF....... | ...... | E.AGTNDI...R | A..A........ | 0.01 | 1 |

TABLE 6

AAV capsid proteins having increased specificity for and/or transduction of
CD44$^+$/133$^+$ GSC (pool of Round 2 selection). Amino acid numbers correspond to the
amino acid sequence of VP1 (SEQ ID NO: 1). Sequences below correspond to SEQ ID
NOs: 8 and 4668-4705 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| G...T | ................. | ..HDR....NF....... | ....D. | ............ | A..A........ | 11.20 | 236 |
| TT..T | ................. | .QPTG....NF....... | ...DDR | E.GNG.D.E.DS | A..A........ | 10.28 | 223 |
| ..... | ................. | ................. | ....GR | ..AG.N.AA.GQ | A..A........ | 6.88 | 145 |
| TA... | F.....SKA.S..L.E.R | ................. | ...D.. | ............ | A..A........ | 6.36 | 134 |
| ..... | ................. | .........DF....... | ...D.. | E.ASGG.A..GS | A..A........ | 6.07 | 128 |
| GT... | F.....AEG.LK.M.H.L | ................. | ...... | ............ | ............ | 6.07 | 128 |
| T.... | F.....SRA.SK.N.A.H | .Q.S......F....... | G..D.. | ............ | A..A........ | 6.03 | 127 |
| ..... | F................. | .V........F....... | ...... | ............ | GERTP..ART.D | 5.60 | 118 |
| ..... | ................. | ................. | ...DD. | .NGST.....GG | A..A........ | 5.55 | 117 |
| ..... | ................. | ................. | ...N.. | ...G.N.A.... | A..A........ | 5.03 | 106 |
| DA... | F.....DNA.NA.M.N.K | ..PNG....DF....... | G..NDR | ............ | A..A........ | 5.03 | 106 |
| ..... | F.....AEG.LK.M.H.L | ..DGE....DF....... | ...... | ............ | ............ | 4.03 | 85 |
| ..... | ................. | ................. | ...N.. | ENAGGD..E..R | A..A........ | 3.27 | 69 |
| ..... | ................. | ................. | ...DDR | ............ | ............ | 3.18 | 67 |
| ..... | F......GT.NM.L.Q.G | .Q.S......F....... | ....D. | ............ | ............ | 2.99 | 63 |
| .A... | F.....ANG.HL.K.K.S | T.P......DF....... | R..D.. | ............ | A..A........ | 2.42 | 51 |
| ..... | F................. | .V.......F....... | ...... | ............ | DRQGN..IGV.. | 1.85 | 39 |
| N.... | F................. | .V.......F....... | ...... | ...........R | A..A........ | 1.33 | 28 |
| ..... | F................. | .V.......F....... | ...... | ............ | GRKGG...NV.E | 1.14 | 24 |

TABLE 6-continued

AAV capsid proteins having increased specificity for and/or transduction of CD44+/133+ GSC (pool of Round 2 selection). Amino acid numbers correspond to the amino acid sequence of VP1 (SEQ ID NO: 1). Sequences below correspond to SEQ ID NOs: 8 and 4668-4705 from top to bottom.

| 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % | # |
|---|---|---|---|---|---|---|---|
| ..... | .................. | ................. | ...ADR | .......... | A..A........ | 0.81 | 17 |
| TA... | .................. | ................. | ....D. | .DTAA...EF.G | A..A........ | 0.57 | 12 |
| ..... | .................. | .QD.E.....F..P.... | ...D.. | .......... | .......... | 0.33 | 7 |
| ..... | .................. | ................. | ...... | E.AG...TAVGN | A..A........ | 0.28 | 6 |
| ..... | F................. | .V........F...... | ...... | .......... | DHRAT..SNN.D | 0.19 | 4 |
| GT... | F.....AEG.LK.M.H.L | ..DGE....DF....... | .G.... | .......... | .......... | 0.09 | 2 |
| ..... | .................. | ........G......... | ....GR | ..AG.N.AA.GQ | A..A........ | 0.09 | 2 |
| G...T | .................. | ..HDR....NF....... | ....D. | .......... | A..T........ | 0.09 | 2 |
| SA... | .................. | ..DGE....DF....... | ...... | ENASGG.AE.DS | A..A........ | 0.09 | 2 |
| TA... | F.....SKA.S..L.EFR | ................. | ...D.. | .......... | A..A........ | 0.09 | 2 |
| ..... | F................. | .V........F...... | ...... | .......... | TRSAP..FNT.E | 0.05 | 1 |
| ..... | .................. | ........DF....... | ...D.. | E.ASEAMPTSAS | A..A........ | 0.05 | 1 |
| ..... | ....A............. | ................. | ...N.. | ENAGGD..E..R | A..A........ | 0.05 | 1 |
| ..... | .................. | ................. | ....G. | E.AG...IAVDR | A..A........ | 0.05 | 1 |
| ..... | .................. | ................. | ....D. | E.GGTG.AEFDQ | A..A........ | 0.05 | 1 |
| ..... | .................. | ..DGE....DF....... | ...... | E.......... | A..A........ | 0.05 | 1 |
| ..... | .................. | ................. | ....GG | ..AG.N.AA.GQ | A..A........ | 0.05 | 1 |
| TA... | .................. | .QANH....DF....... | ...DDR | .......... | .......... | 0.05 | 1 |
| A.... | .................. | .........NF....... | R...D. | ..AK.ADT..GN | A..A........ | 0.05 | 1 |

TABLE 7

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | .................. | ................. | ....GR | ..AG.N.AA.GQ | A..A........ | 1.75 | 287 |
| E.... | F.....ASA.S..T.T.G | .QPG.....DF....... | ...DDR | .......... | .......... | 1.47 | 240 |
| ..... | .................. | ................. | ...DDR | .......... | A..A........ | 0.83 | 136 |
| ..... | F.....AEG.LK.M.H.L | ..DGE....DF....... | ...... | .......... | .......... | 0.78 | 127 |
| ..... | .................. | ................. | ...... | .......... | A..A........ | 0.76 | 125 |
| ..... | F................. | .V........F...... | ...... | .......... | .......... | 0.74 | 121 |
| TA... | .................. | .QANH....DF....... | ...DDR | .......... | A..A........ | 0.59 | 97 |
| ..... | .................. | ................. | R..DD. | .......... | .......... | 0.58 | 95 |
| D...T | F......GT.NM.L.Q.G | .Q.S.....F....... | ....D. | .......... | .......... | 0.56 | 92 |
| ..... | .................. | ................. | R...D. | .......... | A..A........ | 0.53 | 87 |
| GT... | F.....AEG.LK.M.H.L | ..DGE....DF....... | ...... | .......... | .......... | 0.52 | 85 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| H.... | ................... | ..DGE....DF....... | R...D. | ........... | ........... | 0.51 | 83 |
| ..... | ................... | ................... | E..ND. | ........... | A..A........ | 0.51 | 83 |
| ..... | ................... | ................... | ...NDR | ..AKG...AV.. | A..A........ | 0.46 | 75 |
| ..... | ................... | ................... | ...N.. | ........... | A..A........ | 0.45 | 74 |
| TT..T | ................... | ................... | ...... | ........... | ........... | 0.44 | 72 |
| ..... | F.................. | .V........F....... | ...... | ........... | GPHGP..DGM.. | 0.43 | 71 |
| GT... | ................... | ..HG.....NF......T | E..DD. | ........... | ........... | 0.42 | 68 |
| ..... | F.....ASA.S..T.T.G | .QPG.....DF....... | ...DDR | ........... | ........... | 0.38 | 63 |
| ..... | ................... | ..P.G....NF....... | R...D. | ...NG....VDG | A..A........ | 0.38 | 62 |
| A...T | ................... | TQP.R....NF......T | ...D.. | ........... | A..A........ | 0.33 | 54 |
| ..... | ................... | ................... | G..KD. | ESAGAN....GG | A..A........ | 0.32 | 53 |
| ..... | ................... | ................... | E..AG. | ........... | ........... | 0.32 | 53 |
| ..... | ................... | .Q.S.....F........ | ...... | E.AS.N.IE.GS | A..A........ | 0.32 | 53 |
| ..... | ................... | .QD.E.....F..P.... | ...D.. | ........... | ........... | 0.32 | 52 |
| ..... | ................... | ................... | R...AD | ........... | A..A........ | 0.32 | 52 |
| ..... | ................... | ................... | E..N.. | ..AG.N.AA.GQ | A..A........ | 0.31 | 51 |
| ..... | F.................. | .QDT......F......T | ...D.. | ESGNRN.IAF.E | A..A........ | 0.30 | 49 |
| G...T | ................... | ..HDR....NF....... | ....D. | ........... | A..A........ | 0.30 | 49 |
| ..... | F.................. | .V........F....... | ...... | ........... | A..A........ | 0.30 | 49 |
| ..... | ................... | ................... | G..DG. | ........... | ........... | 0.30 | 49 |
| .A... | F.....DRG.S..T.A.S | ..DGE....DF....... | ...... | ........... | ........... | 0.29 | 47 |
| E.... | F.....AEG.LK.M.H.L | ..DGE....DF....... | ...... | ........... | ........... | 0.29 | 47 |
| ..... | ................... | TQYDR....NF....... | E...G. | ........... | A..A........ | 0.29 | 47 |
| GT... | ................... | ................... | G..N.. | ........... | A..A........ | 0.28 | 46 |
| ..... | ................... | ................... | E..TG. | ........... | ........... | 0.27 | 44 |
| ..... | ................... | ................... | R..AG. | ........... | A..A........ | 0.27 | 44 |
| ..... | ................... | ................... | E..DD. | ........... | A..A........ | 0.26 | 43 |
| ..... | ................... | ................... | ...D.. | E.AKGG..A.DQ | A..A........ | 0.26 | 43 |
| E.... | F.....ASA.S..T.T.G | .QPG.....DF....... | ...DDR | ........... | A..A........ | 0.26 | 42 |
| A.... | F.....DA..IA.L.K.R | .KDSR....DF......T | R..DD. | ........... | A..A........ | 0.25 | 41 |
| NA..T | F.....ANG.HL.K.K.S | T.P......DF....... | ...D.. | ........... | A..A........ | 0.25 | 41 |
| NA... | ................... | ..HG.....NF....... | ...NGR | ........... | A..A........ | 0.24 | 40 |
| ..... | ................... | .PHD.....DF......T | ...DG. | ........... | A..A........ | 0.24 | 39 |
| ..... | ................... | ................... | ...DDR | ..AS...I..G. | A..A........ | 0.24 | 39 |
| ..... | ................... | ................... | ...D.. | ........... | A..A........ | 0.24 | 39 |
| ..... | F.................. | .V........F....... | ...... | ........... | SHRA...ATV.H | 0.23 | 37 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | .................. | .PPNG.....F......T | ...DDR | E.TR.N.....Q | A..A........ | 0.23 | 37 |
| GT..T | G.....G.G.IN.L...V | .........DF....... | ...DDR | .STSA..AAY.D | A..A........ | 0.22 | 36 |
| TA... | .................. | TQPTH....NF...... | R..DD. | ............ | A..A........ | 0.22 | 36 |
| ET... | F.....SGT.S..P.A.K | ..HG.....NF...... | ...... | E........... | A..A........ | 0.21 | 35 |
| ..... | F.....DRG.S...T.A.S | ..DGE....DF...... | ...... | ............ | ............ | 0.21 | 35 |
| ..... | .................. | .PPNG.....F......T | ...DDR | E.ATRA..A.DE | A..A........ | 0.21 | 35 |
| ..... | .................. | .................. | R...D. | ...AAS.A.VGQ | A..A........ | 0.21 | 34 |
| ..... | .................. | .................. | R...D. | E.AG..D.A.GR | A..A........ | 0.21 | 34 |
| ..... | F................. | .QD.E.....F..P.... | ...D.. | ............ | ............ | 0.21 | 34 |
| ..... | .................. | .................. | E..N.. | ..TK...AE..D | ............ | 0.20 | 33 |
| DT... | ......AST.IN.L.T.. | ..DGE....DF....... | ...... | ............ | ............ | 0.20 | 32 |
| D...T | F.....NA..LV.I.D.R | .QPG.....NF...... | ...DDR | .DAG.S.A..DR | A..A........ | 0.20 | 32 |
| RA... | .................. | .................. | ..AG. | ............ | A........... | 0.20 | 32 |
| ..... | F................. | .V........F....... | ...... | ............ | GRSAD..DTS.H | 0.19 | 31 |
| E.... | .................. | .................. | ...DDR | ............ | ............ | 0.19 | 31 |
| ..... | F................. | .V........F...... | ...... | ............ | ANSNP..SDS.Q | 0.19 | 31 |
| D...T | F.....ASA.S..T.T.G | .QPG.....DF....... | ...DDR | ............ | A..A........ | 0.19 | 31 |
| ..... | .................. | .................. | ...... | E.TARG.A.F.S | A..A........ | 0.19 | 31 |
| GT... | .................. | .QPN......F......T | ....D. | ............ | A..A........ | 0.18 | 30 |
| ..... | .................. | .................. | ...DDR | .D.AG..T..GQ | A..A........ | 0.18 | 30 |
| ..... | .................. | .................. | R..DD. | EN.KAN....GG | A..A........ | 0.18 | 30 |
| ..... | .................. | .................. | R..A.. | ED.NCN.IA.D. | A..A........ | 0.18 | 30 |
| ..... | .................. | .................. | ...N.. | .SAKAA.AA.DE | A..A........ | 0.18 | 29 |
| ....T | .................. | ..AGR....DF......T | ....D. | ............ | A..A........ | 0.18 | 29 |
| S.... | F.....SRA.SK.N.A.H | TKP.....DF....... | G..K.. | ............ | A..A........ | 0.18 | 29 |
| ..... | .................. | .................. | T..TG. | ............ | A..A........ | 0.18 | 29 |
| ..... | F.....S.T.NV.L.D.. | .QPSQ....NF....... | ...... | E.AS.A.TAV.H | A..A........ | 0.18 | 29 |
| ..... | .................. | .................. | ...DG. | ............ | A..A........ | 0.17 | 28 |
| .A... | F.....SNG.RE.L...K | TQ.TG....NF...... | ...... | ............ | A..A........ | 0.17 | 28 |
| ..... | .................. | .................. | ...A.. | .NAGRDD.A..E | A..A........ | 0.17 | 28 |
| TA... | .................. | .QAS......F....... | ...... | .DATA..A.Y.H | A..A........ | 0.17 | 28 |
| R.... | .................. | TKAT....NF......T | G..TG. | ............ | A..A........ | 0.17 | 28 |
| ..... | .................. | .DGG.....NF....... | R..ND. | E.ATGD..EV.. | A..A........ | 0.17 | 28 |
| ..... | .................. | .................. | ...DD. | ............ | A..A........ | 0.16 | 27 |
| .A... | .................. | ..PNG....DF....... | ...DDR | E.ADGS..E.GN | A..A........ | 0.16 | 27 |
| ..... | .................. | ..AGR....DF......T | R..D.. | .D.......... | A..A........ | 0.16 | 27 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | .................. | ..DGE....DF....... | R...D. | ............ | ............ | 0.16 | 27 |
| GA... | .................. | ..HG.....NF......T | ...DDR | .S.SGN.I..GN | A..A........ | 0.16 | 27 |
| ..... | .................. | .QDT......F......T | ...T.R | ............ | A..A........ | 0.16 | 27 |
| ..... | .................. | .................. | G..N.. | ............ | ............ | 0.16 | 27 |
| ..... | F................. | .V........F....... | ...... | ............ | TERGT..SD... | 0.16 | 27 |
| EA... | F.....ATT..N.L...L | .................. | ...... | ..TNESD..... | A..A........ | 0.16 | 27 |
| RA... | .................. | .................. | E..KG. | ............ | ............ | 0.16 | 27 |
| ..... | .................. | .................. | ...... | E.ADGA..AYDR | A..A........ | 0.16 | 26 |
| ..... | F.....A.A.RE.I.... | TKAT.....NF......T | R..AG. | ESAG....A.GE | A..A........ | 0.16 | 26 |
| ..... | F.....AQ...A.L.... | ..DNH....NF....... | G...G. | ............ | A..A........ | 0.15 | 25 |
| ..... | .................. | .................. | ...DDR | .N.G.N.A.VDN | A..A........ | 0.15 | 25 |
| T...T | F.....ATT.NV.T.K.S | T.P......DF....... | ...D.. | ..AAE.D....N | A..A........ | 0.15 | 25 |
| ..... | .................. | .................. | ...NGR | ............ | A..A........ | 0.15 | 25 |
| ..... | .................. | .................. | R..D.. | .SAGAN..E..S | A..A........ | 0.15 | 25 |
| ..... | F................. | .V........F....... | ...... | ............ | TARTA..SQV.H | 0.15 | 25 |
| NA..T | F......KA.LA.K.D.M | .V........F....... | ...... | E.AT.S.AAF.E | A..A........ | 0.15 | 24 |
| ..... | .................. | .................. | ...... | .NGGAADAE..H | A..A........ | 0.15 | 24 |
| ..... | .................. | .................. | ...DDR | E.A........ | A..A........ | 0.15 | 24 |
| ..... | F................. | .QHNQ.....F......T | R..DD. | ............ | A..A........ | 0.15 | 24 |
| ..... | .................. | .................. | ....D. | ............ | A..A........ | 0.15 | 24 |
| ..... | .................. | ........F....... | R..ND. | ENAA.G.TA.DE | A..A........ | 0.15 | 24 |
| ..... | ......SG..IK.K.D.R | .KPDQ....DF....... | ...D.. | .NATG....VGS | A..A........ | 0.15 | 24 |
| ..... | .................. | .................. | G..A.R | ............ | A..A........ | 0.14 | 23 |
| ..... | F.....AEG.LK.M.H.L | ..DGE....DF....... | ...D.. | ............ | ............ | 0.14 | 23 |
| ..... | .................. | ........F....... | ....DR | ..GKED...VDQ | A..A........ | 0.14 | 23 |
| ..... | .................. | ........D....... | G..K.. | ............ | A..A........ | 0.14 | 23 |
| ..... | .................. | .................. | ...AGR | ..AG.DD...GG | A..A........ | 0.14 | 23 |
| ..... | .................. | .KYT.....NF....... | ...NDR | ED.R.S.A...G | A..A........ | 0.14 | 23 |
| DT... | F.....SRT.IQ.....G | ..YN......F......T | ...... | ............ | A..A........ | 0.14 | 23 |
| N.... | .................. | ..HDR....NF....... | ....D. | EDAGAA..EFGQ | A..A........ | 0.14 | 23 |
| RA... | F.....G.G.HA.T.G.R | .Q.GQ...DF....... | R...D. | .DGTGA..E..E | A..A........ | 0.13 | 22 |
| ..... | F.....NN..N..M...G | ..PDG....DF....... | R..D.. | .DAAG..IAFDQ | A..A........ | 0.13 | 22 |
| ..... | .................. | .................. | ...DDR | ...GT..AA.GD | A..A........ | 0.13 | 22 |
| NT... | F.....DQT.PL.T...R | ..AGQ....NF....... | ...D.. | .DGGGAD.A.D. | A..A........ | 0.13 | 22 |
| D.... | F.....ATT.HP.L.T.L | TQADR....NF......T | G..TD. | .SAKAA.AA.DE | A..A........ | 0.13 | 22 |
| ..... | F................. | .V........F....... | ...... | ............ | G.RN...F.V.A | 0.13 | 22 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 | 444 | 490 | 527 | 545 | 585 | % | # |
| QSGAS | YLSRTNTPSGTTTQSRLQ | KTSADNNNSEYSWTGATK | KKDEEK | QGSEKTNVDIEK | RGNRQAATADVN | | |
|---|---|---|---|---|---|---|---|
| TA..T | F.....AGG.IV.L.G.R | ..DGE....DF....... | ...... | E.GA.N..A..G | A..A........ | 0.13 | 22 |
| ..... | .................. | .................. | R..N.. | E.GAGAD...GQ | A..A........ | 0.13 | 22 |
| ..... | .................. | .................. | E....R | ............ | A..A........ | 0.13 | 22 |
| SA... | .................. | .KYT.....NF......T | R..AGR | ENAG.SD.E..H | A..A........ | 0.13 | 22 |
| ..... | .................. | .........DF....... | ...DDR | ............ | A..A........ | 0.13 | 22 |
| ..... | .................. | .................. | R..DD. | ............ | A..A........ | 0.13 | 21 |
| ..... | .................. | ................T | ...DDR | E.ANG...E.G. | A..A........ | 0.13 | 21 |
| TA..T | .................. | .........DF....... | ....D. | ESGS.S.IA.DQ | A..A........ | 0.13 | 21 |
| ..... | .................. | .................. | R...D. | ..TG.A.I..D. | A..A........ | 0.13 | 21 |
| TA... | F.....GGG.LD.T...R | .Q.DR.....F....... | ....D. | ............ | A..A........ | 0.13 | 21 |
| N.... | .................. | TQ.TH....DF....... | ....D. | EN.GTN.AE.DN | A..A........ | 0.13 | 21 |
| ..... | .................. | .................. | ....DR | .NAATD...V.H | A..A........ | 0.13 | 21 |
| N.... | F.....GS..NM.N.T.R | ..DGE....DF....... | ...... | E.TTGNDI...R | A..A........ | 0.13 | 21 |
| R.... | .................. | ..DGE....DF....... | ...A.. | ..TK.GD..FGQ | A..A........ | 0.13 | 21 |
| ..... | .................. | .Q.DR.....F....... | ....D. | .NAA.A....GD | A..A........ | 0.13 | 21 |
| ..... | .................. | ................T | ...DDR | EDGDGA..A.DR | A..A........ | 0.13 | 21 |
| AT..N | .................. | ........F......T | ...DDR | ..AG.S...NGQ | A..A........ | 0.13 | 21 |
| NA... | F.....GRG.H..P.E.R | .QAS......F....... | ...... | .S.SGN.IE..D | A..A........ | 0.12 | 20 |
| AA... | F.....DG..PE.K.K.L | .V........F....... | ...... | E.AAG..T..GR | A..A........ | 0.12 | 20 |
| A.... | .................. | .QYGQ....DF......T | E..TGR | ...R.G....E | A..A........ | 0.12 | 20 |
| S.... | .................. | TKDDR....DF....... | ....D. | ...AAA.IE..Q | A..A........ | 0.12 | 20 |
| ..... | .................. | .........NF......T | G..DD. | ..TG.D..A.GG | A..A........ | 0.12 | 20 |
| HT... | F.....AGA.NK.L...K | .QAS.....NF......T | ...... | ............ | A..A........ | 0.12 | 20 |
| ..... | .................K | .................. | G..ND. | E.AG...IAVDR | A..A........ | 0.12 | 20 |
| ..... | F.....GGG.HN.H.T.M | ..HG.....NF......T | R..DR | ............ | A..A........ | 0.12 | 20 |
| N.... | F.....NKG.S..H.K.G | T..SE....DF..P...T | ....GR | ............ | A..A........ | 0.12 | 20 |
| ..... | .................. | .................. | ...... | .D.GA..IEV.Q | A..A........ | 0.12 | 20 |
| ..... | .................. | .................. | ...... | ..A..NDI..GR | A..A........ | 0.12 | 20 |
| ..... | .................. | .................. | ...DDR | ...GTND.AYDE | A..A........ | 0.12 | 19 |
| ..... | .................. | .................. | ...D.R | .DANRN..E.GQ | A..A........ | 0.12 | 19 |
| .A... | .................. | .................. | R..DD. | ............ | ............ | 0.12 | 19 |
| D...T | .................. | .QAS.....NF......T | ....GR | .NGGTG..A.DR | A..A........ | 0.12 | 19 |
| ..... | .F................ | .V........F....... | ...... | ............ | SRQNT...TN.D | 0.12 | 19 |
| SA... | .................. | .QPN......F......T | ...N.. | .D.GRAD.AF.S | A..A........ | 0.12 | 19 |
| ..... | .................. | .................. | ...ADR | .SAKAA.AA.DE | A..A........ | 0.12 | 19 |
| ..... | .F................ | .V........F....... | ...... | ............ | GSRSR..FE..T | 0.12 | 19 |

TABLE 7-continued

AAV capsid proteins having increased specificity for and/or transduction of
CD44+ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F.....SA..SI.M.G.R | T.PNE....DF....... | R...D. | E.......... | ............ | 0.12 | 19 |
| ..... | .................. | ..DGE....DF....... | R...DR | ..T.GNDI..GN | A...A........ | 0.12 | 19 |
| ..... | .................. | .................. | E..NG. | ............ | ............ | 0.12 | 19 |
| ..... | .................. | .V........F....... | ...... | ..TGGSD.A.DN | A...AE....... | 0.12 | 19 |
| ..... | .................. | .................. | ...DDR | E.A.AD.AAF.. | A...A........ | 0.12 | 19 |
| ..... | .................. | .................. | R..D.. | ESAAGD.IE.GD | A...A........ | 0.12 | 19 |
| ..... | .................. | .................. | R..TGR | .NAG.DD...DQ | A...A........ | 0.11 | 18 |
| ..... | .................. | .................. | R...D. | .DGST.....GG | A...A........ | 0.11 | 18 |
| ..... | F.....DHT.R..M.G.R | .................. | ...... | ............ | A...A........ | 0.11 | 18 |
| ..... | F................. | .V........F....... | ...... | ............ | GPRDR..VKE.A | 0.11 | 18 |
| HT... | F......TA.PL.P.... | .QPG.....NF....... | ...DDR | ............ | A...A........ | 0.11 | 18 |
| ..... | F................. | .V........F....... | ...... | ............ | .AQTR..D.A.H | 0.11 | 18 |
| ..... | .................. | .................. | E..KD. | ............ | ............ | 0.11 | 18 |
| ..... | .................. | .................. | G..ND. | E..G.S.T.FDS | A...A........ | 0.11 | 18 |
| ..... | .................. | .........NF......T | R..TG. | .DGG.....Y.Q | A...A........ | 0.11 | 18 |
| ..... | F................. | .V........F....... | ...... | ............ | GTRNS..FRE.. | 0.11 | 18 |
| ..... | .................. | .................. | R..TD. | ............ | A...A........ | 0.11 | 18 |
| ..... | F................. | .................. | ...N.. | .SAKAA.AA.DE | A...A........ | 0.10 | 17 |
| ..... | .................. | .........DF....... | ...DDR | .SGTRA..A.GE | A...A........ | 0.10 | 17 |
| ..... | .................. | .................. | ...DD. | ..GNGN..E..S | A...A........ | 0.10 | 17 |
| GA... | .................. | .Q.DH....NF....... | ...DD. | ED.G.N....GR | A...A........ | 0.10 | 17 |
| ..... | F................. | .V........F....... | ...... | ............ | DKRDG..FKV.D | 0.10 | 17 |
| ..... | ..........P.A.K | .QPG.....NF....... | ...DDR | E.GGEN..EF.S | A...A........ | 0.10 | 17 |
| SA... | F......KT.NV.K.T.H | .................. | ...... | EDAG.AD.E.G. | A...A........ | 0.10 | 17 |
| ..... | .................. | .................. | ...... | E.AG.S...... | A...A........ | 0.10 | 17 |
| ..... | .................. | .................. | ...DDR | ..TNGA.IA..G | A...A........ | 0.10 | 17 |
| AA... | F.....AEG.LK.M.H.L | .DGE.....DF....... | ...... | ............ | ............ | 0.10 | 17 |
| ..... | F.....SGA..V.T.G.G | .V........F....... | ...... | ............ | A...A........ | 0.10 | 17 |
| ..... | .................. | .................. | ...NDR | ..TGAS.A..DH | A...A........ | 0.10 | 17 |
| GT... | .................. | .................. | ...... | ............ | ............ | 0.10 | 17 |
| ..... | .................. | .................. | ....D. | .DAGES..A.GD | A...A........ | 0.10 | 17 |
| ..... | F.....GDG....K.Q.R | .V........F....... | ...... | .NATG....VGS | A...A........ | 0.10 | 17 |
| AA... | .................. | .KAS.....NF......T | E..DD. | ............ | A...A........ | 0.10 | 17 |
| T.... | F.....ATA..V.H...R | .QAS......F....... | ...... | .SGDE.D.E.DR | A...A........ | 0.10 | 17 |
| ..... | .................. | .................. | E..NDR | ............ | A...A........ | 0.10 | 16 |
| G.... | .................. | .QANH....DF....... | ...DDR | ............ | A...A........ | 0.10 | 16 |

TABLE 7-continued

AAV capsid proteins having increased specificity for and/or transduction of CD44<sup>+</sup> GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | .Q.G.....F..P.... | ...... | E..TA.D...GR | A..A........ | 0.10 | 16 |
| ..... | F................. | .V........F....... | ...... | ............ | GRKGG...NV.E | 0.10 | 16 |
| ..... | F.....GS..NK.M.A.F | ..YN......F......T | ...D.R | ............ | A..A........ | 0.10 | 16 |
| ..... | F................. | .V........F...... | ...... | ............ | ATRA...VDN.. | 0.10 | 16 |
| D.... | F.....NTG.LH.T...R | ................. | ...DD. | EDGNAA....DQ | A..A........ | 0.10 | 16 |
| ..... | ................. | .QPGQ....NF....... | E..AD. | .SASEN.I..DR | A..A........ | 0.10 | 16 |
| NA..T | F.....GRG.HD...T.K | ..HG.....NF......T | ...A.. | E.ANGG.A...D | A..A........ | 0.10 | 16 |
| .A... | F.....NGG.NN.K.T.R | .V........F....... | ...... | ............ | A..A........ | 0.10 | 16 |
| ..... | ................. | ................. | ...D.. | .SAS.N.IA..E | A..A........ | 0.10 | 16 |
| ..... | F.....SD..HP.L.Q.K | .Q.DH....NF....... | ...DD. | ............ | A..A........ | 0.10 | 16 |
| ..... | ................. | ................. | ...D.. | ............ | GNKGS..VDI.T | 0.10 | 16 |
| ..... | F.....AAT.IN.N.D.K | ..DGE....DF......T | R...D. | ............ | A..A........ | 0.10 | 16 |
| ST... | F.....SAG..L.H...K | .QAS......F....... | ...... | ENAAGGDAE.GE | A..A........ | 0.10 | 16 |
| ..... | ................. | ..DGE....DF....... | R...D. | EN.GT..AA.GD | A..A........ | 0.10 | 16 |
| ..... | F.....GRT.PQ.T.T.R | ..YN......F......T | ...... | .N.KGAD.A.GE | A..A........ | 0.10 | 16 |
| ..... | ................. | ................. | ....GR | ENRAG......E | A..A........ | 0.10 | 16 |
| ..... | ................. | ................. | R..DDR | ............ | A..A........ | 0.10 | 16 |
| SA... | F.....GHA.SK.T.E.K | ...DG....DF....... | E..KD. | ............ | A..A........ | 0.10 | 16 |
| ..... | ................. | ..AGR....DF....... | ...D.. | .NAG.DD...DQ | A..A........ | 0.10 | 16 |
| ..... | ................. | ..PNG....DF....... | R..AGR | ............ | A..A........ | 0.10 | 16 |
| ..... | ................. | ................. | ...... | E.TGTA.AGVGE | A..A........ | 0.10 | 16 |
| E.... | F.....GH..P..P.S.V | .........NF....... | R...D. | ............ | A..A........ | 0.10 | 16 |
| ..... | F................. | .V........F....... | ...... | ............ | NTRDH..S.V.K | 0.10 | 16 |
| ..... | ................. | ....E.....F....... | ...... | .SAT.N.IA..H | A..A........ | 0.10 | 16 |
| ..... | F................. | .V........F....... | ...... | ............ | GQQTP..STT.H | 0.10 | 16 |
| HT... | F.....NTG.HP.T.G.M | T.P......DF....... | ...D.. | ............ | ............ | 0.10 | 16 |
| T.... | F.....NA..LV.I.D.R | ..PN.....NF....... | ...NDR | ............ | A..A........ | 0.10 | 16 |
| ..... | ................. | ................. | ....D. | EDGSED..A..Q | A..A........ | 0.10 | 16 |
| ..... | ................. | ................. | ....D. | ..TTGA..AY.D | A..A........ | 0.10 | 16 |
| TA... | F.....DGA.R..P.A.K | ..YN......F......T | R..DD. | ............ | A..A........ | 0.09 | 15 |
| ..... | ................K | .Q.DH....NF....... | ...DD. | E.AT.A.AEVDS | A..A........ | 0.09 | 15 |
| ST... | F.....NR..RE.I...G | T.PSE............ | ...... | ............ | A..A........ | 0.09 | 15 |
| TA... | ......STT.HA.L.T.K | ..YNH.....F....... | ....D. | .DAAGN..A..E | A..A........ | 0.09 | 15 |
| N.... | F.....GRT.ND.L.Q.R | T.PTG....DF....... | ...DDR | ............ | A..A........ | 0.09 | 15 |
| ..... | ................. | .........DF......T | ...TG. | ............ | A..A........ | 0.09 | 15 |
| ..... | ................. | ................. | ...D.. | E.AGANDA.AV.H | A..A........ | 0.09 | 15 |

TABLE 7-continued

AAV capsid proteins having increased specificity for and/or transduction of
CD44+ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F................. | .V........F....... | ...... | ............ | GPKNP..DRT.D | 0.09 | 15 |
| ..... | ................. | ...............T | ...D.. | ............ | ............ | 0.09 | 15 |
| TA... | F.....SRA.SK.N.A.H | .QDT.....DF....... | ...DDR | ...G.S..AFGD | A..A........ | 0.09 | 15 |
| A.... | F.....SA..RA.....R | ..YN......F......T | ...D.. | ............ | A..A........ | 0.09 | 15 |
| R...T | ................. | .V........F....... | E..TD. | ............ | ............ | 0.09 | 15 |
| ST... | F.....NKG.N..K.G.G | .........NF....... | R...D. | ............ | A..A........ | 0.09 | 15 |
| ..... | ................. | ................. | ...DD. | E..T.G.TA.DH | A..A........ | 0.09 | 15 |
| ..... | F.....DA..IA.L.K.R | .KDSR............ | E..AD. | ............ | ............ | 0.09 | 15 |
| ..... | ................. | ................. | G..K.. | E.AGRDD..V.E | A..A........ | 0.09 | 15 |
| ..... | ................. | ................. | G..D.R | ............ | A..A........ | 0.09 | 15 |
| ..... | ................. | ................. | R..D.. | ESG.RAD..V.Q | A..A........ | 0.09 | 15 |
| ..... | ................. | ................. | ...DD. | EDGR.GD.E.GS | A..A........ | 0.09 | 15 |
| ..... | ................. | ..........F...... | R..TGR | ............ | A..A........ | 0.09 | 15 |
| ..... | ................. | ................. | R..DD. | ...ARS.A.FDG | A..A........ | 0.09 | 15 |
| DA... | F.......T.SV...H.R | ..DGE....DF....... | ...... | EN.G.SD..VDR | A..A........ | 0.09 | 15 |
| DT... | ................. | .Q.GQ....DF....... | ...ADR | ............ | A..A........ | 0.09 | 15 |
| ..... | F................ | ................. | R..DD. | ............ | ............ | 0.09 | 15 |
| ..... | F.....DRG.SL.M...I | ................. | ...NGR | ............ | A..A........ | 0.09 | 14 |
| ..... | F................ | .V........F....... | ...... | ............ | TRQS...FSM.. | 0.09 | 14 |
| ..... | ................. | ................. | ...D.. | ..TNE..I..DG | A..A........ | 0.09 | 14 |
| ..... | ................. | ................. | R..... | ..AAG..AA..R | A..A........ | 0.09 | 14 |
| ..... | ................. | .........DF......T | ...... | ..ANTN.TA.DS | A..A........ | 0.09 | 14 |
| E.... | F.....DS..NH.I.P.R | ..PNG....DF....... | ...NGR | ............ | A..A........ | 0.09 | 14 |
| ..... | ................. | ................. | R...D. | .SAG...TEYD. | A..A........ | 0.09 | 14 |
| ..... | ................. | .KYT.....NF..P...T | R..D.. | ............ | A..A........ | 0.09 | 14 |
| G.... | F.....AEG.LK.M.H.L | ....TE....F....... | ...DDR | ............ | A..A........ | 0.09 | 14 |
| EA... | F.....DAA.IK.T.Q.N | ..DGE....DF....... | ...... | E........... | ............ | 0.09 | 14 |
| ..... | ................. | ................. | G..TDR | E.AGGN..E.DD | ............ | 0.09 | 14 |
| ..... | F................ | .V........F....... | ...... | ............ | G.QTT..Y.G.E | 0.09 | 14 |
| ..... | ................. | .........DF...... | R...D.. | ..TAGA.AA.DN | A..A........ | 0.09 | 14 |
| G.... | F.....STA..Q.H.Q.L | .Q.DR.....F....... | ....D. | ............ | A..A........ | 0.09 | 14 |
| AT... | F.....AST.PI.K.Q.K | TQ.TH....DF....... | ...... | ............ | A..A........ | 0.09 | 14 |
| R.... | ......NKT.I....... | .........DF....... | ...D.R | .DANRN.A.VDH | A..A........ | 0.09 | 14 |
| ..... | F......GT.NM.L.Q.G | .Q.S......F....... | ....D. | ............ | ............ | 0.09 | 14 |
| ..... | ................. | ................. | ....D. | .DGKGS.IA..G | A..A........ | 0.09 | 14 |
| ..... | ................. | ................. | E..DGR | ............ | ............ | 0.09 | 14 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................ | .................... | ...DDR | ENTTGNDAE.GQ | A..A........ | 0.09 | 14 |
| D...T | F.....GRT.ND.L.Q.R | ..PNG....DF....... | G..NDR | E..GGG..EF.G | A..A........ | 0.09 | 14 |
| ..... | ................ | .................... | ...... | .DTAAA...VGE | A..A........ | 0.09 | 14 |
| ..... | F............... | .V........F...... | ...... | ............ | ERRTS....V.. | 0.09 | 14 |
| ..... | F............... | .V........F...... | ...... | ............ | DHRAT..SNN.D | 0.09 | 14 |
| ..... | F............... | .V........F...... | ...... | ............ | G.RG...SGA.. | 0.09 | 14 |
| ..... | ................ | ........DF....... | ...DDR | .NG..G.I...G | A..A........ | 0.08 | 13 |
| SA..T | F.....NET.NA.P...K | ..HG.....NF......T | ...A.. | ............ | A..A........ | 0.08 | 13 |
| G.... | ................ | .Q.S......F....... | ....D. | ............ | ............ | 0.08 | 13 |
| NT... | F.....ATG.NV.T.G.R | .Q.DR.....F....... | ....D. | EDAGT...AFD. | A..A........ | 0.08 | 13 |
| A.... | F.....NA..RL.T.P.G | T.P.......F....... | R..DD. | ............ | A..A........ | 0.08 | 13 |
| ..... | F............... | .V........F...... | ...... | ............ | DTRSG...R..A | 0.08 | 13 |
| ..... | ................ | .................... | ...DD. | E.TGAN.AE.GE | A..A........ | 0.08 | 13 |
| ..... | ................ | .................... | G..KGR | ..AAE..A.F.E | A..A........ | 0.08 | 13 |
| ..... | ................ | ........DF....... | ...D.R | E.GDEAD...DR | A..A........ | 0.08 | 13 |
| ..... | F............... | .V........F...... | ...... | ............ | NETRT..FHT.D | 0.08 | 13 |
| E.... | F.....AA...K.T.E.L | TQ.GG....NF....... | ...D.R | ............ | A..A........ | 0.08 | 13 |
| ..... | ................ | .................... | ...AG. | ..AARS..AF.. | A..A........ | 0.08 | 13 |
| T.... | ................ | ..PNG....DF....... | G..NDR | ............ | ............ | 0.08 | 13 |
| ..... | ................ | .................... | ...D.. | E.TGAN.AE.GE | A..A........ | 0.08 | 13 |
| A.... | ................ | TQ.TG....DF....... | ...... | ..ARAA.I..GQ | A..A........ | 0.08 | 13 |
| ..... | F............... | .V........F...... | ...... | ............ | GPRTP..FDI.A | 0.08 | 13 |
| .A... | F.....NQG....P.K.I | TK.NE....DF......T | ...... | ..AGAN..A.GD | A..A........ | 0.08 | 13 |
| ..... | ................ | .................... | R...D. | .D.NGA.TE.GD | A..A........ | 0.08 | 13 |
| ..... | ................ | .................... | R...DR | ES.GEG...VDS | A..A........ | 0.08 | 13 |
| G...T | F.....AHA.SH.M.S.R | ..DGE....DF....... | ...... | .SGGRS..E.DQ | A..A........ | 0.08 | 13 |
| ..... | F............... | .V........F...... | ...... | ............ | AR.G...IDV.H | 0.08 | 13 |
| ..... | ................ | .................... | ....GR | .SAKGG..EYGD | A..A........ | 0.08 | 13 |
| ..... | ................ | .................... | ...KD. | .DTA.N....DS | A..A........ | 0.08 | 13 |
| G.... | F.....DTA.PK...P.R | ..HG.....NF......T | ...AD. | E.AG.ADIE.G. | A..A........ | 0.08 | 13 |
| RT... | F.....ART..V.N.K.. | ..........F....... | G..AD. | ............ | A..A........ | 0.08 | 13 |
| ..... | F.....DAT.NL.H.Q.L | ..........F.....T | ...DG. | ............ | ............ | 0.08 | 13 |
| GA..T | F.....STG..N.M.Y.. | ..YN.....F.....T | ....D. | ............ | A..A........ | 0.08 | 13 |
| ..... | ................ | ........DF.....T | G..AD. | ESG..N.I..DG | A..A........ | 0.08 | 13 |
| A.... | F.....SA..RA.....R | TKPDR.....F....... | R..D.. | .SAGAN..E..S | A..A........ | 0.08 | 13 |
| TA..T | ................ | ..HG.....NF......T | ...TDR | .SA....AEVDD | A..A........ | 0.08 | 13 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| .A... | F.....ATT..N.L...L | ..ADG....DF....... | ...DDR | ............ | A..A........ | 0.08 | 13 |
| ..... | .................. | .PPNG.....F......T | ...DDR | E.TR.N.....Q | ............ | 0.08 | 13 |
| ..... | .................. | .................. | ...DDR | .STAAG...VDG | A..A........ | 0.08 | 13 |
| D...T | F.....SRA.SK.N.A.H | ..DGE....DF....... | ...... | ..AST..AA..D | A..A........ | 0.08 | 13 |
| ..... | F.....NDG.NH.L.A.R | TKPS.....DF......T | ...DDR | ............ | A..A........ | 0.08 | 13 |
| GA... | F.....STA..Q.H.Q.L | T.P......DF....... | R...D. | ............ | ............ | 0.08 | 13 |
| R.... | .................. | TQASG....DF....... | ...... | E.AG..D.A.GR | A..A........ | 0.08 | 13 |
| RA... | F.....DGA.R..P.A.K | .........NF....... | R...D. | ............ | A..A........ | 0.07 | 12 |
| E.... | .................. | .................. | ...... | ............ | ............ | 0.07 | 12 |
| ..... | .................. | .................. | R..TDR | .D.RA......S | A..A........ | 0.07 | 12 |
| RA... | .................. | ..AGR....DF......T | G..N.. | ............ | A..A........ | 0.07 | 12 |
| .A... | F.....DG..I..K.K.G | .QPSG....NF....... | E..TGR | ............ | ............ | 0.07 | 12 |
| TT..T | .................. | ..HG.....NF......T | E..DD. | ............ | A..A........ | 0.07 | 12 |
| GA... | F......DG.HV.M.A.R | .........DF....... | R..DD. | ............ | A..A........ | 0.07 | 12 |
| ..... | .................. | .................. | ...N.. | EDGKGA....GE | A..A........ | 0.07 | 12 |
| ..... | .................. | .................. | R...G. | EN.AGGD.E... | A..A........ | 0.07 | 12 |
| ..... | .................. | .................. | ...... | E.GGANDT...G | A..A........ | 0.07 | 12 |
| ..... | F.....SN..PL.K.T.. | .................. | G..DG. | ............ | ............ | 0.07 | 12 |
| RA... | F.....SG..IK.K.D.R | ..ADH....DF....... | E..AD. | .SADAG..A..S | A..A........ | 0.07 | 12 |
| ..... | F.....SN..PL.K.T.. | T.ADG...DF......T | ...D.. | ............ | ............ | 0.07 | 12 |
| ..... | .................. | .QANH.....F......T | ...DDR | .DTAGN...Y.R | A..A........ | 0.07 | 12 |
| ..... | .................. | .................. | ...AG. | ............ | A..A........ | 0.07 | 12 |
| ET..T | F.....ANG.HL.K.K.S | ..........F......T | ...D.. | ............ | A..A........ | 0.07 | 12 |
| ..... | .................. | ...TG....NF....... | R..AD. | EDAKGG.....R | A..A........ | 0.07 | 12 |
| ..... | .................. | .................. | ...DDR | .NGST.....GG | A..A........ | 0.07 | 12 |
| ..... | .................. | .........NF....... | G..TDR | .DGG.....Y.Q | A..A........ | 0.07 | 12 |
| ..... | .................. | .................. | R...DR | ............ | A..A........ | 0.07 | 12 |
| ..... | ......HK.P.N.G | .........NF....... | ...NDR | ............ | ............ | 0.07 | 12 |
| ..... | .................R | .................. | ...... | ..ATESD..FDQ | A..A........ | 0.07 | 12 |
| ..... | .................. | .................. | ....GR | ............ | A..A........ | 0.07 | 12 |
| TA..T | .................. | .PPNG.....F......T | ...DDR | ............ | A..A........ | 0.07 | 12 |
| ..... | F.....ANG.HL.K.K.S | .................. | G..N.. | ............ | A..A........ | 0.07 | 12 |
| SA... | F......TT.HN.L.G.R | ..DGE....DF....... | ...... | E.AKGG..A.DQ | A..A........ | 0.07 | 12 |
| ..... | F................. | .V.......F........ | ...... | ............ | GRHGT...K..A | 0.07 | 12 |
| ..... | .................. | .................. | G..DG. | ............ | ARSNR..FDV.H | 0.07 | 12 |
| ..... | F.....DGA.R..P.A.G | .........NF......T | R..... | .DA..N..A..E | A..A........ | 0.07 | 12 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| SA..T | F.....NAA.I..M.G.R | .Q.S......F....... | ...D.. | ........... | A..A........ | 0.07 | 12 |
| .A... | F.....DNA.NA.M.N.K | ..PNC....DF....... | G..NDR | ........... | A..A........ | 0.07 | 12 |
| ..... | F................. | .V........F....... | ...... | ........... | T.KGR...N..Q | 0.07 | 12 |
| ..... | ................. | ................. | ...A.. | ..AKGD.AEYDQ | A..A........ | 0.07 | 12 |
| N.... | F.....NTG.RN.T.T.L | ..DGE....DF....... | ...... | ........... | A..A........ | 0.07 | 12 |
| GA... | F.....GAT.RL.H.Q.E | .QPN......F......T | ...DD. | ........... | A..A........ | 0.07 | 12 |
| T.... | ................. | ................. | ...... | ........... | A..A........ | 0.07 | 12 |
| ..... | F.....AE...A.T...R | ................. | ...... | E.TGTA.AEVGE | A..A........ | 0.07 | 12 |
| ST... | F.....GR..HD.L.N.L | ..AGR.....F......T | ....D. | ........... | A..A........ | 0.07 | 12 |
| ST... | F.....SKA.S..L.E.R | .QPG.....NF....... | G..AG. | ........... | A..A........ | 0.07 | 12 |
| E.... | ................. | T.AG......F......T | ...DD | ..TKRDD.A.DE | A..A........ | 0.07 | 11 |
| ..... | F................. | .V........F....... | ...... | ........... | GRHAA..NDA.P | 0.07 | 11 |
| GT... | ................. | ................. | ...... | EN.TTG.IE.DR | A..A........ | 0.07 | 11 |
| RT... | F......S..PM.T.S.K | .Q.......DF....... | ...AD. | ........... | A..A........ | 0.07 | 11 |
| ..... | ................. | ................T | ...DDR | .SAKAA.AA.DE | A..A........ | 0.07 | 11 |
| TA... | ................. | .QPN......F......T | ...N.. | .DTAG.D.A.DG | A..A........ | 0.07 | 11 |
| NA... | F.....NRA..I.T...S | .KDDG....NF......T | ...DG. | ........... | A..A........ | 0.07 | 11 |
| ..... | F.....GGG.HN.H.T.M | ..HG.....NF......T | R...DR | .........D. | A..A........ | 0.07 | 11 |
| ..... | ................. | ................T | E..ND. | ........... | A..A........ | 0.07 | 11 |
| ..... | ................. | ................. | E..ND. | ........... | ........... | 0.07 | 11 |
| ..... | F................. | .V........F....... | ...... | ........... | GRSGR...EG.T | 0.07 | 11 |
| GT... | F.....GKA.SE.N...K | T.AG.....NF......T | ...N.. | ........... | A..A........ | 0.07 | 11 |
| ..... | ................. | ................. | R...GR | EDGDGA..A.DR | A..A........ | 0.07 | 11 |
| ..... | F.....GN..NK.P.P.N | TQPTE....DF....... | ...DDR | ........... | A..A........ | 0.07 | 11 |
| ..... | F.....NGG.NV.N.K.G | .QAS......F....... | ...... | E.AGGN..A.DG | A..A........ | 0.07 | 11 |
| .A... | F.....SKA.S..L.E.R | ................. | ...D.. | ........... | A..A........ | 0.07 | 11 |
| SA... | ................. | ..HG.....NF......T | ...A.. | ........... | A..A........ | 0.07 | 11 |
| D.... | F.....S.T.NV.L.D.. | .........NF....... | R...D. | ........... | A..A........ | 0.07 | 11 |
| DA... | F......RT.LA.L.G.K | TQ.TG....DF....... | ...DDR | ........... | A..A........ | 0.07 | 11 |
| GT... | F.....AGA.LQ.T.E.R | .PPNG.....F......T | ....GR | E.AG..D.A.GR | A..A........ | 0.07 | 11 |
| DA..T | F.....STA..Q.H.Q.L | ................. | ...A.. | .N.KA.DAE..D | A..A........ | 0.07 | 11 |
| ..... | ................. | ................. | ...... | ..GGTD....DR | A..A........ | 0.07 | 11 |
| ..... | F................. | .V........F....... | ...... | ........... | GPRTG...HT.E | 0.07 | 11 |
| ..... | F................. | .V........F....... | ...... | ........... | .P.T...AHG.H | 0.07 | 11 |
| ..... | ................. | ................. | E..KD. | .S.TAA.TEFDE | A..A........ | 0.07 | 11 |
| ..... | ................. | ................. | G..DD. | ........... | A..A........ | 0.07 | 11 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| D...T | F.....AN..SI.L.H.R | .........NF....... | R...D. | E.TA.S..EY.. | A..A........ | 0.07 | 11 |
| NT..T | F.....AA..IQ.T.K.R | TQ.TG....DF....... | ...DDR | ..AGRADI...S | A..A........ | 0.07 | 11 |
| ..... | ................. | ................. | ...KG. | | A..A........ | 0.07 | 11 |
| ..... | ................. | ................. | ....D. | ESAGRSDTA.DE | ............ | 0.07 | 11 |
| D...T | F.....STA..Q.H.Q.L | ..YN......F......T | ...D.. | | A..A........ | 0.07 | 11 |
| G.... | F.....A...ND.T...K | .QPN......F......T | ...ADR | .D.GRA...F.. | A..A........ | 0.07 | 11 |
| D...T | F.....DGA.RN.T.S.G | ..HG.....NF....... | ...D.. | | A..A........ | 0.07 | 11 |
| AA... | F.....NKG.IP.N.H.R | .QDT.....DF....... | G..DG. | ..GGG.D.E... | A..A........ | 0.07 | 11 |
| ..... | ................. | .V........F....... | E..TD. | | ............ | 0.07 | 11 |
| ..... | ................. | ................. | ....... | | GRKNA..FQN.E | 0.07 | 11 |
| ..... | F......S..PM.T.S.K | ................. | ...D.. | | A..A........ | 0.07 | 11 |
| ..... | ................. | ................. | ....D. | ENAS.N.AEYDR | A..A........ | 0.07 | 11 |
| DT... | F......N..IL.T.T.R | .QPSQ....NF....... | G...GR | | A..A........ | 0.07 | 11 |
| ..... | ................. | ................. | ...DDR | | ............ | 0.07 | 11 |
| ..... | ................. | .QP.G.....F......T | ...DDR | | A..A........ | 0.07 | 11 |
| ..... | F................. | .V........F....... | ...... | | TPRAR..DNI.D | 0.07 | 11 |
| DT... | ................. | ..DGE....DF....... | ...... | | ............ | 0.07 | 11 |
| ..... | ................. | ................. | ...DDR | EDGSR...E.GE | A..A........ | 0.07 | 11 |
| ..... | F................. | .V........F....... | ...... | | GARA...ISG.Q | 0.07 | 11 |
| E.... | ................. | ................. | ...... | | A..A........ | 0.07 | 11 |
| ..... | ................. | ................. | ...ADR | .SGGA.....DG | A..A........ | 0.07 | 11 |
| RT... | F.....SA..RA.....F | .KDT......F......T | ...DD. | EN.D.A..EVDD | A..A........ | 0.07 | 11 |
| ..... | ................. | ................. | ....GR | ..AGA..AA.GS | A..A........ | 0.07 | 11 |
| ..... | F................. | .V........F....... | ...... | | GTRST..FRE.T | 0.07 | 11 |
| GT... | F.....GG..SL.L...B | ..DGE....DF....... | ...... | ES.DRN.....Q | A..A........ | 0.06 | 10 |
| ..... | F................. | .V........F....... | ...... | | ARRDA..NR..T | 0.06 | 10 |
| S.... | ................. | TKA......NF....... | ...... | ESAK..D.E..N | A..A........ | 0.06 | 10 |
| ..... | F................. | .V........F....... | ...... | | ADKTA..VKG.Q | 0.06 | 10 |
| ..... | F................. | .V........F....... | ...... | | KRQAG...HE.A | 0.06 | 10 |
| NT... | F.....AT..SM.L.H.R | .V........F......T | ...A.. | | A..A........ | 0.06 | 10 |
| GT... | ................. | ................. | ...DG. | | A..A........ | 0.06 | 10 |
| ..... | ................. | ..YN......F......T | ...D.R | EDGKGN..AF.. | A..A........ | 0.06 | 10 |
| ..... | F................. | .V........F....... | ...... | | DKQTS..FRG.Q | 0.06 | 10 |
| ..... | F................. | .V........F....... | ...... | | GNRNN...TN.T | 0.06 | 10 |
| TT... | F.....GRG.H..P.E.M | ..DGE...DF....... | ...... | ..AG.N.AA.GQ | A..A........ | 0.06 | 10 |
| ..... | F................. | .V................ | R..DD. | | THRDT..FRM.T | 0.06 | 10 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................ | ................ | R...D. | ..AAG..AA..R | A..A........ | 0.06 | 10 |
| TT... | F.....GGT.IV.K.G.K | .Q.DR....DF....... | ...DDR | ............ | GQKDR..ST..H | 0.06 | 10 |
| ..... | ................ | ................ | E..TD. | ............ | A..A........ | 0.06 | 10 |
| ..... | ................ | ........NF....... | E..ND. | ES.GAN..EVDG | A..A........ | 0.06 | 10 |
| NA... | F.....DSG.RV.P.G.H | ..P.E....NF......T | R..TGR | E.AG.S..E.DN | A..A........ | 0.06 | 10 |
| A.... | F................ | .V........F...... | ...... | ............ | TASSA..Y.A.. | 0.06 | 10 |
| ..... | ................ | ........DF....... | ...... | .DAAGS.AAVD. | A..A........ | 0.06 | 10 |
| TA... | F................ | .V........F...... | ...... | ............ | A..A........ | 0.06 | 10 |
| TA... | F................ | .V........F...... | ...... | ............ | ERRTH...TE.. | 0.06 | 10 |
| ..... | ................ | TQ.TG....DF....... | ...DDR | ............ | A..A........ | 0.06 | 10 |
| ..... | ................ | ................ | ....GR | ..ARRGD.A.DE | A..A........ | 0.06 | 10 |
| ..... | F................ | .V........F...... | ...... | ............ | A.RAG..VR..H | 0.06 | 10 |
| ..... | F.....DEA.RQ.T.N.L | .........NF....... | R...D. | ..ASE...E.D. | A..A........ | 0.06 | 10 |
| ..... | ................ | ................ | ...... | E.AG.A.T.V.N | A..A........ | 0.06 | 10 |
| ..... | F................ | .V........F...... | ...... | ............ | THRDA...EG.E | 0.06 | 10 |
| ..... | ................ | ................ | ...DDR | ENGGGSDAE.DD | A..A........ | 0.06 | 10 |
| .A... | F.....NAG.P..T.T.M | .........DF....... | ...DDR | ..AGAS...FDR | ............ | 0.06 | 10 |
| ..... | ................ | ................ | R..A.. | ............ | A..A........ | 0.06 | 10 |
| NA... | ................ | .V........F...... | ...... | ESTARN.A.V.Q | A..A........ | 0.06 | 10 |
| .A... | ................ | ..A......DF....... | ...DG. | EN.G.A.....Q | A..A........ | 0.06 | 10 |
| ..... | ................ | ................ | ....G. | ..ATGSD.A..H | A..A........ | 0.06 | 10 |
| ..... | ................ | ................ | ...DDR | .DAKGN..EVGQ | A..A........ | 0.06 | 10 |
| ..... | ................ | ................ | ...DDR | .STTEA....GQ | A..A........ | 0.06 | 10 |
| ..... | ................ | ................ | ...... | EDGTA..IE..E | A..A........ | 0.06 | 10 |
| SA..T | ................ | .QPG.....NF....... | ...DDR | .DTRTG.A..GG | A........... | 0.06 | 10 |
| .A... | F.....DRG.S..T.A.S | ..DGE....DF....... | ...... | ............ | A..A........ | 0.06 | 10 |
| NA... | ................ | ................ | E..NG. | ............ | ............ | 0.06 | 10 |
| ..... | F................ | .V........F...... | ...... | ............ | AK.TE...G... | 0.06 | 10 |
| ..... | F.....ASA.S..T.T.G | .QPG.....DF....... | ...DDR | ............ | A..A........ | 0.06 | 10 |
| ..... | F................ | .V........F...... | ...... | ............ | GNRGN....... | 0.06 | 10 |
| RA... | ................ | .KYT.....NF......T | R..DD. | E.TGAN.AE.GE | A..A........ | 0.06 | 10 |
| AA... | F.....GRG.SP.K...G | .QPG.....NF....... | ...DDR | ............ | DRRSA..YTT.Q | 0.06 | 10 |
| ..... | F................ | .V........F...... | ...... | ............ | THRAA..SR... | 0.06 | 10 |
| ..... | ................ | ................ | R..DD. | E.TS.D..AFDQ | A..A........ | 0.06 | 10 |
| ..... | F................ | .V........F...... | ...... | ............ | G..T...VRM.T | 0.06 | 10 |
| G.... | ................ | .QHNQ.....F......T | G..NDR | ..TGAS..EV.N | A..A........ | 0.06 | 10 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F................. | .V........F....... | ...... | ............ | DQRGT...RG.D | 0.06 | 10 |
| ..... | ................. | TKDDR....DF........ | ...DGR | ESAGAN.AE.CE | A..A........ | 0.06 | 10 |
| .A... | F................. | .........DF....... | ...DDR | ..AGAS...FDR | ............ | 0.06 | 10 |
| R.... | ................. | TKDDR....DF....... | ...DDR | ............ | A..A........ | 0.06 | 10 |
| GT... | ................. | TQ.TG....DF....... | ...DDR | .SADAG..A..S | A..A........ | 0.06 | 10 |
| TA... | F.....GGG.LD.T...R | .Q.S......F....... | E..N.. | ............ | A..A........ | 0.06 | 10 |
| ..... | ................. | .........DF....... | ...A.. | ..AN.A..AV.G | A..A........ | 0.06 | 10 |
| A.... | F.....AEG.NI.L.K.R | TPPSQ....NF......T | R..AGR | ............ | A..A........ | 0.06 | 10 |
| ..... | F.....AEG.LK.M.H.L | ..DGE....DF....... | ...... | ............ | A..A........ | 0.06 | 10 |
| ..... | ................. | ..HG.............. | ...AG. | ............ | A..A........ | 0.06 | 10 |
| ..... | F................. | .V........F....... | ...... | ............ | GERTP..ART.D | 0.06 | 10 |
| ..... | F................. | .V........F....... | ...... | ............ | TRRD...N.S.P | 0.06 | 10 |
| ..... | F................. | .V........F....... | ...... | ............ | AASAG..YNN.A | 0.05 | 9 |
| ....T | F.....GRT.ND.L.Q.R | T..NE....DF......T | ...DD. | ............ | A..A........ | 0.05 | 9 |
| GA... | F.....DQ..R..P.S.R | ..DGE....DF....... | ...... | .N.ARS..E.GQ | A..A........ | 0.05 | 9 |
| ..... | ................. | .................. | E..AD. | ............ | A..A........ | 0.05 | 9 |
| ..... | F................. | .V........F....... | ...... | ............ | GTRSP..S.N.D | 0.05 | 9 |
| ..... | ................. | .................. | ...D.. | E.GGEG..E.DG | A..A........ | 0.05 | 9 |
| ..... | ................. | ..HGH....NF......T | ...D.. | ............ | A..A........ | 0.05 | 9 |
| ..... | ................. | .........DF....... | ...D.. | .S.KA..TE.DS | A..A........ | 0.05 | 9 |
| ..... | ................. | .QD.E.....F..P.... | E..N.. | ............ | A..A........ | 0.05 | 9 |
| ..... | ................. | .................. | ...DDR | ESGTA.D..VDR | A..A........ | 0.05 | 9 |
| T.... | F.....DDG.LA.K...R | .................. | ...... | ............ | A..A........ | 0.05 | 9 |
| ..... | ................. | .................. | R..N.. | .D.TGN.I...Q | A..A........ | 0.05 | 9 |
| DT..T | F................. | .V........F....... | ...... | ............ | SNST...YHV.E | 0.05 | 9 |
| ..... | ................. | ..A......DF....... | ...A.. | ESAGRN.IE.GG | A..A........ | 0.05 | 9 |
| ..... | ................. | .................. | ...D.R | EDGATG...VDR | A..A........ | 0.05 | 9 |
| ..... | ................. | .................. | E..ND. | E.AGGND....R | A..A........ | 0.05 | 9 |
| ..... | F................. | .V........F....... | ...... | ............ | GNRAP..IS..E | 0.05 | 9 |
| ..... | F................. | .V........F....... | ...... | ............ | GRRDN..YRT.T | 0.05 | 9 |
| AT... | ................. | .................. | ...DD. | ..GNGN..E..S | A..A........ | 0.05 | 9 |
| ..... | ................. | .................. | ...... | .D.N.A...VGE | A..A........ | 0.05 | 9 |
| .A... | F................. | .................. | ...D.. | ............ | A..A........ | 0.05 | 9 |
| ..... | ................. | .................. | R..ADR | ..ADA..TEVDS | A..A........ | 0.05 | 9 |
| D.... | F.....SRT..A...T.N | T.P......DF....... | ...D.. | ............ | ............ | 0.05 | 9 |
| AA... | F.....GRG.SP.K...G | .QPG.....NF....... | ...DDR | ............ | A..A........ | 0.05 | 9 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | ................... | R..... | E.GTEGDA.... | A..A........ | 0.05 | 9 |
| EA... | F.....DH..ID.K...V | ................... | ...... | ..AG.DD...GG | A..A........ | 0.05 | 9 |
| ..... | ................. | ................... | ...D.. | ESGAAA..EV.Q | A..A........ | 0.05 | 9 |
| ..... | ................. | ................... | R..DG. | .SGKRA..E.DQ | A..A........ | 0.05 | 9 |
| H.... | ................. | .Q.S......F...... | E..NG. | ............ | ............ | 0.05 | 9 |
| G.... | ................. | ................... | G..KD. | ............ | A..A........ | 0.05 | 9 |
| .T..T | ................. | ..AGR.....F......T | R..D.. | ............ | A..A........ | 0.05 | 9 |
| ..... | ................. | ................... | ...DD. | ...RTD..A..H | A..A........ | 0.05 | 9 |
| ..... | ................. | ................... | ...DGR | E.ADGA..AYDR | A..A........ | 0.05 | 9 |
| A.... | ................. | TKDDR....DF...... | ...DDR | ............ | ............ | 0.05 | 9 |
| ..... | ................. | ................... | ...KD. | ............ | A..A........ | 0.05 | 9 |
| ..... | ................. | ................... | ...D.. | .DAGRG..AYDH | A..A........ | 0.05 | 9 |
| ..... | ................. | ................... | ...NGR | EDAT.D.A..D. | A..A........ | 0.05 | 9 |
| ..... | ................. | ....E...DF...... | ...... | E.GTEGDIA..D | A.KA........ | 0.05 | 9 |
| ..... | ................. | ..YG......F.....T | E..DD. | ............ | A..A........ | 0.05 | 9 |
| ..... | ................. | ................... | ...AG. | ESTTEA...... | A..A........ | 0.05 | 9 |
| ..... | ................. | TKDDR....DF...... | ...DDR | ............ | A..A........ | 0.05 | 9 |
| EA... | F.....SN..PL.K.T.. | .Q.DR.....F...... | ....D. | ...NRAD.E..Q | A..A........ | 0.05 | 9 |
| ..... | F................G | ..PDG.....F...... | E..N.. | ............ | A..A........ | 0.05 | 9 |
| ..... | ..........K.L...G | ................T | G..DD. | ESAA.D..E.GD | A..A........ | 0.05 | 9 |
| ..... | ................. | TK.G.....DF...... | ...D.. | ..GTA.D.EFD. | A..A........ | 0.05 | 9 |
| ..... | ................. | ................... | ...... | .DAKG..I.FDG | A..A........ | 0.05 | 9 |
| ..... | ................. | ................... | ...DDR | ..ATGS..EYGS | A..A........ | 0.05 | 9 |
| ..... | ................. | ................... | ...D.R | ..ARTADTE.DS | A..A........ | 0.05 | 9 |
| A.... | F.....SA..RA.....F | ................... | ...... | ............ | A..A........ | 0.05 | 9 |
| ..... | ................. | ................... | ...DDR | .STAES.IH.DG | A..A........ | 0.05 | 9 |
| ..... | ................. | ................... | ...D.R | EDAGRGD...GN | A..A........ | 0.05 | 9 |
| DA... | F................ | .V........F...... | ...... | ............ | TRRDP..DNM.T | 0.05 | 9 |
| ..... | ................. | ................... | ...DDR | E..GRD..AVDG | A..A........ | 0.05 | 9 |
| E.... | F................ | .V........F...... | ...... | ............ | NKQNG..NHE.T | 0.05 | 9 |
| N.... | ................. | ................... | ...DDR | ENTTGNDAE.GQ | A..A........ | 0.05 | 9 |
| TA... | F.....AEG.LK.M.H.L | ..DGE....DF...... | ...... | ............ | A..A........ | 0.05 | 9 |
| ..... | ................. | ................... | ....D. | ..ATESD..FDQ | A..A........ | 0.05 | 9 |
| GT... | F.....SD..I..H.D.R | ................... | ...... | ............ | ............ | 0.05 | 9 |
| DA... | F.....GNG.HV.H.G.R | ........DF...... | ...... | ............ | ............ | 0.05 | 9 |
| DT... | F.....SAG..L.P.H.S | ..YN......F......T | ...D.. | ............ | A..A........ | 0.05 | 9 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| E.... | F.....GAT.IN.M.K.L | ..DGE....DF....... | ...N.. | .......... | A..A........ | 0.05 | 9 |
| GT..T | F................. | .V........F....... | ...... | .......... | NPRNN..AR..H | 0.05 | 9 |
| ..... | .................. | .........DF....... | G..DD. | ED.NGN.IA.D. | A..A........ | 0.05 | 9 |
| ..... | .................. | ...............T | G..ND. | ESAGAN....GG | A..A........ | 0.05 | 9 |
| RA... | ......AST.IN.L.T.. | ..DGE....DF....... | ...... | .......... | ............ | 0.05 | 9 |
| ..... | .................. | .V........F....... | ...... | EDATRS..E..G | A..A........ | 0.05 | 9 |
| ..... | .................. | .QPG.....NF.....T | ...... | .......... | GRHAA..NDA.P | 0.05 | 9 |
| ..... | .................. | ................. | R..DD. | E..KT.D.A..D | A..A........ | 0.05 | 9 |
| .A... | .................. | ................. | ...DDR | .......... | ............ | 0.05 | 9 |
| ..... | .................. | ...............T | ...DDR | .SAS.N.IA..E | A..A........ | 0.05 | 9 |
| ..... | .................. | ................. | R..D.. | E.AGG.DI..GH | A..A........ | 0.05 | 9 |
| ..... | .................. | ................. | ....D. | ...DGSDT..GG | A..A........ | 0.05 | 9 |
| ..... | .................. | ................. | E..DDR | E.AGG.D.E.DG | A..A........ | 0.05 | 9 |
| ..... | .................. | ................. | ...AG. | EDAAR.D.A.D. | A..A........ | 0.05 | 9 |
| TA... | F.....GDG.RH.L.K.G | .Q.DR....DF....... | R...D. | .......... | .......... | 0.05 | 9 |
| ..... | .................. | .V........F....... | R..AD. | .......... | A..A........ | 0.05 | 8 |
| NA..T | F.....NKG.N..K.G.S | ..DSH....DF.....T | ...D.. | .......... | A..A........ | 0.05 | 8 |
| ..... | .................. | ................. | E..DDR | .NA.AS.A..DR | A..A........ | 0.05 | 8 |
| ..... | .................. | ................. | ...... | .......... | DHRAR..FG... | 0.05 | 8 |
| ..... | F................. | .V........F....... | ...... | .......... | GPRT....RV.D | 0.05 | 8 |
| ..... | F................. | .V........F....... | ...... | .......... | AARDG...TV.H | 0.05 | 8 |
| ..... | F................. | ................R | ...ADR | E.GTEGDIA..D | A..A........ | 0.05 | 8 |
| ET..T | F.....STA..Q.H.Q.G | .........NF....... | R...D. | .......... | A..A........ | 0.05 | 8 |
| ..... | .................. | ................. | R..A.. | E.ATRA.IE.DD | A..A........ | 0.05 | 8 |
| ..... | .................. | ................. | T..DD. | ..ASE...E.D. | A..A........ | 0.05 | 8 |
| GA..T | F......AG.NP.P.D.R | .QAS.....NF.....T | ...... | .......... | A..A........ | 0.05 | 8 |
| DT... | F.....AR..SL...H.G | ..HG.....NF.....T | ...A.. | .......... | A..A........ | 0.05 | 8 |
| ..... | F................. | ................. | ...D.. | ..ASES.I..DG | A..A........ | 0.05 | 8 |
| GA..T | F......QG.NQ...A.R | .KYT.....NF.....T | ...D.. | .......... | A..A........ | 0.05 | 8 |
| S.... | .................. | ................. | R..... | EN.NES.T..DG | A..A........ | 0.05 | 8 |
| ..... | .................. | ..PN.....NF....... | ....G. | .N.TA.DAA.GD | A..A........ | 0.05 | 8 |
| ..... | .................. | ................. | ...... | E.AGG.D.E.DS | A..A........ | 0.05 | 8 |
| .A..T | F.....GKG.RK.L.N.E | ...GG.....F.....T | ...D.. | .......... | A..A........ | 0.05 | 8 |
| G.... | .................. | ..........F.....T | R..N.. | ENAAEG.I..DR | A..A........ | 0.05 | 8 |
| .T... | .................. | ...............T | ...... | .NAAAN..EF.H | A..A........ | 0.05 | 8 |
| TA... | F.....GS..NM.N.T.R | .QPN......F.....T | ....D. | E.TG.D.IAF.Q | A..A........ | 0.05 | 8 |

TABLE 7-continued

AAV capsid proteins having increased specificity for and/or transduction of CD44$^+$ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................. | ................. | ...... | E..R.N.AEFGE | A..A........ | 0.05 | 8 |
| ..... | F................ | ................. | R...DR | .DA.TSD..VDR | A..A........ | 0.05 | 8 |
| ET... | F......QT..M.T...R | .KDT......F......T | ...DD. | E....ND.EF.Q | A..A........ | 0.05 | 8 |
| NA..T | ................. | .........DF....... | ...AD. | ............ | A..A........ | 0.05 | 8 |
| ..... | ................. | ..........F...... | ...... | ............ | A.SDT...R..A | 0.05 | 8 |
| ..... | ................. | ................. | ...DDR | .DAGTA...FGG | A..A........ | 0.05 | 8 |
| ..... | ................. | ..HG.....NF...... | E..DD. | ............ | ............ | 0.05 | 8 |
| ..... | ................. | ................. | ...D.. | .SAGRGDAAVDE | A..A........ | 0.05 | 8 |
| ..... | F......GA.NM.T.A.R | ..DGE....DF...... | ...... | E.AAAD.I..GQ | A..A........ | 0.05 | 8 |
| ..... | ................. | ................. | ...DDR | E.AGGN.TE..G | A..A........ | 0.05 | 8 |
| ..... | F................ | .V.......F...... | ...... | .SA.GG....DG | A..A........ | 0.05 | 8 |
| ..... | ................. | ................. | G..N.. | ............ | A..A........ | 0.05 | 8 |
| ..... | F................ | .V.......F...... | ...... | ............ | ADRTA..AH..H | 0.05 | 8 |
| ..... | ................. | ................T | ....D. | E.TGRA..A..G | A..A........ | 0.05 | 8 |
| ..... | F................ | .V.......F...... | ...... | ............ | G.RDE..DRT.. | 0.05 | 8 |
| ..... | ................. | ................. | ...D.R | .DAGES..AF.Q | A..A........ | 0.05 | 8 |
| ..... | ................. | .QANH.....F......T | R..A.. | E..A.ADA..GD | A..A........ | 0.05 | 8 |
| ..... | ................. | ................. | ....D. | ED.R.S.A...G | A..A........ | 0.05 | 8 |
| .A..T | F.......I | ..........F...... | R..DG. | ..ATESD..FDQ | A..A........ | 0.05 | 8 |
| ..... | ................. | ................. | ....D. | ..TD.N...VGQ | A..A........ | 0.05 | 8 |
| ..... | F................ | .V.......F...... | ...... | ............ | THRTT..F.E.T | 0.05 | 8 |
| NT... | F................ | ..........F...... | ...... | EN.RGNDIEF.D | A..A........ | 0.05 | 8 |
| DT... | F.....AEG.SV.P.G.S | .QPG.....NF......T | ...DDR | ............ | A..A........ | 0.05 | 8 |
| ..... | F.....DRG.SL.M...I | ................. | ...... | ............ | ............ | 0.05 | 8 |
| ..... | ................. | ................. | ....DR | ENAAA...A..G | A..A........ | 0.05 | 8 |
| ..... | ................. | ................. | ...AG. | ............ | A..A........ | 0.05 | 8 |
| GT... | F.....ARG.HP.L.Q.K | ...DG....NF...... | ...DDR | ............ | A..A........ | 0.05 | 8 |
| D.... | ................. | .KYT.....NF......T | R..NG. | ............ | A..A........ | 0.05 | 8 |
| ..... | F.....SK..LD.L.T.G | .Q.......DF...... | ...AD. | ............ | A..A........ | 0.05 | 8 |
| .A... | F......GT.NM.L.Q.G | .Q.S......F...... | ...... | ............ | ............ | 0.05 | 8 |
| ..... | ................. | ................. | ...A.. | ............ | A..A........ | 0.05 | 8 |
| G.... | ................. | .QHNQ.....F......T | ...N.. | ............ | A..A........ | 0.05 | 8 |
| ..... | ................. | ................. | ...DDR | ..TGAS..EV.N | A..A........ | 0.05 | 8 |
| .T... | F.....SRG.SP.T...G | .........NF...... | R...D. | .SAKAA.AA.DE | A..A........ | 0.05 | 8 |
| .T... | F.....G...LL.L.G.K | T.P......DF...... | ...D.. | EN.KAGDA..GE | A..A........ | 0.05 | 8 |
| ..... | F.....STA..Q.H.Q.G | ................. | R...D. | ............ | A..A........ | 0.05 | 8 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| GT... | F.....SGA..N...G.R | .Q.......DF....... | ...AD. | .NAAEND...GE | A..A........ | 0.05 | 8 |
| NA... | ................. | ................. | ...... | .DAKG..I.FDG | A..A........ | 0.05 | 8 |
| .T... | F.....AAT.N..P.P.R | TQADR....NF......T | R...D. | ............ | A..A........ | 0.05 | 8 |
| ..... | F.....DH..ID.K...V | T.PGG....NF....... | ...DD. | ESGGGN.IA.DQ | A..A........ | 0.05 | 8 |
| A...T | F.....GRA..L.K.A.S | .QAS......F....... | ...... | ENTGEA....G. | A..A........ | 0.05 | 8 |
| TA... | F.....GG..NK.M.... | ..A......DF....... | ...DG. | ..GT.N..A.DE | A..A........ | 0.05 | 8 |
| ..... | F................. | .PPNG.....F......T | ...DDR | E.TR.N.....Q | ............ | 0.05 | 8 |
| ..... | ................. | ................T | ....GR | ..TGAS..EV.N | A..A...... | 0.05 | 8 |
| GT... | F.....SA..RA.....R | ...DG....DF....... | R..TDR | ..A.AN..AV.Q | A..A........ | 0.05 | 8 |
| AT... | F.....GRG.SP.K...G | T.P......DF....... | ...... | EN.G.A.....Q | A..A........ | 0.05 | 8 |
| ..... | F.....STA..Q.H.Q.L | ..DGE....DF....... | ...... | ............ | A..A........ | 0.05 | 8 |
| ..... | F................. | .V........F....... | ...... | ............ | GHRGT..VTE.T | 0.05 | 8 |
| H.... | F.....SGA..N...G.R | .PANG.....F....... | ...DDR | E.ANGG.A...D | A..A........ | 0.05 | 8 |
| ..... | ................. | .V.......NF....... | E..AD. | ..GGA.D.E.GN | A..A........ | 0.04 | 7 |
| GT... | F................. | ................. | G..DG. | ............ | ............ | 0.04 | 7 |
| ..... | ......GRG.H..P.E.R | ..PNG...RDF....... | G..NDR | ............ | A..A........ | 0.04 | 7 |
| ..... | ................. | .V................ | ...... | ............ | .PRDG..SNV.A | 0.04 | 7 |
| GA... | F.....SAA.NM.M.A.L | TQP.R....DF....... | ...DDR | ............ | A..A........ | 0.04 | 7 |
| E.... | F.....ASA.S..T.T.G | .Q.DH....NF....... | ...DD. | ............ | A..A........ | 0.04 | 7 |
| ..... | ......D.G.IN.L.P.K | .QPG.....DF....... | ...DDR | ............ | A..A........ | 0.04 | 7 |
| ..... | ................. | ................. | R..A.. | .S.G.S.IA..G | A..A........ | 0.04 | 7 |
| E.... | F.....AA..IQ.T.K.R | .QAS......F....... | ...... | E.AARSD...GS | A..A........ | 0.04 | 7 |
| ..... | ................. | ................. | ...... | ESG.GN..EVDR | A..A........ | 0.04 | 7 |
| ..... | ................. | ................. | ...N.. | ..TG.A.I..D. | A..A........ | 0.04 | 7 |
| TT... | F.....DRG.SD.K.K.. | ..DNH....DF....... | ...ADR | ............ | A..A........ | 0.04 | 7 |
| ..... | F.....DRG.SL.M...I | ................. | ...... | .SAKAA.AA.DE | A..A........ | 0.04 | 7 |
| ..... | ................. | ................. | ...D.. | E.TAE..I.... | A..A........ | 0.04 | 7 |
| G.... | ................. | ................. | ...... | .SARG..A..DE | A..A........ | 0.04 | 7 |
| GT... | ................. | TQDT.....DF..P.... | R..DD. | ............ | A..A........ | 0.04 | 7 |
| T.... | G.....GS..NK.M.A.T | .QPSR.....F....... | ...... | ESAAG.D.AF.S | A..A........ | 0.04 | 7 |
| NA... | F......S..PM.T.S.K | ..DGE....DF....... | ...... | .S.SGN.IE..D | A..A........ | 0.04 | 7 |
| G.... | ................. | .QPTG....NF....... | E..AGR | ............ | A..A........ | 0.04 | 7 |
| ..... | ................. | ................. | ...AD. | E.AAGA.IA.GD | A..A........ | 0.04 | 7 |
| DA... | F.....DTG.SK.T.T.R | .QPTG.....F....... | ...NGR | ............ | A..A........ | 0.04 | 7 |
| ..... | F................. | .V........F....... | ...... | ............ | DSRGG..FSE.. | 0.04 | 7 |
| ..... | ................. | .........NF......T | G..DD. | E.ANGG.A...D | A..A........ | 0.04 | 7 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ET..T | F.....SG..IQ.M.Q.T | .KPDQ.....F....... | R..... | ............ | A..A........ | 0.04 | 7 |
| GA... | F.....GQ..LN.L.D.R | .Q.GQ....DF....... | ....GR | ............ | A..A....... | 0.04 | 7 |
| ..... | ................. | ................. | R..DD. | ...TG..T..GQ | A..A........ | 0.04 | 7 |
| ..... | ................. | ................. | ...AGR | .N.NRN.....G | A..A........ | 0.04 | 7 |
| ..... | F.....DAA.IK.T.Q.N | ..DGE....DF....... | ...... | E........... | ............ | 0.04 | 7 |
| TT..T | F......EA.SL.K.Q.R | ..DDG...DF....... | ...DDR | ............ | ............ | 0.04 | 7 |
| ..... | F................. | .V........F....... | ...... | ............ | GAKSG..Y.N.. | 0.04 | 7 |
| A.... | ................. | .QPN......F......T | ...N.. | E.AGAND.AV.H | A..A........ | 0.04 | 7 |
| ..... | ................. | ................. | ....D. | .SAAGAD.A.DS | A..A........ | 0.04 | 7 |
| ..... | ................. | ..HG.....NF......T | ..A... | ............ | A..A........ | 0.04 | 7 |
| D...T | F.....GSA.RV.L.A.R | ................. | ...D.R | E.TR.N...... | A..A........ | 0.04 | 7 |
| NA..T | ................. | ..HG.....NF......T | ...A.. | EDAG.AD.E.G. | A..A........ | 0.04 | 7 |
| SA... | ................. | ................. | E..N.. | ..ATAAD.E.DG | A..A........ | 0.04 | 7 |
| ..... | F.....DQ..R..P.S.R | .Q.DR.....F....... | ....D. | ............ | A..A........ | 0.04 | 7 |
| ..... | F................. | .V........F....... | R..ND. | ..AG...IAYGN | A..A........ | 0.04 | 7 |
| ..... | ................. | ................. | R..DD. | ..AGAD...FDG | A..A........ | 0.04 | 7 |
| HA... | F.....GKG.ND.T.N.G | ..A......DF....... | ...DG. | ............ | ............ | 0.04 | 7 |
| ..... | F................. | .V........F....... | ...... | ............ | GAHAN..DGM.A | 0.04 | 7 |
| ..... | ................. | ................. | ....D. | ..TGAS..EV.N | A..A........ | 0.04 | 7 |
| G.... | ................. | TQTPH....NF....... | R..DD. | E.AGGN...FGE | A..A........ | 0.04 | 7 |
| ..... | ................. | ................. | G..ND. | ED.A.G.T..DN | A..A........ | 0.04 | 7 |
| ..... | ................. | ..........F....... | ...NGR | .DAG.S.A..DR | A..A........ | 0.04 | 7 |
| ..... | F................. | .V.......F....... | ...... | ............ | ATKDG..SRA.Q | 0.04 | 7 |
| ..... | F................. | ................. | R..TGR | ............ | A..A........ | 0.04 | 7 |
| ..... | ................. | ................. | ...D.. | E.GTEGDA..D. | A..A........ | 0.04 | 7 |
| A...T | ................. | TQDS.....NF....... | ...A.. | E.AGTNDI.... | A..A........ | 0.04 | 7 |
| ....T | ................. | ..PN.....NF....... | R...D. | ESTGGND.EYDQ | A..A........ | 0.04 | 7 |
| RT... | ................. | ...DR....DF......T | G...D. | E.TR.N.....Q | A..A........ | 0.04 | 7 |
| ..... | F................. | .V........F....... | ...... | ............ | .RHDT..YET.H | 0.04 | 7 |
| .A... | F.....ST..SV.K.H.M | T.ASH....DF......T | ...D.. | ............ | A..A...NEA.H | 0.04 | 7 |
| ..... | ................. | .........NF....... | R...D. | EDTAASDA...R | A..A........ | 0.04 | 7 |
| ..... | ................. | ................. | ...DD. | EN.G.A....KQ | A..A........ | 0.04 | 7 |
| ..... | ................. | ................. | ...... | ENGGTN..E.GN | A..A........ | 0.04 | 7 |
| ..... | F................. | ..DGE....DF....... | ...DDR | ............ | ............ | 0.04 | 7 |
| ..... | ................. | ................. | ...DDR | ES.AA..I.... | A..A........ | 0.04 | 7 |
| G.... | F.....GNG.HV.H.G.R | ..DGE....DF....... | ...... | .N.TA.DI.VDG | A..A........ | 0.04 | 7 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | .................K | .........DF......T | R...G. | .DAD.A.AEFGQ | A..A........ | 0.04 | 7 |
| ..... | .................. | ..HG.....NF......T | ..A... | E.TSGGD.E..Q | A..A........ | 0.04 | 7 |
| .T... | F.....GN..IK.L.G.K | .Q.DR.....F | ....D. | ............ | A..A........ | 0.04 | 7 |
| TA... | .................. | ..ADH....DF....... | G..A.R | ............ | A..A........ | 0.04 | 7 |
| ..... | .................. | | R..AGR | ............ | A..A........ | 0.04 | 7 |
| AA... | F......G..RP.L.A.G | T..NE....DF......T | E..... | ............ | ............ | 0.04 | 7 |
| .A... | .................. | TQDS.....NF....... | ...... | .DGGGN.....R | A..A........ | 0.04 | 7 |
| ..... | F................. | .V........F....... | ...... | ............ | KQSSA..VR..H | 0.04 | 7 |
| N.... | F.....GRG.N......H | .........NF....... | R...D. | ............ | A..A........ | 0.04 | 7 |
| G.... | F.....SA..RA.....R | .PPNG.....F......T | ...DDR | E.AGG.D.E.DS | A..A........ | 0.04 | 7 |
| A.... | F.....GSA.RP.N.H.K | ..DGE....DF....... | ....GR | ENAGASDIA.DH | ............ | 0.04 | 7 |
| TA... | F................. | .V........F....... | ....D. | ............ | A..A........ | 0.04 | 7 |
| AA... | .................. | TQP.R....NF......T | R...D. | ..A.G...AYD. | A..A........ | 0.04 | 7 |
| ..... | .................. | .................. | ...... | .S.ATGDTE.DG | ............ | 0.04 | 7 |
| DA... | .................. | .................. | R..A.. | E.GG.....FD. | A..A........ | 0.04 | 7 |
| ..... | .................. | .................. | ...ADR | E.AG..D.A.GE | A..A........ | 0.04 | 7 |
| ..... | F................. | .V........F....... | ...... | ............ | TASSA..Y.A.. | 0.04 | 7 |
| ..... | .................. | .................. | R..ND. | ..AG.N.AA.GQ | A..A........ | 0.04 | 7 |
| ..... | .................. | ..HG.....NF......T | R..AGR | ............ | A..A........ | 0.04 | 7 |
| ..... | .................. | T.AG.....NF......T | ...... | .D.GGGD.EVDE | A..A........ | 0.04 | 7 |
| ..... | F................. | .................. | G..N.. | ............ | A..A........ | 0.04 | 7 |
| ..... | .................. | .................. | ...TD. | .SGGRS..E.DQ | A..A........ | 0.04 | 7 |
| ..... | F................. | .V........F....... | ...... | ............ | KTKTP..FDG.. | 0.04 | 7 |
| ..... | .................. | .........DF....... | ...A.. | ............ | A........... | 0.04 | 7 |
| ..... | .................. | .................. | R..ND. | E..RRDD..V.Q. | A..A........ | 0.04 | 7 |
| ..... | .................. | .................. | G...D. | ............ | A..A........ | 0.04 | 7 |
| GT... | F.....AEG.LK.M.H.L | ..DGE....DF.R..... | ...... | ............ | ............ | 0.04 | 7 |
| ..... | F................. | .V........F....... | ...... | ............ | KRSNG..V.G.D | 0.04 | 7 |
| RA..T | .................. | T.P......DF....... | ...DDR | ..AGG..T..GR | A..A........ | 0.04 | 7 |
| TA..T | .................. | .................. | ...D.. | .SGS.NDIA..D | A..A........ | 0.04 | 7 |
| A.... | ......SRT..A...... | T.P......DF....... | ...DD. | ............ | A..A........ | 0.04 | 7 |
| E.... | F.....AGG.P..L...G | .V........F....... | ...... | EN.GE..IA.DR | ............ | 0.04 | 7 |
| ..... | .................. | .................. | E..NG. | ............ | GTRGT..ADA.Q | 0.04 | 7 |
| ..... | .................. | .................. | E..ND. | ............ | GARGN...Q..K | 0.04 | 7 |
| ..... | F................. | .V........F....... | ...... | ............ | G.HAP..SER.. | 0.04 | 7 |
| D.... | ......ARG.IA.I.E.G | .Q.DR.....F | ....D. | ..AST..AA..D | A..A........ | 0.04 | 7 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................. | .................. | R...D. | EDANG...EVDR | A..A........ | 0.04 | 7 |
| ..... | F................ | ..........F....... | ...DD. | ............ | GPHAG..FDT.A | 0.04 | 7 |
| ..... | ................. | .................. | ...A.R | ............ | A..A........ | 0.04 | 7 |
| ..... | ................. | .................. | ...DDR | .DAD.A....G. | A..A........ | 0.04 | 7 |
| TA... | F................ | .V........F....... | ...... | ............ | SARSA..AD..A | 0.04 | 7 |
| ..... | F................ | ...............T | ...A.. | .SAKAA.AA.DE | ............ | 0.04 | 7 |
| ..... | ................. | T..SG....DF......T | ...DD. | E.GSAA.A.VDQ | A..A........ | 0.04 | 7 |
| ..... | ................. | .................. | E..AG. | ............ | A..A........ | 0.04 | 7 |
| ..... | ................. | .................. | R..D.. | ..ASAAD.E..D | A..A........ | 0.04 | 7 |
| ..... | ................. | .................. | ...... | ...TG..T..GQ | A..A........ | 0.04 | 7 |
| ..... | ................. | .................. | G..KD. | ............ | A..A........ | 0.04 | 7 |
| ..... | ................. | ..ATR....DF....... | ....D. | ............ | A..A........ | 0.04 | 7 |
| ST..T | F................ | .V........F....... | ...... | ............ | GTRT...DRA.. | 0.04 | 7 |
| R.... | F.....DEA.RQ.T.N.L | .........NF...... | R...D. | ..ASE...E.D. | A..A........ | 0.04 | 7 |
| ..... | F.....NTG.PP.T.Q.S | ........DF....... | ...... | ............ | ............ | 0.04 | 7 |
| DA... | F.....DEA.RQ.T.N.L | .........NF...... | R...D. | ..ASE...E.D. | A..A........ | 0.04 | 7 |
| ..... | ................. | .................. | R...GR | .SAKAA.AA.DE | A..A........ | 0.04 | 7 |
| AA... | ................. | .Q.......DF....... | G..AGR | E..TGSD..VDR | A..A........ | 0.04 | 7 |
| ..... | F.....NTG.RN.T.T.L | .QP.G.....F....... | ...... | ............ | A..A........ | 0.04 | 7 |
| DA..T | F.....SKT.NE.P...M | .K.TG....DF....... | R..DR | ............ | A..A........ | 0.04 | 7 |
| NT..T | F.....NN..SA.N...R | ...SG....DF......T | ...... | ............ | A..A........ | 0.04 | 7 |
| ..... | ................. | .................. | R..DGR | ............ | A..A........ | 0.04 | 6 |
| ..... | ................. | .................. | ...DDR | ..ASES...VDG | A..A........ | 0.04 | 6 |
| ..... | F................ | .V........F....... | ...... | ............ | GTKDG..YQE.A | 0.04 | 6 |
| ..... | ................. | .................. | ....GR | ...GAD.IA..F | A..A........ | 0.04 | 6 |
| GT... | ................. | .................. | ...DDR | ............ | TRRDP..DNM.T | 0.04 | 6 |
| ..... | ................. | ........DF....... | ..D... | ENGT.G.I.... | A..A........ | 0.04 | 6 |
| ..... | F................ | .V........F....... | ...... | ............ | GPRTA..AGE.A | 0.04 | 6 |
| ..... | F................ | .V........F....... | ...... | ............ | S.KGG..VTT.A | 0.04 | 6 |
| ..... | F.....AEG.LK.M.H.L | ..ADH....DF....... | ...... | ............ | A..A........ | 0.04 | 6 |
| GT... | ................. | ..........F....... | ...... | ES.GEG...VDS | A..A........ | 0.04 | 6 |
| ..... | F.....GGG.HN.H.T.M | .V........F....... | ...... | ............ | A..A........ | 0.04 | 6 |
| GT... | ................. | .................. | E..NG. | ............ | A..A........ | 0.04 | 6 |
| ..... | ................. | .V........ | R..N.. | ............ | TPRNN...EV.D | 0.04 | 6 |
| ..... | ................. | .................. | ....D. | ............ | ............ | 0.04 | 6 |
| ..... | ................. | .................. | R...DR | .N.AGNDAAVDE | A..A........ | 0.04 | 6 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| GA... | ................. | .QDT......F......T | R..KD. | ............ | A..A........ | 0.04 | 6 |
| NT... | ................. | .KAS.....NF......T | E..DD. | ............ | A..A........ | 0.04 | 6 |
| SA... | F.....NGG.IM.L.E.R | ..DGE....DF....... | ...... | ENAAAN.A.Y.S | A..A........ | 0.04 | 6 |
| ..... | ................. | .Q.S.....DF....... | ...D.. | ENGRGG.AEV.D | A..A........ | 0.04 | 6 |
| ..... | ................. | ................T | G..TG. | ............ | ............ | 0.04 | 6 |
| ..... | ................. | ................. | ....DR | ............ | ............ | 0.04 | 6 |
| ..... | ................. | ................. | R..DD. | EN.SAGD..... | A..A........ | 0.04 | 6 |
| ..... | ................. | .........DF......T | ...D.. | E.AGEG.I...R | A..A........ | 0.04 | 6 |
| ..... | F................. | .V........F....... | ...... | ............ | NARNT..A...T | 0.04 | 6 |
| TT... | F.....DNG..D.M.G.R | .KDSR....DF....... | ...DD. | ............ | A..A........ | 0.04 | 6 |
| ..... | ................. | TKDT.....NF......T | G..A.F | ............ | A..A........ | 0.04 | 6 |
| T...T | ................. | ................. | R..DDR | .NAG.DD...DQ | A..A........ | 0.04 | 6 |
| ..... | ................. | ................. | ...D.. | ..TARN.....R | A..A........ | 0.04 | 6 |
| ..... | F................. | .V........F....... | ...... | ............ | GQ.TP..IRT.A | 0.04 | 6 |
| NA..T | F.....NNG.R....N.G | T.ASH....DF....... | ...D.R | ..AG.N.AA.GQ | A..A........ | 0.04 | 6 |
| NA... | F.....NGG.NV.N.K.G | .Q.DR.....F....... | ....D. | ............ | A..A........ | 0.04 | 6 |
| ..... | ................. | ................. | ....GR | ...G.S..AFGD | A..A........ | 0.04 | 6 |
| ..... | F................. | .V........F....... | ...... | ............ | NTKSG..SSG.D | 0.04 | 6 |
| AA... | F.....NAT.RD.M.T.K | .QPN......F......T | ...N.. | ............ | A..A........ | 0.04 | 6 |
| ..... | ................. | ................. | G..N.. | .SARG..A..DE | A..A........ | 0.04 | 6 |
| ..... | F................. | .V........F... | ...... | ............ | TQRT...DRS.. | 0.04 | 6 |
| D.... | ................. | T.PTG....DF....... | ...DDR | .NATG....VGS | A..A........ | 0.04 | 6 |
| ....T | ................. | ................. | ...... | ............ | ............ | 0.04 | 6 |
| A.... | F.....DQ..R..P.S.R | T.ASH....DF....... | ...... | ..ASE...E.D. | A..A........ | 0.04 | 6 |
| NT..T | F.....GRT.S..L.G.R | .V........F....... | ...... | ES.AA..I.... | A..A........ | 0.04 | 6 |
| ..... | ................. | ................. | ...... | E.T..S.IE.GD | A..A........ | 0.04 | 6 |
| ..... | ................. | ................. | ...DDR | ............ | AD.GG..VQG.A | 0.04 | 6 |
| ..... | ................. | ................. | E..KD. | ............ | A..A........ | 0.04 | 6 |
| ..... | ................. | ................. | ...... | ESAN...I...H | A..A........ | 0.04 | 6 |
| A.... | F................. | .V........F....... | .Y.... | ............ | GKRGT..DDS.. | 0.04 | 6 |
| ..... | ................. | ................. | ....D. | ENTATDD...GH | A..A........ | 0.04 | 6 |
| E.... | ................. | .Q.S......F....... | E..N.. | .DASGSD..Y.R | A..A........ | 0.04 | 6 |
| ....T | F.....GTG..P.T.D.R | ..AGQ....NF....... | ...DD. | E.AGTNDI...R | A..A........ | 0.04 | 6 |
| ..... | F.....SAA..D.I.... | ..HG.....NF......T | ...A.. | .SAKAA.AA.DE | A..A........ | 0.04 | 6 |
| ..... | ................. | ................. | ...DDR | .SAKGS.AAYDS | A..A........ | 0.04 | 6 |
| ..... | F................. | .QP.G.....F....... | ...D.R | ............ | A..A........ | 0.04 | 6 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| RA..T | F......G..NL.I...R | .Q.DR.....F....... | ....D. | ........... | ........... | 0.04 | 6 |
| ..... | F.....NNA.S..T.E.G | T.PNE....DF....... | R...D. | E.......... | ........... | 0.04 | 6 |
| ..... | F.....GS..NM.N.T.R | .KDSR....DF....... | ...DDR | .DATA..A.Y.H | A..A........ | 0.04 | 6 |
| GT... | F.....AEG.LK.M.H.L | ..DGE....DF....... | ...... | ........... | A..A........ | 0.04 | 6 |
| R.... | ................. | TKDDR....NF....... | ....D. | ...AAA.IE..Q | A..A........ | 0.04 | 6 |
| ..... | F................. | .V........F....... | ...... | ........... | KRQST..STE.Q | 0.04 | 6 |
| T...T | ................. | .QPN......F......T | ...N.. | ..TG.D..A.GG | A..A........ | 0.04 | 6 |
| H.... | F.....SNG.P....T.R | ..YN.....DF....... | ...D.. | .SGGA...AFGD | A..A........ | 0.04 | 6 |
| ..... | F.....NR..NM.L.Q.G | .Q.S......F....... | ....G. | ........... | A..A........ | 0.04 | 6 |
| AA... | F......RG.SP.K.S.N | ..DGE....DF....... | ...... | ........... | A..A........ | 0.04 | 6 |
| ..... | ................. | .QAS......F....... | ...... | ........... | A..A........ | 0.04 | 6 |
| ..... | F.....GKT.I..N...S | TQASG.....F....... | ...D.. | E.ATAS.AAFDE | A..A........ | 0.04 | 6 |
| HA... | F.....GT.....L...S | T.P......DF....... | ...D.. | ........... | A..A........ | 0.04 | 6 |
| ..... | F................. | .V........F....... | ...... | .SADGSD...DR | A..A........ | 0.04 | 6 |
| TA..T | ................. | ................. | G..DG. | ........... | ........... | 0.04 | 6 |
| ..... | ................. | ................. | ...DD. | ...NRAD.E.DR | A..A........ | 0.04 | 6 |
| AA... | F.....SKG.NV.L.T.G | .QP.G.....F....... | E..AD. | ........... | A..A........ | 0.04 | 6 |
| ..... | ................. | ................. | ...D.R | .SAKAA.AA.DE | A..A........ | 0.04 | 6 |
| ..... | F................. | .V........F....... | ...... | ........... | DERGH..SDN.E | 0.04 | 6 |
| ..... | ................. | ................. | ...NDR | E.A.AD.AAF.. | A..A........ | 0.04 | 6 |
| ..... | ................. | .Q.GQ....DF....... | R..TDR | .DAG.S.A..DR | A..A........ | 0.04 | 6 |
| ..... | ................. | ..DGE....DF....... | R...D. | .STDRA...... | A..A........ | 0.04 | 6 |
| ..... | F................. | .V........F....... | ...DDR | E.A.G..A...N | A..A........ | 0.04 | 6 |
| ..... | ........N........ | ................. | R..DD. | ED.KAN..A.D. | A..A........ | 0.04 | 6 |
| HT..T | ................. | ..PN.....NF....... | R...D. | ESTGGND.EYDQ | A..A........ | 0.04 | 6 |
| ..... | F................. | .QPTR.....F....... | E..NG. | ........... | A..A........ | 0.04 | 6 |
| TA... | F.....ANG.HL.K.K.S | ................. | G..N.. | ........... | A..A........ | 0.04 | 6 |
| GA... | F.....ANG.HL.K.K.S | .Q.S......F....... | ...DDR | E.AGGS..AVDG | A..A........ | 0.04 | 6 |
| ..... | ................. | ..HG.....NF......T | E..DD. | ........... | AARTT..SGG.D | 0.04 | 6 |
| TT..T | F......EA.SL.K.Q.R | .QPG......F....... | ....D. | ........... | A..A........ | 0.04 | 6 |
| ..... | ................. | ................. | ...ND. | ..AGTN...NDE | A..A........ | 0.04 | 6 |
| ..... | ................. | ................. | ...N.. | ESAGA....Y.R | A..A........ | 0.04 | 6 |
| RT... | ................. | ..YN......F......T | ...D.R | ...TG..T..GQ | A..A........ | 0.04 | 6 |
| DA... | F......EG.LQ.M.A.K | .KDSR....DF....... | ...DDR | ........... | A..A........ | 0.04 | 6 |
| ..... | ................. | ................. | ...D.R | E.AST...E.GH | A..A........ | 0.04 | 6 |
| ..... | ................. | ........F......T | ...DG. | ........... | A..A........ | 0.04 | 6 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| EA... | .................... | .QD......DF..P.... | G..K.. | .S.G.S.IA..G | A..A........ | 0.04 | 6 |
| N.... | F.....GN..RM.T...E | ..HG.....NF......T | ...A.. | E.AG...IA.DD | A..A...SDR... | 0.04 | 6 |
| ..... | .................... | .QD......DF......T | R..DG. | .STAEG...F.. | A..A........ | 0.04 | 6 |
| ..... | F.....SN...P.H.T.K | TQ.TG............. | ...... | .DAKG..I.FDG | A..A........ | 0.04 | 6 |
| SA..T | F.....DGA.R..P.A.K | .Q.GQ....DF...... | ....G. | ...AAS.A.VGQ | A..A........ | 0.04 | 6 |
| G.... | .................... | TK.NE...NF....... | ...DDR | ............ | A..A........ | 0.04 | 6 |
| DT..T | .................... | ..........F...... | ...D.. | ............ | SNST...YHV.E | 0.04 | 6 |
| ..... | F.................. | .................. | ...DD. | .STGAD.....Q | A..A........ | 0.04 | 6 |
| ..... | .................... | TK.D.....NF......T | R..AG. | ............ | A..A........ | 0.04 | 6 |
| G...T | .................... | .KYT.....NF....... | ...NDR | ED.R.S.A...G. | A..A........ | 0.04 | 6 |
| G.... | .................... | .QP.G.....F....... | R..DDR | ............ | A..A........ | 0.04 | 6 |
| ..... | F.....S.T.NM.N.T.R | TQDS.....NF....... | ...A.. | .SAKAA.AA.DE | A..A........ | 0.04 | 6 |
| ..... | .................... | ..DGE....DF....... | ...... | ..TNESD..... | A..A........ | 0.04 | 6 |
| ..... | F.................. | .V........F....... | ...... | ............ | DPRAS..FKR.D | 0.04 | 6 |
| ..... | .................... | .QANH....NF......T | ...... | ............ | A..A........ | 0.04 | 6 |
| H.... | .................... | .PPNG.....F......T | ...DDR | E.TR.N.....Q | A..A........ | 0.04 | 6 |
| G.... | F.....NTG.LH.T...R | .PPN......F....... | ...D.. | ............ | A..A........ | 0.04 | 6 |
| ..... | .................... | ..............R... | ...D.. | ..TG.N.AA.GQ | A..A........ | 0.04 | 6 |
| EA... | .................... | .................. | G..DG. | ............ | ............ | 0.04 | 6 |
| ..... | ......SDT.I..L.... | ..PN.....NF....... | ...NDR | ............ | A..A........ | 0.04 | 6 |
| ..... | F.................. | .V........F....... | ...... | ............ | G.RSG..FTG.. | 0.04 | 6 |
| AA... | F.....GN..HM.P...R | TKDT.....NF....... | ...DDR | EDAGT...AFD. | A..A........ | 0.04 | 6 |
| ..... | .................... | .................. | ...DDR | ESGRANDA...S | A..A........ | 0.04 | 6 |
| G.... | .................... | .................. | ...... | ............ | ............ | 0.04 | 6 |
| ..... | F.....ANG.HL.K.K.S | ..DGE....DF....... | ...... | ............ | A..A........ | 0.04 | 6 |
| ..... | ....S.............. | .V........F....... | E..TD. | ............ | ............ | 0.04 | 6 |
| ..... | .................... | ..DD.....DF....... | E..AD. | E..RRA.....Y | A..A........ | 0.04 | 6 |
| NA... | F.....GQG.IA.....K | .................. | ...... | ............ | A..A........ | 0.04 | 6 |
| TA... | F.................. | .V........F....... | ...... | ............ | .R.T...SDV.D | 0.04 | 6 |
| NA... | F.....ATG.NV.T.G.R | .Q.DR.....F....... | ....D. | EDAGT...AFD. | A..A........ | 0.04 | 6 |
| R.... | .................... | TQ.TG...DF....... | ...DDR | E..KAS..AVDH | A..A........ | 0.04 | 6 |
| ..... | .............T.R | ..PN.....NF....... | ...NDR | ............ | A..A........ | 0.04 | 6 |
| ..... | F......A..NV...T.. | .................. | ...DDR | ............ | A..A........ | 0.04 | 6 |
| ..... | F.....S.G.RM.L.G.. | .Q.......DF....... | ...D.. | ............ | A..A........ | 0.04 | 6 |
| TT..T | .................... | ..DGE...DF....... | R...D. | ............ | ............ | 0.04 | 6 |
| ..... | .................... | .................. | ....D. | ENGAGN.TEV.N | A..A........ | 0.04 | 6 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | ................. | R...D. | EN.SAGD..... | A..A........ | 0.04 | 6 |
| A...T | ................. | TQ.TG....DF....... | ...D.. | .SG..ND...DG | A..A........ | 0.04 | 6 |
| ..... | F......TG.KA.I.G.K | .QPN......F......T | R..... | .DAS.N...VDG | A..A........ | 0.04 | 6 |
| ..... | ................. | .........NF......T | E..NG. | E.GAA.D...DQ | A..A........ | 0.04 | 6 |
| N.... | F.....GRT.S..L.G.L | .QD.E.....F..P.... | ...... | ............ | A..A........ | 0.04 | 6 |
| ..... | F..S............. | .V........F....... | ...... | ............ | GARTR..DNV.E | 0.04 | 6 |
| ..... | ................. | ..........F......T | ...D.R | ..G..AD.A.GD | A..A........ | 0.04 | 6 |
| ..... | ................. | .K.T.....DF....... | E..ND. | ...TG..T..GQ | A..A........ | 0.04 | 6 |
| AA... | ................. | .V........F....... | E..TDR | ............ | ............ | 0.04 | 6 |
| ..... | F.....A...ND.T...K | .QPN......F......T | ...ADR | .D.GRA...F.. | A..A........ | 0.04 | 6 |
| E.... | ......SK..PA.K.A.G | .V.......VF....... | ...... | .DGGGN.....R | A..A........ | 0.04 | 6 |
| RA... | ................. | ................. | ...DD. | ES.TG..I.FDR | A..A........ | 0.04 | 6 |
| GA... | F................ | ................. | ...ADR | ............ | A..A........ | 0.04 | 6 |
| ..... | F.....DRG.SL.M...I | ................. | ...DDR | ............ | A..A........ | 0.04 | 6 |
| ..... | ................. | T.P......F........ | ...DDR | ............ | ............ | 0.04 | 6 |
| ..... | ................. | ..DGE....DF....... | ...D.. | ............ | ............ | 0.04 | 6 |
| ..... | F................ | .V........F....... | ...... | ............ | GAKGN..SG..T | 0.04 | 6 |
| ..... | ................. | .PPNG.....F......T | ...DDR | E.TR.N..AV.. | A..A........ | 0.04 | 6 |
| D...T | .......GT.NM.L.Q.G | .Q.S......F....... | ....D. | ............ | ............ | 0.04 | 6 |
| TT... | F.....ASA.S..T.T.G | ..YN......F......T | R..TG. | ............ | A..A........ | 0.03 | 5 |
| NA... | F.....SA..RA.....R | ..DGE....DF....... | ...... | .NGG.ND....Q | A..A........ | 0.03 | 5 |
| ..... | ................. | ................. | ...... | E..TGS..EYDR | A..A........ | 0.03 | 5 |
| ..... | F................ | .V........F....... | ...... | ............ | NTRGP..NGI.. | 0.03 | 5 |
| NA... | F.....GTG.S..H.T.N | ..PN.....NF....... | ...NDR | ............ | A..A........ | 0.03 | 5 |
| ..... | ................. | .QAS......F....... | ...... | .SGKE.D...GQ | A..A........ | 0.03 | 5 |
| ET... | ................. | ................. | E..TG. | ............ | ............ | 0.03 | 5 |
| D.... | F.....GA..SQ.H.G.M | .PANG.....F....... | ...DDR | ............ | A..A........ | 0.03 | 5 |
| TA... | ................. | .QPN......F......T | ...N.. | ...G.D..EVGQ | A..A........ | 0.03 | 5 |
| RA... | ................. | .QYGQ....DF......T | ...K.. | ............ | A..A........ | 0.03 | 5 |
| ..... | F.....SRG.IE.K...L | ..YN......F......T | R..DG. | ............ | A..A........ | 0.03 | 5 |
| ..... | ................. | .........NF......T | ...D.R | .DTGEADA.VDG | A..A........ | 0.03 | 5 |
| AT..T | ................. | .Q.DR.....F....... | ....D. | ..TR.ND.A.DE | A..A........ | 0.03 | 5 |
| SA... | F.....DNT.SK.L...K | TKAGE....NF......T | R...G. | .SG..ND...DG | A..A........ | 0.03 | 5 |
| ....T | F................ | .V........F....... | ...... | ............ | THRAT..ADG.Q | 0.03 | 5 |
| RA... | F.....AHT.LK.N...G | .V........F....... | ...... | ..AGRADIEVGS | A..A........ | 0.03 | 5 |
| ..... | ................. | TKAG.....NF....... | ....GR | ............ | A..A........ | 0.03 | 5 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| TA..T | F.....SGT.S..T.T.. | .Q.DH....NF....... | ...DD. | ............ | A..A........ | 0.03 | 5 |
| ..... | F................. | .V........F....... | ...... | ............ | THRAT..ADG.Q | 0.03 | 5 |
| ..... | F.....NDG.PA.K.T.R | ..PN.....NF....... | ...NDR | ............ | A..A........ | 0.03 | 5 |
| DA... | F......NG.LQ.H...N | T.P......DF....... | ...D.. | ............ | A..A.....N.A | 0.03 | 5 |
| S.... | F.....GHA.SK.T.E.K | .Q.S......F....... | E..N.. | EDAKGND.A..N | A..A........ | 0.03 | 5 |
| ..... | ................. | .................. | R..DD. | EDGAGD.IEVDQ | A..A........ | 0.03 | 5 |
| ..... | F................. | .........F....... | E..TD. | ............ | ............ | 0.03 | 5 |
| ..... | ................. | ........DF....... | E..N.. | E........... | ............ | 0.03 | 5 |
| ..... | F................. | .V........F....... | ...... | ............ | DRSGR..NRG.D | 0.03 | 5 |
| ..... | F................. | .V........F....... | ...... | ............ | GPRDG..V.N.A | 0.03 | 5 |
| D...T | ................. | ..PDG....NF....... | ....DR | ............ | A..A........ | 0.03 | 5 |
| TA... | F.....S.G.RM.L.G.. | .V........F....... | ...... | ............ | A..A........ | 0.03 | 5 |
| G.... | F.....G.G.RA.N.E.R | .KYT.....NF......T | ...DD. | ............ | A..A........ | 0.03 | 5 |
| TA... | ................. | .V........F....... | ...... | ............ | ............ | 0.03 | 5 |
| ..... | F................. | .V........F....... | ...... | ............ | A.QNR..VDT.H | 0.03 | 5 |
| E.... | F................. | .QANH....DF....... | ...DDR | ............ | A..A........ | 0.03 | 5 |
| AT..T | F.....SSA.NV.K.G.R | ..HG.....NF......T | R..N.. | .SAGAN..E..S | A..A........ | 0.03 | 5 |
| ..... | F................. | .V........F....... | ...... | ............ | GRQSH..FTM.D | 0.03 | 5 |
| ..... | ................. | .................. | ...... | ............ | KDRNG...GK.D | 0.03 | 5 |
| TA... | ................. | .................. | G..K.. | E..G.A..E.GR | A..A........ | 0.03 | 5 |
| GA... | F................. | .V........F....... | ...... | ............ | AR.G...IDV.H | 0.03 | 5 |
| ..... | ................. | ....G...NG....... | ...TGR | ............ | A..A........ | 0.03 | 5 |
| ..... | ................. | .Q.S......F....... | ...T.. | ............ | A..A........ | 0.03 | 5 |
| ..... | ................. | ...............T | ...D.. | E..KAS..AVDR | A..A........ | 0.03 | 5 |
| EA... | ................. | ..YG.....F......T | ...D.R | ENGD....E.DR | A..A........ | 0.03 | 5 |
| .A... | F................. | .V........F....... | ...... | ............ | ............ | 0.03 | 5 |
| DT... | F.....GAG.RA.L.D.R | .................. | ....GR | ..AG.N.AA.GQ | A..A........ | 0.03 | 5 |
| ..... | ................. | .V........F....... | ...... | ............ | K.QNG..VEG.H | 0.03 | 5 |
| E.... | F.....SGA..V...Q.G | .QP.G.....F....... | R..NDR | ............ | A..A........ | 0.03 | 5 |
| AA... | F................. | .V........F....... | ...... | ............ | SERTG..DGT.T | 0.03 | 5 |
| ..... | F................. | .V........F....... | ...... | ............ | SHRTO..DNE.A | 0.03 | 5 |
| GT..T | F.....NGG.NI.K.E.R | .................. | ...... | ESGARND...DS | A..A........ | 0.03 | 5 |
| ..... | ................. | .................. | ...... | E.AG..D.A.GR | A..A........ | 0.03 | 5 |
| TA... | F.....STG..N.M.T.. | .K.TG....DF....... | ...... | ............ | A..A........ | 0.03 | 5 |
| ..... | ................. | ..P......DF....... | ...ND. | E.AKGSD.AY.G | A..A........ | 0.03 | 5 |
| GT... | ................. | .................. | E..ND. | ............ | ............ | 0.03 | 5 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| EA... | F................. | .V........F....... | ...... | ............ | DRSGA...RS.A | 0.03 | 5 |
| EA... | F................. | ................ | ...D.. | ............ | A..A........ | 0.03 | 5 |
| SA... | ................ | .KPSG....NF....... | ....D. | ESGTTA.A...H | A..A........ | 0.03 | 5 |
| ..... | F................. | .QPSR.....F....... | ...D.. | ............ | A..A........ | 0.03 | 5 |
| ..... | ................ | ................ | R..D.. | .NGST.....GG | A..A........ | 0.03 | 5 |
| ..... | ...............R | ................ | ...AG. | E.GGTS.AE.D. | A..A........ | 0.03 | 5 |
| TA... | F.........LA...H.G | .V........F....... | ...... | ............ | ............ | 0.03 | 5 |
| TT... | F.....GRT.IE.N.T.R | .QAS.....NF......T | E..DGR | ............ | ............ | 0.03 | 5 |
| A.... | F.....SGT.S..T.T.. | ..DGE....DF....... | ...... | .S.D.D...FGE | A..A........ | 0.03 | 5 |
| ..... | F.....DGA.R..P.A.K | T.P......DF....... | ....D. | ............ | A..A........ | 0.03 | 5 |
| ..... | F................. | .V........F....... | ...... | ............ | GRRDP..DGT.H | 0.03 | 5 |
| ..... | ................ | ................ | ....D. | E........... | A..A........ | 0.03 | 5 |
| G.... | ................ | .Q.GQ....DF....... | ....G. | E..TEG...VDS | A..A........ | 0.03 | 5 |
| ..... | ................ | ................ | R..KG. | ............ | A..A........ | 0.03 | 5 |
| SA... | ................ | .Q.GQ....DF....... | ....G. | ............ | A..A........ | 0.03 | 5 |
| SA... | F......TT..V.M.T.E | T.P......DF....... | ...D.. | ............ | A..A........ | 0.03 | 5 |
| ..... | .......SA.RI.T.G.R | .KDDG....NF....... | ...DDR | ED.AGNDIA.GE | A..A........ | 0.03 | 5 |
| GT... | F.....A...ND.T...K | .QPN......F......T | ...ADR | .D.GRA...F.. | A..A........ | 0.03 | 5 |
| ..... | F.....AGT.RD.M.A.L | .........NF....... | ....D. | ............ | A..A........ | 0.03 | 5 |
| ..... | F................. | .V........F....... | ...... | ............ | GARTP..F.G.H | 0.03 | 5 |
| RA... | F.....SRG..L.P.G.G | .QPSE....DF....... | ...DD. | ............ | A..A........ | 0.03 | 5 |
| GT... | F.....AEG.LK.M.H.L | ................ | ...... | ............ | A..A........ | 0.03 | 5 |
| .A... | ................ | ................ | ...DDR | ..AAGADTA.DD | A..A........ | 0.03 | 5 |
| SA... | ................ | .Q.S......F....... | ...DDR | ............ | A..A........ | 0.03 | 5 |
| NA..T | ................ | TQASG....NF....... | ....D. | E.AS...IEYGQ | A..A........ | 0.03 | 5 |
| ..... | ................ | .QPSR.....F....... | ...... | ............ | A..A........ | 0.03 | 5 |
| ..... | ................ | ................ | ...... | E...GA.AA..E | A..A........ | 0.03 | 5 |
| G.... | ................ | .QATQ....NF......T | ...N.R | EDAGT...AFD. | A..A........ | 0.03 | 5 |
| NA... | F......KT.NV.K.T.H | TKA......NF......T | R..D.R | E..R.N.AEFGE | A..A........ | 0.03 | 5 |
| NA..T | F................. | .V........F....... | ...... | ............ | SRQAH..SDM.E | 0.03 | 5 |
| G.... | F.....GDG....K.Q.R | .........F......T | ...DDR | ESAGRSDTA.DE | A..A........ | 0.03 | 5 |
| ..... | ................ | .........NF....... | ...DD. | E.G.RBD.EVDE | A..A........ | 0.03 | 5 |
| D...T | F.....AEG.LK.M.H.L | ..DGE....DF....... | ...... | ............ | ............ | 0.03 | 5 |
| G.... | ................ | .QDT.....DF....... | G..DG. | ............ | ............ | 0.03 | 5 |
| TA... | ................ | ................ | R..DD. | ............ | ............ | 0.03 | 5 |
| EA... | ................ | ................ | ....GR | E..TRS.AE.GS | A..A........ | 0.03 | 5 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| D...T | ................ | ................ | ...NDR | ..AKG...AV.. | A..A........ | 0.03 | 5 |
| TA... | F.....DAA.IK.T.Q.N | ..DGE....DF....... | ...... | E.......... | ............ | 0.03 | 5 |
| TA... | F.....SAA.NK.L.G.L | ..PNG....DF....... | R..DD. | ............ | A..A........ | 0.03 | 5 |
| ..... | ................ | ................ | ...D.. | EDGMGSD.E.DQ | A..A......T. | 0.03 | 5 |
| A.... | ................ | .QD.E.....F..P.... | ...D.. | ............ | ............ | 0.03 | 5 |
| ..... | ................ | ................ | ...D.R | ..ASES...VDG | A..A........ | 0.03 | 5 |
| SA..T | F.....AAG.RV.L.K.R | ..DGE....DF....... | ...... | ............ | A..A........ | 0.03 | 5 |
| .A... | F.....AST.HD.T.E.R | T.P......DF....... | ...DG. | ............ | ............ | 0.03 | 5 |
| ..... | ................ | .QDT.............. | ....D. | ............ | A..A........ | 0.03 | 5 |
| D.... | F.....DGA.RN.T.S.G | .RPT.....DF....... | G..KGR | ............ | A..A........ | 0.03 | 5 |
| ..... | F................ | .V........F....... | ...... | ............ | TR.NP..DGV.T | 0.03 | 5 |
| ..... | F................ | .V........F....... | ...... | ............ | GP.N...VGA.K | 0.03 | 5 |
| ..... | F................ | .V........F....... | ...... | ............ | GARGA..VHN.A | 0.03 | 5 |
| ..... | F................ | ................ | E..N.. | ............ | A..A........ | 0.03 | 5 |
| ..... | F................ | ..........F....... | ...... | ............ | TAQA...AP..T | 0.03 | 5 |
| E.... | ................ | ................ | R..TD. | ............ | A..A........ | 0.03 | 5 |
| GT... | F................ | TQ.TG....DF....... | ...A.. | ............ | GQKDR...ST..H | 0.03 | 5 |
| ..... | ................ | ................ | ...D.. | ENTKGD....D. | A..A........ | 0.03 | 5 |
| TT..T | ................ | ..........F....... | ...... | ............ | ............ | 0.03 | 5 |
| RA... | F................ | TQDGE....DF....... | ....D. | ED.GAG..AV.G | A..A........ | 0.03 | 5 |
| ..... | F................ | .V........F....... | ...... | ............ | GKQTT..SEG.T | 0.03 | 5 |
| AA... | ................ | ................ | ...DDR | ............ | A..A........ | 0.03 | 5 |
| TA... | ................ | .QPN......F......T | ...N.. | ..TG.D..A.GG | A..A........ | 0.03 | 5 |
| ..... | ................ | ..........NF......T | E..N.. | E.TR.N.....Q | A..A........ | 0.03 | 5 |
| ..... | F......GA.NM.T.A.G | .KDSR....DF......T | R..D.. | ..A.A.D.AFDS | A..A........ | 0.03 | 5 |
| ST... | F.....G.T.II.P.D.R | ..DGE....DF....... | ...... | ..AGAN...FGE | ............ | 0.03 | 5 |
| ..... | ................ | ................ | ...NDR | E.ATA...E.DD | A..A........ | 0.03 | 5 |
| SA... | F.....GNG.HV.H.G.R | ..DGE....DF....... | ...... | .SARG.D.AVDD | A..A........ | 0.03 | 5 |
| ..... | ................ | ................ | ...... | E.ASTA..A.GQ | A..A........ | 0.03 | 5 |
| A.... | ......ASA.S..T.T.G | .QPG.....NF......T | E..DD. | ............ | A..A........ | 0.03 | 5 |
| ..... | F................ | .V........F....... | ...... | ............ | TARNP..FER.T | 0.03 | 5 |
| NA... | F................ | ..AGR...........T | E..N.. | ............ | A..A........ | 0.03 | 5 |
| NA... | F.....A.A.RE.I.... | .K.T......F....... | ...N.. | ............ | A..A........ | 0.03 | 5 |
| RA... | F.....DAG.LL.T.A.G. | .QPG.....NF....... | ...NGR | ............ | A..A........ | 0.03 | 5 |
| GT... | F.....SG..IK.K.D.R | .QDT.....DF....... | ...... | ............ | A..A........ | 0.03 | 5 |
| ..... | F................ | .PPNG.....F......T | ...DDR | E.ATRA..A.DE | A..A........ | 0.03 | 5 |

TABLE 7-continued

AAV capsid proteins having increased specificity for and/or transduction of
CD44+ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................ | ................. | ...ND. | ............ | A..A........ | 0.03 | 5 |
| ..... | ................ | ................. | ...D.. | ............ | ...A........ | 0.03 | 5 |
| D...T | ................ | ................. | E..ND. | ............ | A..A........ | 0.03 | 5 |
| ..... | F............... | ................. | ...... | EDAGGSDI.Y.S | A..A........ | 0.03 | 5 |
| ..... | F.....NQG.R..P.T.L | .Q.S......F......T | ...N.. | ............ | A..A........ | 0.03 | 5 |
| ..... | ................ | ................. | R...GR | .STGAD.....Q | A..A........ | 0.03 | 5 |
| GA... | ................ | ...T....NF......T | ...DDR | .SAKAA.AA.DE | A..A........ | 0.03 | 5 |
| NA... | F......KA.SA.T.A.G | .QAS......F......T | ...ND. | .NTGR..AA..Q | A..A........ | 0.03 | 5 |
| E.... | ................ | ................. | E..T.. | ............ | ............ | 0.03 | 5 |
| ..... | F............... | .V........F...... | ...... | ............ | GPRTH..DKA.. | 0.03 | 5 |
| ..... | F......GT.NM.L.Q.G | .Q.S......F...... | E..TD. | ............ | ............ | 0.03 | 5 |
| G.... | F.....STG.NP.M.E.R | ................. | ...... | ............ | A..A........ | 0.03 | 5 |
| RA... | ................ | TQ.TG....DF....... | ...DDR | E..RRD.AA..H | A..A........ | 0.03 | 5 |
| ..... | ................ | T.P......DF....... | G..D.F | .SGTAN.IEFGQ | A..A........ | 0.03 | 5 |
| ..... | ................ | ................. | ....G. | ............ | GNQT....TG.P | 0.03 | 5 |
| D...T | F.....GR..HD.L.N.L | ..DGE....DF....... | R...D. | ............ | ............ | 0.03 | 5 |
| ....T | F.....SA..RA.....R | TKDDW....DF....... | ...ND. | ............ | A..A........ | 0.03 | 5 |
| ..... | F............... | .V........F...... | ...... | ............ | .R.T...SDV.D | 0.03 | 5 |
| .A... | F.....NQA.SV...A.R | .QYT.....NF......T | E..DD. | ..AGAND.AY.N | A..A........ | 0.03 | 5 |
| NT... | F.....STA..Q.H.Q.L | T.PNE....DF....... | R...D. | .DAKRA..AV.E | A..A........ | 0.03 | 5 |
| RT... | ................ | .KYT.....NF......T | ...D.R | ............ | A..A........ | 0.03 | 5 |
| G...T | F.....NGG.NV.N.K.G | .QDT......F......T | ...D.. | ............ | ............ | 0.03 | 5 |
| ..... | F............... | .V........F...... | ...... | ............ | AARNG..FGT.D | 0.03 | 5 |
| .A... | ................ | ................. | ...D.. | .NTSTSD.E.DG | ............ | 0.03 | 5 |
| ..... | ......ASA.S..T.T.G | .QPG.....NF......T | E..DD. | ............ | A..A........ | 0.03 | 5 |
| NT..T | F.....SEA.IH...Q.L | .Q.DR.....F....... | ....D. | .NAGA.D...GS | A..A........ | 0.03 | 5 |
| ..... | F............... | .V........F...... | ...... | ............ | G.QSP..DGA.T | 0.03 | 5 |
| NA..T | F.....GKT.SL...G.R | ..DGE....DF....... | ...DG. | ..ATG..I.F.R | A..A........ | 0.03 | 5 |
| ..... | ................ | TQ.TG....DF....... | ...DDR | .S..RA.....G | A..A........ | 0.03 | 5 |
| ..... | F............... | .V........F...... | ...... | ............ | AERAT..ANN.E | 0.03 | 5 |
| TA... | F......QT.P..L.Q.R | TQP.R...NF......T | ...... | ............ | A..A........ | 0.03 | 5 |
| TA... | ................ | ..DNH....NF...... | ...D.. | .NGGTG..A.DR | A..A........ | 0.03 | 5 |
| GA... | ................ | ................. | ....GR | ..AG.N.AA.GQ | A..A........ | 0.03 | 5 |
| ..... | F............... | .V........F...... | ...... | ............ | GHHG...SGG.H | 0.03 | 5 |
| A...T | F............... | ................. | ...D.. | ..ASES.I..DG | A..A........ | 0.02 | 4 |
| NA..T | F.....GNG.HV.H.G.T | ................. | ...... | ............ | A..A........ | 0.02 | 4 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F......RA.SQ.L.A.G | .........NF....... | R...D. | ..AGTSDIA.DR | A..A........ | 0.02 | 4 |
| ..... | F................. | .V........F....... | ...... | ........... | E.RS...F.E.H | 0.02 | 4 |
| ..... | ................. | ................. | ...D.. | .DADT..TE..H | A..A........ | 0.02 | 4 |
| AA... | F.....GGT.PM.K.D.R | ................. | ...... | ........... | GP.NA..YRE.Q | 0.02 | 4 |
| ..... | ................. | .V........F....... | ...... | ........... | ANSNP..SDS.Q | 0.02 | 4 |
| A.... | ................. | ................. | R..TG. | ........... | A..A........ | 0.02 | 4 |
| ..... | ................. | ................. | ....D. | ..AG...IA.GQ | A..A........ | 0.02 | 4 |
| GA... | ................. | .........NF....... | R...D. | .DGGGS.....G | A..A........ | 0.02 | 4 |
| EA... | F................. | .V........F....... | ...... | ........... | GPRNT..NST.A | 0.02 | 4 |
| G.... | F.....GA..SM.N.G.R | ..DGE....DF....... | ...... | ES.GAN..EVDG | A..A........ | 0.02 | 4 |
| ..... | F.....GTG..P.T.D.G | .QPG.....DF....... | ...D.. | ........... | A..A........ | 0.02 | 4 |
| ..... | F................. | .V........F....... | ...... | ........... | AQRDH..SEA.H | 0.02 | 4 |
| A.... | F.....GGG.NV.K.Q.G | T.YNH.....F....... | ...D.. | ........... | A..A........ | 0.02 | 4 |
| ..... | F................. | .V........F....... | ...D.. | ........... | ........... | 0.02 | 4 |
| ..... | ................. | ..........F......T | ...DDR | ENTSENDIE.DR | A..A........ | 0.02 | 4 |
| ..... | F................. | .V........F....... | ...... | ........... | TRKNP..VS..E | 0.02 | 4 |
| SA... | ................. | ................. | ...AGR | ........... | A..A........ | 0.02 | 4 |
| .A... | F.....SD..NP.H.D.R | ..YN......F......T | ...D.R | ENAGRAD.AFD. | A..A........ | 0.02 | 4 |
| TA..T | ................. | .Q.D.....DF..P.... | ...A.. | ........... | ........... | 0.02 | 4 |
| AA... | F......KT.NK...A.G | ..DGE....DF....... | ...... | E..G...D.AVGE | A..A........ | 0.02 | 4 |
| DT... | ................. | .QP.G.....F....... | ...DDR | ENGGR..IE..S | A..A........ | 0.02 | 4 |
| AA..T | F.....ANG.NV.L...G | .........NF......T | ...DG. | ........... | A..A........ | 0.02 | 4 |
| N.... | F.....DA..IA.L.K.R | TQ.TH....DF....... | R..ADS | ........... | A..A........ | 0.02 | 4 |
| D...T | G......SA.S..T.T.G | .QPG.....DF....... | ...DDR | ........... | ........... | 0.02 | 4 |
| ..... | ................. | ................. | ....GR | .DAT....A.GG | A..A........ | 0.02 | 4 |
| ..... | ................. | ................. | ...DDR | ESGS.S.IA.DQ | A..A........ | 0.02 | 4 |
| ..... | F................. | .V........F....... | ...... | ........... | GRQGG..S.V.E | 0.02 | 4 |
| ..... | ................. | .PHD.....DF......T | ...DG. | ........... | ........... | 0.02 | 4 |
| G.... | ................. | ................. | ...... | ESAREN.AE.DE | A..A........ | 0.02 | 4 |
| GG... | ................. | ................. | R..D.R | ........... | A..A........ | 0.02 | 4 |
| NT... | F.....SG..IK.K.D.R | TKDDR....DF....... | ...DDR | ........... | A..A........ | 0.02 | 4 |
| ..... | F................. | ................. | ...D.. | ........... | KERTP..ADT.. | 0.02 | 4 |
| ST..T | F.....G.T.II.P.D.R | ..HG.....NF....... | R..D.. | ..ASE....E.D | A..A........ | 0.02 | 4 |
| TA..T | F.....DQG.S......R | ..DGE....DF....... | ...DDR | .NAG.DD...DQ | A..A........ | 0.02 | 4 |
| ..... | ................. | .KYT.....NF......T | ...AD. | ........... | A..A........ | 0.02 | 4 |
| RA... | F......TG..Q.T.T.G | .Q.......DF....... | ...AD. | ........... | A..A........ | 0.02 | 4 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F.....NGG.NN.K.T.R | T.P......DF....... | ...DDR | E..G.A..E.GR | A..A........ | 0.02 | 4 |
| G.... | F.....NTG.LH.T...R | ..PN.....NF....... | ...D.. | E........... | A..A........ | 0.02 | 4 |
| ..... | F.....NG..H..I.A.R | ................. | ...... | ............ | A..A........ | 0.02 | 4 |
| ..... | F.....DH..ID.K...V | ................. | ...... | ..AG.DD...GG | A..A........ | 0.02 | 4 |
| ..... | ................. | ................. | ...DDR | ESGGTD....DR | A..A........ | 0.02 | 4 |
| A.... | F.....DAA.IA.L.K.R | .PPNG.....F......T | ...DD. | ............ | A..A........ | 0.02 | 4 |
| G.... | F................ | ..HG.....NF......T | ...A.. | ............ | A..A........ | 0.02 | 4 |
| ..... | ................. | ................. | R..KD. | ............ | A..A........ | 0.02 | 4 |
| ..... | F.....NN..SA.N...R | T.P......DF....... | ...D.. | E.TTG.DAE.DN | A..A........ | 0.02 | 4 |
| AA... | ................. | .V........F....... | ...... | ............ | A..A........ | 0.02 | 4 |
| EA... | ................. | ................. | ...D.. | ............ | A..A........ | 0.02 | 4 |
| ..... | ......G....K.L...G | TKDDR....DF....... | ...... | ............ | A..A........ | 0.02 | 4 |
| ..... | ................. | ................. | E..ND. | ...G.D..EVGQ | A..A........ | 0.02 | 4 |
| NA..T | F.....GTG..P.T.D.R | .QPSE....DF....... | ...DDR | ............ | ............ | 0.02 | 4 |
| ..... | F.....NT.....K.A.R | .V........F....... | ...... | ............ | ............ | 0.02 | 4 |
| RA... | F.....SS..RA.....R | T.P......DF....... | ...D.. | E.AG.DDA...R | A..A........ | 0.02 | 4 |
| ..... | ................. | ................. | R...DR | .NGG.S..G..S | A..A........ | 0.02 | 4 |
| GA... | ................. | ................. | G..ND. | ED.A.G.T..DN | A..A........ | 0.02 | 4 |
| ..... | ................. | ................. | ...... | .D...S..A.GG | A..A........ | 0.02 | 4 |
| G.... | F......GG.NV...G.M | ................. | ...DD. | ............ | A..A........ | 0.02 | 4 |
| AA... | F.....SA..RA.....R | ................. | G..ND. | ............ | A..A........ | 0.02 | 4 |
| ..... | ................. | ...NG....NF......T | G..TG. | ............ | A..A........ | 0.02 | 4 |
| ET..T | ................. | ..HG.....NF......T | ...N.. | E.AG...IAVDR | A..A........ | 0.02 | 4 |
| ..... | F................ | .V........F....... | ...... | ............ | .R.NG..Y.G.D | 0.02 | 4 |
| ..... | ................. | .........NF....... | R...D. | .DGAGGD.A..Q | A..A........ | 0.02 | 4 |
| ....T | ................. | .KDSR....DF....... | ...D.. | ............ | A..A........ | 0.02 | 4 |
| ..... | F................ | .V........F....... | ...... | ............ | .P.GT..STT.A | 0.02 | 4 |
| ..... | F................ | .QPSE....DF....... | ...AGR | ED.A.A.T..DR | A..A........ | 0.02 | 4 |
| ..... | F................ | .V........F....... | ...... | ............ | GP.GA..VQE.. | 0.02 | 4 |
| GT... | ................. | ................. | ...... | ..AG.D..E.GG | A..A........ | 0.02 | 4 |
| GT... | ................. | T.PTG....DF....... | ...DDR | .DAG.A.I..DG | A..A........ | 0.02 | 4 |
| SA... | F.....GN..NA.T...M | TQ.TG............ | ...... | E..K.GDA...S | A..A........ | 0.02 | 4 |
| SA... | ...............T.L | .Q.S......F......T | ...N.. | ............ | A..A........ | 0.02 | 4 |
| RT... | F................ | ................. | ...D.. | .N.AGNDAAVDE | A..A........ | 0.02 | 4 |
| GA..T | ................. | ................. | ...D.R | E.AG..D.A.GR | A..A........ | 0.02 | 4 |
| ..... | F.....NGG.NN.K.T.R | TQYDR....NF....... | R...D. | ............ | A..A........ | 0.02 | 4 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| E.... | ................. | ................. | ...AGR | .N.NRN.....G | A..A........ | 0.02 | 4 |
| ..... | F.....AQ...A.L.... | TKDDR....DF....... | ...DDR | ..AG..D.A.GR | A..A........ | 0.02 | 4 |
| ..... | F................. | .V........F....... | ...... | ............ | KSKAA..V.S.D | 0.02 | 4 |
| TA... | F.....ASA.S..T.T.G | .QPG.....DF....... | ...DDR | ............ | ............ | 0.02 | 4 |
| ..... | F.....SGA..K.S.S.S | ..A......DF....... | ...... | ............ | ANRTA..DKA.. | 0.02 | 4 |
| ..... | F................. | .V........F....... | ...... | ............ | TRRGP..DRI.E | 0.02 | 4 |
| ..... | ................. | .........NF......T | R..AG. | .STGAD.....Q | A..A........ | 0.02 | 4 |
| E.... | F.....SN..PL.K.T.. | .........F..P.... | R..... | ............ | ............ | 0.02 | 4 |
| ....T | ................. | .KYT.....NF......T | ...DDR | ............ | A..A........ | 0.02 | 4 |
| DA... | ................. | .KYT.....NF......T | R..ND. | ............ | A..A........ | 0.02 | 4 |
| ..... | ................. | ...T.....NF......T | ...ADR | E..RRD.AA..H | A..A........ | 0.02 | 4 |
| E.... | F.....AG..RE.L...K | .QPN......F......T | ...N.. | ESGG.G..E..Q | A..A........ | 0.02 | 4 |
| ..... | ................. | .........NF....... | E..KG. | ............ | A..A........ | 0.02 | 4 |
| GA..T | F.....SNG.P....T.R | ..A......DF....... | ...DG. | ............ | A..A........ | 0.02 | 4 |
| EA... | ................. | TQHTG....NF....... | ...DDR | ............ | A..A........ | 0.02 | 4 |
| N.... | F.....A...ND.T...K | .QD......DF..P.... | G..K.. | E.GG.....FD. | A..A........ | 0.02 | 4 |
| ..... | ................. | ..HG.....NF......T | ...A.. | .SAKAA.AA.DE | A..A........ | 0.02 | 4 |
| .T... | F................. | .V........F....... | ...... | ............ | SERAG..YQ..Q | 0.02 | 4 |
| TA..T | F.....DNG.SP.I.N.R | ..HG.....NF......T | ...A.. | ............ | ............ | 0.02 | 4 |
| HA... | F.....GKG.ND.T.N.G | ..A......DF....... | ...DG. | ............ | A..A........ | 0.02 | 4 |
| ..... | F...........H.... | .V........F....... | ...... | ............ | DQRNS..ARN.T | 0.02 | 4 |
| ..... | ................. | ................. | ...... | .DGTG..A..GN | A..A........ | 0.02 | 4 |
| ..... | F................. | TKAT.....NF......T | ...... | .SGR.N.T..GD | A..A........ | 0.02 | 4 |
| ..... | ................. | ................. | ...N.. | ...G.N.A.... | A..A........ | 0.02 | 4 |
| ET..T | F.....ANG.HL.K.K.S | .........F......T | G..N.. | ............ | A..A........ | 0.02 | 4 |
| ..... | F.....NGG.NN.K.T.R | ..A......DF....... | ...DG. | ESGG.S..E.GD | A..A........ | 0.02 | 4 |
| .A... | ................. | ................. | R..DD. | ............ | A..A........ | 0.02 | 4 |
| ..... | F.....A.A.RE.I.... | .Q.S......F....... | E..NG. | ............ | A..A........ | 0.02 | 4 |
| R.... | ................. | .........KF..P...T | R...D. | .SAKAA.AA.DE | A..A........ | 0.02 | 4 |
| ..... | ................. | ..AGR....NF....... | ...NDR | ............ | ............ | 0.02 | 4 |
| AA... | F......GG.NV...K.. | .PPNG.....F......T | ...DDR | ............ | A..A........ | 0.02 | 4 |
| GT... | ......AEG.LK.M.H.L | ..DGE....DF....... | ...... | ............ | A..A........ | 0.02 | 4 |
| E.... | ................. | .V........F....... | ...DDR | E.GAEGD..FDG | ............ | 0.02 | 4 |
| ..... | ................. | ................. | ...D.R | ..TAE...E..E | A..A........ | 0.02 | 4 |
| GT... | ................. | TQPGG............ | ...DDR | E..AAND...GG | A..A........ | 0.02 | 4 |
| N.... | F.....GRT.PQ.T.T.R | ..DGE....DF....... | ...... | E.ARRA.AE.D. | A..A........ | 0.02 | 4 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F.....NG..SN.M...K | ...G.....DF....... | G..ADR | .NAA.A....GD | A..A........ | 0.02 | 4 |
| .T..T | F.....AG..RV.L.N.G | .V........F....... | ...... | E..AAS....GG | A..A........ | 0.02 | 4 |
| ..... | .................. | .................. | E..KG. | .......I..G. | A..A........ | 0.02 | 4 |
| N.... | F.....DRG.S..T.A.S | ..DGE....DF....... | ...... | ............ | ............ | 0.02 | 4 |
| RA... | F................. | .V........F....... | ...... | ............ | GRRSP......A | 0.02 | 4 |
| ..... | F................. | .................. | R..TG. | ............ | A..A........ | 0.02 | 4 |
| A.... | F................. | ..............F... | R...D. | ............ | ............ | 0.02 | 4 |
| DA... | F.....GKG.ND.T.N.R | .V........F....... | ...... | ENGGTN..E.GN | A..A........ | 0.02 | 4 |
| ..... | F................. | .V........F....... | ...... | ............ | DR.NA..F.G.. | 0.02 | 4 |
| G...T | F.....G.T.IN.T...H | .QPG.....NF....... | ...DDR | ............ | A..A........ | 0.02 | 4 |
| GT... | F.....DRG.S..T.A.S | ..DGE....DF....... | ...... | ............ | A..A........ | 0.02 | 4 |
| ..... | .................. | ................T | ...D.. | .D..RND.A..S | A..A........ | 0.02 | 4 |
| ..... | .................. | .................. | ....D. | E.GGGA.AEVGD | A..A........ | 0.02 | 4 |
| ..... | .................. | .................. | ....D. | .DAG.S.A..DR | A..A........ | 0.02 | 4 |
| E.... | ......ASA.S..T.T.G | .QPG.....NF......T | E..DD. | ............ | A..A........ | 0.02 | 4 |
| ..... | F.....NTT.IL.T.T.K | .QPNG....DF....... | R..DD. | E.AR..DAE.DN | A..A........ | 0.02 | 4 |
| ..... | .................. | .................. | R..DD. | ESGSES.IA..D | A..A........ | 0.02 | 4 |
| R.... | F.....ATG.NV.T.G.R | ..ATR....DF....... | E..N.. | ............ | A..A........ | 0.02 | 4 |
| SA... | F.....S.G.RQ.T.E.R | .QD.E.....F..P.... | .....R | ............ | A..A........ | 0.02 | 4 |
| SA... | .................. | ..A.......DF....... | ...DG. | .SGS.N..AV.D | A..A........ | 0.02 | 4 |
| ET..T | ......ANG.HL.K.K.S | .........DF......T | G..N.. | ............ | A..A........ | 0.02 | 4 |
| E.... | F.....ASA.S..T.T.G | .QD.E.....F..P.... | ...DDR | ............ | ............ | 0.02 | 4 |
| SA..T | .................. | ..............F... | ...... | ............ | DRSGA...RS.A | 0.02 | 4 |
| ..... | .................. | ...........DF......T | E..ND. | ............ | A..A........ | 0.02 | 4 |
| R.... | F.....GA..SM.N.G.R | ..DGE....DF....... | ...... | ES.GAN..EVDG | A..A........ | 0.02 | 4 |
| G.... | .................. | ..HG.....NF......T | ...A.. | E.TSGGD.E..Q | A..A........ | 0.02 | 4 |
| ..... | F................. | .................. | ...D.. | ............ | A..A........ | 0.02 | 4 |
| .A... | .................. | .QPN......F......T | ...N.. | ..TG.D..A.GG | A..A........ | 0.02 | 4 |
| ..... | .................. | .................. | G..DG. | ............ | A..A........ | 0.02 | 4 |
| K.... | F.....GNG.HV.H.G.R | .................. | ...DD. | ............ | A..A........ | 0.02 | 4 |
| DA... | .................. | .................. | ...DDR | ESGST.DAA.GQ | A..A........ | 0.02 | 4 |
| ..... | .................. | .Q.S......F....... | ....D. | ............ | ............ | 0.02 | 4 |
| ..... | F.....NGG.LN.I.G.R | TKPDR....NF......T | ...... | ............ | A..A........ | 0.02 | 4 |
| ..... | F................. | .V........F....... | ...... | ............ | T.HD...YHS.Q | 0.02 | 4 |
| ..... | F................. | .V........F....... | ...... | ............ | DKRTP..DRR.E | 0.02 | 4 |
| ..... | .................. | .................. | ...... | .S.ATGDTE.DG | A..A........ | 0.02 | 4 |

TABLE 7-continued

AAV capsid proteins having increased specificity for and/or transduction of CD44$^+$ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ....T | ................. | ..AGR.....F......T | ....D. | ............ | A..A........ | 0.02 | 4 |
| ...S. | ................. | ................. | ...... | ............ | ............ | 0.02 | 4 |
| R.... | F.....NGG.NN.K.T.R | .........NF....... | R...D. | .DTG.GD.A..H | A..A........ | 0.02 | 4 |
| ..... | F.....DTG.PA.L.T.K | .........NF....... | R...D. | ..ASGD....GR | A..A........ | 0.02 | 4 |
| ..... | ................. | ................T | ...ADR | E..GR..IAFDG | A..A........ | 0.02 | 4 |
| NA... | F.....DRG.S..T.A.S | ..DGE....DF....... | ...... | ............ | ............ | 0.02 | 4 |
| ..... | ................. | .............NF....... | E..A.. | E..G.SDAA.GD | A..A........ | 0.02 | 4 |
| ..... | F................. | .V........F....... | ...... | ............ | NTRSG..AK..H | 0.02 | 4 |
| ..... | F................. | .V........F....... | ...... | ............ | AAQS...NTA.T | 0.02 | 4 |
| G.... | F................. | .V........F....... | ...... | ............ | SRSGR...E..P | 0.02 | 4 |
| E.... | ................. | .QPN......F......T | ...N.. | E.AGAND.AV.H | A..A........ | 0.02 | 4 |
| .A... | F................. | .V........F....... | ...DG. | ............ | ............ | 0.02 | 4 |
| ..... | ................. | ..YN......F......T | ...D.R | ............ | A..A........ | 0.02 | 4 |
| ..... | F................. | .V........F....... | ...... | ............ | NPRDP..NNG.. | 0.02 | 4 |
| ..... | ................. | .QPN......F......T | ...N.. | ..TG.D..A.GG | A..A........ | 0.02 | 4 |
| NA..T | F................. | ................. | ...DD. | ..ASTDDA.VGE | A..A........ | 0.02 | 4 |
| ..... | ................. | ...V.....NF....... | R...D. | ............ | A..A........ | 0.02 | 4 |
| ..... | ................. | .Q.......DF....... | ....D. | E.AG.GDIAYGD | A..A........ | 0.02 | 4 |
| ..... | ................. | ................. | ...DDR | E.A.G..A...N | A..A........ | 0.02 | 4 |
| ..... | ................. | ................. | ...D.R | ESGT.A.A..GH | A..A........ | 0.02 | 4 |
| ..... | F................. | .V........F....... | ...... | ............ | KRHDG..SHM.E | 0.02 | 4 |
| TA... | F.....DRG.S..T.A.S | ..DGE....DF....... | ...... | ............ | ............ | 0.02 | 4 |
| A...T | ................. | ...V.....NF....... | R...D. | ............ | A..A........ | 0.02 | 4 |
| GT... | ................. | .QPDR.....F......T | ...... | ..TTGND..VDG | A..A........ | 0.02 | 4 |
| ..... | F................. | .V........F....... | ...... | ............ | GARNP..ATA.E | 0.02 | 4 |
| ..... | F.....GDT..L.....R | ..HG.....NF......T | ...D.. | ESGGGGDT.V.G | A..A........ | 0.02 | 4 |
| ..... | F.....DTG.SK.T.T.R | .QDT......F......T | ...D.. | ............ | A..A........ | 0.02 | 4 |
| RA... | F.....DTG.SK.T.T.R | .Q.S......F....... | ...D.. | .NGR.G..A..E | A..A........ | 0.02 | 4 |
| ..... | F................. | .V........F....... | ...... | ............ | SSRSG..AGN.T | 0.02 | 4 |
| ..... | ......DKA.IK.K.S.G | .QPN......F......T | ...N.. | E.TAG.DI..D | A..A........ | 0.02 | 4 |
| A.... | F.....GQ..RV.T...L | .A.......DF....... | ...DG. | ............ | A..A........ | 0.02 | 4 |
| ..... | F.....GN..RM.T...E | .HG......NF......T | ...A.. | E.AG...IA.DD | A..A........ | 0.02 | 4 |
| G.... | ................. | TKAT.....NF......T | G..TG. | ............ | A..A........ | 0.02 | 3 |
| ..... | ................. | .PHD.....DF......T | ...DG. | .NTGGG....DG | A..A........ | 0.02 | 3 |
| A.... | ................. | .QANH.....F......T | R..A.. | E..A.ADA..GD | A..A........ | 0.02 | 3 |
| ..... | ................. | ................T | ...ADR | E.GTEGDIA..D | A..A........ | 0.02 | 3 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ....T | F.....GAT.LA.M.H.R | .........NF....... | R...D. | ............ | A..A........ | 0.02 | 3 |
| ..... | ................. | ...............T | ...AGR | ............ | A..A........ | 0.02 | 3 |
| SA... | F.....GHG.NK.I.N.T | ..PSH....DF....... | ....D. | ............ | A..A........ | 0.02 | 3 |
| DT... | F.....AQ...A.L.... | .QPN......F......T | ....N. | E.AG.A..EF.R | A..A........ | 0.02 | 3 |
| NA... | F.....DR.......H.V | ..DGE....DF....... | ...... | ............ | A..A........ | 0.02 | 3 |
| R.... | F.....NKT.I..K..... | ..DGE....DF....... | ...... | E.AGAADA.VDH | A..A........ | 0.02 | 3 |
| NT..T | ................. | ................. | ...... | .DTAAA...VGE | A..A........ | 0.02 | 3 |
| ..... | ................. | ...............T | E..AD. | ............ | A..A........ | 0.02 | 3 |
| ..... | ................. | .V........F....... | ...... | ............ | GPQGR..SR..A | 0.02 | 3 |
| ..... | ................. | .QPSE....DF....... | ...AGR | ED.A.A.T..DR | A..A........ | 0.02 | 3 |
| ..... | ................. | ........DF....... | ...DG. | ..TG.A.I..DR | A..A........ | 0.02 | 3 |
| ..... | ................. | ..........F....... | ....D. | ............ | ............ | 0.02 | 3 |
| AA... | ................. | ..DGE....DF....... | R...D. | ............ | ............ | 0.02 | 3 |
| SA..T | F.....DKA.PD.K.A.R | ..A.R....DF....... | ...D.. | .DAG.GD.AY.Q | A..A........ | 0.02 | 3 |
| ..... | ................. | ................. | ...DD. | .DTA.A.AA.GE | A..A........ | 0.02 | 3 |
| ..... | F................. | .V........F....... | ...... | ............ | SRHGG..FTE.T | 0.02 | 3 |
| ..... | F................. | .V........F....... | ...... | ............ | TTRTT..VTN.H | 0.02 | 3 |
| ..... | F................. | .V........F....... | ...... | ............ | .PRDA..V.I.. | 0.02 | 3 |
| ..... | F................. | .V........F....... | ...... | ............ | SNRAG..N.G.T | 0.02 | 3 |
| ..... | ................. | ................. | ....G. | ............ | A..A........ | 0.02 | 3 |
| ..... | ................. | ................. | R..DD. | ..TG.N.IAF.D | A..A........ | 0.02 | 3 |
| GT... | F.....NRA.LA.N.K.E | ..DGE....DF....... | ....D. | ..AG.N.AA.GQ | A..A........ | 0.02 | 3 |
| TA... | ................. | .Q.GQ....DF....... | ....G. | ENAGASDIA.DH | A..A........ | 0.02 | 3 |
| ..... | ................. | ................. | R..NDR | E.AG..D.A.GR | A..A........ | 0.02 | 3 |
| ..... | F................. | .V........F....... | ...... | ............ | ..RAP..FSE.. | 0.02 | 3 |
| ..... | ................. | ...NE.....F....... | R..N.. | E.AKGSDA.FDN | A..A........ | 0.02 | 3 |
| ..... | ................. | .QANH.....F......T | R...G. | ..ASTDDA.VGE | A..A........ | 0.02 | 3 |
| TA..T | F.....DQG.S..L...G | ..P.G....KF....... | ...DDR | .NAG.DD...DQ | A..A........ | 0.02 | 3 |
| .A... | ................. | .K.TG....DF....... | R...DR | ESAN...I...H | A..A........ | 0.02 | 3 |
| ..... | ................. | ................. | ...DD. | ESGNR.D.EV.D | A..A........ | 0.02 | 3 |
| ..... | F................. | ................. | ...... | ............ | GTRGT..ADA.Q | 0.02 | 3 |
| ..... | ................. | TKDDR....DF....... | ...DDR | .D...A..AVDD | A..A........ | 0.02 | 3 |
| A.... | F.....GG..I.P...R | ................. | ...... | ..........GE | A..A........ | 0.02 | 3 |
| ..... | ................. | ................. | ...N.. | .S.G.S.IA..G | A..A........ | 0.02 | 3 |
| E.... | ................. | .QANH.....F......T | R..D.. | .SAKAA.AA.DE | A..A........ | 0.02 | 3 |
| ..... | F................. | .V........F....... | ...... | ............ | SRQNA..S...K | 0.02 | 3 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F................. | .................T | G..TDR | E.AGGN..E.DD | ............ | 0.02 | 3 |
| SA... | F.....ASA.S..T.T.G | .QPG.....DF....... | ...DDR | ............ | ............ | 0.02 | 3 |
| ..... | F................. | .V........F....... | ...... | ............ | GT.TG..DKG.Q | 0.02 | 3 |
| ..... | ................. | ................. | ...... | ..TNESD..... | A..A........ | 0.02 | 3 |
| S.... | ................. | ................. | ...... | .DTA.A.AA.GE | A..A........ | 0.02 | 3 |
| E.... | ................. | ................. | E..AG. | ............ | ............ | 0.02 | 3 |
| .A... | F.....DGA.RN.T.S.G | ..HG.....NF....... | ...D.. | ............ | A..A........ | 0.02 | 3 |
| TA... | ................. | .KDSR....DF....... | R..DD. | ..AAE.D....N | A..A........ | 0.02 | 3 |
| ..... | ................. | ................. | G..KGR | ............ | A..A........ | 0.02 | 3 |
| SA..T | ................. | .PPNG.....F......T | ...DDR | ............ | A..A........ | 0.02 | 3 |
| ..... | F................. | ................. | ...D.R | E.AG..D.A.GR | A..A........ | 0.02 | 3 |
| ..... | F................. | ................. | ...NGR | ..ASAAD.E..D | A..A........ | 0.02 | 3 |
| G.... | F.....DGG.NK.T...L | .Q.DR.....F....... | ...DDR | EDGG.S..E.DR | A..A........ | 0.02 | 3 |
| ..... | ................. | .KD.E.....F......T | ...DDR | ENAKT.DAEFGQ | A..A........ | 0.02 | 3 |
| TA... | F.......T.SV...H.R | TQ.TG....DF....... | ...DDR | ............ | A..A........ | 0.02 | 3 |
| ..... | ................. | ................T | ...TGR | ............ | A..A........ | 0.02 | 3 |
| ..... | F................. | .V........F....... | ...... | ............ | ARSNR..FDV.H | 0.02 | 3 |
| ..... | ................. | ..DGE....DF....... | ...... | ED.A.G.T..DN | A..A........ | 0.02 | 3 |
| ..... | ................. | ..........F....... | R...DR | E.ATEN..EFDS | A..A........ | 0.02 | 3 |
| ..... | F................. | .V........F....... | ...... | ............ | ARSSA..VEM.E | 0.02 | 3 |
| DT... | F......TG.IL...T.R | .QPG.....NF....... | ...... | E.TA.S..EY.. | A..A........ | 0.02 | 3 |
| DA... | F......NG.LQ.H...N | T.P......DF....... | ...D.. | ............ | ............ | 0.02 | 3 |
| EA... | ................. | ................. | ...AD. | ............ | ............ | 0.02 | 3 |
| ....T | F......GRG.H.P.E.R | .Q.......DF....... | ...AD. | ............ | A..A........ | 0.02 | 3 |
| G.... | F......DK..P.M.T.R | .QPN......F......T | ...N.. | ESATGG.T..GG | A..A........ | 0.02 | 3 |
| GT... | ................. | T.AG......F......T | ...DD. | .SAKAA.AA.DE | ............ | 0.02 | 3 |
| ..... | F.....GRG.H..P.E.R | .V........F....... | R..A.. | ............ | A..A........ | 0.02 | 3 |
| A.... | F.....DD..IH.K.K.K | .Q.DR.....F....... | ....D. | ..AT..DIA.DR | A..A........ | 0.02 | 3 |
| GT... | ................. | ................. | G..N.. | ............ | ............ | 0.02 | 3 |
| D...T | ................. | ................. | ....GR | ..AG.N.AA.GQ | A..A........ | 0.02 | 3 |
| ..... | F................. | .V........F....... | ...... | ............ | GPRAP..SET.Q | 0.02 | 3 |
| ..... | F.....NKT.I..K.... | ..DGE....DF....... | ...... | E.AGAADA.VDG | A..A........ | 0.02 | 3 |
| .A... | ................. | ..YN......F......T | R..DDR | .SARTGDTA..G | A..A........ | 0.02 | 3 |
| DT... | F.....AR..SL...H.G | ..YN......F......T | ...D.R | ............ | A..A........ | 0.02 | 3 |
| R.... | ................. | ................. | R...DR | E.ATEN..EFDS | A..A........ | 0.02 | 3 |
| ..... | F................. | .QPN......F......T | ...DD. | ..TGAS..EV.N | A..A........ | 0.02 | 3 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................. | .................. | ...... | EDGAGD..E..R | A..A........ | 0.02 | 3 |
| ..... | F......NG.LQ.H...N | T.P......DF....... | ...D.. | ............ | ............ | 0.02 | 3 |
| ..... | F................. | .V.........F...... | ...... | ............ | GARSS...EI.K | 0.02 | 3 |
| ..... | F.....SN...P.H.T.K | .V........F...... | ...... | ............ | ............ | 0.02 | 3 |
| GT... | F................. | .Q.S.....DF...... | ...DD. | ES.G.AD.EFGE | A..A........ | 0.02 | 3 |
| ..... | F................. | .................. | ....GR | ............ | A..A........ | 0.02 | 3 |
| .A... | ................. | ..DDG....NF..P.... | R..DD. | ENGKE..I..DG | A..A........ | 0.02 | 3 |
| AT... | F.....DGT.SM.N.G.R | .KDDG...NF......T | E..AG. | ............ | ............ | 0.02 | 3 |
| ..... | ................. | TQDDR....DF....... | ...DDR | E.TR.N.....Q | A..A........ | 0.02 | 3 |
| G.... | ................. | .................. | R..AG. | ............ | A..A........ | 0.02 | 3 |
| .A... | F.....GKA.LD.P.D.R | ..PN.....NF....... | ...... | ............ | A..A........ | 0.02 | 3 |
| .A... | ................. | .KD.E.....F....... | ...N.. | ............ | ............ | 0.02 | 3 |
| G.... | F.....SA..RA.....R | ..DGE....DF....... | ...DDR | E.TGGSD.E..R | A..A........ | 0.02 | 3 |
| ..... | ................. | .................. | ...D.R | ESATGG.T..GG | A..A........ | 0.02 | 3 |
| EA... | F....SA..SM.M.T.K | TKASG.....F....... | ...DDR | E.AGAND.AY.N | A..A....... | 0.02 | 3 |
| ..... | ................. | .................. | R..DD. | ED.NGN.IA.D. | A..A........ | 0.02 | 3 |
| ..... | F.....DRG.S..T.A.S | ..DGE....DF....... | ...... | ............ | A..A........ | 0.02 | 3 |
| DT... | F.....SG..RV.I.G.R | .V........F....... | R..... | ESGG.G..E..Q | A..A........ | 0.02 | 3 |
| .A... | F.....NGG.NN.K.T.R | .QHNQ.....F......T | ...N.. | ............ | A..A........ | 0.02 | 3 |
| ..... | ................. | ..AS.....DF....... | ...N.. | ..GTAG...V.G | A..A........ | 0.02 | 3 |
| H.... | F.....SGT.SQ.K.E.. | .Q.......DF....... | ...DDR | ............ | A..A........ | 0.02 | 3 |
| RA... | F................. | .................. | E..N.. | ............ | A..A........ | 0.02 | 3 |
| HA... | F.....ATT.NV.T.K.S | .Q.DR.....F....... | ....D | E.TGAN.AE.GE | A..A........ | 0.02 | 3 |
| E.... | ................. | .................. | E..TG. | ............ | ............ | 0.02 | 3 |
| .T... | F.......T.SV...H.R | ...TE.....F......T | ...... | E.AAASDAAY.N | A..A........ | 0.02 | 3 |
| E.... | F.....DRG.S..T.A.S | .V........F....... | ...... | ............ | G.RAG..DTE.Q | 0.02 | 3 |
| ..... | F................. | .V........F... | ...... | ............ | TTSGP...QK.. | 0.02 | 3 |
| .T... | F.....AGG.IV.L.G.R | TKDDR....DF....... | ...DDR | EDAGRND.AFDH | A..A........ | 0.02 | 3 |
| ..... | ................. | .................. | G...GR | .SGS.NDIA..D | A..A........ | 0.02 | 3 |
| ..... | ................. | .................. | E..NG. | ..ANR.D...DR | A..A........ | 0.02 | 3 |
| ..... | ................. | .................. | E..KG. | ............ | A..A........ | 0.02 | 3 |
| ..... | F.....ASA.S..T.T.G | .QPG.....DF....... | E..T.. | ............ | ............ | 0.02 | 3 |
| ..... | F.....ST...D.I...S | .QPG.....DF....... | ...DDR | ............ | A..A........ | 0.02 | 3 |
| EA..T | ................. | .................. | ...D.. | .DGA.....VGR | A..A........ | 0.02 | 3 |
| ..... | F.....SG..IQ.M.Q.R | .QYSR....NF....... | R..D.. | E.AG..D.A.GR | A..A........ | 0.02 | 3 |
| ..... | ................. | .................. | ...... | .DGNGA.I.V.G | A..A........ | 0.02 | 3 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| GT... | F.....SG..IK.K.D.R | .Q.G.....NF......T | ...NGR | ............ | A..A........ | 0.02 | 3 |
| ..... | .................. | .................. | ....D. | E.GGA.D.AV.E | A..A........ | 0.02 | 3 |
| TA... | F................. | .V........F....... | ...... | ............ | GPRAS..VNV.P | 0.02 | 3 |
| ..... | .................. | ..........DF...... | ...DDR | ESAGAG..A.GR | A..A........ | 0.02 | 3 |
| E.... | F.....SK..PA.K.A.G | .V........F....... | ...... | .DGGGN.....R | A..A........ | 0.02 | 3 |
| ..... | .................. | .................. | ...DG. | ESGGRA..EV.S | A..A........ | 0.02 | 3 |
| ..... | .................. | .................. | ...D.. | .DGKTGD..VGE | A..A........ | 0.02 | 3 |
| D.... | F.....GQ..LN.L.D.R | ..HG.....NF......T | G..KD. | ............ | A..A........ | 0.02 | 3 |
| .T... | .................. | .V........F....... | ...... | ............ | KERSP..I.T.. | 0.02 | 3 |
| ..... | F................. | .V........F....... | ...... | ............ | TTHST..FET.D | 0.02 | 3 |
| .A... | F.....NA..HE.L.G.R | T.P......DF...... | ...D.. | ............ | ............ | 0.02 | 3 |
| ..... | .................. | ..HG.....NF......T | ...... | E........... | A..A........ | 0.02 | 3 |
| G...T | F.....DQ..R..P.S.R | .Q.S......F....... | ...D.. | ............ | A..A........ | 0.02 | 3 |
| ..... | .................. | ..........F....... | ....D. | ESTGT..AAV.Q | A..A........ | 0.02 | 3 |
| ..... | .................. | .................. | ....G. | .SGS.NDIA..D | A..A........ | 0.02 | 3 |
| ..... | F................. | .V........F....... | ...... | ............ | TEHNP..FRS.T | 0.02 | 3 |
| SA... | F......KT.NV.K.T.G | TKPS.....DF......T | R..N.. | ............ | A..A........ | 0.02 | 3 |
| ..... | F......KT.NK...A.G | T.PGG....NF....... | ...DD. | .SAKAA.AA.DE | A..A........ | 0.02 | 3 |
| ..... | ..........A.N...R | .KYT.....NF......T | R...D. | ...G.D..EVGQ | A..A........ | 0.02 | 3 |
| S.... | F.....S...NV...T.. | TQDGE....DF....... | ...DG. | ............ | A..A........ | 0.02 | 3 |
| ..... | .................. | .................. | ...D.R | ..GAAND....H | A..A........ | 0.02 | 3 |
| N.... | F.....SD..HP.L.Q.K | .KYTE.....F....... | E..TGR | ............ | ............ | 0.02 | 3 |
| NA... | .................. | .................. | ...... | E.TDA...AVDQ | ............ | 0.02 | 3 |
| AA... | ......DHT..D.P...R | ...NG.....F....... | R...D. | EDAR.D..EVGE | A..A........ | 0.02 | 3 |
| DT... | .................. | .................. | R..DD. | ............ | A..A........ | 0.02 | 3 |
| SA... | F.....ASA.S..T.T.G | .Q.S......F....... | ....D. | ............ | ............ | 0.02 | 3 |
| NT..T | F.....AHT.LK.N...G | ..YN......F......T | ...D.R | ..TK...AE..D | A..A........ | 0.02 | 3 |
| ..... | F................. | .................. | R...D. | ............ | A..A........ | 0.02 | 3 |
| D.... | F......GT.NM.L.Q.G | .Q.S......F....... | ....D. | ............ | ............ | 0.02 | 3 |
| NA... | .................. | TQ..H....NF......T | ...D.. | ............ | A..A........ | 0.02 | 3 |
| HT..T | F.....GS..NM.N.T.R | TQPG.....NF....... | R..ND. | ............ | A..A........ | 0.02 | 3 |
| ..... | .................. | .................T | ...N.. | .DTSANDT..DG | A..A........ | 0.02 | 3 |
| A.... | F......G..NQ.N.A.G | TKAT.....NF......T | ...DDR | ............ | A..A........ | 0.02 | 3 |
| ..... | F................. | .V........F....... | ...... | ............ | ADHT...V.A.Q | 0.02 | 3 |
| GA... | F.....GTT....M.T.L | .K.TQ.....F....... | ...DDR | ...D.D..E..G | A..A........ | 0.02 | 3 |
| TA... | F.....AKG.P..H...G | .Q.S......F....... | E..N.. | ............ | A..A........ | 0.02 | 3 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | .................. | .PPNG.....F....... | ...DDR | ........... | ............ | 0.02 | 3 |
| E.... | F.....A...ND.T...K | .KDSR....DF....... | R..D.. | .STA..DA.FDS | A..A........ | 0.02 | 3 |
| ..... | .................. | ..........F | R...D. | EN.KA.DAE..D | A..A........ | 0.02 | 3 |
| HT..T | .................. | .QPTG....NF....... | R..DG. | ..AATNDAEF.E | A..A........ | 0.02 | 3 |
| GA... | F................. | .V........F....... | ....GR | ..AG.N.AA.GQ | A..A........ | 0.02 | 3 |
| ..... | F................. | .V........F....... | ...... | ........... | T.RDG..ITG.T | 0.02 | 3 |
| SA... | F.....S.T..I.K.N.M | ..........F....... | ...... | ........... | A..A........ | 0.02 | 3 |
| A.... | .................. | ...............T | ...N.. | ........... | A..A........ | 0.02 | 3 |
| ..... | .................. | .................. | ..AG. | ........... | A.......... | 0.02 | 3 |
| ..... | .................. | .................. | ...D.R | ...GGGDAA..G | A..A........ | 0.02 | 3 |
| DA... | F.....AGA.SL.....R | .........DF......T | ...DG. | ........... | A..A........ | 0.02 | 3 |
| G.... | .................. | .................. | ....GR | ..GAAS.AAFDE | A..A........ | 0.02 | 3 |
| ..... | ......DKA.IK.K.S.G | .................. | ...D.R | ..TG.N.IAF.D | A..A........ | 0.02 | 3 |
| NT... | .................. | .KAS.....NF......T | E..DD. | ........... | ............ | 0.02 | 3 |
| HA... | F.....NKT.I..K.... | ..DGE....DF....... | ...... | E.AGAADA.VDH | A..A........ | 0.02 | 3 |
| ..... | F................. | .QANH....DF....... | ...DDR | ........... | A..A........ | 0.02 | 3 |
| G...T | F.....GGG.NQ.I.S.G | TQ.TG....DF....... | ...DDR | ESAG.DD.A.DQ | A..A........ | 0.02 | 3 |
| G.... | F.....GDT.H..I...G | .QPTG.....F....... | ...N.. | ........... | A..A........ | 0.02 | 3 |
| ..... | .................. | ..........F....... | ....DR | EDGG.S..E.DR | A..A........ | 0.02 | 3 |
| .A... | F.....AEG.LK.M.H.L | ..DGE....DF....... | ...... | ........... | ............ | 0.02 | 3 |
| ..... | F................. | .Q.S.....F....... | E..NG. | ........... | ............ | 0.02 | 3 |
| ..... | F................. | .V........F....... | ...... | ........... | DTRTG..AGK.D | 0.02 | 3 |
| RA... | .................. | T.YNH.....F....... | ...DD. | .D.GG.....GH | A..A........ | 0.02 | 3 |
| DT... | F.....SNA.PK.N.A.S. | ..PN.....NF....... | ...... | .DGGGAD.A.D. | A..A........ | 0.02 | 3 |
| ..... | F................. | .QPTR.....F....... | ....GR | ........... | A..A........ | 0.02 | 3 |
| TA..T | .................. | .PPNG.....F......T | ...DDR | E.GKA....FDG | A..A........ | 0.02 | 3 |
| RA... | .................. | .................. | ...... | ........... | A..A........ | 0.02 | 3 |
| GT... | F.....A...ND.T...K | TQ.TG....DF....... | ...DDR | E.T......... | A..A........ | 0.02 | 3 |
| ..... | .................. | .................. | R..ND. | ........... | A..A........ | 0.02 | 3 |
| NA... | F.....AAT.N..P.P.R | ..PSH...DF..S.... | R..... | E.AG...IAVDR | A..A........ | 0.02 | 3 |
| GA... | F.....G.G.NQ.I.K.N | ..A......DF....... | ...DG. | ........... | A..A........ | 0.02 | 3 |
| ..... | .................. | .KDDR....DF....... | ...DDR | E.GTGA.IE.GD | A..A........ | 0.02 | 3 |
| ..... | F.....AHA.SH.M.S.R | ..DGE...DF....... | ...... | .SGGRS..E.DQ | A..A........ | 0.02 | 3 |
| G.... | F.....AQ...A.L.... | ...........P.... | ...... | ........... | ............ | 0.02 | 3 |
| .A... | .................. | ..........NF....... | R...D. | ..TGAS.A..DH | A..A........ | 0.02 | 3 |
| ..... | .................. | .................. | ...DDR | E.AGTNDI...R | A..A........ | 0.02 | 3 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F................. | .................. | ....GR | .......... | ............ | 0.02 | 3 |
| ..... | .................. | .................. | ...DDR | ..AAGADTA.DD | A..A........ | 0.02 | 3 |
| AA... | F.....GRG.N......H | T.P.....DF | ...... | .......... | ............ | 0.02 | 3 |
| DT... | F.....S.T.NV.L.D.. | .................. | ...ADR | ..AS...I..G. | A..A........ | 0.02 | 3 |
| ..... | .................. | .................. | R...D. | .SARGA.A.YDD | A..A........ | 0.02 | 3 |
| NA... | F......GG.NA.H.Q.R | .................. | ...... | E.AG...IAVDR | A..A........ | 0.02 | 3 |
| D...T | F......G..NL.T.E.R | .Q.DR.....F | ....D. | .......... | A..A........ | 0.02 | 3 |
| E.... | .................. | .........DF....... | R...D. | ESGTTS....GG | A..A........ | 0.02 | 3 |
| ..... | .................. | .................. | E..ND. | ..AD.A....G. | A..A........ | 0.02 | 3 |
| ..... | .................. | .................. | R...D. | .NGSAS..A.DN | A..A........ | 0.02 | 3 |
| ..... | F.....NG..IQ.M.N.R | .Q.......DF....... | ....AD | .......... | A..A........ | 0.02 | 3 |
| G.... | F......GT.NM.L.Q.G | .Q.S......F | ....D. | .......... | ............ | 0.02 | 3 |
| ..... | .................. | .................. | G..ND. | E.AR.S..EVGE | A..A........ | 0.02 | 3 |
| ..... | F.....AT..ND.K.P.K | .Q.GQ....DF....... | ....G. | .......... | ............ | 0.02 | 3 |
| ..... | .................. | .................. | ...DD. | E.AGGN..E.DD | A..A........ | 0.02 | 3 |
| ..... | .................. | .V........F | ...... | .......... | NNHGP......Q | 0.02 | 3 |
| GA... | F.....ASA.S..T.T.G | .QPG.....DF....... | ...DDR | .......... | A..A........ | 0.02 | 3 |
| ..... | .................. | .V........F | ...... | .......... | TRHTR..AEA.E | 0.02 | 3 |
| ..... | .................. | ..DGE....DF....... | ...ND. | ENAAGGDT..GR | ............ | 0.02 | 3 |
| ..... | .................. | .KYT.....NF......T | ...D.R | ESATGD..E.GQ | A..A........ | 0.02 | 3 |
| RT... | F.....ARG.I..T.A.K | ..DGE....DF....... | ...... | E.AG.S..E.DN | A..A........ | 0.02 | 3 |
| T.... | .................. | ..P.E.....F.......T | R..DD. | .......... | A..A........ | 0.02 | 3 |
| ..... | F................. | .V | ...AG. | .......... | A..A........ | 0.02 | 3 |
| ..... | F.....DGA.R..P.A.K | ..YN......F.......T | R..DD. | .......... | A..A........ | 0.02 | 3 |
| ..... | F................. | .V........F | ...... | .......... | AHSGG..FET.A | 0.02 | 3 |
| ..... | ......STA..Q.H.Q.L | .........NF | E..NGR | .......... | A..A........ | 0.02 | 3 |
| ..... | F................. | .V........F | ...... | .......... | GNHAA..FDM.. | 0.02 | 3 |
| ..... | .................. | .........DF......T | R..AGR | EDAGT...AFD. | A..A........ | 0.02 | 3 |
| D...T | F......GT.NM.L.Q.G | .Q.S......F | ....D. | .......... | A..A........ | 0.02 | 3 |
| G...T | F......S..PM.T.S.K | ..DGE....DF | ...... | .......... | A..A........ | 0.02 | 3 |
| ..... | .................. | T.Y.G....NF | ....GR | E.T..S..A..R | A..A........ | 0.02 | 3 |
| ..... | F................. | .V........F | ...... | .......... | A.QAP..ATE.Q | 0.02 | 3 |
| ..... | .................. | .................. | G..K.. | EN.G.A....Q | A..A........ | 0.02 | 3 |
| GT... | F.....AEG.LK.M.H.L | ..ADH....DF | ...... | .......... | A..A........ | 0.01 | 2 |
| DA... | F.....DAG.PM.I.N.R | ................T | R..D.. | .......... | A..A........ | 0.01 | 2 |
| GA... | F.....G.G.NQ.I.K.N | ..A......DF....... | ....D. | E.TGAN.AE.GE | A..A........ | 0.01 | 2 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F.....AEG.LK.M.H.L | ..DGE....DF....... | ...... | ............ | ATRA...VDN.. | 0.01 | 2 |
| HA... | ................. | TKAT.....NF......T | ...DDR | .D.AAS..EFGQ | A..A........ | 0.01 | 2 |
| DT... | R.....ASA.S..T.T.G | .QPG.....DF....... | ...DDR | ............ | ............ | 0.01 | 2 |
| ..... | ................. | .V........F....... | ...... | ............ | NPRDP..NNG.. | 0.01 | 2 |
| ..... | ................. | TQDS.....NF....... | ...A.. | E.AGTNDI.... | A..A........ | 0.01 | 2 |
| RA... | F.....G.G.HA.T.G.R | ..YN......F......T | ....D. | ............ | A..A........ | 0.01 | 2 |
| ..... | F.....SEA.IH...Q.L | .Q.DR.....F....... | ....D. | .NAGA.D...GS | A..A........ | 0.01 | 2 |
| ..... | F.....GG..NE.K.G.V | .QPN......F..P.... | ...... | ..AG.N..EV.S | A..A........ | 0.01 | 2 |
| DA..T | F......EG.S..T.K.K | ..A......DF....... | ...DG. | ..AGE....VG. | A..A........ | 0.01 | 2 |
| EA... | ................. | .QAS.....NF......T | ....GR | E.AGRDD..V.E | A..A........ | 0.01 | 2 |
| ..... | F................ | .V........F....... | ...... | ............ | NSRAT..S.G.H | 0.01 | 2 |
| ..... | F................ | .V........F....... | ....D. | ............ | ............ | 0.01 | 2 |
| A.... | F.....DK...M.K.P.M | .........NF....... | ...D.. | ED.A.G.T..DN | A..A........ | 0.01 | 2 |
| ..... | ................. | ................. | E..T.. | ............ | ............ | 0.01 | 2 |
| ..... | F.....STG.NP.M.E.R | ...TE.....F......T | ...... | ............ | A..A........ | 0.01 | 2 |
| ..... | F................ | .V........F....... | ...... | ............ | STKSG..YSA.Q | 0.01 | 2 |
| ..... | ................. | ................. | ...ADR | ............ | A..A........ | 0.01 | 2 |
| G.... | ................. | .PPNG.....F......T | ...... | ..ADGA..AYDR | A..A........ | 0.01 | 2 |
| ..... | ................. | ................. | ...DD. | ESAGRS...VDR | A..A........ | 0.01 | 2 |
| ..... | F.....GK..LA.K.N.G | ................. | ...... | ..AGT.D.EYGQ | A..A........ | 0.01 | 2 |
| GA... | ................. | ................. | ....D. | .D..TD....GD | A..A........ | 0.01 | 2 |
| ..... | ................. | ................. | ....D. | .NATG....VGS | A..A........ | 0.01 | 2 |
| GT... | F......S..PM.T.S.K | ..DGE....DF....... | ...... | E.TGGS.I.YDR | A..A........ | 0.01 | 2 |
| ..... | ................. | .KPSE....DF......T | ...D.. | ............ | A..A........ | 0.01 | 2 |
| ..... | ................. | TQADR....NF......T | ....D. | EDAK.N...Y.N | A..A........ | 0.01 | 2 |
| ..... | ................. | .........DF......T | R..TDR | .DGGR....VDG | ............ | 0.01 | 2 |
| TA... | F.....SRA.SK.N.A.H | .QDT.....DF....... | ...DDR | ...G.S..E.DR | A..A........ | 0.01 | 2 |
| GT... | F.....DGT.IA.L...R | ................. | R..N.. | E.A.GS....GG | A..A........ | 0.01 | 2 |
| N.... | F.....GS..NM.N.T.R | ................. | ...D.. | E.AGAND.AV.H | A..A........ | 0.01 | 2 |
| ..... | F.....G.G.NQ.I.K.N | ..A......DF....... | ...DG. | ............ | A..A........ | 0.01 | 2 |
| AA... | ................. | .........NF......T | ...DDR | E..G.SDAA.GD | A..A........ | 0.01 | 2 |
| DT... | ................. | .QPN......F......T | ....D. | ............ | A..A........ | 0.01 | 2 |
| ..... | ................. | ................. | E..KD. | .SAAAA.I.F.H | A..A........ | 0.01 | 2 |
| ..... | ................. | ..DGE....DF....... | R...D. | ............ | A........... | 0.01 | 2 |
| DT... | F.....AEG.LK.M.H.L | ..DGE....DF......T | R..DD. | ............ | A..A........ | 0.01 | 2 |
| NA... | F.....SRG..L.P.G.G | .QPSE....DF....... | ...DD. | ............ | A..A........ | 0.01 | 2 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| NA... | .................. | ..DGE....DF....... | ...... | ........... | A..A........ | 0.01 | 2 |
| ..... | .................. | .................. | R...D. | ....AG..AV.D | A..A........ | 0.01 | 2 |
| ..... | F.....SGT.S..P.A.K | ..HG.....NF....... | ...... | E.......... | A..A........ | 0.01 | 2 |
| ..... | F................. | .V........F....... | ...... | ........... | SAKDS..DNG.. | 0.01 | 2 |
| TA... | F.....DKA.IK.K.S.G | .................. | ...D.R | ..TG.N.IAF.D | A..A........ | 0.01 | 2 |
| TA... | .................. | .................. | ....D. | E.......... | A..A........ | 0.01 | 2 |
| H.... | F.....ASA.S..T.T.G | ..HG.....NF......T | ...A.. | ........... | A..A........ | 0.01 | 2 |
| ..... | F......QG.NQ...A.R | .KYT.....NF......T | ...D.. | ........... | A..A........ | 0.01 | 2 |
| A.... | .................. | TQ.TQ....DF....... | ...DDR | E..RRD.AA..H | A..A........ | 0.01 | 2 |
| ..... | ................K | ........F........ | ...... | ........... | ARSNR..FDV.H | 0.01 | 2 |
| ..... | .................. | ..AGR....DF......T | ....D. | ........... | A..A........ | 0.01 | 2 |
| D.... | F.....ATT.HP.L.T.L | TQADR.D..NF......T | G..TD. | .SAKAA.AA.DE | A..A........ | 0.01 | 2 |
| G.... | F................. | .V........F....... | ...... | ........... | NPRGA..S.G.E | 0.01 | 2 |
| ..... | F................. | .V........F....... | ...... | ........... | G.RTH...S..H | 0.01 | 2 |
| ..... | .................. | .........DF......T | R..D.. | E.TA.S..EY.. | A..A........ | 0.01 | 2 |
| EA... | F................. | TQDGE....DF....... | ....D. | ED.GAG..AV.G | A..A........ | 0.01 | 2 |
| .A... | F.....SG..IK.K.D.R | ..HG.....NF......T | E..N.. | ........... | A..A........ | 0.01 | 2 |
| E.... | F.....ASA.S..T.T.G. | .QD.E.....F..P.... | ...D.. | ........... | A..A........ | 0.01 | 2 |
| TA..T | F......EG.LQ.M.A.K | .KDSR....DF....... | ...DDR | ........... | A..A........ | 0.01 | 2 |
| ..... | .................. | .........NF....... | R...D. | .DGGGS.....G | A..A........ | 0.01 | 2 |
| ET..T | F.....AKG.NM.L...K | ..YN......F......T | ...D.R | ES.G..D..VGG | A..A........ | 0.01 | 2 |
| D...T | .................. | .........F......T | R..N.. | ........... | A..A........ | 0.01 | 2 |
| NA... | F.....SG..IK.K.D.R | ..DGE....DF....... | ...... | EDANRN..E..R | A..A........ | 0.01 | 2 |
| ..... | .................. | .................. | ...DDR | EDAA...AAVDQ | A..A........ | 0.01 | 2 |
| ..... | .................. | .QAS.....NF......T | ....GR | .NGGTG..A.DR | A..A........ | 0.01 | 2 |
| NT..T | .................. | .................. | G..DG. | ........... | ........... | 0.01 | 2 |
| GT... | F.....SR..NE.M...S | ..DGE....DF....... | ...NDR | ........... | A..A........ | 0.01 | 2 |
| ..... | F.....GKT.SL...G.R | ..DGE....DF....... | ...DG. | ..ATG..I.F.R | A..A........ | 0.01 | 2 |
| ..... | F.....SAG..L.H...K | .........NF....... | E..NG. | ........... | A..A........ | 0.01 | 2 |
| ....T | F......TT.HN.L.G.R | .Q.DH....NF....... | ...DD. | ........... | A..A........ | 0.01 | 2 |
| E.... | .................. | .QANH.....F......T | R..D.. | .SAKAA.AA.DE | ........... | 0.01 | 2 |
| .T... | .................. | .V........F....... | R..ND. | ..AG...T.V.N | A..A........ | 0.01 | 2 |
| ..... | .................. | .Q.......DF....... | ...DDR | ES.SED....GG | A..A........ | 0.01 | 2 |
| TT... | F.....NGT.IL.T.A.K | TKA......NF......T | ...... | ........... | A..A........ | 0.01 | 2 |
| ..... | .................. | .................. | ....G. | ..TTGAD.EVGG | A..A........ | 0.01 | 2 |
| AT... | F.....ATG.NV.T.G.R | ..HDG....F........ | ...... | ........... | A..A........ | 0.01 | 2 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | ..HG.....NF......T | ...A.. | .SA....AEVDD | A..A........ | 0.01 | 2 |
| SA... | F.....S.T..I.K.N.M | ................. | E..KD. | ............ | ............ | 0.01 | 2 |
| ..... | ................. | ..P.E.....F......T | R..DD. | ............ | A..A........ | 0.01 | 2 |
| .T... | ................. | ................. | E..DDR | E.AAAD.I..GQ | A..A........ | 0.01 | 2 |
| NA... | F.....GQT.SP.T.D.K | .V........F....... | E..AGR | E...GG.DIAY.E | A..A........ | 0.01 | 2 |
| ..... | ................. | .Q.DR.....F....... | ....D. | ............ | A..A........ | 0.01 | 2 |
| GT... | F................. | ................. | R..D.. | ..ASAAD.E..D | A..A........ | 0.01 | 2 |
| G.... | F.....AT..ND.K.P.K | .Q.GQ....DF....... | ....G. | ............ | A..A........ | 0.01 | 2 |
| ..... | .......GT.NM.L.Q.G | .Q.S......F....... | ....D. | ............ | A..A........ | 0.01 | 2 |
| ..... | ................. | ................. | G..K.. | E.AGG.DI..GH | A..A........ | 0.01 | 2 |
| GT... | F.....AEG.LK.M.H.L | ................. | G..DG. | ............ | ............ | 0.01 | 2 |
| ..... | ................. | .V........F....... | ...... | ............ | NARSG..SR..H | 0.01 | 2 |
| A.... | ................. | TQ.TG....DF....... | ...... | ..ARAA.I..GQ | ............ | 0.01 | 2 |
| ..... | F................. | .V........F....... | ...... | ............ | AESSG..AEI.E | 0.01 | 2 |
| G.... | F.....ATT.NV.T.K.S | .........NF....... | R...D. | ............ | A..A........ | 0.01 | 2 |
| HA... | ................. | ................. | ...DD. | ..ASTDDA.VGE | A..A........ | 0.01 | 2 |
| RA... | ................. | .KYT......F....... | ...... | E.TAAA.A..DG | A..A........ | 0.01 | 2 |
| SA... | ................. | ................. | E..KG. | ............ | ............ | 0.01 | 2 |
| ..... | F................. | .V........F....... | ...... | ............ | SRQTG..YTN.P | 0.01 | 2 |
| GT... | F.....GG..NK.M.... | .QPSE....DF....... | R..D.. | ............ | A..A........ | 0.01 | 2 |
| TA... | F.....ASA.S..T.T.G | .QD.E.....F..P.... | ...D.. | ............ | ............ | 0.01 | 2 |
| ..... | ................. | ................. | ...DD. | .N.GA.D.A.GG | A..A........ | 0.01 | 2 |
| ..... | ................. | ................. | ...N.. | E.AG...IAVDR | A..A........ | 0.01 | 2 |
| RA... | ................. | ..DNH....NF....... | ...D.. | .NGGTG..A.DR | A..A........ | 0.01 | 2 |
| EA... | F.....SD..HP.L.Q.K | .Q.DH....NF....... | ...DD. | ............ | A..A........ | 0.01 | 2 |
| E.... | ................. | .KDDG....NF......T | ...DDR | .SGATG.AA.GE | A..A........ | 0.01 | 2 |
| SA... | ................. | TQYDR....NF....... | R...D. | .SAKAA.AA.DE | A..A........ | 0.01 | 2 |
| ..... | ................. | ..........F....... | ...D.. | ............ | A..A........ | 0.01 | 2 |
| DT... | ......AST.IN.L.T.. | ..DGE....DF....... | ...G.. | ............ | ............ | 0.01 | 2 |
| SA... | ................K | ................. | G..ND. | E.AG...IAVDR | A..A........ | 0.01 | 2 |
| ..... | ................. | ................. | ...... | ..TGAS..EV.N | A..A........ | 0.01 | 2 |
| DA... | F.......G.SE.N...R | .PPNG.....F....... | ...... | ENAATA.AA..E | A..A........ | 0.01 | 2 |
| TA... | F.....SRA.SK.N.A.H | ................. | ....GR | ..AG.N.AA.GQ | A..A........ | 0.01 | 2 |
| N.... | ................. | .QANH.....F......T | ...ADR | E.ANGG.A...D | A..A........ | 0.01 | 2 |
| R.... | ................. | ................. | R...D. | ............ | A..A........ | 0.01 | 2 |
| SA... | ................. | ................. | ....GR | ..AG.N.AA.GQ | A..A........ | 0.01 | 2 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................. | ..DGE....DF....... | ...... | E.ASGSDIE.DR | A..A........ | 0.01 | 2 |
| E.... | F.....DGA.R..P.A.K | .QPTR....DF....... | E..NG. | ............ | A..A........ | 0.01 | 2 |
| .A... | F................ | .V........F....... | ...... | ............ | GQ.TP..IRT.A | 0.01 | 2 |
| ..... | ................. | ................. | ....GR | ..AG.N.AA.GQ | ............ | 0.01 | 2 |
| AA... | ................. | .Q.DR.....F....... | ....D. | ..AKG...AV.. | A..A........ | 0.01 | 2 |
| AA... | ................. | .QHNQ.....F......T | ...N.. | ..AST..AA..D | A..A........ | 0.01 | 2 |
| SA..T | F.....GGG.HK.T...G | .K.T......F....... | ...... | ............ | A..A........ | 0.01 | 2 |
| ..... | F................ | .V........F....... | ...... | ............ | GPRST..S.E.P | 0.01 | 2 |
| ..... | ................. | ................. | G..K.. | ............ | A..A........ | 0.01 | 2 |
| E.... | F.....ASA.S..T.T.G | .QPG.....DF....... | ...... | ..TNESD..... | A..A........ | 0.01 | 2 |
| T.... | F.....DAG.SA...H.R | ..HG.....NF......T | ...A.. | ............ | A..A........ | 0.01 | 2 |
| G.... | F................ | ................. | R..TG. | ............ | A..A........ | 0.01 | 2 |
| .A... | F.....ASA.S..T.T.G | .Q.DH....NF....... | ...DD. | ............ | A..A........ | 0.01 | 2 |
| ..... | ................. | .PPNG.....F......T | R...D. | EDAGT...AFD. | A..A........ | 0.01 | 2 |
| ..... | ................. | ................. | ...TG. | ............ | A..A........ | 0.01 | 2 |
| ..... | ................. | ................. | ...... | ..TNESD..... | ............ | 0.01 | 2 |
| ..... | ................. | .........NF....... | R...D. | EDGGGS..E.GR | A..A........ | 0.01 | 2 |
| G.... | ................. | ................. | ...DDR | ............ | ............ | 0.01 | 2 |
| ..... | F.....DQ..R..P.S.R | .KD.E.....F..P...T | R...D. | ............ | A..A........ | 0.01 | 2 |
| ..... | ................. | ..DGE....DF....... | ...... | .DGTGGD.A..R | A..A........ | 0.01 | 2 |
| ..... | ................. | .........DF....... | G..NDR | .D.SAG...Y.G | A..A........ | 0.01 | 2 |
| E.... | F.....DRG.S..T.A.S | .V........F....... | ...... | ............ | ..RAG..DTE.Q | 0.01 | 2 |
| DT... | ......AST.IN.L.T.. | ..EGE....DF....... | ...... | ............ | ............ | 0.01 | 2 |
| ..... | ................. | ................. | ...... | ............ | GP.NA..YRE.Q | 0.01 | 2 |
| ..... | ................. | ................. | E..AD. | ............ | ............ | 0.01 | 2 |
| E.... | ................. | ..P.G....KF....... | ...D.R | ENGT.G.I... | A..A........ | 0.01 | 2 |
| E.... | ......SK..PA.K.A.G | ................. | ...A.. | ............ | A..A........ | 0.01 | 2 |
| GT... | F.....NTG.RN.T.T.L | .QP.G.....F....... | ...... | ............ | A..A........ | 0.01 | 2 |
| ..... | F......GG.NV...K.. | .PPNG.....F......T | ...DDR | ............ | A..A........ | 0.01 | 2 |
| DA..T | ................. | .........NF....... | R...D. | E..G.A..E.GR | A..A........ | 0.01 | 2 |
| ..... | F.....NN..N..M...G | ..PDG....DF....... | ...DDR | ............ | GQKDR..ST..H | 0.01 | 2 |
| ..... | F................ | .V........F....... | ...... | ............ | ATKAP..SDG.T | 0.01 | 2 |
| ..... | ................. | ................. | ...DDR | .DAKGN..EVGQ | AA.A.......D | 0.01 | 2 |
| ..... | ................. | ................. | E..KD. | ..AS...I..G. | A..A........ | 0.01 | 2 |
| .T... | F................ | .V........F....... | ...... | R.......... | SERAG..YQ..Q | 0.01 | 2 |
| TA..T | F................ | .V........F....... | ...... | ............ | SRQAH..SDM.E | 0.01 | 2 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | ................ | .................. | G..DD. | E.AG...TAVGN | A..A........ | 0.01 | 2 |
| ..... | ................ | .................. | E..AD. | ENG.AN.AE.DE | A..A........ | 0.01 | 2 |
| ..... | ................ | .................. | R..N.. | ..AKAND...GS | A..A........ | 0.01 | 2 |
| E.... | F............... | .................. | ...DD. | ..ASTDDA.VGE | A..A........ | 0.01 | 2 |
| ..... | ................ | N................. | R..A.. | ED.NGN.IA.D. | A..A........ | 0.01 | 2 |
| RT... | ................ | .................. | ...... | ............ | ............ | 0.01 | 2 |
| NT... | F.....AGA.NK.L...K | .................T | G..D.R | ............ | A..A........ | 0.01 | 2 |
| RA... | F.....ASA.S..T.T.G | .QPG.....DF....... | ...DDR | ............ | ............ | 0.01 | 2 |
| NA... | ................ | .................. | E..NG. | ............ | A........... | 0.01 | 2 |
| ..... | ......ASA.S..T.T.G | .QPG.....DF....... | ...DDR | ............ | ............ | 0.01 | 2 |
| ET... | F.....SGT.SQ.K.E.. | ..DGE....DF....... | ...... | EDTGAD....DS | A..A........ | 0.01 | 2 |
| ..... | ................ | .........NF....... | ...... | ..GGTD....DR | A..A........ | 0.01 | 2 |
| ..... | ................ | .QPN......F......T | ...DD. | ..TGAS..EV.N | A..A........ | 0.01 | 2 |
| ..... | ................ | TQ.TG....DF....... | ...... | ..ARAA.I..GQ | A..A........ | 0.01 | 2 |
| NA..T | F.....STA..Q.H.Q.L | TQPTE....DF....... | ....D. | ..AAE.D....N | A..A........ | 0.01 | 2 |
| ..... | F.....GKG.RK.L.N.E | ...GG.....F......T | ...D.. | ............ | A..A........ | 0.01 | 2 |
| ..... | ................ | .................. | R..DD. | E.ARAN.IEVDQ | A..A........ | 0.01 | 2 |
| ..... | F.....NQG....P.K.I | TK.NE....DF......T | ...... | ..AGAN..A.GD | A..A........ | 0.01 | 2 |
| A.... | F.....AGG.IN.L.T.. | .QD.E.....F..P.... | R..DDR | ............ | A..A........ | 0.01 | 2 |
| ..... | F............... | .................. | R..DD. | ............ | ..D......... | 0.01 | 2 |
| ..... | ................ | .................. | ...... | ED.A.A....GQ | A..A........ | 0.01 | 2 |
| RA... | ................ | TQP.R....NF......T | ...D.. | ............ | A..A........ | 0.01 | 2 |
| NA..T | F......ET.SP.I.G.. | .QAS.....NF......T | ....GR | E.GATG...VD. | A..A........ | 0.01 | 2 |
| A.... | ................ | .QPN......F......T | ...N.. | .D.GRAD.AF.S | A..A........ | 0.01 | 2 |
| ..... | ................ | ..HG.....NF......T | ...A.. | EDAG.AD.E.G. | A..A........ | 0.01 | 2 |
| E.... | ................ | T.PGG....NF....... | ...DD. | ..GAGS..AV.E | A..A........ | 0.01 | 2 |
| ..... | ................ | .................. | R..D.R | EDGARA..A.GE | A..A........ | 0.01 | 2 |
| GT... | F.....STA.HA.M.S.V | ..DGE....DF....... | ...... | .SAKAA.AA.DE | A..A........ | 0.01 | 2 |
| E.... | F.....NTT.SK.M.K.R | .QD.E.....F..P... | ...... | ............ | A..A........ | 0.01 | 2 |
| ..... | ................ | .................. | ...DDR | ENAAAN.A.Y.S | A..A........ | 0.01 | 2 |
| ..... | F............... | ..DGE....DF....... | ...D.. | ESGT.G.AEVDD | A..A........ | 0.01 | 2 |
| ..... | ................ | ..PDH....DF....... | ...NGR | ED.T.D..A.DR | A..A........ | 0.01 | 2 |
| TT..T | F.....SA..RA.....R | .................. | G..ND. | ............ | ............ | 0.01 | 2 |
| ..... | ................ | ..........DF...... | ...DD. | .D..R.D.E... | A..A........ | 0.01 | 2 |
| G.... | F.....GE..LQ.N.T.R | ..PTG....DF....... | ...DDR | ESGTAND...DR | A..A........ | 0.01 | 2 |
| G.... | ................ | ..DGE....DF....... | ...... | .SGARD.A..DG | A..A........ | 0.01 | 2 |

TABLE 7-continued

AAV capsid proteins having increased specificity for and/or transduction of CD44$^+$ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| TA..T | F.....NGG.IM.L.E.R | T.P......DF....... | ....D. | ........... | ........... | 0.01 | 2 |
| TA... | ................. | .................. | ...DDR | ..AGES.A.Y.Q | A..A........ | 0.01 | 2 |
| ..... | ................. | .............F | ...DDR | EN.DGNDT..DG | A..A........ | 0.01 | 2 |
| A.... | ................. | ................T | ...DDR | EDGDGA..A.DR | A..A........ | 0.01 | 2 |
| ..... | ................. | .................. | ....GR | .STAAG...VDG | A..A........ | 0.01 | 2 |
| G.... | ................. | .................. | ...D.R | ..TGAS.A..DH | A..A........ | 0.01 | 2 |
| E.... | ................K | ..YN......F......T | ...D.R | .NGR.G..A..E | A..A........ | 0.01 | 2 |
| GT... | F................. | .KAS.....NF......T | ....GR | ........... | ........... | 0.01 | 2 |
| NA... | ................. | .................. | ...DDR | ..AGES.A.Y.Q | A..A........ | 0.01 | 2 |
| .A... | ................. | ..........NF....... | ...DDR | ...TG..T..GQ | A..A.......T | 0.01 | 2 |
| ..... | ................. | TKPAH.....F | ...... | ........... | T.STR..DEK.. | 0.01 | 2 |
| ..... | ................. | .................. | ....D. | .DAAGN..A..E | A..A........ | 0.01 | 2 |
| AA... | F.....A.G.NQ.T.G.R | .................. | ...... | .S.GTGDIAVDQ | A..A........ | 0.01 | 2 |
| ST... | ................. | TQDS.....NF....... | ...A.. | E.AGNTDI.... | A..A........ | 0.01 | 2 |
| ..... | .....AHA.SH.M.S.R | ..DGE....DF....... | ...D.. | .SGGRS..E.DQ | A..A........ | 0.01 | 2 |
| ..... | ................. | ................A. | ...D.. | E.AGAND.AV.H | A..A........ | 0.01 | 2 |
| ..... | ................. | TKAT.....NF......T | G..TG. | ........... | A..A........ | 0.01 | 2 |
| GT... | ................. | .QANH....DF....... | ...DDR | ........... | A..A........ | 0.01 | 2 |
| G.... | F.....GN..HM.P.... | .QPN......F......T | R...D. | ........... | A..A........ | 0.01 | 2 |
| ..... | ................. | .Q.DR.....F....... | ....D. | E.TD.A....DG | A..A........ | 0.01 | 2 |
| ..... | ................. | .................. | R..DG. | E.TT.A...VGD | A..A........ | 0.01 | 2 |
| DT... | F.....GG..RV.I.G.R | .V........F....... | R..... | ESGG.G..E... | A..A........ | 0.01 | 2 |
| ....T | ................. | .................. | ....D. | ........... | A..A........ | 0.01 | 2 |
| ..... | ................. | .................. | ...D.R | ...NRSD.A..S | A..A........ | 0.01 | 2 |
| RA..T | F......GD.HP.K...V | ..DGE....DF....... | ...... | ........... | A..A........ | 0.01 | 2 |
| ..... | ................. | .................. | ...... | ........... | KPHSP..VSE.T | 0.01 | 2 |
| TA... | F.....GN..NA.T.... | TQ.TG............. | ...... | E..K.GDA...S | A..A........ | 0.01 | 2 |
| ..... | ................. | ..HQ.....NF......T | ...A.. | E.TKGS.AEF.G | A..A........ | 0.01 | 2 |
| ..... | ................. | ..P......DF....... | ....G. | ........... | ........... | 0.01 | 2 |
| ..... | ................. | .................. | R..N.. | ...G.N.A.... | A..A........ | 0.01 | 2 |
| DT... | F................. | .Q.S......F....... | E..NG. | ........... | ........... | 0.01 | 2 |
| RA... | F.....GRT.S..L.G.R | .QANH.....F......T | E..T.. | ........... | A..A........ | 0.01 | 2 |
| E.... | ................. | ..DGE....DF....... | R...DR | ..T.GNDI..GN | A..A........ | 0.01 | 2 |
| ..... | F.....AGG.IV.L.G.R | ..DGE....DF....... | ...... | E.GA.N..A..H | A..A........ | 0.01 | 2 |
| ..... | ................. | TQ.TG...DF....... | ...DDR | ENATASD...GS | A..A........ | 0.01 | 2 |
| G.... | F......S..PM.T.S.K | T.P......DF....... | ...D.. | ........... | A..A........ | 0.01 | 2 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| G.... | ................. | .................. | G..TDR | E.AGGN..E.DD | A..A........ | 0.01 | 2 |
| ..... | F................. | .V........F....... | ...... | ............ | .R.DG..AT..A | 0.01 | 2 |
| TA... | ................. | .................. | ....GR | ..AG.N.AA.GQ | A..A........ | 0.01 | 2 |
| TA... | ................. | ..HG.....NF......T | E..DD. | ............ | A..A........ | 0.01 | 2 |
| ..... | ................. | .................. | ...DD. | .SGR.N.T..GD | A..A........ | 0.01 | 2 |
| ..... | ................. | .KPQG.....F......T | ...N.. | ENAGRAD.AFD. | A..A........ | 0.01 | 2 |
| RA... | F.....SGA..N...G.R | .Q.......DF....... | ...AD. | .NAAEND...GE | A..A........ | 0.01 | 2 |
| ..... | ................. | .................. | ...D.. | E.TS.D..AFDQ | A..A........ | 0.01 | 2 |
| A...T | ................. | .QANH.....F......T | R..A.. | E..A.ADA..GD | A..A........ | 0.01 | 2 |
| EA... | F................. | .................. | ...DDR | E.AAGADT...S | ............ | 0.01 | 2 |
| ..... | F.....GRG.NN.T.G.. | .................. | ...... | ENAG.ND.E.DH | A..A........ | 0.01 | 2 |
| ..... | ................. | .................. | ....GR | E.ARGGDA.F.Q | A..A........ | 0.01 | 2 |
| GT... | ......ASA.S..T.T.G | .QPG.....DF....... | ...DDR | ............ | ............ | 0.01 | 2 |
| A...T | F......K.....L.G.L | .Q.S......F....... | E..N.. | ............ | A..A........ | 0.01 | 2 |
| R.... | F.....NG..SN.M...K | ...G.....DF....... | G..ADR | .NAA.A....GD | A..A........ | 0.01 | 2 |
| ..... | ................. | .V........F....... | ...... | ..AGRADIEVGS | A..A........ | 0.01 | 2 |
| GT... | F.....DTG.PA.L.T.K | ..DGE....DF....... | ...... | E.AGAND.AY.N | A..A........ | 0.01 | 2 |
| ..... | ..............R.... | ..DGE....DF....... | ...... | ............ | ............ | 0.01 | 2 |
| ..... | ................. | ................T | G..DD. | ESAA.D..E.GD | A..A........ | 0.01 | 2 |
| ..... | F.....ARA.L..L.Q.G | ...NG.....F....... | R...GR | ............ | A..A........ | 0.01 | 2 |
| ..... | ................. | .................. | E..N.. | E.AGGN...FGE | A..A........ | 0.01 | 2 |
| AA... | F.....ASA.S..T.T.G | .QPG.....DF....... | ...DDR | ............ | ............ | 0.01 | 2 |
| RA... | ................. | .................. | ...DDR | .STAES.IH.DG | A..A........ | 0.01 | 2 |
| ..... | ................. | .Q.GQ....DF....... | ....G. | E.AGAD..AVGE | A..A........ | 0.01 | 2 |
| ..... | ................. | .................. | ....D. | EDAGRND.AFDH | A..A........ | 0.01 | 2 |
| ..... | ................. | .................. | ...DD. | ............ | GPHAG..FDT.A | 0.01 | 2 |
| G.... | F.....DSG.NM.H.A.R | .Q.DH....NF....... | ...... | ............ | A..A........ | 0.01 | 2 |
| ..... | ................. | .................. | G..ND. | E..RADD.E..Q | A..A........ | 0.01 | 2 |
| ET..T | ................. | .................. | R...D. | ...AAS.A.VGQ | A..A........ | 0.01 | 2 |
| TT... | F.....DNG..D.M.G.R | .KDSR....DF....... | ...DG. | ............ | A..A........ | 0.01 | 2 |
| AT... | F.....DA..IA.L.K.R | .QPN......F....... | ...DG. | ............ | A..A........ | 0.01 | 2 |
| ..... | ..............T.. | ..HG.....NF......T | ...A.. | ..AG.SD.EVG. | A..A........ | 0.01 | 2 |
| DT... | F................. | .........F......T | R..TDR | ............ | ............ | 0.01 | 2 |
| SA... | ................. | .K.TG....DF....... | G..ND. | ............ | A..A........ | 0.01 | 2 |
| R.... | ................. | T.D.R...NF....... | ...... | ..ANAG.A.V.Q | A..A........ | 0.01 | 2 |
| ..... | F................. | .................. | R..N.. | ..AKAND...GS | A..A........ | 0.01 | 2 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| GA... | F......S..SE.T...R | TQYT.....NF......T | R..AD. | .SAGAN..E..S | A..A........ | 0.01 | 2 |
| ..... | .................. | .................. | ...D.R | ..TGAS.A..DH | A..A........ | 0.01 | 2 |
| GA... | F.....SG..IK.K.D.R | ..ADH....DF....... | E..AD. | .SADAG..A..S | A..A........ | 0.01 | 2 |
| E.... | F.....S.T.NV.L.D.. | .QPSQ....NF....... | ...... | E.AS.A.TAV.H | A..A........ | 0.01 | 2 |
| E.... | .................. | .................. | E..NG. | ............ | ............ | 0.01 | 2 |
| D...T | .................. | .V........F....... | ....GR | ..AG.N.AA.GQ | A..A........ | 0.01 | 2 |
| ..... | F................. | .................. | ...DDR | E.A.AD.AAF.. | A..A........ | 0.01 | 2 |
| ..... | .................. | .V........F....... | ...... | ............ | DPKTA..VRG.. | 0.01 | 2 |
| DT... | .................. | .................. | R...D. | ............ | A..A........ | 0.01 | 2 |
| A.... | F.....GHA.SK.T.E.K | .Q.S......F....... | E..N.. | EDAKGND.A..N | A..A........ | 0.01 | 2 |
| G.... | .................. | .PPNG.....F......T | ...DDR | EDGNGSDT..DS | A..A........ | 0.01 | 2 |
| TA... | F.....DEA.RQ.T.N.L | .........NF....... | R...D. | ..ASE...E.D. | A..A........ | 0.01 | 2 |
| ..... | F................. | .V....D...F....... | ...... | ............ | AARDG...TV.H | 0.01 | 2 |
| ..... | .................. | .........DF......T | R...G. | .NASEN...FDR | ............ | 0.01 | 2 |
| ..... | .................. | ..HGH....NF......T | ...D.. | ............ | GPQGR..SR..A | 0.01 | 2 |
| ..... | F.....SG..IK.K.D.R | .Q.G.....NF......T | ...NGR | ............ | A..A........ | 0.01 | 2 |
| ..... | F.....ATT.NV.T.K.S | .PHD.....DF......T | ...DG. | ............ | ............ | 0.01 | 2 |
| SA..T | F.....NTG.RN.T.T.L | ..DDG....NF....... | ...DD. | ............ | A..A........ | 0.01 | 2 |
| ..... | F.....GRG.SP.K...G | .QPG.....NF....... | ...DDR | ............ | DRRSA..YTT.Q | 0.01 | 2 |
| ..... | .................. | .................. | ...DDR | EDAGGS.AEYD. | A..A........ | 0.01 | 2 |
| ..... | F................. | .V........F....... | ...... | ............ | TAKDA..F.R.E | 0.01 | 2 |
| GT... | F......GT.NM.L.Q.G | .Q.S......F....... | ....D. | ............ | ............ | 0.01 | 2 |
| ..... | F................. | .................. | ...D.R | E.AG...IAYGN | A..A........ | 0.01 | 2 |
| ..... | F................. | .V........FL...... | ...... | ............ | GARA...ISG.Q | 0.01 | 2 |
| A.... | F......G..NQ.N.A.G | TKAT.....DF......T | ...DDR | ............ | A..A........ | 0.01 | 2 |
| ..... | .........K.L...G | .................. | ...DDR | ............ | A..A........ | 0.01 | 2 |
| RA... | .................. | .QYGQ....DF....... | ...... | ............ | G.QSP..DGA.T | 0.01 | 2 |
| TT... | F.....NGT.IL.T.A.K | TKPS.....DF......T | ...DG. | E.AG.A..EF.R | A..A........ | 0.01 | 2 |
| ..... | .................. | .........DF....... | ...DDR | .SGATG.AA.GE | A..A........ | 0.01 | 2 |
| ..... | F................. | .V........F....... | ...... | ............ | TQRNT..V.E.H | 0.01 | 2 |
| ..... | F.....STA..Q.H.Q.L | T.P......DF....... | R...D. | ............ | ............ | 0.01 | 2 |
| ..... | F................. | .V........F....... | ...... | ............ | GPQGR..SR..A | 0.01 | 2 |
| ..... | .................. | ......D........... | E..TD. | ............ | A..A........ | 0.01 | 2 |
| G.... | F.....G.T.IN.T...H | .QPG.....NF....... | ...DDR | ............ | A..A........ | 0.01 | 2 |
| ..... | F................. | .V........F....... | ...... | ............ | SAKTA..FE... | 0.01 | 2 |
| A.... | .................. | .KYT.....NF......T | ....GR | ..G..AD.A.DE | A..A........ | 0.01 | 2 |

TABLE 7-continued

AAV capsid proteins having increased specificity for and/or transduction of
CD44$^+$ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | F................. | .V........F....... | ...... | ............ | GERAS..ID..Q | 0.01 | 2 |
| .A... | F.....DGA.R..P.A.K | .QPNQ....NF......T | G..N.. | ............ | A...A........ | 0.01 | 2 |
| G...T | ................. | .Q.S......F....... | ....D. | ............ | ............ | 0.01 | 2 |
| ..... | ................. | ................. | G..KD. | ...NRAD.E..Q | A...A........ | 0.01 | 2 |
| ..... | ................. | ................. | ...DDR | E.A.TD.AAF.. | A...A........ | 0.01 | 2 |
| TT... | F......AG.NV.N.S.R | .QAS.....NF......T | ...N.. | ............ | A...A........ | 0.01 | 2 |
| RA... | F.....ANG.NV...G.R | TQADR....NF......T | ....D. | ............ | A...A........ | 0.01 | 2 |
| ..... | F................. | .V........F....... | ...... | ............ | SARGP..AQG.Q | 0.01 | 2 |
| A.... | ................. | ................. | ...DG. | ............ | A...A........ | 0.01 | 2 |
| SA..T | F.....AGG.SI.T.G.M | .PNNG....DF......T | ....G. | ENAAAN.A.Y.S | A...A........ | 0.01 | 2 |
| N.... | F.....SKT.LM.T.N.R | TQPNH.....F....... | ...DDR | .DAG.A.I..DG | A...A........ | 0.01 | 2 |
| E.... | F.....ASA.S..T.T.G | .QPG.............. | ...D.. | E.TAE..I.... | A...A........ | 0.01 | 2 |
| D...T | F.....NKG.S..H.K.G | ..YN......F......T | ...D.R | ..ASAAD.E..D | A...A........ | 0.01 | 2 |
| GT... | F.....SAG..L.H...K | .........NF....... | ....GR | ............ | A...A........ | 0.01 | 2 |
| ..... | F................. | .V........F....... | .....S | ............ | GPHGP..DGM.. | 0.01 | 2 |
| ..... | ......STT.HA.L.T.K | ..YNH.....F....... | ....D. | .DAAGN..A..E | A...A........ | 0.01 | 2 |
| G.... | ................. | .V........F....... | ...... | .N.SGNDIE.DQ | A...A........ | 0.01 | 2 |
| GT... | F......TG.IL...T.R | .QAS.....NF......T | ....GR | .DAGA.D.EVDE | ............ | 0.01 | 2 |
| NA..T | F.....NR..N..I.T.G | .QHNH....DF....... | ....G. | ESAGAA..AY.D | A...A........ | 0.01 | 2 |
| ..... | ................. | ................T | ...AGR | E..G.SDAA.GD | A...A........ | 0.01 | 2 |
| ..... | ................. | ........DF......T | R..TDR | ............ | A...A........ | 0.01 | 2 |
| ..... | F.....DTG.PA.L.T.K | .KYT.....DF....... | ...N.. | EDAA...AAVDQ | A...A........ | 0.01 | 2 |
| RA... | F.....DKG..L.N...R | ..DGE....DF....... | ...... | E.TGAN.AE.GE | A...A........ | 0.01 | 2 |
| ..... | ................. | ................T | G..DG. | ............ | ............ | 0.01 | 2 |
| ..... | F................. | .V........F....... | ...... | ............ | ADRNG..VRM.T | 0.01 | 2 |
| DA... | F......NG.LQ.H.... | T.P......DF....... | ...D.. | ............ | ............ | 0.01 | 2 |
| ..... | ................. | ....G....NF....... | ...D.. | E..R.N.AEFGE | A...A........ | 0.01 | 2 |
| .A... | F.....DRG.S..T.A.S | ..DGE....DF....... | ...DDR | .NTNEG.IA.DE | A...A........ | 0.01 | 2 |
| RA... | ................. | ................. | ...... | E.TAAA.A..DG | A...A........ | 0.01 | 2 |
| ..... | F................. | ................T | ...N.. | .DTSANDT..DG | A...A........ | 0.01 | 2 |
| ..... | ................. | ................. | E..TD. | ............ | ............ | 0.01 | 2 |
| ..... | .......GT.NM.L.Q.G | .Q.S......F....... | ....D. | ............ | GRSAS..VEG.Q | 0.01 | 2 |
| HT... | ................. | .QAS......F....... | ...... | ESAG....A.GE | A...A........ | 0.01 | 2 |
| E.... | ................. | ........F......T | R...D. | .D.NGA.TE.GD | A...A........ | 0.01 | 2 |
| ..... | F................. | .V........F....... | ...... | ............ | GRRDG..FTE.H | 0.01 | 2 |
| T.... | F.....DAG.SA...H.R | ..HG.....NF......T | ...A.. | ............ | ............ | 0.01 | 2 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ....T | F................. | .........NF....... | ...ND. | ...TG..T..GQ | A..A........ | 0.01 | 2 |
| TT..T | ................. | .QPTG....NF....... | ...DDR | E.GNG.D.E.DS | A..A........ | 0.01 | 2 |
| ..... | ................. | ................. | R..... | .DTSTN..E..G | A..A........ | 0.01 | 2 |
| A.... | F.....DA..IA.L.K.R | .QPN......F....... | ...DG. | ............ | A..A........ | 0.01 | 2 |
| DT... | F......TG..Q.T.T.G | .Q.......DF....... | ...AD. | ............ | A..A........ | 0.01 | 1 |
| ..... | ................. | TKDDR....DF....... | ...... | ............ | A..A........ | 0.01 | 1 |
| ST... | F......GT.NM.L.Q.G | .Q.S......F....... | ....D. | ............ | ............ | 0.01 | 1 |
| ..... | ................. | ................. | ...DDR | ..AAG..AA..R | A..A........ | 0.01 | 1 |
| SA... | F.....DNT.SK.L...K | TKAGE....NF......T | R..... | ............ | G.QSP..DGA.T | 0.01 | 1 |
| GT... | F.....AEG.LK.M.H.L | ..DGE....DF....... | ...... | ............ | GRSAS..VEG.Q | 0.01 | 1 |
| DT... | ................. | ................. | R..DD. | ............ | ............ | 0.01 | 1 |
| NA..T | F.....STG.HE.L...M | ..DGE....DF....... | ...... | E.AAASD.EYGE | A..A........ | 0.01 | 1 |
| ..... | ................. | .........NF......T | ...K.. | ..GSA..I..GG | A..A........ | 0.01 | 1 |
| E.... | ................. | ................. | ...D.R | ..TAE...E..E | A..A........ | 0.01 | 1 |
| GT... | ................. | ................. | ...NDR | ..AKG...AV.. | A..A........ | 0.01 | 1 |
| ..... | ................. | .........DF....... | ...D.. | ES.AGGDAAFDQ | A..A........ | 0.01 | 1 |
| ..... | ................. | ................. | R..DD. | .D.......... | A..A........ | 0.01 | 1 |
| ..... | F.....AST.PI.K.Q.K | TQ.TH....DF....... | ...... | ............ | A..A........ | 0.01 | 1 |
| ..... | ................. | ................. | ...D.R | ERGT.A.A..GH | A..A........ | 0.01 | 1 |
| GA..T | F.....STG..N.M.T.. | ..YN......F....... | G..NDR | ............ | ............ | 0.01 | 1 |
| TA... | F.....S.A.IA.M.T.R | ..DGE....DF....... | E..ND. | E.ARGADI..GD | A..A........ | 0.01 | 1 |
| ..... | ................. | .QD.E.....F..P...E | ...D.. | ............ | ............ | 0.01 | 1 |
| E.... | ......A.......... | ................. | ...DDR | ............ | ............ | 0.01 | 1 |
| ..... | ................. | ................. | ...... | .NA.AS.A..DR | A..A........ | 0.01 | 1 |
| ..... | F......TT..V.M.T.E | T.P.....DF....... | ...D.. | ............ | A..A........ | 0.01 | 1 |
| NT... | F.....AGA.NK.L...K | .V........F....... | ...... | ENARASDA..GS | A..A........ | 0.01 | 1 |
| TA..T | ................. | .PPNG.....F......T | ...DDR | ............ | A..A......A. | 0.01 | 1 |
| EA... | ................. | .Q.DH....NF....... | ...DD. | E.AGAND.AY.N | A..A........ | 0.01 | 1 |
| ET..T | ......ANG.HL.K.K.S | ................. | E..ND. | ............ | A..A........ | 0.01 | 1 |
| DT... | F.....DHT.R..M.G.R | ................. | ...... | ............ | A..A........ | 0.01 | 1 |
| ..... | F.....DNT.SK.L...K | T.PSH....DF......T | ...DD. | ............ | A..A........ | 0.01 | 1 |
| T.... | ................. | ................. | R...D. | ............ | A..A........ | 0.01 | 1 |
| EA... | F.....DG..I..K.K.G | .QPSQ....NF....... | E..TGR | E.GAGAD...GQ | A..A........ | 0.01 | 1 |
| D.... | F.....NTG.LH.T...R | ................. | ...DD. | E.TR.N.....Q | A..A........ | 0.01 | 1 |
| T...T | F.....GTG..P.T.D.R | .Q.S......F....... | E..N.. | ............ | A..A........ | 0.01 | 1 |
| G.... | F................. | .Q.S.....DF....... | ...DD. | ES.G.AD.EFGE | A..A........ | 0.01 | 1 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| .A... | F.....DG..I..K.K.G | .QPSQ..D.NF....... | E..TGR | ............ | ............ | 0.01 | 1 |
| E.... | F......AT.SN.I.Q.R | .................. | ...... | ....T.DTEFDS | A..A........ | 0.01 | 1 |
| ..... | .................. | TQ.TG....DF....... | ...DDR | ............ | AASAG..YNN.A | 0.01 | 1 |
| ..... | F......S..PM.T.S.K | .................E | ...D.. | ............ | A..A........ | 0.01 | 1 |
| GT... | F.....AEG.LK.M.H.L | ..DGE....DF....... | ...... | ............ | TTQS...IHA.A | 0.01 | 1 |
| ..... | F.....GKT.SL...G.R | TQHTE....DF....... | R..DD. | ..AT.DD..FDG | A..A........ | 0.01 | 1 |
| ..... | .................. | .QPSQ....NF....... | ...... | E.AS.A.TAV.H | A..A........ | 0.01 | 1 |
| ..... | .................. | .................. | ...DD. | E.TGRA..A..G | A..A........ | 0.01 | 1 |
| ..... | .................. | .................. | ...D.. | EDGNGSDT..DS | A..A........ | 0.01 | 1 |
| ..... | F.....STG.NP.M.E.R | ...TE.....F....... | ...D.. | E.TTG.DAE.DN | A..A........ | 0.01 | 1 |
| AT..T | .................. | .KYT.....NF......T | ...D.R | ESATGD..E.GQ | A..A........ | 0.01 | 1 |
| ..... | .................. | .PANG.....F....... | ..ND.. | E.TD...A..DN | A..A........ | 0.01 | 1 |
| DA... | .................. | .................. | ....GR | .SAKGG.EYGD | A..A........ | 0.01 | 1 |
| ..... | .................. | .................. | E..TGR | ............ | ............ | 0.01 | 1 |
| ..... | F................. | .V........F....... | ...... | ............ | GSRAT..FDE.. | 0.01 | 1 |
| NA... | .................. | .................. | ...AG. | EDAAR.D.A.D. | A..A........ | 0.01 | 1 |
| ..... | .................. | .................. | ...... | E.TDA...AVDQ | ............ | 0.01 | 1 |
| TA... | F.....NAA.I..M.G.R | .QPN......F......T | ...N.. | ............ | A..A........ | 0.01 | 1 |
| ..... | F................. | .................. | G..TDR | E.AGGN..E.DD | A..A........ | 0.01 | 1 |
| ..... | .................K | .Q.DH....NF....... | ...DD. | ..TK...AE..D | ............ | 0.01 | 1 |
| ..... | F......QT.P..L.Q.R | TQP.R....NF......T | ...... | ............ | A..A........ | 0.01 | 1 |
| DA... | F.....ASA.S..T.T.G | .QPG.....DF....... | ....G. | ............ | ............ | 0.01 | 1 |
| ..... | F.....AG..RV.L.N.G | .QPN......F......T | ...N.. | ............ | A..A........ | 0.01 | 1 |
| GT... | .................. | .................. | R..DD. | ED.NGN.IA.D. | A..A........ | 0.01 | 1 |
| S.... | .................. | .................. | ...... | E.AS.A.TAV.H | A..A........ | 0.01 | 1 |
| G.... | .................. | TQ.GR....DF....... | ...DDR | ............ | A..A........ | 0.01 | 1 |
| NA... | F.....GG..NE.K.G.V | .QPN......F..P.... | ...... | ..AG.N..EV.S | A..A........ | 0.01 | 1 |
| ..... | .................. | .................. | ...DDR | .D.AAS..EFGQ | A..A........ | 0.01 | 1 |
| G.... | .................. | .................. | R...D. | ............ | A..A........ | 0.01 | 1 |
| E.... | F.....G.G.HA.T.G.R | .Q.GQ....DF....... | R...D. | .DGTGA..E..E | A..A........ | 0.01 | 1 |
| E.... | F................. | .V........F....... | ...... | ............ | GQHGP..SNA.H | 0.01 | 1 |
| GT..T | F.....DN...Q.N...R | ..HG.....NF......T | ...A.. | ............ | A..A........ | 0.01 | 1 |
| ..... | .................. | ..........F....... | ...... | ............ | DSRGG..FSE.. | 0.01 | 1 |
| RA... | F......AG.L..L.K.G | T.ANH....DF....... | ...... | ..AATD.AA.DQ | A..A........ | 0.01 | 1 |
| TA..T | F......A..NV...T.. | .................. | ...DDR | ............ | A..A........ | 0.01 | 1 |
| AA... | F.....AEG.LK.M.H.H | .................. | ....G. | ............ | GNQT....TG.P | 0.01 | 1 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | F................ | .V........F....... | ...... | ............ | GTRTG..NTK.D | 0.01 | 1 |
| E.... | ................ | .QPN......F......T | ...N.. | ..TG.D..A.GG | A..A........ | 0.01 | 1 |
| S.... | ................ | TKTTW....DF....... | ....D. | ...AAA.IE..Q | A..A........ | 0.01 | 1 |
| DA... | F.....AEG.LK.M.H.L | ..DGE...DF.....T | R..DD. | ............ | A..A........ | 0.01 | 1 |
| ..... | F.....SA..RA.....R | .PPNG.....F......T | ...DDR | E.AGG.D.E.DS | A..A........ | 0.01 | 1 |
| ..... | F.....DTG.SK.T.T.R | .QDT......F....... | ...... | ............ | ............ | 0.01 | 1 |
| R.... | F................ | .V........F....... | ...... | ............ | G.RN...F.V.A | 0.01 | 1 |
| ..... | ................ | .KYT......F....... | ....D. | ............ | A..A........ | 0.01 | 1 |
| TT... | F.....DRG.SD.K.K.. | .V........F....... | ...... | ............ | GPRTP..FDI.A | 0.01 | 1 |
| R.... | ................ | .KYT.....NF......T | ....G. | E.GT.ND...GG | A..A........ | 0.01 | 1 |
| AT... | ................ | .Q.S......F....... | ...DDR | ............ | A..A........ | 0.01 | 1 |
| TA..T | F.....ASA.S..T.T.G | .QPG.....DF....... | ...DDR | ............ | ............ | 0.01 | 1 |
| DT... | F.....ASA.S..T.T.G | .QPG.....DF....... | ...DDR | ............ | A..A........ | 0.01 | 1 |
| H.... | ................ | ................ | ....D. | ............ | A..A........ | 0.01 | 1 |
| ..... | F................ | .V........F....... | ...... | ............ | NRQDG..VRA.A | 0.01 | 1 |
| ..... | ................ | ................ | ...ADR | .....K...... | A..A........ | 0.01 | 1 |
| ..... | ................ | ................ | ...... | E.TGTA.AEVGE | A..A........ | 0.01 | 1 |
| ..... | ................ | .QYGQ....DF......T | ...K.. | ............ | A..A........ | 0.01 | 1 |
| ..... | ................ | ........NF....... | R...D. | .DATA..A.Y.H | A..A........ | 0.01 | 1 |
| DT... | F.....SKA.S..L.E.R | .Q.......DF....... | ...AD. | ..AGGADIEFDQ | A..A........ | 0.01 | 1 |
| ..... | ................ | .V........F....... | R...D. | ............ | A..A........ | 0.01 | 1 |
| DA... | ................ | ................ | ...D.. | .DADT..TE..H | A..A........ | 0.01 | 1 |
| NA... | ................ | ........DF....... | R...D. | ESGTTS....GG | A..A........ | 0.01 | 1 |
| AA... | F.....SS..NM.T.T.L | T..SE....NF....... | E..N.. | ............ | A..A........ | 0.01 | 1 |
| ..... | F.....NT.....K.A.R | .V........F....... | ...... | ............ | A..A........ | 0.01 | 1 |
| SA... | ................ | .KIHR....DF....... | G..ND. | ............ | A..A........ | 0.01 | 1 |
| E.... | ................ | .V........F....... | ...... | ............ | TRHTR..AEA.E | 0.01 | 1 |
| ...S. | ................ | ........K....... | ...... | ............ | ............ | 0.01 | 1 |
| TA... | F.....A...ND.T...K | .QPN......F......T | ...ADR | .D.GRA...F.. | A..A........ | 0.01 | 1 |
| TA... | ................ | ................ | E..N.. | ..TK...AE..D | ............ | 0.01 | 1 |
| ..... | F................ | .V........F....... | ...... | ............ | ARQAG..FDS.. | 0.01 | 1 |
| GA... | F.....ATT.IM.T.T.G | .........NF....... | R...D. | .DAG.S.A..DR | A..A........ | 0.01 | 1 |
| ..... | F................ | .V........F....... | ...... | ............ | KDRTH..FDM.. | 0.01 | 1 |
| ..... | ................ | ................ | ...D.. | ..ARGADAE..S | A..A........ | 0.01 | 1 |
| A.... | ................ | TQ.TG....DF....... | ...... | .NGGAADAE..H | A..A........ | 0.01 | 1 |
| ..... | F.....SGA..N...G.R | .Q.......DF....... | ...AD. | .NAAEND...GE | A..A........ | 0.01 | 1 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| TA..T | ................. | ................. | E..TG. | ........... | ........... | 0.01 | 1 |
| ..... | ................. | ................. | ...DD. | E.GGGSD.EFDG | A..A........ | 0.01 | 1 |
| ..... | ................. | ................. | N...GR | ..AG.N.AA.GQ | A..A........ | 0.01 | 1 |
| .A... | F................ | .V........F....... | ...... | ........... | .R.NG..Y.G.D | 0.01 | 1 |
| ..... | F.....NE..SD.H...K | .Q.DR.....F....... | R...D | ........... | A..A........ | 0.01 | 1 |
| ..... | ................. | .V........F....... | ...... | ........... | GAKGN..SG..T | 0.01 | 1 |
| G.... | ......SS..SV.P.D.H | .QPG............. | ...... | ........... | A..A........ | 0.01 | 1 |
| ..... | F......GA.NN...G.R | .QHNQ.....F....... | E..ND. | ........... | A..A........ | 0.01 | 1 |
| ..... | F................ | .QAS......F......T | ...ND. | .NTGR..AA..Q | A..A........ | 0.01 | 1 |
| GT... | F................ | .QANH....DF....... | ...DDR | ........... | A..A........ | 0.01 | 1 |
| ..... | F.....SR...V.P.G.M | ..PN.....NF....... | E..AG. | .SAKAA.AA.DE | A..A........ | 0.01 | 1 |
| TA... | F.....GRG.NI.K.P.H | TQ.TG....DF....... | ...DDR | ...G.S..AFGD | A..A........ | 0.01 | 1 |
| TT..T | ................. | ...V.....NF....... | R...D | ........... | A..A........ | 0.01 | 1 |
| ..... | ................. | ................. | ...DD | EDATGS.IA.DQ | A..A........ | 0.01 | 1 |
| GA..T | F.....AG..L.T.N.R | .QANH.....F.....T | ...D. | .NTGG.....GQ | A..A........ | 0.01 | 1 |
| TA..T | F.....DGT.SM.N.G.R | ..PNG....DF....... | ...D. | .S.SGN.I..GH | A..A........ | 0.01 | 1 |
| GA... | F.....DQ..R..P.S.R | .Q.DR.....F....... | ....D | ........... | A..A........ | 0.01 | 1 |
| T...T | ................. | ................. | R..DDR | ESTARN.A.V.Q | A..A....E... | 0.01 | 1 |
| ..... | ................. | ................. | D..DG. | ........... | A..A........ | 0.01 | 1 |
| ..... | ................. | .V.......DF....... | ...D.. | .D.GRN.A.FDG | A..A........ | 0.01 | 1 |
| ..... | ................. | .........F....... | R..AD. | ........... | A..A........ | 0.01 | 1 |
| ..... | F................ | .V........F....... | ...... | ........... | GPKA...D.R.Q | 0.01 | 1 |
| ST... | F.....GHA.SK.T.E.K | .Q.S......F....... | E..N.. | EDAKGND.A..N | A..A........ | 0.01 | 1 |
| A.... | F................ | .V........F....... | .Y.... | ........... | GRKNA..FQN.E | 0.01 | 1 |
| D...T | F.....ASA.S..T.T.G | .QPG............. | ...... | ........... | A..A........ | 0.01 | 1 |
| D...T | F.....SD..HP.L.Q.K | .Q.DH....NF....... | ...DD | ........... | A..A........ | 0.01 | 1 |
| H.... | ................. | ................. | ...DDR | ........... | TRRDP..DNM.T | 0.01 | 1 |
| ..... | ................. | .............R... | ...... | ..TNESD..... | ........... | 0.01 | 1 |
| GT... | F.....AEG.LK.M.H.L | ................. | ...... | ........... | A..A....EI.K | 0.01 | 1 |
| ..... | ................. | ................. | G..NDR | E..GGG..EF.D | A..A........ | 0.01 | 1 |
| ..... | F................ | .V........F....... | ...... | EDAG.AD.E.G. | A..A........ | 0.01 | 1 |
| ..... | F.....GGG.NV.K.Q.G | T.YNH.....F....... | ...D.. | ........... | A..A........ | 0.01 | 1 |
| GT... | ................. | ...V.....NF....... | R...D | ........... | A..A........ | 0.01 | 1 |
| ..... | ................. | .Q.S......F....... | E..N.. | .DASGSD..Y.R | A..A........ | 0.01 | 1 |
| DT... | ......DA..IA.L.K.R | .QPN......F....... | ...DG. | ........... | A..A........ | 0.01 | 1 |
| D.... | F.....GA..SQ.H.G.M | .PANG............ | ...... | ..TGAS..EV.N | A..A........ | 0.01 | 1 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| ..... | F......KT.NV.K.T.H | ................. | ...AG. | .SAKAA.AA.DE | A..A........ | 0.01 | 1 |
| G.... | ................. | .QDT......F....... | ...... | ............ | G.RDE..DRT.. | 0.01 | 1 |
| NA..T | ................. | ................. | ....GR | ............ | A..A........ | 0.01 | 1 |
| ..... | ................. | .QP.G.....F....... | R..DDR | ............ | A..A........ | 0.01 | 1 |
| ..... | F................ | .V........F....... | ...... | ............ | GKQGG..NKA.. | 0.01 | 1 |
| ..... | F.....SD..NP.H.D.R | ..YN......F......T | ...D.R | ENAGRAD.AFD. | A..A........ | 0.01 | 1 |
| ..... | F.....DG..I..K.K.G | .QPSG....NF....... | E..TGR | E.GAGAD...GQ | A..A........ | 0.01 | 1 |
| E.... | ................. | ................. | ....D. | ............ | A..A........ | 0.01 | 1 |
| GT... | F.....SGT.S..P.A.K | ..HG.....NF....... | ...... | E........... | A..A........ | 0.01 | 1 |
| A.... | F.....SA..RA.....R | ..YN......F......T | ...... | ............ | A..A........ | 0.01 | 1 |
| ..... | F................ | .V........F....... | ...... | ............ | GTRGG..FGM.H | 0.01 | 1 |
| D...T | F.....ASA.S..T.T.G | .QPG.....DF....... | ...DDR | ......A..... | A..A........ | 0.01 | 1 |
| RA... | ................. | ................. | ...D.. | ............ | A..A........ | 0.01 | 1 |
| ..... | ................. | ................. | ...DG. | ............ | GTRGT..ADA.Q | 0.01 | 1 |
| TT... | F.....NDG.PA.K.T.R | ..PN.....NF....... | ...NDR | ............ | A..A........ | 0.01 | 1 |
| GA... | F................ | .V........F....... | ...... | ............ | ARSNR..FDV.H | 0.01 | 1 |
| A.... | F.....DAA.IK.T.Q.N | ..DGE....DF....... | ...... | E........... | ............ | 0.01 | 1 |
| ..... | F.....NGG.NN.K.T.R | .V........F....... | ...... | ............ | A..A........ | 0.01 | 1 |
| ..... | ................. | TQP.R....NF......T | R...D. | ..A.G...AYD. | A..A........ | 0.01 | 1 |
| SA... | ................. | ................. | ...... | ..GGTD....DR | A..A........ | 0.01 | 1 |
| ..... | F.....S.T.NV.L.D.. | .QPSQ....NF....... | R...G. | .SG..ND...DG | A..A........ | 0.01 | 1 |
| E.... | ................. | ................. | ....GR | ..AG.N.AA.GQ | A..A........ | 0.01 | 1 |
| H.... | ................. | ................. | G..KD. | ESAGAN....GG | A..A........ | 0.01 | 1 |
| ..... | ................. | ................. | ...D.. | ESTGGN..AVGQ | A..A........ | 0.01 | 1 |
| D...T | F.....ASA.S..T.T.G | ................. | ....D. | .DGKGS.IA..G | A..A........ | 0.01 | 1 |
| ..... | F.....AG..RV.L.N.G | .QPN......F......T | ...N.. | E..GASD.A..Q | ............ | 0.01 | 1 |
| ..... | F................ | ................. | ...N.. | ............ | A..A........ | 0.01 | 1 |
| ..... | F................ | .........D....... | ...D.. | ............ | A..A........ | 0.01 | 1 |
| EA... | F......A..NV...T.. | ................. | ...DDR | ............ | A..A........ | 0.01 | 1 |
| ..... | F................ | ................. | ...DDR | .DAKGN..EVGQ | A..A........ | 0.01 | 1 |
| DT... | F.....DRG.S..T.A.S | ..DGE....DF....... | ...... | ............ | ............ | 0.01 | 1 |
| ..... | ................. | ................. | R..AG. | ............ | A..A.T...... | 0.01 | 1 |
| TA... | F................ | .V........F....... | ...... | ............ | ............ | 0.01 | 1 |
| ..... | F................ | .V........F....... | ...... | ............ | GHRD...DKG.D | 0.01 | 1 |
| ..... | F................ | ..........F....... | R..AGR | .NA.RA.T..G. | A..A........ | 0.01 | 1 |
| D...T | F................ | .V........F....... | ...... | ............ | ..RAP..FSE.. | 0.01 | 1 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| E.... | F.....DRG.S..T.A.S | ..DGE....DF....... | ...... | .......... | ............ | 0.01 | 1 |
| ..... | F.....NKG.N..K.G.G | .........NF....... | R...D. | .......... | A..A........ | 0.01 | 1 |
| TT... | F.....GGG.L..T.E.R | TQ.TG....DF....... | ...DDR | .......... | A..A........ | 0.01 | 1 |
| ..... | .................. | .V........F....... | ...DDR | E.GAEGD..FDG | ............ | 0.01 | 1 |
| ..... | F................. | .V........F....... | R..... | .......... | KPHSP..VSE.T | 0.01 | 1 |
| .A... | .................. | .................. | R...DR | .......... | A..A........ | 0.01 | 1 |
| ..... | F.....A........... | .V........F....... | ...... | .......... | TNRDA..ANT.T | 0.01 | 1 |
| RA... | .................. | .K.TG....DF....... | R...DR | ESAN...I...H | A..A........ | 0.01 | 1 |
| ..... | .................. | .........DF....... | ...DDR | .STSA..AAY.D | A..A........ | 0.01 | 1 |
| ..... | .................. | ..P.G....NF....... | E..DDR | .NA.AS.A..DR | A..A........ | 0.01 | 1 |
| A.... | .................. | .................. | ...D.. | .N.TAN...VGS | A..A........ | 0.01 | 1 |
| ..... | ......GK..LA.K.N.G | .................. | ...... | ..AGT.D.EYGQ | A..A........ | 0.01 | 1 |
| ..... | F................. | .V................ | R...DR | .DA.TSD..VDR | A..A........ | 0.01 | 1 |
| E.... | F.....GH..P..P.S.V | ..AGR....DF......T | R..D.. | .D......... | A..A........ | 0.01 | 1 |
| ..... | .................. | .V........F....... | ...... | ESGTAND...DR | A..A........ | 0.01 | 1 |
| TA... | F................. | .V........F....... | ...... | .......... | SRQNT...TN.D | 0.01 | 1 |
| ..... | .................. | .................. | G..NDR | ED.GGVD.E.DR | ............ | 0.01 | 1 |
| ..... | .................. | .................. | RTMRAG | .......... | A..A........ | 0.01 | 1 |
| EA... | F.....SN..PL.K.T.. | .Q.DR.....F....... | ....D. | ...NRAD.E..Q | ............ | 0.01 | 1 |
| ..... | .................. | TK.NE....DF......T | ...... | ..AGAN..A.GD | A..A........ | 0.01 | 1 |
| TA..T | .................. | .QPN......F......T | ...N.. | ..TG.D..A.GG | A..A........ | 0.01 | 1 |
| ..... | F.....GRT.PQ.T.T.R | ..YN.............. | G..DG. | .......... | ............ | 0.01 | 1 |
| ..... | .................. | .................. | ....D. | ..AKG...AV.. | A..A........ | 0.01 | 1 |
| GA... | F.....ATT.IM.T.T.R | .........NF....... | R...D. | .DAG.G.A..DR | A..A........ | 0.01 | 1 |
| NA... | .................. | .........NF......T | ...K.. | ..GSA..I..GG | A..A........ | 0.01 | 1 |
| SA... | .................. | .QPN......F......T | ...N.. | .DTG.N..A..R | A..A........ | 0.01 | 1 |
| D.... | F.....SK..LD.L.T.G | .QPN......F......T | ...... | .......... | A..A........ | 0.01 | 1 |
| ..... | .............T.R | ..PN......NF....... | ...DD. | ES.A...AAYGE | A..A........ | 0.01 | 1 |
| EA... | .................. | .QHNQ.....F......T | ...D.. | .DGARDDAA..D | A..A........ | 0.01 | 1 |
| ..... | F................. | .V........F....... | ...... | .......... | GPKSR..DDV.T | 0.01 | 1 |
| CA... | .................. | .................. | E..KG. | .......... | ............ | 0.01 | 1 |
| TA..T | F.....AGG.IV.L.G.R | ..DGE....DF....... | ...... | .......... | A..A........ | 0.01 | 1 |
| GT... | F.....AEG.LK.M.H.L | .QPG.....DF....... | ...DDR | .......... | ............ | 0.01 | 1 |
| ..... | .................. | .................. | ...... | .DGGGS.AAFDE | A..A........ | 0.01 | 1 |
| ..... | F................. | .V........F....... | ...... | .......... | GAHDG..ARG.Q | 0.01 | 1 |
| DT... | F.....DDG.LA.K...R | .................. | ...... | .......... | A..A........ | 0.01 | 1 |

TABLE 7-continued

AAV capsid proteins having increased specificity for and/or transduction of CD44+ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | .KDSR....DF......T | R..DD. | ........... | A..A........ | 0.01 | 1 |
| TA... | ................. | .QANH....DF....... | ...DDR | ........... | ............ | 0.01 | 1 |
| G.... | F.....AHA.SH.M.S.R | ..DGE....DF....... | ...... | E.AA.DD.AV.. | A..A........ | 0.01 | 1 |
| .A... | ................. | ..A......DF....... | G..N.. | ........... | A..A........ | 0.01 | 1 |
| GA..T | ................. | .QPN......F......T | ...N.. | .DTG.N..A..R | A..A........ | 0.01 | 1 |
| NA... | F.....NT...M.M...R | ..DGE....DF....... | ....D. | .N.ARS..E.GG | A..A........ | 0.01 | 1 |
| ..... | ................. | ................. | ...N.. | ........... | P..A........ | 0.01 | 1 |
| GT..T | ................. | ................. | ...... | ...TG..T..GQ | A..A........ | 0.01 | 1 |
| ..... | ................. | .QPNQ....NF......T | ...N.. | E.TD.A....DG | A..A........ | 0.01 | 1 |
| ST..T | F.....DA..IA.L.K.R | TQ.TH....DF....... | R..ADS | ........... | A..A........ | 0.01 | 1 |
| ..... | ......AEG.LK.M.H.L | ..DGE....DF....... | ...DD. | ........... | ............ | 0.01 | 1 |
| ..... | .......GT.NM.L.Q.G | .Q.S......F....... | ....D. | ........... | ............ | 0.01 | 1 |
| ..... | ................. | TQDS.....NF....... | ...DDR | E........... | A..A........ | 0.01 | 1 |
| ..... | ................. | ..PNG....DF....... | ...DDR | E.ADGS..E.GN | A..A........ | 0.01 | 1 |
| E.... | ................. | ................. | R..NG. | ........... | ............ | 0.01 | 1 |
| TA... | F.....DMG.S..T.A.S | ..DGE....DF....... | ...... | ........... | ............ | 0.01 | 1 |
| SA... | ................. | ................. | ...D.. | E.TAE..I.... | A..A........ | 0.01 | 1 |
| GA..T | ................. | ................. | ...N.. | EDGKGA....GE | A..A........ | 0.01 | 1 |
| RA... | F.....AGA.NK.L...K | .QAS.....NF......T | ...... | ........... | A..A........ | 0.01 | 1 |
| D...T | F.....ASA.S..T.T.G | .QPG.....DF....... | ...DDR | ........... | ............ | 0.01 | 1 |
| G.... | ................. | .QPG.....NF....... | ...DDR | EDATRS..E..G | A..A........ | 0.01 | 1 |
| .A... | F.....GK..NE.L.Q.V | .QPG.....NF....... | ...D.. | E.TGA.D.EYDQ | A..A........ | 0.01 | 1 |
| TA... | ................. | ................. | E..TD. | ........... | A..A........ | 0.01 | 1 |
| RA... | ......GRT.S..L.G.R | .QANH.....F......T | E..T.. | ........... | A..A........ | 0.01 | 1 |
| A.... | ................. | TQ.TG....DF....... | ...DDR | ..AGT.D.EYGQ | A..A........ | 0.01 | 1 |
| ..... | F................. | .V........F....... | ...DD. | E.GGSD.EFDG | A..A........ | 0.01 | 1 |
| ..... | F................. | .V........F....... | R..DD. | ........... | E.RS...F.E.H | 0.01 | 1 |
| ..... | ................. | ................. | G..DG. | .DANRN..E.GQ | A..A........ | 0.01 | 1 |
| TA... | ................. | ................. | ...D.R | E.AG..D.A.GR | A..A........ | 0.01 | 1 |
| .A... | F.....DG..I..K.K.G | .QPSQ....NF....... | E..TGR | E.GAGAD...GQ | A..A........ | 0.01 | 1 |
| .A..T | F.......I......... | .........F....... | ...... | ENGGTN..E.GN | A..A........ | 0.01 | 1 |
| DA... | F.....NTG.LH.T...R | T.ASH....DF....... | R..DD. | ........... | A..A........ | 0.01 | 1 |
| A.... | ................. | .QPGQ....NF....... | E..AD. | .SASEN.I..DR | A..A........ | 0.01 | 1 |
| NT... | F................. | ................. | R..TG. | ........... | A..A........ | 0.01 | 1 |
| GA..T | F.....GTG..P.T.D.G | .QPG.....DF....... | ...D.. | ........... | ...A........ | 0.01 | 1 |
| DT... | F................. | ................. | E..N.. | ........... | A..A........ | 0.01 | 1 |

TABLE 7-continued

AAV capsid proteins having increased specificity for and/or transduction of
CD44<sup>+</sup> GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| G.... | .................. | .........DF....... | ....D. | ESGS.S.IA.DQ | A..A........ | 0.01 | 1 |
| ....T | F................. | .................. | ....D. | ............ | A..A........ | 0.01 | 1 |
| ..... | .................. | .................. | ...D.. | .N.TAN...VGS | A..A........ | 0.01 | 1 |
| TA... | .................. | .................. | R..N.. | .D.TGN.I...Q | A..A........ | 0.01 | 1 |
| E.... | .................. | .................. | G..KD. | ESAGAN....GG | A..A........ | 0.01 | 1 |
| GA..T | F......QG.NQ...A.R | .................. | E..DDR | .NA.AS.A..DR | A..A........ | 0.01 | 1 |
| ..... | .................. | .................. | ...... | E.AAASDAAY.N | A..A........ | 0.01 | 1 |
| RA... | F.....NAG.LL.T.H.K | .................. | G...G. | ............ | ............ | 0.01 | 1 |
| DT... | F.....NN..N..M...G | .................. | E..KD. | ............ | A..A........ | 0.01 | 1 |
| ..... | .................. | .................. | E..ND. | .SAGAA.IA..Q | A..A........ | 0.01 | 1 |
| GA... | .................. | .................. | ...DDR | E.A.AD.AAF.. | A..A........ | 0.01 | 1 |
| ..... | .................. | .................. | G..DD. | EDAG.AD.E..R | ............ | 0.01 | 1 |
| ..... | F.....GG..NK.M.... | .QPSE....DF....... | R..D.. | ............ | A..A........ | 0.01 | 1 |
| ..... | F................. | .V........F....... | ...... | ............ | GKRD...AGE.K | 0.01 | 1 |
| ..... | .................. | .................. | G..TDR | E.AGGN..E.DD | ....R....... | 0.01 | 1 |
| EA... | .................. | T..SG....DF......T | ...ADR | .SGATG...FDG | A..A........ | 0.01 | 1 |
| E.... | F.....AA..IQ.T.K.R | T.ASH....DF....... | ...... | ..ASE...E.D. | A..A........ | 0.01 | 1 |
| ET... | F.....GG..I..P...R | .PPN......F......T | ...ADR | ENAGRSD..FGG | A..A........ | 0.01 | 1 |
| ..... | .................. | .................. | R...GR | EDTG.A....GN | A..A........ | 0.01 | 1 |
| ..... | .................. | .................. | G..K.. | ..GNGN..E..S | A..A........ | 0.01 | 1 |
| ..... | .................. | .................. | ...DDR | .DAKGN..EVGQ | AA.A........ | 0.01 | 1 |
| TT..T | F.....ASA.S..T.T.G | .QPG.....DF....... | ...DDR | ............ | ............ | 0.01 | 1 |
| EA... | F................. | .................. | ...D.. | ............ | A..T........ | 0.01 | 1 |
| GT... | .................. | TQPGG............. | ...DDR | E..TAA.AAFD. | A..A........ | 0.01 | 1 |
| ..... | .................. | ..HG.....NF.....T | ...TDR | .SA....AEVDD | A..A........ | 0.01 | 1 |
| AA... | F.....NKG.N..K.G.G | .........NF....... | R...D. | ............ | A..A........ | 0.01 | 1 |
| ..... | .................. | ...V.....DF....... | ...DD. | .D..R.D.E... | A..A........ | 0.01 | 1 |
| A...T | .................. | .................. | ...AG. | ............ | A........... | 0.01 | 1 |
| ..... | .................. | .QYGQ....DF......T | E..TGR | ...R.G.....E | A..A........ | 0.01 | 1 |
| ..... | .................. | .V........F....... | R..ND. | ..AG...IYAGN | A..A........ | 0.01 | 1 |
| ..... | F.....DTG.PA.L.T.K | ..DGE....DF....... | ...... | E.AGAND.AY.N | A..A........ | 0.01 | 1 |
| H.... | ......NKT.I....... | .........DF....... | ...D.R | .DANRN.A.VDH | A..A........ | 0.01 | 1 |
| NA... | F................. | ..AGR...........T | E..D.. | ............ | A..A........ | 0.01 | 1 |
| RA... | F................. | .V........F....... | R..ND. | ..AG...IAYGN | A..A........ | 0.01 | 1 |
| ..... | .................. | .................. | G..TDR | E.AGGN..E.DD | A..A........ | 0.01 | 1 |
| TA..T | .................. | .........NF....... | R...D. | EDGGGS..E.GR | A..A........ | 0.01 | 1 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| AA... | ......DHT..D.P...R | ...NG.....F.R..... | R...D. | EDAR.D..EVGE | A..A........ | 0.01 | 1 |
| E.... | F.....AEG.LK.M.H.L | ..DGE....DF....... | ...... | ............ | A..A........ | 0.01 | 1 |
| ST... | F.....ASA.S..T.T.G | .QPG.....DF....... | ...DDR | ............ | ............ | 0.01 | 1 |
| DT... | F.....GKA.SE.N...K | T.AG.....NF......T | ...N.. | ............ | A..A........ | 0.01 | 1 |
| E.... | F.....GN..RM.T...E | ..HG.....NF......T | ...A.. | E.AG...IA.DD | A..A........ | 0.01 | 1 |
| A.... | .................. | .................. | ....GR | ..AG.N.AA.GQ | A..A........ | 0.01 | 1 |
| E.... | F.....ASA.S..T.T.G | .QPG.....DF....... | G..N.. | ............ | ............ | 0.01 | 1 |
| E.... | .................. | .................. | R..D.. | ESAAGD.IE.GD | A..A........ | 0.01 | 1 |
| ..... | .................. | .V........F....... | ...... | ............ | THRAT..ADG.Q | 0.01 | 1 |
| ..... | .................. | .................. | E..N.. | ............ | A..A........ | 0.01 | 1 |
| GT..T | F.....GRG.SP.K...G | .QPG.....NF....... | ...DDR | ............ | DRRSA..YTT.Q | 0.01 | 1 |
| ..... | ..........NAVKAS | .................. | E..ND. | ............ | A..A........ | 0.01 | 1 |
| DA..A | F.....STA..Q.H.Q.L | .................. | ...A.. | .N.KA.DAE..D | A..A........ | 0.01 | 1 |
| ..... | F................. | .................. | G..N.. | ............ | ............ | 0.01 | 1 |
| ..... | .................. | .................. | ...D.R | ESGKAS..A.GE | A..A........ | 0.01 | 1 |
| GT... | F.....SA..RA.....R | ...DG....DF....... | R..TDR | ..A.AN..AV.Q | GAKGN..SG..T | 0.01 | 1 |
| ..... | .................. | .........DF....... | ...... | ............ | ............ | 0.01 | 1 |
| TA... | F.........NL.T.S.L | ..A......DF....... | ...D.. | .STREGD....N | A..A........ | 0.01 | 1 |
| ..... | F.....NGG.IM.L.E.R | ..DGE....DF....... | ...... | ENAAAN.A.Y.S | A..A........ | 0.01 | 1 |
| A.... | F.....DGT.SM.N.G.R | .KDDG....NF......T | E..AG. | ............ | ............ | 0.01 | 1 |
| AT... | F.....DR..II...A.R | ..HG.....NF......T | ...A.. | ............ | A..A........ | 0.01 | 1 |
| TA... | .................. | ..DGE....DF....... | R...D. | ............ | ............ | 0.01 | 1 |
| ..... | .................. | .........F....... | R..TG. | ..ATAA..AVDN | A..A........ | 0.01 | 1 |
| ..... | .................. | .................. | ...DG. | ESTARN.A.V.Q | A..A....E... | 0.01 | 1 |
| GA... | F.....GT..I..N.T.G | .V........F....... | ...... | .SGS.NDIA..D | A..A........ | 0.01 | 1 |
| ..... | .................. | TKAT.....NF......T | R..AG. | E..G.DD.EYDQ | A..A........ | 0.01 | 1 |
| ..... | F.....ATT.NV.T.K.S | .Q.DR.....F....... | ....D. | E.TGAN.AE.GE | A..A........ | 0.01 | 1 |
| A.... | F.....AEG.NI.L.K.R | TPPSQ....NF......T | ...DDR | ............ | TRRDP..DNM.T | 0.01 | 1 |
| ..... | F......AT.IA.P.K.M | .........NF....... | R...D. | ............ | A..A........ | 0.01 | 1 |
| ..... | F................. | .V........F....... | ...... | ............ | SERTG..DGT.T | 0.01 | 1 |
| SA..T | .................. | .................. | R..DD. | ............ | A..A........ | 0.01 | 1 |
| ....T | F.....DGA.RN.T.S.G | ..HG.....NF....... | ...D.. | ............ | A..A........ | 0.01 | 1 |
| NT... | F................. | .V........F....... | ...... | ............ | GARGE..YNV.A | 0.01 | 1 |
| ..... | F.....GS..NM.N.T.R | ..DGE....DF....... | ...... | E.TTGNDI...R | A..A........ | 0.01 | 1 |
| ..... | .................. | .................. | G..D.R | ..ASE...E.D. | A..A........ | 0.01 | 1 |
| TT... | .................. | .................. | ...NDR | ..AKG...AV.. | A..A........ | 0.01 | 1 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| AT... | F.....AEG.LK.M.H.L | ..DGE....DF....... | ...... | ............ | ............ | 0.01 | 1 |
| RA... | F.....DK..P..M.T.R | .QPN......F......T | ...N.. | ESATGG.T..GG | A..A........ | 0.01 | 1 |
| ..... | F.....DDG.LA.K...R | .................. | ...... | ............ | A..A........ | 0.01 | 1 |
| AT... | .................. | ..AGR.....F....... | ....GR | ............ | A..A........ | 0.01 | 1 |
| E.... | ......DQ..R..P.S.R | ..DGE....DF....... | ...... | .N.ARS..E.GQ | A..A........ | 0.01 | 1 |
| ..... | .................. | ................E. | R...AG. | ............ | A..A........ | 0.01 | 1 |
| ..... | F......NG.LQ.H...N | T.P......DF....... | ...D.. | ............ | A..A........ | 0.01 | 1 |
| SA... | .................. | .................. | ...... | E.AS.A.TAV.H | A..A........ | 0.01 | 1 |
| AA... | .................. | ...T.....NF......T | ...DDR | .SAKAA.AA.DE | A..A........ | 0.01 | 1 |
| ..... | .................. | .................. | ...... | ESGGAD.I...R | A..A........ | 0.01 | 1 |
| ..... | F.....GHG.NK.I.N.R | ..PSH....DF....... | ....D. | ............ | A..A........ | 0.01 | 1 |
| D...T | .................. | TQ.TH....DF....... | ....D. | EN.GTN.AE.DN | A..A........ | 0.01 | 1 |
| ..... | .................. | .................T | R...AG. | E.ASG..I.VGR | A..A........ | 0.01 | 1 |
| ..... | .................. | .................. | ...... | ..GTAG...V.G | A..A........ | 0.01 | 1 |
| N.... | .................. | .................. | G..K.. | E.AGRDD..V.E | A..A........ | 0.01 | 1 |
| .A... | F......GT.NM.L.Q.G | .Q.S.....NF......T | ...... | ............ | A..A........ | 0.01 | 1 |
| S.... | .................. | .................T | ...D.. | ............ | ............ | 0.01 | 1 |
| GT... | .................. | .................. | R...GR | EDGDGA..A.DR | A..A........ | 0.01 | 1 |
| ..... | .................. | ..PNG....DF....... | G..NDR | ............ | ............ | 0.01 | 1 |
| H.... | F................. | ..DGE....DF....... | ...... | E.TDAND..VGQ | A..A........ | 0.01 | 1 |
| E.... | .................. | .................. | G..DD. | ............ | A..A........ | 0.01 | 1 |
| ..... | .................. | .........DF....... | E..ND. | ............ | ............ | 0.01 | 1 |
| A.... | F.....DA..IA.L.K.R | .................. | ...N.. | ............ | A..A........ | 0.01 | 1 |
| E.... | F......SA.S..T.T.G | .QPG.....DF....... | ...DDR | ............ | ............ | 0.01 | 1 |
| N.... | F.....DTT.LH.K.T.G | .Q.S......F....... | E..N.. | ............ | A..A........ | 0.01 | 1 |
| SA... | F.....GRG.NI.K.P.H | .V........F....... | ...... | ............ | A..A........ | 0.01 | 1 |
| ..... | F................. | .V.........F...... | ...... | ............ | GNHSP..D.M.Q | 0.01 | 1 |
| ..... | .................. | .................. | ...D.. | E.TAGN.IE.DG | A..A........ | 0.01 | 1 |
| ..... | ...........R..... | ..DGE....DF....... | ...... | ..AG.DD...GG | A..A........ | 0.01 | 1 |
| GA... | .................. | .........F........ | ...... | ............ | ANSNP..SDS.Q | 0.01 | 1 |
| D...T | .................. | .........DF......T | E..NG. | E.GKA....FDG | A..A........ | 0.01 | 1 |
| A.... | .................. | .................. | R..DD. | E.GAR.D.E.GE | A..A........ | 0.01 | 1 |
| ..... | F................. | .................. | E..DGR | ............ | ............ | 0.01 | 1 |
| RA... | .................. | .................. | G..KD. | ESAGAN....GG | A..A........ | 0.01 | 1 |
| ..... | F.....STG..N.M.T. | .K.TG....DF....... | ...... | ............ | A..A........ | 0.01 | 1 |
| ..... | F.....SRT..A...T.N | T.P......DF....... | ...D.. | ............ | ............ | 0.01 | 1 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263<br>QSGAS | 444<br>YLSRTNTPSGTTTQSRLQ | 490<br>KTSADNNNSEYSWTGATK | 527<br>KKDEEK | 545<br>QGSEKTNVDIEK | 585<br>RGNRQAATADVN | % | # |
|---|---|---|---|---|---|---|---|
| TA... | F................. | .V................ | R...D. | E.AG..D.A.GR | A..A........ | 0.01 | 1 |
| D.... | .................. | .................. | ....D. | ..ARRNDAEFGS | A..A........ | 0.01 | 1 |
| GA... | F.....S.T.NV.L.D.. | .QPSQ....NF....... | ...... | E.AS.A.TAV.H | A..A........ | 0.01 | 1 |
| ..... | .................. | ........DF....... | ...... | ..AST..AA..D | A..A........ | 0.01 | 1 |
| N.... | .................. | .................. | ...DD. | ES.A...AAYGE | A..A........ | 0.01 | 1 |
| ..... | F................. | .V........F....... | .....S | .SA.GG....DG | A..A........ | 0.01 | 1 |
| ..... | .................. | .QANH.....F......T | R..D.. | .SAKAA.AA.DE | A..A........ | 0.01 | 1 |
| ..... | F................. | .V........F....... | E..ND. | E.AGGND....R | A..A........ | 0.01 | 1 |
| ..... | .................. | .................. | ...DG. | .N.GA.D.A.GG | A..A........ | 0.01 | 1 |
| GT... | .................. | .Q.S......F....... | ....D. | ............ | ............ | 0.01 | 1 |
| D...T | F......GT.NM.L.Q.G | .V........F....... | ...... | ............ | TEHNP..FRS.T | 0.01 | 1 |
| ..... | .................. | ..PN....NF....... | R...D. | ESTGGND.EYDQ | A..A........ | 0.01 | 1 |
| ..... | F.....EA.SL.K.Q.R | ..DDG....DF....... | ...DDR | ............ | ............ | 0.01 | 1 |
| T...T | F.....GTG..P.T.D.R | .Q.S......F....... | E..N.. | ............ | TPRNN...EV.D | 0.01 | 1 |
| ..... | .................. | ........DF....... | ...A.. | ............ | GPRTG...HT.E | 0.01 | 1 |
| ..... | .................. | .................. | ...DDR | E..GGND....R | A..A........ | 0.01 | 1 |
| RA... | .................. | ..DGE....DF....... | R...D. | ............ | ............ | 0.01 | 1 |
| ET..T | .................. | .................. | ...D.R | ............ | A..A........ | 0.01 | 1 |
| GT... | .................. | .Q.D.....DF..P.... | ...A.. | ............ | ............ | 0.01 | 1 |
| GA... | F.....STT.HV.K...I | .QAS......F....... | ...DD. | ENASG.....GN | A..A........ | 0.01 | 1 |
| TA... | .................. | ..........F....... | E..TD. | ............ | ............ | 0.01 | 1 |
| ..... | F................. | .V........F....... | ...DDR | ESGGTD....DR | A..A........ | 0.01 | 1 |
| .A... | .................. | .................. | E..KG. | ............ | ............ | 0.01 | 1 |
| ..... | F.....NET.NA.P...K | ..HG.....NF......T | ...A.. | ............ | A..A........ | 0.01 | 1 |
| ..... | .................. | TQP.R....NF......T | ...D.. | ............ | A..A........ | 0.01 | 1 |
| TA..T | F................. | .V........F....... | ...... | ............ | SRQNT...TN.D | 0.01 | 1 |
| .A... | F.....DH..ID.K...V | T.PGG....NF....... | ...DG. | ESGGGN.IA.DQ | A..A........ | 0.01 | 1 |
| ..... | F................. | .V........F....... | ...... | ............ | TRSSG..SNA.D | 0.01 | 1 |
| EA... | F.....DAA.IK.T.Q.N | ..DGE....DF....... | ...N.. | ............ | A..A........ | 0.01 | 1 |
| E.... | F.....AEG.LK.M.H.L | ..DGE....DF....... | .....S | ............ | ............ | 0.01 | 1 |
| G.... | F................. | ..HG.....NF......T | ...A.. | ..AG.SD.EVG. | A..A........ | 0.01 | 1 |
| ..... | F.....AEG.LK.M.H.L | ..........F....... | ...... | ............ | A..A........ | 0.01 | 1 |
| EA... | ......SG..IK.K.D.R | .KPDQ....DF....... | ...D.. | .NATG....VGS | A..A........ | 0.01 | 1 |
| ..... | .................. | .................. | ....R. | E.ADGA..AYDR | A..A........ | 0.01 | 1 |
| ..... | F.....DRG.SL.M...I | .................. | ...NDR | ............ | A..A........ | 0.01 | 1 |
| ..... | .................. | .Q.GQ....DF....... | R..ND. | ..AK.ADT..GN | A..A........ | 0.01 | 1 |

TABLE 7-continued

AAV capsid proteins having increased specificity for and/or transduction of CD44⁺ GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| AA..T | F.....GS..NK.M.A.R | ..AGR....DF......T | R..D.. | ........... | A..A........ | 0.01 | 1 |
| ..... | ................. | .........NF....... | R..D. | ........... | A..A........ | 0.01 | 1 |
| ..... | ................. | ................. | E..NG. | ENASGG.AE.DS | ........... | 0.01 | 1 |
| ..... | ................. | ................. | ....D. | .D..TD....GD | A..A........ | 0.01 | 1 |
| D...T | ................. | ................. | R..DD. | ........... | ........... | 0.01 | 1 |
| .A... | F................. | .V........F....... | ....D. | ........... | A..A.......A. | 0.01 | 1 |
| ..... | ................. | T.AG......F......T | ...DD. | ..TKRDD.A.DE | A..A........ | 0.01 | 1 |
| DT... | F.....GKG.ND.T.N.G | ..ATR...DF....... | E..N.. | ........... | A..A........ | 0.01 | 1 |
| GT... | ................. | .PPNG.....F......T | ...DDR | E.TR.N.....Q | A..A........ | 0.01 | 1 |
| ..... | F.....STA..Q.H.Q.L | ..DGE............T | ...AGR | ........... | A..A........ | 0.01 | 1 |
| ET... | F......QT..M.T...R | .KDT......F......T | ...DD. | E....ND.EF.Q | A..A.....E.. | 0.01 | 1 |
| SA... | ................. | ...............T | ....D. | E.TGRA..A..G | A..A........ | 0.01 | 1 |
| ..... | F................. | ................. | E..NG. | ..ANR.D...DR | A..A........ | 0.01 | 1 |
| D...T | F.....SN..PL.K.T.. | ..HG.....NF......T | ...DDR | ........... | A..A........ | 0.01 | 1 |
| ..... | F................. | .K.T.....DF....... | E..ND. | ...TG..T..GQ | A..A........ | 0.01 | 1 |
| ..... | ................. | ................. | R..DD. | .DTRAD..EF.D | A..A........ | 0.01 | 1 |
| .A... | F.....DRG.S...T.A.S | ................. | G..N.. | ........... | A..A........ | 0.01 | 1 |
| RA... | F......TG..Q.T.T.G | ................. | G..DG | ........... | ........... | 0.01 | 1 |
| AT... | F.....ASA.S..T.T.G | .QPG.....DF....... | ...DDR | ........... | ........... | 0.01 | 1 |
| RA... | ................. | ................. | ...DDR | ..AAGADTA.DD | A..A........ | 0.01 | 1 |
| ..... | F................. | .V........F....... | E..... | ........... | SHRA...ATV.H | 0.01 | 1 |
| ..... | F................. | .V........F....... | ...... | ........... | GPHNN..ADA.T | 0.01 | 1 |
| ..... | F................. | .V........F....... | ...... | ........... | TNRDA..ANT.T | 0.01 | 1 |
| ..... | ................. | ........NF....... | ...TD. | ........... | A..A........ | 0.01 | 1 |
| ..... | F................. | .V........F....... | ...... | ........... | GTRT...DRA.. | 0.01 | 1 |
| ..... | F.....NGG.NN.K.T.. | ................. | R..DD. | E.ARAN.IEVDQ | ........... | 0.01 | 1 |
| ..... | ................. | ........N......... | ...D.R | ...GGGDAA..G | A..A........ | 0.01 | 1 |
| ..... | ................. | ...............T | ...DDR | E..G.SDAA.GD | A..A........ | 0.01 | 1 |
| ..... | F.....GGG.NH...H.R | ..DGE....DF....... | ...... | ESAAASD..VGQ | A..A........ | 0.01 | 1 |
| GT... | F................. | .V........F....... | ...... | ........... | GRRDN..YRT.T | 0.01 | 1 |
| RA..T | ................. | ................. | R..KD. | ........... | A..A........ | 0.01 | 1 |
| AT... | ................. | ..HG.....NF......T | R..DG. | ........... | A..A........ | 0.01 | 1 |
| ..... | ................. | ................. | R..DD. | ........... | ...........D | 0.01 | 1 |
| NA... | F................. | .V........F....... | ...... | ........... | GTRST..FRE.T | 0.01 | 1 |
| RA... | ................. | TQP.R.....F....... | ...D.. | ........... | A..A........ | 0.01 | 1 |
| N.... | ................. | ................. | ...N.. | ........... | A..A........ | 0.01 | 1 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| RA... | ................. | .V........F....... | ...... | ............ | KDRNG...GK.D | 0.01 | 1 |
| SA... | F................. | .V........F....... | ...... | ............ | ............ | 0.01 | 1 |
| ..... | ................. | .........DF....... | ...DDR | .NG..A.I...G | A..A........ | 0.01 | 1 |
| ..... | ................. | ................. | ...... | ............ | TTSGP...QK.. | 0.01 | 1 |
| DT... | ................. | ................. | G..DG. | ............ | ............ | 0.01 | 1 |
| DT... | F......KT.NV.K.T.H | ................. | ...... | EDAG.AD.E.G. | A..A........ | 0.01 | 1 |
| T.... | ................. | ..PNG....DF....... | G..NDR | ............ | A..A........ | 0.01 | 1 |
| SA..T | F.....AR..L..P.D.K | .KYT.....NF......T | R...D. | E........... | A..A........ | 0.01 | 1 |
| GA... | F.....AA..IQ.T.K.R | .QAS......F....... | ...... | E.AARSD...GS | A..A........ | 0.01 | 1 |
| ..... | F.....SGA..V.T.G.G | .QPN......F......T | ...N.. | .D.GRAD.AF.S | A..A........ | 0.01 | 1 |
| EA... | F.....ATG.NV.T.G.R | .KDSR....DF....... | R...D. | .DAG.S.A..DR | A..A........ | 0.01 | 1 |
| ..... | F................. | .V........F....... | ...... | ............ | NEKDG...RG.Q | 0.01 | 1 |
| AA... | ................. | .........F......T | ...DDR | E..G.SDAA.GD | A..A........ | 0.01 | 1 |
| ..... | F.....ASA.S..T.T.G | .Q.DH....NF....... | ...DD. | ............ | A..A........ | 0.01 | 1 |
| GT... | F................. | ................. | ...... | E.TGRA..A..G | A..A........ | 0.01 | 1 |
| ..... | ................. | T.P......DF....... | ...D.. | .NTSTSD.E.DG | ............ | 0.01 | 1 |
| GT... | F.....NDG.NH.L.A.R | TKPS.....DF......T | ...DDR | ............ | A..A........ | 0.01 | 1 |
| A...T | ................. | TQASG....NF....... | ....D. | E.AS....IEYGQ | A..A........ | 0.01 | 1 |
| ST... | ................. | ................. | G..DG. | ............ | ............ | 0.01 | 1 |
| ..... | F................. | .V........F....... | ...... | ............ | GS.AR..SDV.E | 0.01 | 1 |
| ..... | ................R | .........F....... | ...... | ............ | A..A........ | 0.01 | 1 |
| ..... | F................. | .V........F....... | ...... | ............ | DSRTP...D..E | 0.01 | 1 |
| ..... | ................. | ................. | E..KG. | ............ | ............ | 0.01 | 1 |
| RA... | ................. | .QYGQ....DF......T | E..TGR | ...R.G.....E | A..A........ | 0.01 | 1 |
| T.... | F.....DDG.LA.K...R | ................. | ...... | ............ | ............ | 0.01 | 1 |
| ST... | ................. | ................. | ...DDR | ............ | ............ | 0.01 | 1 |
| ..... | F................. | .V.......F.. | ...... | ............ | TPHGS..FTM.. | 0.01 | 1 |
| ..... | F.....NQG..V.L.N.R | ..A......DF....... | ...DG. | EDAGGS.AEYD. | A..A........ | 0.01 | 1 |
| .A... | ................. | .........DF......T | ...... | E..G.A....DR | A..A........ | 0.01 | 1 |
| D...T | F................. | ................. | R..DD. | ............ | ............ | 0.01 | 1 |
| ..... | ................. | ................. | ...D.. | .DGA.....VGR | A..A........ | 0.01 | 1 |
| G.... | F.....AEG.LK.M.H.L | ..DGE....DF....... | ...... | ............ | A..A........ | 0.01 | 1 |
| SA..T | F......TG.IL...T.R | .QAS.....NF......T | ....GR | .DAGA.D.EVDE | ............ | 0.01 | 1 |
| T.... | ................. | .KDT......F......T | ...DD. | ESGA.A.AAV.G | A..A........ | 0.01 | 1 |
| ..... | ................. | ................. | R..DD. | E.TGAN.AE.GE | A..A........ | 0.01 | 1 |
| AA... | F.....AAT.N..P.P.R | ................T | ...DDR | ............ | ............ | 0.01 | 1 |

TABLE 7-continued

AAV capsid proteins having increased specificity for and/or transduction of CD44[+] GSC (pool of Round 1 selection). Amino acid numbers correspond to the amino acid sequence of VP1 (SEQ ID NO: 1). Sequences below correspond to SEQ ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| ..... | ................. | .QANH....DF....... | ...DDR | ............ | A..A........ | 0.01 | 1 |
| ..... | ................. | ................. | ...D.R | ..ARTADETE.DS | A..A....V... | 0.01 | 1 |
| ..... | ................. | T..SE....NF....... | ...D.R | E.GRGA..AV.E | A..A........ | 0.01 | 1 |
| N.... | F.....AEG.LK.M.H.L | ..DGE....DF....... | ...... | ............ | ............ | 0.01 | 1 |
| ..... | ..............T.T.R | ..YN......F......T | ...D.R | E.ATA...E.DD | A..A........ | 0.01 | 1 |
| ..... | F.....GQ..RV.T...L | ..A......DF....... | ...DG. | ............ | A..A........ | 0.01 | 1 |
| E.... | F.....DRG.SD.K.K.. | ..DNH....DF....... | ...ADR | ............ | A..A........ | 0.01 | 1 |
| ..... | F................. | ................. | ...DD. | ES.A...AAYGE | A..A..P..... | 0.01 | 1 |
| HT... | F......KT.NV.K.T.H | .V........F....... | ...... | ............ | A..A........ | 0.01 | 1 |
| G.... | ................. | ................. | R..DD. | .D.......... | A..A........ | 0.01 | 1 |
| A.... | ................. | ................. | G..T.R | ............ | A..A........ | 0.01 | 1 |
| G.... | ................. | TK.NE....NF....... | ...DDR | ............ | A..T........ | 0.01 | 1 |
| .A... | ................. | ................. | R..A.. | E.ATRA.IE.DD | A..A........ | 0.01 | 1 |
| TT..T | ................. | ..DGE....DF.R..... | ...... | ............ | ............ | 0.01 | 1 |
| ..... | ................. | ................. | ....G. | ..TG.D..A.GG | A..A........ | 0.01 | 1 |
| ..... | ................. | ................. | ...... | EDGRGD.TEVDQ | A..A........ | 0.01 | 1 |
| ..... | ................. | ...............T | ...DDR | ............ | A........... | 0.01 | 1 |
| SA..T | F................. | .V........F....... | ...... | ............ | GPRTP..FDI.A | 0.01 | 1 |
| GT... | F.....GSA.RP.N.H.K | ..DGE....DF....... | ....GR | ENAGASDIA.DH | ............ | 0.01 | 1 |
| EA... | F................. | .V........F....... | ...... | ............ | KRQAG...HE.A | 0.01 | 1 |
| TT... | F.....DRG.S..T.A.S | ..DGE....DF....... | ...... | ............ | ............ | 0.01 | 1 |
| ..... | F.....DA..IA.L.K.R | .KDSR............. | R..AG. | ESAG....A.GE | A..A........ | 0.01 | 1 |
| ..... | ................. | ................. | ...AD. | ESAG.DD.A.DQ | A..A........ | 0.01 | 1 |
| ..... | F......NG.PL.K...L | .V........F....... | ...... | ............ | A..A........ | 0.01 | 1 |
| ..... | ................. | ................. | ...... | .SARG..A..DE | A..A........ | 0.01 | 1 |
| G.... | ................. | ................. | ....GR | ..AG.N.AA.GQ | A..A........ | 0.01 | 1 |
| E.... | F................. | ................. | ....D. | .SAS.N.IA..D | A..A........ | 0.01 | 1 |
| ..... | F................. | .V........F....... | ...... | ............ | DR.SG..Y...H | 0.01 | 1 |
| NA... | F.....NKT.IV.T.E.R | TPPG.....DF....... | ...D.. | ............ | A..A........ | 0.01 | 1 |
| D...T | F.....SN..PL.K.T.. | ..HG.....NF......T | ...DD. | ESAGRS...VDR | A..A........ | 0.01 | 1 |
| ..... | F.....SKA.S..L.E.R | .QPG.....NF....... | G..AG. | ............ | A..A........ | 0.01 | 1 |
| .A... | ................. | .KYT.....NF......T | ...D.R | ESATGD..E.GQ | A..A........ | 0.01 | 1 |
| TA... | ................. | .QPG.....NF......T | ...D.. | ............ | A..A........ | 0.01 | 1 |
| .A... | F................. | ..........F....... | E..TD.. | ............ | ............ | 0.01 | 1 |
| ....T | F................. | .KYT.....NF......T | ...DDR | ............ | A..A........ | 0.01 | 1 |
| .A... | F.....NQA.SV...A.R | .........NF......T | ...DDR | E..G.SDAA.GD | A..A........ | 0.01 | 1 |

TABLE 7-continued

AAV capsid proteins having increased specificity for and/or transduction of
CD44⁺ GSC (pool of Round 1 selection). Amino acid numbers correspond to the
amino acid sequence of VP1 (SEQ ID NO: 1). Sequences below correspond to SEQ
ID NOs: 8 and 4706-6981 from top to bottom.

| 263 QSGAS | 444 YLSRTNTPSGTTTQSRLQ | 490 KTSADNNNSEYSWTGATK | 527 KKDEEK | 545 QGSEKTNVDIEK | 585 RGNRQAATADVN | % | # |
|---|---|---|---|---|---|---|---|
| EA... | F.....GGG....K.G.R | .KDT......F......T | ...DD. | ENGT.AD.AFDH | A..A........ | 0.01 | 1 |
| ..... | .................. | ..........F....... | G..AD. | ............ | A..A........ | 0.01 | 1 |
| .A... | .................. | .................. | E....R | ............ | A..A........ | 0.01 | 1 |
| ..... | .................. | ..........F....... | ...... | ............ | THRDA...EG.E | 0.01 | 1 |
| G.... | .................K | ..YN......F......T | ...D.R | .NGR.G..A..E | A..A........ | 0.01 | 1 |
| NA..T | F................. | .V........F....... | ...... | ............ | TRKNP..VS..E | 0.01 | 1 |
| ..... | .................. | .................. | ...D.. | ............ | ............ | 0.01 | 1 |
| T.... | .................. | .................. | G..DG. | ............ | ............ | 0.01 | 1 |
| GA... | F.....D....V.T.E.R | .................. | ...DD. | ............ | ............ | 0.01 | 1 |
| RA... | .................. | .................. | ...NDR | E.A.AD.AAF.. | A..A........ | 0.01 | 1 |
| ..... | .................. | ................T | G..D.R | ............ | A..A........ | 0.01 | 1 |
| ..... | .................. | .Q.D.....DF..P.... | ...A.. | ............ | ............ | 0.01 | 1 |
| A.... | .................. | .KYT.....NF....... | R...D. | ED.GGND.EV.D | A..A........ | 0.01 | 1 |
| .A... | .................. | .................. | R..DD. | EN.SAGD..... | A..A........ | 0.01 | 1 |
| ..... | .................. | .Q.DR....NF....... | G...D. | .SGS.N..AV.D | A..A........ | 0.01 | 1 |
| GA... | F......S..SA.I.K.K | .QHNH....DF....... | ...DD. | .NAGASDA.FDQ | A..A........ | 0.01 | 1 |
| ..... | .................. | .................. | R..DDE | ............ | ............ | 0.01 | 1 |
| G.... | .................. | TQP.R....NF......T | ...D.. | ............ | A..A........ | 0.01 | 1 |
| ..... | F................. | .................. | ...... | ............ | ............ | 0.01 | 1 |
| .A... | .................. | ................T | ....D. | E.TGRA..A..G | A..A........ | 0.01 | 1 |
| ..... | .................. | ..A......DF....... | ...DG. | EN.G.A.....Q | A..A........ | 0.01 | 1 |
| EA... | F.....DAA.IK.T.Q.N | .V........F....... | ...... | ............ | TT.D...DGV.A | 0.01 | 1 |
| ..... | .................. | .................. | RTMTTS | ............ | ............ | 0.01 | 1 |
| NA..T | .................. | .................. | ...... | ESGGAD.I...R | A..A....... | 0.01 | 1 |
| ..... | F.....GRT.S..L.G.R | .V........F....... | ...... | ES.AA..I.... | A..A........ | 0.01 | 1 |
| G...T | G.....GTG..P.T.D.R | ..AGQ....NF....... | ...DD. | E.AGTNDI...R | A..A........ | 0.01 | 1 |
| GA... | .................. | ..DGE...DF......T | ...N.. | ............ | A..A........ | 0.01 | 1 |
| ..... | .................. | T.PTG....DF....... | ...DDR | .DAG.A.I..DG | A..A........ | 0.01 | 1 |
| D.... | F.....NTG.LH.T...R | .................. | ...DG. | ............ | A..A........ | 0.01 | 1 |
| ..... | .................. | .................. | R...D. | E.AGRN.T..DD | A..A........ | 0.01 | 1 |
| NT... | F......GA.NM.T.A.R | .KDSR....DF......T | R..D.. | ..A.A.D.AFDS | A..A........ | 0.01 | 1 |
| ..... | .................. | .Q.G......F..P.... | ...... | ES.GEG...VDS | ............ | 0.01 | 1 |

TABLE 8

AAV capsid proteins having increased specificity for and/or transduction of CD44⁺ GSC (pool of Round 2 selection). Amino acid numbers correspond to the amino acid sequence of VP1 (SEQ ID NO: 1). Sequences below correspond to SEQ ID NOs: 8 and 6982-6986 from top to bottom.

| | 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN | % |
|---|---|---|---|---|---|---|---|
| # 65 | HA... | F.....GKG.ND.T.N.G | ..A......DF | ....... | ...DG. | ........... | ........... | 81.25 |
| 10 | GT... | F.....AEG.LK.M.H.L | ..DGE....DF | ...... | ...... | ........... | ........... | 12.50 |
| 2 | ..... | F.....ASA.S..T.T.G | .QPG.....DF | ....... | ...D.. | ........... | ........... | 2.50 |
| 2 | ST... | ................. | ..DGE....DF | ....... | R...D. | ........... | ........... | 2.50 |
| 1 | ..... | F.....SGT.NM.K.T.E | .Q.GQ....DF | ....... | ....G. | ........... | A..A........ | 1.25 |

Example 4

Validation of GBM-Specific Mutants

Figure 5:
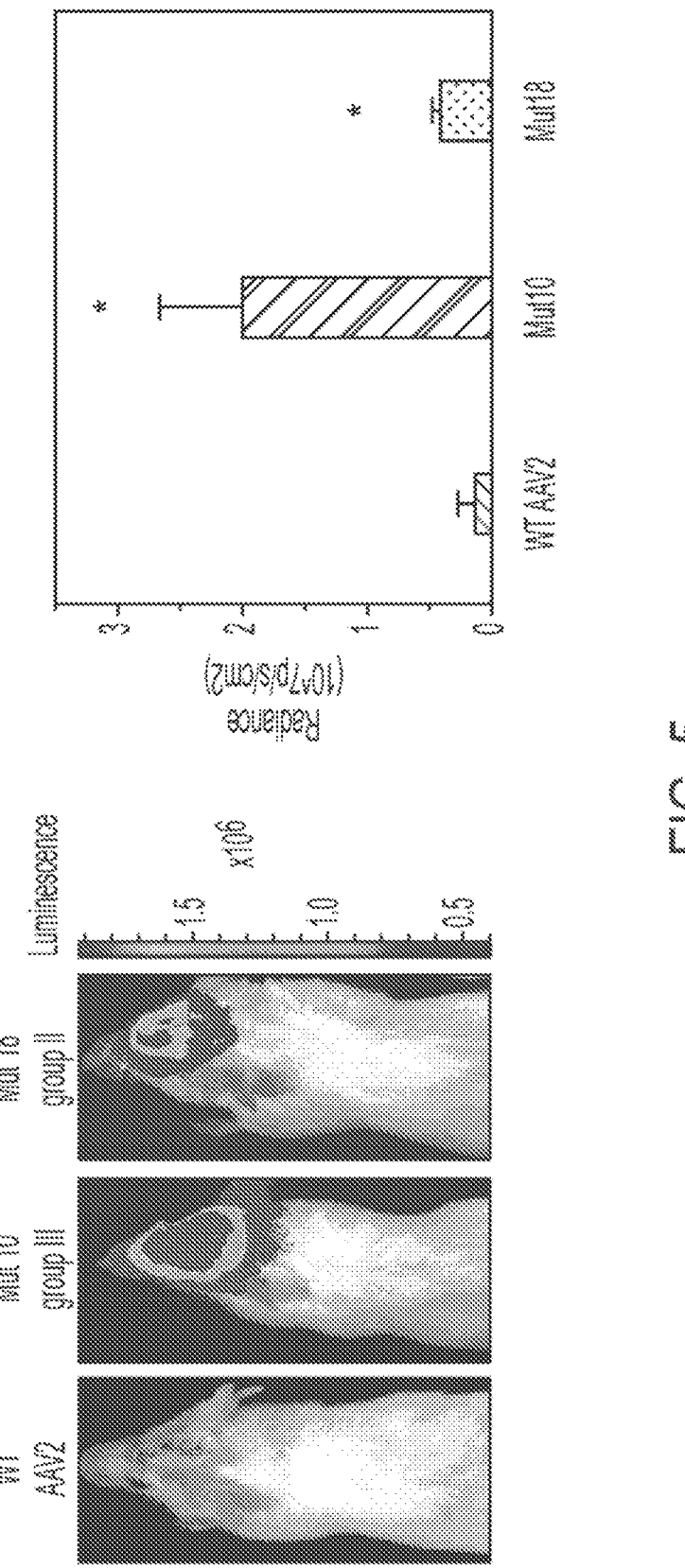
FIG. 5. Variants 10 and 18 exhibited greatly higher efficiency and specificity for GBM compared to WT AAV2, as measured by Antares BLI. *T-test $p\leq0.05$.

Variants (or mutants) numbered 1, 9, 19 and 23 (FIG. 4) and a control WT AAV2 were synthesized to express reporter gene Antares. An equal titer of mutants and two-fold higher titer of the WT was injected once into a cohort of D-luciferase-tagged glioblastoma multiforme (GBM) patient-derived xenograft (PDX) animals. Antares bioluminescence (using furimazine) was measured 4 days after injection. Antares bioluminescence was normalized against baseline D-luciferase bioluminescence (using D-luciferin). Results from Mutants 9 and 19, shown in (FIG. 5), were significantly elevated in efficiency and specificity for GBM compared to the unselected WT AAV2 control, as predicted by NGS analysis.

Figure 6A:
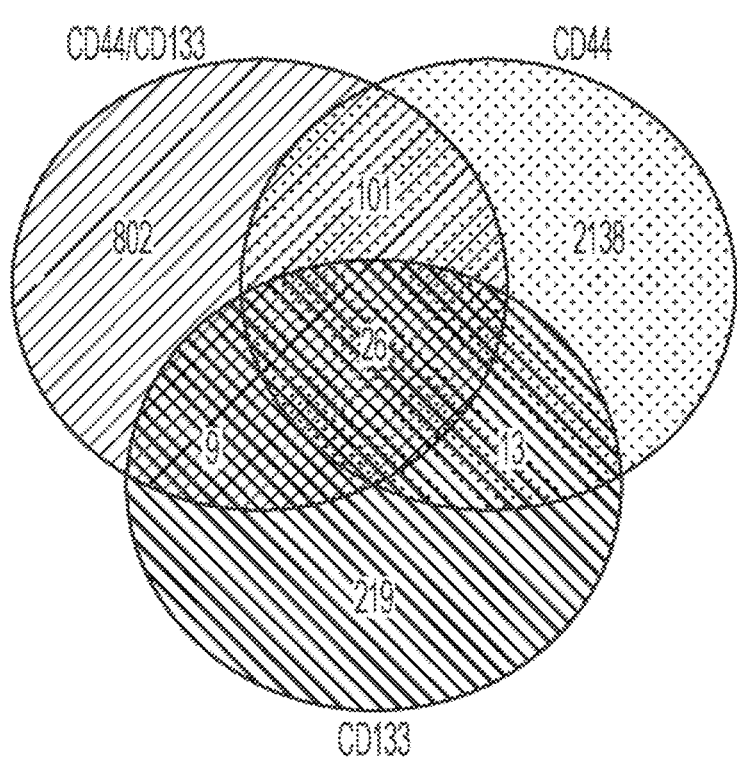
FIG. 6A. Overlapping of CD44+/133+, CD44+, CD133+ mutants after first round of selection.
Figure 6B:
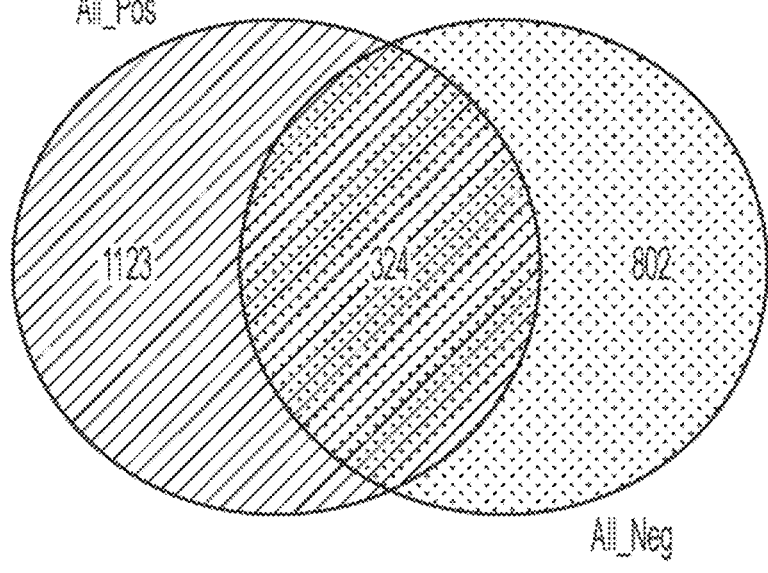
FIG. 6B. Overlapping of pooled library all-CD-positive (pooled library of DNA from CD44+/133+, CD44+, CD133+) and all-CD-negative (CD44−/133−).
Figure 7:
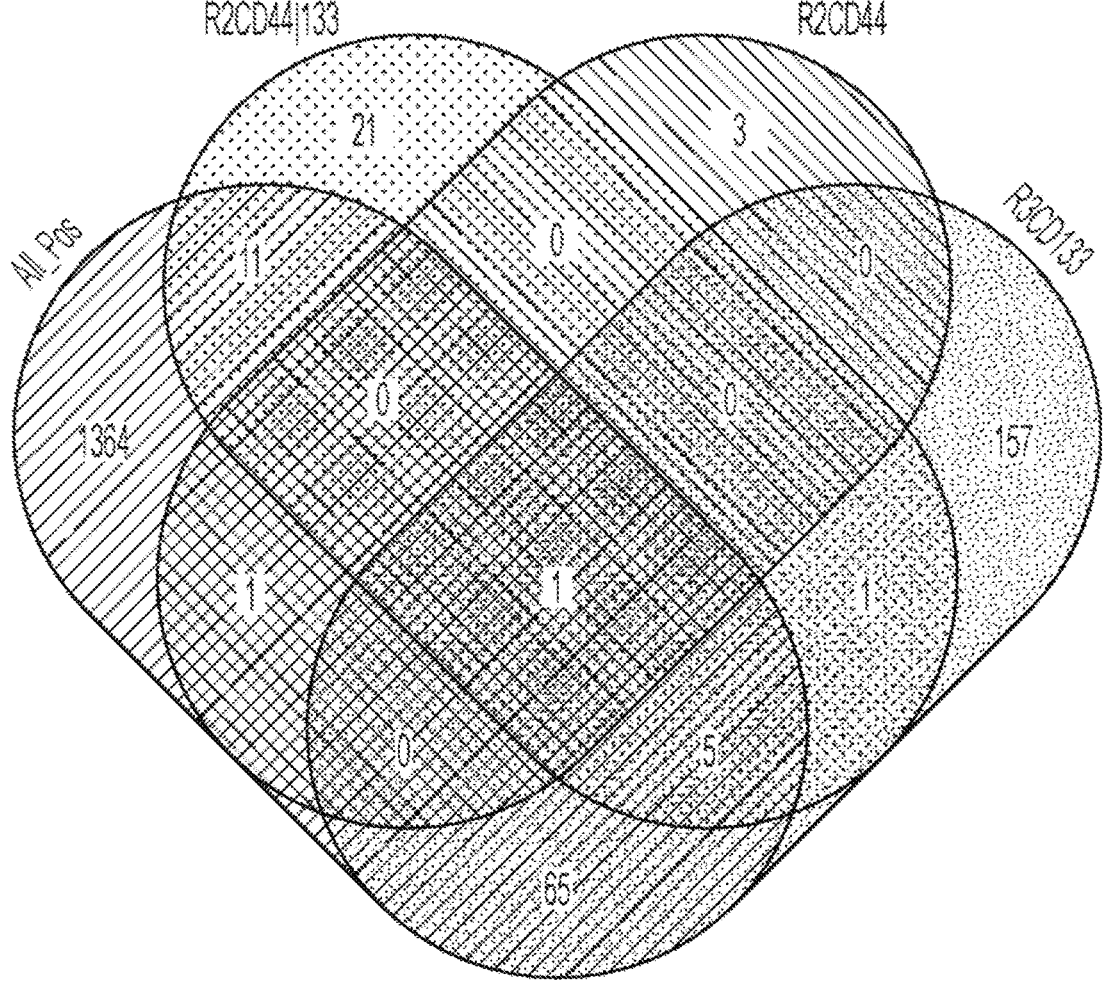
FIG. 7. Overlapping of pooled library all-CD-positive (injection mix) with mutants after 2nd round of selection: CD44+/133+, CD44+, CD133+.

As shown in FIGS. 6A, 6B, and 7, the pools of particular capsid variants that confer enhaned affinity for and transduction in cells following two rounds of selection from among different cell populations have significant overlap.

Several of the capsid variants conferring the highest transduction properties comprise substitutions at one of the following combinations of amino acid positions:

(a) Q263, 5264, Y444, T450, P451, 5452, T454, Q457, R459, Q461, 5492, A493, D494, E499, and Y500F, or (b) E531, K532, S547, E548, D553, R585, and R588 relative to SEQ ID NO: 1 (the AAV2 VP1 amino acid sequence).

TABLE 9

Variant Capsid Proteins: amino acid substitutions. Amino acid (AA) sequences of the top 23 capsid variants selected by three rounds of directed evolution targeting all four GSC and GBM cell populations. The numbers at the top of the list designate AA residue position within the WT AAV2 VP1 capsid sequence. The conserved, not mutated residues in the selected variants are identified by a dot, the positions of mutant AAs shown below the respective WT AAs. Variants with numbers 9, 10, 18, 19, and 23 are shown in bold. The frequency (in %) of the selected variants in NGS database are shown in four columns to the right of the sequences. In addition, variant designated '10*' was synthesized. Sequences below correspond to SEQ ID NOs: 8 and 6987-7010 from top to bottom.

| Variant | 263 QSGAS | 444 YLSRTNTPSGTTTQSRLQ | 490 KTSADNNNSEYSWTGATK | 527 KDDEEK | 545 QGSEKTNVDIEK | 585 RGNRQAATADVN |
|---|---|---|---|---|---|---|
| 1 | ..... | ................. | ................... | G..DG. | ........... | ........... |
| 2 | TA... | ................. | .QANH....DF....... | ...DDR | ........... | A..A........ |
| 3 | ..... | F................ | .V........F........ | ...... | ........... | A..A........ |
| 4 | ..... | ................. | ................... | ...N.. | ........... | A..A........ |
| 5 | ..... | F................ | .V........F........ | ...... | ........... | ........... |
| 6 | ..... | ................. | ................... | R..TG. | ........... | A..A........ |
| 7 | ..... | ................. | ................... | E..ND. | ........... | ........... |
| 8 | A.... | F.....DA..IA.L.K.R | .KDSR....DF......T | R..DD. | ........... | A..A........ |
| 9 (I) | ..... | ................. | ................... | ....GR | ..AG.N.AA.GQ | A..A........ |
| 10 (III) | .A... | F.....DRG.S..T.A.S | ..DGE....DF....... | ...... | ........... | ........... |
| 11 | RA... | F.....DTG.SK.T.T.R | .Q.S......F........ | ...D.. | .NGR.G..A..E | A..A........ |

TABLE 9-continued

Variant Capsid Proteins: amino acid substitutions. Amino acid (AA) sequences of
the top 23 capsid variants selected by three rounds of directed evolution targeting all four
GSC and GBM cell populations. The numbers at the top of the list designate AA residue
position within the WT AAV2 VP1 capsid sequence. The conserved, not mutated residues in
the selected variants are identified by a dot, the positions of mutant AAs shown below the
respective WT AAs. Variants with numbers 9, 10, 18, 19, and 23 are shown in bold. The
frequency (in %) of the selected variants in NGS database are shown in four columns to the
right of the sequences. In addition, variant designated '10*' was synthesized. Sequences
below correspond to SEQ ID NOs: 8 and 6987-7010 from top to bottom.

```
12          .....    ...................    .PPNG.....F......T    ...DDR    E.ATRA..A.DE    A..A........

13          .....    ...................    .QD.E.....F..P....    ...D..    ............    ............

14          .....    ...................    .Q.DR.....F.......    ....D.    ............    A..A........

15          .....    ...................    ...................    ......    ............    A..A........

16          .....    ...................    ...................    ...DDR    ...GT..AA.GD    A..A........

17          .....    ...................    ...................    ....D.    ............    A..A........

18 (II)     GT...    F.....AEG.LK.M.H.L     ..DGE....DF.......    ......    ............    ............

19          .....    ...................    ...................    ...NDR    ..AKG...AV..    A..A........

20          .....    ...................    ...................    R..AGR    ............    A..A........

21          .....    ...................    ...................    R..DD.    ............    A..A........

22          E....    F.....DRG.S..T.A.S     ..DGE....DF.......    ......    ............    ............

23 (IV)     E....    F.....ASA.S..T.T.G     .QPG.....DF.......    ...DDR    ............    ............

10*         AA...    F.....DRG.S..T.A.S     ..DGE....DF.......    ......    ............    ............
```

| | CD status | | | |
|---|---|---|---|---|
| Variant | 44+/133+ | 44-/133- | 44 + | 133+ |
| 1 | 0.31 | 0.80 | 0.30 | 0.43 |
| 2 | 0.45 | 0.55 | 0.59 | 0.07 |
| 3 | 0.10 | 0.16 | 0.30 | 0.14 |
| 4 | 0.08 | 0.16 | 0.45 | 0.62 |
| 5 | 0.29 | 0.23 | 0.74 | 1.01 |
| 6 | 0.02 | 0.09 | 0.18 | 0.57 |
| 7 | 0.05 | 0.23 | 0.07 | 0.09 |
| 8 | 0.27 | 0.34 | 0.25 | 0.56 |
| 9 (I) | 1.70 | 1.91 | 1.75 | 3.23 |
| 10 (III) | 0.88 | 0.88 | 0.29 | 0.56 |
| 11 | 0.14 | 0.15 | 0.02 | 0.43 |
| 12 | 0.43 | 0.26 | 0.21 | 0.07 |
| 13 | 0.35 | 0.16 | 0.32 | 0.51 |
| 14 | 0.13 | 0.04 | 0.01 | 0.30 |
| 15 | 0.46 | 0.65 | 0.76 | 0.46 |
| 16 | 0.15 | 0.08 | 0.13 | 0.61 |
| 17 | 0.02 | 0.19 | 0.15 | 0.95 |
| 18 (II) | 0.08 | 0.85 | 0.52 | 2.17 |
| 19 | 0.78 | 0.75 | 0.46 | 3.25 |
| 70 | 0.02 | 0.03 | 0.04 | 0.30 |

TABLE 9-continued

Variant Capsid Proteins: amino acid substitutions. Amino acid (AA) sequences of
the top 23 capsid variants selected by three rounds of directed evolution targeting all four
GSC and GBM cell populations. The numbers at the top of the list designate AA residue
position within the WT AAV2 VP1 capsid sequence. The conserved, not mutated residues in
the selected variants are identified by a dot, the positions of mutant AAs shown below the
respective WT AAs. Variants with numbers 9, 10, 18, 19, and 23 are shown in bold. The
frequency (in %) of the selected variants in NGS database are shown in four columns to the
right of the sequences. In addition, variant designated '10*' was synthesized. Sequences
below correspond to SEQ ID NOs: 8 and 6987-7010 from top to bottom.

| | | | |
|---|---|---|---|
| 21 | 0.29 | 0.47 | 0.13 | 0.33 |
| 22 | 0.02 | 0.01 | 0.01 | 0.53 |
| 23 (IV) | 0.92 | 1.15 | 1.47 | 0.95 |
| 10* | | | |

Full amino acid sequences for above variants #9, #10,
18, and #23 (indicated with boldface and Roman numerals
in the chart) are shown below.

Variant 9-
```
                              SEQ ID NO: 4
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNPSGTTTQSRLQFSQAGASDI

RDQSRNWLPGPCYRQQRVSKTSADNNNSEYSWTGATKYHLNGRDSLV

NPGPAMASHKDDEGRFFPQSGVLIFGKQGAGKNNAAIGQVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 10-
```
                              SEQ ID NO: 5
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQAGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS
```

-continued
```
YAHSQSLDRLMNPLIDQYLYFLSRTNDRGGSTTTSALSFSQAGASDI

RDQSRNWLPGPCYRQQRVSKTDGENNNSDFSWTGATKYHLNGRDSLV

NPGPAMASHKDDEEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 18-
```
                              SEQ ID NO: 6
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSGTGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNAEGGLKTMSHLLFSQAGASDI

RDQSRNWLPGPCYRQQRVSKTDGENNNSDFSWTGATKYHLNGRDSLV

NPGPAMASHKDDEEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 23-
```
                              SEQ ID NO: 7
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG
```

-continued

```
KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSESGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNASAGSTTTSTLGFSQAGASDI

RDQSRNWLPGPCYRQQRVSKQPGDNNNSDFSWTGATKYHLNGRDSLV

NPGPAMASHKDDDDRFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Full amino acid sequences for the remaining capsid variants in Table 9 are shown below.

Variant 1-

SEQ ID NO: 9
```
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHGDDDGKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 2-

SEQ ID NO: 10
```
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSTAGASNDNHYFGYSTPWGYF

DFNRFHCHFSPRDWQRLINNNWGFRPKRLNFKLFNIQVKEVTQNDGT
```

-continued

```
TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKQANHNNNSDFSWTGATKYHLNGRDSLV

NPGPAMASHKDDDDRFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 3-

SEQ ID NO: 11
```
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNTPSGTTTQSRLQFSQAGASDI

RDQSRNWLPGPCYRQQRVSKVSADNNNSEFSWTGATKYHLNGRDSLV

NPGPAMASHKDDEEKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Variant 4-

SEQ ID NO: 12
```
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHKDDNEKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS
```

TTFSAAKFASFITQYSTGQVSVEIEWELQKENSKRWNPEIQYTSNYN

KSVNVDFTVDTNGVYSEPRPIGTRYLTRNL

Variant 5-

SEQ ID NO: 13

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNTPSGTTTQSRLQFSQAGASDI

RDQSRNWLPGPCYRQQRVSKVSADNNNSEFSWTGATKYHLNGRDSLV

NPGPAMASHKDDEEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 6-

SEQ ID NO: 14

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHRDDTGKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 7-

SEQ ID NO: 15

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHEDDNDKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 8-

SEQ ID NO: 16

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSASGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNDASGIATLSKLRFSQAGASDI

RDQSRNWLPGPCYRQQRVSKKDSRNNNSDFSWTGATTYHLNGRDSLV

NPGPAMASHRDDDDKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 11-

SEQ ID NO: 17

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSRAGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNDTGGSKTTSTLRFSQAGASDI

-continued

RDQSRNWLPGPCYRQQRVSKQSSDNNNSEFSWTGATKYHLNGRDSLV

NPGPAMASHKDDDEKFFPQSGVLIFGKQNGRKGNVAIEEVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 12-

SEQ ID NO: 18

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKPPNGNNNSEFSWTGATTYHLNGRDSLV

NPGPAMASHKDDDDRFFPQSGVLIFGKEGATRANVAIDEVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 13-

SEQ ID NO: 19

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKQDAENNNSEFSWPGATKYHLNGRDSLV

NPGPAMASHKDDDEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 14-

SEQ ID NO: 20

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKQSDRNNNSEFSWTGATKYHLNGRDSLV

NPGPAMASHKDDDEDKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 15-

SEQ ID NO: 21

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHKDDEEKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 16-

SEQ ID NO: 22

MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

-continued

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHKDDDDRFFPQSGVLIFGKQGSGTTNAAIGDVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 17-
                                        SEQ ID NO: 23
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHKDDEDKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 19-
                                        SEQ ID NO: 24
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHKDDNDRFFPQSGVLIFGKQGAKGTNVAVEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 20-
                                        SEQ ID NO: 25
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHRDDAGRFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 21-
                                        SEQ ID NO: 26
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSQSGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYYLSRTNTPSGTTTQSRLQFSQAGASDI

RDQSRNWLPGPCYRQQRVSKTSADNNNSEYSWTGATKYHLNGRDSLV

NPGPAMASHRDDDDKFFPQSGVLIFGKQGSEKTNVDIEKVMITDEEE

IRTTNPVATEQYGSVSTNLQAGNAQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 22-
                                        SEQ ID NO: 27
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

-continued

```
HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSESGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNDRGGSTTTSALSFSQAGASDI

RDQSRNWLPGPCYRQQRVSKTDGENNNSDFSWTGATKYHLNGRDSLV

NPGPAMASHKDDEEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL

Variant 10*-
                                        SEQ ID NO: 28
MAADGYLPDWLEDTLSEGIRQWWKLKPGPPPPKPAERHKDDSRGLVL

PGYKYLGPFNGLDKGEPVNEADAAALEHDKAYDRQLDSGDNPYLKYN

HADAEFQERLKEDTSFGGNLGRAVFQAKKRVLEPLGLVEEPVKTAPG

KKRPVEHSPVEPDSSSGTGKAGQQPARKRLNFGQTGDADSVPDPQPL

GQPPAAPSGLGTNTMATGSGAPMADNNEGADGVGNSSGNWHCDSTWM

GDRVITTSTRTWALPTYNNHLYKQISSAAGASNDNHYFGYSTPWGYF

DFNRFHCHFSPRDWQRLINNNWGFRPKRLNFKLFNIQVKEVTQNDGT

TTIANNLTSTVQVFTDSEYQLPYVLGSAHQGCLPPFPADVFMVPQYG

YLTLNNGSQAVGRSSFYCLEYFPSQMLRTGNNFTFSYTFEDVPFHSS

YAHSQSLDRLMNPLIDQYLYFLSRTNDRGGSTTTSALSFSQAGASDI

RDQSRNWLPGPCYRQQRVSKTDGENNNSDFSWTGATKYHLNGRDSLV

NPGPAMASHKDDEEKFFPQSGVLIFGKQGSEKTNVDIEKVMITDEEE

IRTTNPVATEQYGSVSTNLQRGNRQAATADVNTQGVLPGMVWQDRDV

YLQGPIWAKIPHTDGHFHPSPLMGGFGLKHPPPQILIKNTPVPANPS

TTFSAAKFASFITQYSTGQVSVEIEWELQKENSKRWNPEIQYTSNYN

KSVNVDFTVDTNGVYSEPRPIGTRYLTRNL
```

Example 5

Validation of Capsid Variants In Vitro

The directed evolution screen identified capsid variants #9, #10, #18, and #23 as four of the best-transducing capsids in GBM and GSC cells. Recombinant AAV particles comprising these capsids were evaluated in vitro in patient-derived cells in 3D perfused neurosphere assays (FIG. 8A). A neurosphere is a culture system composed of free-floating clusters of cells. As used herein, the Neurosphere Assay (NSA) involves patient-derived GBM and GSC cells cultured in defined serum-free conditions. NSA permits a model reflective of in vivo tumorigenic potential and growth in the use of clonal spheres of cells. The polyacrylamide neurosphere assay (pNSA) involves the use of 10-20 μm microgels composed of transparent polyacrylamide hydrogel particles immersed in an aqueous solution of polyethylene glycol (PEG) (FIG. 8B). AAV perfusion, or dynamic passage, is shown. As used herein, the pNSA assay indicates support in patient-derived GBM clonal spheres and enables in situ fluorescence acquisition at the resolution of a single cell.

AAV particles comprising each of these four capsids were engineered to express the Antares gene. Particles were administered to GBM cells and GSC cells, and fluorescence (mFI) was evaluated on days 1, 3, and 5 post-transduction. As shown in FIGS. 8C-8D, the kinetics and tropism of transduction in serum-free GBM cells of were favorable. The transduction kinetics for particles comprising capsid variant #9 in particular were excellent, as shown in FIG. 8C. A ranking of transduction kinetics as of day 5 for these four variants is shown in FIG. 8D. Mutant #9 is indicated at the bar furthest to the right. The efficient transduction of these capsids in a serum-free perfusion suggests that these particles may be suitable for scalable rAAV production and confirm the directed evolution screen and the in vivo validation experiment shown in Example 4.

AAV particles comprising each of these four capsids were engineered to express GFP with or without one of three short hairpin RNAs (shRNA): a scrambled shRNA, an shRNA targeting the Nkx6-2 and Ascl-1 genes for knockdown, or an shRNA targeting Nkx6-2 alone. Particles were expression of GFP (i.e., measuring AAV transduction), sphere size, and propidium iodide (PI) uptake (a measure of cell death). As shown in FIGS. 9A-9C, particles containing capsid variant #9 carrying either shRNA targeting Nkx6-2 or the Nkx6-2/Ascl1 combination effectively transduced GBM and GSC and silenced both Nkx6-2 and Ascl-1 expression leading to reduction of GBM sphere size and increase in cell death as compared to the control scrambled shRNA containing AAV, as determined in a pNSA assay. Compared to scrambled shRNA (the control, X), cell survival is substantially reduced in Nkx6-2/Ascl-1 (Y) and Nkx6-2 (Z) short hairpin RNA over days 4-8 post-transduction (FIGS. 9B-9C). Size reduction and increased death was mediated by shRNA depletion of MR, as captured by PI uptake using an expert confocal algorithm. The chart in FIG. 9C shows the differential kinetics of cell killing (survival %) for particles expressing the three shRNA cassettes. Nkx6-2/Ascl-1 shRNA-expressing vectors caused the most cell death, while Nkx6-2 (alone) vectors caused the most dramatic single-day increase in cell death (between days 7 and 8). These kinetics enabled further screening of these four lead AAV variants.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

SEQUENCE LISTING

The patent contains a lengthy sequence listing. A copy of the sequence listing is available in electronic form from the USPTO web site (https://seqdata.uspto.gov/docdetail?docId=US12630845B2). An electronic copy of the sequence listing will also be available from the USPTO upon request and payment of the fee set forth in 37 CFR 1.19(b)(3).

What is claimed is:

1. An adeno-associated virus (AAV) particle comprising a capsid protein comprising amino acid substitutions E531G, K532R, S547A E548G, T550N, V552A, D553A, E555G, K556Q, R585A, and R588A relative to the amino acid sequence of SEQ ID NO: 1, or corresponding substitutions in a wild-type VP1 capsid sequence of an AAV serotype other than AAV2.

2. The AAV particle of claim 1, wherein the capsid protein has an amino acid sequence comprising the amino acid sequence of SEQ ID NO: 4.

3. The AAV particle of claim 1, wherein the AAV particle comprises a recombinant genome comprising at least one heterologous nucleic acid sequence.

4. The AAV particle of claim 3, wherein the heterologous nucleic acid sequence encodes a therapeutic peptide or protein.

5. The AAV particle of claim 4, wherein the therapeutic peptide comprises a repair enzyme, a checkpoint inhibitor, a transcription factor, a growth factor receptor, a growth factor ligand, a tumor suppressor protein, or fragments or combinations thereof.

6. An adeno-associated virus (AAV) particle comprising a capsid protein comprising amino acid substitutions Q263G, S264T, Y444F, T450A, P451E, S452G, T454L, T455K, Q457M, R459H, Q461L, S492D, A493G, D494E, E499D, and Y500F relative to the amino acid sequence of SEQ ID NO: 1, or corresponding substitutions in a wild-type VP1 capsid sequence of an AAV serotype other than AAV2.

7. The AAV particle of claim 6, wherein the capsid protein has an amino acid sequence comprising the amino acid sequence of SEQ ID NO: 6.

8. The AAV particle of claim 6, wherein the AAV particle comprises a recombinant genome comprising at least one heterologous nucleic acid sequence.

9. The AAV particle of claim 8, wherein the heterologous nucleic acid sequence encodes a therapeutic peptide or protein.

10. The AAV particle of claim 9, wherein the therapeutic peptide comprises a repair enzyme, a checkpoint inhibitor, a transcription factor, a growth factor receptor, a growth factor ligand, a tumor suppressor protein, or fragments or combinations thereof.

*    *    *    *    *